United States Patent
Dias et al.

(10) Patent No.: US 11,559,561 B2
(45) Date of Patent: Jan. 24, 2023

(54) COMPOSITION AND METHODS FOR TREATMENT OF PRIMARY CILIARY DYSKINESIA

(71) Applicant: Translate Bio, Inc., Lexington, MA (US)

(72) Inventors: Anusha Dias, Lexington, MA (US); Darshan Parekh, Lexington, MA (US); Jeffrey S. Dubins, Lexington, MA (US); Christian Cobaugh, Lexington, MA (US); Shrirang Karve, Lexington, MA (US); Zarna Patel, Lexington, MA (US); Sara J. Dunaj, Lexington, MA (US); Frank DeRosa, Lexington, MA (US); Michael Heartlein, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 67 days.

(21) Appl. No.: 16/736,417

(22) Filed: Jan. 7, 2020

(65) Prior Publication Data

US 2020/0215157 A1    Jul. 9, 2020

Related U.S. Application Data

(60) Provisional application No. 62/789,414, filed on Jan. 7, 2019.

(51) Int. Cl.
| | |
|---|---|
| *A61K 9/127* | (2006.01) |
| *A61K 31/7105* | (2006.01) |
| *A61K 38/17* | (2006.01) |
| *A61K 9/00* | (2006.01) |
| *A61P 11/00* | (2006.01) |
| *A61K 31/711* | (2006.01) |

(52) U.S. Cl.
CPC ........ *A61K 38/1709* (2013.01); *A61K 9/0053* (2013.01); *A61K 9/1272* (2013.01); *A61K 31/711* (2013.01); *A61K 31/7105* (2013.01); *A61P 11/00* (2018.01)

(58) Field of Classification Search
CPC ............... A61K 9/1271; A61K 9/1272; A61K 31/7105; A61K 31/7115; A61K 38/1709
See application file for complete search history.

(56) References Cited

FOREIGN PATENT DOCUMENTS

| WO | WO 2015/148247 A1 | 10/2015 | |
|---|---|---|---|
| WO | WO 2017/205767 A1 | 11/2017 | |
| WO | WO-2018165257 A1 * | 9/2018 | ........... A61K 9/1272 |
| WO | WO 2019/207060 A1 | 10/2019 | |

OTHER PUBLICATIONS

Sequence Alignment: WO 2017/205767, SEQ ID No. 17, vs. U.S. Appl. No. 16/736,417, SEQ ID No. 16, alignment performed Oct. 14, 2021. (Year: 2021).*
Sequence Alignment: WO 2017/205767, SEQ ID No. 18, vs. U.S. Appl. No. 16/736,417, SEQ ID No. 16, alignment performed Oct. 14, 2021. (Year: 2021).*
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).
Hornef et al., "DNAH5 Mutations Are a Common Cause of Primary Ciliary Dyskinesia with Outer Dynein Arm Defects", American Journal of Respiratory and Critical Care Medicine, vol. 174, No. 2, pp. 120-126, (2006).
Lai et al., "Gene editing of DNAH11 restores normal cilia motility in primary ciliary dyskinesia", Journal of Medical Genetics, vol. 53, No. 4, pp. 242-249, (2016).
International Search Report and Written Opinion for PCT/US2020/012529, dated Mar. 30, 2020 (11 pages).
International Preliminary Report on Patentability for PCT/US2020/012529, dated Jun. 16, 2021 (6 pages).

* cited by examiner

*Primary Examiner* — Jeffrey E. Russel
(74) *Attorney, Agent, or Firm* — Proskauer Rose LLP

(57) ABSTRACT

The present invention provides, among other things, methods and compositions for treating primary ciliary dyskinesia (PCD) based on mRNA therapy. The compositions used in treatment of PCD comprise an mRNA comprising a dynein axonemal heavy chain 5 (DNAH5) coding sequence and are administered at an effective dose and an administration interval such that at least one symptom or feature of PCD is reduced in intensity, severity, or frequency or has a delayed onset. mRNAs with optimized DNAH5 coding sequences are provided that can be administered without the need for modifying the nucleotides of the mRNA to achieve sustained in vivo function.

17 Claims, 4 Drawing Sheets

Specification includes a Sequence Listing.

COMPOSITION AND METHODS FOR TREATMENT OF PRIMARY CILIARY DYSKINESIA

CROSS-REFERENCE TO RELATED APPLICATIONS

This application claims benefit of, and priority to, U.S. Provisional Patent Application Ser. No. 62/789,414 filed on Jan. 7, 2019, the contents of which are incorporated herein in its entirety

INCORPORATION-BY-REFERENCE OF SEQUENCE LISTING

The contents of the text file named "MRT-2060US_ST25.txt" which was created on Jan. 6, 2020 and is 504 KB in size, are hereby incorporated by reference in its entirety.

BACKGROUND

Primary ciliary dyskinesia (PCD) is an auto recessive disorder characterized by abnormal cilia and flagella that are found in the linings of the airway, the reproductive system, and other organs and tissues. PCD occurs in approximately 1 in 16,000. Symptoms are present as early as at birth, with breathing problems, and the affected individuals develop frequent respiratory tract infections beginning in early childhood. People with PCD also have year-round nasal congestion and chronic cough. Chronic respiratory tract infections can result in condition called bronchiectasis, which damages the passages, called bronchi, and can cause life-threatening breathing problems. Some individuals with PCD also have infertility, recurrent ear infections, abnormally placed organs within their chest and abdomen.

Mutations in the DNAH1 or DNAH5 genes account for about a third of all cases of primary ciliary dyskinesia. The DNAH5 gene encodes dynein axonemal heavy chain 5, which forms the inner structure of cilia. With an absent or abnormal dynein axonemal heavy chain 5, defective cilia cannot produce the force and movement needed to eliminate fluid, bacteria, and particles from the lungs. The movement of cilia also helps establish the left-right axis during embryonic development and propel the sperm cells forward to the female egg cell.

There is currently no cure for PCD. Current standard of care includes aggressive measures to enhance clearance of mucus and with antibiotic therapy for bacterial infections of the airways. Routine immunizations are administered to prevent respiratory infections and other secondary complications. For some patients, lobectomy, lung transplantation, and sinus surgery are considered. Gene therapy has been studied to address the urgent need for new, more effective treatments of PCD. However, due to the large size of DNAH5 conventional gene therapy methods remain challenging.

SUMMARY OF THE INVENTION

The present invention provides, among other things, methods and compositions for use in the treatment of primary ciliary dyskinesia (PCD). The present invention is based, in part, on the surprising discovery that DNAH5 mRNA, which is approximately 14 kb in length, can be successfully encapsulated in a liposome and effectively delivered to target tissues in vivo.

In some aspects, the present invention provides a method of delivery of a 10 kb or greater mRNA encoding for a protein or peptide in vivo comprising administering to a subject in need of delivery a 10 kb or greater mRNA encoding a protein or peptide. In some embodiments, the 10 kb or greater mRNA is encapsulated in a liposome. In some embodiments, the 10 kb or greater mRNA is 11 kb or greater in length. In some embodiments, the 10 kb or greater mRNA is 12 kb or greater in length. In some embodiments, the 10 kb or greater mRNA is 13 kb or greater in length. In some embodiments, the 10 kb or greater mRNA is 14 kb or greater in length.

In some aspects, the present invention provides a method of delivery of human axonemal dynein heavy chain 5 (DNAH5) in vivo comprising administering to a subject in need of delivery an mRNA encoding a human DNAH5 protein. In some embodiments, the DNAH5 mRNA is encapsulated in a liposome.

In some aspects, the present invention provides a method of treating primary ciliary dyskinesia (PCD) comprising administering to a subject in need of treatment an mRNA encoding human axonemal dynein heavy chain 5 (DNAH5) at an effective dose and an administration interval such that at least one symptom or feature of PCD is reduced in intensity, severity, or frequency or has delayed in onset.

In some embodiments, the DNAH5 mRNA is encapsulated in a liposome.

In some embodiments, the liposome comprises one or more cationic lipids, one or more non-cationic lipids and one or more PEG-modified lipids.

In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLinSSDMA, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), ccBene, ML7 and combinations thereof.

In some embodiments, the cationic lipid is ICE.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)) or combinations thereof. In some embodiments, the non-cationic lipid is DOPE.

In some embodiments, the one or more PEG-modified lipids comprise a poly(ethylene) glycol chain of up to 5 kDa in length covalently attached to a lipid with alkyl chain(s) of $C_6$-$C_{20}$ length.

In some embodiments, the cationic lipid constitutes about 30-60% of the liposome by molar ratio.

In some embodiments, the cationic lipid constitutes about 30%, 40%, 50%, or 60% of the liposome by molar ratio.

In some embodiments, the liposome comprises ICE, DOPE and DMG-PEG2K.

In some embodiments, the liposome has a size of about 80 nm to 200 nm, optionally wherein the liposome has a size of about 100 nm or less than 100 nm.

In some embodiments, the DNAH5 mRNA is codon optimized.

In some embodiments, the DNAH5 mRNA comprises one or more modified nucleotides.

In some embodiments, the one or more modified nucleotides are selected from pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the mRNA is unmodified.

In some embodiments, the mRNA comprises a 5'-untranslated region (5'-UTR) that has a sequence set forth in SEQ ID NO: 2 or SEQ ID NO: 3.

In some embodiments, the mRNA comprises a 3'-untranslated region (3'-UTR) that has a sequence set forth in SEQ ID NO: 4 or SEQ ID NO: 5.

In some embodiments, the mRNA comprises a coding sequence at least 70%, 75%, 80%, 85%, 90%, or 95% identical to any one of SEQ ID NO: 6 to SEQ ID NO: 31. In some embodiments, the mRNA comprises a coding sequence at least 70% identical to any one of SEQ ID NO: 6 to SEQ ID NO: 31. In some embodiments, the mRNA comprises a coding sequence at least 80% identical to any one of SEQ ID NO: 6 to SEQ ID NO: 31. In some embodiments, the mRNA comprises a coding sequence at least 90% identical to any one of SEQ ID NO: 6 to SEQ ID NO: 31. In some embodiments, the mRNA comprises a coding sequence at least 95% identical to any one of SEQ ID NO: 6 to SEQ ID NO: 31. In some embodiments, the mRNA comprises a coding sequence at least 96%, at least 97%, at least 98%, or at least 99% identical to SEQ ID NO: 6 to SEQ ID NO: 31. In some embodiments, the mRNA comprises a coding sequence set forth in SEQ ID NO: 6 to SEQ ID NO: 31.

In some embodiments, the mRNA comprises a coding sequence at least 70%, 75%, 80%, 85%, 90%, or 95% identical to SEQ ID NO: 6. In some embodiments, the mRNA comprises a coding sequence at least 70% identical to SEQ ID NO: 6. In some embodiments, the mRNA comprises a coding sequence at least 80% identical to SEQ ID NO: 6. In some embodiments, the mRNA comprises a coding sequence at least 90% identical to SEQ ID NO: 6. In some embodiments, the mRNA comprises a coding sequence at least 95% identical to SEQ ID NO: 6. In some embodiments, the mRNA comprises a coding sequence at least 96%, at least 97%, at least 98%, or at least 99% identical to SEQ ID NO: 6. In some embodiments, the mRNA comprises a coding sequence set forth in SEQ ID NO: 6.

In some embodiments, the mRNA comprises a coding sequence at least 70%, 75%, 80%, 85%, 90%, or 95% identical to SEQ ID NO: 7. In some embodiments, the mRNA comprises a coding sequence at least 70% identical to SEQ ID NO: 7. In some embodiments, the mRNA comprises a coding sequence at least 80% identical to SEQ ID NO: 7. In some embodiments, the mRNA comprises a coding sequence at least 90% identical to SEQ ID NO: 7. In some embodiments, the mRNA comprises a coding sequence at least 95% identical to SEQ ID NO: 7. In some embodiments, the mRNA comprises a coding sequence at least 96%, at least 97%, at least 98%, or at least 99% identical to SEQ ID NO: 7. In some embodiments, the mRNA comprises a coding sequence set forth in SEQ ID NO: 7.

In some embodiments, the mRNA comprises a coding sequence at least 70%, 75%, 80%, 85%, 90%, or 95% identical to SEQ ID NO: 8. In some embodiments, the mRNA comprises a coding sequence at least 70% identical to SEQ ID NO: 8. In some embodiments, the mRNA comprises a coding sequence at least 80% identical to SEQ ID NO: 8. In some embodiments, the mRNA comprises a coding sequence at least 90% identical to SEQ ID NO: 8. In some embodiments, the mRNA comprises a coding sequence at least 95% identical to SEQ ID NO: 8. In some embodiments, the mRNA comprises a coding sequence at least 96%, at least 97%, at least 98%, or at least 99% identical to SEQ ID NO: 8. In some embodiments, the mRNA comprises a coding sequence set forth in SEQ ID NO: 8.

In some embodiments, the mRNA comprises a coding sequence at least 70%, 75%, 80%, 85%, 90%, or 95% identical to SEQ ID NO: 9. In some embodiments, the mRNA comprises a coding sequence at least 70% identical to SEQ ID NO: 9. In some embodiments, the mRNA comprises a coding sequence at least 80% identical to SEQ ID NO: 9. In some embodiments, the mRNA comprises a coding sequence at least 90% identical to SEQ ID NO: 9. In some embodiments, the mRNA comprises a coding sequence at least 95% identical to SEQ ID NO: 9. In some embodiments, the mRNA comprises a coding sequence at least 96%, at least 97%, at least 98%, or at least 99% identical to SEQ ID NO: 9. In some embodiments, the mRNA comprises a coding sequence set forth in SEQ ID NO: 9.

In some embodiments, the mRNA comprises a coding sequence at least 70%, 75%, 80%, 85%, 90%, or 95% identical to SEQ ID NO: 10. In some embodiments, the mRNA comprises a coding sequence at least 70% identical to SEQ ID NO: 10. In some embodiments, the mRNA comprises a coding sequence at least 80% identical to SEQ ID NO: 10. In some embodiments, the mRNA comprises a coding sequence at least 90% identical to SEQ ID NO: 10. In some embodiments, the mRNA comprises a coding sequence at least 95% identical to SEQ ID NO: 10. In some embodiments, the mRNA comprises a coding sequence at least 96%, at least 97%, at least 98%, or at least 99% identical to SEQ ID NO: 10. In some embodiments, the mRNA comprises a coding sequence set forth in SEQ ID NO: 10.

In some embodiments, the mRNA comprises a coding sequence at least 70%, 75%, 80%, 85%, 90%, or 95% identical to SEQ ID NO: 11. In some embodiments, the mRNA comprises a coding sequence at least 70% identical to SEQ ID NO: 11. In some embodiments, the mRNA comprises a coding sequence at least 80% identical to SEQ ID NO: 11. In some embodiments, the mRNA comprises a coding sequence at least 90% identical to SEQ ID NO: 11. In some embodiments, the mRNA comprises a coding sequence at least 95% identical to SEQ ID NO: 11. In some embodiments, the mRNA comprises a coding sequence at least 96%, at least 97%, at least 98%, or at least 99% identical to SEQ ID NO: 11. In some embodiments, the mRNA comprises a coding sequence set forth in SEQ ID NO: 11.

In some embodiments, the mRNA comprises a coding sequence at least 70%, 75%, 80%, 85%, 90%, or 95% identical to SEQ ID NO: 12. In some embodiments, the mRNA comprises a coding sequence at least 70% identical to SEQ ID NO: 12. In some embodiments, the mRNA comprises a coding sequence at least 80% identical to SEQ ID NO: 12. In some embodiments, the mRNA comprises a coding sequence at least 90% identical to SEQ ID NO: 12. In some embodiments, the mRNA comprises a coding sequence at least 95% identical to SEQ ID NO: 12. In some embodiments, the mRNA comprises a coding sequence at least 96%, at least 97%, at least 98%, or at least 99% identical to SEQ ID NO: 12. In some embodiments, the mRNA comprises a coding sequence set forth in SEQ ID NO: 12.

In some embodiments, the mRNA comprises a coding sequence at least 70%, 75%, 80%, 85%, 90%, or 95% identical to SEQ ID NO: 13. In some embodiments, the mRNA comprises a coding sequence at least 70% identical to SEQ ID NO: 13. In some embodiments, the mRNA comprises a coding sequence at least 80% identical to SEQ ID NO: 13. In some embodiments, the mRNA comprises a coding sequence at least 90% identical to SEQ ID NO: 13. In some embodiments, the mRNA comprises a coding sequence at least 95% identical to SEQ ID NO: 13. In some embodiments, the mRNA comprises a coding sequence at least 96%, at least 97%, at least 98%, or at least 99% identical to SEQ ID NO: 13. In some embodiments, the mRNA comprises a coding sequence set forth in SEQ ID NO: 13.

In some embodiments, the mRNA comprises a coding sequence at least 70%, 75%, 80%, 85%, 90%, or 95% identical to SEQ ID NO: 14. In some embodiments, the mRNA comprises a coding sequence at least 70% identical to SEQ ID NO: 14. In some embodiments, the mRNA comprises a coding sequence at least 80% identical to SEQ ID NO: 14. In some embodiments, the mRNA comprises a coding sequence at least 90% identical to SEQ ID NO: 14. In some embodiments, the mRNA comprises a coding sequence at least 95% identical to SEQ ID NO: 14. In some embodiments, the mRNA comprises a coding sequence at least 96%, at least 97%, at least 98%, or at least 99% identical to SEQ ID NO: 14. In some embodiments, the mRNA comprises a coding sequence set forth in SEQ ID NO: 14.

In some embodiments, the mRNA comprises a coding sequence at least 70%, 75%, 80%, 85%, 90%, or 95% identical to SEQ ID NO: 15. In some embodiments, the mRNA comprises a coding sequence at least 70% identical to SEQ ID NO: 15. In some embodiments, the mRNA comprises a coding sequence at least 80% identical to SEQ ID NO: 15. In some embodiments, the mRNA comprises a coding sequence at least 90% identical to SEQ ID NO: 15. In some embodiments, the mRNA comprises a coding sequence at least 95% identical to SEQ ID NO: 15. In some embodiments, the mRNA comprises a coding sequence at least 96%, at least 97%, at least 98%, or at least 99% identical to SEQ ID NO: 15. In some embodiments, the mRNA comprises a coding sequence set forth in SEQ ID NO: 15.

In some embodiments, the mRNA comprises a coding sequence at least 70%, 75%, 80%, 85%, 90%, or 95% identical to SEQ ID NO: 16. In some embodiments, the mRNA comprises a coding sequence at least 70% identical to SEQ ID NO: 16. In some embodiments, the mRNA comprises a coding sequence at least 80% identical to SEQ ID NO: 16. In some embodiments, the mRNA comprises a coding sequence at least 90% identical to SEQ ID NO: 16. In some embodiments, the mRNA comprises a coding sequence at least 95% identical to SEQ ID NO: 16. In some embodiments, the mRNA comprises a coding sequence at least 96%, at least 97%, at least 98%, or at least 99% identical to SEQ ID NO: 16. In some embodiments, the mRNA comprises a coding sequence set forth in SEQ ID NO: 16.

In some embodiments, the mRNA comprises a coding sequence at least 70%, 75%, 80%, 85%, 90%, or 95% identical to SEQ ID NO: 17. In some embodiments, the mRNA comprises a coding sequence at least 70% identical to SEQ ID NO: 17. In some embodiments, the mRNA comprises a coding sequence at least 80% identical to SEQ ID NO: 17. In some embodiments, the mRNA comprises a coding sequence at least 90% identical to SEQ ID NO: 17. In some embodiments, the mRNA comprises a coding sequence at least 95% identical to SEQ ID NO: 17. In some embodiments, the mRNA comprises a coding sequence at least 96%, at least 97%, at least 98%, or at least 99% identical to SEQ ID NO: 17. In some embodiments, the mRNA comprises a coding sequence set forth in SEQ ID NO: 17.

In some embodiments, the mRNA comprises a coding sequence at least 70%, 75%, 80%, 85%, 90%, or 95% identical to SEQ ID NO: 18. In some embodiments, the mRNA comprises a coding sequence at least 70% identical to SEQ ID NO: 18. In some embodiments, the mRNA comprises a coding sequence at least 80% identical to SEQ ID NO: 18. In some embodiments, the mRNA comprises a coding sequence at least 90% identical to SEQ ID NO: 18. In some embodiments, the mRNA comprises a coding sequence at least 95% identical to SEQ ID NO: 18. In some embodiments, the mRNA comprises a coding sequence at least 96%, at least 97%, at least 98%, or at least 99% identical to SEQ ID NO: 18. In some embodiments, the mRNA comprises a coding sequence set forth in SEQ ID NO: 18.

In some embodiments, the mRNA comprises a coding sequence at least 70%, 75%, 80%, 85%, 90%, or 95% identical to SEQ ID NO: 19. In some embodiments, the mRNA comprises a coding sequence at least 70% identical to SEQ ID NO: 19. In some embodiments, the mRNA comprises a coding sequence at least 80% identical to SEQ ID NO: 19. In some embodiments, the mRNA comprises a coding sequence at least 90% identical to SEQ ID NO: 19. In some embodiments, the mRNA comprises a coding sequence at least 95% identical to SEQ ID NO: 19. In some embodiments, the mRNA comprises a coding sequence at least 96%, at least 97%, at least 98%, or at least 99% identical to SEQ ID NO: 19. In some embodiments, the mRNA comprises a coding sequence set forth in SEQ ID NO: 19.

In some embodiments, the mRNA comprises a coding sequence at least 70%, 75%, 80%, 85%, 90%, or 95% identical to SEQ ID NO: 20. In some embodiments, the mRNA comprises a coding sequence at least 70% identical to SEQ ID NO: 20. In some embodiments, the mRNA comprises a coding sequence at least 80% identical to SEQ ID NO: 20. In some embodiments, the mRNA comprises a coding sequence at least 90% identical to SEQ ID NO: 20. In some embodiments, the mRNA comprises a coding sequence at least 95% identical to SEQ ID NO: 20. In some embodiments, the mRNA comprises a coding sequence at least 96%, at least 97%, at least 98%, or at least 99% identical to SEQ ID NO: 20. In some embodiments, the mRNA comprises a coding sequence set forth in SEQ ID NO: 20.

In some embodiments, the mRNA comprises a coding sequence at least 70%, 75%, 80%, 85%, 90%, or 95% identical to SEQ ID NO: 21. In some embodiments, the mRNA comprises a coding sequence at least 70% identical to SEQ ID NO: 21. In some embodiments, the mRNA comprises a coding sequence at least 80% identical to SEQ ID NO: 21. In some embodiments, the mRNA comprises a coding sequence at least 90% identical to SEQ ID NO: 21. In some embodiments, the mRNA comprises a coding sequence at least 95% identical to SEQ ID NO: 21. In some embodiments, the mRNA comprises a coding sequence at least 96%, at least 97%, at least 98%, or at least 99% identical to SEQ ID NO: 21. In some embodiments, the mRNA comprises a coding sequence set forth in SEQ ID NO: 21.

In some embodiments, the mRNA comprises a coding sequence at least 70%, 75%, 80%, 85%, 90%, or 95% identical to SEQ ID NO: 22. In some embodiments, the mRNA comprises a coding sequence at least 70% identical to SEQ ID NO: 22. In some embodiments, the mRNA comprises a coding sequence at least 80% identical to SEQ ID NO: 22. In some embodiments, the mRNA comprises a coding sequence at least 90% identical to SEQ ID NO: 22. In some embodiments, the mRNA comprises a coding sequence at least 95% identical to SEQ ID NO: 22. In some embodiments, the mRNA comprises a coding sequence at least 96%, at least 97%, at least 98%, or at least 99% identical to SEQ ID NO: 22. In some embodiments, the mRNA comprises a coding sequence set forth in SEQ ID NO: 22.

In some embodiments, the mRNA comprises a coding sequence at least 70%, 75%, 80%, 85%, 90%, or 95% identical to SEQ ID NO: 23. In some embodiments, the mRNA comprises a coding sequence at least 70% identical to SEQ ID NO: 23. In some embodiments, the mRNA comprises a coding sequence at least 80% identical to SEQ ID NO: 23. In some embodiments, the mRNA comprises a coding sequence at least 90% identical to SEQ ID NO: 23. In some embodiments, the mRNA comprises a coding sequence at least 95% identical to SEQ ID NO: 23. In some embodiments, the mRNA comprises a coding sequence at least 96%, at least 97%, at least 98%, or at least 99% identical to SEQ ID NO: 23. In some embodiments, the mRNA comprises a coding sequence set forth in SEQ ID NO: 23.

In some embodiments, the mRNA comprises a coding sequence at least 70%, 75%, 80%, 85%, 90%, or 95% identical to SEQ ID NO: 24. In some embodiments, the mRNA comprises a coding sequence at least 70% identical to SEQ ID NO: 24. In some embodiments, the mRNA comprises a coding sequence at least 80% identical to SEQ ID NO: 24. In some embodiments, the mRNA comprises a coding sequence at least 90% identical to SEQ ID NO: 24. In some embodiments, the mRNA comprises a coding sequence at least 95% identical to SEQ ID NO: 24. In some embodiments, the mRNA comprises a coding sequence at least 96%, at least 97%, at least 98%, or at least 99% identical to SEQ ID NO: 24. In some embodiments, the mRNA comprises a coding sequence set forth in SEQ ID NO: 24.

In some embodiments, the mRNA comprises a coding sequence at least 70%, 75%, 80%, 85%, 90%, or 95% identical to SEQ ID NO: 25. In some embodiments, the mRNA comprises a coding sequence at least 70% identical to SEQ ID NO: 25. In some embodiments, the mRNA comprises a coding sequence at least 80% identical to SEQ ID NO: 25. In some embodiments, the mRNA comprises a coding sequence at least 90% identical to SEQ ID NO: 25. In some embodiments, the mRNA comprises a coding sequence at least 95% identical to SEQ ID NO: 25. In some embodiments, the mRNA comprises a coding sequence at least 96%, at least 97%, at least 98%, or at least 99% identical to SEQ ID NO: 25. In some embodiments, the mRNA comprises a coding sequence set forth in SEQ ID NO: 25.

In some embodiments, the mRNA comprises a coding sequence at least 70%, 75%, 80%, 85%, 90%, or 95% identical to SEQ ID NO: 26. In some embodiments, the mRNA comprises a coding sequence at least 70% identical to SEQ ID NO: 26. In some embodiments, the mRNA comprises a coding sequence at least 80% identical to SEQ ID NO: 26. In some embodiments, the mRNA comprises a coding sequence at least 90% identical to SEQ ID NO: 26. In some embodiments, the mRNA comprises a coding sequence at least 95% identical to SEQ ID NO: 26. In some embodiments, the mRNA comprises a coding sequence at least 96%, at least 97%, at least 98%, or at least 99% identical to SEQ ID NO: 26. In some embodiments, the mRNA comprises a coding sequence set forth in SEQ ID NO: 26.

In some embodiments, the mRNA comprises a coding sequence at least 70%, 75%, 80%, 85%, 90%, or 95% identical to SEQ ID NO: 27. In some embodiments, the mRNA comprises a coding sequence at least 70% identical to SEQ ID NO: 27. In some embodiments, the mRNA comprises a coding sequence at least 80% identical to SEQ ID NO: 27. In some embodiments, the mRNA comprises a coding sequence at least 90% identical to SEQ ID NO: 27. In some embodiments, the mRNA comprises a coding sequence at least 95% identical to SEQ ID NO: 27. In some embodiments, the mRNA comprises a coding sequence at least 96%, at least 97%, at least 98%, or at least 99% identical to SEQ ID NO: 27. In some embodiments, the mRNA comprises a coding sequence set forth in SEQ ID NO: 27.

In some embodiments, the mRNA comprises a coding sequence at least 70%, 75%, 80%, 85%, 90%, or 95% identical to SEQ ID NO: 28. In some embodiments, the mRNA comprises a coding sequence at least 70% identical to SEQ ID NO: 28. In some embodiments, the mRNA comprises a coding sequence at least 80% identical to SEQ ID NO: 28. In some embodiments, the mRNA comprises a coding sequence at least 90% identical to SEQ ID NO: 28. In some embodiments, the mRNA comprises a coding sequence at least 95% identical to SEQ ID NO: 28. In some embodiments, the mRNA comprises a coding sequence at least 96%, at least 97%, at least 98%, or at least 99% identical to SEQ ID NO: 28. In some embodiments, the mRNA comprises a coding sequence set forth in SEQ ID NO: 28.

In some embodiments, the mRNA comprises a coding sequence at least 70%, 75%, 80%, 85%, 90%, or 95% identical to SEQ ID NO: 29. In some embodiments, the mRNA comprises a coding sequence at least 70% identical to SEQ ID NO: 29. In some embodiments, the mRNA comprises a coding sequence at least 80% identical to SEQ ID NO: 29. In some embodiments, the mRNA comprises a coding sequence at least 90% identical to SEQ ID NO: 29. In some embodiments, the mRNA comprises a coding sequence at least 95% identical to SEQ ID NO: 29. In some embodiments, the mRNA comprises a coding sequence at least 96%, at least 97%, at least 98%, or at least 99% identical to SEQ ID NO: 29. In some embodiments, the mRNA comprises a coding sequence set forth in SEQ ID NO: 29.

In some embodiments, the mRNA comprises a coding sequence at least 70%, 75%, 80%, 85%, 90%, or 95% identical to SEQ ID NO: 30. In some embodiments, the mRNA comprises a coding sequence at least 70% identical to SEQ ID NO: 30. In some embodiments, the mRNA comprises a coding sequence at least 80% identical to SEQ ID NO: 30. In some embodiments, the mRNA comprises a coding sequence at least 90% identical to SEQ ID NO: 30. In some embodiments, the mRNA comprises a coding sequence at least 95% identical to SEQ ID NO: 30. In some embodiments, the mRNA comprises a coding sequence at least 96%, at least 97%, at least 98%, or at least 99% identical to SEQ ID NO: 30. In some embodiments, the mRNA comprises a coding sequence set forth in SEQ ID NO: 30.

In some embodiments, the mRNA comprises a coding sequence at least 70%, 75%, 80%, 85%, 90%, or 95% identical to SEQ ID NO: 31. In some embodiments, the mRNA comprises a coding sequence at least 70% identical to SEQ ID NO: 31. In some embodiments, the mRNA comprises a coding sequence at least 80% identical to SEQ ID NO: 31. In some embodiments, the mRNA comprises a coding sequence at least 90% identical to SEQ ID NO: 31. In some embodiments, the mRNA comprises a coding sequence at least 95% identical to SEQ ID NO: 31. In some embodiments, the mRNA comprises a coding sequence at least 96%, at least 97%, at least 98%, or at least 99% identical to SEQ ID NO: 31. In some embodiments, the mRNA comprises a coding sequence set forth in SEQ ID NO: 31.

In some embodiments, administering the mRNA to the subject is performed by intratracheal, intranasal, intravenous, intramuscular or subcutaneous delivery.

In some embodiments, administering the mRNA to the subject is performed by intratracheal delivery.

In some embodiments, administering the mRNA to the subject is performed by intranasal delivery.

In some embodiments, administering the mRNA to the subject is performed by aerosol delivery.

In some embodiments, administering the mRNA to the subject is performed by nebulized delivery.

In some embodiments, administering the mRNA to the subject is performed by dry powder inhalation.

In some embodiments, the composition is administered once a week.

In some embodiments, the composition is administered once every two weeks.

In some embodiments, the composition is administered twice a month.

In some embodiments, the composition is administered once a month.

In some embodiments, the administering the mRNA results in DNAH5 protein expression detectable in one or more internal organs selected from lung, heart, liver, spleen, kidney, brain, stomach, intestines, ovary and testis.

In some embodiments, the administering the mRNA results in DNAH5 protein expression detectable in the lung.

In some embodiments, the administering the mRNA results in DNAH5 protein expression detectable in the lung epithelium.

In some aspects, the invention provides a composition for use in the treatment of primary ciliary dyskinesia (PCD), the composition comprising an mRNA encoding human axonemal dynein heavy chain 5 (DNAH5) encapsulated in a liposome, wherein the liposome comprises one or more cationic lipids, one or more non-cationic lipids and one or more PEG-modified lipids.

In some embodiments, the mRNA comprises a DNAH5 coding sequence at least 70%, 75%, 80%, 85%, 90%, or 95% identical to any one of SEQ ID NO: 6 to SEQ ID NO: 31.

In some embodiments, mRNA comprises a coding sequence at least 70%, at least 80%, at least 90%, at least 95% or at least 98% identical to SEQ ID NO: 6. In some embodiments, mRNA comprises a coding sequence at least 70%, at least 80%, at least 90%, at least 95% or at least 98% identical to SEQ ID NO: 7.

In some embodiments, the mRNA comprises a coding sequence set forth in SEQ ID NO: 6. In some embodiments, the mRNA comprises a coding sequence set forth in SEQ ID NO: 7.

In some embodiments, the mRNA has a 5'-untranslated region (5'-UTR) that has a sequence set forth in SEQ ID NO: 2 or SEQ ID NO: 3, and a 3'-untranslated region (3'-UTR) that has a sequence set forth in SEQ ID NO: 4 or SEQ ID NO: 5.

In some embodiments, wherein the mRNA has one or more modified nucleotides.

In some embodiments, the modified one or more nucleotides is selected from pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the mRNA is unmodified.

In some embodiments, the liposome is 100 nm in diameter or less.

In some embodiments, the invention provides a pharmaceutical composition comprising the composition described above and a suitable excipient.

In some aspects, the present invention provides a method of delivery of a mRNA encoding for a protein or peptide in vivo comprising administering to a subject in need of delivery a mRNA encoding a protein or peptide and having a 5'-untranslated region (5'-UTR) that has a sequence at least 70%, 75%, 80%, 85%, 90%, or 95% identical to SEQ ID NO: 2 and that is not SEQ ID NO: 3. In some embodiments, the mRNA comprises a 5'-untranslated region (5'-UTR) that has a sequence at least 70% identical to SEQ ID NO: 2 that is not SEQ ID NO: 3. In some embodiments, the mRNA comprises a 5'-untranslated region (5'-UTR) that has a sequence at least 75% identical to SEQ ID NO: 2 that is not SEQ ID NO: 3. In some embodiments, the mRNA comprises a 5'-untranslated region (5'-UTR) that has a sequence at least 80% identical to SEQ ID NO: 2 that is not SEQ ID NO: 3. In some embodiments, the mRNA comprises a 5'-untranslated region (5'-UTR) that has a sequence at least 85% identical to SEQ ID NO: 2 that is not SEQ ID NO: 3. In some embodiments, the mRNA comprises a 5'-untranslated region (5'-UTR) that has a sequence at least 90% identical to SEQ ID NO: 2 that is not SEQ ID NO: 3. In some embodiments, the mRNA comprises a 5'-untranslated region (5'-UTR) that has a sequence at least 95% identical to SEQ ID NO: 2 that is not SEQ ID NO: 3. In some embodiments, the mRNA comprises a 5'-untranslated region (5'-UTR) that is at least 96%, at least 97%, at least 98%, or at least 99% identical to SEQ ID NO: 2 that is not SEQ ID NO: 3. In some embodiments, the mRNA comprises a 5'-untranslated region (5'-UTR) set forth in SEQ ID NO: 2. Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

FIG. 1B (left) shows data from Group 1 mice who were administered MRT-1 hDNA5 mRNA; FIG. 1B (right) shows data from Group 2 mice who were administered MRT-1 hDNA5-GFP mRNA.

FIG. 2A depicts representative IHC data for hDNA-5 protein staining in MRT-1 hDNA5 mRNA treated mice compared to saline-treated control (Group 1, left); and IHC data for GFP protein staining in MRT-1 hDNA5-GFP mRNA treated mice compared to saline-treated control (Group 2, right). FIG. 2B shows detailed localization of the respective hDNA5 mRNA derived protein in epithelial tissue of the airways in Group 1 (upper panel) and Group 2 (lower panel) mice.

DEFINITIONS

Figure 1A:
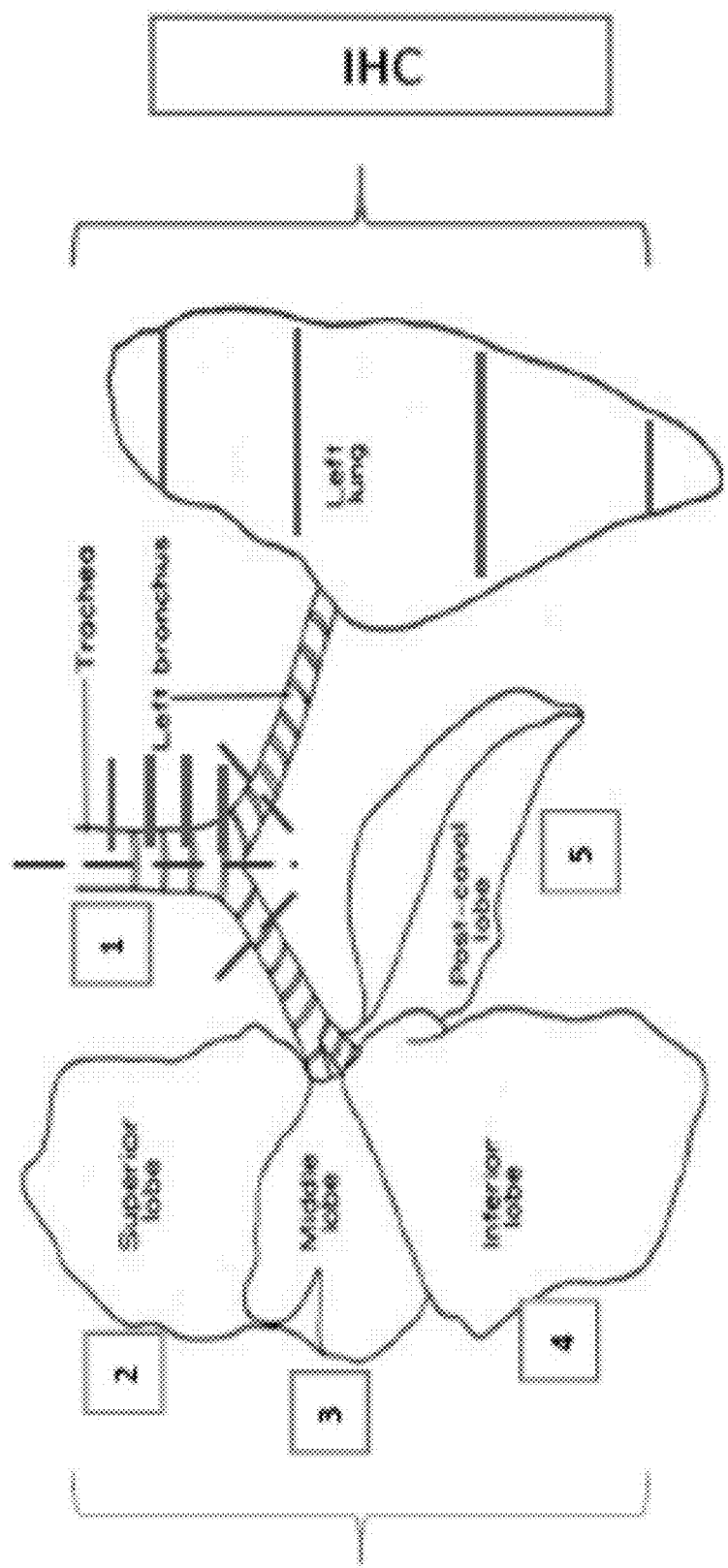
FIG. 1A is a schematic diagram that shows the dissection and usage of various parts of mouse trachea and lungs for quantitative PCR analysis (qPCR) and immunohistochemistry (IHC) analysis, 24 hours after mRNA administration.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("C1-15 alkyl"). In some embodiments, an alkyl group has 1 to 3 carbon atoms ("C1-3 alkyl"). Examples of C1-3 alkyl groups include methyl (C1), ethyl (C2), n-propyl (C3), and isopropyl (C3). In some embodiments, an alkyl group has 8 to 12 carbon atoms ("C8-12 alkyl"). Examples of C8-12 alkyl groups include, without limitation, n-octyl (C8), n-nonyl (C9), n-decyl (C10), n-undecyl (C11), n-dodecyl (C12) and the like. The prefix "n-" (normal) refers to unbranched alkyl groups. For example, n-C8 alkyl refers to (CH2)7CH3, n-C10 alkyl refers to (CH2)9CH3, etc.

Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Typically, the term "approximately" or "about" refers to a range of values that within 10%, or more typically 1%, of the stated reference value.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Codon-optimized: As used herein, the term describes a nucleic acid in which one or more of the nucleotides present in a naturally occurring nucleic acid sequence (also referred to as 'wild-type' sequence) has been substituted with an alternative nucleotide to optimize protein expression without changing the amino acid sequence of the polypeptide encoded by the naturally occurring nucleic acid sequence. For example, the codon AAA may be altered to become AAG without changing the identity of the encoded amino acid (lysine). In some embodiments, the nucleic acids of the invention are codon optimized to increase protein expression of the protein encoded by the nucleic acid. For the purpose of this application, nucleobase thymidine (T) and uracil (U) are used interchangeably in narration of mRNA sequences.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Dosing interval: As used herein dosing interval in the context of a method for treating a disease is the frequency of administering a therapeutic composition in a subject (mammal) in need thereof, for example an mRNA composition, at an effective dose of the mRNA, such that one or more symptoms associated with the disease is reduced; or one or more biomarkers associated with the disease is reduced, at least for the period of the dosing interval. Dosing frequency and dosing interval may be used interchangeably in the current disclosure.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Effective dose: As used herein, an effective dose is a dose of the mRNA in the pharmaceutical composition which when administered to the subject in need thereof, hereby a mammalian subject, according to the methods of the invention, is effective to bring about an expected outcome in the subject, for example reduce a symptom associated with the disease.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polyribonucleotide that encodes at least one polypeptide. mRNA may contain one or more coding and non-coding regions. mRNA can be purified from natural sources, produced using recombinant expression systems and optionally purified, in vitro transcribed, chemically synthesized, etc. An mRNA sequence is presented in the 5' to 3' direction unless otherwise indicated. Typically, the mRNA of the present invention is synthesized from adenosine, guanosine, cytidine and uridine nucleotides that bear no modifications. Such mRNA is referred to herein as mRNA with unmodified nucleotides or 'unmodified mRNA' for short. Typically, this means that the mRNA of the present invention does not comprise any of the following nucleoside analogs: 2-aminoadenosine, 2-thiothymidine, inosine, pyrrolo-pyrimidine, 3-methyl adenosine, 5-methyl-cytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine. An mRNA suitable for practising the claimed invention commonly does not comprise nucleosides comprising chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

Primary Ciliary Dyskinesia (PCD)

Primary ciliary dyskinesia (PCD) is an autosomal recessive disorder characterized by abnormal cilia and flagella that are found in the linings of the airway, the reproductive system, and other organs and tissues. Mutations in the DNAH5 gene, which encodes the dynein axonemal heavy chain 5 protein that forms the inner structure of cilia, cause PCD. Over 80 different mutations in the DNAH5 gene have been identified in patients with PCD.

Mutations in the DNAH5 gene result in an absent or abnormal dynein axonemal heavy chain 5, which is required for the proper functioning of cilia. Without a normal version of dynein axonemal heavy chain 5, defective cilia cannot produce the force and movement needed to eliminate fluid, bacteria, and particles from the lungs, to establish the left-right axis during embryonic development, and to propel the sperm cells. PCD can lead to chronic respiratory tract infections, bronchiectasis, year-round nasal congestion, abnormally placed organs within their chest and abdomen, and infertility.

Polyribonucleotides of the disclosure can be used, for example, to treat a subject having or at risk of having primary ciliary dyskinesia or any other condition associated with a defect or malfunction of a gene whose function is linked to cilia maintenance and function. Non limiting examples of genes that have been associated with primary ciliary dyskinesia include: armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin O (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GAS8), axonemal central pair apparatus protein (HYDIN), leucine rich repeat containing 6 (LRRC6), ME/M23 family member 8 (NME8), oral-facial-digital syndrome 1 (OFD1), retinitis pigmentosa GTPase regulator (RPGR), radial spoke head 1 homolog (Chlamydomonas) (RSPH1), radial spoke head 4 homolog A (Chlamydomonas) (RSPH4A), radial spoke head 9 homolog (Chlamydomonas) (RSPH9), sperm associated antigen 1 (SPAG1), and zinc finger MY D-type containing 10 (ZMYND10).

Dynein Axonemal Heavy Chain 5 (DNAH5) Gene and Protein Sequence

In some embodiments, the present invention provides methods and compositions for delivering mRNA encoding to a subject for the treatment of PCD. A suitable DNAH5 mRNA encodes any full length, fragment or portion of a DNAH5 protein which can be substituted for naturally-occurring DNAH5 protein activity and/or reduce the intensity, severity, and/or frequency of one or more symptoms associated with PCD.

In some embodiments, a suitable mRNA sequence is an mRNA sequence encoding a human DNAH5 protein. The naturally-occurring human DNAH5 mRNA coding sequence and the corresponding amino acid sequence are shown in Table 1:

The naturally-occurring human DNAH5 mRNA coding sequence and the corresponding amino acid sequence are shown in Table 1:

TABLE 1

Human DNAH5 Amino Acid Sequence

| | |
|---|---|
| Human DNAH5 Protein Sequence | (SEQ ID NO: 1)<br>MFRIGRRQLWKHSVTRVLTQRLKGEKEAKRALLDARHNYLFAIVASCLDL<br>NKTEVEDAILEGNQIER1DQLFAVGGLRHLMFYYQDVEEAETGQLGSLGGV<br>NLVSGKIKKPKVFVTEGNDVALTGVCVFFIRTDPSKAITPDNIHQEVSFNML<br>DAADGGLLNSVRRLLSDIFIPALRATSHGWGELEGLQDAANIRQEFLSSLEG<br>FVNVLSGAQESLKEKVNLRKCDILELKTLKEPTDYLTLANNPETLGKIEDCM<br>KVWIKQTEQVLAENNQLLKEADDVGPRAELEHWKKRLSKFNYLLEQLKSP<br>DVKAVLAVLAAAKSKLLKTWREMDIRITDATNEAKDNVKYLYTLEKCCDP<br>LYSSDPLSMMDAIPTLINAIKMIYSISHYYNTSEKITSLFVKVTNQIISACKAYI<br>TNNGTASIWNQPQDVVEEKILSAIKLKQEYQLCFHKTKQKLKQNPNAKQFD<br>FSEMYIFGKFETPHRRLAKIIDIFTTLKTYSVLQDSTIEGLEDMATKYQGIVAT<br>IKKKEYNFLDQRKMDFDQDYEEFCKQTNDLHNELRKFMDVTFAKIQNTNQ<br>ALRMLKKFERLNIPNLGIDDKYQLILENYGADIDMISKLYTKQKYDPPLARN<br>QPPIAGKILWARQLFHRIQQPMQLFQQHPAVLSTAEAKPIIRSYNRMAKVLL<br>EFEVLFHRAWLRQIEEIHVGLEASLLVKAPGTGELFVNFDPQILILFRETECM<br>AQMGLEVSPLATSLFQKRDRYKRNFSNMKMMLAEYQRVKSKIPAAIEQLIV<br>PHLAKVDEALQPGLAALTWTSLNIEAYLENTFAKIKDLELLLDRVNDLIEFRI<br>DAILEEMSSTPLCQLPQEEPLTCEEFLQMTKDLCVNGAQILHFKSSLVEEAV<br>NELVNMLLDVEVLSEEESEKISNENSVNYKNESSAKREEGNFDTLTSSINAR<br>ANALLLTTVTRKKKETEMLGEEARELLSHFNHQNMDALLKVTRNTLEAIRK<br>RIFISSSHTINFRDSNSASNMKQNSLPIFRASVTLAIPNIVMAPALEDVQQTLNK<br>AVECIISVPKGVRQWSSELLSKKKIQERKMAALQSNEDSDSDVEMGENELQ<br>DTLEIASVNLPIPVQTKNYYKNVSENKEIVKLVSVLSTIINSTKKEVITSMDCF<br>KRYNHIWQKGKEEAIKTFITQSPLLSEFESQILYFQNLEQEINAEPEYVCVGSI<br>ALYTADLKFALTAETKAWMVVIGRHCNKKYRSEMENIFMLIEEFNKKLNRP<br>IKDLDDIRIAMAALKEIREEQISIDFQVGPIEESYALLNRYGLLIAREEIDKVDT<br>LHYAWEKLLARAGEVQNKLVSLQPSFKKELISAVEVFLQDCHQFYLDYDLN<br>GPMASGLKPQEASDRLIMFQNQFDNIYRKYITYTGGEELFGLPATQYPQLLE<br>IKKQLNLLQKIYTLYNSVIETVNSYYDILWSEVNIEKINNELLEFQNRCRKLP<br>RALKDWQAFLDLKKIIDDFSECCPLLEYMASKAMMERHWERITTLTGHSLD<br>VGNESFKLRNIMEAPLLKYKEEIEDICISAVKERDIEQKLKQVINEWDNKTFT<br>FGSFKTRGELLLRGDSTSEIIANMEDSLMLLGSLLSNRYNMPFKAQIQKWVQ<br>YLSNSTDIIESWMTVQNLWIYLEAVFVGGDIAKQLPKEAKRFSNIDKSWVKI<br>MTRAHEVPSVVQCCVGDETLGQLLPHLLDQLEICQKSLTGYLEKKRLCFPR<br>FFFVSDPALLEILGQASDSHTIQAHLLNVFDNIKSVKFHEKIYDRILSISSQEGE<br>TIELDKPVMAEGNVEVWLNSLLEESQSSLHLVIRQAAANIQETGFQLTEFLSS<br>FPAQVGLLGIQMIWTRDSEEALRNAKFDKKIMQKTNQAFLELLNTLIDVTTR<br>DLSSTERVKYETLITIHVHQRDIFDDLCHMHIKSPMDFEWLKQCRFYFNEDS<br>DKMMIHITDVAFIYQNEFLGCTDRLVITPLTDRCYITLAQALGMSMGGAPA<br>GPAGTGKTETTKDMGRCLGKYVVVFNCSDQMDFRGLGRIFKGLAQSGSWG<br>CFDEFNRIDLPVLSVAAQQISIILTCKKEHKKSFIFTDGDNVTMNPEFGLFLT<br>MNPGYAGRQELPENLKINFRSVAMMVPDRQIIIRVKLASCGFIDNVVLARKF<br>FTLYKLCEEQLSKQVHYDFGLRNILSVLRTLGAAKRANPMDTESTIVMRVL |

TABLE 1 -continued

Human DNAH5 Amino Acid Sequence

```
RDMNLSKLIDEDEPLFLSLIEDLFPNILLDKAGYPELEAAISRQVEEAGLINHP
PWKLKVIQLFETQRVRHGMMTLGPSGAGKTTCIFITLMRAMTDCGKPHREM
RMNPKAITAPQMFGRLDVATNDWTDGIFSTLWRKTLRAKKGEHIWIILDGP
VDAIWIENLNSVLDDNKTLTLANGDRIPMAPNCKIIFEPHNIDNASPATVS RN
GMVFMSSSILDWSPILEGFLKKRSPQEAEILRQLYTESFPDLYRFCIQNLEYK
MEVLEAFVITQSINMLQGLIPLKEQGGEVSQAHLGRLFVFALLWSAGAALEL
DGRRRLELWLRSRPTGTLELPPPAGPGDTAFDYYVAPDGTWTHWNTRTQE
YLYPSDTTPEYGSILVPNVDNVRTDFLIQTIAKQGKAVLLIGEQGTAKTVIIK
GFMSKYDPECHMIKSLNFSSATTPLMFQRTIESYVDKRMGTTYGPPAGKKM
TVFIDDVNMPIINEWGDQVTNEIVRQLMEQNGFYNLEKPGEFTSIVDIQFLA
AMIHPGGGRNDIPQRLKRQFSIFNCTLPSEASVDKIFGVIGVGHYCTQRGFSE
EVRDSVTKLVPLTRRLWQMTKIKMLPTPAKFHYVFNLRDLSRVWQGMLNT
TSEVIKEPNDLLKLWKHECKRVIADRFTVSSDVTWFDKALVSLVEEEFGEEK
KLLVDCGIDTYFVDFLRDAPEAAGETSEEADAETPKIYEPIESFSHLKERLNM
FLQLYNESIRGAGMDMVFFADAMVHLVKISRVIRTPQGNALLVGVGGSGK
QSLTRLASFIAGYVSFQITLTRSYNTSNLMEDLKVLYRTAGQQGKGITFIFTD
NEIKDESFLEYMNNVLSSGEVSNLFARDEIDEINSDLASVMKKEFPRCLPTNE
NLHDYFMSRVRQNLHIVLCFSPVGEKFRNRALKFPALISGCTIDWFSRWPKD
ALVAVSEHFLTSYDIDCSLEIKKEVVQCMGSFQDGVAEKCVDYFQRFRRST
HVTPKSYLSFIQGYKFIYGEKHVEVRTLANRMNTGLEKLKEASESVAALSKE
LEAKEKELQVANDKADMVLKEVTMKAQAAEKVKAEVQKVKDRAQAIVD
SISKDKAIAEEKLEAAKPALEEAEAALQTIRPSDIATVRTLGRPPHLIMRIMD
CVLLLFQRKVSAVKIDLEKSCTMPSWQESLKLMTAGNFLQNLQQFPKDTIN
EEVIEFLSPYFEMPDYNIETAKRVCGNVAGLCSWTKAMASFFSINKEVLPLK
ANLVVQENRHLLAMQDLQKAQAELDDKQAELDVVQAEYEQAMTEKQTLL
EDAERCRHKMQTASTLISGLAGEKERWTEQSQEFAAQTKRLVGDVLLATAF
LSYSGPFNQEFRDLLLNDWRKEMKARKIPFGKNLNLSEMLIDAPTISEWNLQ
GLPNDDLSIQNGIIVTKASRYPLLIDPQTQGKIWIKNKESRNELQITSLNHKYF
RNHLEDSLSLGRPLLIEDVGEELDPALDNVLERNFIKTGSTFKVKVGDKEVD
VLDGFRLYITTKLPNPAYTPEISARTSIIDFTVTMKGLEDQLLGRVILTEKQEL
EKERTHLMEDVTANKRRMKELEDNLLYRLTSTQGSLVEDESLIVVLSNTKR
TAEEVTQKLEISAETEVQINSAREEYRPVATRGSILYFLITEMRLVNEMYQTS
LRQFLGLFDLSLARSVKSPITSKRIANIIEHMTYEVYKYAARGLYEEHKFLFT
LLLTLKIDIQRNRVKHEEFLTLIKGGASLDLKACPPKPSKWILDITWLNLVEL
SKLRQFSDVLDQISRNEKMWKIWFDKENPEEEPLPNAYDKSLDCFRRLLLIR
SWCPDRTIAQARKYIVDSMGEKYAEGVILDLEKTWEESDPRTPLICLLSMGS
DPTDSIIALGKRLKIETRYVSMGQGQEVHARKLLQQTMANGGWALLQNCH
LGLDFMDELMDIIIETELVHDAFRLWMTTEAHKQFPITLLQMSIKFANDPPQ
GLRAGLKRTYSGVSQDLLDVSSGSQWKPMLYAVAFLHSTVQERRKFGALG
WNIPYEFNQADFNATVQFIQNHLDDMDVKKGVSWTTIRYMIGEIQYGGRVT
DDYDKRLLNTFAKVWFSENMFGPDFSFYQGYNIPKCSTVDNYLQYIQSLPA
YDSPEVFGLHPNADITYQSKLAKDVLDTILGIQPKDTSGGGDETREAVVARL
ADDMLEKLPPDYVPFEVKERLQKMGPFQPMNIFLRQEIDRMQRVLSLVRST
LTELKLAIDGTIIMSENLRDALDCMFDARIPAWWKKASWISSTLGFWFTELI
ERNSQFTSWVFNGRPHCFWMTGFFNPQGFLTAMRQEITRANKGWALDNM
VLCNEVTKWMKDDISAPPTEGVYVYGLYLEGAGWDKRNMKLIESKPKVLF
ELMPVIRIYAENNTLRDPRFYSCPIYKKPVRTDLNYIAAVDLRTAQTPEHWV
LRGVALLCDVK
```

In some embodiments, a suitable mRNA is a wild-type human DNAH5 mRNA of sequence. In some embodiments, a suitable therapeutic candidate mRNA is a codon-optimized hDNAH5 sequence that can encodes a DNAH5 amino acid sequence shown in Table 1 as SEQ ID NO: 1 or an amino acid sequence at least 70%, 75%, 80%, 85%, 90%, 95%, 96%, 97%, 98%, or 99% identical to SEQ ID NO: 1. In some embodiments, an mRNA according to the present invention encodes a DNAH5 protein with an amino acid sequence that is identical to SEQ ID NO: 1.

Codon Optimization

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Despite these obstacles, the inventors have arrived at a codon-optimized hDNAH5 sequence that improves expression of the DNAH5 protein at least threefold over the coding sequence of the wild type gene. The increase in expression is not limited to cell cultures of mammalian cells but was also observed in vivo in a mouse model. It is expected that the observed improvement in expression of the codon-optimised DNAH5 coding sequence will result in an improved, more cost-effective mRNA replacement therapy for patients suffering from PCD, because it does not require the use of modified nucleotides for the preparation of the mRNA and allows treatment with a reduced dose and/or at extended dosing intervals.

Exemplary Codon Optimized DNAH5 mRNA Sequences

The sequences that follow recite select, exemplary codon-optimized DNAH5 mRNA sequences.

In some embodiments, a suitable mRNA may be a codon-optimized sequence, as shown in SEQ ID NO: 6.

In some embodiments, a suitable mRNA may be a codon-optimized sequence, as shown in SEQ ID NO: 7.

In some embodiments, a suitable mRNA may be a codon-optimized sequence, as shown in SEQ ID NO: 8.

In some embodiments, a suitable mRNA may be a codon-optimized sequence, as shown in SEQ ID NO: 9.

In some embodiments, a suitable mRNA may be a codon-optimized sequence, as shown in SEQ ID NO: 10.

In some embodiments, a suitable mRNA may be a codon-optimized sequence, as shown in SEQ ID NO: 11.

In some embodiments, a suitable mRNA may be a codon-optimized sequence, as shown in SEQ ID NO: 12.

In some embodiments, a suitable mRNA may be a codon-optimized sequence, as shown in SEQ ID NO: 13.

In some embodiments, a suitable mRNA may be a codon-optimized sequence, as shown in SEQ ID NO: 14.

In some embodiments, a suitable mRNA may be a codon-optimized sequence, as shown in SEQ ID NO: 15.

In some embodiments, a suitable mRNA may be a codon-optimized sequence, as shown in SEQ ID NO: 16.

In some embodiments, a suitable mRNA may be a codon-optimized sequence, as shown in SEQ ID NO: 17.

In some embodiments, a suitable mRNA may be a codon-optimized sequence, as shown in SEQ ID NO: 18.

In some embodiments, a suitable mRNA may be a codon-optimized sequence, as shown in SEQ ID NO: 19.

In some embodiments, a suitable mRNA may be a codon-optimized sequence, as shown in SEQ ID NO: 20.

In some embodiments, a suitable mRNA may be a codon-optimized sequence, as shown in SEQ ID NO: 21.

In some embodiments, a suitable mRNA may be a codon-optimized sequence, as shown in SEQ ID NO: 22.

In some embodiments, a suitable mRNA may be a codon-optimized sequence, as shown in SEQ ID NO: 23.

In some embodiments, a suitable mRNA may be a codon-optimized sequence, as shown in SEQ ID NO: 24.

In some embodiments, a suitable mRNA may be a codon-optimized sequence, as shown in SEQ ID NO: 25.

In some embodiments, a suitable mRNA may be a codon-optimized sequence, as shown in SEQ ID NO: 26.

In some embodiments, a suitable mRNA may be a codon-optimized sequence, as shown in SEQ ID NO: 27.

In some embodiments, a suitable mRNA may be a codon-optimized sequence, as shown in SEQ ID NO: 28.

In some embodiments, a suitable mRNA may be a codon-optimized sequence, as shown in SEQ ID NO: 29.

In some embodiments, a suitable mRNA may be a codon-optimized sequence, as shown in SEQ ID NO: 30.

In some embodiments, a suitable mRNA may be a codon-optimized sequence, as shown in SEQ ID NO: 31.

In some embodiments, a suitable mRNA sequence may be an mRNA sequence a homolog or an analog of human DNAH5 protein. For example, a homolog or an analog of human DNAH5 protein may be a modified human DNAH5 protein containing one or more amino acid substitutions, deletions, and/or insertions as compared to a wild-type or naturally-occurring human DNAH5 protein while retaining substantial DNAH5 protein activity. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more homologous to SEQ ID NO: 1. In some embodiments, an mRNA suitable for the present invention encodes a protein substantially identical to human DNAH5 protein. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more identical to SEQ ID NO: 1. Typically, an mRNA according to the present invention encodes a DNAH5 protein with an amino acid sequence that is identical to SEQ ID NO: 1.

In some embodiments, an mRNA suitable for the present invention encodes a fragment or a portion of human DNAH5 protein. In some embodiments, an mRNA suitable for the present invention encodes a fragment or a portion of human DNAH5 protein, wherein the fragment or portion of the protein still maintains DNAH5 activity similar to that of the wild-type protein.

In some embodiments, a suitable mRNA encodes a fusion protein comprising a full length, fragment or portion of a DNAH5 protein fused to another protein (e.g., an N or C terminal fusion). In some embodiments, the protein fused to the mRNA encoding a full length, fragment or portion of a DNAH5 protein encodes a signal or a cellular targeting sequence.

In some embodiments, an mRNA suitable for the present invention comprises a nucleotide sequence at least 85%, 90%, 91%, 92%, 93%, 94%, 95%, 96%, 97%, 98%, 99% or more identical to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31. More typically, an mRNA in accordance with the present invention comprises a nucleotide sequence at least 95% identical to SEQ ID NO: 6. Preferably, an mRNA according to the present invention comprises a nucleotide sequence at least 99% identical to SEQ ID NO: 7. For example, an mRNA according to the present invention comprises the nucleotide sequence of SEQ ID NO: 6 or SEQ ID NO: 7.

Messenger RNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Typically, the mRNA according to the present invention is synthesized as unmodified mRNA. Accordingly, the mRNAs of the invention are synthesized from naturally occurring nucleotides including purines (adenine (A), guanine (G)) or pyrimidines (cytosine (C), uracil (U)).

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., DNAH5-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, mRNAs (e.g., DNAH5-encoding mRNAs) include a 3' poly(A) tail structure. A poly-A tail on the 3' terminus of mRNA typically includes about 10 to 800 adenosine nucleotides (e.g., about 300 to 500 adenosine nucleotides, about 300 to 800 adenosine nucleotides, about 10 to 500 adenosine nucleotides, about 10 to 300 adenosine nucleotides, about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long. More commonly, the poly-A tail is about 300 adenosine nucleotides long. In some embodiments, the poly(A) tail structure comprises at least 85%, 90%, 95% or 100% adenosine.

In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNA further comprises a 5' untranslated region (5' UTR) comprising a nucleotide sequence and positioned between the 5' cap structure and coding sequence, and/or a 3' untranslated region (3' UTR) comprising a nucleotide sequence and positioned between the coding sequence and the poly(A) tail structure. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Modified mRNA mRNAs according to the present invention are typically synthesized as unmodified mRNAs. In some embodiments, it may be advantageous to synthesize an mRNA encoding a codon-optimized DNAH5 coding sequence of the present invention with one or more modified nucleotides. Typically, mRNAs are modified to enhance their stability or reduce their immunogenic properties, in particular when administered to a subject as naked mRNAs or in complexed form. Therefore, providing an mRNA encoding a codon-optimized DNAH5 coding sequence of the present invention may have synergistic effects, resulting in sustained in vivo function that exceeds that observed with unmodified mRNAs.

Modifications of mRNA can include, for example, modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methyl-thio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs of the present invention may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs of the present invention may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs of the present invention may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m7G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m7G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m7G(5')ppp(5')G ("m7GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH3.

Additional cap analogs include, but are not limited to, a chemical structures selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m72'dGpppG, m7,3'OmeGpppG, m7,3'dGpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m7G") linked via a triphosphate bridge to the 5'-end of the first transcribed nucleotide, resulting in m7G (5')ppp(5')N, where N is any nucleoside. A preferred embodiment of a m7G cap utilized in embodiments of the invention is m7G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m7G cap analogs are known in the art, many of which are commercially available. These include the m7GpppG described above, as well as the ARCA 3'-OCH3 and 2'-OCH3 cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly-A tail is thought to stabilize natural messengers and synthetic sense RNA. Therefore, in certain embodiments a long poly-A tail can be added to an mRNA molecule thus rendering the RNA more stable. Poly-A tails can be added using a variety of art-recognized techniques. For example, long poly-A tails can be added to synthetic or in vitro transcribed RNA using poly A polymerase (Yokoe, et al. Nature Biotechnology. 1996; 14: 1252-1256). A transcription vector can also encode long poly-A tails. In addition, poly-A tails can be added by transcription directly from PCR products. Poly-A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly-A tail can be at least about 10, 50, 100, 200, 300, 400 or 500 nucleotides in length. In some embodiments, a poly-A tail on the 3' terminus of mRNA typically includes about 10 to 800 adenosine nucleotides (e.g., about 300 to 500 adenosine nucleotides, about 300 to 800 adenosine nucleotides, about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long. More commonly, the poly-A tail is about 300 adenosine nucleotides long.

In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' untranslated region (UTR). In some embodiments, mRNAs include a 3' untranslated region. In some embodiments, mRNAs include both a 5' untranslated region and a 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and 5' untranslated region sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

In certain embodiments, the codon-optimized DNAH5 mRNA includes a coding region having a codon-optimized coding region flanked by 5' and 3' untranslated regions as represented as X and Y, respectively (vide infra)

X-Coding Region-Y where the coding region sequence is SEQ ID NO: 6, or a sequence 70%, 75%, 80%, 85%, 90%, 91%, 92%, 93%, 94%, 95%, 96%, 97%, 98%, 99% or more identical to SEQ ID NO: 6; or SEQ ID NO: 7 or a sequence 70%, 75%, 80%, 85%, 90%, 91%, 92%, 93%, 94%, 95%, 96%, 97%, 98%, 99% or more identical to SEQ ID NO: 7; SEQ ID NO: 8 or a sequence 70%, 75%, 80%, 85%, 90%, 91%, 92%, 93%, 94%, 95%, 96%, 97%, 98%, 99% or more identical to SEQ ID NO: 8; SEQ ID NO: 9 or a sequence 70%, 75%, 80%, 85%, 90%, 91%, 92%, 93%, 94%, 95%, 96%, 97%, 98%, 99% or more identical to SEQ ID NO: 9; SEQ ID NO: 10 or a sequence 70%, 75%, 80%, 85%, 90%, 91%, 92%, 93%, 94%, 95%, 96%, 97%, 98%, 99% or more identical to SEQ ID NO: 10; SEQ ID NO: 11 or a sequence 70%, 75%, 80%, 85%, 90%, 91%, 92%, 93%, 94%, 95%, 96%, 97%, 98%, 99% or more identical to SEQ ID NO: 11; SEQ ID NO: 12 or a sequence 70%, 75%, 80%, 85%, 90%, 91%, 92%, 93%, 94%, 95%, 96%, 97%, 98%, 99% or more identical to SEQ ID NO: 12; SEQ ID NO: 13 or a sequence 70%, 75%, 80%, 85%, 90%, 91%, 92%, 93%, 94%, 95%, 96%, 97%, 98%, 99% or more identical to SEQ ID NO: 13; SEQ ID NO: 14 or a sequence 70%, 75%, 80%, 85%, 90%, 91%, 92%, 93%, 94%, 95%, 96%, 97%, 98%, 99% or more identical to SEQ ID NO: 14; SEQ ID NO: 15 or a sequence 70%, 75%, 80%, 85%, 90%, 91%, 92%, 93%, 94%, 95%, 96%, 97%, 98%, 99% or more identical to SEQ ID NO: 15; SEQ ID NO: 16 or a sequence 70%, 75%, 80%, 85%, 90%, 91%, 92%, 93%, 94%, 95%, 96%, 97%, 98%, 99% or more identical to SEQ ID NO: 16; SEQ ID NO: 17 or a sequence 70%, 75%, 80%, 85%, 90%, 91%, 92%, 93%, 94%, 95%, 96%, 97%, 98%, 99% or more identical to SEQ ID NO: 17; SEQ ID NO: 18 or a sequence 70%, 75%, 80%, 85%, 90%, 91%, 92%, 93%, 94%, 95%, 96%, 97%, 98%, 99% or more identical to SEQ ID NO: 18; SEQ ID NO: 19 or a sequence 70%, 75%, 80%, 85%, 90%, 91%, 92%, 93%, 94%, 95%, 96%, 97%, 98%, 99% or more identical to SEQ ID NO: 19; SEQ ID NO: 20 or a sequence 70%, 75%, 80%, 85%, 90%, 91%, 92%, 93%, 94%, 95%, 96%, 97%, 98%, 99% or more identical to SEQ ID NO: 20; SEQ ID NO: 21 or a sequence 70%, 75%, 80%, 85%, 90%, 91%, 92%, 93%, 94%, 95%, 96%, 97%, 98%, 99% or more identical to SEQ ID NO: 21; SEQ ID NO: 22 or a sequence 70%, 75%, 80%, 85%, 90%, 91%, 92%, 93%, 94%, 95%, 96%, 97%, 98%, 99% or more identical to SEQ ID NO: 22; SEQ ID NO: 23 or a sequence 70%, 75%, 80%, 85%, 90%, 91%, 92%, 93%, 94%, 95%, 96%, 97%, 98%, 99% or more identical to SEQ ID NO: 23; SEQ ID NO: 24 or a sequence 70%, 75%, 80%, 85%, 90%, 91%, 92%, 93%, 94%, 95%, 96%, 97%, 98%, 99% or more identical to SEQ ID NO: 24; SEQ ID NO: 25 or a sequence 70%, 75%, 80%, 85%, 90%, 91%, 92%, 93%, 94%, 95%, 96%, 97%, 98%, 99% or more identical to SEQ ID NO: 25; SEQ ID NO: 26 or a sequence 70%, 75%, 80%, 85%, 90%, 91%, 92%, 93%, 94%, 95%, 96%, 97%, 98%, 99% or more identical to SEQ ID NO: 26; SEQ ID NO: 27 or a sequence 70%, 75%, 80%, 85%, 90%, 91%, 92%, 93%, 94%, 95%, 96%, 97%, 98%, 99% or more identical to SEQ ID NO: 27; SEQ ID NO: 28 or a sequence 70%, 75%, 80%, 85%, 90%, 91%, 92%, 93%, 94%, 95%, 96%, 97%, 98%, 99% or more identical to SEQ ID NO: 28; SEQ ID NO: 29 or a sequence 70%, 75%, 80%, 85%, 90%, 91%, 92%, 93%, 94%, 95%, 96%, 97%, 98%, 99% or more identical to SEQ ID NO: 29; SEQ ID NO: 30 or a sequence 70%, 75%, 80%, 85%, 90%, 91%, 92%, 93%, 94%, 95%, 96%, 97%, 98%, 99% or more identical to SEQ ID NO: 30; SEQ ID NO: 31 or a sequence 70%, 75%, 80%, 85%, 90%, 91%, 92%, 93%, 94%, 95%, 96%, 97%, 98%, 99% or more identical to SEQ ID NO: 31; and where X (5' UTR Sequence) is AGACAGAUCGCCUGGA-GACGCCAUCCACGCUGUUUUGACCUCCAUAGAA-GACACC GGGACCGAUCCAGCCUCCGCGGCCGG-GAACGGUGCAUUGGAACGCGGAUUCCCG UGCCAAGAGUGACUCACCGUCCUUGACACG [SEQ ID NO.: 2] or a sequence 70%, 75%, 80%, 85%, 90%, 91%, 92%, 93%, 94%, 95%, 96%, 97%, 98%, 99% or more identical to SEQ ID NO: 2,
or GGACAGAUCGCCUGGAGACGCCAUCCACGCU-GUUUUGACCUCCAUAGAAGACACC GGGACCGAUCCAGCCUCCGCGGCCGGGAACG-GUGCAUUGGAACGCGGAUUCCCG UGC-CAAGAGUGACUCACCGUCCUUGACACG (SEQ ID NO: 3) or a sequence 70%, 75%, 80%, 85%, 90%, 91%, 92%, 93%, 94%, 95%, 96%, 97%, 98%, 99% or more identical to SEQ ID NO: 3; and where Y (3' UTR Sequence) is CGGGUGGCAUCCCUGUGACCCCUCCCCAGUGC-CUCUCCUGGCCCUGGAAGUUGCC ACUCCAGUGCCCACCAGCCUUGUCC-UAAUAAAAUUAAGUUGCAUCAAGCU (SEQ ID NO: 4) or a sequence 70%, 75%, 80%, 85%, 90%, 91%, 92%, 93%, 94%, 95%, 96%, 97%, 98%, 99% or more identical to SEQ ID NO: 4, or GGGUGGCAUCCCUGUGACCC-CUCCCCAGUGCCUCUCCUGGCCCUG-GAAGUUGCCA CUCCAGUGCCCACCAGCCUUGUC-CUAAUAAAAUUAAGUUGCAUCAAAGCU (SEQ ID NO: 5) or a sequence 70%, 75%, 80%, 85%, 90%, 91%, 92%, 93%, 94%, 95%, 96%, 97%, 98%, 99% or more identical to SEQ ID NO: 5.

In Vitro Transcription

In certain embodiments of the invention, a codon-optimized human dynein axonemal heavy chain 5 messenger RNA (DNAH5 mRNA) is synthesized by in vitro transcription from a plasmid DNA template encoding the gene, which is followed by the addition of a 5' cap structure (Fechter, P.; Brownlee, G. G. "Recognition of mRNA cap structures by viral and cellular proteins" J. Gen. Virology 2005, 86, 1239-1249) and a 3' poly(A) tail of approximately 100, 200, 250, 300, 400, 500 or 800 nucleotides in length as determined by gel electrophoresis.

Delivery Vehicles

According to the present invention, mRNA encoding a DNAH5 protein (e.g., a full length, fragment or portion of a DNAH5 protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding a DNAH5 protein may be delivered via a single delivery vehicle. In some embodiments, mRNAs encoding a DNAH5 protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

Liposomes

In some embodiments, a suitable delivery vehicle is a liposome. As used herein, liposomes are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, liposome typically serves to transport a desired mRNA to a target cell or tissue. A typical liposome in accordance with the invention comprises one or more cationic lipids, one or more non-cationic lipids, one or more cholesterol-based lipids and one or more PEG-modified lipids.

Cationic Lipids

As used herein, the phrase "cationic lipids" refers to any of a number of lipid species that have a net positive charge at a selected pH, such as physiological pH.

Several cationic lipids have been described in the literature, many of which are commercially available. Suitable cationic lipids for use in the compositions and methods of the invention include the cationic lipids as described in International Patent Publication WO 2010/144740, which is incorporated herein by reference.

In certain embodiments, the compositions and methods of the present invention include a cationic lipid, (6Z,9Z,28Z, 31Z)-heptatriaconta-6,9,28,31-tetraen-19-yl 4-(dimethylamino) butanoate, having a compound structure of:

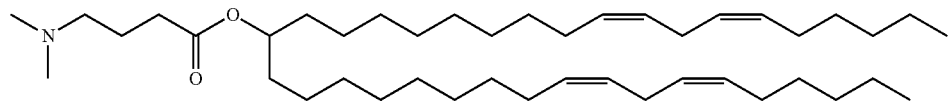

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

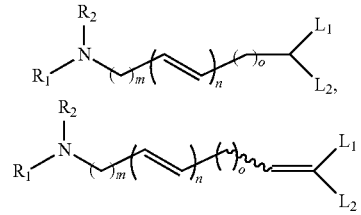

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

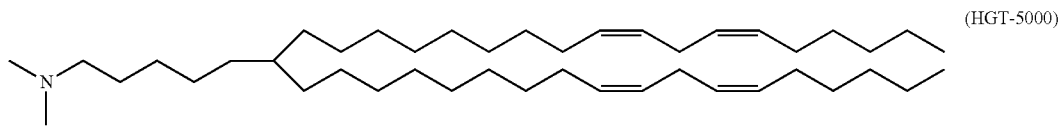 [SMILES: CCCCC/C=C\C/C=C\CCCCCCCCC(CCCCCCCC/C=C\C/C=C\CCCCC)CCCCCN(C)C]

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

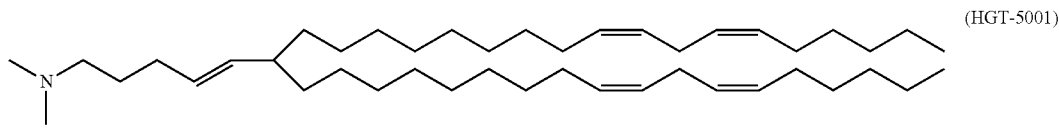 [SMILES: CCCCC/C=C\C/C=C\CCCCCCCCC(/C=C/CCCN(C)C)CCCCCCCC/C=C\C/C=C\CCCCC]

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

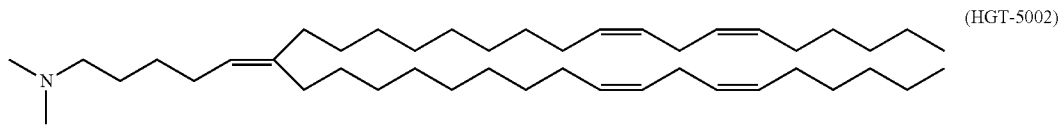 [SMILES: CCCCC/C=C\C/C=C\CCCCCCCCC(=CCCCCN(C)C)CCCCCCCC/C=C\C/C=C\CCCCC]

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

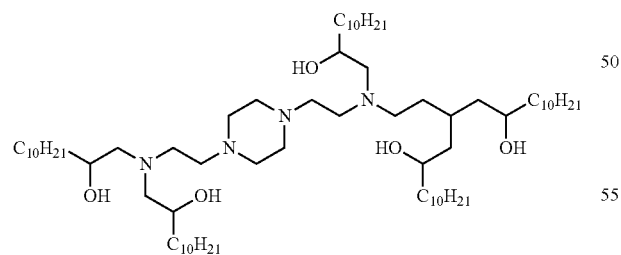

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

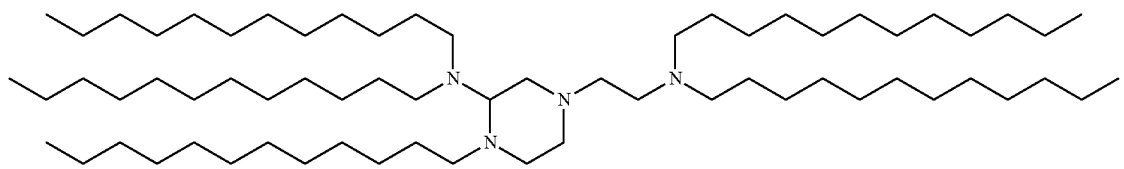 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

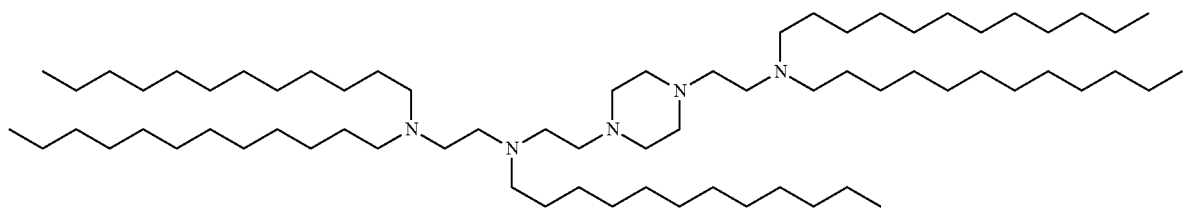 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

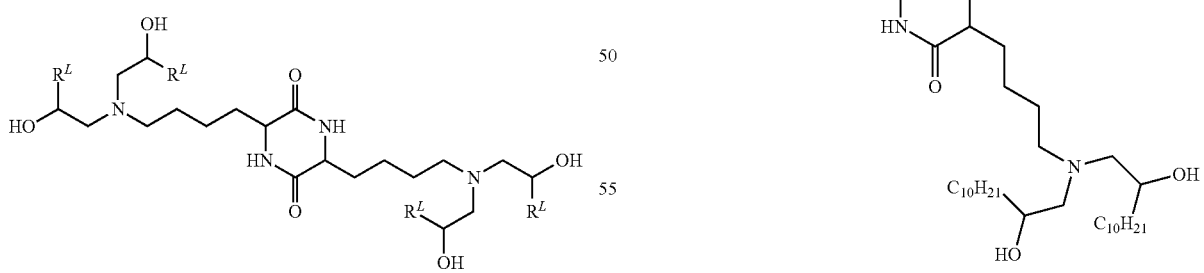

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

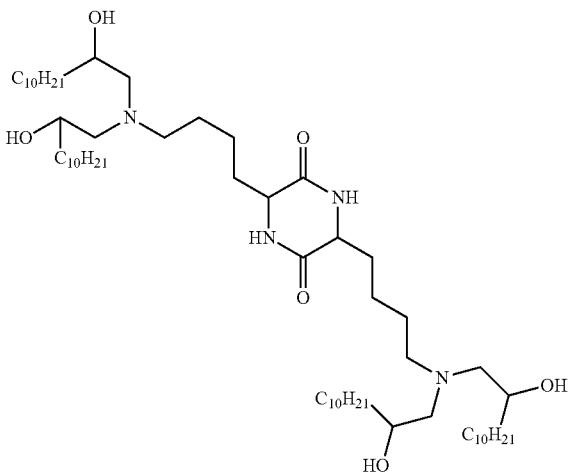

and pharmaceutically acceptable salts thereof. In certain embodiments, the compositions and methods of the present invention include a cationic lipid having a compound structure of:

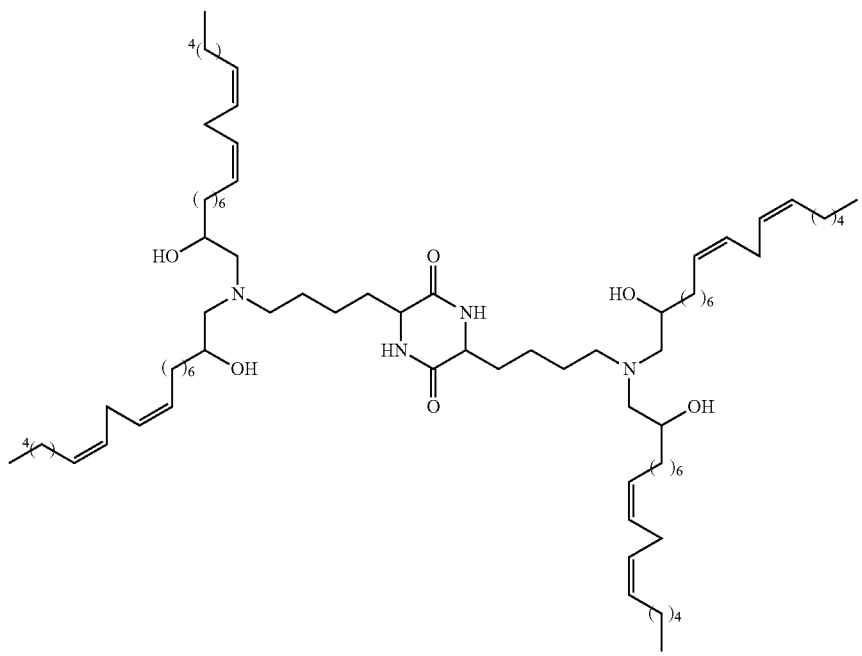

and pharmaceutically acceptable salts thereof. In certain embodiments, the compositions and methods of the present invention include a cationic lipid having a compound structure of:

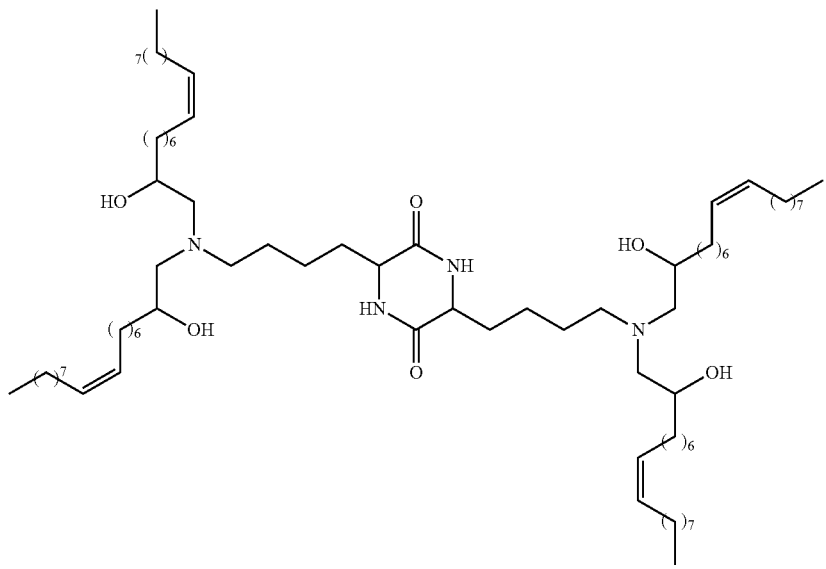

and pharmaceutically acceptable salts thereof. In certain embodiments, the compositions and methods of the present invention include a cationic lipid having a compound structure of:

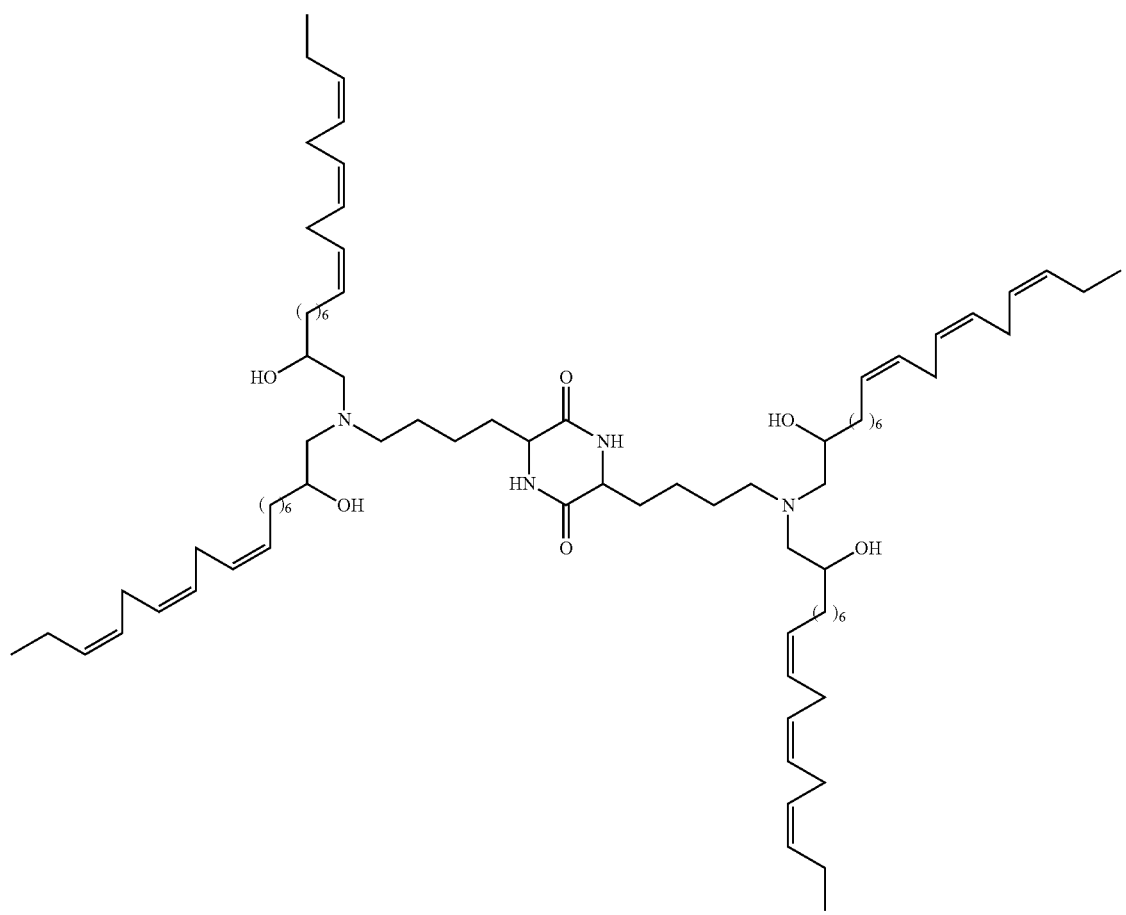

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

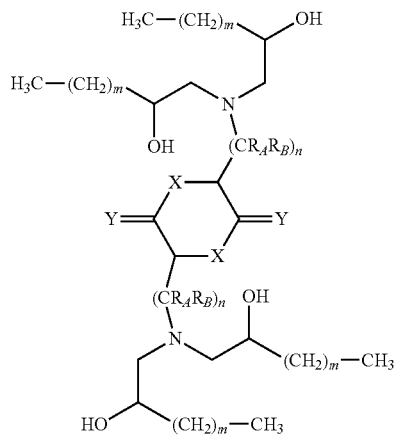

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

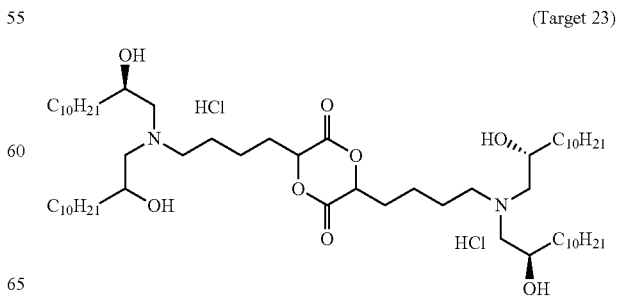

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

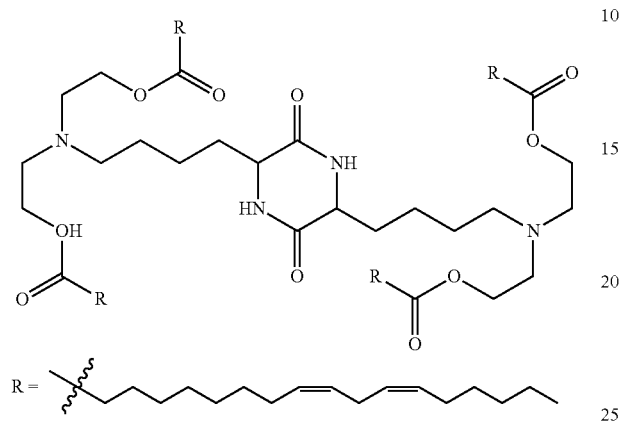

or a pharmaceutically acceptable salt thereof. In some embodiments, the compositions and methods of the present invention include a cationic lipid having the compound structure:

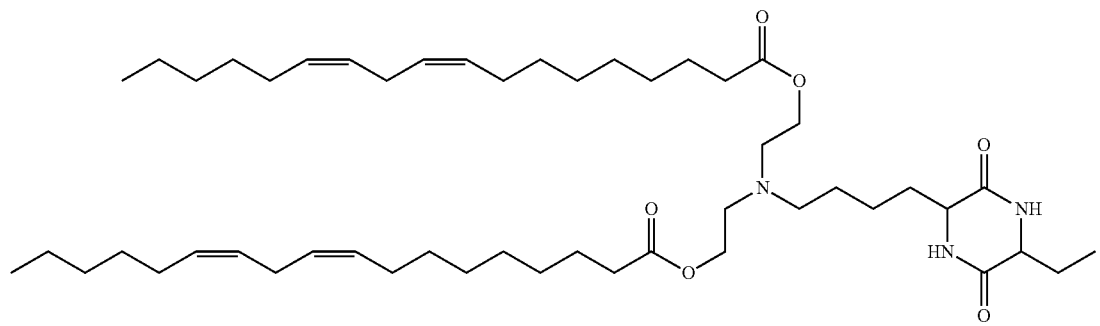 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

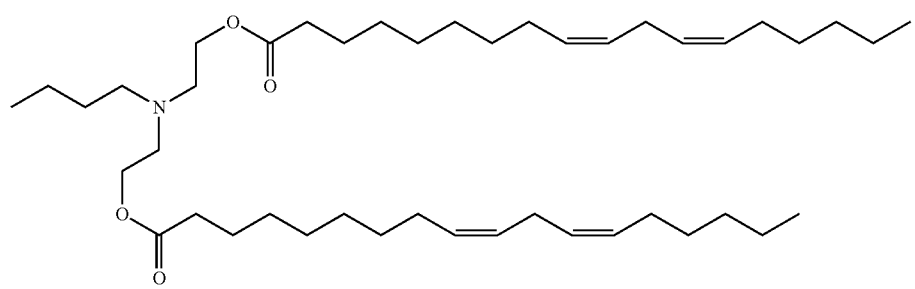 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

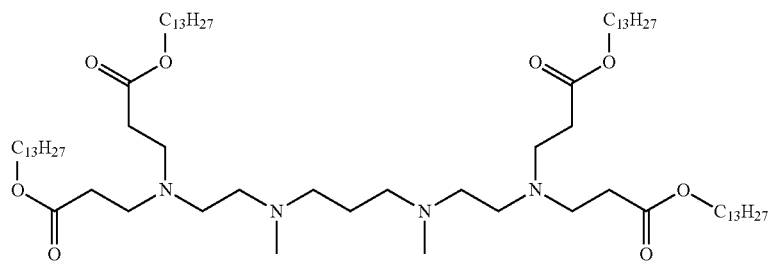

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

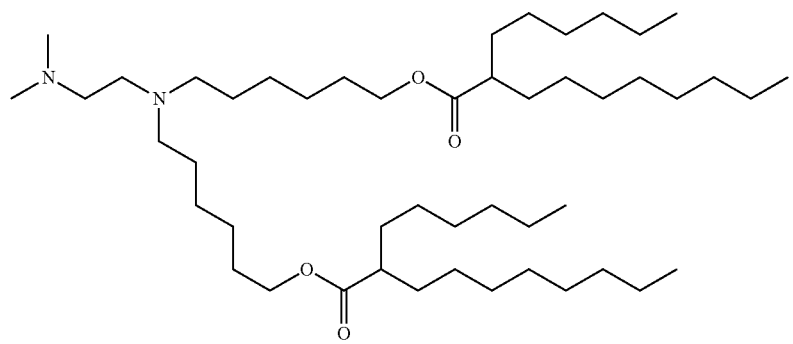 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

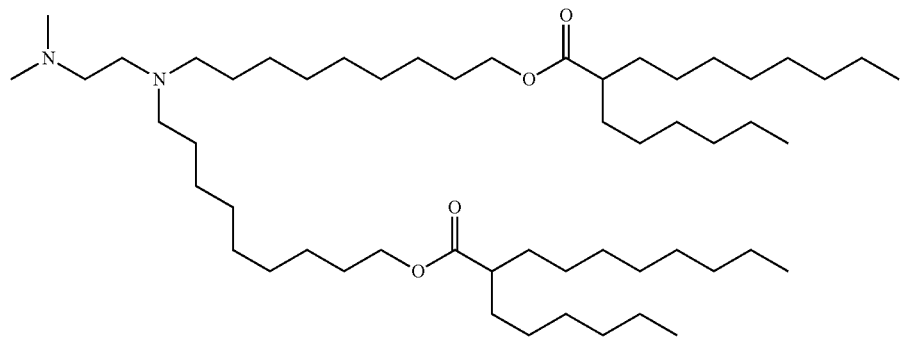 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

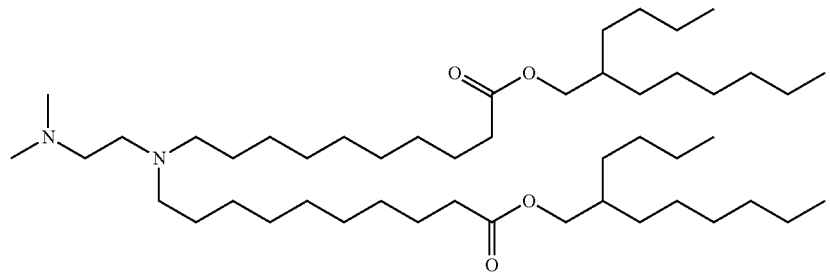 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

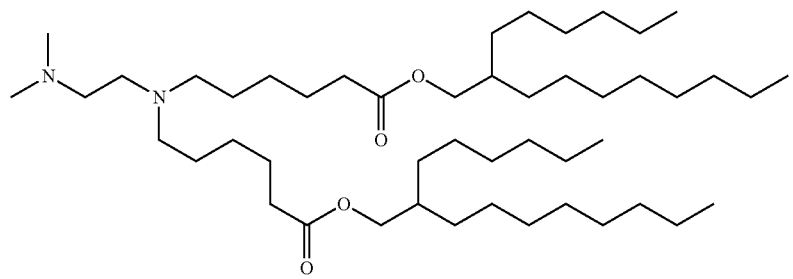 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

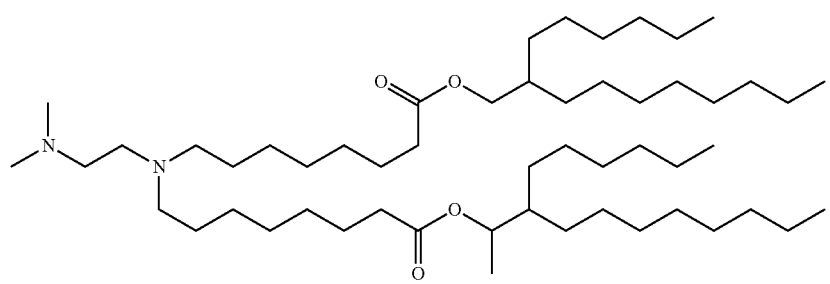 [SMILES: CCCCCCCCC(CCCCCC)COC(=O)CCCCCCCN(CCCCCCCC(=O)OC(C)C(CCCCCC)CCCCCCCC)CCN(C)C]

and pharmaceutically acceptable salts thereof. In some embodiments, the compositions and methods of the present invention include a cationic lipid having the compound structure:

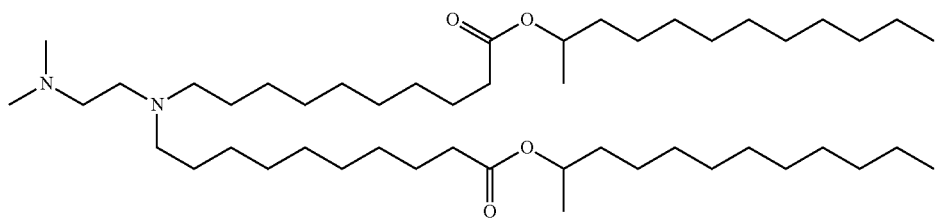 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

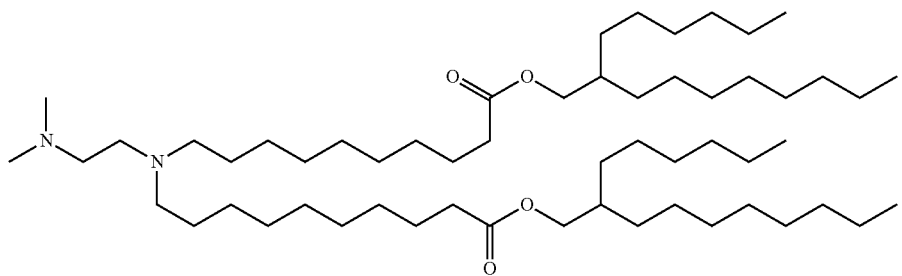 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

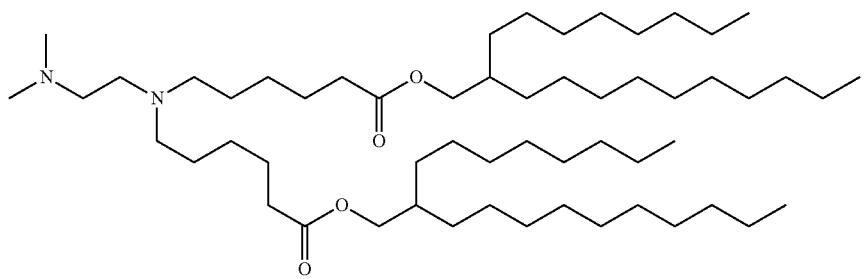 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

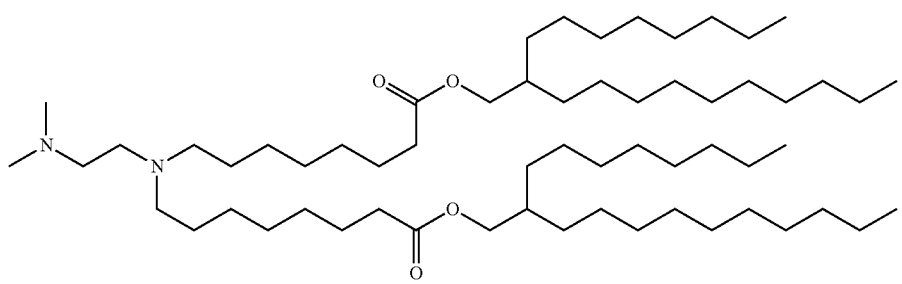 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

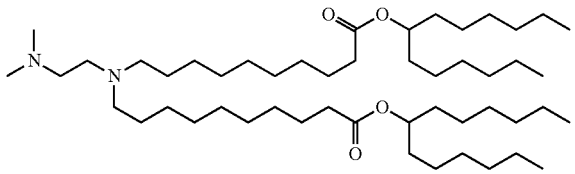 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

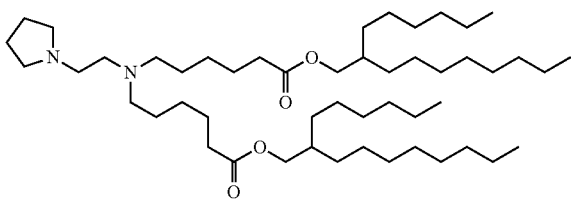 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

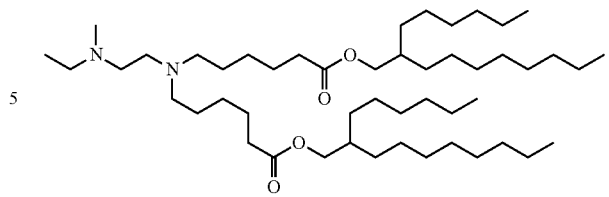

and pharmaceutically acceptable salts thereof. In some embodiments, the compositions and methods of the present invention include a cationic lipid having the compound structure:

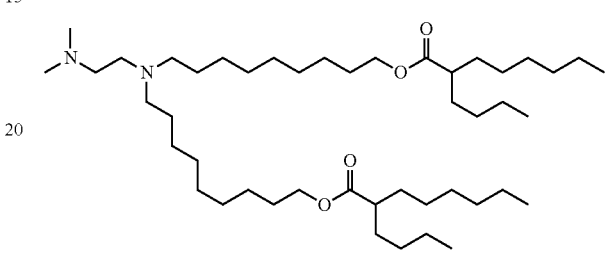

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

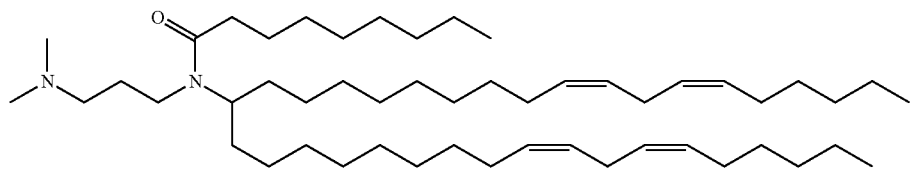 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

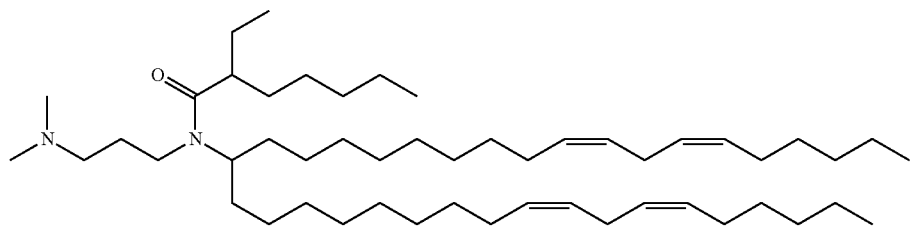 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

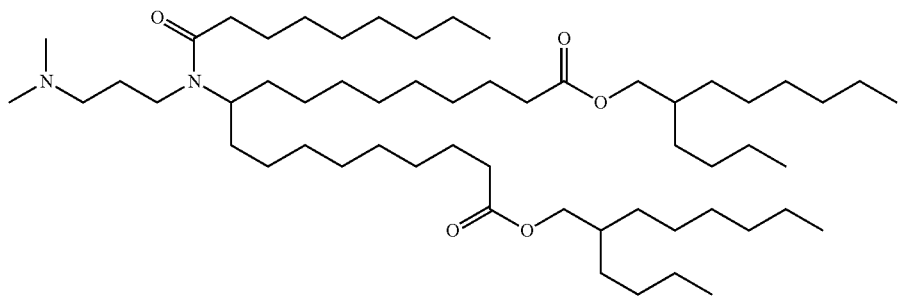 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

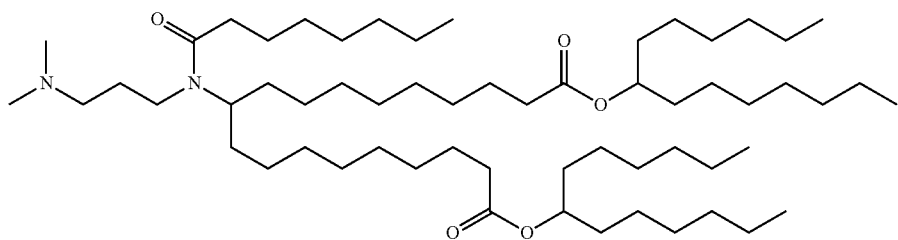 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCCC]

and pharmaceutically acceptable salts thereof. In some embodiments, the compositions and methods of the present invention include a cationic lipid having the compound structure:

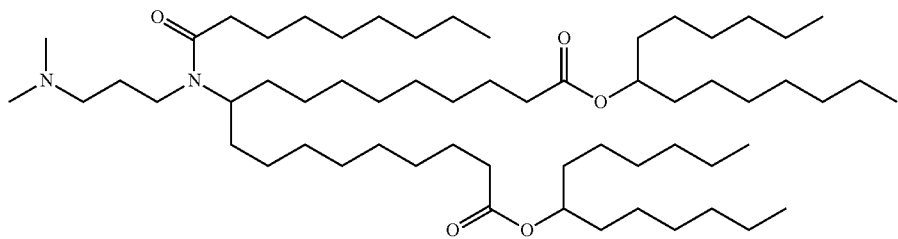 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCCC]

and pharmaceutically acceptable salts thereof. In some embodiments, the compositions and methods of the present invention include a cationic lipid having the compound structure:

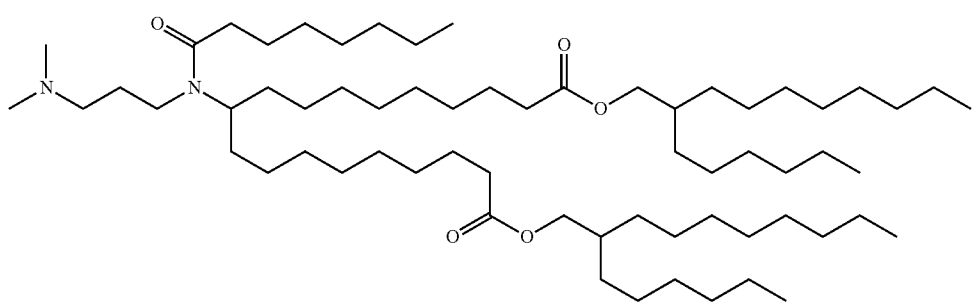 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

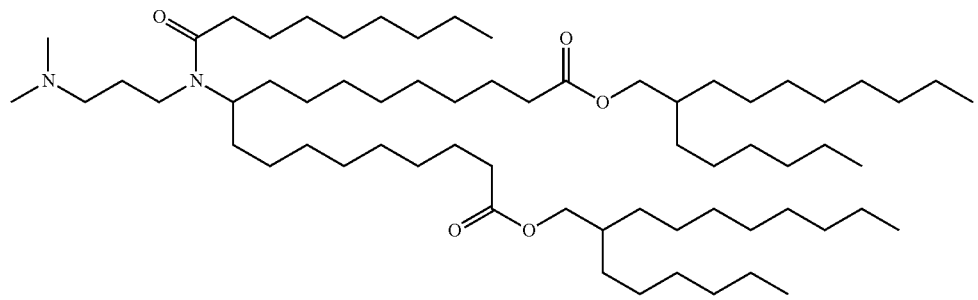 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

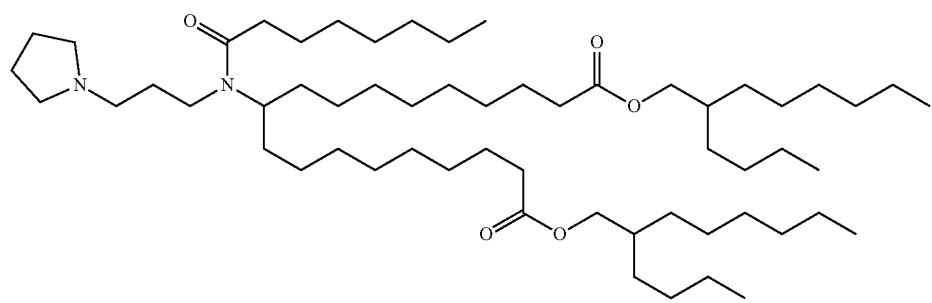 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

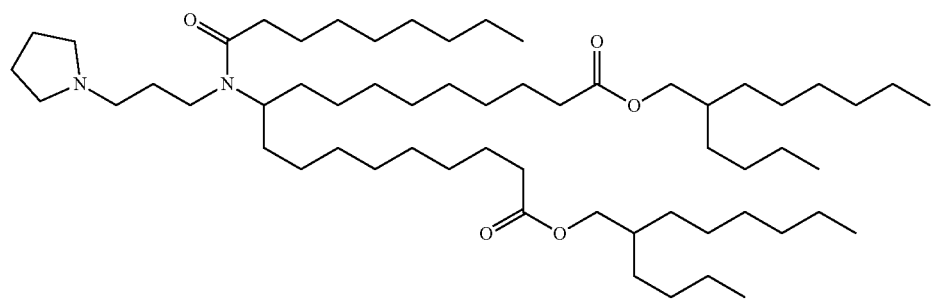 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

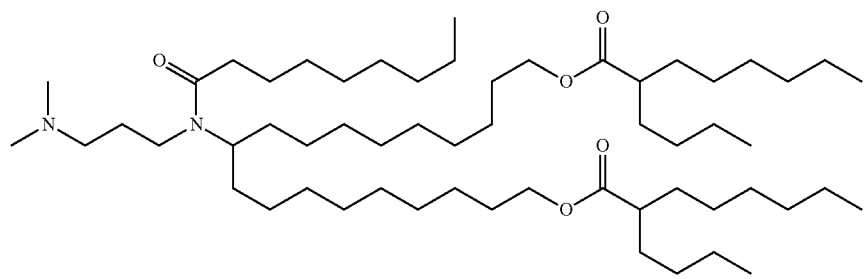 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

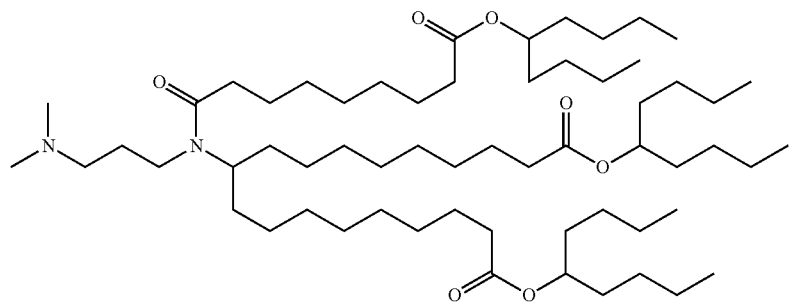 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

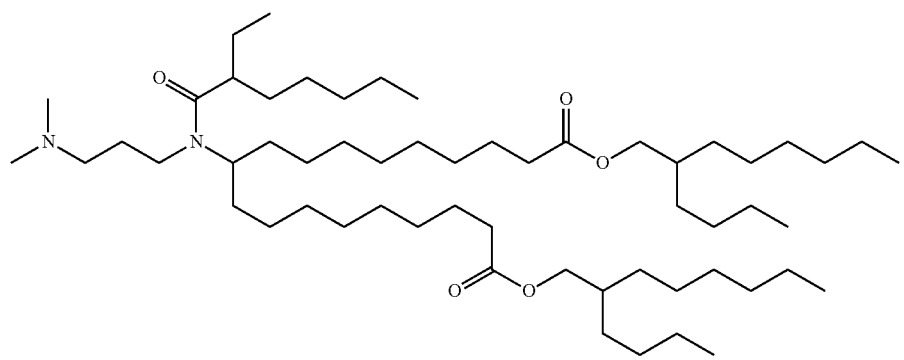 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

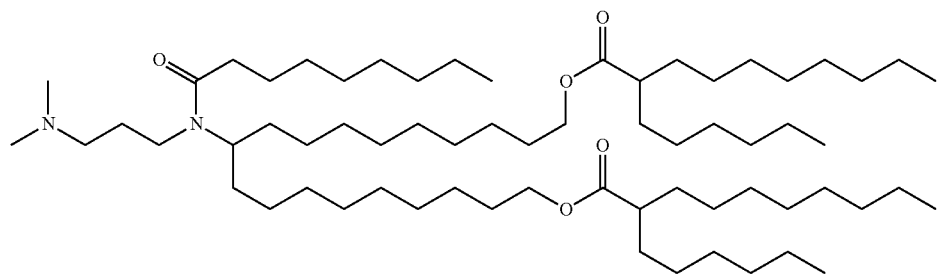 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

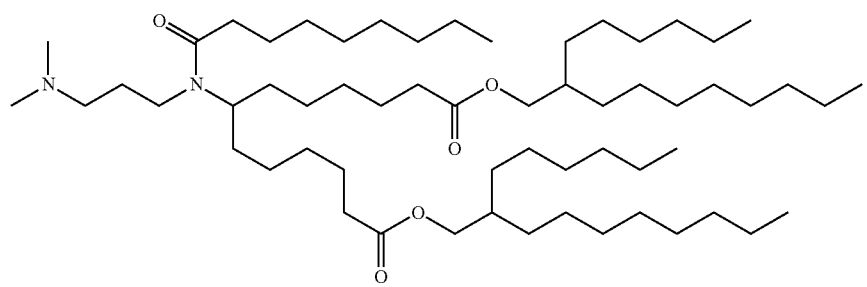 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

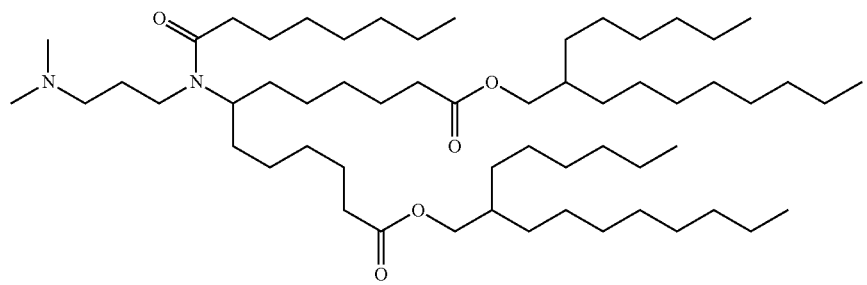 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

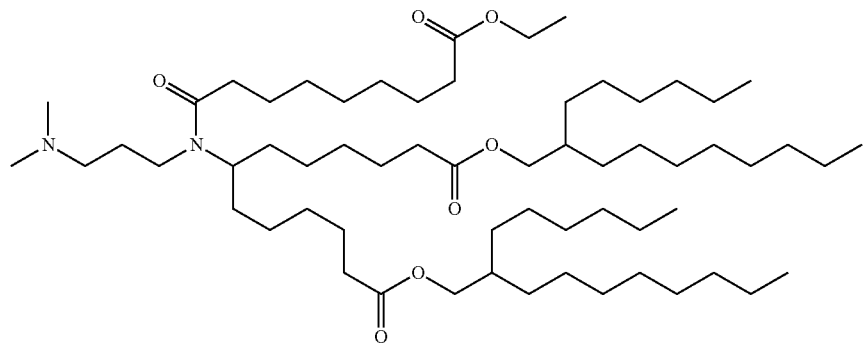 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

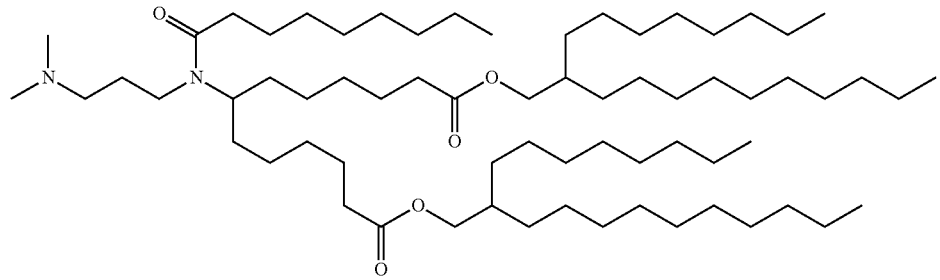 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

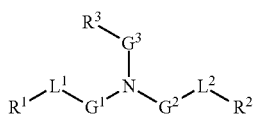

or a pharmaceutically acceptable salt thereof, wherein one of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

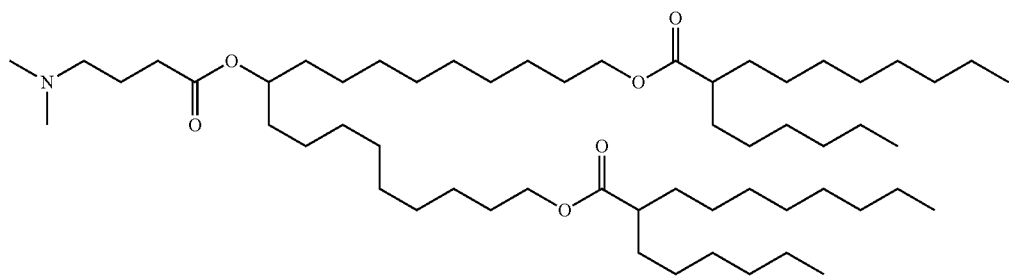 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

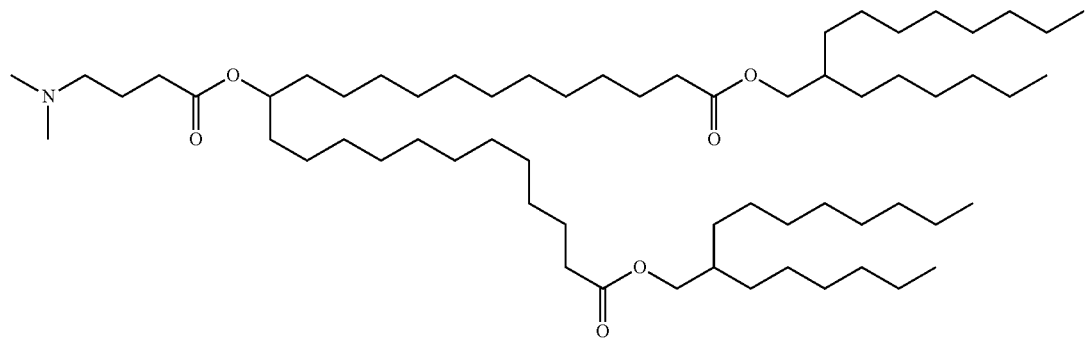 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

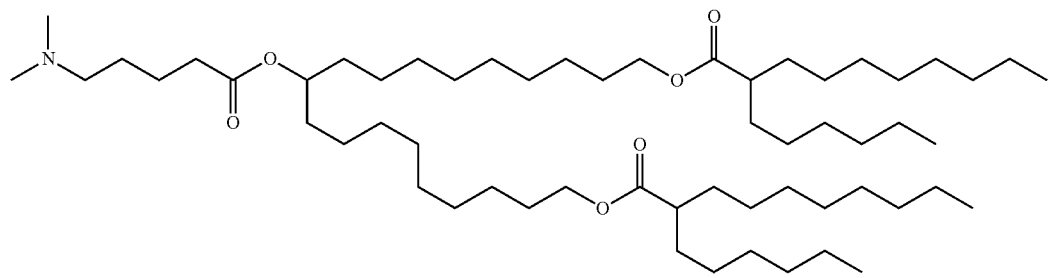 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

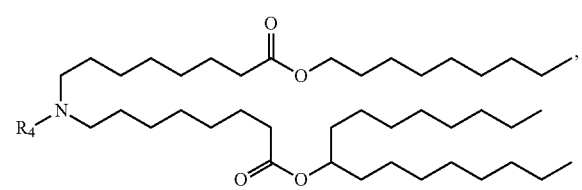

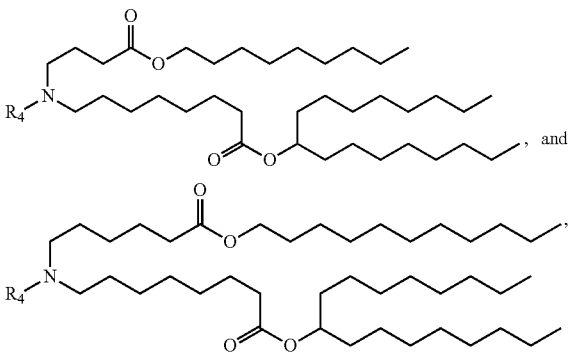

and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle; and n is 1, 2, or 3. In certain embodiments, the compositions and methods of the present invention include a cationic lipid having a compound structure of:

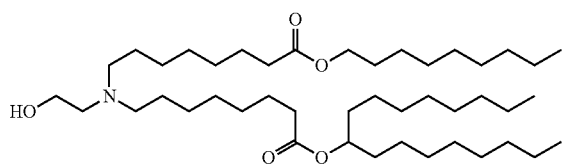 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

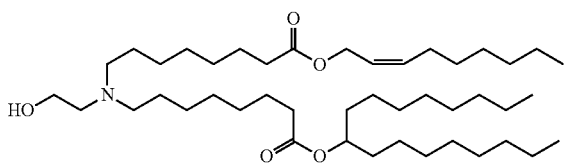 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

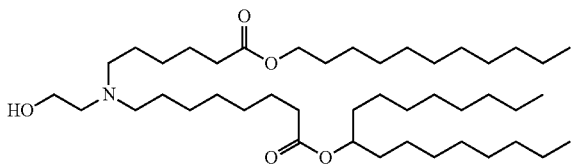 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

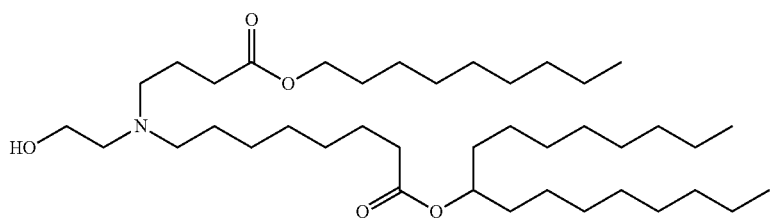 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

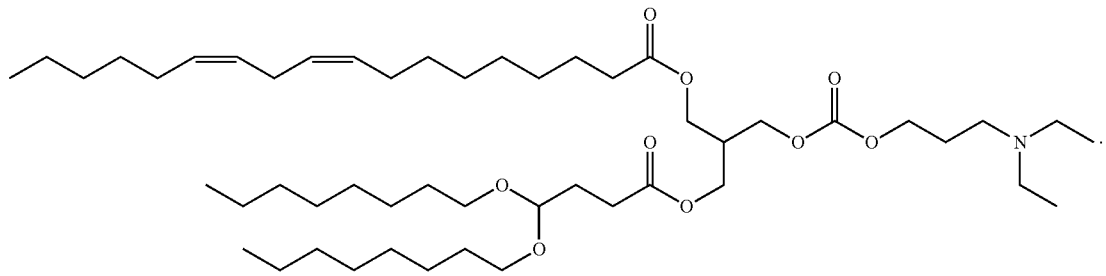 [SMILES: CCCCC/C=C\C/C=C\CCCCCCCC(=O)OCC(COC(=O)CCC(OCCCCCCCC)OCCCCCCCC)COC(=O)OCCCN(CC)CC ; "."]

and pharmaceutically acceptable salts thereof. In certain embodiments, the compositions and methods of the present invention include a cationic lipid having a compound structure of:

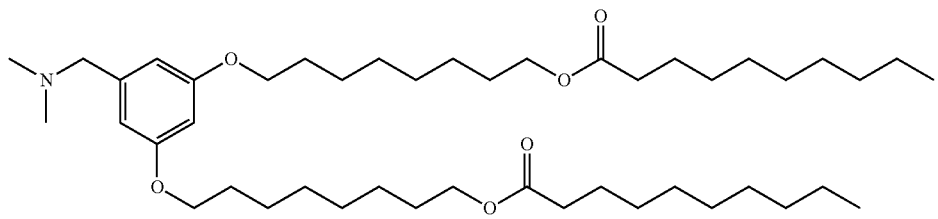 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

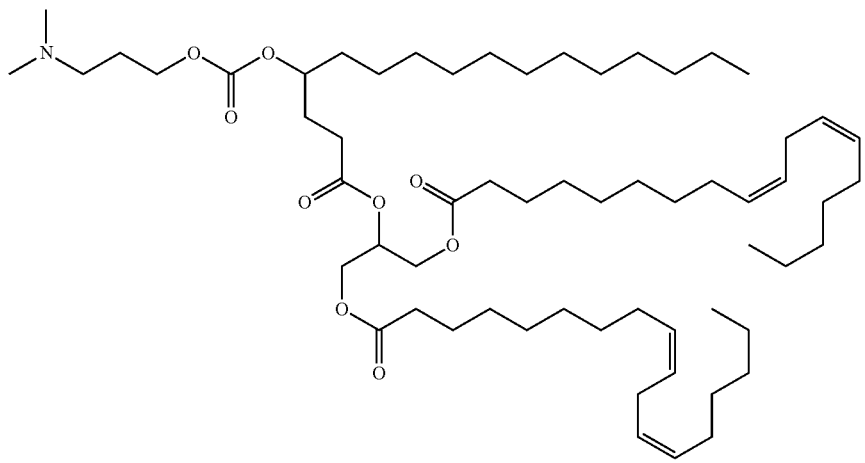 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

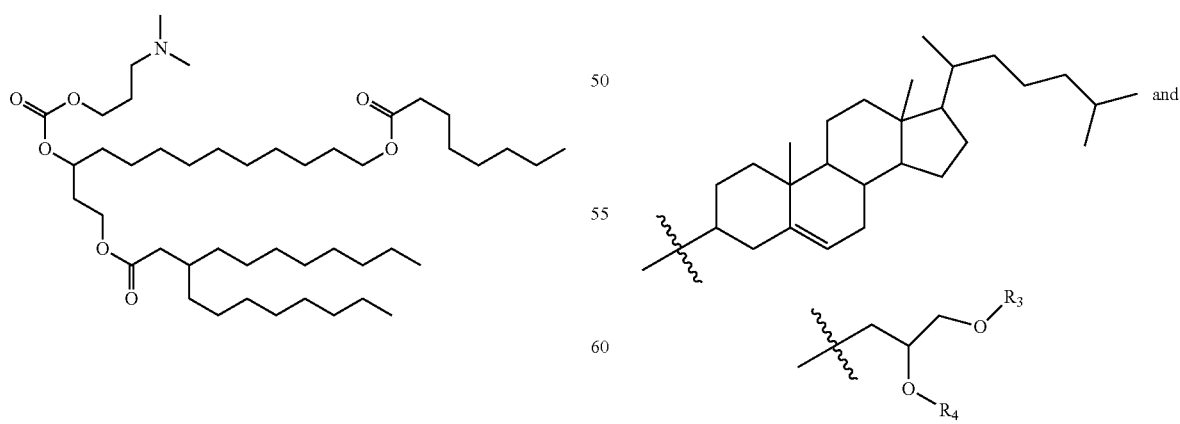

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

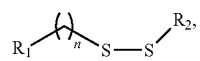

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

and pharmaceutically acceptable salts thereof. In certain embodiments, the compositions and methods of the present invention include a cationic lipid, "HGT4002", having a compound structure of:

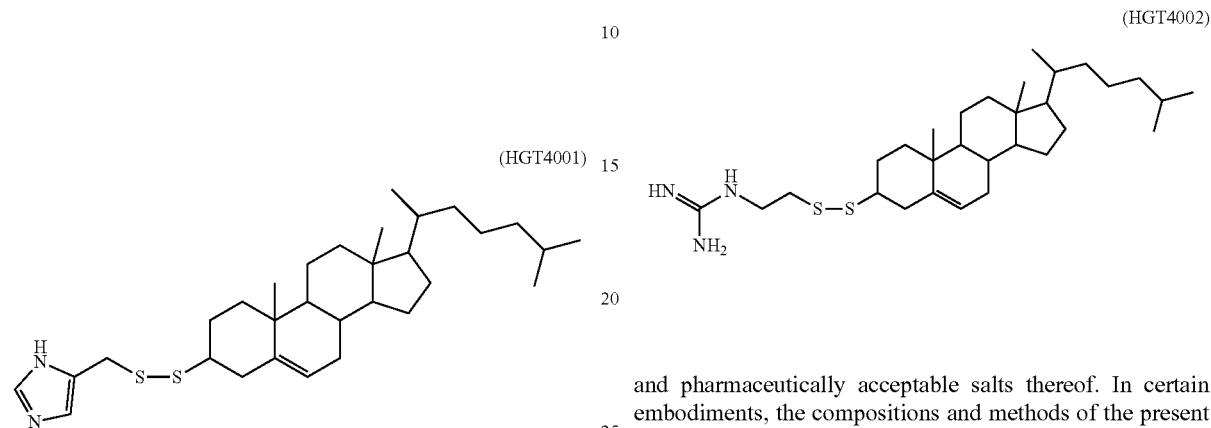

and pharmaceutically acceptable salts thereof. In certain embodiments, the compositions and methods of the present invention include a cationic lipid, "HGT4003", having a compound structure of:

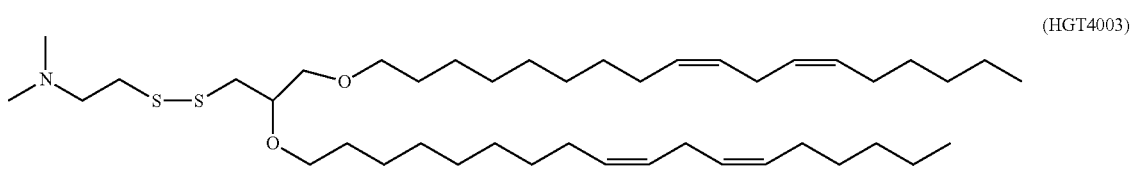 [SMILES: CCCCC/C=C\C/C=C\CCCCCCCCOCC(CSSCCN(C)C)OCCCCCCCC/C=C\C/C=C\CCCCC]

and pharmaceutically acceptable salts thereof. In certain embodiments, the compositions and methods of the present invention include a cationic lipid, "HGT4004", having a compound structure of:

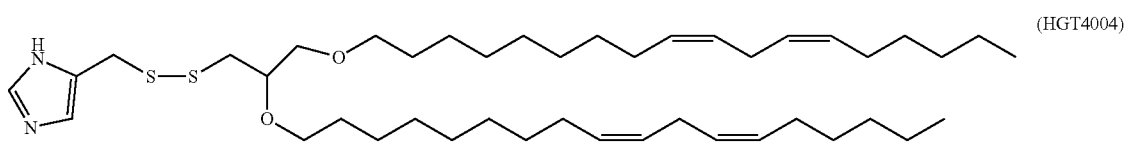 [SMILES: CCCCC/C=C\C/C=C\CCCCCCCCOCC(CSSCc1cnc[nH]1)OCCCCCCCC/C=C\C/C=C\CCCCC]

and pharmaceutically acceptable salts thereof. In certain embodiments, the compositions and methods of the present invention include a cationic lipid "HGT4005", having a compound structure of:

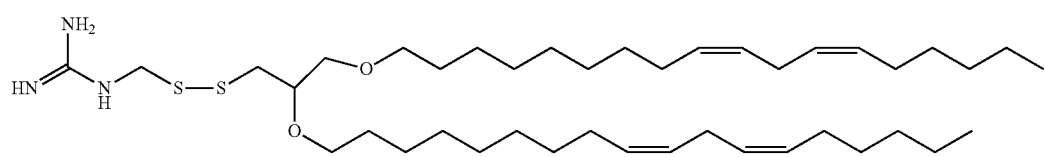

(HGT4005)

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

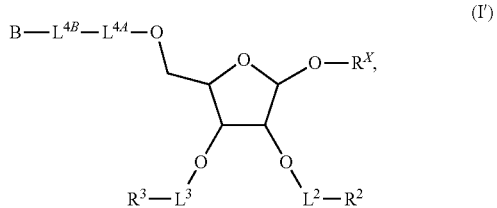

(I')

wherein:

$R^X$ is independently —H, $-L^1-R^1$, or $-L^{5A}-L^{5B}-B'$;

each of $L^1$, $L^2$, and $L^3$ is independently a covalent bond, —C(O)—, —C(O)O—, —C(O)S—, or —C(O)NR$^L$—;

each $L^{4A}$ and $L^{5A}$ is independently —C(O)—, —C(O)O—, or —C(O)NR$^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is NR$^4$R$^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

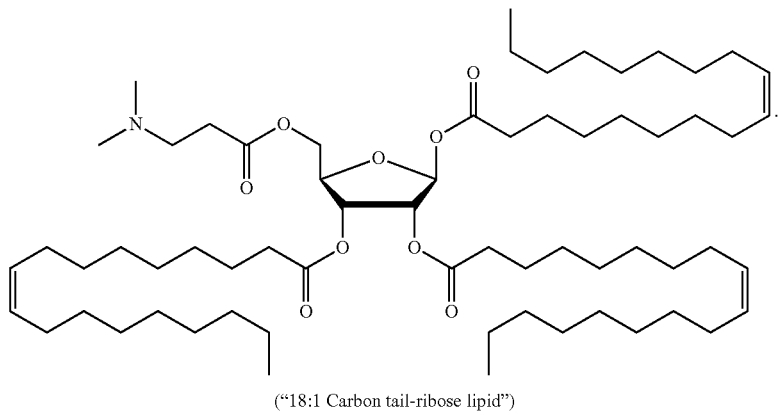

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3 aR,5s,6aS)—N,N-dimethyl-2,2-di ((9Z,12Z)-octadeca-9,12-dienyl)tetrahydro-3aH-cyclopenta [d][1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by the following structure:

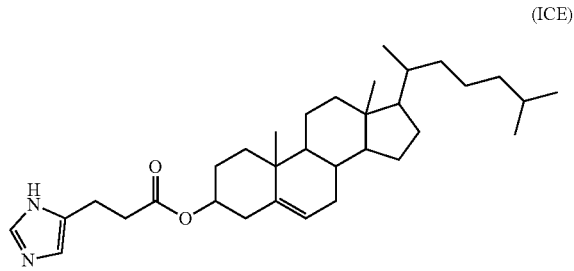 [SMILES: CC(C)CCCC(C)C1CCC2C3CC=C4CC(OC(=O)CCc5cnc[nH]5)CCC4(C)C3CCC12C]

(ICE)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the liposome may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 2 kDa, up to 3 kDa, up to 4 kDa or 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). In some embodiments, a PEG-modified or PEGylated lipid is PEGylated cholesterol or PEG-2K. In some embodiments, particularly useful exchangeable lipids are PEG-ceramides having shorter acyl chains (e.g., C14 or C18).

In some embodiments, particularly useful exchangeable lipids are PEG-ceramides having shorter acyl chains (e.g., C14 or C18). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome. PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

According to various embodiments, the selection of cationic lipids, non-cationic lipids and/or PEG-modified lipids which comprise the liposome, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

Liposome Formulations

A suitable liposome for the present invention may include one or more of any of the cationic lipids, non-cationic lipids, cholesterol lipids, PEGylated lipids and/or polymers described herein at various ratios. Typically, a liposome in accordance with the present invention comprises a cationic lipid, a non-cationic lipid, a cholesterol lipid and a PEGylated lipid. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase then may be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. In a typical embodiment, the mRNA of the invention is encapsulated in a liposome using the methods described in WO 2018/089801 (the teachings of which are incorporated herein by reference in their entirety). Briefly, the mRNA is encapsulated by mixing of a solution comprising pre-formed liposomes with mRNA such that liposomes encapsulating mRNA are formed.

Typically, the liposome-incorporated nucleic acids are completely located in the interior space of the liposome within the bilayer membrane of the liposome, although as discussed above, some of the mRNA (e.g., no more than 10% of total mRNA in the liposome composition) may also be associated with the exterior surface of the liposome membrane. The incorporation of a nucleic acid into liposomes is also referred to herein as "encapsulation". Typically, the purpose of incorporating an mRNA into a liposome is to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). Liposomes with a size of 80-200 nm are particularly suitable for some application. In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Liposome Formulations for DNAH5 mRNA Delivery and Expression

This section provides exemplary liposome formulations for effective delivery and expression of DNAH5 mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding DNAH5 protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, OF-02, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Exemplary Formulation Protocols

A. cKK-E12

Aliquots of 50 mg/mL ethanolic solutions of cKK-E12, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution was injected rapidly into the aqueous mRNA solution and shaken to yield a final suspension in 20% ethanol. The resulting liposome suspension was filtered, diafiltrated with 1×PBS (pH 7.4), concentrated and stored at 2-8° C. The final concentration, Zave, Dv(50) and Dv(90) of the DNAH5 encapsulated mRNA were determined.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of DNAH5mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of DNAH5T mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

Clinical or therapeutic candidate mRNA formulations are selected from the exemplary codon-optimized mRNA sequences having a 5'-cap and a 3'-poly A tail, which is formulated in a suitable lipid combination as described above. Clinically relevant mRNA candidates are characterized by efficient delivery and uptake by in vivo tissue, high level of expression and sustained protein production, without detectable adverse effects in the subject to whom the therapeutic is administered, either caused by the pharmacologically active ingredient or by the lipids in the liposome, or by any excipients used in the formulation. In general, high efficiency with low dose administration is favorable for the selection process of a relevant candidate therapeutic.

Pharmaceutical Compositions

The present invention provides compositions for use in the treatment of primary ciliary dyskinesia (PCD). The compositions of the present invention are for use in the manufacture of a medicament for the treatment of primary ciliary dyskinesia (PCD).

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject, the mammal, (e.g., treating, modulating, curing, preventing and/or ameliorating PCD). For example, a therapeutically effective amount may be an amount sufficient to achieve a desired therapeutic and/or prophylactic effect. Generally, the amount of a therapeutic agent (e.g., mRNA encoding aDNAH5 protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, an effective therapeutic dose of the pharmaceutical composition comprising an mRNA encoding dynein axonemal heavy chain 5 protein is administered to the mammal at a dosing interval sufficient to reduce for the period of the dosing interval or longer the level of at least one symptom or biomarker associated with PCD in the mammal relative to its state prior to the treatment.

In some embodiments the mammal is a human. A suitable therapeutic dose that may be applicable for a human being can be derived based on animal studies. A basic guideline for deriving a human equivalent dose from studies performed in animals can be obtained from the U.S>Food and Drug Administration (FDA) website at https://www.fda.gov/downloads/drugs/guidances/ucm078932.pdf, entitled, "Guidance for Industry Estimating the Maximum Safe Starting Dose in Initial Clinical Trials for Therapeutics in Adult Healthy Volunteers." Based on the guidelines for allometric scaling, a suitable dose of, for example, 0.6 mg/kg in a mouse, would relate to a human equivalent dose of 0.0048 mg/kg. Thus, considering the derived human equivalent dose, a projected human therapeutic dose can be derived based on studies in other animals.

In some embodiments, the dosing interval is once every 15 days or longer, or once every 20 days or longer, or once every 21 days, or once every 22 days, or once every 23 days, or once every 24 days, or once every 25 days, once every 26 days, or once every 27 days, or once every 28 days, or once every 29 days or longer, or once every 30 days or longer, or once every 31 days or longer. In some embodiments, the dosing interval is once every 40, 45 or 50 days or 60 days, or any number of days in between. In some embodiments, the dosing interval is once every 80, 90 or 120 days or 150 days, or any number of days in between.

In some embodiments, the therapeutic low dose is administered at a dosing interval of once every 2 weeks or longer, which is sufficient to reduce the level of at least one symptom or biomarker associated with PCD in the mammal relative to the state prior to the treatment. In some embodiments, the therapeutic low dose is administered at a dosing interval of once every 3 weeks or longer, which is sufficient to reduce the level of at least one symptom or biomarker associated with PCD in the mammal relative to the state prior to the treatment. In some embodiments, the dosing interval is once every 4 weeks or longer. In some embodiments, the dosing interval is once every 5 weeks or longer. In some embodiments, the dosing interval is once every 6 weeks or longer. In some embodiments, the dosing interval is once every 8 weeks or longer. In some embodiments, the dosing interval is once every 12 or 15 or 18 weeks or longer.

In some embodiments, the dosing interval is once a month. In some embodiments, the dosing interval is once in every two months. In some embodiments, the dosing interval is once every three months, or once every four months or once every five months or once every six months or anywhere in between.

In some embodiments, administering the provided composition results in an increased dynein axonemal heavy chain 5 mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased DNAH5 mRNA expression level by at least about 10%, 20%, 30%, 40%, 50%, 60%, 70%, 80%, 90%, or 95% as compared to the baseline level immediately before treatment. In some embodiments, administering the provided composition results in an increased DNAH5 mRNA expression level as compared to a DNAH5 mRNA expression level in subjects who are not treated According to the present invention, a therapeutically effective dose of the provided composition, when administered regularly, results in an increased DNAH5 protein expression or activity level in a subject as compared to a baseline DNAH5 protein expression or activity level before treatment. Typically, the DNAH5 protein expression or activity level is measured in a biological sample obtained from the subject such as blood, plasma or serum, urine, or solid tissue extracts. In some embodiments, the administering of a composition of the invention results in DNAH5 expression detectable in the liver. In some embodiments, administering the provided composition results in an increased DNAH5 protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased DNAH5 protein expression or activity level in a biological sample (e.g., plasma/serum or urine) by at least about 10%, 20%, 30%, 40%, 50%, 60%, 70%, 80%, 90%, or 95% as compared to a baseline level before treatment for at least 24 hours, at least 48 hours, at least 72 hours, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days.

In some embodiments, the therapeutic dose is sufficient to achieve at least some stabilization, improvement or elimination of symptoms and other indicators, such as biomarkers, are selected as appropriate measures of disease progress, disease regression or improvement by those of skill in the art.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

In some embodiments, the therapeutically effective dose comprising the mRNA encoding dynein axonemal heavy chain protein is administered to the subject by intramuscular administration.

In some embodiments, the therapeutically effective dose comprising the mRNA encoding dynein axonemal heavy chain protein is administered to the subject by subcutaneous administration.

In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Most commonly, the therapeutically effective dose comprising the mRNA encoding dynein axonemal heavy chain protein is administered to the subject by intravenous administration.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In particular embodiments, DNAH5 encoding mRNA is administered intravenously, wherein intravenous administration is associated with delivery of the mRNA to hepatocytes.

In some embodiments, the therapeutically effective dose comprising the mRNA encoding dynein axonemal heavy chain protein is administered for suitable delivery to the mammal's liver. In some embodiments, the therapeutically effective dose comprising the mRNA encoding dynein axonemal heavy chain protein is administered for suitable expression in hepatocytes of the administered mammal.

Provided methods of the present invention contemplate single as well as multiple administrations of a therapeutically effective amount of the therapeutic agents (e.g., mRNA encoding a DNAH5 protein) described herein. Therapeutic agents can be administered at regular intervals, depending on the nature, severity and extent of the subject's condition (e.g., PCD). In some embodiments, a therapeutically effective amount of the therapeutic agents (e.g., mRNA encoding a DNAH5 protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In some embodiments, the compositions of the present invention are administered to a subject twice a week, once a week, once every 7 days, once every 10 days, once every 14 days, once every 28 days, once every 30 days, once every two weeks, once every three weeks, once every four weeks, once a month, twice a month, once every six weeks, once every eight weeks, once every other month, once every three months, once every four months, once every six months, once every eight months, once every nine months or annually.

In a preferred embodiment, the compositions of the present invention are administered to a subject once a week, once every two weeks or once a month. In a more preferred embodiment, the compositions of the present invention are administered to a subject once every two weeks or once every month. In the most preferred embodiment, the compositions of the present invention are administered to a subject once every month.

In some embodiments the mRNA is administered concurrently with an additional therapy.

Also contemplated are compositions and liposomes which are formulated for depot administration (e.g., intramuscularly, subcutaneously, intravitreally) to either deliver or release an mRNA over extended periods of time. Preferably, the extended-release means employed are combined with modifications made to the mRNA to enhance stability.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts. According to the present invention, a therapeutically effective dose of the provided composition, when administered regularly, results in at least one symptom or feature of PCD is reduced in intensity, severity, or frequency or has delayed onset.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

In some embodiments, the pharmaceutical composition comprises a lyophilized liposomal delivery vehicle that comprises a cationic lipid, a non-cationic lipid, a PEG-modified lipid and cholesterol. In some embodiments, the pharmaceutical composition has a Dv50 of less than 500 nm, 300 nm, 200 nm, 150 nm, 125 nm, 120 nm, 100 nm, 75 nm, 50 nm, 25 nm or smaller upon reconstitution. In some embodiments, the pharmaceutical composition has a Dv90 of less than 750 nm, 700 nm, 500 nm, 300 nm, 200 nm, 150 nm, 125 nm, 100 nm, 75 nm, 50 nm, 25 nm or smaller upon reconstitution. In some embodiments, the pharmaceutical composition has a polydispersity index value of less than 1, 0.95, 0.9, 0.8, 0.75, 0.7, 0.6, 0.5, 0.4, 0.3, 0.25, 0.2, 0.1, 0.05 or less upon reconstitution. In some embodiments, the pharmaceutical composition has an average particle size of less than 500 nm, 400 nm, 300 nm, 200 nm, 175 nm, 150 nm, 125 nm, 100 nm, 75 nm, 50 nm, 25 nm or upon reconstitution.

In some embodiments, the lyophilized pharmaceutical composition further comprises one or more lyoprotectants, such as sucrose, trehalose, dextran or inulin. Typically, the lyoprotectant is sucrose. In some embodiments, the pharmaceutical composition is stable for at least 1 month or at least 6 months upon storage at 4° C., or for at least 6 months upon storage at 25° C. In some embodiments, the biologic activity of the mRNA of the reconstituted lyophilized pharmaceutical composition exceeds 75% of the biological activity observed prior to lyophilization of the composition.

Provided liposomes and compositions may be administered to any desired tissue. In some embodiments, the DNAH5 mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in a reduced methylmalonic acid level in a subject as compared to a baseline methylmalonic acid level before treatment.

In some embodiments, administering the provided composition results in an increased level of DNAH5 protein in a liver cell (e.g., a hepatocyte) of a subject as compared to a baseline level before treatment. Typically, the baseline level is measured immediately before treatment. In some embodiments, administering the provided composition results in an increased DNAH5 protein level in the liver cell by at least about 10%, 20%, 30%, 40%, 50%, 60%, 70%, 80%, 90%, or 95% as compared to a baseline level before treatment. In some embodiments, administering the provided composition results in an increased DNAH5 protein level in a liver cell as compared to the DNAH5 protein level a liver cell of subjects who are not treated.

In some embodiments, administering the provided composition results in an increased DNAH5 protein level in plasma or serum of subject as compared to a baseline level before treatment. Typically, the baseline level is measured immediately before treatment. In some embodiments, administering the provided composition results in an increased DNAH5 protein level in plasma or serum by at least about 10%, 20%, 30%, 40%, 50%, 60%, 70%, 80%, 90%, or 95% as compared to a baseline level before treatment. In some embodiments, administering the provided composition results in an increased DNAH5 protein level in plasma or serum as compared to a DNAH5 protein level in plasma or serum of subjects who are not treated.

In some embodiments, administering the provided composition results in increased DNAH5 enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased DNAH5 enzyme activity by at least about 10%, 20%, 30%, 40%, 50%, 60%, 70%, 80%, 90%, or 95% as compared to a baseline level immediately before treatment. In some embodiments, administering the provided composition results in an increased DNAH5 enzyme activity as compared to DNAH5 enzyme activity in subjects who are not treated.

In some embodiments the subject is a mammal. In some embodiments, the mammal is an adult. In some embodiments the mammal is an adolescent. In some embodiments the mammal is an infant or a young mammal. In some embodiments, the mammal is a primate. In some embodiments, the mammal is a human. In some embodiments the subject is 6 years to 80 years old.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for DNAH5 mRNA Delivery and Expression This example provides exemplary liposome formulations for effective delivery and expression of hDNAH5 mRNA in vivo.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate human dynein axonemal heavy chain 5 (hDNAH5) mRNA. Unless otherwise specified, the multi-component lipid mixture used in the following Examples were ethanolic solutions of an imidazole cholesterol ester ("ICE") cationic lipid, a non-cationic lipid such as DOPE, and a PEGylated lipid such as DMG-PEG2K.

Messenger RNA Material

Codon-optimized hDNAH5 messenger RNA was synthesized by in vitro transcription from a plasmid DNA template encoding the gene. Following in vitro transcription, a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail were added. The poly(A) tail was approximately 135 nucleotides in length on average. The 5' and 3' untranslated regions present in each mRNA product are represented as X and Y, respectively, and defined as stated (vide infra).

```
Codon-Optimized hDNAH5 mRNA:
X-Coding region-Y
5' and 3' UTR Sequences
X (5' UTR Sequence) =
                                          [SEQ ID NO.: 2]
AGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACG
```

```
OR
                                          [SEQ ID NO.: 3]
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACG

Y (3' UTR Sequence) =
                                          [SEQ ID NO.: 4]
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UCAAGCU
OR
                                          [SEQ ID NO.: 5]
GGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAU

CAAAGCU
Coding regions
```

The MRT-1 codon-optimized hDNAH5 messenger RNA coding region comprised the sequence of SEQ ID NO. 6 or SEQ ID NO. 7. A 3'-GFP-tagged version of MRT-1 codon-optimized hDNA5 was likewise prepared, MRT-hDNA5-GFP using molecular cloning techniques well known in the art.

Formulation Protocol hDNAH5 mRNA was encapsulated in multi-component liposomes as described in WO 2018/089790, published May 17, 2018 (incorporated herein by reference), at an N/P ratio of approximately 10.

Example 2. In Vivo Administration and Delivery of hDNAH5 mRNA to the Lung and Expression of hDNAH5 Protein This example illustrates exemplary methods of administering hDNAH5 mRNA-loaded liposome nanoparticles and methods for analyzing delivered mRNA and subsequently expressed hDNAH5 protein in lung epithelium in vivo.

The studies in this Example were performed using male 129S1/SvimJ mice, which were of approximately 10-12 weeks of age. Three groups of mice (each n=5) were exposed by a single intratracheal aerosol administration via Microsprayer® (50 µL/animal) a test article (Groups 1 and 2) or a control. The test article for Group 1 was 10 µg/animal of MRT-1 hDNAH5 mRNA prepared as described in Example 1. The test article for Group 2 was 10 µg/animal (unless otherwise specified) of hDNAH5-GFP mRNA (i.e., a sequence including both MRT1 hDNAH5 mRNA and green fluorescent protein (GFP) mRNA) prepared as described in Example 1. The control included either saline administered at the same volume or an irrelevant mRNA in the same delivery vehicle as the test articles. Mice were euthanized at 24 hours (±5%) post dose administration.

Isolation of Plasma for Analysis

All animals were euthanized by isoflurane overdose via nose cone followed by thoracotomy and terminal blood collection. Whole blood (maximal obtainable volume) was collected via cardiac puncture on euthanized animals and discarded. The animals were then and perfused with saline.

Isolation of Organ Tissues for Analysis

Following perfusion, the liver and the entire airway (trachea to lungs) of each mouse was harvested. The entire airway for the top of the trachea to, and including, the lungs was dissected in one piece and then sagitally cut to provide left and right sections of the entire airway. FIG. 1A depicts the dissection scheme of the lung. The left section of the entire airway was fixed in buffer for subsequent immunohistochemical and histological analysis. The right section of the entire airway was snap-frozen and stored at −70° C. for subsequent qPCR analysis of the trachea (1), superior lobe (2), middle lobe (3), inferior lobe (4), and post-caval lobe (5). The liver also was snap-frozen and stored at −70° C.

qPCR Assay

Figure 1B:
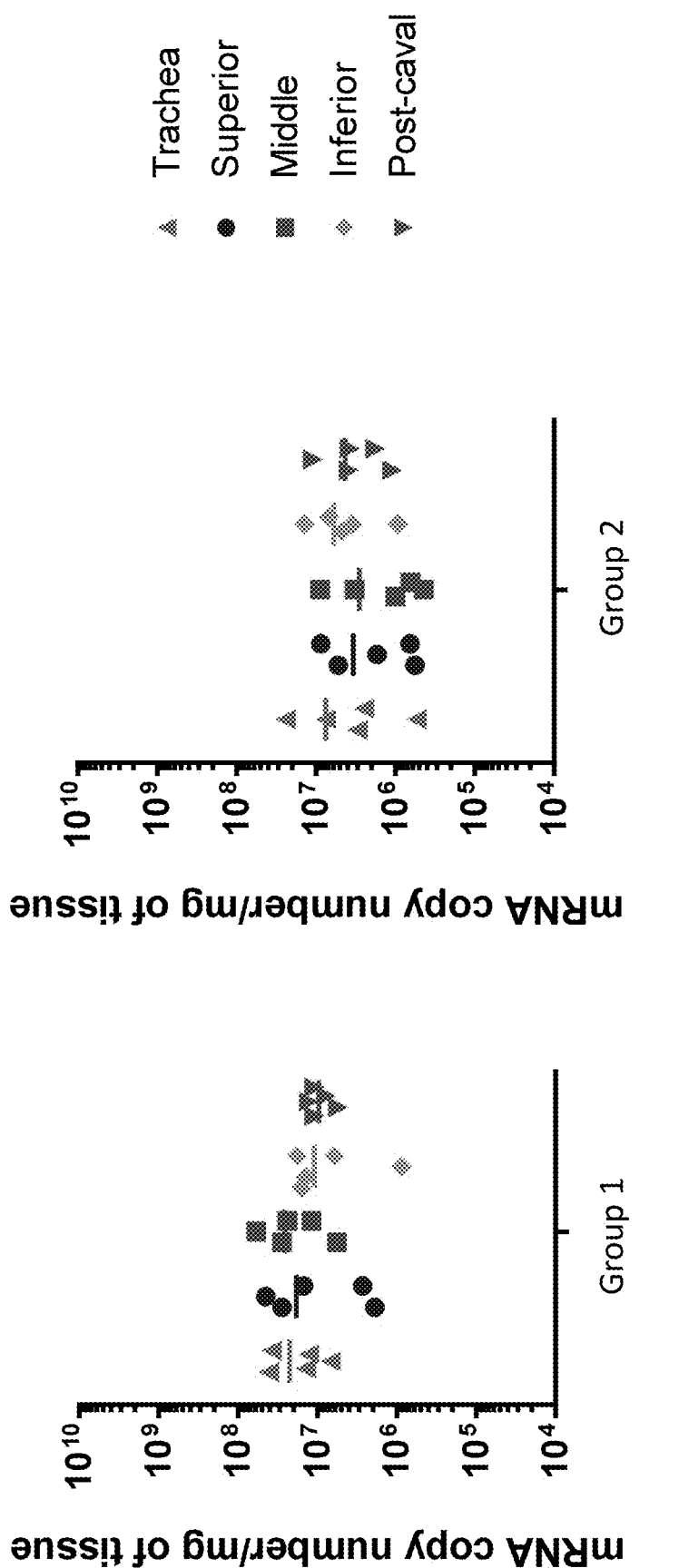
FIG. 1B (left) and (right), are graphs that show qPCR data for hDNA5 mRNA in the different regions of the respiratory system as indicated in the figure.

Mouse trachea and each lung lobes were homogenized in presence of trizol for complete lysis, followed by RNA extraction using silica-membrane based spin columns. The codon optimized hDNAH5 mRNA levels are determined using RT-qPCR. First, the purified RNA is reverse transcribed (RT) into cDNA using random primers. Then, a PCR reaction is performed using sequence specific primers and quantified in real-time using a taqman fluorophore probe (qPCR). Purified, in vitro transcribed hDNAH5 which is run as a reference in the qPCR assay is used to generate a standard curve and calculate hDNAH5 copy numbers per milligram of the analyzed tissue. Results of the qPCR analysis are shown in FIG. 1B.

Immunohistochemical (IHC) Analysis—DNAH5 or GFP

The hDNAH5 and GFP protein in the trachea and lungs was characterized by IHC staining. Briefly, the harvested tissues were fixed in formalin and embedded in paraffin blocks. Sections (5 micron thick) along the length of the tissues were mounted on glass slides for staining. Antigen retrieval was performed using EDTA based buffer, followed by blocking with hydrogen peroxide and goat serum. Primary antibodies against hDNAH5 (Ab122390) and GFP (Ab290) were incubated with respective samples overnight at 4° C. Enzyme-conjugated secondary antibodies were used for detection of the bound primary antibodies. The images of the stained slides were captured at 20× magnification. Results of the IHC analysis are shown in FIG. 2.

Results

Figure 2A:
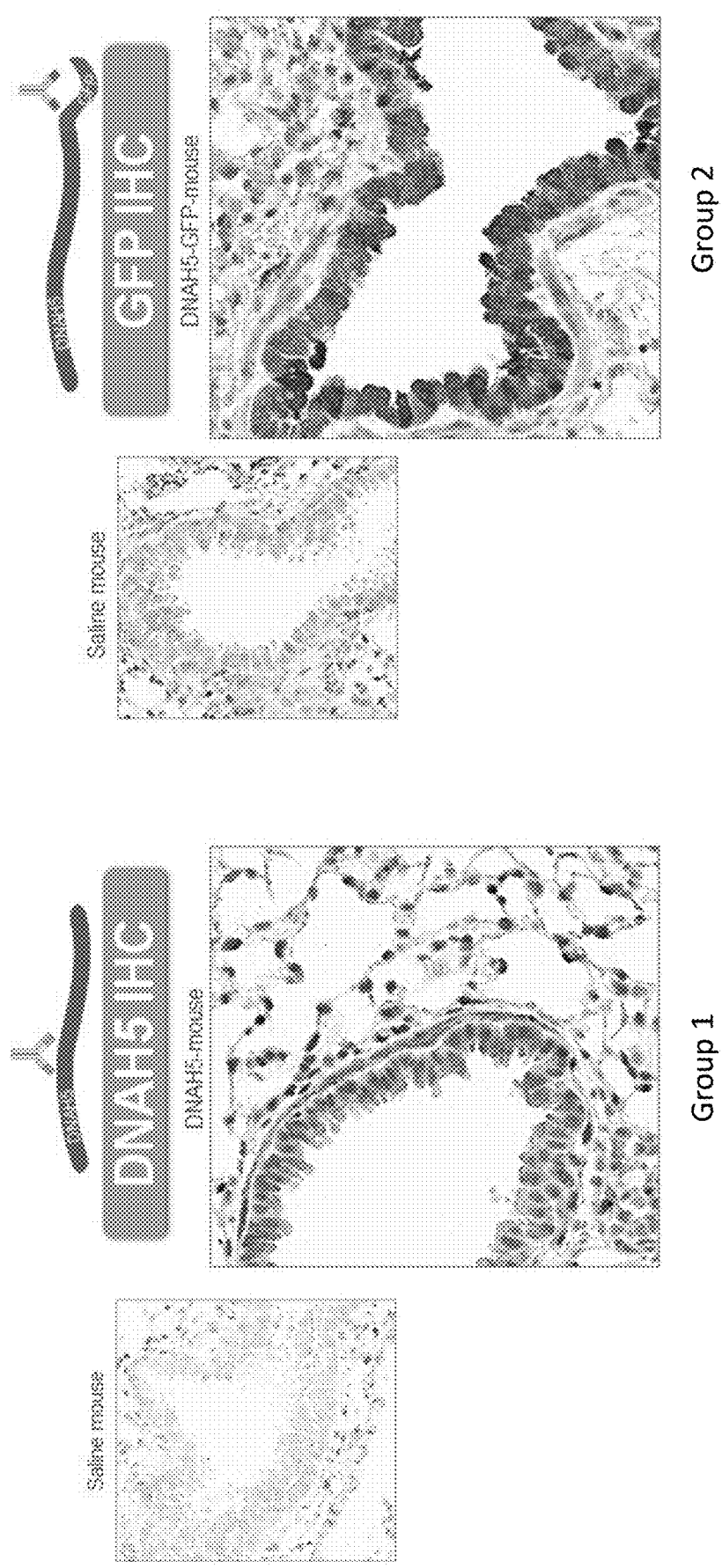
FIG. 2A and FIG. 2B show series of photomicrographs depicting results from IHC analysis for hDNA protein expression in the respiratory airways.
Figure 2B:
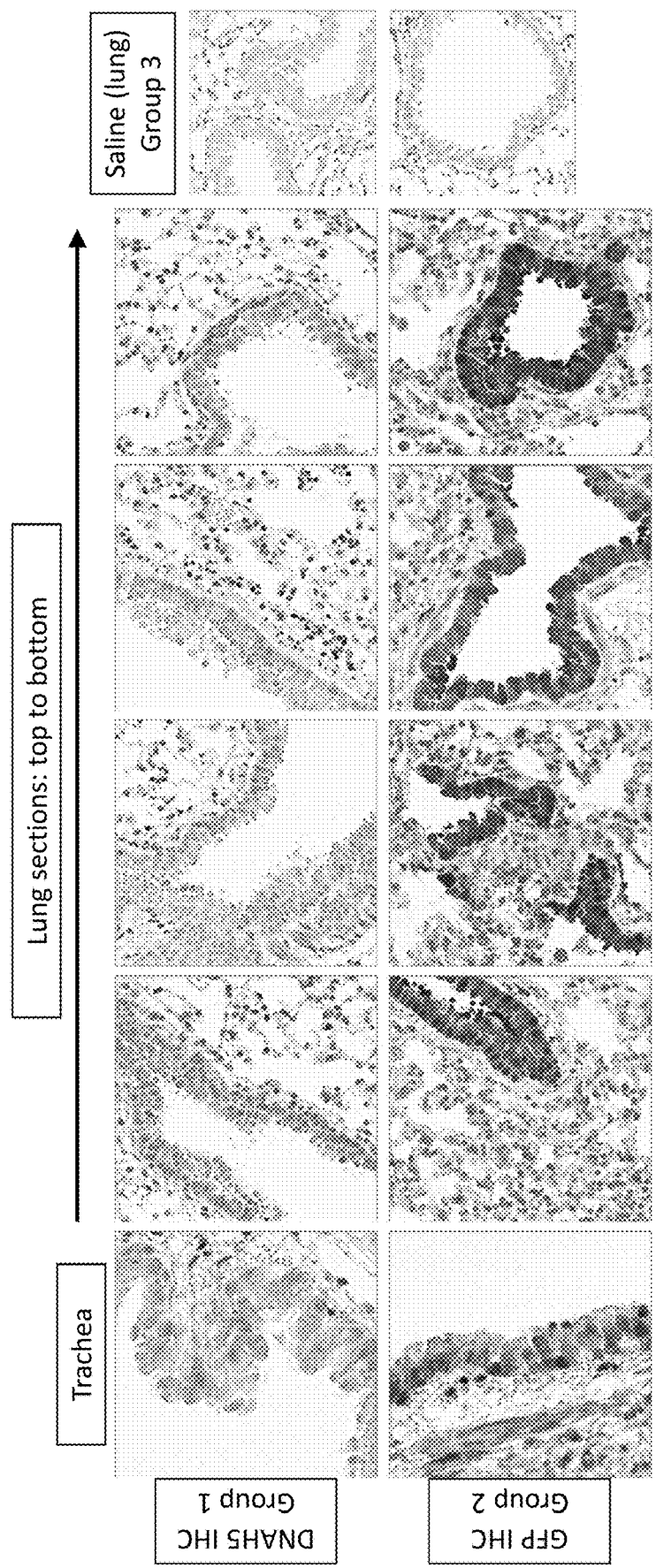

This Example shows the successful in vivo administration, delivery and expression of a greater than 10 kb therapeutic mRNA. In particular, in this Example, hDNAH5 mRNA, a 14 kb mRNA, was successfully encapsulated, administered by nebulization and delivered in vivo to the lung. FIG. 1B provides qPCR data showing successful hDNAH5 mRNA deposition in cells in each of the trachea (1), superior lobe (2), middle lobe (3), inferior lobe (4), and post-caval lobe (5) of the lung for each mouse in Groups 1 and 2. FIG. 2A provides exemplary IHC images showing positive staining for hDNAH5 protein expressed from the hDNAH5 mRNA lung tissue from mice in each of Groups 1 and 2. Further, FIG. 2B shows IHC images with positive staining for hDNAH5 protein, from mice in Groups 1 and 2, in tissue from the trachea as well as tissue across the entire lung, from top to bottom (left to right in FIG. 2B).

Exemplary Sequences

Exemplary codon-optimized mRNA sequences are shown in SEQ ID NO: 6-31. For the purpose of the sequence disclosure, U and T are used interchangeably.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of delivery of human axonemal dynein heavy chain 5 (DNAH5) in vivo comprising administering to a subject in need of delivery an mRNA encoding a human DNAH5 protein, wherein the mRNA comprises a coding sequence at least 90% identical to any one of SEQ ID NO: 6 to SEQ ID NO: 31.

2. A method of treating primary ciliary dyskinesia (PCD) comprising administering to a subject in need of treatment an mRNA encoding human axonemal dynein heavy chain 5 (DNAH5) at an effective dose and an administration interval such that at least one symptom or feature of PCD is reduced in intensity, severity, or frequency or has delayed in onset, wherein the mRNA comprises a coding sequence at least 90% identical to any one of SEQ ID NO: 6 to SEQ ID NO: 31.

3. The method of claim 1, wherein the DNAH5 mRNA is encapsulated in a liposome.

4. The method of claim 3, wherein the liposome comprises one or more cationic lipids, one or more non-cationic lipids and one or more PEG-modified lipids.

5. The method of claim 3, wherein the liposome has a diameter of about 80 nm to 200 nm.

6. The method of claim 1, wherein the DNAH5 mRNA is codon optimized.

7. The method of claim 1, wherein the mRNA comprises a coding sequence at least 95% identical to any one of SEQ ID NO: 6 to SEQ ID NO: 31.

8. The method of claim 1, wherein the mRNA comprises a coding sequence set forth in SEQ ID NO: 6 to SEQ ID NO: 31.

9. The method of claim 1, wherein administering the mRNA to the subject is performed by intratracheal, intranasal, intravenous, intramuscular or subcutaneous delivery.

10. The method of claim 1, wherein administering the mRNA to the subject is performed by intratracheal delivery.

11. The method of claim 1, wherein the composition is administered once daily.

12. The method of claim 1, wherein the administering the mRNA results in DNAH5 protein expression detectable in one or more internal organs selected from lung, heart, liver, spleen, kidney, brain, stomach, intestines, ovary and testis.

13. The method of claim 1, wherein the administering the mRNA results in DNAH5 protein expression detectable in the lung.

14. A composition for use in the treatment of primary ciliary dyskinesia (PCD), the composition comprising an mRNA encoding human axonemal dynein heavy chain 5 (DNAH5) encapsulated in a liposome, wherein the liposome comprises one or more cationic lipids, one or more non-cationic lipids and one or more PEG-modified lipids, and wherein the mRNA comprises a coding sequence at least 90% identical to any one of SEQ ID NO:6 to SEQ ID NO:31.

15. The composition of claim 14, wherein the mRNA comprises a coding sequence at least 95% identical to any one of SEQ ID NO: 6 to SEQ ID NO: 31.

16. The composition of claim 14, wherein the liposome is 100 nm in diameter or less.

17. A pharmaceutical composition comprising the composition of claim 14 and a suitable excipient.

* * * * *

SEQUENCE LISTING

```
<160> NUMBER OF SEQ ID NOS: 31

<210> SEQ ID NO 1
<211> LENGTH: 4624
<212> TYPE: PRT
<213> ORGANISM: Homo sapiens

<400> SEQUENCE: 1

Met Phe Arg Ile Gly Arg Arg Gln Leu Trp Lys His Ser Val Thr Arg
1               5                   10                  15

Val Leu Thr Gln Arg Leu Lys Gly Glu Lys Glu Ala Lys Arg Ala Leu
            20                  25                  30

Leu Asp Ala Arg His Asn Tyr Leu Phe Ala Ile Val Ala Ser Cys Leu
        35                  40                  45

Asp Leu Asn Lys Thr Glu Val Glu Asp Ala Ile Leu Glu Gly Asn Gln
    50                  55                  60

Ile Glu Arg Ile Asp Gln Leu Phe Ala Val Gly Gly Leu Arg His Leu
65                  70                  75                  80

Met Phe Tyr Tyr Gln Asp Val Glu Glu Ala Glu Thr Gly Gln Leu Gly
                85                  90                  95

Ser Leu Gly Gly Val Asn Leu Val Ser Gly Lys Ile Lys Lys Pro Lys
            100                 105                 110

Val Phe Val Thr Glu Gly Asn Asp Val Ala Leu Thr Gly Val Cys Val
        115                 120                 125

Phe Phe Ile Arg Thr Asp Pro Ser Lys Ala Ile Thr Pro Asp Asn Ile
    130                 135                 140
```

-continued

```
His Gln Glu Val Ser Phe Asn Met Leu Asp Ala Asp Gly Gly Leu
145                 150                 155                 160

Leu Asn Ser Val Arg Arg Leu Leu Ser Asp Ile Phe Ile Pro Ala Leu
                165                 170                 175

Arg Ala Thr Ser His Gly Trp Gly Glu Leu Glu Gly Leu Gln Asp Ala
            180                 185                 190

Ala Asn Ile Arg Gln Glu Phe Leu Ser Ser Leu Glu Gly Phe Val Asn
        195                 200                 205

Val Leu Ser Gly Ala Gln Ser Leu Lys Glu Lys Val Asn Leu Arg
    210                 215                 220

Lys Cys Asp Ile Leu Glu Leu Lys Thr Leu Lys Glu Pro Thr Asp Tyr
225                 230                 235                 240

Leu Thr Leu Ala Asn Asn Pro Glu Thr Leu Gly Lys Ile Glu Asp Cys
                245                 250                 255

Met Lys Val Trp Ile Lys Gln Thr Glu Gln Val Leu Ala Glu Asn Asn
            260                 265                 270

Gln Leu Leu Lys Glu Ala Asp Asp Val Gly Pro Arg Ala Glu Leu Glu
        275                 280                 285

His Trp Lys Lys Arg Leu Ser Lys Phe Asn Tyr Leu Leu Glu Gln Leu
    290                 295                 300

Lys Ser Pro Asp Val Lys Ala Val Leu Ala Val Leu Ala Ala Ala Lys
305                 310                 315                 320

Ser Lys Leu Leu Lys Thr Trp Arg Glu Met Asp Ile Arg Ile Thr Asp
                325                 330                 335

Ala Thr Asn Glu Ala Lys Asp Asn Val Lys Tyr Leu Tyr Thr Leu Glu
            340                 345                 350

Lys Cys Cys Asp Pro Leu Tyr Ser Ser Asp Pro Leu Ser Met Met Asp
        355                 360                 365

Ala Ile Pro Thr Leu Ile Asn Ala Ile Lys Met Ile Tyr Ser Ile Ser
    370                 375                 380

His Tyr Tyr Asn Thr Ser Glu Lys Ile Thr Ser Leu Phe Val Lys Val
385                 390                 395                 400

Thr Asn Gln Ile Ile Ser Ala Cys Lys Ala Tyr Ile Thr Asn Asn Gly
                405                 410                 415

Thr Ala Ser Ile Trp Asn Gln Pro Gln Asp Val Val Glu Glu Lys Ile
            420                 425                 430

Leu Ser Ala Ile Lys Leu Lys Gln Glu Tyr Gln Leu Cys Phe His Lys
        435                 440                 445

Thr Lys Gln Lys Leu Lys Gln Asn Pro Asn Ala Lys Gln Phe Asp Phe
    450                 455                 460

Ser Glu Met Tyr Ile Phe Gly Lys Phe Glu Thr Phe His Arg Arg Leu
465                 470                 475                 480

Ala Lys Ile Ile Asp Ile Phe Thr Thr Leu Lys Thr Tyr Ser Val Leu
                485                 490                 495

Gln Asp Ser Thr Ile Glu Gly Leu Glu Asp Met Ala Thr Lys Tyr Gln
            500                 505                 510

Gly Ile Val Ala Thr Ile Lys Lys Lys Glu Tyr Asn Phe Leu Asp Gln
        515                 520                 525

Arg Lys Met Asp Phe Asp Gln Asp Tyr Glu Glu Phe Cys Lys Gln Thr
    530                 535                 540

Asn Asp Leu His Asn Glu Leu Arg Lys Phe Met Asp Val Thr Phe Ala
545                 550                 555                 560

Lys Ile Gln Asn Thr Asn Gln Ala Leu Arg Met Leu Lys Lys Phe Glu
```

```
                565                 570                 575
Arg Leu Asn Ile Pro Asn Leu Gly Ile Asp Asp Lys Tyr Gln Leu Ile
            580                 585                 590

Leu Glu Asn Tyr Gly Ala Asp Ile Asp Met Ile Ser Lys Leu Tyr Thr
        595                 600                 605

Lys Gln Lys Tyr Asp Pro Pro Leu Ala Arg Asn Gln Pro Pro Ile Ala
    610                 615                 620

Gly Lys Ile Leu Trp Ala Arg Gln Leu Phe His Arg Ile Gln Gln Pro
625                 630                 635                 640

Met Gln Leu Phe Gln Gln His Pro Ala Val Leu Ser Thr Ala Glu Ala
                645                 650                 655

Lys Pro Ile Ile Arg Ser Tyr Asn Arg Met Ala Lys Val Leu Leu Glu
            660                 665                 670

Phe Glu Val Leu Phe His Arg Ala Trp Leu Arg Gln Ile Glu Glu Ile
        675                 680                 685

His Val Gly Leu Glu Ala Ser Leu Leu Val Lys Ala Pro Gly Thr Gly
    690                 695                 700

Glu Leu Phe Val Asn Phe Asp Pro Gln Ile Leu Ile Leu Phe Arg Glu
705                 710                 715                 720

Thr Glu Cys Met Ala Gln Met Gly Leu Glu Val Ser Pro Leu Ala Thr
                725                 730                 735

Ser Leu Phe Gln Lys Arg Asp Arg Tyr Lys Arg Asn Phe Ser Asn Met
            740                 745                 750

Lys Met Met Leu Ala Glu Tyr Gln Arg Val Lys Ser Lys Ile Pro Ala
        755                 760                 765

Ala Ile Glu Gln Leu Ile Val Pro His Leu Ala Lys Val Asp Glu Ala
    770                 775                 780

Leu Gln Pro Gly Leu Ala Ala Leu Thr Trp Thr Ser Leu Asn Ile Glu
785                 790                 795                 800

Ala Tyr Leu Glu Asn Thr Phe Ala Lys Ile Lys Asp Leu Glu Leu Leu
                805                 810                 815

Leu Asp Arg Val Asn Asp Leu Ile Glu Phe Arg Ile Asp Ala Ile Leu
            820                 825                 830

Glu Glu Met Ser Ser Thr Pro Leu Cys Gln Leu Pro Gln Glu Glu Pro
        835                 840                 845

Leu Thr Cys Glu Glu Phe Leu Gln Met Thr Lys Asp Leu Cys Val Asn
    850                 855                 860

Gly Ala Gln Ile Leu His Phe Lys Ser Ser Leu Val Glu Glu Ala Val
865                 870                 875                 880

Asn Glu Leu Val Asn Met Leu Leu Asp Val Glu Val Leu Ser Glu Glu
                885                 890                 895

Glu Ser Glu Lys Ile Ser Asn Glu Asn Ser Val Asn Tyr Lys Asn Glu
            900                 905                 910

Ser Ser Ala Lys Arg Glu Glu Gly Asn Phe Asp Thr Leu Thr Ser Ser
        915                 920                 925

Ile Asn Ala Arg Ala Asn Ala Leu Leu Leu Thr Thr Val Thr Arg Lys
    930                 935                 940

Lys Lys Glu Thr Glu Met Leu Gly Glu Glu Ala Arg Glu Leu Leu Ser
945                 950                 955                 960

His Phe Asn His Gln Asn Met Asp Ala Leu Leu Lys Val Thr Arg Asn
                965                 970                 975

Thr Leu Glu Ala Ile Arg Lys Arg Ile His Ser Ser His Thr Ile Asn
            980                 985                 990
```

-continued

```
Phe Arg Asp Ser Asn Ser Ala Ser  Asn Met Lys Gln Asn  Ser Leu Pro
        995                1000                1005

Ile Phe Arg Ala Ser Val Thr  Leu Ala Ile Pro Asn  Ile Val Met
    1010                1015                1020

Ala Pro Ala Leu Glu Asp Val  Gln Gln Thr Leu Asn  Lys Ala Val
    1025                1030                1035

Glu Cys Ile Ile Ser Val Pro  Lys Gly Val Arg Gln  Trp Ser Ser
    1040                1045                1050

Glu Leu Leu Ser Lys Lys Lys  Ile Gln Glu Arg Lys  Met Ala Ala
    1055                1060                1065

Leu Gln Ser Asn Glu Asp Ser  Asp Ser Asp Val Glu  Met Gly Glu
    1070                1075                1080

Asn Glu Leu Gln Asp Thr Leu  Glu Ile Ala Ser Val  Asn Leu Pro
    1085                1090                1095

Ile Pro Val Gln Thr Lys Asn  Tyr Tyr Lys Asn Val  Ser Glu Asn
    1100                1105                1110

Lys Glu Ile Val Lys Leu Val  Ser Val Leu Ser Thr  Ile Ile Asn
    1115                1120                1125

Ser Thr Lys Lys Glu Val Ile  Thr Ser Met Asp Cys  Phe Lys Arg
    1130                1135                1140

Tyr Asn His Ile Trp Gln Lys  Gly Lys Glu Glu Ala  Ile Lys Thr
    1145                1150                1155

Phe Ile Thr Gln Ser Pro Leu  Leu Ser Glu Phe Glu  Ser Gln Ile
    1160                1165                1170

Leu Tyr Phe Gln Asn Leu Glu  Gln Glu Ile Asn Ala  Glu Pro Glu
    1175                1180                1185

Tyr Val Cys Val Gly Ser Ile  Ala Leu Tyr Thr Ala  Asp Leu Lys
    1190                1195                1200

Phe Ala Leu Thr Ala Glu Thr  Lys Ala Trp Met Val  Val Ile Gly
    1205                1210                1215

Arg His Cys Asn Lys Lys Tyr  Arg Ser Glu Met Glu  Asn Ile Phe
    1220                1225                1230

Met Leu Ile Glu Glu Phe Asn  Lys Lys Leu Asn Arg  Pro Ile Lys
    1235                1240                1245

Asp Leu Asp Asp Ile Arg Ile  Ala Met Ala Ala Leu  Lys Glu Ile
    1250                1255                1260

Arg Glu Glu Gln Ile Ser Ile  Asp Phe Gln Val Gly  Pro Ile Glu
    1265                1270                1275

Glu Ser Tyr Ala Leu Leu Asn  Arg Tyr Gly Leu Leu  Ile Ala Arg
    1280                1285                1290

Glu Glu Ile Asp Lys Val Asp  Thr Leu His Tyr Ala  Trp Glu Lys
    1295                1300                1305

Leu Leu Ala Arg Ala Gly Glu  Val Gln Asn Lys Leu  Val Ser Leu
    1310                1315                1320

Gln Pro Ser Phe Lys Lys Glu  Leu Ile Ser Ala Val  Glu Val Phe
    1325                1330                1335

Leu Gln Asp Cys His Gln Phe  Tyr Leu Asp Tyr Asp  Leu Asn Gly
    1340                1345                1350

Pro Met Ala Ser Gly Leu Lys  Pro Gln Glu Ala Ser  Asp Arg Leu
    1355                1360                1365

Ile Met Phe Gln Asn Gln Phe  Asp Asn Ile Tyr Arg  Lys Tyr Ile
    1370                1375                1380
```

```
Thr Tyr Thr Gly Gly Glu Glu Leu Phe Gly Leu Pro Ala Thr Gln
1385                1390                1395

Tyr Pro Gln Leu Leu Glu Ile Lys Lys Gln Leu Asn Leu Leu Gln
1400                1405                1410

Lys Ile Tyr Thr Leu Tyr Asn Ser Val Ile Glu Thr Val Asn Ser
1415                1420                1425

Tyr Tyr Asp Ile Leu Trp Ser Glu Val Asn Ile Glu Lys Ile Asn
1430                1435                1440

Asn Glu Leu Leu Glu Phe Gln Asn Arg Cys Arg Lys Leu Pro Arg
1445                1450                1455

Ala Leu Lys Asp Trp Gln Ala Phe Leu Asp Leu Lys Lys Ile Ile
1460                1465                1470

Asp Asp Phe Ser Glu Cys Cys Pro Leu Leu Glu Tyr Met Ala Ser
1475                1480                1485

Lys Ala Met Met Glu Arg His Trp Glu Arg Ile Thr Thr Leu Thr
1490                1495                1500

Gly His Ser Leu Asp Val Gly Asn Glu Ser Phe Lys Leu Arg Asn
1505                1510                1515

Ile Met Glu Ala Pro Leu Leu Lys Tyr Lys Glu Ile Glu Asp
1520                1525                1530

Ile Cys Ile Ser Ala Val Lys Glu Arg Asp Ile Glu Gln Lys Leu
1535                1540                1545

Lys Gln Val Ile Asn Glu Trp Asp Asn Lys Thr Phe Thr Phe Gly
1550                1555                1560

Ser Phe Lys Thr Arg Gly Glu Leu Leu Leu Arg Gly Asp Ser Thr
1565                1570                1575

Ser Glu Ile Ile Ala Asn Met Glu Asp Ser Leu Met Leu Leu Gly
1580                1585                1590

Ser Leu Leu Ser Asn Arg Tyr Asn Met Pro Phe Lys Ala Gln Ile
1595                1600                1605

Gln Lys Trp Val Gln Tyr Leu Ser Asn Ser Thr Asp Ile Ile Glu
1610                1615                1620

Ser Trp Met Thr Val Gln Asn Leu Trp Ile Tyr Leu Glu Ala Val
1625                1630                1635

Phe Val Gly Gly Asp Ile Ala Lys Gln Leu Pro Lys Glu Ala Lys
1640                1645                1650

Arg Phe Ser Asn Ile Asp Lys Ser Trp Val Lys Ile Met Thr Arg
1655                1660                1665

Ala His Glu Val Pro Ser Val Val Gln Cys Cys Val Gly Asp Glu
1670                1675                1680

Thr Leu Gly Gln Leu Leu Pro His Leu Leu Asp Gln Leu Glu Ile
1685                1690                1695

Cys Gln Lys Ser Leu Thr Gly Tyr Leu Glu Lys Lys Arg Leu Cys
1700                1705                1710

Phe Pro Arg Phe Phe Phe Val Ser Asp Pro Ala Leu Leu Glu Ile
1715                1720                1725

Leu Gly Gln Ala Ser Asp Ser His Thr Ile Gln Ala His Leu Leu
1730                1735                1740

Asn Val Phe Asp Asn Ile Lys Ser Val Lys Phe His Glu Lys Ile
1745                1750                1755

Tyr Asp Arg Ile Leu Ser Ile Ser Ser Gln Glu Gly Glu Thr Ile
1760                1765                1770

Glu Leu Asp Lys Pro Val Met Ala Glu Gly Asn Val Glu Val Trp
```

```
            1775                1780                1785

Leu Asn Ser Leu Leu Glu Glu Ser Gln Ser Ser Leu His Leu Val
    1790                1795                1800

Ile Arg Gln Ala Ala Ala Asn Ile Gln Glu Thr Gly Phe Gln Leu
    1805                1810                1815

Thr Glu Phe Leu Ser Ser Phe Pro Ala Gln Val Gly Leu Leu Gly
    1820                1825                1830

Ile Gln Met Ile Trp Thr Arg Asp Ser Glu Glu Ala Leu Arg Asn
    1835                1840                1845

Ala Lys Phe Asp Lys Lys Ile Met Gln Lys Thr Asn Gln Ala Phe
    1850                1855                1860

Leu Glu Leu Leu Asn Thr Leu Ile Asp Val Thr Thr Arg Asp Leu
    1865                1870                1875

Ser Ser Thr Glu Arg Val Lys Tyr Glu Thr Leu Ile Thr Ile His
    1880                1885                1890

Val His Gln Arg Asp Ile Phe Asp Asp Leu Cys His Met His Ile
    1895                1900                1905

Lys Ser Pro Met Asp Phe Glu Trp Leu Lys Gln Cys Arg Phe Tyr
    1910                1915                1920

Phe Asn Glu Asp Ser Asp Lys Met Met Ile His Ile Thr Asp Val
    1925                1930                1935

Ala Phe Ile Tyr Gln Asn Glu Phe Leu Gly Cys Thr Asp Arg Leu
    1940                1945                1950

Val Ile Thr Pro Leu Thr Asp Arg Cys Tyr Ile Thr Leu Ala Gln
    1955                1960                1965

Ala Leu Gly Met Ser Met Gly Gly Ala Pro Ala Gly Pro Ala Gly
    1970                1975                1980

Thr Gly Lys Thr Glu Thr Thr Lys Asp Met Gly Arg Cys Leu Gly
    1985                1990                1995

Lys Tyr Val Val Val Phe Asn Cys Ser Asp Gln Met Asp Phe Arg
    2000                2005                2010

Gly Leu Gly Arg Ile Phe Lys Gly Leu Ala Gln Ser Gly Ser Trp
    2015                2020                2025

Gly Cys Phe Asp Glu Phe Asn Arg Ile Asp Leu Pro Val Leu Ser
    2030                2035                2040

Val Ala Ala Gln Gln Ile Ser Ile Ile Leu Thr Cys Lys Lys Glu
    2045                2050                2055

His Lys Lys Ser Phe Ile Phe Thr Asp Gly Asp Asn Val Thr Met
    2060                2065                2070

Asn Pro Glu Phe Gly Leu Phe Leu Thr Met Asn Pro Gly Tyr Ala
    2075                2080                2085

Gly Arg Gln Glu Leu Pro Glu Asn Leu Lys Ile Asn Phe Arg Ser
    2090                2095                2100

Val Ala Met Met Val Pro Asp Arg Gln Ile Ile Ile Arg Val Lys
    2105                2110                2115

Leu Ala Ser Cys Gly Phe Ile Asp Asn Val Val Leu Ala Arg Lys
    2120                2125                2130

Phe Phe Thr Leu Tyr Lys Leu Cys Glu Glu Gln Leu Ser Lys Gln
    2135                2140                2145

Val His Tyr Asp Phe Gly Leu Arg Asn Ile Leu Ser Val Leu Arg
    2150                2155                2160

Thr Leu Gly Ala Ala Lys Arg Ala Asn Pro Met Asp Thr Glu Ser
    2165                2170                2175
```

```
Thr Ile Val Met Arg Val Leu Arg Asp Met Asn Leu Ser Lys Leu
        2180            2185                2190

Ile Asp Glu Asp Glu Pro Leu Phe Leu Ser Leu Ile Glu Asp Leu
    2195            2200                2205

Phe Pro Asn Ile Leu Leu Asp Lys Ala Gly Tyr Pro Glu Leu Glu
    2210            2215                2220

Ala Ala Ile Ser Arg Gln Val Glu Glu Ala Gly Leu Ile Asn His
    2225            2230                2235

Pro Pro Trp Lys Leu Lys Val Ile Gln Leu Phe Glu Thr Gln Arg
    2240            2245                2250

Val Arg His Gly Met Met Thr Leu Gly Pro Ser Gly Ala Gly Lys
    2255            2260                2265

Thr Thr Cys Ile His Thr Leu Met Arg Ala Met Thr Asp Cys Gly
    2270            2275                2280

Lys Pro His Arg Glu Met Arg Met Asn Pro Lys Ala Ile Thr Ala
    2285            2290                2295

Pro Gln Met Phe Gly Arg Leu Asp Val Ala Thr Asn Asp Trp Thr
    2300            2305                2310

Asp Gly Ile Phe Ser Thr Leu Trp Arg Lys Thr Leu Arg Ala Lys
    2315            2320                2325

Lys Gly Glu His Ile Trp Ile Ile Leu Asp Gly Pro Val Asp Ala
    2330            2335                2340

Ile Trp Ile Glu Asn Leu Asn Ser Val Leu Asp Asp Asn Lys Thr
    2345            2350                2355

Leu Thr Leu Ala Asn Gly Asp Arg Ile Pro Met Ala Pro Asn Cys
    2360            2365                2370

Lys Ile Ile Phe Glu Pro His Asn Ile Asp Asn Ala Ser Pro Ala
    2375            2380                2385

Thr Val Ser Arg Asn Gly Met Val Phe Met Ser Ser Ser Ile Leu
    2390            2395                2400

Asp Trp Ser Pro Ile Leu Glu Gly Phe Leu Lys Lys Arg Ser Pro
    2405            2410                2415

Gln Glu Ala Glu Ile Leu Arg Gln Leu Tyr Thr Glu Ser Phe Pro
    2420            2425                2430

Asp Leu Tyr Arg Phe Cys Ile Gln Asn Leu Glu Tyr Lys Met Glu
    2435            2440                2445

Val Leu Glu Ala Phe Val Ile Thr Gln Ser Ile Asn Met Leu Gln
    2450            2455                2460

Gly Leu Ile Pro Leu Lys Glu Gln Gly Gly Glu Val Ser Gln Ala
    2465            2470                2475

His Leu Gly Arg Leu Phe Val Phe Ala Leu Leu Trp Ser Ala Gly
    2480            2485                2490

Ala Ala Leu Glu Leu Asp Gly Arg Arg Arg Leu Glu Leu Trp Leu
    2495            2500                2505

Arg Ser Arg Pro Thr Gly Thr Leu Glu Leu Pro Pro Pro Ala Gly
    2510            2515                2520

Pro Gly Asp Thr Ala Phe Asp Tyr Tyr Val Ala Pro Asp Gly Thr
    2525            2530                2535

Trp Thr His Trp Asn Thr Arg Thr Gln Glu Tyr Leu Tyr Pro Ser
    2540            2545                2550

Asp Thr Thr Pro Glu Tyr Gly Ser Ile Leu Val Pro Asn Val Asp
    2555            2560                2565
```

```
Asn Val Arg Thr Asp Phe Leu  Ile Gln Thr Ile Ala  Lys Gln Gly
2570                    2575              2580

Lys Ala Val Leu Leu Ile Gly  Glu Gln Gly Thr Ala  Lys Thr Val
    2585                2590              2595

Ile Ile Lys Gly Phe Met Ser  Lys Tyr Asp Pro Glu  Cys His Met
    2600                2605              2610

Ile Lys Ser Leu Asn Phe Ser  Ser Ala Thr Thr Pro  Leu Met Phe
    2615                2620              2625

Gln Arg Thr Ile Glu Ser Tyr  Val Asp Lys Arg Met  Gly Thr Thr
    2630                2635              2640

Tyr Gly Pro Pro Ala Gly Lys  Lys Met Thr Val Phe  Ile Asp Asp
    2645                2650              2655

Val Asn Met Pro Ile Ile Asn  Glu Trp Gly Asp Gln  Val Thr Asn
    2660                2665              2670

Glu Ile Val Arg Gln Leu Met  Glu Gln Asn Gly Phe  Tyr Asn Leu
    2675                2680              2685

Glu Lys Pro Gly Glu Phe Thr  Ser Ile Val Asp Ile  Gln Phe Leu
    2690                2695              2700

Ala Ala Met Ile His Pro Gly  Gly Gly Arg Asn Asp  Ile Pro Gln
    2705                2710              2715

Arg Leu Lys Arg Gln Phe Ser  Ile Phe Asn Cys Thr  Leu Pro Ser
    2720                2725              2730

Glu Ala Ser Val Asp Lys Ile  Phe Gly Val Ile Gly  Val Gly His
    2735                2740              2745

Tyr Cys Thr Gln Arg Gly Phe  Ser Glu Glu Val Arg  Asp Ser Val
    2750                2755              2760

Thr Lys Leu Val Pro Leu Thr  Arg Arg Leu Trp Gln  Met Thr Lys
    2765                2770              2775

Ile Lys Met Leu Pro Thr Pro  Ala Lys Phe His Tyr  Val Phe Asn
    2780                2785              2790

Leu Arg Asp Leu Ser Arg Val  Trp Gln Gly Met Leu  Asn Thr Thr
    2795                2800              2805

Ser Glu Val Ile Lys Glu Pro  Asn Asp Leu Leu Lys  Leu Trp Lys
    2810                2815              2820

His Glu Cys Lys Arg Val Ile  Ala Asp Arg Phe Thr  Val Ser Ser
    2825                2830              2835

Asp Val Thr Trp Phe Asp Lys  Ala Leu Val Ser Leu  Val Glu Glu
    2840                2845              2850

Glu Phe Gly Glu Glu Lys Lys  Leu Leu Val Asp Cys  Gly Ile Asp
    2855                2860              2865

Thr Tyr Phe Val Asp Phe Leu  Arg Asp Ala Pro Glu  Ala Ala Gly
    2870                2875              2880

Glu Thr Ser Glu Glu Ala Asp  Ala Glu Thr Pro Lys  Ile Tyr Glu
    2885                2890              2895

Pro Ile Glu Ser Phe Ser His  Leu Lys Glu Arg Leu  Asn Met Phe
    2900                2905              2910

Leu Gln Leu Tyr Asn Glu Ser  Ile Arg Gly Ala Gly  Met Asp Met
    2915                2920              2925

Val Phe Phe Ala Asp Ala Met  Val His Leu Val Lys  Ile Ser Arg
    2930                2935              2940

Val Ile Arg Thr Pro Gln Gly  Asn Ala Leu Leu Val  Gly Val Gly
    2945                2950              2955

Gly Ser Gly Lys Gln Ser Leu  Thr Arg Leu Ala Ser  Phe Ile Ala
```

```
                2960                2965                2970
Gly Tyr Val Ser Phe Gln Ile Thr Leu Thr Arg Ser Tyr Asn Thr
        2975                2980                2985
Ser Asn Leu Met Glu Asp Leu Lys Val Leu Tyr Arg Thr Ala Gly
        2990                2995                3000
Gln Gln Gly Lys Gly Ile Thr Phe Ile Phe Thr Asp Asn Glu Ile
        3005                3010                3015
Lys Asp Glu Ser Phe Leu Glu Tyr Met Asn Asn Val Leu Ser Ser
        3020                3025                3030
Gly Glu Val Ser Asn Leu Phe Ala Arg Asp Glu Ile Asp Glu Ile
        3035                3040                3045
Asn Ser Asp Leu Ala Ser Val Met Lys Lys Glu Phe Pro Arg Cys
        3050                3055                3060
Leu Pro Thr Asn Glu Asn Leu His Asp Tyr Phe Met Ser Arg Val
        3065                3070                3075
Arg Gln Asn Leu His Ile Val Leu Cys Phe Ser Pro Val Gly Glu
        3080                3085                3090
Lys Phe Arg Asn Arg Ala Leu Lys Phe Pro Ala Leu Ile Ser Gly
        3095                3100                3105
Cys Thr Ile Asp Trp Phe Ser Arg Trp Pro Lys Asp Ala Leu Val
        3110                3115                3120
Ala Val Ser Glu His Phe Leu Thr Ser Tyr Asp Ile Asp Cys Ser
        3125                3130                3135
Leu Glu Ile Lys Lys Glu Val Val Gln Cys Met Gly Ser Phe Gln
        3140                3145                3150
Asp Gly Val Ala Glu Lys Cys Val Asp Tyr Phe Gln Arg Phe Arg
        3155                3160                3165
Arg Ser Thr His Val Thr Pro Lys Ser Tyr Leu Ser Phe Ile Gln
        3170                3175                3180
Gly Tyr Lys Phe Ile Tyr Gly Glu Lys His Val Glu Val Arg Thr
        3185                3190                3195
Leu Ala Asn Arg Met Asn Thr Gly Leu Glu Lys Leu Lys Glu Ala
        3200                3205                3210
Ser Glu Ser Val Ala Ala Leu Ser Lys Glu Leu Glu Ala Lys Glu
        3215                3220                3225
Lys Glu Leu Gln Val Ala Asn Asp Lys Ala Asp Met Val Leu Lys
        3230                3235                3240
Glu Val Thr Met Lys Ala Gln Ala Ala Glu Lys Val Lys Ala Glu
        3245                3250                3255
Val Gln Lys Val Lys Asp Arg Ala Gln Ala Ile Val Asp Ser Ile
        3260                3265                3270
Ser Lys Asp Lys Ala Ile Ala Glu Glu Lys Leu Glu Ala Ala Lys
        3275                3280                3285
Pro Ala Leu Glu Glu Ala Glu Ala Ala Leu Gln Thr Ile Arg Pro
        3290                3295                3300
Ser Asp Ile Ala Thr Val Arg Thr Leu Gly Arg Pro Pro His Leu
        3305                3310                3315
Ile Met Arg Ile Met Asp Cys Val Leu Leu Phe Gln Arg Lys
        3320                3325                3330
Val Ser Ala Val Lys Ile Asp Leu Glu Lys Ser Cys Thr Met Pro
        3335                3340                3345
Ser Trp Gln Glu Ser Leu Lys Leu Met Thr Ala Gly Asn Phe Leu
        3350                3355                3360
```

-continued

```
Gln Asn Leu Gln Gln Phe Pro Lys Asp Thr Ile Asn Glu Glu Val
3365                3370                3375

Ile Glu Phe Leu Ser Pro Tyr Phe Glu Met Pro Asp Tyr Asn Ile
3380                3385                3390

Glu Thr Ala Lys Arg Val Cys Gly Asn Val Ala Gly Leu Cys Ser
3395                3400                3405

Trp Thr Lys Ala Met Ala Ser Phe Phe Ser Ile Asn Lys Glu Val
3410                3415                3420

Leu Pro Leu Lys Ala Asn Leu Val Val Gln Glu Asn Arg His Leu
3425                3430                3435

Leu Ala Met Gln Asp Leu Gln Lys Ala Gln Ala Glu Leu Asp Asp
3440                3445                3450

Lys Gln Ala Glu Leu Asp Val Val Gln Ala Glu Tyr Glu Gln Ala
3455                3460                3465

Met Thr Glu Lys Gln Thr Leu Leu Glu Asp Ala Glu Arg Cys Arg
3470                3475                3480

His Lys Met Gln Thr Ala Ser Thr Leu Ile Ser Gly Leu Ala Gly
3485                3490                3495

Glu Lys Glu Arg Trp Thr Glu Gln Ser Gln Glu Phe Ala Ala Gln
3500                3505                3510

Thr Lys Arg Leu Val Gly Asp Val Leu Leu Ala Thr Ala Phe Leu
3515                3520                3525

Ser Tyr Ser Gly Pro Phe Asn Gln Glu Phe Arg Asp Leu Leu Leu
3530                3535                3540

Asn Asp Trp Arg Lys Glu Met Lys Ala Arg Lys Ile Pro Phe Gly
3545                3550                3555

Lys Asn Leu Asn Leu Ser Glu Met Leu Ile Asp Ala Pro Thr Ile
3560                3565                3570

Ser Glu Trp Asn Leu Gln Gly Leu Pro Asn Asp Asp Leu Ser Ile
3575                3580                3585

Gln Asn Gly Ile Ile Val Thr Lys Ala Ser Arg Tyr Pro Leu Leu
3590                3595                3600

Ile Asp Pro Gln Thr Gln Gly Lys Ile Trp Ile Lys Asn Lys Glu
3605                3610                3615

Ser Arg Asn Glu Leu Gln Ile Thr Ser Leu Asn His Lys Tyr Phe
3620                3625                3630

Arg Asn His Leu Glu Asp Ser Leu Ser Leu Gly Arg Pro Leu Leu
3635                3640                3645

Ile Glu Asp Val Gly Glu Glu Leu Asp Pro Ala Leu Asp Asn Val
3650                3655                3660

Leu Glu Arg Asn Phe Ile Lys Thr Gly Ser Thr Phe Lys Val Lys
3665                3670                3675

Val Gly Asp Lys Glu Val Asp Val Leu Asp Gly Phe Arg Leu Tyr
3680                3685                3690

Ile Thr Thr Lys Leu Pro Asn Pro Ala Tyr Thr Pro Glu Ile Ser
3695                3700                3705

Ala Arg Thr Ser Ile Ile Asp Phe Thr Val Thr Met Lys Gly Leu
3710                3715                3720

Glu Asp Gln Leu Leu Gly Arg Val Ile Leu Thr Glu Lys Gln Glu
3725                3730                3735

Leu Glu Lys Glu Arg Thr His Leu Met Glu Asp Val Thr Ala Asn
3740                3745                3750
```

```
Lys Arg Arg Met Lys Glu Leu Glu Asp Asn Leu Leu Tyr Arg Leu
3755                3760                3765

Thr Ser Thr Gln Gly Ser Leu Val Glu Asp Glu Ser Leu Ile Val
3770                3775                3780

Val Leu Ser Asn Thr Lys Arg Thr Ala Glu Glu Val Thr Gln Lys
3785                3790                3795

Leu Glu Ile Ser Ala Glu Thr Glu Val Gln Ile Asn Ser Ala Arg
3800                3805                3810

Glu Glu Tyr Arg Pro Val Ala Thr Arg Gly Ser Ile Leu Tyr Phe
3815                3820                3825

Leu Ile Thr Glu Met Arg Leu Val Asn Glu Met Tyr Gln Thr Ser
3830                3835                3840

Leu Arg Gln Phe Leu Gly Leu Phe Asp Leu Ser Leu Ala Arg Ser
3845                3850                3855

Val Lys Ser Pro Ile Thr Ser Lys Arg Ile Ala Asn Ile Ile Glu
3860                3865                3870

His Met Thr Tyr Glu Val Tyr Lys Tyr Ala Ala Arg Gly Leu Tyr
3875                3880                3885

Glu Glu His Lys Phe Leu Phe Thr Leu Leu Thr Leu Lys Ile
3890                3895                3900

Asp Ile Gln Arg Asn Arg Val Lys His Glu Glu Phe Leu Thr Leu
3905                3910                3915

Ile Lys Gly Gly Ala Ser Leu Asp Leu Lys Ala Cys Pro Pro Lys
3920                3925                3930

Pro Ser Lys Trp Ile Leu Asp Ile Thr Trp Leu Asn Leu Val Glu
3935                3940                3945

Leu Ser Lys Leu Arg Gln Phe Ser Asp Val Leu Asp Gln Ile Ser
3950                3955                3960

Arg Asn Glu Lys Met Trp Lys Ile Trp Phe Asp Lys Glu Asn Pro
3965                3970                3975

Glu Glu Glu Pro Leu Pro Asn Ala Tyr Asp Lys Ser Leu Asp Cys
3980                3985                3990

Phe Arg Arg Leu Leu Leu Ile Arg Ser Trp Cys Pro Asp Arg Thr
3995                4000                4005

Ile Ala Gln Ala Arg Lys Tyr Ile Val Asp Ser Met Gly Glu Lys
4010                4015                4020

Tyr Ala Glu Gly Val Ile Leu Asp Leu Glu Lys Thr Trp Glu Glu
4025                4030                4035

Ser Asp Pro Arg Thr Pro Leu Ile Cys Leu Leu Ser Met Gly Ser
4040                4045                4050

Asp Pro Thr Asp Ser Ile Ile Ala Leu Gly Lys Arg Leu Lys Ile
4055                4060                4065

Glu Thr Arg Tyr Val Ser Met Gly Gln Gly Gln Glu Val His Ala
4070                4075                4080

Arg Lys Leu Leu Gln Gln Thr Met Ala Asn Gly Gly Trp Ala Leu
4085                4090                4095

Leu Gln Asn Cys His Leu Gly Leu Asp Phe Met Asp Glu Leu Met
4100                4105                4110

Asp Ile Ile Ile Glu Thr Glu Leu Val His Asp Ala Phe Arg Leu
4115                4120                4125

Trp Met Thr Thr Glu Ala His Lys Gln Phe Pro Ile Thr Leu Leu
4130                4135                4140

Gln Met Ser Ile Lys Phe Ala Asn Asp Pro Pro Gln Gly Leu Arg
```

```
                4145                4150                4155
Ala Gly Leu Lys Arg Thr Tyr Ser Gly Val Ser Gln Asp Leu Leu
        4160                4165                4170
Asp Val Ser Ser Gly Ser Gln Trp Lys Pro Met Leu Tyr Ala Val
        4175                4180                4185
Ala Phe Leu His Ser Thr Val Gln Glu Arg Arg Lys Phe Gly Ala
        4190                4195                4200
Leu Gly Trp Asn Ile Pro Tyr Glu Phe Asn Gln Ala Asp Phe Asn
        4205                4210                4215
Ala Thr Val Gln Phe Ile Gln Asn His Leu Asp Asp Met Asp Val
        4220                4225                4230
Lys Lys Gly Val Ser Trp Thr Thr Ile Arg Tyr Met Ile Gly Glu
        4235                4240                4245
Ile Gln Tyr Gly Gly Arg Val Thr Asp Asp Tyr Asp Lys Arg Leu
        4250                4255                4260
Leu Asn Thr Phe Ala Lys Val Trp Phe Ser Glu Asn Met Phe Gly
        4265                4270                4275
Pro Asp Phe Ser Phe Tyr Gln Gly Tyr Asn Ile Pro Lys Cys Ser
        4280                4285                4290
Thr Val Asp Asn Tyr Leu Gln Tyr Ile Gln Ser Leu Pro Ala Tyr
        4295                4300                4305
Asp Ser Pro Glu Val Phe Gly Leu His Pro Asn Ala Asp Ile Thr
        4310                4315                4320
Tyr Gln Ser Lys Leu Ala Lys Asp Val Leu Asp Thr Ile Leu Gly
        4325                4330                4335
Ile Gln Pro Lys Asp Thr Ser Gly Gly Gly Asp Glu Thr Arg Glu
        4340                4345                4350
Ala Val Val Ala Arg Leu Ala Asp Asp Met Leu Glu Lys Leu Pro
        4355                4360                4365
Pro Asp Tyr Val Pro Phe Glu Val Lys Glu Arg Leu Gln Lys Met
        4370                4375                4380
Gly Pro Phe Gln Pro Met Asn Ile Phe Leu Arg Gln Glu Ile Asp
        4385                4390                4395
Arg Met Gln Arg Val Leu Ser Leu Val Arg Ser Thr Leu Thr Glu
        4400                4405                4410
Leu Lys Leu Ala Ile Asp Gly Thr Ile Ile Met Ser Glu Asn Leu
        4415                4420                4425
Arg Asp Ala Leu Asp Cys Met Phe Asp Ala Arg Ile Pro Ala Trp
        4430                4435                4440
Trp Lys Lys Ala Ser Trp Ile Ser Ser Thr Leu Gly Phe Trp Phe
        4445                4450                4455
Thr Glu Leu Ile Glu Arg Asn Ser Gln Phe Thr Ser Trp Val Phe
        4460                4465                4470
Asn Gly Arg Pro His Cys Phe Trp Met Thr Gly Phe Phe Asn Pro
        4475                4480                4485
Gln Gly Phe Leu Thr Ala Met Arg Gln Glu Ile Thr Arg Ala Asn
        4490                4495                4500
Lys Gly Trp Ala Leu Asp Asn Met Val Leu Cys Asn Glu Val Thr
        4505                4510                4515
Lys Trp Met Lys Asp Asp Ile Ser Ala Pro Pro Thr Glu Gly Val
        4520                4525                4530
Tyr Val Tyr Gly Leu Tyr Leu Glu Gly Ala Gly Trp Asp Lys Arg
        4535                4540                4545
```

| Asn | Met | Lys | Leu | Ile | Glu | Ser | Lys | Pro | Lys | Val | Leu | Phe | Glu | Leu |
|     | 4550 |     |     |     | 4555 |     |     |     | 4560 |     |     |     |     |     |

| Met | Pro | Val | Ile | Arg | Ile | Tyr | Ala | Glu | Asn | Asn | Thr | Leu | Arg | Asp |
|     | 4565 |     |     |     | 4570 |     |     |     | 4575 |     |     |     |     |     |

| Pro | Arg | Phe | Tyr | Ser | Cys | Pro | Ile | Tyr | Lys | Lys | Pro | Val | Arg | Thr |
|     | 4580 |     |     |     | 4585 |     |     |     | 4590 |     |     |     |     |     |

| Asp | Leu | Asn | Tyr | Ile | Ala | Ala | Val | Asp | Leu | Arg | Thr | Ala | Gln | Thr |
|     | 4595 |     |     |     | 4600 |     |     |     | 4605 |     |     |     |     |     |

| Pro | Glu | His | Trp | Val | Leu | Arg | Gly | Val | Ala | Leu | Leu | Cys | Asp | Val |
|     | 4610 |     |     |     | 4615 |     |     |     | 4620 |     |     |     |     |     |

Lys

<210> SEQ ID NO 2
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 2
agacagaucg ccuggagacg ccauccacgc uguuuugacc uccauagaag acaccgggac    60
cgauccagcc uccgcggccg ggaacggugc auuggaacgc ggauccccg ugccaagagu    120 gacucaccgu ccuugacacg                                                140

<210> SEQ ID NO 3
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 3
ggacagaucg ccuggagacg ccauccacgc uguuuugacc uccauagaag acaccgggac    60
cgauccagcc uccgcggccg ggaacggugc auuggaacgc ggauccccg ugccaagagu    120 gacucaccgu ccuugacacg                                                140

<210> SEQ ID NO 4
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 4
cggguggcau cccugugacc cucccccagu gccucuccug gcccuggaag uugccacucc    60
agugcccacc agccuugucc uaauaaaauu aaguugcauc aagcu                    105

<210> SEQ ID NO 5
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 5
ggguggcauc ccugugaccc ucuccccagug ccucuccugg cccuggaagu ugccaccca   60 gugcccacca gccuuguccu aauaaaauua aguugcauca aagcu                    105

<210> SEQ ID NO 6
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 6

| | | | | | |
|---|---|---|---|---|---|
| atgttcagaa | ttggacgccg | ccagctctgg | aagcattccg | tcacccgggt | cctgactcag | 60 |
| aggctgaagg | gggaaaagga | agcgaaacgc | gccctgctgg | acgcccgcca | taactacctc | 120 |
| tttgccatcg | tggcctcctg | cctggacctc | aacaagacag | aagtcgagga | cgccattctc | 180 |
| gaagggaacc | agattgagcg | gatcgaccaa | ctcttcgccg | tcggaggact | tcggcacctc | 240 |
| atgttctact | accaggacgt | ggaggaggca | gaaaccggcc | agctcggcag | cctgggtgga | 300 |
| gtgaacctcg | tgtcgggaa | gattaagaag | ccaaaagtgt | tcgtgaccga | aggaaatgac | 360 |
| gtggcactca | ccggagtgtg | cgtgttcttc | attcggacag | accctcgaa | ggcgattacc | 420 |
| ccagacaata | tccaccaaga | agtgtcgttc | aacatgctgg | acgctgcgga | tggcgggctg | 480 |
| ttgaactccg | tgcggcggtt | gctgtccgac | attttcattc | cggccctgcg | agctacttcg | 540 |
| cacggctggg | gcgaactgga | gggcttgcag | gatgcggcta | acattcggca | ggagttcctt | 600 |
| tcctctctgg | aaggcttcgt | caacgtcctg | tccggcgctc | aggagtcact | gaaggagaag | 660 |
| gtgaaccta | gaaatgcga | catcctggag | ctcaagaccc | tgaaggagcc | caccgattac | 720 |
| cttaccctgg | ccaacaaccc | tgaaacactg | ggaaagattg | aggattgcat | gaaggtctgg | 780 |
| attaagcaga | ctgaacaagt | gctggccgaa | acaaccagc | tgctgaagga | agccgacgat | 840 |
| gtggggcctc | gcgcggagct | tgaacactgg | aagaagagac | tctcgaagtt | caactacctc | 900 |
| ctggagcaat | tgaagtcccc | tgatgtgaag | gccgtgctgg | ccgtcctggc | cgccgccaag | 960 |
| tccaagctgc | tcaagacctg | gagggaaatg | gacataagaa | ttactgacgc | gaccaatgag | 1020 |
| gccaaggaca | acgtgaaata | cttgtacacc | ctggaaaagt | gctgcgaccc | gctctactcc | 1080 |
| tccgacccgc | tcagcatgat | ggacgccatt | ccgaccctta | tcaacgcgat | caagatgatc | 1140 |
| tactccattt | cccactacta | caacacctcc | gagaagatta | cttcgctgtt | cgtcaaggtg | 1200 |
| accaaccaga | tcatctcagc | ctgcaaggcc | tacattacca | caacggaac | cgcctccatc | 1260 |
| tggaaccagc | cgcaggacgt | ggtgaagaa | aaaatccttt | ccgccattaa | gctcaagcag | 1320 |
| gaataccagt | tgtgcttcca | caagaccaag | cagaagctca | gcagaaccc | taacgccaag | 1380 |
| cagttcgact | tctccgaaat | gtacatcttc | ggcaaatttg | agacattcca | ccgccggctc | 1440 |
| gctaagatca | ttgacatttt | caccacgctc | aagacctact | ccgtcctgca | agactcgacc | 1500 |
| attgagggac | ttgaggacat | ggcgaccaag | taccagggca | tcgtcgccac | catcaagaag | 1560 |
| aaggagtaca | acttcctcga | ccaaaggaag | atggacttcg | accaggatta | cgaggaattc | 1620 |
| tgcaaacaga | ctaacgacct | ccacaacgag | ctgcgcaagt | tcatggacgt | caccttcgcg | 1680 |
| aagattcaga | acaccaacca | agcgctgagg | atgcttaaaa | agttcgaacg | gctcaacatc | 1740 |
| cccaacctgg | ggatcgatga | caagtaccaa | ctcatcctgg | aaaactacgg | cgccgatatc | 1800 |
| gacatgatct | ccaagctgta | taccaagcag | aagtacgacc | cccgctggc | acgcaaccaa | 1860 |
| ccccccattg | ccgggaagat | tctgtgggcg | aggcaactgt | tccacagaat | tcagcaaccc | 1920 |
| atgcaactct | tccagcagca | ccccgccgtg | ctctcgaccg | ccgaagccaa | acccatcatt | 1980 |
| cggtcctaca | accgcatggc | caaggtcctt | ttggagttcg | aagtcctgtt | ccaccgcgcg | 2040 |
| tggctccggc | agattgagga | gattcatgtg | gggcttgagg | ccagcctgct | cgtcaaggct | 2100 |

```
cccggcactg gagaactgtt cgtgaatttt gacccgcaaa tcctgatcct gttcagggag    2160
acagagtgta tggcccagat gggccttgaa gtgtctccgc tcgccacctc actgttccag    2220
aagcgcgaca gatacaagag aaacttcagc aacatgaaga tgatgctggc cgagtaccag    2280
agagtcaagt ccaagatccc cgcagccatc gagcagctca ttgtgccgca ccttgcgaag    2340
gtcgacgagg cacttcagcc aggactcgcc gccctgactt ggacttccct caacatcgaa    2400
gcctacctgg agaacacctt cgcgaagatc aaagacttgg aactgctgct ggatagagtc    2460
aacgatctga tcgagttcag aattgacgcc atcctggaag aaatgtctag caccccgctc    2520
tgtcaacttc ctcaggaaga acccctcact tgcgaagagt tcctgcagat gactaaggat    2580
ctgtgcgtga atggggccca gatcctgcac ttcaagtcgt ccctggtgga ggaagccgtg    2640
aacgagctgg tcaacatgct cctggacgtc gaggtgctgt ccgaggagga gtcggagaag    2700
attagcaacg aaaacagcgt gaactacaaa acgaatcct ccgccaagag agaagaggga    2760
aacttcgaca ccctgacctc ctcgataaat gcgcgggcca acgccctgct cctgaccacc    2820
gtcactcgga agaaaaagga aactgagatg ctgggcgaag aggcccggga gctgctctcc    2880
cacttcaacc accaaaacat ggacgccctg ctcaaggtga cccgcaacac cctggaggcc    2940
attcgaaagc ggattcattc ctcccacacg attaacttcc gggacagcaa ctccgcgtcc    3000
aacatgaagc agaactccct cccaatcttc agggcttcgg tgaccctcgc cattcccaac    3060
atcgtgatgg cgcctgccct cgaggacgtg cagcagacgc tgaacaaggc agtcgagtgc    3120
attatctccg tgcccaaggg cgtgcgccag tggtccagcg agttgcttag caagaaaaag    3180
atccaagagc gcaagatggc cgccctgcaa tcaaacgaag attcggactc cgacgtggaa    3240
atgggagaaa acgaactgca ggacaccctc gagatcgcct ccgtgaactt gcccatcccg    3300
gtgcaaacca agaactacta taagaacgtg tccgaaaaca aggaaatcgt caagctcgtg    3360
agcgtcctct cgaccatcat caactccacc aagaaagagg tgatcacctc catggactgc    3420
ttcaagcgct acaaccacat ctggcagaaa gggaagaag aggccattaa gaccttcatc    3480
acccagtcac cactgctgtc agagttcgag tcgcagatcc tgtacttcca gaacctcgag    3540
caggaaatca acgcggaacc agaatacgtc tgcgtcggat cgattgccct gtacacggca    3600
gacctgaagt tcgcactcac tgcagagact aaagcctgga tggtcgtgat cgggcgccat    3660
tgcaacaaga gtatagaag cgagatggaa aacatattca tgctgatcga ggaattcaac    3720
aagaaattga accggcctat caaggacctg gacgacatcc gcatcgccat ggccgccctg    3780
aaggagattc gcgaggaaca aatttcgata gatttccaag tgggacccat tgaggagtcc    3840
tacgccctgc tgaaccggta cggactgctg atcgctagag aggagattga caaggtggac    3900
accctgcact acgcctggga aaagctgctg gccagggccg tgaagtgca gaacaagctg    3960 gtcagcctcc agccttcctt caagaaggaa ctgatttccg cggtcgaagt gttcctgcaa    4020
gactgccacc agttctacct ggactatgac ctcaacggac cgatggccag cggtctgaaa    4080
ccgcaggagg cctccgaccg cctgatcatg ttccaaaacc agttcgacaa catataccgg    4140
aaatacatca cttacactgg aggagaagaa ctcttcggcc tgcccgccac ccaataccct    4200
caactgctgg agatcaagaa gcagctgaat ctgctgcaaa agatctacac cctctacaac    4260
tccgtcattg agactgtgaa ttcatactac gatatcctgt ggtccgaagt gaacatcgaa    4320
aagattaaca acgagctcct ggagtttcag aacagatgcc ggaagctgcc gcgggccctc    4380
aaggattggc aggctttcct tgacctgaag aagataatcg acgacttctc ggagtgttgc    4440
cccctcctcg agtacatggc ctcgaaggcc atgatggaac gccactggga aaggatcact    4500
```

```
actctgactg ggcacagcct ggatgtgggt aacgagtcct tcaagctgcg gaacatcatg    4560
gaggccccgc ttctgaaata caaggaggaa atcgaggaca tctgcatctc ggccgtcaag    4620
gaacgcgaca ttgagcaaaa gctgaagcaa gtgatcaacg agtgggacaa caagactttc    4680
accttcggat ccttcaaaac ccggggagag ctcctgctga gaggagactc cacttccgaa    4740
atcattgcga acatggagga ctccctcatg ctcctcgggt cgctcctgag caacagatac    4800
aacatgccgt tcaaggccca gatccagaag tgggtgcagt acctgtcgaa ctccactgac    4860
atcattgaga gctggatgac tgtgcagaac ctctggatct acttagaggc cgtgttcgtg    4920
ggaggcgaca ttgctaagca gctcccaaag gaagcaaagc gcttcagcaa catcgacaag    4980
tcgtgggtga agattatgac ccgcgcgcat gaggtgccca gcgtggtgca gtgttgcgtg    5040
ggcgatgaaa cgctgggcca gcttctgccg catctgctgg accagctgga gatttgccag    5100
aagtccctca ccggatacct ggagaagaag cggctgtgct cccccggtt cttcttcgtg    5160 tccgaccctg ccctgctgga aattcttgga caggcctctg acagccatac tatccaggcc    5220
cacctcctga acgtgttcga caacatcaag tccgtgaagt tccacgaaaa gatatatgac    5280
cgcatcctgt cgattagcag ccaggaaggg gaaaccatcg agctcgacaa gcctgtgatg    5340
gccgaaggaa acgtcgaggt gtggctgaac tcgctcctgg aggagagcca gagcagcctg    5400
cacctcgtta taagacaggc cgccgccaac atccaggaga ctggattcca gctcactgaa    5460
ttcttgtcgt ccttccctgc ccaagtgggc ttgctgggaa ttcaaatgat ctggacccgc    5520
gactccgaag aggccctcag gaacgccaag ttcgacaaaa agatcatgca gaaaaccaat    5580
caggcgttcc tggagcttct gaacaccctc attgatgtga ccactaggga cctgtcaagc    5640
accgaacggg tgaagtacga aaccctcatc accatccacg tccatcagcg ggatattttc    5700
gatgacctgt gtcacatgca tatcaagtcc cctatggact tcgaatggct gaagcaatgc    5760
cgcttctact tcaatgagga ctcggacaag atgatgatcc atatcacaga tgtcgccttc    5820
atctaccaga acgaattcct gggatgcacc gaccgcttgg tgatcacccc cctcactgac    5880
cggtgctaca ttaccttggc ccaggccctg ggaatgtcca tgggaggggc gcctgccggg    5940
ccagccggca ccggaaaaac cgaaacaaca aaggacatgg gccgctgcct ggggaagtac    6000
gtggtggtgt tcaattgctc cgatcaaatg gacttcagag gtctggggcg gatcttcaag    6060
ggtctggctc agtccggctc ctgggatgc ttcgacgaat tcaaccggat cgacttgccg    6120
gtgctgagcg tcgccgccca gcagatctcc atcatcctga cctgtaagaa ggaacacaag    6180
aagtcgttca ttttcaccga cggagacaac gtgacgatga cccggagtt cgggctattc    6240 ttgaccatga acccgggtta cgccggccga caagagctgc ccgaaaactt gaagatcaac    6300
ttccgcagcg tggctatgat ggtcccggat cggcagatta ttattagagt gaagctggct    6360
tcgtgcggat tcatcgataa cgtcgtgctg gcccggaagt tcttcacgct gtacaagctc    6420
tgcgaggaac agctgagcaa gcaagtccac tacgacttcg ggctgcgcaa cattctctcc    6480
gtgctgcgca ctctgggagc ggccaagcgg gcgaacccta tggataccga gagcaccatt    6540
gtcatgcgcg tgctccggga catgaacctc tcaaagttga tcgacgagga cgagcctctc    6600
ttcctctccc tgatcgagga cctctttccc aacatcctgc tcgataaggc cgggtacccc    6660
gagctggagg ccgccattag ccgccaggtg aagaggctg gcctcatcaa ccaccctcct    6720
tggaagttga aggtcataca gctgttcgaa actcagcgcg tgcgacatgg catgatgacc    6780 ctgggaccctt cgggagccgg caaaactact tgcatccaca ccctgatgcg ggctatgacc    6840
```

```
gactgcggga agcctcaccg ggagatgagg atgaacccga aggccatcac cgccccgcaa    6900
atgttcggcc ggctggacgt ggccactaat gattggaccg acgggatctt ctcaaccctc    6960
tggcgcaaaa ccctgcgcgc aaagaaggga gagcacatct ggatcatcct ggatggcccg    7020
gtcgatgcca tctggattga gaacctgaac agcgtgctgg acgacaacaa gactctcact    7080
ctcgcgaacg gcgacagaat tcccatggcc ccgaactgca agatcatttt cgagccacac    7140
aacattgaca acgcctcccc ggctaccgtg tcgagaaacg gaatggtgtt tatgtccagc    7200
tcgatcctcg attggtcccc catcctggaa ggcttcctga agaagaggtc gccgcaagag    7260
gccgaaattt tgagacagct gtacaccgaa tccttcccgg acctgtaccg cttctgcatc    7320
cagaacctcg agtacaagat ggaagtgctg gaggcattcg tgatcactca gagcattaac    7380
atgctgcagg gactcatccc tcttaaggaa caggggggcg aagtctctca ggctcacctc    7440
ggccggctgt tcgtgttcgc cctcctctgg agcgcgggtg cggccctgga gctggatggc    7500
cgccgcagac tcgagctgtg gctgagatcc agacccaccg gaactctcga gttgcccccg    7560
cccgccggcc ccggagatac ggccttcgac tactacgtgg cccccgacgg gacgtggact    7620
cattggaaca cacgcacaca ggaatacctg taccctagcg acaccactcc ggaatacgga    7680
tcgatcctgg tgcccaacgt ggataacgtg aggaccgatt tccttataca aaccatcgcc    7740
aagcaaggaa aggcggtcct cctcatcggg gagcagggga ccgccaagac cgtgatcatt    7800
aagggattca tgtccaagta cgaccccgaa tgccacatga tcaagtctct caactttagc    7860
tccgccacca ccccactgat gttccaacgg actatcgaaa gctacgtcga caagcgcatg    7920
ggaactactt acggccctcc ggcaggaaag aaaatgaccg tgttcatcga cgacgtcaac    7980
atgcccatca ttaacgaatg gggggaccag gtgacgaacg agatcgtgcg ccagctcatg    8040
gaacaaaacg gtttctacaa ccttgagaag cccggagagt ttacttcaat tgtggacatc    8100
cagttcctcg cggcaatgat tcatcccggc ggaggaagaa acgacatccc gcagcgcctc    8160
aaacgccagt tctcgatctt caactgcacg ctgccgtccg aggctagcgt cgacaagata    8220
tttggcgtga ttggtgtggg acattactgc acccagaggg gattctcgga ggaagtgcgg    8280
gacagcgtga ccaagctggt gccgctgact aggcggctct ggcagatgac caagatcaag    8340
atgctcccta cacccgccaa gttccactac gtgttcaatc tgcgcgacct gtcacgcgtg    8400
tggcagggaa tgctgaacac tacctccgaa gtcatcaagg aaccgaacga tctccttaaa    8460
ctttggaagc acgaatgcaa gcgcgtaatc gcagaccggt tcaccgtgag ctccgatgtg    8520
acctggttcg acaaggccct ggtgtccctc gtggaggaag agttcggaga ggaaaagaaa    8580
cttctcgtag actgcggtat agatacgtac ttcgtggact tcctgcgcga cgccccgaa    8640 gccgccggcg aaacctccga agaagctgac gccgaaacac caaagatata cgagcctatc    8700
gaatccttca gccatctgaa ggagagactc aacatgttcc tgcaattgta taatgagtcc    8760
atccgcggcg ccggcatgga catggtgttc tttgcggatg ccatggtgca cctggtgaag    8820
atctcgcggg tgattcggac tccccagggc aacgcgctgc tcgtgggcgt gggggggctcc    8880 gggaagcaga gccttacccg gctggcctcc ttcattgccg gctatgtgag cttccagatc    8940
actctgactc gctcgtacaa taccagcaac ctcatggagg atctcaaggt cctgtaccgg    9000
accgccggac aacagggcaa gggtatcacc ttcatctttta ccgacaacga gatcaaggat    9060
gagtccttcc tggagtacat gaacaacgtg ctgtcctccg gtgaagtctc caacctcttt    9120 gccccgggacg agattgatga gatcaactcg gacttggcgt cagtgatgaa gaaggaattc    9180
ccgaggtgtc tgcctaccaa cgagaacctc cacgactact tcatgagccg ggtgcggcag    9240
```

| | |
|---|---|
| aatctgcaca tcgtgctttg cttcagcccg gtgggagaaa agtttcggaa ccgcgccctc | 9300 |
| aagttcccgg cccttatctc gggatgcacc attgactggt tttcacggtg gccgaaggat | 9360 |
| gctctggtcg cggtgtccga acacttcctt acttcgtacg acattgactg ctccctggaa | 9420 |
| atcaagaaag aagtggtcca gtgtatgggc tccttccagg acggtgtcgc cgaaaagtgc | 9480 |
| gtggactact tccagcgctt ccgcagatcc acgcacgtga cccctaagtc ctacctgtcg | 9540 |
| ttcatccaag gatacaagtt catctacggg gaaaagcacg tcgaagtgcg gaccctggcc | 9600 |
| aaccgaatga acacaggact ggaaaagctg aaggaggcgt ccgagtccgt ggctgccctg | 9660 |
| agcaaggagc tggaagctaa agagaaggag ctccaggtcg ccaacgacaa ggccgacatg | 9720 |
| gtcctgaagg aggtgaccat gaaggctcaa gccgccgaga agtcaaggc ggaggtgcaa | 9780 |
| aaggtcaagg atagagcgca agccatcgtg gactccatct ccaaagacaa ggctattgcg | 9840 |
| gaggagaagc tcgaggccgc caagcctgcc ttggaagagg ccgaagccgc tctgcagacc | 9900 |
| attcggccga gcgatatagc caccgtgcgg acgctgggac ggcctcctca cctgattatg | 9960 |
| cggatcatgg actgtgtgct cctgctgttt caacggaagg tgtccgccgt gaagatcgat | 10020 |
| ctcgagaaat cctgcactat gccgagctgg caggagtccc tgaagctgat gaccgccggc | 10080 |
| aacttcctcc agaacctcca gcagttccca aaagatacca ttaacgagga ggtgatcgaa | 10140 |
| ttcctgagcc cgtacttcga aatgcccgat tacaacatcg aaaccgccaa gagggtgtgc | 10200 |
| ggcaacgtgg ctgggctctg ctcgtggact aaggccatgg cctccttctt ctcaatcaac | 10260 |
| aaggaagtgc tgccctgaa ggccaacctc gtggtgcagg aaaatcgcca ccttctcgcc | 10320 |
| atgcaggatc tgcagaaggc acaggctgaa ctggacgaca acaggcaga gctggatgtg | 10380 |
| gtgcaggccg agtacgaaca ggccatgacg gagaagcaaa ccctgttgga ggatgcggag | 10440 |
| agatgcagac ataagatgca gactgcctcc accctgattt caggcctggc cggagaaaag | 10500 |
| gaacgctgga ctgaacaatc ccaggaattc gcggcccaga caagagact cgtgggagat | 10560 |
| gtgctgcttg cgactgcctt tctgagctac tctggaccgt tcaaccagga attccgggac | 10620 |
| ctcctgctca cgactggcg caaggagatg aaggcccgga agatccccctt cgggaagaac | 10680 |
| ctcaacctga gcgagatgct gatcgacgcc cccaccatct ccgagtggaa cctccaggga | 10740 |
| ctgcctaacg acgacctctc cattcagaac ggcatcatcg tgactaaggc gtcccgctac | 10800 |
| ccgctgctca ttgaccctca gacccaggga agatttgga tcaaaaataa ggagtcccgc | 10860 |
| aacgagctgc agatcacctc cctgaaccac aagtactttc gcaaccatct ggaagattcc | 10920 |
| ctcagcctgg gacggccgct tctgatagag gatgtgggag aagaactgga cccggctctc | 10980 |
| gacaacgtcc tggagaggaa cttcatcaag accgggtcca ccttcaaggt gaaggtgggc | 11040 |
| gacaaggagg tggacgtcct ggatggattc cgcctgtaca ttaccactaa gctcccaaac | 11100 |
| cccgcttaca ctcctgagat cagcgcgcgg accagcatca ttgatttcac cgtgactatg | 11160 |
| aagggccttg gaccagct gctgggtcgc gtgatcttga ccgagaagca ggaacttgaa | 11220 |
| aaggaacgca ctcacctcat ggaggacgtg accgccaata agcgccggat gaaggaactg | 11280 |
| gaagataact tgctgtacag gcttacttcc actcagggtt ccctggtgga ggacgagtcg | 11340 |
| ctgattgtgg tgctgagcaa caccaagcgg actgccgaag aagtgaccca aaaactggag | 11400 |
| atctcggcgg aaaccgaggt gcagatcaat agcgcgcggg aggagtaccg gccagtcgca | 11460 |
| accagagggt ccatcctgta cttcctgatt accgaaatga ggctggtcaa cgaaatgtac | 11520 |
| cagacgtccc tgaggcagtt cctggggttg ttcgacctga gccttgcccg ctcggtgaag | 11580 |

```
tcaccaatca cttccaagag aattgccaac attattgagc acatgaccta cgaggtctat   11640
aagtacgccg cgcggggact gtacgaggaa cacaaattcc tgttcactct gctgctcacc   11700
ctgaaaatcg atattcagcg gaaccgcgtc aagcacgagg agttcctcac cctgattaag   11760
ggaggagcca gcctggacct gaaggcgtgc cctcctaagc cctccaagtg gattcttgac   11820
atcacctggc tgaacctggt ggaactcagc aagttgcggc aattctccga cgtgcttgac   11880
caaatttccc gcaacgagaa gatgtggaag atttggttcg acaaagagaa cccggaggaa   11940
gaacccctgc ctaacgccta cgacaagtcg ctcgattgtt tccggcgcct cctgctgatt   12000
aggagctggt gccctgacag gaccattgcc caagctcgga agtacattgt ggactccatg   12060
ggcgagaagt atgccgaagg ggtcattctc gacctggaga aaacttggga agagtccgac   12120
ccgagaactc cactgatctg cctcctgtcc atgggctccg accccaccga tagcatcatc   12180
gcgctgggaa agcggctgaa gatcgaaact agatacgtga gcatgggaca agggcaggag   12240
gtgcacgcga ggaagctcct ccaacaaacc atggccaacg gaggctgggc cttgctgcag   12300
aactgtcacc tcggactcga ctttatggac gagctgatgg acattatcat cgagactgaa   12360
cttgtgcatg acgccttcag actgtggatg accaccgaag cccacaagca gttcccgatt   12420
acactgctcc aaatgtccat caaattcgca acgacccgc ctcagggact ccgggccgga   12480
ctgaagcgga cctactcggg agtgtcccaa gacctcctgg atgtgagctc agggagccaa   12540
tggaagccaa tgctctacgc cgtggccttc ctgcattcga ccgtgcagga acggcgcaag   12600
ttcggcgccc tgggctggaa catcccgtac gaattcaacc aggccgactt caatgccacc   12660
gtgcagttca tccagaacca ccttgacgac atggacgtga agaagggagt gtcgtggact   12720
accatccgct acatgattgg cgaaattcag tatggcggcc gcgtgaccga cgactacgat   12780
aagagactcc tcaacaccct tcgccaaggtc tggttctcgg aaaacatgtt cggtccagac   12840
ttctccttct accaaggata caacatcccc aagtgctcca ccgtggataa ttaccttcag   12900
tacatccagt cgctgccggc ctacgattca ccggaagtgt tcggactgca tcctaacgcg   12960
gacattactt accagagcaa gctcgccaag gatgtcctgg acactatcct gggaattcag   13020
cctaaggata cttcaggagg gggagatgag actagagagg cggtggtcgc tcgcctggcc   13080
gacgacatgt tggaaaagct cccgcctgat tacgtgccgt tcgaggtgaa agagcggctg   13140
cagaagatgg gacctttcca accgatgaac attttttctga cacaggagat cgaccggatg   13200
cagagagtgc tgtccctcgt gcggtccacc ctgaccgaac tgaagttggc tatcgacggg   13260
accattatta tgtcggagaa cctccgggac gccctggact gcatgttcga tgcgcggatt   13320
ccggcctggt ggaagaaggc atcctggatt tccagcaccc tgggcttctg gtttaccgaa   13380
ctgattgaaa gaaattcgca attcacttcc tgggtgttca acgggcgccc gcactgtttt   13440
tggatgaccg gcttcttcaa ccccccaggga tttctcactg cgatgaggca ggaaattacc   13500
cgcgcgaaca agggatgggc cctggataac atggtgctct gcaacgaggt gaccaaatgg   13560
atgaaggatg acatttccgc cccccgacc gaaggagtct acgtctacgg cctgtacctc   13620
gagggtgccg ggtgggacaa gcgaaatatg aagttgatcg aatcaaagcc aaaggtcttg   13680
ttcgaactga tgccggtgat cagaatatac gccgagaaca cacccttgcg cgaccccagg   13740
ttctactcct gccctatcta caagaagcca gtgcgcaccg acctcaacta catcgccgcc   13800
gtcgacctcc ggactgccca aaccccggaa cactgggtgc tgcgcggtgt ggccctgctc   13860
tgcgatgtca agtag                                                    13875
```

```
<210> SEQ ID NO 7
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 7
```

| | | | | | |
|---|---|---|---|---|---|
| atgttccgaa | tcggccggcg | ccagctgtgg | aagcactcag | tgacccgcgt | cctgacccag   60 |
| agactgaagg | gagaaaagga | ggccaaacgg | gccctcctgg | acgcgcggca | caactacctg  120 |
| ttcgctatcg | tggcctcgtg | tctcgacctc | aacaagaccg | aggtggaaga | tgcaatcctg  180 |
| gagggcaatc | aaattgagcg | gattgatcag | ctgttcgcag | tgggcggctt | gcggcacctg  240 |
| atgttttact | accaagacgt | ggaggaggcc | gaaactgggc | agctgggaag | cctgggcgga  300 |
| gtgaacctgg | tgtccggcaa | aatcaaaaag | cccaaggtct | tgtcactga | agggaacgac  360 |
| gtggccctca | ccggagtgtg | cgtgttcttc | atccggacgg | accctagcaa | agccatcacc  420 |
| ccggacaaca | tccaccagga | agtgtccttt | aacatgctgg | acgcggccga | cggggggcctc  480 |
| cttaactcgg | tccggcgcct | cctttccgac | atcttcatcc | cggctctgcg | ggctacgtcc  540 |
| cacggttggg | gagaactgga | aggactgcag | gacgccgcta | acatccgcca | agagttcctc  600 |
| tcatccctcg | agggttttgt | caatgtgctg | tcgggcgccc | aggaatcgct | gaaggagaag  660 |
| gtgaacctcc | gcaagtgcga | tattctggag | ctcaagaccc | tcaaggaacc | gactgactac  720 |
| ctcactctgg | ccaacaaccc | cgaaactctg | ggaaaattg | aggactgcat | gaaggtgtgg  780 |
| atcaagcaga | ccgaacaggt | cctggccgaa | acaaccagc | tgctgaaaga | ggccgatgac  840 |
| gtgggacccc | gggccgagct | ggagcactgg | aagaagcgcc | tctcaaagtt | caactaccct  900 |
| ctcgagcaac | tgaagtcccc | tgacgtgaag | gctgtgctgg | cggtgcttgc | cgcggctaaa  960 |
| tcaaagctcc | tgaaaacctg | gagagaaatg | gatattgaa | tcaccgacgc | gaccaatgaa 1020 |
| gcgaaggaca | acgtgaagta | cctgtacacg | ctggaaaaat | gctgcgaccc | cctctattcc 1080 |
| tccgacccgc | tgtccatgat | ggatgcaatt | cccaccctga | tcaacgccat | caagatgatc 1140 |
| tactcgattt | cacactacta | caatacttcc | gagaagatca | ccagcctgtt | cgtcaaggtc 1200 |
| actaaccaaa | tcatcagcgc | atgcaaggcc | tacatcacca | caacggaac | cgcgtccatt 1260 |
| tggaaccagc | cacaggatgt | ggtcgaggaa | aagatccttt | ccgcaattaa | gctcaagcag 1320 |
| gaataccagc | tgtgcttcca | caagactaag | cagaaactga | acaaaaaccc | gaacgcaaag 1380 |
| cagttcgact | ttagcgagat | gtacattttc | ggaaagttcg | aaaccttcca | tagacggctg 1440 |
| gctaagatca | tcgatatctt | caccaccctc | aagacctact | cggtgttgca | ggacagcacc 1500 |
| atcgaaggtc | tggaggacat | ggcgactaag | taccagggaa | tcgtcgccac | tatcaagaag 1560 |
| aaggagtaca | acttcctgga | tcagcggaag | atggacttcg | accaggatta | cgaagagttc 1620 |
| tgcaagcaga | ccaatgacct | ccacaacgag | ctgcggaagt | tcatggatgt | gactttcgcc 1680 |
| aaaattcaga | caccaacca | ggcgcttcgg | atgctgaaga | agttcgaaag | gcttaacatc 1740 |
| cccaacctgg | gcatcgatga | taaataccag | ttgatccttg | agaactacgg | agccgacatc 1800 |
| gacatgatta | gcaagctgta | caccaaacaa | aaatacgacc | tcctctggc | cagaaaccaa 1860 |
| cctccgattg | ctgaaaagat | tctctgggcc | cggcagctgt | tccaccgcat | ccagcagcct 1920 |
| atgcagctgt | tcaacagca | cccggccgtc | ctgtccaccg | ctgaagccaa | gccgatcatc 1980 |
| aggtcctata | acaggatggc | caaggtgctg | ctggagttcg | aggtgctgtt | ccaccgagcc 2040 |
| tggctgcggc | aaattgaaga | aatccacgtg | ggactggaag | cctccctcct | ggtgaaggcc 2100 |

```
ccagggaccg gcgaactgtt cgtgaatttc gaccctcaga tcctgattct gttccgggaa    2160
accgaatgca tggcccagat gggcctggag gtgtccccc  tggcaacctc actgttccaa    2220
aagcgcgaca ggtacaagag gaacttctcc aatatgaaga tgatgctcgc agagtaccag    2280
agagtcaagt ccaagatccc cgcagccatt gagcagctga ttgtcccgca ccttgctaag    2340
gtggacgaag cgctccagcc cggcctcgcc gccctgacct ggacttcctt gaatatcgag    2400
gcgtatctcg aaaacacttt cgctaaaatc aaggacctgg aattgctgct ggacagggtc    2460
aacgatctca tcgagttcag aattgacgcg atcctggagg aaatgtcctc gaccccctg    2520
tgccagcttc ctcaggagga gccactgacc tgtgaggagt tcctgcagat gaccaaggac    2580
ctgtgtgtga acggagccca gatcctccac tttaagagca gcttggtgga agaagccgtg    2640
aacgaattgg tgaacatgct cctggacgtg gaggtgctgt ccgaagagga gtccgagaag    2700
atttcgaacg agaactcagt gaactacaag aacgaatcct cagcgaagag agaggaaggc    2760
aactttgaca ctctgacctc ctcgattaat gcacgggcca acgctctgct gttgaccacc    2820
gtgactcgga aaagaaggaa aaccgagatg ctgggtgaag aggcccgcga acttctctcg    2880
cacttcaatc accaaaacat ggacgccctg ttgaaggtca ccaggaacac cctggaagcc    2940
atcaggaaga gaattcactc ctcgcacact atcaacttca gagattcaaa ttccgcatcc    3000
aacatgaagc agaacagcct gccgatcttc cgcgcgagcg tgacccttgc catcccaaac    3060
atcgtgatgg ccccagctct cgaggacgtg cagcagactc tgaacaaagc tgtggaatgc    3120
attatttccg tgcccaaggg agtgagacaa tggtcatccg aactgctgag caagaagaag    3180
atccaagagc gcaagatggc cgcactccag agcaacgagg attccgatag cgacgtggaa    3240
atgggcgaga acgaactgca ggatacctg  gagatcgcca gcgtcaacct tcccatcccg    3300
gtgcagacca gaactatta  caagaacgtg tcggaaaaca aggaaatcgt gaaactcgtg    3360
tccgtgctct ccactattat caacagcact aagaaggaag tcatcacttc aatggattgt    3420
ttcaagaggt acaaccacat ctggcaaaag ggcaaagaag aagccatcaa gacttttatt    3480
acccaaagcc ccctgctgtc agagttcgag agccagatcc tgtacttcca gaacctggaa    3540
caagaaatca cgccgaacc  ggagtacgtg tgcgtgggta gcatcgccct ttacactgct    3600
gacctgaagt tcgcactgac cgcagagact aaagcatgga tggtggtgat cggacggcac    3660
tgcaacaaga gtaccgctc  cgaaatggag aacatcttca tgcttatcga ggagttcaac    3720
aagaagctca accggccgat caaggacctg gatgacattc ggattgcgat ggccgccctg    3780
aaagagatta gagaagaaca atctccatc  gatttccaag tcggacccat tgaagaatcc    3840
tacgccctgc tgaaccgcta cggattgctg atcgcccgcg aggaaatcga caaggtggac    3900
accctgcatt acgcctggga aaagctgctg ccagagcag  gagaagtgca aaacaagctc    3960
gtgtccctgc agccgtcgtt taagaaagag ctcatttcgg ccgtggaagt gttcctgcag    4020
gactgtcacc agttctatct ggactacgat ctcaatggac ctatggcttc cgggttgaag    4080
ccgcaggaag cctctgaccg cctcattatg ttccagaatc agttcgacaa tatctaccgc    4140
aagtacatta catacaccgg cggagaagaa ctgttcgggc tcccagcgac ccagtacccc    4200
cagctcctcg agatcaaaaa gcagctgaac cttctgcaga aaatctacac tctatacaac    4260
tccgtgatcg aaactgtcaa ttcctactac gatatcctgt ggtcggaagt caacattgag    4320
aagatcaaca tgaactgct  cgaattccag aaccgctgca ggaagctgcc gcgggccctc    4380
aaggattggc aggccttcct ggacctgaag aagatcatcg acgacttctc cgaatgttgc    4440
cccctcctgg aatacatggc atccaaggcc atgatggagc ggcactggga aaggattacc    4500
```

```
acactcaccg gccactcact ggacgtcggg aacgagtcct tcaagctccg gaacattatg    4560
gaggccccc  tgctgaagta caaggaggag attgaggata tctgcatttc ggccgtgaag   4620
gaaagagaca tagagcagaa gctgaagcaa gtgatcaacg aatgggacaa caagacgttc   4680
actttcggat ccttcaagac gagggtgaa  ctgctgctcc ggggagacag cacctccgag   4740
atcatcgcaa acatggagga ctcgctgatg ctgctggggt ccctgctgtc caaccggtac   4800
aatatgcctt tcaaggccca gattcagaag tgggtccagt acttgagcaa ctcgaccgac   4860
atcatcgagt cctggatgac tgtccaaaac ctgtggatct acctcgaagc ggtgttcgtg   4920
ggaggtgaca ttgccaaaca gctccccaag gaagcgaagc gcttttcgaa cattgacaag   4980
tcctgggtga agatcatgac tcgggctcac gaagtgccgt ccgtcgtcca gtgttgcgtg   5040
ggcgacgaaa ccctgggaca gttgctcccc catctgctgg atcagctcga aatttgccag   5100
aagtcgctga ctggatacct cgagaagaag agattgtgct tcccgagatt cttcttcgtg   5160
tcggacccgg ccctgctgga gatcctgggc caggcctccg atagccacac tattcaagcg   5220
cacctcttga acgtgttcga caatatcaag agcgtgaagt tccacgaaaa gatctatgac   5280
cggatcctgt caattagcag ccaagaagga gaaaccattg aactggacaa gcccgtgatg   5340
gctgagggca acgtggaagt gtggctgaac agcctcttgg aagagtcgca gtcaagcctc   5400
catctggtga tcagacaggc agccgccaac atccaggaaa ccggtttcca actgactgag   5460
ttcctgtcat ccttcccggc tcaagtcggg ctgctcggaa tccagatgat ttggacccgg   5520
gactccgagg aagccctcag gaatgccaag ttcgataaga agatcatgca aaagaccaac   5580
caggcatttt tggagctcct gaacaccctg atcgacgtca caacccggga cctgtccagc   5640
accgagcggg tcaagtacga aaccttgatc accattcacg tgcaccagag agacatcttc   5700
gatgacctgt gtcacatgca catcaagtcc cccatggact tcgaatggct gaagcagtgc   5760
cggttctact ttaacgagga cagcgataag atgatgatcc acatcaccga cgtggccttc   5820
atctaccaaa acgagtttct tggatgcacc gaccgcctgg tcatcacccc cctgacggac   5880
cggtgttaca tcacgctcgc ccaagcactg gcatgagca  tgggcggcgc ccagctgga   5940
cccgcgggaa ctgaaagac  tgaaaccacc aaggacatgg gccggtgcct gggaaagtac   6000
gtcgtggtgt ttaactgctc cgatcagatg gacttcagag gcctcggccg catctttaag   6060
gggctggccc agtccggctc ctgggctgc  ttcgacgagt tcaacaggat cgatctgccg   6120
gtcctgagcg tggctgcgca gcagatctcc attatcctga cttgcaagaa ggaacacaag   6180
aagtcctta  tcttcactga tggcgataac gtcactatga acccgagtt  cgggctgttc   6240
ctgaccatga accccggata cgccggtcgg caggagctgc ctgagaacct caagatcaac   6300
ttccggtccg tggccatgat ggtgcccgac cgccagatta tcatacgggt gaagctcgcc   6360
tcatgcggct ttatcgacaa cgtggtgctg gcccggaagt tctttaccct gtacaagctg   6420
tgcgaggaac agctgtcgaa gcaagtccac tacgacttcg gcctgcgcaa catcttgtcc   6480
gtcctgcgca ccctgggcgc ggccaagcgg gccaaccca  tggatactga gagcaccatt   6540
gtcatgcgcg tgctccggga tatgaacttg agcaagctga ttgatgagga cgagccgctt   6600
tttctgtccc tgattgaaga cttgtttcca aacatcctgc tggacaaagc cggataccca   6660
gagctggagg cagcgatctc ccgccaagtg gaagaagccg gactgatcaa ccacccgcct   6720
tggaaattga agtgatcca  actgttcgaa actcagcggg tccggcacgg catgatgacc   6780
ttgggcccct cggggcggg  aaagacgact tgcatccata ctttgatgcg ggctatgacg   6840
```

```
gattgcggga agccgcatag ggaaatgcgg atgaacccca aggccatcac cgctccacaa    6900
atgttcggta ggcttgacgt ggccaccaac gattggaccg atggcatctt ctcaactctg    6960
tggagaaaga ccctgcgggc taagaagggg gagcatattt ggattatcct cgacggccca    7020
gtggacgcca tctggatcga aaaccttaac tccgtgctcg acgacaacaa gaccctgacc    7080
ctggccaacg gcgaccgcat cccgatggct ccgaactgca agatcatctt cgaaccgcac    7140
aacatcgaca acgcctcccc ggccaccgtg tccagaaacg gaatggtgtt catgtcctcc    7200
tctatcttgg actggtcgcc gatcctggag ggattcctga agaagagaag cccgcaagaa    7260
gccgagatcc tgcgccaact gtatactgaa tcgttccccg atctgtaccg gttttgcatc    7320
caaaacctgg agtacaagat ggaggtgctc gaggcgttcg tgatcactca gagcattaac    7380 atgttcaag gcctgatccc gctcaaggag caggggggcg aagtgtccca ggcccacctg    7440
gggcggctgt tcgtgttcgc cctcctgtgg tcagccggag cggcgctgga gcttgacgga    7500
cgccgcagac tggaactgtg gctgcggtcc cgaccgactg ggactctgga gttgcctccg    7560
ccggccggcc ctggcgatac agcgttcgac tattacgtgg cccctgatgg aacttggacc    7620
cattggaaca ctaggaccca ggaatacctc tacccgagcg acaccacccc agaatacggg    7680
tcaatcctgg tcccgaacgt ggataatgtc cggactgatt tcttgatcca gaccatcgcg    7740
aagcagggaa aagccgtgct gctgattgga gaacagggta ccgctaagac tgtgattatc    7800
aagggattca tgtccaagta cgacccggaa tgtcacatga ttaagtcctt gaacttctca    7860
tcggccacca ccccctgat gttccagcgg accatcgagt cctacgtgga caagcggatg    7920
ggaactacct acgaccgcc ggcagggaag aagatgaccg tgttcattga cgacgtcaac    7980
atgccaatca tcaatgaatg gggcgatcaa gtcaccaacg agatcgtccg ccagctgatg    8040
gaacagaacg gcttctacaa cctcgaaaaa ccggggagaat tcactagcat cgtggacatc    8100
caatttctcg cagccatgat ccaccctggt ggcgggcgga acgatattcc ccagagactg    8160
aagcgccagt ttagcatctt caactgcact ttgcctagcg aagccagcgt cgacaagatc    8220
ttcggcgtga taggagtggg acactactgc actcagcggg gattctcaga agaagtccgg    8280
gactccgtga ctaagctcgt gcctctgaca aggcggctgt ggcagatgac taagatcaag    8340
atgctgccga cccccgcaaa gttccactac gtgtttaacc ttcgggacct gtccagagtc    8400
tggcagggga tgctcaacac cacctcggag gtcattaagg aacccaacga tcttctgaag    8460
ttgtggaagc acgagtgcaa gagggtcatc gccgacagat tcactgtgtc ctcagacgtc    8520
acttggttcg acaaggccct cgtgtcccct gtggaggaag aattcggaga agagaagaag    8580
ttgctcgtgg actgcggcat tgatacttac ttcgtggact tcctccggga tgcgccggag    8640
gccgccggag aaacctctga ggaggccgac gctgaaaccc ccaaaatcta cgagcctatc    8700
gagtcgttct cccatctgaa ggagcggctg aacatgttct tgcagctgta caacgagtcc    8760 atccggggg ccgaatggga catggtgttt tttgccgatg cgatggtgca cctggtgaag    8820
atttccagag tgatccgcac ccccagggaa acgcactcc ttgtgggagt gggaggatcc    8880
ggcaaacaga gcctgactcg cttggcgtcg ttcatcgcgg atacgtgtc gttccagatc    8940 accctgactc gcagctacaa cacctcgaac ctcatggagg acctcaaggt cctgtacagg    9000
accgcaggcc aacaaggcaa aggaattacc ttcattttca ccgacaacga aatcaaggac    9060
gaatcattcc tggagtacat gaacaacgtg ctgagctcag gagaggtgtc aaacctgttc    9120
gcccgcgacg agatcgacga gatcaactcg gatctggctt ccgtgatgaa aaaggaattc    9180
cctcggtgtc tgcctaccaa tgagaacctc catgactact tcatgagccg cgtgcggcag    9240
```

```
aacttgcata tcgtcctgtg cttttccccc gtcggagaaa agttcagaaa cagggccctg    9300
aagttcccgg cgctcatctc cggctgcacc attgattggt ttagccgctg gccaaaggac    9360
gcactcgtgg ccgtgtcgga acatttcctc acatcctacg acatcgattg ctcgcttgag    9420
atcaaaaagg aggtggtgca gtgcatgggc tcgttccaag acggcgtggc tgaaaagtgt    9480
gtggactact tccagaggtt ccgacggtcc actcacgtga ccccaaagtc ctacctgagc    9540
ttcatccagg gatacaagtt catctacgga gagaagcatg tcgaagtgcg caccttggcg    9600
aaccggatga caccgggct cgaaaagctg aaggaggcct ctgaatccgt cgccgccctg    9660
tccaaagagc tggaggccaa ggaaaaggaa ctgcaagtcg ccaacgataa ggccgacatg    9720
gtcctgaagg aagtcaccat gaaggctcag gccgccgaga aggtcaaagc agaggtgcag    9780
aaggtgaagg atcgcgcgca ggccattgtg gacagcattt caaaggacaa ggccatcgcc    9840
gaggaaaaac tggaagccgc gaagccggcc ttggaagagg cagaggccgc gctgcagacc    9900
atacggccct ctgacattgc caccgtgcgg accctcgggc ggccccccgca tctgatcatg    9960 agaattatgg actgcgtgct gctgctgttc caacggaaag tgtccgccgt gaagattgac   10020
ctggagaagt cctgcactat gccgagctgg caggagtcgc tgaagctcat gactgcggga   10080
aacttcctgc agaacctcca acaatttccc aaagacacca ttaacgagga agtgattgag   10140
ttcctgtccc catacttcga gatgcccgac tacaacatcg agactgccaa gagggtgtgc   10200
ggaaacgtgg ccggcctctg ctcgtggacc aaggccatgg cgtcgttttt cagcatcaac   10260
aaggaggtgt tgcctcttaa ggccaacctg gtggtgcaag agaaccggca tctcttggcc   10320
atgcaggacc tccagaaggc ccaggcagag ttggacgaca gcaggccga gctggacgtc   10380 gtccaagccg agtacgaaca ggccatgacc gaaaagcaga ccctcctgga ggatgctgaa   10440
cgctgccgcc acaagatgca gactgccagc actctgatct ccggacttgc cggagaaaag   10500
gagcgctgga ccgagcagtc ccaggagttc gcagcccaga cgaagcgcct cgtggggac   10560 gtgctgctgg cgaccgcctt cctctcgtac tcgggcccgt tcaaccagga gtttcgggat   10620
cttctgttga acgattggcg caaggagatg aaagccagaa aaatcccgtt cggtaaaaac   10680
ctcaatctga gcgagatgct gatcgatgcc cccaccatct ccgaatggaa ccttcaggga   10740
ctgccgaacg atgatttgtc aatccagaac ggtatcattg tcactaaggc ctcccgctac   10800 ccctttattga ttgatcctca gacccagggg aagatttgga tcaaaacaa ggaatcgcgg   10860 aacgagctgc agatcacatc tctgaaccac aagtacttcc gaaaccactt ggaagattcc   10920
ctgtccctgg gccggcccct gctgattgag gacgtgggcg aagaactcga cccggccctg   10980
gataatgtgc tggaacggaa tttcattaag accggtagca ctttcaaggt gaaagtggga   11040
gataaggagg tggacgtcct ggacggattc cgcttgtaca tcacgaccaa gctgcctaac   11100
cccgcgtaca ctccggaaat cagcgcgagg acgtcgatca tcgatttcac tgtgaccatg   11160
aagggtctgg aagatcagct tctgggacgg gtcatcctga ctgagaagca ggaactggaa   11220
aaagagagaa cccacctgat ggaagatgtg accgccaata gcgcaggat gaaagagctc   11280 gaggacaacc tcctttaccg cctgacctcc acccagggtt ccttggtgga ggatgaatcg   11340
ctgattgtgg tgctgtcgaa caccaagagg accgccgaag aagtgaccca aaagttgaa   11400 atctccgccg aaaccgaagt gcagatcaac tcggctcggg aggagtaccg gccggtggcc   11460
actcgaggat caattctgta cttcctgatc accgagatgc ggctcgtgaa cgagatgtat   11520
cagactagcc tccgccagtt ccttggcttg ttcgacctgt cgctggcgag aagcgtgaag   11580
```

```
tccccaatta cctcgaaacg gatcgccaac attattgaac atatgactta cgaagtgtac   11640
aaatacgcgg cacggggget ctacgaagaa cacaagtttc tcttcacgct gctgctgact   11700
ctgaagatcg atattcagcg caaccgggtg aagcacgaag agttcctgac cctgattaag   11760
ggtggcgcct ccctggacct caaggcctgc cccccaagc cgtccaagtg gatcctcgac    11820
attacctggc tcaacctcgt ggaactttca aagctcagac agttctccga cgtgctcgat   11880
cagatctcca ggaacgagaa gatgtggaag atttggttcg ataaggaaaa tcccgaagag   11940
gagcctcttc ctaacgcgta cgacaagtcc ctggattgct tccgccggct gctcctgatc   12000
cggtcgtggt gtccagaccg gactattgcc caagcccgga aatacatcgt ggactcaatg   12060
ggcgagaagt acgcagaggg tgtgatcctg gacctggaaa agacctggga agagtccgat   12120
ccgagaactc ctctgatctg cctgctgtcc atgggttcag accccaccga ctcgatcatc   12180
gccctcggaa agcgcctgaa gatcgaaacc cgatacgtca gcatgggcca aggccaggag   12240
gtccacgccc gcaaactgct gcagcagacc atggctaacg gaggatgggc gctgctgcag   12300
aattgtcacc tgggacttga cttcatggat gagctgatgg acatcatcat cgaaaccgag   12360
ctcgtgcacg atgcattccg gctgtggatg acaactgagg cgcacaagca gttcccgatt   12420
accttgctgc agatgtctat taagttcgcg aacgatccgc cccagggact gagagccgga   12480
ctcaagcgca cctacagcgg cgtgtcccaa gacttgttgg acgtgtcctc gggaagccag   12540
tggaagccga tgctctacgc cgtggcgttc ctccattcaa ccgtccagga cgcagaaag   12600
ttcggcgcac tgggatggaa catcccttac gaattcaacc aggcggattt taacgccacc   12660
gtgcagttca ttcagaacca cctggacgac atggacgtga agaagggggt gtcatggacc   12720
actatccggt acatgatcgg agagatacag tatggaggtc gggtgaccga cgactacgac   12780
aagcgcttgc tgaacacctt cgccaaggtc tggttctccg agaacatgtt cggacccgat   12840
ttcagcttct accagggata caacatccct aagtgctcca ccgtcgacaa ctacctccag   12900
tacattcagt ccctgccagc ctacgacagc ccggaggtgt tcggactcca ccccaacgca   12960
gacatcacct accagtccaa gctcgccaag gatgtgttgg acaccatcct gggaatccag   13020
cctaaggaca cgagcggcgg gggggatgaa actcgggagg ctgtggtggc acggctggcc   13080
gacgatatgc tggaaaagct cccacctgac tacgtgccgt tcgaagtgaa ggagcggctc   13140
cagaagatgg gcccgttcca gcccatgaac atcttcctgc ggcaagaaat tgaccggatg   13200
cagagagtgc tgtccctggt ccggtcaacc ctgactgaac tgaagctggc catcgacgga   13260
accatcatca tgtccgagaa cctcagagat gcgctggatt gcatgttcga cgcccggatc   13320
cctgcctggt ggaaaaaggc ctcctggatc tccagcactt tgggattctg gttcaccgaa   13380
ctgatcgaaa gaaactcaca attcacttcc tgggtgttta acggcagacc acactgtttc   13440
tggatgaccg gcttcttcaa cccacaagga ttcctgacag cgatgagaca ggaaatcacc   13500
cgcgccaaca agggctgggc cctggacaac atggtgctgt gcaacgaagt gaccaagtgg   13560
atgaaggacg acatttccgc accgcctact gaagggtgt acgtgtacgg cctgtacctg    13620
gagggcgctg gatgggacaa gcggaacatg aaactgattg aatccaagcc caaggtcctg   13680
ttcgaactca tgccagtcat taggatctac gcggagaaca cacgctccg ggacccgagg    13740
ttttactcct gccccatcta taagaagccc gtgcggaccg atctgaacta cattgcggcg   13800
gtggacctca ggaccgcgca gacccctgaa cattgggtgc tccgcggcgt ggcccttctg   13860
tgtgacgtga agtag                                                    13875
```

```
<210> SEQ ID NO 8
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 8
```

| | | | | | |
|---|---|---|---|---|---|
| atgttcagaa | tcgggcggcg | gcaactgtgg | aagcattcag | taactcgcgt | cctgactcag | 60 |
| agactgaagg | gagaaaagga | ggcaaaaagg | gccttgctgg | acgcccgcca | caactacctc | 120 |
| ttcgcgattg | tggcctcatg | cctggacctg | aataagactg | aagtggagga | cgctatcctc | 180 |
| gagggaaacc | aaatagagag | aatcgaccaa | ttgttcgccg | tgggtggact | ccggcacctg | 240 |
| atgttctact | accaagacgt | ggaggaagcg | gaaaccggac | agctgggatc | actgggggc | 300 |
| gtgaacctcg | tgagcggaaa | gatcaagaag | cccaaggtgt | tcgtcaccga | aggcaacgat | 360 |
| gtggcgctca | ccggcgtgtg | cgtgttttc | attcgcaccg | acccatcgaa | ggccattact | 420 |
| cccgataaca | tccatcaaga | ggtgtccttc | aacatgctgg | acgctgccga | tggaggactc | 480 |
| ctcaacagcg | tgcgccggct | cctctccgac | attttcatcc | ccgcgctgag | agctaccagc | 540 |
| cacggatggg | gggaactcga | gggactgcag | gacgccgcaa | acattcgcca | gaattcctc | 600 |
| tcctcattgg | agggcttcgt | gaacgtgctc | agcggcgctc | aggaaagcct | gaaagaaaag | 660 |
| gtcaatctcc | gcaagtgcga | catcctagag | ctcaaaacgc | tgaaagagcc | cacagactac | 720 |
| ctcactcttg | ccaataaccc | tgaaacctg | ggaaagatcg | aggactgcat | gaaggtctgg | 780 |
| attaagcaaa | cagaacaagt | cctggccgag | aacaaccagc | tcctgaagga | ggcggatgac | 840 |
| gtgggcccgc | gggcagaatt | agagcactgg | aagaaacgcc | tcagcaagtt | taattacctc | 900 |
| ctggagcaat | tgaagtcccc | tgacgtgaag | gccgtgctcg | cagtgttggc | agcggcaaag | 960 |
| tccaagctgc | tgaaaacttg | gcgggagatg | gacattagaa | ttactgacgc | gacgaacgag | 1020 |
| gcaaaggata | acgtcaaata | cttgtacacg | ctcgagaagt | gctgcgaccc | gttgtattcc | 1080 |
| tcagacccac | tgagcatgat | ggacgccatt | cccaccctca | tcaacgccat | taagatgatt | 1140 |
| tactcaattt | cccattacta | caacaccctca | gagaagatta | cttcactctt | cgtgaaggtg | 1200 |
| accaaccaaa | ttatctccgc | ctgcaaggcc | tacatcacta | caacgggac | agcttcgatc | 1260 |
| tggaaccagc | cgcaggatgt | cgtggaggag | aagatcctgt | cggccatcaa | acttaagcag | 1320 |
| gagtaccaac | tgtgctttca | caaaaccaag | cagaagctga | agcaaaatcc | aaacgccaag | 1380 |
| caattcgact | tctccgagat | gtacatcttc | ggcaagttcg | aaaccttcca | caggagactg | 1440 |
| gccaaaatca | ttgatatttt | cactacccctt | aagacctaca | gcgtgctcca | agacagcact | 1500 |
| atcgagggac | tggaggacat | ggccaccaag | taccaaggca | tcgtcgccac | cattaaaaaa | 1560 |
| aaggaataca | acttcctgga | tcagcggaag | atggacttcg | atcaggatta | tgaagagttc | 1620 |
| tgcaaacaga | ccaatgatct | ccacaacgaa | ctgcggaagt | ttatggacgt | gaccttcgca | 1680 |
| aaaatccaga | acaccaacca | ggcgctgcgc | atgctgaaga | agttcgagag | attgaacatc | 1740 |
| ccgaatctcg | gcatcgacga | taagtaccag | ctcatcctgg | aaaactacgg | ggccgacatc | 1800 |
| gacatgatct | ccaagctgta | cactaagcag | aaatacgacc | cgccactggc | gagaaaccag | 1860 |
| cccccccattg | ccggcaagat | cctctgggcc | cgacagcttt | tccaccgaat | ccagcaaccc | 1920 |
| atgcagcttt | tccagcaaca | ccccgccgtg | ctctcaaccg | ccgaggccaa | gccgatcatt | 1980 |
| agaagctaca | acagaatggc | gaaggtgctg | ctcgaattcg | aggtgttgtt | ccaccgggca | 2040 |
| tggttgaggc | agatcgagga | aatacacgtg | ggactggagg | cctcgctgtt | ggtgaaggcc | 2100 |

```
ccagggaccg gagaactgtt cgtcaacttc gacccgcaaa tcctgatcct gttccgcgaa    2160
actgaatgca tggctcagat gggattggaa gtcagccccc tcgcgacttc cctcttccaa    2220
aagagagata gatacaaacg gaacttctcc aatatgaaga tgatgctggc ggaataccag    2280
agagtgaaat ccaaaattcc ggccgctatt gagcagctga ttgtgcctca ccttgccaag    2340
gtcgacgaag cgttgcagcc tggcctggcc gctctcactt ggaccagcct gaacatcgag    2400
gcctacttgg aaaacacctt cgccaaaatt aaggacctcg aactcctgct cgaccgggtg    2460
aacgacttga tcgagtttag gattgatgcc attctggagg agatgagctc cactccgttg    2520
tgtcaactgc cacaggagga accccctcaca tgcgaggaat tcctgcaaat gactaaggac    2580
ctgtgcgtca acggggccca atcctgcac ttcaaatcct ccctggtcga ggaagcagtc    2640
aacgagttgg tgaacatgct cctggatgtg gaggtgctgt ccgaggagga gtccgagaag    2700
atctccaacg aaaactccgt gaactataag aatgaatcct ccgcaaagcg ggaggagggg    2760
aatttcgata ccctgacttc ctccatcaac gcccgcgcca acgccttgct gctaactacc    2820
gtgactagaa agaagaaaga aactgaaatg ctgggggagg aggcacgcga actcctgtcc    2880
cactttaacc accagaacat ggacgccctg ctgaaggtca cccggaacac cttggaggcc    2940
attcgcaagc ggatccatag cagccacacc attaacttca gagactcaaa ctcggcatcc    3000
aacatgaagc agaattcact cccgatcttc agggcaagcg tgactttggc tatcccgaac    3060
attgtcatgg cgcctgctct ggaggacgtc cagcagacgc tgaacaaggc cgtggaatgc    3120
atcatcagcg tcccgaaggg tgtgagacag tggtcctccg aattgttgtc aaagaagaag    3180
atccaagaga ggaagatggc ggcgctccag tccaatgaag atagcgatag cgacgtggag    3240
atgggcgaga acgaactcca ggatacccctg gagatcgcgt ccgtcaacct ccctatcccg    3300
gtccagacca gaactactaa caagaatgtc tcggaaaaca aggagatcgt gaagctcgtg    3360
tcggtcctgt ccaccattat caactccacc aagaaggagg tcattactag catggactgc    3420
ttcaagcgct ataaccacat ctggcaaaag gggaaggaag aggccatcaa gacctttatc    3480
acccagtcgc cgctcttgtc agagtttgag tcacagattc tgtacttcca gaacctggaa    3540
caggagatta atgctgaacc agagtacgtg tgcgtgggct ccatcgcgct gtatactgcg    3600
gacctcaagt tcgcgttgac cgcagaaact aaggcctgga tggtggtcat cggcagacac    3660
tgcaataaga agtaccgcag cgaaatggaa aacatcttca tgttgattga agagttcaac    3720
aagaagctca accggcccat taaggacctc gatgatattc gcatcgccat ggcggccctc    3780
aaagaaatcc gggaggagca aatctccatc gacttccagg tcggccccat tgaagagagc    3840
tacgcactgc tgaaccgcta tggactgtta atcgcccggg aagaaatcga taaggtggat    3900
accctgcatt acgcttggga aaagttgctg gcccgggcag gagaggtgca gaacaagctc    3960
gtgagcctcc aaccctcctt caaaaaagaa ctgatcagcg cggtggaagt gtttctccag    4020
gactgccacc agttctacct cgactatgac ctgaacggcc ccatggctag cggcttgaag    4080
cctcaggagg cctcagaccg cctgatcatg tttcagaacc aattcgataa catctaccgg    4140
aagtacatta cctataccgg cggcgaggag ttgtttggat tgccagccac ccagtaccct    4200
caactcctgg agatcaaaaa gcaactgaac ttgctccaga gatctacac cctctacaac    4260
tcggtcatcg aaactgtgaa ctcgtactac gacattcttt ggagcgaggt caacatcgaa    4320
aagatcaata cgaactcct ggaattccag aaccgatgca ggaagctgcc ccgggccctg    4380
aaagattggc aagccttctt ggacctgaag aagattattg atgacttctc agaatgttgc    4440
cccctcctgg agtacatggc ctccaaggcc atgatggaac ggcattggga gcggattact    4500
```

```
acccttacgg gccacagcct ggacgtcggc aacgagagct tcaaactgag aaacatcatg    4560
gaggccccac tcctgaagta caaggaagag attgaggata tttgcatttc cgccgtgaag    4620
gaacgcgaca tcgaacagaa acttaagcaa gtcattaacg agtgggacaa caaaaccttc    4680
acgttcggat ccttcaagac gagaggcgag ctcctcctga ggggagactc aaccagcgaa    4740
attatcgcca acatggagga ctccctgatg ctcctggggt cgctgctgtc gaacaggtac    4800
aacatgccct tcaaggccca gatccagaag tgggtccagt acctcagcaa ctccaccgac    4860
atcatcgagt cctggatgac tgtgcagaac ttgtggatct acctggaggc cgtgttcgtg    4920
ggaggagata tcgccaaaca attgcctaag gaagccaaga ggttctcgaa tattgacaag    4980
agctgggtga agatcatgac cagggcacac gaagtgcctt cggtggtgca atgttgcgtg    5040
ggggatgaaa ctctcggaca gttgctgcct cacctcctgg accaactcga gatttgtcag    5100
aagtccctga ctggatacct cgagaagaaa cgcttgtgct cccaaggtt tttcttcgtg     5160 tcggatcctg ccctcttgga aatcctcggt caggcctcag actcacacac cattcaagcc    5220
cacctcctta acgtctttga taacattaag agcgtcaagt tccatgagaa aatctacgac    5280
cggatcctct ccatttcgtc ccaagaggga gaaacgattg aacttgacaa gccagtgatg    5340
gccgaaggga atgtcgaggt gtggctcaac agcctcctgg aagaatccca aagctccctt    5400
catcttgtga tccggcaggc cgccgccaat atccaggaaa ccggattcca actcaccgag    5460
ttcctttcct ccttccccgc acaagtggga ctgctcggca ttcaaatgat ctggacgcgg    5520
gattccgagg aggccctgag gaacgccaag ttcgacaaga gatcatgca aaaacaaac     5580 caggccttcc tcgaacttct caatacctg atcgatgtga ccactagaga tctctcctcg     5640
acggaacggg tgaaatacga aaccctcatc accatccacg tgcaccagag agatatttc     5700 gacgacctct gccacatgca tattaagtcg ccaatggact tcgaatggtt gaaacaatgc    5760
agattttact ttaacgagga cagcgataag atgatgatcc atatcaccga cgtcgccttc    5820
atctaccaga acgaattcct gggatgcacc gataggctgg tgattacccc gctgactgac    5880
cggtgctaca ttaccctggc ccaggccctg gaatgagca tgggcggcgc ccctgccgga    5940
ccggcgggca ccggcaagac cgaaaccacc aaggatatgg gacggtgcct cggaaagtac   6000
gtggtggtgt ttaactgctc ggaccagatg gatttccgcg gactgggcag gatcttcaaa   6060
ggcctggctc agagcggttc atggggctgc ttcgacgagt tcaaccgaat tgacttgccg   6120
gtgctgtccg tcgcagcgca gcaaatctcg atcatcctga cttgtaagaa ggaacataaa   6180
aagtccttca tttttaccga cggagacaac gtgacaatga acccggagtt cggactgttc   6240
ctgactatga accctgggta cgccgggcgc caggagctcc ctgaaaacct taagatcaac   6300
ttccgctccg tggcaatgat ggtgcctgac agacagatta tcattcgcgt gaagctggcg   6360
tcatgcggct tcatcgacaa cgtggtgctg gcgaggaagt tttccacact gtacaaactt   6420
tgcgaggagc agctctccaa acaggtgcac tacgacttcg gactgagaaa catcctgagc   6480
gtcctgagga ccctgggggc tgctaagcgc gccaaccca tggataccga atccaccatt    6540
gtcatgcggg tcctgaggga catgaacctg tccaagctca tcgacgagga tgaaccctg    6600 ttcctgagcc tgattgaaga tctgtttcca aacatcttgc tggacaaggc gggttacccc   6660
gagctggaag ccgccatctc ccgccaagtg gaggaggctg gactcattaa ccacccaccc   6720
tggaagctca aggtcatcca actgttcgaa acgcagagag tgcgacacgg catgatgaca   6780
ctggggccat caggtgcagg aaagaccacg tgcatccaca ccttgatgcg ggcgatgacc   6840
```

```
gactgcggga agccacatcg ggagatgcgc atgaacccga aggcgatcac tgcacctcaa    6900
atgttcggac ggctcgacgt ggccactaac gactggaccg acgggatttt ctcgaccttg    6960
tggcgcaaga ccctacgggc caagaaagga gagcacatct ggattatcct ggatggtcca    7020
gtggatgcga tctggatcga gaaccttaac tccgtgctgg acgacaacaa gaccctgacc    7080
ctggctaacg gcgaccggat cccaatggcg cccaactgca aaatcatctt cgaaccccac    7140
aacattgaca acgcctcgcc cgccactgtg tcgcggaacg ggatggtgtt catgtcgtcg    7200
tccatcttgg actggtcccc cattctcgaa ggcttcctga agaagcgcag ccctcaagaa    7260
gccgagatac tccgccaact ctacaccgag tcgttcccgg atttgtaccg gttctgtatc    7320
cagaacttgg agtacaagat ggaggtgctt gaggcattcg tgatcaccca atcgatcaac    7380
atgctgcaag gactcatccc cctgaaagaa cagggaggtg aagtctccca agctcacctg    7440
ggacgcctct tcgtgttcgc gctgctttgg agcgcgggag ccgcgctcga gctcgacggg    7500
cggcgcaggc tggagctctg gctgcgctcc cgcccgaccg gaaccctgga gctgccgccc    7560
ccggccggcc cgggcgacac cgcctttgac tactacgtgg cccccgacgg gacctggact    7620
cactggaaca ctagaaccca ggaataccct taccctccg cactactcc gaatacgga      7680 agcatccttg tgccgaacgt ggacaacgtg cgcaccgact tcctaattca gaccatcgcc    7740
aagcagggaa aggccgtgct gcttattgga gaacagggta ccgcaaagac cgtgatcatc    7800
aagggattca tgtcaaagta cgaccctgaa tgtcacatga ttaagtcact taacttctcc    7860
agcgccacca cccctctgat gttccagaga accatcgaga gctacgtgga caaacgcatg    7920
ggcaccacgt acggtccccc ggccggaaag aagatgaccg tattcatcga cgacgtgaac    7980
atgccgatca ttaacgaatg gggagatcag gtgaccaacg aaatcgtgcg ccagttaatg    8040
gagcagaacg gtttctacaa ccttgaaaaa cccggagagt tcacttcaat cgtggacatc    8100
cagttcctgg ccgccatgat ccacccgggc ggaggtagaa cgacatccc gcagagactg     8160 aagagacagt tctcaatctt caactgcacc ctgccctccg aagcatcagt cgataagatt    8220
ttcggggtga tcggagtggg ccactactgc acgcagaggg gtttctcaga ggaggtgcgc    8280
gactccgtga ccaaactggt cccactcact cgaaggctgt ggcagatgac caagattaag    8340
atgctcccta ctcctgccaa gttccattac gtctttaacc ttcgggactt gtcccgggtc    8400
tggcagggaa tgctgaatac cacctccgaa gtgattaagg aacctaacga cctcctgaag    8460
ctctggaaac acgagtgcaa gagggtgatc gccgatagat tcaccgtgtc ctccgacgtg    8520
acctggttcg acaaggccct cgtgtccttg gtggaagaag agttcggtga agaaaagaag    8580
ctcctcgtgg actgcggaat cgacacctac ttcgtcgact tcctcagaga tgcccccgag    8640
gctgccggag aaacctcaga agaggccgat cgggagactc cgaagattta cgaacccatc    8700
gaatccttca gccacttgaa ggagaggctc aacatgttcc tgcagctcta caacgaaagc    8760
atcaggggag ctggcatgga catggtgttc ttcgccgacg cgatggtgca ccttgtcaag    8820
atctcccggg tcattcgaac gccgcaggga aacgcattgc tcgtgggcgt cggaggttcc    8880
ggaaaacagt ccctcacgag gctggcgtcc ttcattgcgg atacgtgag cttccaaatt     8940 accctcaccc gcagctacaa tacctccaac cttatggagg acttgaaggt cttgtaccgc    9000
actgccggac agcagggaaa ggggatcacc ttcatcttca ccgacaacga aatcaaggat    9060
gagagcttct ggagtacat gaacaacgtc ctttcgtccg gagaagtgtc caacctcttc     9120
gctcgcgatg aaatcgacga gatcaactcc gacctcgcca gcgtcatgaa aaagaattc     9180 cctcgctgtc tccccaccaa cgagaacctc cacgattact ttatgtcccg ggtccgccaa    9240
```

```
aacttgcata ttgtgctgtg cttctcgccc gtgggggaga agtttcggaa ccgggcgctg     9300
aagttccccg ccctgattag cggatgtact atcgactggt tctcgagatg gcccaaagac     9360
gccctggtcg ccgtgagcga acatttcctg acttcctacg acatcgactg cagcctcgaa     9420
atcaagaagg aagtggtgca gtgcatgggg tcatttcagg atggagtggc cgagaagtgc     9480
gtcgactact tccagagatt ccggcggtca acccatgtga cgcccaaaag ctacctttcg     9540
ttcatccagg gctacaagtt catctacggg gaaaagcatg tcgaagtgcg gacccttgca     9600
aaccgcatga acaccggcct tgagaagttg aaagaggcct cggaatccgt ggccgcgctc     9660
agcaaagaac tggaagctaa ggagaaggaa ctccaagtcg ccaacgataa agcggacatg     9720
gtgctgaagg aagtgaccat gaaggcccag gccgccgaga aggtcaaggc cgaggtccag     9780
aaggtgaagg accgcgcaca agcaatcgtg gatagcatct ccaaggacaa agcaatcgca     9840
gaagagaagc tcgaggcggc aaagcccgcg ctcgaagagg cggaagcggc gctgcagact     9900
atccggccgt ccgacattgc aaccgtgaga accctgggcc gccccccaca cctcatcatg     9960
cgcattatgg actgcgtgct cttgctcttt caacggaagg tgtccgccgt gaagatcgac    10020
cttgagaagt cctgcaccat gccaagctgg caggagtcgc tgaaactcat gaccgccgga    10080
aacttcctgc agaacttgca acagttcccg aaagacacca tcaacgaaga agtcatcgag    10140 ttccttttccc cgtacttcga aatgcctgat tacaacattg aaaccgccaa gagagtgtgc    10200
ggaaatgtcg cgggcctgtg ctcgtggacc aaggccatgg cgtcgttctt tagcatcaac    10260
aaggaggtgc tccccctgaa ggccaacctc gtggtgcagg aaaatcgcca cttgctggcc    10320
atgcaagatc ttcagaaggc tcaagcggag ctggacgata acaggccga acttgacgtg    10380 gtccaggccg agtacgagca ggctatgacg gaaaagcaga ccctcctgga ggatgcagaa    10440
cgctgcaggc acaagatgca gaccgcctcc acccttattt ccggcctggc gggcgaaaag    10500
gagcggtgga ccgagcagtc ccaggaattc gcagctcaga ccaagcggct cgtgggcgat    10560
gtgctgctgg ccactgcctt cttgagctac tccggcccct tcaaccagga atttcgggac    10620
ctcctgctga cgactggag gaaggagatg aaggcgcgga agatcccatt cgggaagaac    10680
ttgaacctct ccgagatgct catcgacgct cccaccatca gcgaatggaa cctccaggga    10740
ctgcccaacg atgaccttag cattcaaaac ggaatcatcg tgaccaaggc ctcgcgctac    10800
ccgctgctta tcgacccaca aactcaagga aagatttgga ttaagaacaa ggagtcacgc    10860
aacgagctgc agatcacctc cctgaaccat aaatacttta gaaaccatct cgaggattcc    10920
ctgagcctgg gcagacccct tctcatcgag gacgtgggcg aggagctcga tccagcgctg    10980
gacaacgtcc tggagagaaa cttcattaag accggatcca cgttcaaggt caaggtcggc    11040
gacaaggaag tggatgtcct ggacggcttc cgcctgtaca tcaccaccaa attgcctaac    11100
cccgcataca ccccggaaat ctcagctcgc acgtcgatca ttgattttac cgtcactatg    11160
aaaggactgg aggaccagct gctgggcaga gtcattctca ccgaaaagca agagctgaa    11220 aaggaacgca cccatctcat ggaggacgtg actgcgaata agcggcggat gaaagagctg    11280
gaagataact tgctgtaccg cctgacttcc actcaggggt ccctcgtcga agatgagtca    11340
ctgatcgtgg tcctgtcaaa cacgaagagg accgccgagg aagtaaccca gaagctggag    11400
atttccgccg aaaccgaagt gcagatcaac tccgcaagag aggaatatag acccgtagct    11460 acgcgggga gcattctgta cttcctcatc acggagatga gacttgtcaa cgaaatgtac    11520
cagacctcat tgcggcagtt cctcggactg tttgacctgt ccctcgcaag aagcgtcaag    11580
```

```
tccccaatta cttcaaagcg catcgcgaac attattgagc acatgactta cgaagtgtac   11640
aagtacgcgg ccaggggtt gtatgaggag cacaagtttc tcttcaccct gctgctgacc    11700
ttgaagatcg acattcaacg aatagagtg aagcatgaag agttcctgac cctcatcaaa    11760
ggcggcgctt ccctcgatct gaaggcttgc cctccgaaac cgtcaaaatg gatcctggac   11820
attacctggc tgaaccttgt cgagctgtcc aagttgcgcc aattctccga cgtgctggac   11880
cagatctccc ggaacgagaa gatgtggaag atctggttcg acaaggaaaa cccagaggag   11940
gagcctctgc ccaacgccta tgacaaaagc ctggactgct ccggcggct ccttctcatt    12000
cgctcttggt gtcccgaccg gaccattgcc caggcccgca agtacatcgt ggattcaatg   12060
ggggagaagt acgctgaggg ggtgatcctt gacctggaga aaacttggga ggagagcgat   12120
ccgcggaccc cgctgatttg cttgctttca atgggatctg accccaccga ctccatcatc   12180
gccctgggaa agaggcttaa gatcgaaact cgctacgtca gcatgggaca aggacaggag   12240
gtgcacgccc ggaagctgct ccagcagacc atggccaacg ggggatgggc gctgctgcag   12300
aactgccacc ttggactgga tttcatggac gaactcatgg acatcattat cgagactgaa   12360
ttggtccatg acgccttcag actgtggatg actactgagg cccataagca gttccccatc   12420
acacttctgc agatgagcat caagttgcgc aacgatcctc ctcaaggcct gagagccgga   12480
ttgaaaagga cgtactccgg ggtgtcccaa gacctcctgg atgtgtcctc cggatcccaa   12540
tggaagccaa tgctctacgc ggtggcgttc cttcacagca ctgtgcagga gaggcggaag   12600
tttggagccc tgggatggaa cattccatac gagttcaacc aagccgactt caacgcgact   12660
gtgcaattca tccagaacca cctggacgat atggatgtga aaaaggggt gtcctggacg   12720
accatccgct acatgatcgg ggagatccag tacggggaa gagtgaccga tgattacgac   12780
aagaggctcc tgaacacttt cgccaaggtc tggttctccg aaaacatgtt cggccccgac   12840
ttctcgttct accaggggta taacattccg aagtgctcga cggtggataa ctacctccag   12900
tacattcaat cgctgccggc ctacgactcc cccgaggtgt tcggcctcca ccccaacgcc   12960
gacattacct accagagcaa gctggctaag gacgtgctag acaccatact ggggatccaa   13020
ccgaaggata cttccggcgg aggggatgaa acccgcgaag cagtggtggc acggctggct   13080
gacgacatgc tggagaaact gccccctgac tacgtcccct ttgaggtcaa ggaaaggctc   13140
cagaagatgg gacctttcca gccaatgaac atcttcttgc ggcaagagat cgaccggatg   13200
cagagagtgc tctccctcgt gcgctcaacc ctcactgagc tcaagctggc aatcgacggt   13260
accattatca tgtcggagaa cctccgggac gcactggact gcatgttcga tgcgcggatc   13320
cctgcgtggt ggaagaaggc ctcctggatc tcgtcaaccc tggggttctg gttcaccgag   13380
ctgattgaaa ggaactccca attcacctcc tgggtctttta acggccgccc gcactgcttc   13440
tggatgaccg gctttttcaa ccccccaggga tttctcaccg ccatgcggca ggaaatcacc   13500
agggccaaca agggctgggc gttggataac atggtgctgt gcaacgaagt gaccaagtgg   13560
atgaaagatg acatttcagc cccgcgacc gaaggcgtct acgtctacgg gctctacttg    13620
gaaggggccg gatgggacaa gcggaatatg aaactcattg agtccaagcc caaggtcctg   13680
ttcgagctga tgccagtgat ccgcatctac gccgaaaata cacccctccg ggatccgagg   13740
ttctactcgt gcccaattta caagaagccc gtgcggaccg acctgaatta catcgccgct   13800
gtcgaccttc gcactgccca aactccggaa cactgggtgc tgcggggagt cgccctgctt   13860
tgcgacgtga agtag                                                    13875
```

```
<210> SEQ ID NO 9
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 9
```

| | | | | | |
|---|---|---|---|---|---|
| atgtttagga | ttggtcggcg | ccagctgtgg | aaacatagcg | tcactcgcgt | cctcacgcaa       60 |
| agacttaaag | gagaaaagga | ggcaaaacgg | gcgttgctcg | acgctcggca | taactacctg      120 |
| tttgcaatcg | tcgcatcgtg | tcttgatctt | aacaagacgg | aggtggaaga | cgctattctg      180 |
| gaaggtaatc | agatcgagag | aattgaccag | ttgttcgctg | tgggcggtct | tcgccacctt      240 |
| atgttctatt | atcaagatgt | cgaagaggcg | gagactgggc | agttggggag | cttgggtgga      300 |
| gtcaatttgg | tcagcggtaa | aatcaaaaaa | ccaaaagtgt | tcgtcacgga | gggcaatgac      360 |
| gtcgcgctga | cgggtgtctg | cgtcttcttt | atccggacgg | accccagcaa | ggctatcacg      420 |
| ccagataaca | tccatcagga | ggtgtcattc | aatatgttgg | atgccgcaga | tggaggactc      480 |
| cttaattccg | tgaggcgcct | tctttccgac | atttttattc | cggctctgcg | cgccacctcg      540 |
| catggttggg | gagagctcga | gggacttcaa | gatgcagcga | atattcggca | agaattttg       600 |
| tcctccctgg | aaggattcgt | caatgtgctt | tcgggagcac | aggagtccct | taagaaaaaa      660 |
| gtcaatttgc | ggaagtgtga | catcctggag | cttaaaactt | tgaaagaacc | cacgactat       720 |
| cttactttgg | cgaacaatcc | agaaacgttg | gggaagattg | aagactgtat | gaaagtgtgg      780 |
| attaaacaga | ctgaacaggt | gttggcagaa | aataatcaat | tgctcaaaga | agccgacgat      840 |
| gtgggcccga | gagcggaact | cgaacattgg | aaaaagagac | tgagcaagtt | taattaccctt     900 |
| cttgaacagc | ttaaatcccc | ggacgtcaaa | gcagtgctgg | cagtgttggc | ggctgctaag      960 |
| tcgaaacttt | tgaaaacttg | gcgggagatg | gacattcgga | ttacggatgc | cacgaacgag     1020 |
| gccaaagata | tgtgaaata  | tctttatacc | ctcgagaagt | gctgcgaccc | actttattca     1080 |
| tccgacccgc | tctcaatgat | ggacgctatt | cctaccctga | tcaacgcaat | taagatgatt     1140 |
| tactcaattt | cgcattacta | caataccagc | gagaaaatca | cttcgttgtt | cgtgaaagtg     1200 |
| accaatcaaa | tcattagcgc | atgcaaggcc | tatatcacga | caatggcac  | ggcctcaatc     1260 |
| tggaaccaac | cgcaagatgt | ggtcgaggaa | aagattttgt | cggcaattaa | gttgaagcaa     1320 |
| gaataccagc | tctgctttca | taaaaccaag | caaaagttga | aacaaaaccc | caatgccaaa     1380 |
| caattcgact | tcagcgaaat | gtacatcttt | gggaaattcg | agacgtttca | caggcggctg     1440 |
| gcaaaaatca | tcgatatctt | taccacgctt | aaaacgtact | cggtcctcca | agattcgacg     1500 |
| atcgaggggt | tggaggacat | ggcgacgaag | tatcaaggta | ttgtggcaac | tatcaagaaa     1560 |
| aaagagtata | acttcttgga | ccagagaaaa | atggactttg | accaagatta | cgaggagttc     1620 |
| tgtaagcaaa | ccaacgattt | gcacaacgag | cttcgcaagt | tcatggacgt | caccttgcg      1680 |
| aaaatccaga | acaccaatca | ggcgctccgc | atgctgaaaa | agtttgaacg | gctcaacatt     1740 |
| cccaatcttg | gaattgacga | caagtatcaa | ctcattctcg | aaaattatgg | ggcagatatc     1800 |
| gatatgatca | gcaagttgta | taccaagcag | aaatatgacc | cgccgttggc | taggaatcag     1860 |
| ccgcccatcg | ctggcaaaat | cctttgggca | cgccagctct | tccatcggat | tcagcagccc     1920 |
| atgcaactgt | ttcaacagca | tcccgcggtc | ctgtcgaccg | ccgaagccaa | gccaattatt     1980 |
| cggtcgtata | acagaatggc | taaggtcttg | ctcgagttcg | aagtcctgtt | ccaccgcgct     2040 |
| tggctgcgcc | aaattgagga | aattcacgtc | ggtcttgaag | caagccttt  | ggtcaaagct     2100 |

```
cctggcactg gcgaactctt tgtcaatttt gacccgcaga ttttgattct gttcagagaa   2160
actgagtgta tggctcagat gggactcgaa gtgagccctt tggccacttc cctgtttcaa   2220
aagagagata ggtataagcg caacttctcg aatatgaaga tgatgcttgc tgaatatcaa   2280
agggtgaaaa gcaagattcc cgcggcgatt gaacagctca ttgtgccgca cctcgcgaag   2340
gtggatgagg cattgcaacc cggacttgcg gcgttgacct ggacttcgct caacattgaa   2400
gcctacttgg agaacacttt tgccaaaatc aaagatctgg agcttttgct cgacagggtg   2460
aatgatttga tcgagttcag aatcgacgcg atcctggaag agatgtcatc cactccactg   2520
tgtcagttgc ctcaggagga accacttacc tgcgaagaat ttctgcagat gacgaaagac   2580
ctctgtgtca acggcgcaca aattttgcac tttaaatcat cattggtgga agaagcggtc   2640
aatgaacttg tgaacatgtt gcttgatgtg gaagtgttgt ccgaggagga atcggagaaa   2700
atttcgaacg aaaattcggt caactacaag aatgaatcgt ccgcgaaacg cgaggagggg   2760
aattttgaca ctctgacctc ctcaattaat gccagagcca atgccctctt gctgactacc   2820
gtgacgagaa agaagaagga gaccgagatg cttggagagg aagctaggga attgctctcc   2880
cactttaacc atcagaacat ggacgcgttg ctcaaggtga cgcgcaatac tcttgaggcc   2940
attaggaagc gcatccactc gtcccacacg atcaacttcc gggattcaaa ctccgcttcc   3000
aatatgaaac agaactcgct cccgatcttt agagcttcag tgactctggc cattcctaat   3060
attgtcatgg cacctgcttt ggaggacgtc cagcaaacgc tcaacaaggc cgtcgagtgt   3120
attatttcgg tcccgaaggg agtcagacag tggtcctcag aactcttgtc caagaagaag   3180
atccaagaac gcaaaatggc agcccttcaa tccaacgaag attcggattc agatgtggaa   3240
atgggcgaaa atgagctcca ggataccctg gaaattgcat cggtcaatct tccaatccct   3300
gtccagacta gaactattta taagaatgtc tcagaaaaca aagaaatcgt caagttggtg   3360
tcagtcctgt cgacgatcat taatagcact aagaaggaag tgattacgtc gatggactgc   3420
ttcaaaaggt ataaccatat ctggcagaaa ggcaaggaag aagcaattaa aacctttatc   3480
acgcagtcac cgctgctgtc agagtttgag agccagattt tgtacttcca gaatcttgag   3540
caagaaatta atgcagagcc ggagtatgtc tgcgtcggtt ccatcgctct gtacacggcc   3600
gatttgaagt ttgctcttac cgcagaaacg aaagcatgga tggtggtgat cggcagacat   3660
tgtaataaga ataccggtc ggagatggaa atatcttta tgcttattga ggaattcaat   3720
aaaaaattga accggcctat taaggatctg gatgatatcc gcatcgccat ggccgccctg   3780
aaagagatta gagaagaaca aatctcaatc gatttccagg tgggccccat cgaagaatca   3840
tatgcgctcc ttaataggta cggactgctc attgccagag aggagatcga caaagtcgac   3900
accctccatt acgcttggga gaagctgctc gccagagcgg gggaagtgca aaacaaactt   3960
gtgagcttgc aaccgtcctt taagaaagaa ctcatttcag ccgtcgaggt gtttctgcaa   4020
gattgtcatc aattctacct cgattatgat ctgaacggtc caatggcttc gggactgaaa   4080
ccccaggaag ccagcgaccg gctgattatg ttccagaacc agtttgacaa catttatcgg   4140
aaatacatta cgtacacggg gggtgaggaa cttttcggtc tgccagcaac gcagtatcct   4200
cagctgttag aaattaaaaa acaactgaac ctgctccaaa agatttacac cctctacaat   4260
tcagtcattg agaccgtgaa ctcatactac gacattctct ggtcagaggt gaatatcgag   4320
aagattaata tgaactcct tgaattccag aacaggtgca ggaagcttcc acgggcactc   4380
aaggattggc aggcgttctt ggatctcaaa aaaattattg acgatttctc agagtgttgc   4440
cctcttctgg agtatatggc ctcgaaagcg atgatggaaa ggcattggga aaggattacc   4500
```

```
accttgacgg gccacagcct tgatgtcggg aatgagtcat ttaaactcag aaacattatg    4560 gaagccccttt tgctgaagta taaggaggag atcgaggata tctgcattag cgctgtgaaa    4620
gagcgcgata tcgagcagaa attgaagcaa gtgattaacg aatgggacaa caaaacgttc    4680
acgtttggga gcttcaagac cagaggggaa ctcctcctgc ggggcgactc cacttccgaa    4740
attatcgcga acatggaaga ctcgcttatg cttctcggct cgctgttgtc caacaggtac    4800
aatatgccat ttaaggcaca gattcaaaaa tgggtgcaat acctcagcaa ctcgacggat    4860
attatcgagt catggatgac cgtgcaaaac ttgtggattt atctggaagc ggtgtttgtg    4920
ggaggagaca tcgctaaaca gctcccgaaa gaagcaaagc gcttttcgaa cattgacaaa    4980
agctgggtga aaattatgac gagggcccac gaagtgccct ccgtcgtgca atgttgtgtc    5040
ggcgacgaga ccctcggcca gctgcttccc cacctcctcg atcagctcga aatttgtcag    5100
aaatcgttga cgggatatct tgagaaaaaa aggttgtgct cccgagatt ttttttcgtg    5160 agcgaccccg ctctcttgga gattttgggt caggcctccg attcgcatac catccaagca    5220
catctgctca acgtctttga caacattaag tcagtgaagt tcatgaaaaa gatttacgat    5280
agaatcctta gcatctcatc ccaagaggga gaaactattg aactggacaa gcccgtgatg    5340
gcagagggga acgtcgaggt ctggcttaat tcgttgctgg aagagtccca atcatcactg    5400
catcttgtca ttcgccaagc cgcggccaat atccaggaaa cggggttcca gctcactgaa    5460
ttcctttcaa gcttcccggc tcaggtcgga ctgttgggaa ttcaaatgat ttggacgcgg    5520
gattccgaag aggctttgag aaacgcgaag tttgacaaaa aaattatgca aaagaccaat    5580
caggctttct tggaactcct taatacgttg attgacgtca ccactagaga tttgtcatcg    5640
acggagcggg tgaagtacga aaccctgatc acgatccacg tgcatcagag agacatcttc    5700
gacgacttgt gtcatatgca cattaagagc ccaatggact ttgaatggct gaaacaatgt    5760
agattctact tcaacgagga ctccgataaa atgatgattc atatcacgga cgtggcattt    5820
atctatcaaa acgaattctt gggatgcact gatagactcg tgattactcc ccttaccgac    5880
agatgttata ttacttttggc gcaagcactg ggcatgtcaa tgggtggcgc accggccgga    5940
cccgctggca ctggtaaaac cgaaaccacc aaggatatgg ggcggtgtct ggggaaatac    6000
gtcgtggtgt ttaattgctc cgaccagatg gatttccgcg gcctcggccg catctttaag    6060
ggcctcgccc aatcgggctc atgggggtgc tttgacgagt tcaatagaat tgacctgcct    6120
gtcttgtcgg tcgcagccca acaaatttca attatcttga cctgcaaaaa ggagcataaa    6180
aaatcgttta tctttactga cggggataat gtcactatga atccggagtt cggactcttt    6240
ttgacgatga acccgggtta cgccggaaga caagaactgc ctgagaatct caaaatcaat    6300
tttagatccg tggcaatgat ggtccccgac cgccaaatta ttattagagt caaacttgcc    6360
tcgtgtgggt tcattgataa cgtcgtgctc gcccggaaat ttttttaccct gtacaaactg    6420 tgtgaagaac aactttcgaa gcaggtgcat tatgatttcg ggcttcggaa tatcctgagc    6480
gtgctccgga cgctgggtgc agcgaaaagg gccaacccaa tggacaccga gtcaactatt    6540
gtgatgcggg tccttagaga catgaatttg tccaaactga ttgatgagga cgagcctctg    6600
ttcctttcgc tgatcgagga tcttttcccg aacattcttc tggataaagc tggatatcct    6660
gaattggaag cggcaatcag cagacaggtg gaggaagcag gtttgatcaa ccatcccccT    6720
tggaaattga aagtcatcca gttgttcgag acgcagcgcg tcaggcacgg tatgatgacc    6780
ctggggccct caggcgcagg gaagactacg tgtatccaca ctttgatgag ggcgatgact    6840
```

```
gattgcggta agccccacag ggaaatgaga atgaatccaa aagcaattac tgctccacag   6900
atgtttggtc ggctcgacgt ggccacgaat gattggacgg acggaatttt tagcactttg   6960
tggagaaaaa ctctcagagc taaaaagggt gaacatatct ggattattct cgatggcccg   7020
gtggatgcga tttggatcga gaatctgaat tcagtgctgg acgacaataa aactttgacg   7080
ctcgcgaacg gtgatcggat tcccatggcc cctaattgta aaattatttt cgaacctcac   7140
aacattgata atgctagccc ggccactgtc tccaggaacg ggatggtgtt tatgtcgtcg   7200
tccattttgg actggtcccc gattctggag ggcttcctga agaaaaggag cccacaggag   7260
gcagaaattt tgagacagtt gtacactgag tccttcccag atctctatcg gttctgcatc   7320
cagaacctcg aatacaaaat ggaggtgctc gaggcctttg tcattaccca gtcaattaat   7380
atgttgcagg ggcttattcc ccttaaggag caggggggtg aggtgagcca ggcccatctg   7440
gggcgcttgt tcgtctttgc tcttctgtgg tcggccgggg ctgctctgga gcttgacggc   7500
cggagacggt tggaattgtg gctgaggagc agacctacgg gtacgctcga attgccccg   7560 ccagccgggc ccgggggacac ggcgttcgat tactacgtcg cgcccgatgg gacttggacc   7620
cactggaaca ctcggacgca agagtatttg tatccctccg ataccacccc ggaatacggt   7680
agcatcctcg tgcctaacgt cgataacgtc cgcacggact ttcttatcca aaccatcgcg   7740
aagcagggca aggcagtgct gttgattggg gagcaaggca ctgccaaaac ggtgatcatc   7800 aaaggttttca tgtcgaagta tgatccagaa tgccatatga ttaaatcgct gaacttcagc   7860
tccgcgacta ccccgctcat gtttcaacgc accatcgagt cgtacgtcga taagaggatg   7920
ggcaccacgt acggtccgcc agccggtaaa aaaatgaccg tctttattga tgatgtgaat   7980
atgcctatca ttaatgagtg gggtgatcag gtcactaatg aaatcgtgcg ccagcttatg   8040
gaacagaatg gcttttacaa tctcgagaaa cccggcgaat tcacttcaat tgtggatatc   8100
caatttctgg ctgccatgat tcacccaggt ggaggaagga atgacattcc gcagagactc   8160
aaacggcagt tcagcatttt taattgcact ctcccttcgg aggcgtcagt ggacaagatc   8220
tttggagtca tcggggtcgg tcattactgt acccagagag gattttcgga ggaggtccgc   8280
gactcggtca ccaagcttgt ccctcttact aggcgcctct ggcaaatgac taagatcaag   8340
atgcttccca ccccggcgaa attccactac gtgtttaatc ttagggacct gtcccgggtc   8400
tggcagggca tgttgaacac tacgtcggag gtgattaagg aacccaacga tttgcttaaa   8460
ctgtggaagc acgagtgcaa acgcgtcatc gctgaccgct ttactgtgtc ctcagacgtg   8520
acctggtttg acaaagcctt ggtctccttg gtcgaggagg aatttggtga ggaaaaaaa   8580 ttgctggtgg attgcggaat tgacacttac ttcgtggatt tcctccgcga tgcaccagaa   8640
gctgccggtg aaacctcgga ggaagcggac gccgagaccc ccaaaattta cgaaccgatt   8700
gaatcgttct cccacttgaa agagcggctc aacatgtttc tccaactgta taacgagtcg   8760 atcagggag ctgggatgga catggtgttc ttcgccgatg ccatggtcca ccttgtcaag   8820
atctcgcggg tcatccgcac gcctcaaggt aacgctctct tggtcggtgt gggagggagc   8880
ggcaaacaaa gcctcactcg cctcgcgtcg ttcattgcag gttatgtctc atttcaaatt   8940
actctcaccc gctcctataa tacttcgaat ttgatggagg atttgaaggt cctttatagg   9000
accgctgggc aacaaggcaa aggaatcacc ttcatcttca ccgacaacga aattaaggac   9060
gaatcctttt tggaatatat gaataatgtc ctcagctcgg gagaagtgag caacctgttt   9120
gcaagagatg agattgatga aatcaattcc gaccttgctt ccgtgatgaa aaaggagttc   9180
ccaaggtgcc tgcccaccaa tgagaatctt cacgactact ttatgagccg cgtccggcaa   9240
```

```
aatctgcata tcgtgttgtg tttctcaccc gtcggtgaga agtttagaaa tcgcgccctc  9300
aagtttccgg ctttgatctc aggctgcacc attgattggt tttccagatg gccgaaggat  9360
gcactggtgg cagtctccga acatttcctg acttcatacg atattgactg ttcactggaa  9420
attaagaagg aagtggtcca atgcatggga tcattccagg atggcgtcgc agaaaagtgt  9480
gtggattact tccaaaggtt tcggaggagc acccacgtca cgcccaaatc atatttgtca  9540
ttcattcagg gctacaaatt tatctacggc gaaaagcacg tcgaggtccg gactttggca  9600
aacaggatga acaccggcct tgaaaaactg aaggaagcta gcgagtccgt ggctgcactc  9660
tcgaaggagc tggaggccaa agaaaaagag ctgcaagtcg ctaatgacaa ggccgacatg  9720
gtcttgaaag aggtgactat gaaagcgcag gctgctgaga aggtgaaggc tgaggtgcaa  9780
aaggtgaaag accgggctca ggccatcgtg gactcaattt caaggataaa ggctatcgct  9840
gaggaaaagt tggaagccgc taagcccgca ttggaggagg cagaggctgc gcttcaaacc  9900
atcaggccct ccgacattgc gactgtgagg accctgggaa ggccgcccca tctcatcatg  9960
cggattatgg actgtgtgct cctcctcttc aacgcaagg tctcagcagt caaaatcgat  10020
cttgaaaaaa gctgtacgat gccctcctgg caagagtcgc ttaaacttat gactgcgggc  10080
aattttctcc agaatcttca acagttccct aaagacacca ttaacgaaga agtcattgaa  10140
tttctttcgc cgtatttcga gatgcccgac tataatatcg agactgccaa acgcgtgtgt  10200
ggaaacgtcg cgggactgtg tagctggacg aaagcaatgg caagcttctt ttcgattaat  10260
aaagaagtcc tgccactgaa agccaatctc gtggtccaag aaaaccgcca ccttttggca  10320
atgcaagatc tccaaaaggc tcaagccgaa ttggacgata agcaagccga gctggacgtg  10380
gtccaggccg aatacgaaca agcaatgacg gagaagcaga cgttgctgga ggacgcagaa  10440
cggtgcaggc ataagatgca gacggcttcg acgcttattt cgggtcttgc cggagaaaag  10500
gaaaggtgga ccgagcaatc gcaagagttc gcagcccaaa ctaaaagact tgtgggagac  10560
gtcttgctcg ccactgcctt tttgtcatac agcggcccat tcaaccagga gttcagggac  10620
ctcttgctta acgattggag aaaggaaatg aaggctcgca aaatcccgtt tggaaagaac  10680
ctgaatttga gcgaaatgct tattgacgca ccgaccattt ccgagtggaa tctgcaaggc  10740
ctcccgaatg acgatcttag catccaaaac ggtattattg tgaccaaggc ctccaggtat  10800
ccactgttga tcgacccgca aactcaagga agatctggaa ttaaaaacaa ggaatcgcgg  10860
aacgaacttc agatcactag cctgaaccac aagtacttcc gcaaccatct cgaggattcc  10920
ctcagcctgg gccgccccct tctgatcgaa gacgtcggtg aggagctcga tcctgcgctc  10980
gataacgtcc tcgagaggaa ctttatcaaa acgggatcaa cgttcaaggt gaaagtcgga  11040
gacaaggaag tggatgtcct ggacgggttt cgcctctaca ttacgactaa gttgccaaac  11100
cctgcttaca cgcccgagat ctcggcaagg acgtcaatca ttgattttac cgtgaccatg  11160
aaaggcctcg aggatcagct tctcgggcgg gtgattctga ctgaaaagca ggaactcgaa  11220
aaagaaagaa cgcatcttat ggaggatgtg accgcgaata aacgccggat gaaagagctc  11280
gaagataacc ttctctacag gcttacctca acgcaaggtt ccctggtcga ggacgaatca  11340
cttattgtcg tgctgtccaa cactaagagg accgcggaag aggtgacgca gaagttggaa  11400
atttcagcag aaacggaagt gcagattaat tcggctcgcg aagaatatag accagtcgca  11460
actcgcggat cgattctcta ttttttgatc actgagatgc ggcttgtcaa tgaaatgtat  11520
caaacctcgc tgcgccagtt tcttggattg tttgacctgt cactcgcacg gagcgtcaaa  11580
```

```
tcgcccatca cgtcaaagcg cattgcgaat atcatcgaac atatgaccta cgaggtctat    11640
aagtatgccg cacggggatt gtacgaagag cacaagttcc tctttactct gctgctgacc    11700
cttaaaatcg acattcagag gaacagagtc aagcacgagg aattccttac gctgattaag    11760
ggaggagctt cactcgattt gaaggcgtgc ccacccaaac cgtccaagtg gattcttgac    11820
attacctggc tgaacctcgt cgagttgtcc aaattgaggc agttctcaga tgtcctggat    11880
cagatctcgc ggaacgagaa aatgtggaaa atttggtttg ataaggaaaa cccggaggag    11940
gagcccctgc cgaatgcgta cgacaaatca cttgattgtt ttagaaggct ccttttgatt    12000
cggtcatggt gccctgacag gacgatcgcc caagctagaa agtacattgt ggactcgatg    12060
ggggaaaagt atgcagaggg agtcatcctg gatcttgaaa agacctggga agagtcagac    12120
cctagaactc ctcttatctg tctgctttcc atgggctcgg atccgacgga ttcaatcatc    12180
gcactcggca agcgcctcaa aatcgagacg cggtacgtgt caatgggtca aggacaagag    12240
gtgcatgcac gcaagttgct gcaacagacc atggcgaacg gtgggtgggc cctgcttcaa    12300
aactgccacc ttgggctgga cttcatggac gaattgatgg atattattat cgagacggag    12360
ttggtgcatg acgcttttag actctggatg actacggaag cccataagca gttccccatc    12420
accctgttgc agatgtcgat taagttcgca aatgatcccc cccagggttt gcgggctggt    12480
ctgaaaagga cgtattcggg agtgtcgcaa gatttgttgg atgtctcctc cgggtcgcaa    12540
tggaaaccaa tgttgtatgc cgtggccttc cttcattcca cggtgcaaga gcgccgcaaa    12600
ttcggggcgc ttggatggaa catcccttat gagttcaatc aagcagattt caatgccacc    12660
gtgcaattca tccagaatca ccttgacgat atggatgtga aaaagggtgt ctcatggacc    12720
acgatccgct atatgatcgg tgagattcag tatggcggtc gcgtgacgga cgattatgat    12780
aagcggttgt tgaacaccct tcgcgaaagtg tggttcagcg agaatatgtt cggacctgac    12840
ttctccttct accaaggcta taacattcca aagtgttcga ccgtcgataa ctacctccag    12900
tacattcaaa gccttcccgc atatgacagc cctgaggtct tcggtttgca cccgaatgcc    12960
gacattactt atcagagcaa gctggcaaag gacgtcctgg acaccatcct gggaatccag    13020
ccaaaagaca cgagcggtgg aggagacgag acgagggagg ccgtcgtggc cagattggca    13080
gacgacatgt tggagaaact gcctcccgac tatgtcccct ttgaggtgaa agaacggctg    13140
cagaaaatgg gtccttttcca gccgatgaac attttcctga ggcaggaaat tgatcggatg    13200
caaagagtgc tttcccttgt cagatcgacc ctgacggaac tgaaacttgc tatcgatggc    13260
actatcatta tgtcggagaa cttgagggat gccttggatt gcatgttcga tgcgagaatc    13320
ccggcatggt ggaagaaagc ttcatggatt tcatccactc tcgggttctg gttcacggaa    13380
cttatcgaga gaaactcaca gtttaccagc tgggtgttca acggtagacc acattgcttt    13440
tggatgactg gtttcttcaa cccgcagggc ttttttgaccg ccatgaggca ggagattacc    13500
cgcgcaaata aaggttgggc tttggacaac atggtcctct gcaacgaagt cactaaatgg    13560
atgaaggacg atatctccgc gccgccaacg gagggcgtgt acgtctacgg gttgtatttg    13620
gagggagccg gatgggataa agaaacatg aagcttatcg aaagcaagcc taaggtgttg    13680
ttcgaactca tgccagtgat cagaatttat gcggaaaaca atacgcttcg ggacccgcgg    13740
ttttattcct gccctatcta taaaaagcct gtccggaccg acctcaacta tattgcagcc    13800
gtggatctgc ggaccgccca aaccccgaa cattgggtgc tgagggggt ggcgcttctc    13860 tgcgacgtga aatag                                                    13875
```

```
<210> SEQ ID NO 10
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 10
atgttccgga ttggtcgccg ccagctttgg aagcacagcg tcactcgcgt cctgactcag      60
aggctgaagg gtgaaaaaga ggccaaaagg gccctgctcg atgcaagaca caattatctc     120
tttgcaattg tggcatcatg cctcgatctt aataagactg aagtcgagga cgcgattctt     180
gaagggaatc aaatcgaaag gattgatcag ctcttcgctg tgggtgggct tagacatctt     240 atgtttttact accaggacgt cgaagaagca gaaaccggcc aattggggag cctcggtggt     300
gtcaatctgg tctccggaaa gattaaaaaa ccgaaggtct tcgtcactga gggtaacgac     360
gtcgcgctca cgggagtctg cgtctttttt attagaactg acccttcaaa agccatcacc     420
cccgacaaca ttcaccagga ggtgtcattc aacatgctgg acgcagcaga cggaggtctt     480
ctgaattcag tcaggcggct tctttccgat attttcattc cggcgcttcg ggccacctcg     540
cacggatggg gcgaactcga aggcctccag gatgctgcga acattagaca ggaattcctc     600
agctcgttgg agggatttgt gaacgtgttg tcaggggcac aggaaagcct gaaagagaag     660
gtgaacctca ggaaatgtga catccttgaa ctgaaaaccc ttaaggagcc aactgattat     720
ttgactctgg ctaataatcc tgaaacccctt ggtaaaatcg aggattgtat gaaagtgtgg     780
atcaaacaga ccgaacaagt cttggccgag aacaatcaac tgctcaagga ggcagacgac     840
gtgggtcctc gggcagaact tgagcattgg aaaaaacggc tgtccaagtt caattatctg     900
cttgaacagc ttaaaagccc ggacgtcaaa gccgtgcttg ctgtcctggc cgccgctaaa     960
tcgaaacttt tgaaaacttg gcgggaaatg gatatccgga ttaccgatgc tactaacgag    1020
gctaaagaca atgtgaagta cttgtacacg ttggagaagt gttgtgatcc tttgtattcc    1080
tcagatccgc tcagcatgat ggacgcgatt ccaaccccta ttaatgcaat taagatgatt    1140
tattcgatca gccattatta caatacctca gagaaaatta cctcactgtt cgtcaaagtg    1200
acgaatcaga ttatctccgc gtgtaaagca tatattacca caacggcac tgcatcaatc    1260 tggaatcaac cacaagacgt cgtcgaagaa aaaattcttt ccgctatcaa gctgaaacaa    1320
gaatatcagc tctgctttca caaactaaa caaaaactaa acagaaccc caatgccaaa    1380 cagtttgatt ttagcgaaat gtatatcttt ggaaagtttg agacgttcca tcggaggttg    1440
gcgaagatta tcgatatctt caccacgctc aagacttatt cagtgctcca ggattcaacc    1500
atcgaaggat tggaggatat ggctacgaag taccaaggaa ttgtcgcaac tatcaaaaaa    1560
aaggaatata acttcttgga tcagcgcaaa atggatttcg atcaggatta cgaggagttt    1620
tgtaagcaaa cgaatgacct ccacaatgaa ctcaggaaat tcatggacgt gacgttcgcc    1680
aaaattcaaa atactaatca agctttgagg atgctcaaga gttcgaaag gcttaacatc    1740 ccaaatcttg gaattgacga taaataccaa cttatcctcg agaactatgg agctgatatc    1800
gacatgattt ccaaattgta cacgaagcag aagtatgacc ctcccccttgc ccggaatcag    1860 cctccgattg caggtaagat cctgtgggcc cgccagctgt ttcacaggat ccaacaacct    1920
atgcagcttt ttcagcagca ccccgcagtc ctgtcgaccg ctgaggccaa acctattatt    1980
agatcatata accgcatggc taaagtcctc ctggagttcg aggtcctgtt ccatagagcc    2040
tggcttaggc agatcgagga aatccacgtc ggcttggagg cttccctgct tgtcaaggcc    2100
```

```
ccggggacgg gcgagctctt cgtgaatttt gatccacaga ttttgatttt gtttcgcgag    2160
acggaatgca tggcacaaat gggtctggaa gtctcgccac ttgctacctc gttgtttcag    2220
aaaagagata ggtacaagcg caacttttcg aacatgaaga tgatgctcgc agaatatcaa    2280
cgggtgaagt ccaaaatccc ggccgcaatc gagcagctca tcgtcccgca cctcgctaaa    2340
gtcgacgaag ccttgcaacc tggactggca gcgctcacgt ggacgtcgct caatatcgag    2400
gcctacctcg aaaatacgtt tgctaagatc aaagacctcg aattgctcct tgatcgggtc    2460
aacgatctga ttgagtttag gattgacgca atcctggagg aaatgtcgtc aaccccctctc   2520 tgtcagctcc cgcaagaaga gccacttacg tgcgaggaat ttttgcaaat gacgaaagac    2580
ctgtgcgtca atggagccca gattcttcac ttcaagtcgt cattggtgga ggaggccgtg    2640
aatgagctcg tcaacatgtt gctcgatgtg gaagtgcttt cggaggagga gtcggaaaaa    2700
atctccaatg agaatagcgt caactataag aacgaatcaa gcgcaaagcg ggaagagggt    2760
aacttcgata ccctgactag ctcaattaac gctagagcga acgctttgct ccttacgacg    2820
gtgactcgga aaaaaaaga gaccgagatg ttgggtgagg aggccaggga gctgctctcg    2880
cacttcaacc atcagaacat ggacgcactc cttaaggtga ccaggaatac tttggaggct    2940
atccgcaaga ggatccattc gagccatact atcaacttcc gcgactccaa tagcgcgtcg    3000
aacatgaaac aaaattcact tccaatcttc agagcgagcg tcacgcttgc cattcctaat    3060
atcgtcatgg ctcctgcact ggaagatgtg cagcaaactt tgaacaaggc cgtggagtgt    3120
atcatttcgg tcccgaaggg ggtgagacaa tggagcagcg agcttcttag caaaaaaaag    3180
attcaagaac gcaagatggc agccctccag tccaacgaag attcagattc agacgtcgaa    3240
atgggtgaaa atgagttgca agatacgttg gaaatcgcga gcgtgaatct tcccattccc    3300
gtccagacta aaaactatta caagaacgtc agcgaaaata aggagattgt caaacttgtc    3360
tcggtccttt caactattat taactcgacg aaaaaagagg tgatcacttc aatggattgc    3420
tttaaaaggt ataaccatat ctggcagaag ggtaaggagg aagcaatcaa aacgttcatc    3480
acccagagcc cccttctctc agaatttgaa agccaaatcc tctatttcca aaaccttgag    3540
caagaaatca acgcggagcc tgaatacgtc tgcgtggggt caattgcgct gtatacggcg    3600
gacctcaagt tcgcgctgac cgcggaaacc aaggcatgga tggtggtcat cggaaggcat    3660
tgtaacaaaa aatatcgctc ggagatggag aacatcttca tgttgatcga ggagttcaac    3720
aagaaactga acagaccgat taaggacctg gatgacatca ggattgccat ggcggcgctc    3780
aaagaaatta gagaggaaca aatttccatc gatttccagg tcggcccaat cgaagaatcc    3840
tatgcattgc tcaacaggta tggccttctg atcgcccgcg aggagattga caaagtggac    3900
acgctgcatt atgcttggga aaaacttctt gctagggcgg gagaagtcca aaacaagctc    3960
gtgagccttc agccaagctt caagaaagag ctgatcagcg ccgtcgaggt gtttcttcag    4020
gattgtcatc aattttacct cgactacgat ttgaatggtc ccatggcatc gggtctgaaa    4080
ccacaagagg cttcggatcg gctcatcatg tttcaaaatc agtttgataa tatctacaga    4140
aaatacatta cgtacacggg aggtgaagag cttttcggac ttcctgcaac tcaatatccg    4200
caacttcttg agatcaaaaa gcaacttaac cttctccaga aaatttatac tctgtataat    4260
tcagtcattg agactgtcaa cagctactac gacatcttgt ggtcagaggt caatattgag    4320
aaaatcaata atgagttgct tgaatttcag aatagatgtc ggaagcttcc tcgggccctc    4380
aaagactggc aggcttttttt ggaccttaaa aaaatcatcg atgatttctc cgaatgttgc    4440
cccttgctcg agtatatggc tagcaaagcg atgatggaac gccattggga gcggatcacg    4500
```

```
acgcttactg gacatagcct ggatgtcggc aacgaatcct ttaaacttcg gaacatcatg   4560
gaggcgccgc ttcttaaata taaggaggaa attgaggaca tttgtatttc ggcggtgaaa   4620
gaaagggaca ttgagcagaa actgaaacag gtgattaacg agtgggacaa taagactttc   4680
actttcggtt cctttaaaac gagaggtgaa ctcctgctga gaggagactc gacgtcagag   4740
attattgcta atatggaaga ttcacttatg ctgttgggct cacttctctc aaataggtat   4800
aacatgccgt ttaaagcaca gatccagaaa tgggtgcaat accttagcaa ctccactgat   4860
attattgaga gctggatgac tgtgcaaaac ttgtggatct atcttgaggc agtgtttgtg   4920
gggggtgata tcgcgaaaca actgcctaaa gaggccaagc ggttctcaaa catcgataaa   4980
tcgtgggtca aaattatgac gcgggcacac gaggtcccta gcgtcgtcca atgctgtgtg   5040
ggggacgaga ctctcgggca actgcttccg cacctgctgg atcagctgga gatctgtcag   5100
aaatcgctga ctggatacct cgaaaagaaa cgcttgtgtt tccccaggtt ctttttttgtg   5160 tcagaccctg ccttgttgga aattttgggg caggcaagcg acagccacac tattcaagcc   5220
cacttgttga acgtctttga taacattaaa tccgtgaagt ttcatgagaa aatttacgat   5280
agaatcttgt cgattagcag ccaggagggt gaaactatcg agctggataa acctgtcatg   5340
gctgagggta atgtcgaagt ctggttgaac agccttctgg aggagtccca gagctcactc   5400
catttggtca ttagacaggc tgcagctaat atccaggaga ctggatttca actgacggag   5460
tttctctcaa gctttcctgc tcaggtgggt ctgcttggaa tccaaatgat ctggacccgc   5520
gattcggagg aggctctgcg gaacgctaag ttcgataaaa agattatgca gaaaacgaat   5580
caggcatttc tggaactctt gaatacccctg attgacgtga cgactcgcga ccttagctca   5640
accgagaggg tcaaatatga gaccctcatt accattcatg tgcatcaacg cgatattttt   5700
gacgacctct gccacatgca tattaaatca ccgatggact tcgagtggct gaagcaatgc   5760
agattttatt tcaacgagga ttcggataaa atgatgatcc atatcacgga tgtcgccttc   5820
atctaccaga atgagttcct tggatgcact gaccgcttgg tcatcactcc attgaccgac   5880
cgctgctaca ttactcttgc ccaggctttg gggatgtcga tgggtggggc cccagcgggc   5940
cctgcaggta cgggcaaaac ggaaactacg aaggacatgg ggaggtgcct tgggaagtac   6000
gtggtcgtgt tcaattgctc agatcagatg gattttaggg ggctcggaag aattttcaaa   6060
ggcctggctc agtccggctc ctgggggtgt ttcgacgaat ttaatcggat tgacttgcct   6120
gtgctttccg tggctgccca gcaaatcagc attattctca cgtgtaagaa ggagcacaag   6180
aaatcattta ttttcactga cggagataac gtgaccatga atcctgaatt cggccttttc   6240
ctcacgatga acccaggtta tgcgggtcgg caggagttgc ctgaaaattt gaagattaac   6300
tttcgctccg tcgctatgat ggtcccggac cggcaaatca ttattagagt gaagttggcc   6360
tcgtgcgggt tcatcgacaa cgtcgtgctg gcaagaaaat tctttacgct ctataagctc   6420
tgcgaagaac agctttcaaa acaggtccat tacgactttg gactcagaaa tattctctca   6480
gtgctcagga cgttgggtgc cgcaaagagg gccaatccca tggataccga atcaaccatc   6540
gtgatgagag tcctgagaga catgaatttg tccaagctta tcgacgagga cgaaccgctc   6600
ttcctgagct tgatcgagga cctttttccca aacatttttgc tcgataaagc gggctaccca   6660
gaattggaag ccgccatttc gcggcaagtc gaggaagcag gtctgatcaa tcatccgcct   6720
tggaagctga agtcattcca attgttcgaa acccaacggg tccggcatgg gatgatgacc   6780
ctcggtccat cgggcgcggg taaaactacc tgtatccaca ctctcatgag ggcaatgacc   6840
```

```
gactgtggaa agccacaccg ggagatgagg atgaacccta aagctattac cgcgcccag    6900 atgttcggaa gactcgatgt ggccaccaat gattggacgg atgggatttt ttcgactttg   6960
tggcggaaga ctttgcgggc caagaagggg gaacacatct ggatcattct tgacggaccg   7020
gtggatgcca tttggatcga aaatctgaat tcggtgttgg acgataataa aactctgacc   7080
cttgcgaatg gtgatcgcat tccgatggcg cccaactgca aaattatctt cgagccccat   7140
aatatcgata tgcttcgcc agctactgtg tccaggaacg ggatggtgtt tatgtcatcc    7200
tcgatcctgg attggagccc aatcctggag gggtttctca aaaaacggtc gcctcaggag   7260
gccgaaattc tcagacagct ttacaccgag tccttcccgg atctctacag gttctgcatc   7320
caaaatctcg aatataagat ggaagtcctc gaagccttcg tgatcaccca atccatcaat   7380
atgcttcagg gactcatccc ccttaaggag caaggaggag aggtgtcgca ggcccatctg   7440
ggaagacttt ttgtcttcgc attgttgtgg agcgccgggg cagctctcga acttgacgga   7500
cgcaggcgcc tggaactttg gcttaggtcc aggcccaccg gaacgctgga acttcctccg   7560
cctgctggcc ccgggggacac tgcttttgac tattatgtcg cccctgacgg tacctggacg   7620
cactggaaca ccaggactca ggaatatctg tacccttcag acaccacgcc cgagtacggg   7680
tccatcttgg tccctaacgt cgacaacgtg agaactgact ttcttatcca gactatcgcg   7740
aagcaaggca aagcagtcct cctgatcggc gaacaaggaa cggctaagac ggtcatcatt   7800
aagggtttca tgtcaaagta tgatcctgag tgccacatga ttaaatcgtt gaattttcc    7860 tcggcgacga cgcccttgat gtttcaacgc actattgagt cgtacgtgga taaagaatg    7920 gggaccacgt acgggccccc ggcgggaaag aagatgactg tgttcatcga cgacgtcaat   7980
atgccgatca tcaacgagtg gggggaccag gtcacgaacg agatcgtgag gcaattgatg   8040
gaacagaatg gtttctacaa tcttgagaag cctggagagt tcacttcaat cgtcgatatt   8100
cagtttctgg ccgctatgat ccatccagga ggtggtcgga atgacattcc gcagaggctc   8160
aaaaggcagt tttcgatttt taattgcact ttgcccagcg aggccagcgt ggataaaatc   8220
ttcggggtga ttggagtggg tcattactgt actcagcggg gattctccga ggaggtgaga   8280
gactcggtca cgaagcttgt cccattgact cggcggcttt ggcaaatgac caagattaag   8340
atgctgccaa ctcccgccaa attccattat gtgttcaatc tcagggacct ttcgcgcgtg   8400
tggcaaggca tgctcaacac cactagcgag gtcattaaag agcccaacga ccttttgaaa   8460
ttgtggaagc atgagtgcaa acgcgtcatc gcagacagat ttacggtgtc ctcagacgtg   8520
acttggttcg acaaagccct cgtgtccctg gtggaagagg aatttggaga ggaaaaaaag   8580
ctgctggtgg actgcggtat tgatacttat ttcgtggact ttcttcggga cgcaccggaa   8640
gcagccggag aaacgtcgga ggaagctgac gccgagactc ctaagatcta tgagcccatc   8700
gagagcttta gccacctcaa agaaaggctt aacatgttcc tccaattgta taatgagtcg   8760
attagaggtg ccggcatgga tatggtgttc tttgctgatg cgatggtgca cctcgtcaaa   8820
atttcgcggg tgatccggac tccacaggga aatgccctgc ttgtgggcgt cggcggatca   8880
gggaaacagt cgctcacgcg cttggcaagc tttatcgccg gttacgtctc attccagatc   8940
actctgacga gatcatataa tacttcgaac ttgatggaag atttgaaagt gttgtaccgc   9000
acggcgggcc aacaagggaa agggattacg ttcattttca ccgataacga aatcaaagac   9060
gaatcgtttc tcgaatacat gaacaacgtc ctgagctccg gggaggtgtc caatctgttt   9120
gctagggatg agattgacga aattaattca gaccttgcaa gcgtgatgaa gaaagagttc   9180
ccgcgctgcc tccccacgaa cgaaaacctg cacgattatt tcatgagcag agtccgccag   9240
```

```
aaccttcata tcgtgctttg ttttagccca gtcggagaga agtttcgaa tagagcactt    9300 aaatttccgg cgctgatctc cgggtgcacc atcgattggt tttcccgctg gcctaaagac    9360
gctctggtcg ccgtgtccga gcactttctc acttcgtatg atattgattg ctcactcgaa    9420
atcaagaagg aggtggtgca gtgcatgggg agcttccaag atggtgtggc agagaagtgc    9480
gtcgattact tccaaaggtt tagacgctcg actcacgtca ctcctaagtc atatctgagc    9540
tttattcaag gttataaatt tatctacggc gaaaagcacg tcgaggtccg gacccttgct    9600
aacagaatga acacggggct tgaaaagttg aaggaagctt cagaatcggt ggcagcactc    9660
tccaaggaac tcgaggccaa agagaaagaa cttcaagtcg caaacgataa agcggatatg    9720
gtcctcaaag aagtgaccat gaaggcacaa gcggcagaaa aagtgaaggc ggaggtgcaa    9780
aaagtgaagg atcgcgcgca agcaatcgtc gatagcatct caaaagacaa ggctattgcg    9840
gaggagaagc tggaggccgc caagcctgct ctggaggaag cagaggcagc tcttcagacc    9900
attcgcccta gcgatatcgc taccgtgaga actcttggta ggccccccca cttgattatg    9960
aggattatgg attgcgtgct tctccttttt caacggaagg tgtcggcggt gaagatcgac   10020
ttggagaagt catgtactat gccgagctgg caagaatcat tgaaattgat gaccgcagga   10080
aacttcttgc agaacctcca acagttccca aaggatacca tcaatgaaga agtcattgaa   10140
tttctctccc catattttga aatgccagac tataatattg aaacggccaa aagggtgtgt   10200
ggaaacgtgg cgggactgtg ctcctggacg aaggcaatgg cgtcgttttt ctcgatcaac   10260
aaggaggtgc ttccgttgaa agcaaacctc gtggtccaag agaaccggca cctgctggcc   10320
atgcaggacc ttcagaaggc tcaagccgag ctggacgaca agcaggcaga actggacgtc   10380
gtgcaagccg aatacgagca agcaatgacg gaaaagcaga cgttgttgga agatgcggaa   10440
cgctgccggc ataaaatgca gacggcttcg acgcttattt ccggactcgc tggggagaaa   10500
gaaaggtgga cggaacagtc acaagaattt gccgcccaaa ctaagagact ggtgggagac   10560
gtgcttctgg caactgcctt tctgtcgtac agcggcccat tcaatcagga attccgggat   10620
ctgttgctga atgattggag aaaagagatg aaagcccgga agatccccctt cgggaaaaat   10680 cttaatctct ccgaaatgct cattgatgcc cctaccatta gcgagtggaa tctccaagga   10740
ttgccgaatg acgatctgtc aattcaaaac ggcatcattg tgacgaaggc ctccaggtac   10800
ccacttctta tcgatccgca aacccagggg aaaatctgga ttaagaataa agaatcgcgg   10860
aacgagctcc agattacctc acttaatcac aaatatttca ggaaccacct tgaggattca   10920
ctgtcgctcg gcggcctct gttgattgag gatgtgggtg aggaactgga tccagctttg   10980
gataatgtcc ttgaacgcaa cttcattaag accggatcaa cctttaaagt caaggtcggc   11040
gataaagagg tggatgtgct ggacggcttt agactctata ttacgactaa gcttcctaat   11100
cctgcgtaca cgccagaaat ttccgcgagg accagcatca tcgacttcac cgtcacgatg   11160
aagggactcg aggaccaatt gctggggagg gtcatcctca ctgaaaagca agaacttgag   11220
aaagagagaa cgcacctcat ggaagatgtg actgctaaca agagacggat gaaggaattg   11280
gaagataatt tgctgtatcg gctgacttca acccagggct cgctggtgga agacgaaagc   11340
cttattgtcg tcttgtcgaa tactaagcgc actgctgagg aagtcactca aaaactcgaa   11400
atttcagcgg agaccgaggt ccagatcaac tcggccaggg aggagtacag gccagtggcc   11460
actagaggtt cgatcttgta ttttcttatt accgagatgc ggctggtgaa tgaaatgtac   11520
caaacgtccc tgcggcaatt ccttggcctt ttcgacttga gccttgctcg ctcggtcaaa   11580
```

```
tcaccaatta cttccaaacg catcgcgaat atcattgagc acatgactta cgaagtgtac    11640
aagtacgcgg ccaggggact gtatgaggaa cacaaattcc tttttacgct cctcctcact    11700
ctcaaaattg atatccaacg caacagggtg aagcatgaag agtttcttac tttgatcaag    11760
ggaggtgcct cactcgacct caaggcctgc cctcccaaac cgtccaaatg gatcttggat    11820
attacttggt tgaacctcgt ggagcttagc aagctgcggc aattctcaga tgtcctcgat    11880
caaatttcac ggaatgaaaa aatgtggaag atttggtttg acaaagagaa ccccgaggag    11940
gaacctcttc ccaatgccta cgacaaaagc ctggactgtt ttaggcggct tctcttgatc    12000
aggtcatggt gtccggatcg cactatcgct caagcgcgga agtatatcgt cgactccatg    12060
ggtgaaaagt acgcagaggg ggtcatcctc gatctggaga aaacctggga agagtcagac    12120
ccaagaactc cgttgatttg cctcttgtca atgggctccg accctaccga ctccatcatc    12180
gcgctgggta aaaggctcaa aatcgaaacc cggtatgtca gcatggggca aggtcaggag    12240
gtgcacgcgc ggaagcttct ccaacagacg atggcaaatg ggggttgggc acttcttcag    12300
aactgccact tgggcctcga cttcatggat gaactgatgg acattattat tgagacggag    12360
ctggtccacg atgcattccg cctctggatg accacggaag cccacaaaca atttcctatc    12420
acgctgctgc agatgtccat taagtttgca aatgatcccc cccaaggtct tcgcgcaggc    12480
cttaagagaa cgtattcagg agtgtcacag gatctccttg atgtctcatc ggggtcacaa    12540
tggaaaccga tgctgtacgc ggtcgctttc cttcactcca ctgtgcagga gcggaggaag    12600
tttggagcgt tgggatggaa tatcccctac gaatttaacc aagccgactt taatgctact    12660
gtgcaattta ttcaaaacca tcttgacgac atggacgtca aaaagggagt gagctggact    12720
accatcagat acatgatcgg tgagattcag tatggaggga gggtcaccga cgactatgac    12780
aaacggcttt tgaacacgtt cgcaaaagtg tggttttcag agaacatgtt tggcccggat    12840
ttctcatttt atcaagggta taatatccct aagtgctcaa ccgtcgataa ctatctccag    12900
tatatccaga gccttcccgc ttatgattcc ccagaggtgt ttgggttgca cccgaatgcg    12960
gatatcactt accagagcaa acttgctaag gacgtgcttg atacgattct cggtattcaa    13020
cccaaagata cgagcggagg aggagacgaa accaggggag ccgtggtcgc taggctcgct    13080
gacgacatgc tcgagaaact tccgcccgac tacgtcccgt ttgaagtcaa ggaaaggttg    13140
cagaagatgg gtcccttcca gccaatgaac attttcctcc ggcaggagat tgatcgcatg    13200
cagagagtgc tgtcattggt ccggtcgacg ctcactgaac ttaaacttgc cattgacggg    13260
actatcatca tgagcgaaaa tctgcgggat gcattggatt gcatgtttga tgcgcggatc    13320
ccagcgtggt ggaagaaagc ttcctggatc agcagcactc tcgggttttg gtttaccgag    13380
ctcattgaaa gaaattcgca gttcacgtca tgggtctttta acgggcgccc tcattgcttt    13440
tggatgacgg gcttctttaa cccgcagggt tttctcacgg ctatgaggca ggaaatcact    13500
agggcaaata aaggctgggc gcttgacaac atggtcctgt gtaatgaggt gactaaatgg    13560
atgaaggacg acatcagcgc tcccccctacg gagggtgtgt atgtgtacgg cctctatttg    13620
gaaggtgctg gatgggataa gcgcaatatg aaacttattg agagcaaacc taaggtgctg    13680
tttgagctga tgcccgtgat ccggatctat gctgaaaata cacgttgag ggaccccagg    13740 ttctattcgt gtccgatcta caaaaagccg gtccgcaccg atttgaatta cattgctgct    13800
gtcgatcttc ggacggccca gacgcctgaa cattgggtcc tcaggggtgt ggcgctgctg    13860
tgtgatgtca aatag                                                     13875
```

<210> SEQ ID NO 11
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 11

```
atgtttcgga ttggcaggcg ccagctgtgg aagcactcag tgactcgggt ccttacgcag      60
cggttgaaag gcgagaagga ggcaaaacgg gcactgttgg acgcaaggca caactatttg     120
ttcgcaattg tggcatcgtg cttggatctt aacaaaacgg aggtcgaaga cgcgatcctg     180
gaggggaatc agattgagag gatcgaccaa ttgttcgccg tcggagggtt gcggcacttg     240
atgttctact atcaagacgt cgaggaggct gagaccggcc agctcgggag cttgggagga     300
gtcaaccttg tgtcgggcaa aatcaaaaaa cccaaggtct tcgtgacgga ggggaatgat     360
gtcgcactga ccggtgtgtg cgtcttcttt atccgcaccg atccgtcaaa agcaattacc     420
cccgacaata tccatcagga agtgtcgttc aatatgctcg atgcggctga tggtggcctc     480
cttaattcag tcagaaggct tctctcagat atttttattc ccgccctccg ggctacgtcg     540
catggctggg gggagctgga ggggcttcaa gacgcagcta atattagaca ggagtttctt     600
tcctcactcg agggcttcgt caatgtcctg tccggcgcgc aggaatcact caaagaaaaa     660
gtcaacctca gaaatgtgaa tatcctcgaa cttaaaaccc ttaaagaacc gaccgattac     720
ctcacgttgg caaataaccc cgaaactctg ggcaaaattg aagattgcat gaaagtgtgg     780
atcaagcaaa ctgagcaggt cctcgccgag aataaccagc tgctgaagga ggcggatgac     840
gtgggacctc gcgcggaact ggaacactgg aagaaacggc tttcaaaatt caactacctt     900
ctggaacagc ttaaatcccc tgatgtgaag gccgtcctgg ccgtgctcgc ggccgccaaa     960
agcaagctgt tgaagacttg gcgggagatg gacatcagaa tcacggacgc gaccaacgaa    1020
gccaaggaca atgtcaagta cctctacacg cttgagaaat gttgtgatcc cctctattca    1080
agcgatcctc ttagcatgat ggacgctatc ccaactctta tcaacgctat taaaatgatc    1140
tatagcatta gccactatta taacacttca gagaaaatca cgagcctctt cgtgaaggtc    1200
actaatcaaa tcatttccgc ttgtaaagcc tacattacta taacggaac ggcatcgatc    1260
tggaaccagc cgcaagacgt ggtggaggaa aaaatccttt ccgcaattaa gcttaaacag    1320
gagtatcagc tttgctttca caagacgaaa cagaagttga acaaaaccc aaacgcaaag    1380
caattcgatt tctcagagat gtatatttc ggaaagttcg aaacgtttca caggagactg    1440
gcgaaaatta tcgacatctt cactacgctt aaaacgtact cggtgctcca ggacagcact    1500
atcgagggtc ttgaggacat ggccaccaag tatcagggga tcgtcgccac cattaagaag    1560
aaggagtaca acttccttga ccaacggaaa atggatttg accaagatta tgaagaattc    1620
tgcaaacaaa ccaatgattt gcataacgaa cttcgcaaat tcatggacgt cacgtttgcg    1680
aaaatccaga atactaacca ggcgctgcgc atgctcaaaa agtttgagag ctgaacatc    1740
ccgaatctcg ggatcgacga caagtatcag ctcattcttg agaactacgg cgccgacatt    1800
gatatgatct cgaaactcta cacgaagcag aaatatgatc cgccgctcgc taggaaccag    1860
cctcctattg ccggaaagat tctctgggcg cgccagctgt tccatcgcat tcagcaacca    1920
atgcagcttt tccagcagca tcctgctgtg ctgtccaccg cagaggcgaa acctattatt    1980
agatcataca acaggatggc caaagtgttg ctggaatttg aggtgctgtt ccaccgggcc    2040
tggctgcgcc aaatcgagga gattcacgtg gggcttgagg catccctctt ggtgaaagct    2100
```

```
ccaggtaccg gggaactgtt cgtcaatttt gacccgcaaa ttttgattct ttttcgggag    2160
actgaatgta tggctcagat gggtttggag gtgtcaccct tggcaactag cctgtttcag    2220
aagagagatc gctataaaag gaacttcagc aacatgaaga tgatgctcgc agagtaccag    2280
cgcgtcaagt ccaagatccc agccgctatc gagcagctga tcgtccccca cctcgctaaa    2340
gtggacgaag cgttgcagcc tgggctcgca gcacttacgt ggactagcct caacatcgaa    2400
gcttatttgg agaatacttt cgcaaagatc aaggacctgg agcttctgct tgatagggtc    2460
aacgatttga tcgagttcag aattgatgct attctcgagg agatgtcctc aacgccgttg    2520
tgccagctcc cacaggaaga accattgact tgcgaggagt tcctgcaaat gaccaaggac    2580
ttgtgtgtca acggtgcgca gattttgcat tttaagtcaa gcttggtgga agaggcggtg    2640
aacgagcttg tcaacatgct cttggacgtc gaggtgttgt cagaggaaga atcggaaaaa    2700
atctcgaatg aaaattccgt gaactataaa aacgaatcgt ccgccaagcg ggaagaaggg    2760
aacttcgata ccctcacctc aagcattaac gcgagggcta acgccctcct gctcactact    2820
gtgacgcgga aaaaaagga aactgaaatg ctgggtgaag aggctcgcga acttttgtca    2880
cattttaatc accagaatat ggacgctctg ctcaaggtca ctcgcaacac tcttgaagcc    2940
atccgcaaac gcatccattc aagccacacg atcaacttca gggattccaa ctcggcaagc    3000
aacatgaaac agaactcact gcccattttt cgggcgtcag tgacgctcgc gatcccgaat    3060
atcgtcatgg cccctgccct tgaagatgtc caacaaactc tcaacaaagc ggtggaatgt    3120
attatttcag tgcctaaggg tgtcaggcaa tggagctcag agcttctgtc gaaaaaaaaa    3180
atccaggaga ggaaaatggc cgcttttgcag agcaatgagg actcggattc cgacgtcgaa    3240
atgggggaaa acgaactgca agacacgctg gaaattgcat cagtcaacct tccaattcct    3300
gtccaaacta aaaactatta taagaacgtc tcggaaaata aggagattgt caaactggtg    3360
agcgtgttga gcactattat taatagcacg aagaaagaag tgatcacgtc catggactgc    3420
ttcaagaggt ataaccatat ctggcagaaa ggtaaagagg aagccattaa gactttatt    3480
acgcaaagcc ccttgttgag cgagtttgag tcccagattc tctacttcca gaatctcgag    3540
caggagatca acgctgaacc cgagtatgtc tgtgtgggta gcattgcctt gtatactgcc    3600
gacctcaagt ttgctctcac ggctgaaact aaagcgtgga tggtcgtgat cgggaggcat    3660
tgtaacaaga agtaccgcag cgaaatggaa aatattttta tgctgatcga agagttcaac    3720
aaaaaactta atcggcccat caaagacttg gatgacattc ggattgcgat ggccgctctc    3780
aaagaaatca gggaggagca gatctccatt gactttcagg tcgggcctat tgaggagtcc    3840
tacgcactcc tgaacagata tggtctgctc atcgctcggg aagaaatcga caaagtggat    3900
accctgcatt atgcatggga aaaattgttg gcacgcgcag gggaggtcca gaacaaactt    3960
gtgagcctcc aaccttcgtt taaaaggag ctgatctccg cagtggaggt cttttttgcag    4020
gactgtcatc aattctatct tgattatgac ctcaatgggc ctatgcgag cgggctcaag    4080
cctcaagaag catccgatcg cttgattatg ttccagaatc agtttgacaa tatctaccgg    4140
aagtatatta cttataccgg cggtgaagaa ttgttcggtc ttcctgcgac ccagtacccg    4200
cagcttctcg aaattaagaa gcaactgaat ctcctccaaa aaatttacac gctttacaac    4260
agcgtgatcg aaaccgtgaa ctcgtattac gatatcctct ggtcggaagt caacattgaa    4320
aaaattaaca atgaactgct ggaatttcag aatagatgca gaaaattgcc acgggctctg    4380
aaagattggc aggcctttt ggacttgaag aaaattatcg acgactttc cgagtgctgc    4440
cccttgctgg aatatatggc ttccaaggcg atgatggaaa gacactggga aaggatcacg    4500
```

```
actctcaccg gtcactcgct tgatgtggga aacgaaagct ttaagctcag aaatatcatg    4560
gaggcaccgc tgttgaagta taaggaggag attgaagata tttgtatttc ggccgtgaag    4620
gaacgggaca tcgagcagaa actgaagcag gtgatcaatg aatgggataa caagactttt    4680
acctttgggt cctttaagac ccggggcgag ctccttctta gaggcgactc gacttccgaa    4740
atcatcgcaa atatggaaga ttccctgatg ctccttggat cattgttgtc aaatcgctac    4800
aacatgccct tcaaggccca gattcagaag tgggtccaat atctgtccaa cagcaccgac    4860
atcatcgaat cctggatgac tgtccagaac ctctggatct acctggaagc ggtgtttgtc    4920
ggcggggata tcgcgaaaca gttgccaaag gaggcgaaaa ggttctcgaa cattgataaa    4980
tcctgggtga aaattatgac tcgcgcccac gaagtgccaa gcgtcgtcca atgctgtgtg    5040
ggggatgaaa ccctgggcca actgctgccc caccttctgg accagcttga gatctgtcag    5100
aaatccctga cgggctacct cgaaaagaaa agactttgct tccccaggtt cttctttgtc    5160
tcagacccgg ccctgctgga gatcctcgga caagcatcgg actcgcatac cattcaggca    5220
catctcctta acgtgttcga taatatcaag tccgtgaaat tccacgaaaa gatttacgac    5280
cggatcctta gcattagcag ccaggaagga gaaactatcg agcttgacaa accagtgatg    5340
gctgaaggaa atgtcgaggt ctggttgaat tcccttcttg aagagtcgca gagctccctc    5400
catcttgtca ttcggcaagc cgcagcgaat attcaggaga cggggtttca acttaccgag    5460
tttcttttcga gcttccccgc tcaagtcggt ttgttgggca ttcagatgat ttggacgagg    5520
gactcggagg aggccctccg caatgctaag ttcgataaaa aaatcatgca aaaaccaac    5580
caggcattcc ttgagcttct taacactctt atcgatgtca ccacccggga cttgtcctcc    5640
acggagaggg tcaagtacga aacgcttatc actatccacg tgcaccaacg ggacatcttt    5700
gatgacttgt gccatatgca tatcaaatcg ccaatggatt tcgagtggct gaaacagtgc    5760
cggttctact tcaacgaaga ttccgataaa atgatgattc acattaccga tgtcgcattc    5820
atttaccaaa atgagttcct cggatgtact gatcggcttg tcattacgcc cctgactgac    5880
aggtgttaca tcactctggc gcaagctctg gtatgtcga tggggggcgc tccggcaggc    5940
cccgcgggta ccgggaagac cgaaactacg aaggatatgg gcagatgctt gggcaaatac    6000
gtggtcgtgt ttaactgttc agatcagatg gacttccggg ggctgggtcg catctttaag    6060
gggttggcac agtcaggctc ctgggatgt ttcgatgaat tcaatcggat cgacttgccg    6120
gtcttgagcg tggcagcgca acagatttca atcatcctta cctgtaagaa ggagcataag    6180
aagtcgttta ttttcacgga cggggacaac gtcaccatga acccagagtt tggattgttc    6240
ctcactatga atccggggta cgcaggccgc caagagctcc cagagaatct caaaattaat    6300
tttagatcag tggctatgat ggtcccggac agacagatca tcattcgggt gaaactcgcc    6360
agctgcggct tcatcgacaa cgtggtgttg gcgcggaaat ttttcacgct ctataaactc    6420
tgcgaagaac agctttcaaa acaggtcac tatgattttg gcctccggaa cattctctcc    6480
gtcctgagaa ctctcggagc ggcgaaaagg gcaaatccta tggataccga gtcgacgatt    6540
gtgatgaggg tcctgagaga tatgaacctt tcaaaactga tcgacgagga cgaaccactg    6600
tttctttcgt tgatcgagga tttgtttccg aacatccttc tggacaaggc tggttacccg    6660
gagcttgaag ctgcgatttc acggcaagtc gaagaggctg gattgattaa ccacccgcca    6720
tggaagctga aagtcatcca attgtttgag actcaaagag tccgccatgg catgatgact    6780
cttggtccta gcggcgcggg gaagacgacg tgtatccaca ctttgatgag ggcaatgacg    6840
```

```
gattgcggta aacctcacag agaaatgagg atgaatccaa aggctattac cgcaccgcag    6900
atgttcggaa ggttggacgt ggcgacgaat gactggactg acggcatttt ctcaacgttg    6960
tggcgcaaga ccttgagagc caaaaaagga gaacatatct ggattatcct cgacggcccc    7020
gtggatgcca tctggattga gaatcttaac tcggtgctcg atgataataa gaccctgacc    7080
ctggctaacg gagataggat cccgatggcc cctaattgca aaatcatctt tgaaccgcat    7140
aacattgata tgcatcacc agcgaccgtc tccaggaatg gtatggtgtt catgagctca    7200
agcattctgg attggtcgcc cattcttgag ggattcctca aaaaaagatc acctcaggag    7260
gcagagattt tgagacaact gtatacggaa tccttcccgg atctgtatag attttgtatc    7320
caaaatctcg agtataaaat ggaggtcctt gaggctttcg tcattacgca aagcatcaat    7380
atgctgcagg gtctgatccc tttgaaagaa caggggggag aggtgtcaca agctcacctg    7440
ggaagactct tcgtgttcgc gttgctctgg agcgcaggcg cagcgctcga gctggatgga    7500
aggaggaggc tcgaattgtg gctgcggagc cgccccacgg gcactttgga actgccgccc    7560
ccggccggtc cgggcgacac cgcattcgac tactacgtgg cgccagatgg tacgtggact    7620
cactggaata cgagaaccca agaatatctt tatccatcgg ataccacgcc tgagtatggt    7680
agcattctgg tccctaatgt cgataatgtc agaacggact tcctcatcca aactattgcc    7740
aaacagggta aagccgtcct cttgatcggt gaacagggta ccgcaaagac cgtcattatc    7800
aaagggttca tgtcaaaata tgacccggag tgtcatatga tcaagagcct caacttctca    7860
tcagccacca ctccgctgat gttccaaagg actatcgagt cgtatgtcga caagaggatg    7920
ggcacgacgt atgggcctcc tgccggcaag aagatgaccg tctttattga tgacgtgaat    7980
atgccgatta ttaacgaatg gggagatcag gtcactaatg aaatcgtccg ccaactgatg    8040
gagcagaacg ggttctataa tctggagaag cccggcgaat tacttcaat tgtggatatt    8100 cagttcttgg cagctatgat ccatccaggc ggaggccgga acgacatccc ccaacggctg    8160
aagagacagt ttagcatctt taactgcacg ttgccctcag aggcatcagt ggataagatc    8220
tttggagtga tcggagtggg tcactactgt acccagcggg gtttctcgga ggaggtccgc    8280
gacagcgtca ctaagctggt gcccttgacg agacggctct ggcagatgac gaagattaag    8340
atgctgccaa ctcccgcgaa gttccactac gtgtttaatc tgcgggactt gagccgcgtg    8400
tggcagggga tgctcaacac cacgtcagag gtcatcaaag agccgaacga cctgctcaag    8460
ttgtggaaac acgaatgcaa acgggtgatt gcggatcgct ttacggtctc ctccgatgtc    8520
acctggttcg ataaggcctt ggtgtcactt gtcgaagagg agttcggcga ggaaaaaaag    8580
cttctcgtcg actgcggaat tgatacgtat tttgtggact tcctgaggga tgccccgaa    8640 gcggcaggag agacttccga ggaagcagat gcggaaaccc ccaaaattta tgaaccgatc    8700
gagtcatttt cacacttgaa ggagcgcctg aacatgttcc tccaactcta taatgaatcg    8760
atccgcggtg caggaatgga catggtgttc tttgctgatg ctatggtcca tctggtcaaa    8820
atttcaagag tgattagaac tccgcaggc aatgcgctcc tcgtcggagt gggggatcc    8880 gggaagcaat cgctcacccg gctggcctcg ttcatcgcgg ggtatgtgtc gttccaaatt    8940
actctcacca ggagctacaa taccagcaac cttatggagg acctcaaggt gctctacagg    9000
actgctggcc agcagggtaa gggcattacc tttattttta ccgataatga aattaaagac    9060
gaatcctttt tggagtacat gaacaatgtc ctttcgtcag gtgaagtgtc aaacctcttc    9120
gcaagggatg aaattgacga gatcaacagc gacctggcta gcgtgatgaa aaaagaattt    9180
ccgcggtgtt tgccaaccaa tgaaaacttg catgactact tcatgtcacg ggtccgccaa    9240
```

```
aacttgcaca tcgtcctctg tttttcgcca gtgggtgaga agtttcggaa cagggcactt    9300
aagttcccgg cactcatctc cggctgtact atcgactggt tctcgaggtg gcctaaagat    9360
gcattggtgg cagtgagcga gcacttcttg acgtcctacg atattgactg ttcgttggaa    9420
attaagaaag aggtggtcca gtgtatgggg tcctttcagg atggagtcgc agaaaaatgc    9480
gtcgactatt tccagagatt caggagatca acgcatgtca ctccgaagtc atatttgagc    9540
tttattcaag gctacaagtt tatttacggg gaaaagcatg tcgaggtcag aacccttgca    9600
aatagaatga ataccggctt ggagaaactc aaagaagcgt cggaatcagt ggcggcattg    9660
tcaaaggagc tcgaagcaaa ggaaaaggaa ttgcaggtgg ctaacgacaa agcggacatg    9720
gtgctgaaag aagtgaccat gaaagcccaa gctgcagaga agtcaaagc tgaagtgcag    9780
aaggtgaagg accgcgcaca ggctatcgtc gattcgatct cgaaggataa ggctattgcc    9840
gaagagaaac ttgaggccgc caagcccgct cttgaagagg cggaagctgc attgcagacc    9900
attagaccct ccgacattgc aacggtcagg actctgggca ggcccctca cttgattatg    9960
agaatcatgg actgcgtgct ccttctgttc caaagaaagg tgtccgccgt gaagatcgat   10020
cttgagaagt catgcacgat gccgtcctgg caggaatcgc ttaagcttat gacggcaggt   10080
aactttctcc aaaatctcca gcaatttccc aaggatacca ttaacgaaga ggtcatcgaa   10140
ttcttgtcac cctactttga aatgcccgat tacaacattg agacggctaa acgggtctgc   10200
gggaatgtcg ccggactgtg tagctggact aaggccatgg caagcttctt ctccatcaac   10260
aaagaagtcc tgcctctgaa agcaaatctg gtggtccaag agaatagaca tcttctggct   10320
atgcaggact tgcaaaaagc ccaggcggag ttggacgata acaagcaga gttggacgtg   10380
gtgcaggccg agtacgaaca ggctatgacc gagaagcaaa cgctcctcga ggatgcagag   10440
cgctgtaggc ataaaatgca gacggcatcc accctcatct cagggctggc tggggaaaag   10500
gagaggtgga ccgaacagtc acaagaattt gccgcccaga ctaagagact tgtgggagat   10560
gtcctgctcg caacggcctt cctgtcgtat agcggtccat ttaatcagga atttcgcgat   10620
ctcttgctta acgattggag aaaagaaatg aaggccagaa aaatcccgtt cggtaaaaac   10680
cttaatttgt cggagatgct gatcgacgcg cctactattt cagaatggaa tctgcaaggg   10740
ctgccaaatg acgacttgtc catccaaaac ggaattatcg tgactaaggc ttcgcggtat   10800
ccactcctca ttgatccgca gactcaaggt aaaatttgga tcaagaataa ggaatcgcgg   10860
aacgagcttc agatcacttc actcaaccac aaatatttcc gcaaccacct ggaggattcc   10920
ttgagccttg aagaccgtt gctcatcgaa gatgtcggcg aagaacttga tccggccttg   10980
gacaacgtcc tggaaaggaa cttcatcaaa actggctcga cttttaaagt gaaggtgggc   11040
gacaaggaag tcgatgtcct ggatggattt aggctttaca ttacgactaa attgccgaat   11100
ccagcataca ccccggaaat ttcggcgagg accagcatca ttgactttac ggtgactatg   11160
aagggattgg aagaccagct cctcggcagg gtgattttga cggaaaaaca ggagctggaa   11220
aaagaaagga cgcacctcat ggaggatgtg accgccaata acgccggat gaaggagctc   11280
gaggataatc tcctttatcg cctcacgagc actcaaggat ccttggtcga ggacgagtcc   11340
cttattgtcg tgcttagcaa cactaagaga acggcggagg aggtcactca gaaactcgaa   11400
attagcgcag aaacggaggt gcaaatcaac tcagctaggg aggaatatcg gccagtcgca   11460
actagaggct ccattctcta tttcctcatc accgaaatgc gcctcgtcaa tgagatgtac   11520
caaacttcac tgcgccaatt cctgggtctt tttgatctgt ccctcgcaag atcggtgaaa   11580
```

```
tcccccatta ccagcaagcg gattgcgaac attatcgaac atatgacgta tgaggtctac    11640
aagtatgccg ccaggggget ttacgaagag cacaagttcc tctttacgtt gttgttgact    11700
cttaagattg acattcagcg gaaccgcgtg aaacatgagg agtttctcac tctgatcaaa    11760
ggaggggcaa gccttgactt gaaggcatgc cccccaaaac catcgaaatg gattcttgat    11820
atcacctggc tcaacttggt cgagctgtca aagctccggc aattctcgga cgtccttgac    11880
caaatttcga ggaacgagaa gatgtggaag atctggttcg ataaagagaa tcccgaagag    11940
gagcctttgc ccaacgccta tgataaatca ttggactgct ttcgccggct ccttctcatc    12000
agaagctggt gtccagacag aacgattgcc caggcgcgga agtatatcgt cgatagcatg    12060
ggggaaaaat acgccgaggg tgtcattctt gaccttgaaa aaacttggga ggaatccgat    12120
ccgcggactc ctttgatttg tttgctgtcc atgggctccg atcccactga tagcatcatt    12180
gcacttggta agaggcttaa aattgaaacg cgctacgtga gcatgggaca gggccaggag    12240
gtccatgctc ggaaacttct gcagcaaacg atggccaacg gtggttgggc ccttttgcag    12300
aattgccact tgggtctcga ttttatggat gaacttatgg acatcattat cgagaccgaa    12360
cttgtccacg acgcatttcg gctctggatg acgactgaag cgcataaaca gtttccgatc    12420
accttgctcc agatgtcgat taaattgcgc aacgaccctc cgcaagggct tagagcgggt    12480
ctcaaaagga cctactcggg ggtgtcacag gatcttcttg acgtctcctc cggcagccag    12540
tggaaaccaa tgctgtacgc tgtggcattc ttgcactcca cggtgcagga aaggcggaag    12600
ttcggagctt tgggctggaa tatcccgtac gaattcaacc aggccgattt taatgcaacg    12660
gtgcaattta tccagaatca tctcgatgac atggatgtga aaaaggggt  ctcatggacc    12720
accattagat atatgatcgg ggaaatccaa tacggtggta gggtcactga tgattatgat    12780
aagagacttc tgaatacgtt cgcaaaggtc tggttctcag agaatatgtt tggtcctgat    12840
ttctcgtttt atcagggcta taacatccct aagtgcagca ccgtggataa ctatctccaa    12900
tatatccaat ccctccctgc ttatgattca ccagaagtct ttggcttgca tcctaatgca    12960
gatattacgt atcagtcaaa actggcgaag gacgtcttgg acactatcct gggtattcag    13020
ccgaaagata cgagcggggg tggagacgaa accagagagg cagtcgtggc gaggctggct    13080
gacgacatgc tggagaagct gcctcccgac tacgtcccct ttgaggtgaa agaaagactg    13140
cagaagatgg gccccttcca acctatgaac atcttcttga caagaaaat   cgacaggatg    13200
caaagagtgc tgagcctcgt gcgctccacc ctgactgaat tgaagctcgc aatcgatgga    13260
acgatcatca tgtcggaaaa cttgcgggac gcacttgact gtatgttcga cgccaggatc    13320
ccagcgtggt ggaaaaaagc atcatggatc tcatcgactc tgggtttctg gtttaccgaa    13380
ctgatcgaaa ggaattcgca gtttacgtcc tgggtgttta acggacggcc acattgcttc    13440
tggatgaccg gcttttttaa ccctcagggt tttcttacgg ctatgcgcca agaaatcacc    13500
cgggcaaaca agggttgggc acttgacaac atggtcttgt gtaacgaggt gactaagtgg    13560
atgaaggatg acatctcagc tccgccgact gaggggggtct acgtgtatgg tctttatctg    13620
gagggcgcag gttgggataa acgcaacatg aagctgatcg agtcgaaacc aaaagtcttg    13680
ttcgagctca tgcccgtcat tagaatctac gccgagaaca atacgcttcg cgaccctaga    13740
ttctatagct gcccgattta taaaaaaccg gtgcggacgg acttgaatta tatcgcggca    13800
gtcgatctgc ggacggcgca gacccctgag cattgggtgc tgcggggagt ggctcttctg    13860
tgcgatgtca agtag                                                    13875
```

-continued

```
<210> SEQ ID NO 12
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 12
atgtttcgca tcgggaggcg gcagctctgg aagcactccg tgacgcgcgt gctgacgcag     60
cgccttaaag gcgaaaagga agcgaagcgg gcccttctgg acgctcggca taactacttg    120
tttgccattg tggcttcctg tcttgatctg aacaagacgg aggtcgagga tgcaatcctt    180
gaaggcaatc aaattgaaag aattgaccag ttgttcgcag tgggcggtct caggcatctt    240
atgtttract atcaagacgt cgaggaggcg gaaacgggcc aattggggag ccttggggga    300
gtcaatctgg tgagcgggaa atcaagaag ccgaaagtct tgtgacgga gggaaacgac     360 gtggcgctta ccggtgtgtg cgtgttcttt attagaaccg acccatcgaa ggccatcacg    420
cccgacaaca ttcatcagga ggtgagcttc aacatgttgg atgcagcaga tggggactg    480 ttgaactcgg tgagaagact cttgtccgac attttatcc cggctttgcg ggcaactagc     540
cacggttggg gtgaattgga agggctccag gacgctgcaa atatccgcca agagtttctt    600
agctcccttg aaggttttgt gaatgtcttg agcggagcgc aggagtccct taaggaaaaa    660
gtcaatctga aaatgtgat tattttggaa ctgaaaacgc tgaaggaacc gactgattac    720
ctgaccttgg cgaataatcc agaaacgttg gggaagatcg aagactgcat gaaagtgtgg    780
attaagcaga ccgagcaagt cttggcagaa acaaccagt tgctcaagga ggctgacgac    840
gtggggcccc gggccgagct cgagcattgg aagaagcggt tgagcaagtt taactatttg    900
ctcgaacagt tgaaatcgcc tgacgtcaag gcggtgctcg cagtcttggc agctgcgaag    960
tcaaagttgc tgaaaacttg gcgcgagatg gacatccgca ttactgacgc taccaatgaa   1020 gcaaagaca acgtgaaata tctgtatact ctcgagaaat gttgtgaccc tttgtattcg    1080
tcggaccccc tttcgatgat ggatgcaatc ccgacgttga tcaacgctat caagatgatt   1140
tattccattt cacactacta caatacgtcg gagaagatca cctccctgtt tgtcaaggtg   1200
acgaatcaga tcatttcggc gtgtaaagca tatatcacta caacggcac ggcatccatt    1260 tggaaccagc ctcaggatgt cgtcgaagag aagatcttgt ccgctatcaa gctgaagcaa   1320
gagtatcaac tgtgttttca caagactaaa cagaagctca agcaaaaccc aaatgcgaag   1380
cagtttgatt tttcagaaat gtacatcttc gggaagttcg agaccttcca caggcggttg   1440
gctaaaatta tcgatatctt cacgacgctt aagacgtata gcgtccttca ggattcgact   1500
atcgaaggac ttgaagatat ggcgacgaag taccaaggga tcgtcgcaac gatcaagaag   1560
aaagagtata actttctcga tcagagaaag atggactttg atcaagacta tgaagagttc   1620
tgcaaacaaa ccaatgatct tcataacgaa ctgcggaaat tcatggatgt cacctttgcg   1680
aagatccaaa acaccaacca agccctcaga atgctcaaga aatttgaaag gcttaatatt   1740
ccaaatctcg gcattgatga taagtaccaa cttatcctcg aaaattacgg agccgacatc   1800
gacatgatta gcaagcttta caccaaacag aaatatgatc ccccattggc gagaaaccag   1860 cccccccattg caggtaaaat tttgtgggcc cgccagctct tcatagaat tcagcagccg   1920 atgcagctgt ttcaacagca tcccgcagtg cttttccacgg cagaggccaa gccaatcatc   1980
cgctcgtata atagaatggc aaaggtgctt ctggaattcg aggtcctttt ccatcgggcc   2040
tggttgcggc agattgagga aatccatgtg ggccttgaag cgtcactgct tgtcaaagcc   2100
```

-continued

```
ccgggtactg gtgagctgtt tgtcaacttt gatccccaaa tcttgatttt gttccgggaa    2160
acggaatgca tggcccagat gggtctcgag gtctccccat tggccacgtc gctctttcaa    2220
aagcgggacc ggtacaaaag gaattttccg aatatgaaaa tgatgctcgc tgaataccaa    2280
cgcgtcaaat cgaagatccc agctgctatt gaacaactca ttgtcccaca ccttgctaaa    2340
gtcgatgagg ccctgcagcc tggtcttgcc gctttgacgt ggactagcct taacattgaa    2400
gcatatcttg aaaatacgtt cgcaaagatc aaagaccttg agctcctgct cgaccgggtg    2460
aatgatctga tcgagttccg gatcgatgca atcttggaag aaatgtcgtc caccccactc    2520
tgtcaacttc cacaggagga acccctgacc tgtgaagaat tcttgcagat gaccaaagat    2580
ctttgcgtca acggtgctca gatcttgcac tttaagagca gcctggtcga ggaggcggtc    2640
aatgagctcg tcaatatgtt gcttgacgtc gaagtgttgt cggaagagga aagcgagaaa    2700
atttccaacg aaaattcagt caactacaaa atgaaagct cggctaagag ggaggaaggc    2760
aatttcgata cgctgaccag ctccattaac gcgcgcgcta acgccctgct tctcaccacc    2820
gtcacccgga agaagaaaga gactgaaatg ctgggagaag aggctcggga gcttctcagc    2880
cactttaatc accaaaatat ggacgcgctc ttgaaggtca cccggaatac cctcgaggcg    2940
atccggaaga ggatccactc atcccacact attaattttc gcgattccaa cagcgctagc    3000
aacatgaaac agaattccct gccgattttt cgggctagcg tgactcttgc cattccaaac    3060
attgtgatgg ctccagcatt ggaagatgtg caacaaacgc ttaacaaggc ggtcgagtgt    3120
atcattagcg tgccaaaggg ggtcaggcaa tggagctccg agttgttgag caagaagaag    3180
attcaagagc ggaagatggc ggcactccaa tccaacgagg attcggattc agatgtcgag    3240
atgggtgaaa atgaactgca agatactctg gaaatcgcaa gcgtgaatct gccaattcct    3300 gtccaaaacca agaattatta taaaaacgtc tcggagaaca agaaatcgt caagctcgtg    3360 tcggtcctct caactatcat taatagcact aaaaaagaag tcattaccag catggactgt    3420
tttaaacggt ataatcatat ctggcagaaa ggaaaggaag aggcaatcaa gacgtttatc    3480
acccagagcc ccttgctctc agaattcgaa tcacagattc tctacttcca gaatcttgaa    3540
caagaaatca atgctgagcc agagtatgtg tgcgtggggt ccatcgcttt gtatacggcc    3600
gatctgaaat ttgcgttgac cgcagaaacg aaggcttgga tggtggtcat tggccgccat    3660
tgcaacaaaa agtatcggtc agaaatggaa aacatcttca tgctgattga agagtttaac    3720
aagaagttga atcggcctat taaagatctc gatgatattc gcattgctat ggctgctctg    3780
aaggagatta gggaagaaca aatttccatc gactttcaag tcggtcctat cgaagaaagc    3840
tacgctctcc tcaacaggta tggtctcctc attgctaggg aagaaatcga taagtcgat    3900 acgttgcact atgcgtggga gaagttgctc gcccgggccg cgcgaggtcca aaataaactt    3960 gtgtccttgc aaccctcgtt caagaaggag ctgatctcag cagtggaggt cttcttgcaa    4020
gactgccatc aattctactt ggattatgat ctgaatggac ctatggcaag cggcctcaag    4080
ccccaagagg cgtcagaccg cctgatcatg ttccaaaatc aatttgataa catttacaga    4140
aagtatatta cgtacaccgg cggagaggaa ctgtttgggc tcccagcaac gcaatatcct    4200
caactcctgg aaattaaaaa gcagcttaat cttcttcaga agatttacac tttgtacaac    4260
tcagtcatcg agaccgtgaa ttcatattat gatatccttt ggtcggaagt gaatatcgag    4320
aagatcaata tgaactcct tgaattccag aatcgctgta ggaaattgcc cagagcactg    4380
aaagattggc aagccttctt ggacctcaaa aagatcattg acgacttctc cgagtgttgt    4440
ccacttctcg agtacatggc ctcgaaggct atgatggaac gccattggga gcggatcacc    4500
```

```
acgctcacgg gacactcgct tgacgtcgga aatgagtcct tcaaattgag gaatattatg   4560
gaggcgcccc tgcttaagta taaggaggag attgaggaca tctgtatttc ggctgtgaag   4620
gaaagggaca ttgaacagaa attgaagcag gtgattaatg aatgggacaa taaaaccttt   4680
accttcggtt cctttaaaac tcgcggagag cttctgttgc ggggagacag cacttcggaa   4740
attatcgcca acatggaaga ttcacttatg ctcctggggt cgctgctctc gaatagatat   4800
aatatgccct tcaaagccca aattcagaaa tgggtgcagt atttgagcaa ctcgactgac   4860
atcattgaat cctggatgac tgtgcagaac ttgtggattt acttggaggc agtcttcgtg   4920
ggaggcgata tcgcaaaaca acttccgaag gaagctaaaa gattctccaa tatcgacaaa   4980
tcctgggtga aaatcatgac tcgggcacat gaagtcccat cggtcgtgca atgctgtgtc   5040
ggtgacgaaa ctcttgggca actgctgccg cacctgttgg atcagctcga gatctgtcaa   5100
aagtcattga cgggatacct ggaaaagaag cgcctgtgtt ttcctcgctt cttctttgtg   5160
tccgaccccg cgctgttgga gatcttgggc caggcttccg actcgcacac tattcaggcc   5220
catctcctta atgtgttcga caatattaaa tccgtgaaat tcatgaaaa gatttatgat   5280 cgcattctgt cgatctcctc acaggaagga gagacgattg aacttgacaa gcctgtcatg   5340
gccgaaggga atgtcgaggt ctggttgaat tccctcttgg aagagtcgca gagctcgttg   5400
cacctcgtca ttaggcaggc cgcagctaac atccaagaga ccggatttca gcttacggaa   5460
ttcctttcga gctttccggc tcaagtcggt ctgctcggca tccagatgat ttggacgcgg   5520
gacagcgaag aggccctcag aaacgcgaaa tttgacaaaa aaatcatgca gaagactaat   5580
caggcatttt tggagttgct gaatacgctg attgacgtga ctacgaggga tttgtcaagc   5640
acggagcgcg tgaagtatga gactttgatc actatccatg tgcaccaaag agatattttc   5700
gacgacttgt gccatatgca tattaaaagc ccgatggact ttgagtggct gaaacaatgt   5760
agattttact tcaatgagga ctcagacaag atgatgattc acatcaccga cgtcgcgttt   5820
atctaccaaa acgaattttt ggggtgcact gatagactcg tgattacgcc cctcactgat   5880
aggtgttata tcaccttggc ccaggcgctt ggtatgagca tgggcggggc gccagcgggc   5940
ccggcaggaa ccggtaaaac ggaaactact aaagatatgg ggcgctgtct gggcaagtat   6000
gtcgtggtct tcaattgtag cgatcagatg gattttcggg gcctcggacg cattttttaag   6060 ggccttgccc aatccggctc ctggggatgt tttgacgagt tcaatcggat tgacttgccg   6120
gtcttgtccg tcgccgccca acaaatctcc atcatcctga cttgcaagaa agagcacaag   6180
aagtcgttca tctttaccga cggtgacaat gtgactatga atcctgagtt tggtctcttt   6240
ctcacgatga atccgggata tgcgggaagg caggaactgc ctgaaaatct caaaatcaat   6300
ttcaggtcag tggctatgat ggtgcccgat cgccaaatca tcattcgcgt caaactggcc   6360
tcgtgcggat ttatcgataa tgtcgtgctg gcgaggaaat ttttcactct ctacaaactc   6420
tgtgaagaac aacttagcaa acaggtccac tacgatttcg gactccggaa catccttagc   6480
gtcttgagaa ccctcggggc tgccaaacgg gcgaacccaa tggatactga gagcaccatt   6540
gtcatgagag tgttgagaga tatgaacctc tccaagctga tcgatgaaga tgaaccccctt   6600 ttcctgagct tgatcgaaga tctctttccc aatatcctgc ttgacaaagc gggttatccc   6660
gaactcgaag ctgctattag caggcaggtg gaggaagcag gactcatcaa ccatcctccg   6720
tggaaactga agtcattca gctgttcgaa acccaagggg tgcggcatgg tatgatgacg   6780
ctggggcctt ccggtgccgg gaaaacgacc tgcatccata ctcttatgag agccatgacg   6840
```

| | |
|---|---|
| gattgcggca aacctcatcg cgaaatgagg atgaatccga aagcgattac cgccccacag | 6900 |
| atgtttggac ggttggatgt ggcgacgaac gactggactg acgggatttt ctcgacgttg | 6960 |
| tggcggaaga cgcttcgggc gaaaaagggg gagcatattt ggatcattct cgatggtccc | 7020 |
| gtggatgcca tttggatcga aaatttgaac tccgtgctcg acgataataa gactcttacg | 7080 |
| ttggcaaatg gtgacagaat tccgatggca ccaaactgca agattatctt cgaaccacac | 7140 |
| aatatcgaca atgcgtcccc cgccaccgtc tcccgcaacg ggatggtctt tatgtcatcg | 7200 |
| agcattttgg actggtcgcc aattctcgaa gggttcctga aaaaacgctc gccgcaggag | 7260 |
| gcggaaattc tgaggcaact ctatacgaaa tcattcccag atctctatcg cttctgcatc | 7320 |
| caaaacctgg aatataaaat ggaagtcctc gaggcttttg tcattacgca atccattaac | 7380 |
| atgctccagg ggctcattcc attgaaagag caaggaggag aggtgagcca agcacacctg | 7440 |
| ggcaggcttt ttgtgttcgc actcttgtgg tcggcggggg ccgctctgga acttgatggg | 7500 |
| agacgcaggc tggaattgtg gcttcggtcg cggccaaccg gtacgttgga actcccacct | 7560 |
| cccgcaggcc caggggacac cgcttttgat tattatgtcg ccccagatgg cacctggacc | 7620 |
| cactggaaca ccagaacgca agaataccttt tatccgtcgg acaccactcc agagtatggg | 7680 |
| tccatccttg tgccgaacgt cgataatgtg agaacggatt ttcttatcca gaccattgcc | 7740 |
| aagcaaggaa aagcggtcct tctgatcgga gaacaaggga ccgctaaaac tgtgatcatc | 7800 |
| aaaggtttta tgtcgaagta tgatcccgaa tgtcacatga tcaaatcatt gaattttagc | 7860 |
| agcgcgacga ccccacttat gttccaaaga acgattgagt catatgtgga taaaagaatg | 7920 |
| ggtacgacct atgggccccc agcgggtaaa aagatgaccg tctttattga tgacgtcaat | 7980 |
| atgccgatta ttaatgagtg gggcgaccag gtcacgaacg agattgtccg gcagctcatg | 8040 |
| gagcaaaacg gcttctacaa tctcgaaaaa cccggagagt tcacgtcaat tgtggatatt | 8100 |
| cagttcctgg cagccatgat ccacccaggt gggggtagaa atgatatccc ccaaaggttg | 8160 |
| aagagacaat tttcgatttt taattgcacc ctcccccagcg aagcctccgt ggataaaatt | 8220 |
| ttcggcgtca ttggagtggg gcactattgc acccaaagag gttttttccga agaagtccgc | 8280 |
| gattcggtca cgaaactcgt gcctctcacg cgccggcttt ggcagatgac taaaattaag | 8340 |
| atgctcccca cgccagctaa attccactac gtcttcaact tgagggacct gtcccgcgtg | 8400 |
| tggcagggca tgctcaacac tacctcggag gtgatcaaag agcccaatga tttgctgaaa | 8460 |
| ctctggaaac acgagtgcaa gagggtgatc gctgatcgct tcactgtctc gagcgacgtc | 8520 |
| acttggtttg acaaggcgct tgtcagcctg gtggaagagg aatttggtga agaaaaaaag | 8580 |
| ctcttggtcg actgtgggat cgatacttac tttgtcgatt ttctgaggga tgcgcccgaa | 8640 |
| gcggcggggg agacctccga agaagctgat gccgagactc cgaaaatcta cgagccgatt | 8700 |
| gaatcctttt cacatctcaa agagagactt aacatgttct tgcaactgta taacgaatca | 8760 |
| atccgggggg ccggaatgga catggtgttc ttcgctgacg caatggtcca tctggtcaaa | 8820 |
| atctcgcgcg tgattcgcac ccctcaaggg aatgctcttc tggtgggtgt gggagggtcc | 8880 |
| ggcaagcaaa gcctgacccg gcttgcctcc tttatcgccg gctacgtctc gtttcaaatt | 8940 |
| acgcttacgc gctcctataa cacgtcaaac cttatggaag atctcaaagt gttgtacaga | 9000 |
| actgctggac aacagggaaa gggaatcact tttatcttca ccgacaacga aatcaaggat | 9060 |
| gagagctttc tcgagtatat gaacaatgtg cttagcagcg gagaggtctc aaatttgttt | 9120 |
| gcgagagacg aaatcgatga gattaatagc gatctggcaa gcgtcatgaa aaaggagttt | 9180 |
| cctcggtgtt tgccgactaa tgaaaatttg cacgattatt tcatgtcacg cgtgcggcag | 9240 |

```
aacctgcaca tcgtcctgtg cttctcacct gtgggtgaaa agtttaggaa ccgggcactc    9300
aagtttccgg cactgatcag cggctgtact attgattggt ttagccgctg gccaaaggat    9360
gccttggtgg cggtctcaga gcatttctc acctcctacg atattgattg cagcctcgag    9420
attaagaaag aagtcgtcca atgcatgggt tcgttccaag acggggtcgc cgaaaagtgt    9480
gtcgactatt tccagagatt caggcggagc actcatgtca ctccgaagtc ctatttgtcg    9540
ttcatccagg gatacaaatt tatttacgga gaaaagcatg tggaggtgag aactttggca    9600
aataggatga acacggggct tgagaaattg aaggaggcta gcgaatcagt ggccgcactc    9660
tcaaaagagt tggaagctaa ggagaaggag ttgcaggtgg ctaatgataa ggctgatatg    9720
gtccttaaag aggtcacgat gaaggcgcaa gccgcagaaa aagtcaaagc ggaagtgcaa    9780
aaagtgaaag atcgggctca ggctattgtc gacagcatct ccaaggataa agccattgcc    9840
gaggagaagc tcgaagctgc taagcctgct cttgaggaag ctgaggcagc actccagacc    9900
atcaggccgt ccgacatcgc aaccgtgagg acgctgggaa ggcctccgca ccttatcatg    9960
agaatcatgg attgcgtcct gctgctcttc aacggaaaag tctccgcggt caagattgat   10020
ttggagaaat cgtgtaccat gccctcatgg caggaatcct tgaagttgat gaccgcaggc   10080
aactttctgc aaaacctgca gcaatttcca aaggacacca tcaacgaaga ggtcatcgag   10140
ttcctcagcc cctattttga gatgccggac tataatatcg aaacggcaaa acgcgtgtgt   10200
ggcaacgtcg caggcttgtg ctcctggacc aaagctatgg cttcgttctt ctcaattaac   10260
aaagaggtgc tgccgttgaa agcaaacctc gtggtgcagg agaatagaca tcttctggca   10320
atgcaggact tgcaaaaagc tcaagctgag ctggatgata agcaagcaga gcttgatgtg   10380
gtccaggctg agtacgagca ggctatgact gaaaagcaaa cgcttctgga ggacgcagaa   10440
cgctgcagac acaagatgca gactgcttcc accttgattt cagggctggc tggagagaaa   10500
gaacggtgga cggaacagtc acaagagttt gccgcacaaa ctaaaaggtt ggtcggtgac   10560
gtcttgcttg cgaccgcgtt tctttcgtac tcagggccat tcaaccaaga gtttcgggat   10620
ttgctgctca atgattggag gaaggaaatg aaagcgcgca agattccatt cggaaagaat   10680
ctcaacctct cggagatgct tatcgacgcc ccgaccattt cagagtggaa cctccaaggg   10740
ctgccgaatg atgatctctc catccagaac gggatcattg tcacgaaagc ctcacgctac   10800
cctctgctca tcgatccgca gactcagggg aagatctgga ttaagaataa ggagtcgagg   10860
aacgaactgc agatcactag cttgaaccac aaatacttta gaaaccacct tgaggattca   10920
ctcagcctcg gtaggccgct gctcattgag gatgtgggcg aggaactgga cccagcccctt  10980 gataacgtcc tggagcggaa cttcatcaaa accgggtcga cgtttaaagt gaaggtcggc   11040
gacaaagagg tcgacgtgct ggatggattc aggctttaca tcactacgaa actgcctaac   11100
ccagcgtaca ctccggagat ttccgcccgg acctcgatta tcgacttcac cgtcaccatg   11160
aaagggcttg aggaccagct ccttggacgc gtgatcctca ctgaaaaaca agaactcgaa   11220
aaggaacgga cccacctgat ggaggatgtc accgccaata aagaaggat gaaagaactt    11280 gaagataatc ttctttatcg cctcacgagc actcagggct cgttggtgga agatgaatcc   11340
cttatcgtcg tcttgtcgaa caccaaacgc actgcgaag aggtcaccca gaagctgaa     11400 atttcggcag aaacggaggt ccaaattaat tccgcaaggg aggagtacag gccggtggcg   11460
acccgcgggt cgattctta ttttctcatt acggagatga ggttggtcaa cgaaatgtat    11520
caaacgtccc tcaggcagtt tcttggcttg ttcgacctgt cacttgctcg ctcggtgaag   11580
```

```
tcgccgatta cgtcgaagag aatcgcaaat atcattgagc atatgaccta tgaggtctat   11640
aaatatgccg cccgggggcct gtatgaggaa cataaatttt tgtttaccct gttgcttacg  11700
ttgaaaatcg acatccaacg gaacagggtc aaacacgagg aattttttgac gctgatcaag  11760
ggtggtgcct ccctggatct gaaggcctgc cccccaagc ctagcaaatg gattcttgat    11820
atcacttggc tcaacctggt cgagctgtca aaattgcgcc agttttcgga tgtgctcgac   11880
cagatctcaa ggaacgaaaa gatgtggaag atctggttcg ataaagagaa cccggaggag   11940
gaaccactgc ctaatgctta tgacaaatca ctggactgtt ttcggagatt gcttctgatc   12000
cggtcctggt gcccggatcg cactatcgcc caggcaagaa agtatatcgt cgattcgatg   12060
ggagagaaat atgcagaagg tgtgatcctc gatcttgaaa agacgtggga agagtcagat   12120
cctcgcactc ctcttatttg cctcctttcg atgggatcag acccaacgga cagcattatt   12180
gcgctgggca agcggttgaa aatcgaaacg cggtatgtgt caatgggtca ggggcaggaa   12240
gtgcatgcac gcaaacttct ccaacaaact atggccaatg ggggctgggc gttgctgcaa   12300
aactgccacc ttggcttgga ctttatggac gaacttatgg atattattat tgagaccgaa   12360
ctggtccatg atgctttcag attgtggatg actacggagg ctcacaagca atttccgatc   12420
actttgctcc aaatgtcgat caaatttgcc aatgaccccc ctcaaggact gcgcgccgga   12480
ttgaaaagaa cttactccgg ggtgtcgcag gatttgcttg acgtctcaag cgggtcccag   12540
tggaagccca tgctttatgc tgtggccttc ttgcattcaa ctgtccaaga acgccggaag   12600
ttcggtgcac ttggctggaa cattccctat gaattcaacc aggctgattt caatgccacg   12660
gtccagttca tccaaaacca cctggatgat atggatgtca agaagggtgt ctcctggact   12720
actatccggt acatgatcgg tgaaattcaa tatggcggta gggtcacgga cgactacgat   12780
aaaaggctct tgaatacttt cgcgaaggtc tggttctcgg aaaacatgtt tggtccagac   12840
tttagctttt accagggata caacatccct aaatgtagca cggtggacaa ttatttgcag   12900
tacattcaaa gccttcctgc ttatgactcg ccggaggtct tcggtttgca tccaaacgcg   12960
gacattacgt atcagtcgaa acttgcaaaa gatgtgctcg acacgatcct ggggattcag   13020
ccgaaagata cgagcggcgg aggggacgaa actcgggaag ccgtcgtggc taggctggcg   13080
gatgacatgt tggaaaagct ccccccccgac tatgtgcctt tcgaagtcaa agagaggctt   13140
caaaagatgg ggccgttcca acctatgaac attttccttc ggcaggagat cgatcgcatg   13200
caacgcgtcc tgagccttgt ccgcagcacc ctcactgaac tcaagctggc cattgatggg   13260
accatcatta tgtccgaaaa cctgcgcgat gcgcttgact gcatgtttga cgcgcgcatt   13320
ccagcttggt ggaagaaggc ctcctggatc tcatccactt tgggtttctg gtttaccgag   13380
ctgattgaac gcaactcgca attcacttcg tgggtcttca atgggcgccc gcactgtttc   13440
tggatgaccg gtttttttaa tcctcaaggt tttcttactg ctatgcgcca agagatcacc   13500
agggccaata agggggtgggc cctcgacaat atggtcctct gcaatgaagt cactaagtgg   13560
atgaaggacg atatctcagc accccccaacg gagggtgtct atgtctacgg cttgtacctg   13620
gaaggtgcgg gatgggacaa aaggaacatg aaacttatcg aatccaagcc caaggtgctt   13680
tttgagttga tgccggtgat ccggatttat gcggaaaata acactctgag agaccctagg   13740
ttctactcat gcccaatttta caaaaaaccg gtccgcacgg acttgaacta cattgcggcg   13800
gtggacctcc gcaccgccca aaccccggaa cattgggtcc tcagaggcgt cgccctgctt   13860
tgcgacgtga agtag                                                    13875
```

```
<210> SEQ ID NO 13
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 13
atgtttcgga ttgggaggag gcaactctgg aaacacagcg tgaccagagt gcttacccag      60
cggctgaagg gagagaaaga agccaaacgc gctttgttgg atgctaggca caactatctc     120
tttgccattg tggcctcgtg cctcgatttg aacaaaactg aagtggagga cgccattctg     180
gaaggcaacc aaattgaaag aattgatcaa ctctttgctg tgggcggttt gagacacctc     240
atgttttatt accaggatgt ggaagaggcc gaaactggac aactgggatc gcttggtggt     300
gtcaatcttg tctccggaaa gatcaaaaag ccaaaagtgt tcgtgacgga aggaaacgat     360
gtcgccctga ctggggtgtg tgtgttcttt attagaaccg accccctccaa agcgatcacc     420
cccgataaca ttcatcagga ggtgtccttt aatatgcttg atgctgccga cggtggtctc     480
ttgaacagcg tgagacggtt gctttcagat atcttcatcc ctgcattgag ggcgacttcc     540
catggttggg gtgaattgga aggcttgcaa gacgctgcca atatccgcca ggagttttg      600
tcgtccttgg aaggatttgt caacgtcctt agcggagcgc aagagtcgct taaggagaag     660
gtcaatttgc gcaaatgcga tatccttgag ctcaaaactc tcaaggaacc cacgattac      720
ttgaccttgg caaataaccc cgaaacctg gggaagatta aggactgcat gaaggtgtgg     780
atcaaacaga cggagcaagt cctcgccgaa aataatcagt tgcttaagga ggctgacgat     840
gtcggcccca gggccgaact tgagcattgg aagaagcggc tctcgaaatt taactatttg     900
ctcgagcaac ttaagtcccc tgacgtcaaa gctgtgctgg cagtgcttgc cgcggccaag     960
tcaaaactgc tcaaaacgtg gagagaaatg gatattgaa tcactgacgc cacgaacgag    1020
gccaaagaca atgtgaaata cttgtacact cttgagaagt gctgcgatcc actgtactcg    1080
tcggatccgt tgagcatgat ggatgcgatc cccactctca tcaatgctat aaaatgatc    1140
tatagcattt cccattacta caacacgtcc gaaaagatca cgtccttgtt tgtgaaagtc    1200
accaatcaga ttatctcagc ttgtaaagca tacattacta ataatgggac tgcgtcaatc    1260
tggaatcagc cacaggacgt ggtggaggaa aagattcttt cggcgatcaa acttaagcaa    1320
gagtaccagc tctgcttcca taaaaccaag caaaagctta agcaaaatcc caatgccaag    1380
caatttgact tttcagagat gtacattttc ggtaagttcg agactttcca ccggcggctc    1440
gctaagatta tcgatatttt cactacccctt aaaacttaca gcgtcctcca agattccacg    1500
atcgaaggac tcgaggacat ggccaccaag taccagggta ttgtggcaac tatcaaaaaa    1560
aaagaatata acttttgga tcagagaaaa atggatttg atcaagatta tgaggagttc    1620
tgtaaacaga ctaacgacct ccacaatgaa ctccggaaat ttatggacgt caccttgcc    1680
aagatccaga acacgaacca agctttgcgg atgcttaaga atttgaaag acttaacatt    1740
ccaaacctcg gcatcgacga taaataccag ctcatccttg aaaattatgg ggcggatatt    1800
gatatgatta gcaaattgta cactaagcag aagtacgacc cgcctttggc acggaaccaa    1860
ccccctatcg cgggcaagat cctttgggcc aggcagttgt ttcatcgcat ccagcagcct    1920
atgcagcttt ttcaacaaca tccggcagtc ctgtcaaccg ccgaagcgaa gcctattatt    1980
aggagctata accgcatggc caaagtgctg ctcgaatttg aggtcttgtt tcacagagca    2040
tggcttagac agattgagga aatccatgtc ggccttgaag catccctgct ggtcaaagct    2100
```

```
ccaggcacgg gcgaactttt cgtcaatttt gaccccccaaa tcctcattct gttcagagag   2160
acggagtgta tggcacaaat ggggttggag gtgtccccct tggcaacgtc ccttttcag     2220
aaacgggacc gctacaagag gaatttagc aacatgaaga tgatgcttgc ggagtaccag     2280
cgggtgaagt ccaaaatccc agctgcaatc gaacaactga tcgtgcccca ccttgccaag    2340
gtcgacgagg ccctgcaacc aggcctcgcc gcgttgactt ggacctcgct gaatatcgaa    2400
gcctatttgg aaaatacttt tgcgaagatc aaagaccttg agctgttgct tgacagggtc    2460
aacgacttga tcgaattccg gattgatgcc atccttgagg aaatgagcag cacccccctc    2520
tgtcaattgc tcaagagga gcctttgacg tgcgaggaat tcctgcaaat gacgaaggat     2580
ctttgcgtga acggggcaca aatccttcac ttcaaatcat ccttggtcga ggaggccgtc    2640
aacgaactcg tcaatatgct tctcgatgtg gaggtcctta gcgaagaaga gagcgagaaa    2700
atttccaatg aaaactccgt gaattacaaa atgagagct ccgcaaaaag ggaggagggg     2760
aacttcgaca ctctgacctc atccatcaac gcaagagcaa atgcattgct gcttactacg    2820
gtgactcgca aaagaaaga gaccgagatg cttggtgagg aggccagaga actcttgtca    2880
cactttaatc atcagaacat ggacgcccct ctcaaggtga ccaggaatac cttggaagcg    2940
atcagaaaga gaatccacag cagccatacc attaacttta gggattcgaa ttcagcctcc    3000
aatatgaagc agaattcgtt gcctatcttc cgggcgtcag tgacccttgc cattccaaac    3060
attgtgatgg cccctgcact cgaagacgtc caacaaacgc ttaacaaagc ggtcgaatgt    3120
atcatttcgg tgccgaaggg agtgcggcaa tggtcatccg aactgttgtc gaaaaagaag    3180
attcaggaaa gaaagatggc cgctctgcaa agcaatgagg attcagattc agatgtcgag    3240
atgggagaaa atgagctcca ggatactctg gagattgctt cggtgaactt gcccatcccc    3300
gtgcaaacga aaaattacta caaaaatgtc tcggagaaca aagagatcgt caaacttgtg    3360
tcggtcctct ccacgattat aacagcacc aaaaaggaag tcattacgtc aatggattgc    3420
tttaaaagat ataaccatat ttggcagaag ggcaaggagg aagctatcaa gacctttatt    3480
acccaatccc ctctcctcag cgagttcgaa agccagattc tctatttcca aaacttggaa    3540
caagagatta acgccgagcc agaatacgtc tgtgtggggt cgatcgcgct gtacacggcg    3600
gacctcaaat ttgcacttac ggcggagacg aaggcctgga tggtcgtcat cggtaggcat    3660
tgtaacaaga aatacagaag cgagatggaa atatatcttca tgcttattga agaattcaat    3720
aagaaactga acaggcctat caaagatctt gatgatatca gaatcgcgat ggctgccctg    3780
aaagaaattc gggaggaaca aatttcgatc gattttcagg tgggtcctat cgaagaaagc    3840
tatgctttgt tgaatagata tgggctcctg atcgcacggg aagaaattga caaagtcgat    3900
actctgcatt acgcctggga aaagcttctc gcgagagccg gggaagtcca gaacaaactt    3960
gtctcccttc agcctagctt taagaaagag ctgatcagcg ctgtggaagt gtttcttcaa    4020
gattgccatc aattctacct cgactacgat ctcaacggtc caatggcctc cggtttgaag    4080
ccccaagagg cctccgacag acttatcatg ttccaaaacc agtttgataa tatctacaga   4140
aaatatatta cgtacacggg tggcgaggaa ctgttcggtc tcccagcaac ccaatacct    4200
cagctgcttg agattaaaaa acaactgaat ttgttgcaga agatttacac gctctataac    4260
tcggtgatcg aaacggtcaa cagctattac gatattctct ggtcagaagt gaatatcgag    4320
aagatcaata tgaattgct cgaatttcag aatcggtgta gaaaactgcc cagggcactc    4380
aaagactggc aagccttcct tgatttgaag aaaattattg atgacttcag cgaatgctgt    4440
ccccttctcg agtacatggc ctcgaaggcc atgatggaga ggcactggga acgcattacc    4500
```

```
actctgactg gccacagcct cgatgtgggt aatgagtcat tcaaattgag aaacatcatg   4560
gaggctcccc ttctgaaata taaggaggag atcgaggata tttgtatttc ggctgtgaag   4620
gagcgcgata ttgagcagaa attgaagcag gtgattaatg aatgggataa caagaccttc   4680
acgtttggtt ccttcaaaac cagaggcgag ctgcttctgc ggggcgactc aacgagcgag   4740
attatcgcaa acatggaaga ttccttgatg ctgttggggt cactgctttc aaatcgctat   4800
aatatgccgt ttaaggcaca aattcagaaa tgggtgcagt atctttccaa ttccaccgat   4860
attattgaat cgtggatgac tgtccaaaac ttgtggatct accttgaagc cgtgttcgtc   4920
ggtggggata ttgctaagca gttgccaaaa gaagctaaac gcttttccaa tatcgataaa   4980
agctgggtga agatcatgac tagagcacat gaggtgcctt ccgtggtgca gtgttgtgtc   5040
ggcgatgaaa cgcttggaca gcttctcccc caccttctcg accaactgga aatctgccaa   5100
aaatccttga ccgggtatct tgaaaagaaa agactttgct ttccaagatt cttttcgtc    5160 tcagatcctg cgcttttgga atcctgggc caggccagcg attcccatac gattcaagca    5220
cacctcctca atgtgttcga taatatcaaa tcagtcaagt ttcatgagaa aatttacgat   5280
cgcatcctgt caatctcctc caagaaggt gagaccatcg agttggataa acctgtcatg     5340
gcggagggga acgtggaagt gtggttgaac tccttgttgg aagaatccca atcatccctg   5400 cacctttgtga ttcgccaggc ggcggctaat atccaggaaa cggggttcca gctcaccgag  5460
tttctcagct cattccctgc tcaggtcggg ctgctcggca ttcagatgat ttggacgcgg   5520
gactcggagg aagccctcag aaatgcgaag tttgacaaaa aaatcatgca aaagaccaat   5580
caagcctttc ttgaactgct gaatacctc atcgatgtga ctaccaggga tctgtcgtcg    5640
accgaacggg tcaaatacga gacgcttatt actatccacg tccaccaaag ggatatcttc   5700
gatgatctct gtcacatgca tatcaaatca ccaatggact ttgaatggct gaagcagtgt   5760
cgcttttact ttaacgagga ttcagacaag atgatgattc acattaccga tgtggcattt   5820
atttatcaaa atgaattcct gggttgcacg gatcgcctgg tgattacgcc actcacggat   5880
cggtgttata tcacgctcgc acaggcattg ggaatgtcaa tggggggggc cccggcaggg   5940
ccagctggaa cgggtaaaac cgaaacgact aaggatatgg gtcggtgtct tggaaagtac   6000
gtggtcgtgt tcaattgcag cgatcaaatg gacttccggg gattgggaag aattttcaag   6060
ggattggccc aatccggatc ctgggggtgt tttgacgaat tcaatagaat tgatcttccg   6120
gtcctgtcag tggccgcgca gcagattagc atcatcctta cttgcaaaaa agaacacaag   6180
aagagcttca tttttacgga cggagataac gtgactatga atccggagtt cgggctcttc   6240
ctgaccatga atccgggcta cgcgggcagg caggagctgc ctgagaatct caaaattaac   6300
tttcggtcag tggctatgat ggtccctgat cgccagatta ttatccgcgt caaacttgcg   6360
tcgtgcggtt ttatcgacaa tgtcgtgttg gcaaggaaat tctttactct ttataagctc   6420
tgtgaggaac aactctccaa gcaagtgcac tacgacttcg gctccggaaa tattctttcc   6480
gtccttcgga cgctcggcgc cgcaaaaagg gctaaccca tggacacgga atccacgatc    6540
gtcatgaggg tgctgcgcga catgaacctg tcgaagctca tcgacgaaga cgagccgctg    6600 ttttgagcc tcatcgaaga cctctttcct aacatccttc ttgacaaggc cgggtaccct   6660
gagcttgaag ccgctatttc gcggcaagtg gaggaggcgg ggcttatcaa tcatccgccc   6720
tggaagctta aggtcatcca attgtttgag acgcagaggg tccgccatgg aatgatgacg   6780
ctgggcccaa gcggtgccgg gaagactacc tgcatccaca ccctcatgag agcgatgacg   6840
```

```
gactgcggga agccccacag agagatgaga atgaacccta aggcaattac tgcacccccaa    6900
atgttcggcc gcctggacgt ggctacgaat gattggaccg acggaatctt ctcgaccctc     6960
tggaggaaaa cgctcagagc gaagaaggga gagcatatct ggattatcct cgacgggcct    7020
gtcgacgcaa tttggattga aaacttgaat tcagtcttgg acgataacaa gacgctgacc    7080
ttggcgaacg gcgatcggat ccctatggct cccaactgca aaatcatctt cgaaccccat    7140
aatatcgaca atgcgtcccc ggctacggtg tcgaggaacg gtatggtctt catgagctca    7200
tccatcctgg attggtcccc gattctggaa gggtttctca aaaagcggtc cccgcaagaa    7260
gcagaaattt tgagacaact ttatactgag agctttcccg acttgtatcg cttttgtatc    7320
caaaacttgg agtataagat ggaggtcttg gaggcatttg tcatcactca gtccatcaac    7380
atgctccagg ggctcattcc gctgaaagag caaggaggtg aggtgtcgca ggcacatctg    7440
ggaaggcttt tcgtgtttgc cctgctgtgg agcgcaggag ctgccctgga gttggacggt    7500
cggagaagac tggagctctg gctgcgctca agaccgacgg gcaccctgga acttccgcct    7560
ccagccgggc cgggcgacac tgcgttcgat tactacgtcg ctccggatgg aacttggacg    7620
cactggaata ctcgcactca agagtatctc tatccttcag ataccactcc ggaatacggc    7680
tcaattctcg tgccgaacgt cgacaatgtc aggaccgatt tccttatcca aaccattgct    7740
aagcaaggga aagccgtcct gcttattggc gagcaaggta ctgctaagac tgtcatcatt    7800
aaagggttca tgtcgaaata tgaccctgaa tgccacatga ttaaaagcct caatttcagc    7860
tcggccacta cgccgcttat gttccaacgc actatcgagt cgtacgtcga caagagaatg    7920
ggtaccactt atggtccacc ggcaggaaaa aaatgactg tgtttattga tgacgtgaac     7980
atgcccatca ttaacgaatg gggtgatcag gtgacgaacg agattgtgcg gcaactcatg    8040
gagcaaaacg gcttttataa tttggaaaag ccaggcgagt ttacctcaat cgtggacatc    8100
cagttcctcg cagcgatgat tcaccccggg ggcgggcgca atgacatccc acagaggctg    8160
aagagacagt tttcaatttt caattgcacg ctgccctcgg aagcaagcgt cgacaaaatt    8220
tttggtgtca tcggagtggg tcactactgc actcaacgcg gcttctccga agaagtgaga    8280
gattcagtca ctaagctggt cccactgact cggcggcttt ggcagatgac gaaaattaaa    8340
atgctgccta ctcccgcgaa attccactac gtctttaatt tgagggatct ttcccgggtc    8400
tggcaaggta tgctcaatac cacttcggag gtcatcaagg agcccaacga tctcttgaaa    8460
ttgtggaagc atgaatgcaa gagagtcatc gccgaccggt tcacggtgag cagcgacgtg    8520
acttggttcg acaaagcgct tgtctcattg gtggaggagg aatttggcga agagaagaag    8580
ttgttggtgg actgtggaat cgatacttac ttcgtggatt ttcttcgcga tgcaccggaa    8640
gctgcgggag aaacgtcgga agaagcagac gccgaaacgc ctaaaatcta cgaaccaatt    8700
gagtcatttt cccaccttaa agaacggctg aatatgtttc tgcaactttta caacgaatca    8760
attgcggtg cagggatgga catggtcttc tttgccgacg caatggtcca tctcgtgaaa    8820
atttcgagag tgattaggac gcctcagggt aatgcactcc ttgtcgggggt gggcggctcc    8880
ggaaaacaat cattgacgcg gcttgcttca tttattgcag ggtacgtctc atttcagatt    8940
acgcttacca gatcgtataa cacctccaat ctcatggagg accttaaagt gttgtatcgg    9000
actgctgggc agcagggaa ggggattacc ttcattttca ctgataatga aattaaagat     9060
gaaagctttc tggaatatat gaataatgtg ctttcatcgg gggaggtctc aaatcttttc    9120
gccagggatg aaattgacga aatcaacagc gaccttgcct ccgtgatgaa gaaagaattc    9180
cctcggtgcc tccctactaa cgagaatctc cacgattatt tcatgtccag agtgcgccaa    9240
```

```
aatctccata tcgtcctgtg tttttcgcca gtcggtgaaa agtttagaaa tagagctctt    9300
aaatttcccg cactcatcag cggctgtacg attgattggt tttcacgctg gcccaaagac    9360
gcgcttgtcg ccgtgtccga gcacttcctg actagctacg acattgactg ctcactggag    9420
attaaaaaag aagtggtcca atgtatgggt tcgtttcaag atggagtggc cgaaaaatgc    9480
gtggattact tccagagatt cagacggtcc acgcacgtga cgccgaaatc atacctgtca    9540
tttatccagg ggtacaagtt tatttacggg gaaaagcatg tggaggtccg cacgcttgct    9600
aacaggatga atacgggcct ggagaagctt aaagaagctt ccgaatcggt cgcggcactg    9660
tcaaaggagc ttgaagccaa agagaaggag ctccaagtcg cgaatgataa agctgacatg    9720
gtcctgaagg aggtcacgat gaaggctcaa gcggcagaaa aggtgaaggc cgaggtgcag    9780
aaagtcaagg atcgcgcaca ggctatcgtc gattcaattt caaaggataa agctatcgcg    9840
gaagaaaagc tggaagctgc aaagccggcc cttgaagagg cggaggccgc tctgcaaact    9900
attcgcccgt ccgatatcgc tacggtgagg actctcggac gcccaccaca tctcatcatg    9960
agaattatgg attgcgtgct gcttcttttc cagagaaaag tcagcgcagt caagatcgat   10020
ctggagaaat catgtactat gccgtcatgg caggagagcc tgaagctgat gacggcagga   10080
aacttcttgc aaaacttgca acagtttccg aaagacacca tcaacgagga agtgattgag   10140
ttcttgtcgc cttactttga gatgccagat tacaatattg agaccgcaaa aagagtctgt   10200
ggcaacgtgg ccgggctttg tagctggact aaagcaatgg cctccttttt ctccatcaac   10260
aaagaggtcc tgcctcttaa ggcgaacctg gtggtgcagg agaataggca tcttctggca   10320
atgcaagacc tccaaaaggc ccaggctgag ttggatgaca agcaggccga actgacgtc    10380 gtccaggctg aatatgaaca ggcaatgacg gagaaacaaa ctctcctgga agatgccgaa   10440
cggtgcaggc ataagatgca aactgcttcc actcttatca gcggattggc gggcgaaaag   10500
gagagatgga cggagcaatc acaagaattc gcggctcaga ccaagcggct ggtcggtgac   10560
gtcctcctcg ccaccgcctt cttgtcgtac tcgggaccct tcaaccagga atttagagat   10620
cttcttttga atgactggag aaaggaaatg aaggctagaa aaatcccatt tggcaagaac   10680
ctcaacctct cggagatgct gattgacgct cccactattt ccgaatggaa ccttcaaggt   10740
ctgccaaacg atgacctcag cattcagaat ggaattattg tgactaaggc atcaaggtat   10800
ccattgctta ttgacccgca gacgcaaggc aaaatttgga tcaaaaataa ggagtccaga   10860
aacgagctgc agattactag ccttaatcac aaatacttta gaaaccattt ggaggactcc   10920
ttgtcactgg ggcgcccgtt gcttatcgag gacgtggggg aggagctgga cccggcgctg   10980
gacaacgtcc ttgaaaggaa tttcatcaag actggaagca cgtttaaagt caaggtcggg   11040
gataaggagg tggatgtcct ggatggattt cggctctata ttacgactaa actccccaac   11100
ccggcgtata ctccggagat ctcagcgcgc acgtcgatca ttgacttcac tgtcactatg   11160
aaaggtcttg aggatcagct tctgggaagg gtgatcctta ctgaaaagca agagctggag   11220
aaagagagga cgcatcttat ggaggatgtg actgcgaata aaaggcggat gaaagagctc   11280
gaagataacc tgttgtaccg cctgacgagc acccagggat cattggtgga agatgaatca   11340
ctgatcgtgg tcctgtcaaa caccaaaagg accgcagagg aggtgaccca aaagctggag   11400
atttcggctg agaccgaagt ccaaattaac tcggccagag aagaatacag gcctgtcgct   11460
actcggggaa gcattctgta ttttcttatt accgagatgc gccttgtgaa tgagatgtat   11520
caaacttcac tgaggcaatt tctcggactc ttcgatctgt cgcttgcgag atcagtgaaa   11580
```

```
tcccctatta cttcaaaacg gattgctaat attattgagc acatgacgta tgaagtctac    11640
aaatacgctg caagaggctt gtacgaggag cacaagtttc tgttcactct cctcttgacg    11700
cttaagattg acatccagcg gaacagagtg aagcatgagg agtttctgac gcttattaag    11760
ggaggtgctt cactggacct gaaagcatgt cctccgaagc cttccaagtg gattctggac    11820
atcacgtggc ttaatctggt ggagctctca aaactcagac aattttcaga cgtgttggat    11880
caaatttcaa ggaacgagaa aatgtggaag atttggttcg acaaagaaaa cccggaagag    11940
gagccattgc cgaacgctta tgacaaatcc ctggactgtt tcagaaggct gttgctcatt    12000
cggagctggt gtcctgatcg caccatcgca caggcgagaa aatatatcgt ggactcaatg    12060
ggtgagaagt acgcagaggg ggtcatcctg gatttggaaa agacttggga ggaatcagat    12120
ccgcgcactc ccctcatttg cctcctgtcc atgggaagcg atcccactga ttcgatcatt    12180
gcgcttggca aacggcttaa gattgaaacg aggtatgtct cgatgggtca aggacaggag    12240
gtccacgcta ggaaattgct tcagcaaacg atggccaatg gtgggtgggc gcttctccag    12300
aactgccatc tcggtcttga cttcatggac gaactgatgg atatcattat tgaaaccgag    12360
ttggtccatg acgcttttag gctgtggatg actaccgagg cccataaaca gttcccaatt    12420
acgttgctcc aaatgtccat taagtttgcg aacgaccctc cgcaaggttt gcgcgcgggc    12480
cttaaacgga cttactccgg agtcagccag gacttgctgg acgtcagcag cggatcacaa    12540
tggaagccca tgctctatgc agtggccttt ttgcacagca ctgtccagga gagaaggaag    12600
tttggagcgc tggggtggaa tatcccctat gaattcaacc aagcggactt taacgctacg    12660
gtccagttca tccagaacca ccttgatgac atggatgtca agaaaggcgt ctcgtggacg    12720
acgatcaggt acatgatcgg ggaaattcag tacggcggta gggtcaccga cgattacgac    12780
aaaaggctct tgaatacttt tgccaaagtg tggttttcag agaacatgtt cgggccggac    12840
ttctcctttt accaaggtta taatatcccc aagtgctcga ccgtcgacaa ttatcttcaa    12900
tacatccagt cgctgccagc atacgattcg ccagaggtct tcggtctgca tcctaacgcg    12960
gacatcacgt accaatccaa gttggcgaaa gatgtcttgg atactatttt gggtatccag    13020
cctaaagaca cctcgggggg gggcgatgaa accaggaggg cagtggtcgc gaggctcgca    13080
gatgatatgc ttgagaagct gccacccgat tacgtgccct tcgaggtgaa ggagaggctc    13140
caaaaaatgg gaccattcca gccgatgaat attttcttgc gccaggagat cgacaggatg    13200
cagcgcgtgc tgtcactcgt ccgcagcact cttaccgagc tgaagcttgc catcgatggc    13260
acgattatta tgtcagagaa ccttagagac gcgctcgact gcatgtttga cgcaagaatt    13320
cccgcttggt ggaagaaggc atcatggatt tcctcgacgt tgggcttttg gttcacggag    13380
cttattgaac ggaattccca gttcacttcc tgggtgttca atggcagacc acactgtttt    13440
tggatgaccg gcttcttcaa cccgcagggg tttctgacgg cgatgaggca ggaaattact    13500
cgggctaata aggggtgggc tcttgacaac atggtgctct gcaacgaagt gactaagtgg    13560
atgaaggacg atatttcggc ccctcctact gaagggggtgt atgtctatgg actttacttg    13620
gaaggggcag gttgggataa gaggaatatg aagcttatcg aatcaaaacc aaaagtgctc    13680
tttgagttga tgcctgtgat cagaatctat gcagaaaaca atactctcag ggatcccaga    13740
ttctactcct gtcctatcta taagaaaccc gtccgcacgg acttgaacta tatcgccgcg    13800
gtcgatctcc gcactgctca gactcccgag cactgggtcc ttcgcggggt cgcgctcctt    13860
tgtgacgtga agtag                                                    13875
```

```
<210> SEQ ID NO 14
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 14
atgttccgga tcggccggag gcaactgtgg aagcattcag tcaccagagt ccttacccaa      60
cgcctcaagg gagagaaaga ggccaaacgc gcgctgctgg acgctcgcca taattacctc     120
tttgcgattg tcgcctcatg cttggatctc aacaagactg aagtcgaaga cgccatcctt     180
gaaggcaacc aaatcgaacg gatcgatcag cttttcgccg tcgggggtct ccggcacctt     240
atgttttact accaggacgt ggaagaagct gaaacgggac agctggggtc acttggtggg     300
gtgaacctgg tgtccgggaa aattaagaag ccgaaggtgt tgtcaccga gggcaatgac      360
gtggccctta ccggagtgtg cgtgttcttt atcagaacgg acccatcaaa agcaattact     420
ccggataaca tccatcaaga ggtcagcttc aacatgcttg atgcggcaga tggtggtttg     480
cttaattcag tccgccggtt gctttcggac atcttcattc ctgcccttcg cgcaacctcc     540
cacggttggg gagaacttga ggggttgcag gacgccgcta acattcgcca agaatttctt     600
tcaagcctcg aaggcttcgt gaatgtgctg tcggggcac aggagtcgct caaagagaaa      660
gtcaatctga aaaatgtga cattctcgag ctcaagactc tcaaggaacc cactgattat     720
ttgacgctcg cgaataatcc agaaaccctc gggaaaatcg aggactgtat gaaagtgtgg     780
attaaacaaa cggagcaagt gctcgcagaa aataatcaac tcctcaagga ggcggatgac     840
gtcggccctc gcgcggagct tgaacattgg aaaaagaggc tttcgaagtt taattatctg     900
ctcgaacagc ttaagtcacc ggatgtgaag gcagtgctgg cggtgcttgc agctgcaaag     960
tcgaaattgc tcaagacttg gcgggagatg gacatcagga tcactgacgc aacgaatgag    1020
gcgaaggata cgtgaagta cctgtatacc ttggaaaagt gctgtgatcc tctttatagc     1080
tccgaccctc tctcgatgat ggatgctatc ccaaccctca ttaatgccat taagatgatt    1140
tattcgattt cgcattatta taatacctcg gaaaaaatta cctcgttgtt cgtgaaggtc    1200
acgaatcaga ttatttcagc atgcaaagct tacattacca ataatggtac cgcttcgatc    1260
tggaatcagc cgcaagatgt ggtggaggag aaaattttga gcgcaatcaa gttgaaacag    1320
gaataccagt tgtgcttcca caagactaag caaaagttga agcaaaaccc caaacgctaaa    1380
caatttgatt ttagcgaaat gtatatttttc gggaagtttg aaacctttca taggagactc    1440
gcgaagatta tcgacatttt cactacgctt aagacttatt cggtgttgca ggactccact    1500
attgagggat tggaggatat ggctactaag taccagggta ttgtcgccac gattaaaaag    1560
aaggaataca actttctgga ccaacgcaaa atggactttg accaagacta tgaagagttc    1620
tgcaagcaga ccaatgacct tcataatgaa ttgagaaagt tcatggacgt cacttttcgcg    1680
aaaatccaga acaccaatca ggcccttagg atgctcaaaa aattcgagag acttaacatt    1740
cccaatctcg gaatcgacga caaatatcag ctcattctcg agaattatgg cgctgacatc    1800
gacatgatct caaaactgta caccaaacaa aagtatgatc cacctctggc taggaaccag    1860
cctccaatcg cggggaagat cctttgggcc cggcagcttt tccataggat ccagcagcct    1920
atgcaacttt tccagcagca tccagctgtg ttgtccacgg cggaggccaa accgattatc    1980
cgctcctata tcggatggc aaaggtcttg ctcgagttcg aagtgctctt ccaccgcgca    2040
tggcttcggc aaatcgagga gattcacgtg ggtctcgaag ctagcctttt ggtcaaggct    2100
```

```
cctggcacgg gggagctttt tgtcaattt  gatcctcaaa ttttgattct gttcagggaa   2160
actgaatgta tggcgcagat gggcttggag gtgtcaccct tggcgacgag cctcttcag    2220
aagagggaca ggtataagcg caatttctcc aatatgaaaa tgatgctggc tgagtaccag   2280
cgggtcaaat caaagatccc cgctgccatt gaacaactta ttgtgccaca tctcgcaaaa   2340
gtggacgaag ccctccaacc cggactcgcc gcgctcactt ggacttcgct gaacatcgag   2400
gcctacttgg aaaataccct cgctaagatc aaagacctgg aattgttgct tgacagagtc   2460
aacgatctga ttgagttccg gattgacgct atcttggaag agatgtcgtc gacgccgctt   2520
tgtcagttgc cccaggagga gccattgact tgtgaagagt tccttcaaat gacgaaggac   2580
ttgtgcgtga acggtgccca atcctccac  ttcaagtcgt cattggtcga agaggctgtg   2640
aatgaactcg tgaatatgtt gcttgatgtc gaggtgctga gcgaggaaga atccgagaaa   2700
atttcgaatg agaattccgt caattataaa aatgaatcca gcgccaaacg ggaggagggg   2760
aactttgaca ctctgacgtc gtcgattaac gcacgcgcaa atgccctgtt gctgactacg   2820
gtgacgcgca agaaaaagga aaccgagatg ttgggcgagg aggccagaga actccttagc   2880
catttcaacc atcaaaatat ggatgctctc ctcaaagtga cccggaacac cctcgaggct   2940
atcagaaagc ggattcactc ctcgcacacc attaatttcc gggactcgaa ctcagcgagc   3000
aatatgaaac aaaactcact gccaatcttt cgcgcaagcg tgactctcgc aatcccaaat   3060
atcgtgatgg ccccgccctt ggaggatgtc cagcagacgc tgaataaggc tgtggagtgc   3120
atcatctcgg tgccaaaagg agtccgccag tggtccagcg agctcttgtc gaagaaaaaa   3180
atccaagagc gcaagatggc cgcccttcaa tccaacgagg atagcgattc agacgtcgag   3240
atgggcgaga acgagttgca agacaccttg gagattgcat ccgtgaatct cccaattcca   3300
gtccagacta gaactacta  taaaaatgtg tccgaaaata aagaaatcgt caaactcgtg   3360
agcgtgctta gcaccattat caattccact aaaaaagagg tgattacgtc aatggactgt   3420
ttcaaacggt acaatcatat ttggcagaag ggcaaggaag aggctattaa aacgttcatt   3480
acgcagagcc cgctcctctc agaattcgaa tccagatttt tgtatttcca aaatttggag   3540
caggagatca atgcggagcc tgaatatgtg tgcgtgggat ccattgctct ttatactgcg   3600
gatctgaagt tcgctctgac ggctgaaact aaggcgtgga tggtggtcat tggcagacat   3660
tgcaataaaa agtataggtc cgaaatggaa aatatcttca tgctgatcga agagtttaat   3720
aagaaactca atcggccgat taaggatctg gatgatatcc gcattgccat ggcagccttg   3780
aaagagatca gagaagagca gatctcgatc gatttccagg tcgggcccat tgaggagagc   3840
tacgctctgc tgaatcgcta cggtcttctg attgcgcggg aggaaatcga caaggtggat   3900
actctccatt acgcatggga aaaacttttg gcacgcgccg gggaagtcca gaataaattg   3960
gtgtcgctgc agccttcgtt caaaaaagag ttgatttccg ccgtggaagt cttttttgcag  4020
gattgccatc agttctatct ggactacgac ctcaacggac ctatggcttc gggccttaaa   4080
ccccaggaag cgtccgaccg gctgatcatg ttccagaatc agtttgataa tatctatagg   4140
aaatacatta cgtacacggg tggggaggag ctgttcggac tgccagcaac ccaatccct    4200
caattgttgg agattaagaa gcagttgaat ttgctccaga gatctacac  gctgtataac   4260
tcggtcattg aaactgtcaa ttcgtactat gacatcttgt ggtcagaagt caacatcgag   4320
aagatcaata acgaattgct cgaattccaa aatcgctgta ggaagttgcc aagggctctg   4380
aaggattggc aagccttcct ggatcttaag aaaattattg acgactttc  agaatgttgc   4440
ccactcctgg aatacatggc gagcaaagct atgatggaaa ggcactggga gcgcattacg   4500
```

```
actttgaccg ggcactcact tgatgtcggc aatgaatcgt ttaaactgcg gaatattatg   4560
gaggcaccgt tgttgaagta caaagaggaa attgaagata tctgtatcag cgcggtcaaa   4620
gaacgcgata tcgaacagaa actcaaacaa gtgattaatg agtgggacaa taagacgttt   4680
acgtttgggt cattcaagac tcggggagaa ctgctcttga ggggagactc cacttccgag   4740
atcattgcca acatggaaga ttccttgatg ttgcttggat ccttgctctc gaatcgctat   4800
aacatgccgt tcaaagccca gatccaaaag tgggtccagt atctctcgaa cagcaccgac   4860
atcatcgaat cgtggatgac ggtccaaaat ttgtggattt acctggaagc cgtcttcgtg   4920
ggcggcgata tcgcaaagca gttgcctaaa gaggcaaaaa gattttccaa tatcgacaaa   4980
agctgggtca aaattatgac cagagcacac gaagtgcctt ccgtggtcca gtgttgcgtg   5040
ggcgacgaaa cgcttggtca actgctcccg caccttttgg atcaactcga gatctgtcag   5100
aaatccctga ccggttatct tgagaaaaaa agactttgct ttcctagatt cttttttcgtc  5160 tcggacccgg cactgctgga gatcctcggt caggcgtcgg actcccacac tattcaagcc   5220
caccttctca acgtcttcga caatatcaaa tcggtcaaat tccatgagaa gatctacgat   5280
agaatcctgt cgatctcgtc acaagaaggc gaaactattg aactcgataa gcctgtgatg   5340
gcagaaggga acgtcgaagt ctggttgaat agcctcctgg aggagtcaca gtcgagcttg   5400
catcttgtca ttcggcaagc cgctgctaat attcaggaga ctggtttcca acttaccgag   5460 ttttttgtcgt cctttccagc tcaggtgggc ctcctgggca ttcagatgat ttggacgagg   5520
gatagcgaag aagcccttcg caacgcaaag ttcgacaaga aaattatgca aaagaccaac   5580
caagcttttc tggaactcct caatactctg attgacgtga ccacgcggga tctcagctcc   5640
accgaaagag tcaagtacga gacgctcatt accatccacg tccatcaaag ggatattttc   5700
gacgacctct gccatatgca catcaaatcg cctatggatt tcgagtggtt gaaacagtgc   5760
cggttttact tcaacgagga ctccgacaaa atgatgattc atattaccga tgtggcattc   5820
atctatcaaa acgagtttct tggttgtacc gacagactcg tcattacccc tttgacggat   5880
aggtgctaca tcacccttgc acaagctctc ggaatgagca tgggaggtgc gcccgccggc   5940
ccggcgggaa ctggcaagac cgaaaccact aaggacatgg gcagatgtct gggcaagtat   6000
gtggtggtgt tcaactgttc cgaccaaatg gactttaggg gcctgggacg catcttcaaa   6060
ggactggcgc agagcggatc atggggctgc tttgacgagt ttaaccgcat cgatctcccg   6120
gtgctctccg tggccgccca gcagatttcg attattctca cctgtaagaa ggaacacaag   6180
aagtcattca ttttcacgga tggtgataat gtcacgatga ccccgaatt tgggctgttt   6240 ctcactatga atccagggta tgctggcaga caagaactgc cagagaacct taaaattaat   6300
tttcggtccg tcgcgatgat ggtgcccgac cgccaaatta ttatccgggt gaaactggcg   6360
tcatgtggct tcattgataa cgtcgtcttg gcgcggaaat ttttttactct ttataagctt   6420 tgtgaagaac agctctccaa gcaggtgcac tacgacttcg gtctgcggaa tatcctcagc   6480
gtcttgcgca cgcttggcgc cgcgaagagg gctaatccca tggatactga agcactatc    6540 gtgatgcgcg tccttcgcga catgaacctg tcaaagttga tcgatgaaga cgaaccactg   6600
tttctgtcgc tgatcgaaga cttgtttccc aatatcctcc tcgacaaggc gggttatcct   6660
gaattggagg cagcgatttc ccggcaagtg gaggaagcgg gcctgatcaa ccatcctccg   6720
tggaagctga aggtgattca gcttttcgag actcaacggg tgcggcatgg gatgatgacg   6780
cttggtccgt ccggggctgg taaaactact tgtattcaca ccctgatgag agccatgacc   6840
```

```
gattgcggta aacctcaccg cgagatgagg atgaatccaa aggccattac ggcacctcag    6900
atgtttgggc gcctggacgt ggccaccaac gattggaccg acggaatttt ttcgaccctg    6960
tggcgcaaaa ctcttagagc caagaaagga gagcatattt ggatcattct ggacggtcca    7020
gtcgatgcta tttggatcga aaacctgaac tcggtcttgg acgacaataa gacgctcacg    7080
cttgctaacg gagaccgcat ccctatggcg cccaattgca aaattatttt cgagccacac    7140
aacatcgata acgcatcacc tgccactgtc agccggaatg gcatggtctt tatgtcgagc    7200
tcgattctgg actggagccc gatcctggaa ggatttctca aaaagcgcag cccgcaagaa    7260
gcagagattc ttaggcaact ctacaccgaa agcttccccg acttgtacag gttttgcatt    7320
cagaatcttg aatacaagat ggaggtcctt gaggccttcg tcatcacgca gtcaattaac    7380
atgcttcagg gcctgatccc actcaaagaa cagggcggag aggtgtcaca ggcacacctc    7440
gggagattgt tgtgtttgc tcttctttgg tcagcgggcg cggcacttga actggatggg    7500
cgccgccgcc ttgagctctg gctgcggtcg agacctaccg gaactcttga actgccgcct    7560
cctgctggtc ctggagacac ggcatttgac tactatgtgg ccccagacgg cacttggact    7620
cattggaaca ccagaactca agaatatctt tacccatccg atactacgcc agagtatggg    7680
agcatccttg tgcctaacgt cgacaatgtc cgcacggatt tccttattca aactattgcg    7740
aaacagggga aggccgtcct gcttatcgga gagcaaggga ctgccaagac tgtcatcatc    7800
aaggggttta tgagcaaata tgacccagag tgccatatga tcaagtcatt gaattttca    7860
tccgccacta cgcctctcat gtttcaacgc accatcgaat cctacgtcga caaaagaatg    7920
ggaactactt atgggccccc tgccgggaag aaaatgactg tgttcatcga tgacgtgaac    7980
atgcccatta ttaatgagtg gggagatcag gtcaccaatg aaattgtcag acagcttatg    8040
gaacagaatg gattctataa tctcgaaaag ccagggaat ttacctccat tgtcgacatt    8100
caattcctcg cagccatgat ccatccagga ggtgggagga acgatattcc gcaacgcctt    8160
aagcggcagt tctccatttt caattgcacc ctccctccg aggctagcgt cgataaaatt    8220
tttggggtca tcggtgtcgg gcactactgc actcaaaggg gcttttcgga agaggtgaga    8280
gattcagtca cgaaactggt gccgttgact agacgcttgt ggcagatgac caaaatcaaa    8340
atgcttccaa ctcccgctaa attccactac gtgtttaatt tgcgggacct ttcgcgcgtg    8400
tggcagggta tgctgaacac tacctccgag gtcatcaaag aacccaacga tttgctgaag    8460
ctctggaaac atgaatgcaa acgcgtcatt gctgatagat tcacggtcag ctccgatgtc    8520
acctggttcg ataaagcgct ggtcagcctg gtcgaggaag agtttgggga agagaagaag    8580
ttgttggtcg attgtggtat tgacacctat tttgtcgatt ttctcagaga cgcgcctgaa    8640
gctgcgggtg agacctccga ggaggctgat gctgaaactc ccaaaattta tgaaccgatc    8700
gagtccttct cccatttgaa ggaacggctg aacatgttcc tgcagctcta taatgagagc    8760
atccgcggtg ccggaatgga catggtcttt ttcgcagatg ctatggtgca cttggtgaaa    8820
atttcaagag tcattaggac gccccagggt aatgcattgc tggtcggggt gggtggatcc    8880
ggtaagcaat ccctgacccg ccttgcatca tttatcgcgg ggtacgtgtc attccagatc    8940
actcttacga gaagctataa tacgagcaat cttatggagg acttgaaagt gttgtatagg    9000
acggccggtc agcagggcaa gggtatcacg ttcatcttca ccgataatga gatcaaagat    9060
gagtccttct tggagtacat gaataacgtg ctcagcagcg gtgaggtgtc gaacctttc    9120
gcaagagacg aaatcgatga aattaactcc gatctggcgt ccgtcatgaa aaaggaattt    9180
ccaaggtgcc tcccgacgaa cgagaatctc cacgactatt tcatgagcag agtccggcag    9240
```

```
aacctgcaca ttgtgttgtg cttctcaccg gtgggcgaaa agtttaggaa ccgcgcgctt   9300
aaattccccg ctctcatttc aggttgcact atcgattggt tctcaaggtg gccgaaggat   9360
gcactggtcg cagtgtcgga acactttctc acttcatatg atatcgattg ctcccttgaa   9420
atcaagaaag aggtggtgca gtgtatggga tcattccagg acggtgtggc ggagaaatgt   9480
gtcgactact ttcaaagatt cagaagaagc acgcacgtga cccctaaatc atacctctca   9540
tttattcagg gatacaagtt tatctacggc gaaaaacatg tcgaggtccg gactttggcg   9600
aaccgcatga acactggttt ggaaaagttg aaagaagcgt cagaatcggt cgctgcactg   9660
tcaaaggaac ttgaagcgaa ggagaaagaa ttgcaggtcg cgaacgacaa ggccgatatg   9720
gtcttgaagg aagtcaccat gaaggcacaa gctgccgaaa aggtgaaggc cgaagtgcaa   9780
aaagtcaaag atcgggcaca agccattgtg gattcaattt cgaaagacaa ggcgattgct   9840
gaagaaaagt tggaggcggc gaagccagcc ctggaagagg ctgaggcggc gcttcaaacc   9900
attaggcctt cagatattgc cacggtcaga accctgggca ggccgcctca ccttattatg   9960
agaattatgg attgcgtcct tctttttgttc cagcgcaaag tctcagctgt caagattgac  10020
ctcgagaaat cgtgtactat gccttcatgg caggaatcgc ttaagcttat gacggctggt  10080
aatttccttc aaaatctcca gcagttcccg aaggatacta tcaatgagga agtgattgag  10140
ttcctctcac cgtacttcga gatgcccgac tataacattg agacggcaaa gagagtgtgc  10200
ggaaacgtcg ccggactgtg ttcgtggacg aaggcaatgg cctcgttctt ttcaatcaat  10260
aaagaagtgt tgcctctgaa ggcaaacctc gtggtgcagg aaaacaggca tcttctcgct  10320
atgcaggatc ttcaaaaagc acaagctgag ctcgatgaca acaggctgaa actcgatgtg  10380
gtgcaagccg agtatgagca agcaatgact gaaaaacaaa cgctccttga ggacgcggaa  10440
aggtgtagac acaagatgca aactgcatca actttgattt cggggcttgc cggagaaaaa  10500
gagagatgga ccgagcaatc acaagagttc gccgctcaaa cgaagaggtt ggtcggtgac  10560
gtcttgctcg caaccgcctt cctgtcctat tcaggtccat ttaaccaaga gtttcgggat  10620
ctcttgttga cgactggcg caaggaaatg aaggcccgca aaatcccatt cggtaagaat  10680
cttaatctga gcgagatgct tatcgacgcg cctaccatta gcgaatggaa tcttcagggt  10740
cttccaaatg acgatctgtc gattcagaat gggatcattg tgacgaaagc gagccgctat  10800
ccgctgctta tcgacccaca gactcagggt aaaatctgga tcaagaacaa ggaaagccgg  10860
aacgaactcc aaatcactag ccttaatcat aagtactttc ggaaccattt ggaggattca  10920
ctgtccttgg ggcggccact gttgattgag gatgtgggtg aagagctcga tccgcgcgctc  10980 gataacgtcc tggaaaggaa tttcattaaa accgggagca ccttcaaggt gaaagtcgga  11040
gacaaggagg tggacgtctt ggatggattc cggctctaca ttacgactaa gctcccaaac  11100
cctgcttata ctcccgagat ctcggcccgc acgagcatca ttgatttcac ggtcacgatg  11160
aaaggtctcg aggaccagtt gttggggagg gtcattctca cggagaagca agagcttgaa  11220
aaggaaagaa cgcatctcat ggaggatgtg accgccaata agcggcggat gaaggagctg  11280
gaagacaacc tgttgtatcg gctgacgagc acccagggca gcctggtgga agacgaaagc  11340
cttatcgtcg tgctgagcaa cactaagagg actgctgaag aagtcactca gaaacttgaa  11400
atctcagctg aaacggaggt gcaaatcaat tccgcgcggg aagagtaccg cccggtcgct  11460
acgagaggtt cgattcttta tttcttgatt accgagatgc gcctggtgaa cgagatgtac  11520
caaacctccc ttcgccagtt tcttggactc ttcgacttga gcctcgcaag atcggtcaag  11580
```

```
agccccatca ctagcaaaag aattgctaat attatcgagc acatgactta tgaagtctac   11640
aagtatgcag caagaggcct gtatgaagaa cataagtttc tgtttacgtt gttgctgacc   11700
ctgaaaattg acattcagag aaatagagtc aagcatgagg agttcctcac gcttattaaa   11760
ggtggagcct cacttgactt gaaagcttgt cctccaaagc cctcaaaatg gattctcgac   11820
attacctggc tcaatcttgt ggagctttcc aaactcagac agttttcaga cgtccttgac   11880
cagatctcgc ggaatgaaaa gatgtggaag atttggttcg acaaggaaaa tcctgaagaa   11940
gaaccacttc ctaatgccta tgacaaatcc ctcgactgtt ttagaagatt gctgcttatt   12000
cggagctggt gtcctgatcg caccattgct caggcaagga aatatatcgt ggactccatg   12060
ggggaaaagt acgcagaagg ggtgattctt gatctggaga agacctggga ggaatcagat   12120
cctcggacgc cccttatttg cctgttgtcg atggggagcg atcccactga ctccattatc   12180
gcacttggca agagattgaa gattgaaacc agatatgtga gcatgggtca aggtcaagaa   12240
gtgcacgcca ggaagttgtt gcaacagacg atggccaatg gagggtgggc actccttcaa   12300
aattgccacc tcggcttgga cttcatggac gaacttatgg acattatcat cgaaaccgag   12360
ctggtccacg atgcgttcag attgtggatg acgactgaag cacacaaaca gttcccaatc   12420
acgctgcttc aaatgtcgat caagtttgcg aatgatccac cacaaggact tcgggccgga   12480
ttgaagcgga cttattcggg cgtctcacag gatctcctcg acgtgtcgtc agggagccaa   12540
tggaagccga tgctttatgc ggtggcgttc ctgcatagca ccgtgcaaga gaggagaaaa   12600
ttcggcgccc ttggatggaa tatcccttac gagtttaacc aggctgattt caatgccacc   12660
gtgcaattta ttcaaaacca cttggacgac atggatgtga agaaaggggg ctcgtggact   12720
acgattcggt acatgattgg agaaatccag tacggaggaa gggtcactga cgattatgac   12780
aagcggctgc ttaacacttt tgccaaagtc tggttctcgg aaaatatgtt tgggcccgat   12840
ttctcatttt accagggcta taatatcccg aagtgctcga ccgtcgataa ctatctccaa   12900
tacatccaat cgttgccagc ctatgacagc ccagaggtgt ttggtcttca cccaaacgct   12960
gatattacct accagtccaa actcgctaag gacgtgctcg acaccatcct gggtatccag   13020
ccaaaagata cgtcaggagg gggggacgaa acccgcgagg cagtggtggc tcgcctcgct   13080
gatgatatgc ttgaaaagtt gccaccagat tatgtgcctt tcgaggtcaa agaaagattg   13140
caaaagatgg gcccgttcca accaatgaac atcttcctca gacaggaaat cgacaggatg   13200
caacgggtgc tctcgttggt cagaagcacg cttacggagt tgaagttggc aatcgacggg   13260
acgatcatta tgtcagaaaa ccttagagac gccttggatt gtatgttcga cgctcgcatt   13320
ccggcttggt ggaaaaaagc gtcatggatt agctcaacgc tcgggttttg gtttacggag   13380
cttattgaaa ggaattcaca gtttacttcc tgggtgttca atggtcggcc acattgcttt   13440
tggatgacgg gtttctttaa ccctcaagga ttcttgactg cgatgaggca ggagatcact   13500
cgggcaaata aggggtgggc gctggataat atggtccttt gcaacgaagt gactaaatgg   13560
atgaaagacg acattagcgc accgcctact gaaggtgtct acgtctacgg cttgtacttg   13620
gagggagcag gttgggacaa aaggaatatg aaactgatcg agtccaaacc gaaggtcctc   13680
tttgaactga tgccggtgat tcggatttac gctgagaata atacgctccg ggacccaaga   13740
ttttatagct gcccgattta caaaaaacct gtcaggacgg atctgaacta cattgcagca   13800
gtggatctca gaaccgctca aacgccagag cattgggtgc tgcgcggggt cgcattgttg   13860
tgtgatgtga aatag                                                    13875
```

<210> SEQ ID NO 15
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 15

| | | | | | |
|---|---|---|---|---|---|
| atgtttcgga | ttggtcggcg | ccagctttgg | aagcactccg | tgactagggt | cctgacccag | 60 |
| agattgaagg | gagaaaagga | agcgaaacgc | gccttgctcg | atgcgcgcca | caattatctc | 120 |
| tttgccattg | tggcctcatg | cctcgatttg | aacaagaccg | aggtcgagga | cgctatcctg | 180 |
| gaaggtaacc | aaattgagag | aattgaccaa | ttgttcgccg | tgggcggact | tcggcacctg | 240 |
| atgttctact | accaggatgt | cgaagaggcc | gaaacgggtc | agcttggtag | cctgggcgga | 300 |
| gtgaaccttg | tctcagggaa | aattaagaaa | cccaaagtct | tgtgactga | aggaaatgac | 360 |
| gtggcattga | ctggggtgtg | tgtctttttt | atccggactg | atccgtccaa | ggctatcact | 420 |
| cctgacaaca | ttcaccagga | ggtctcattc | aatatgctgg | acgctgctga | cggcggtctt | 480 |
| cttaactcag | tcaggcgcct | cctgtccgat | atcttcattc | ctgccctgag | gcaacgagc | 540 |
| cacggatggg | gcgaacttga | ggggttgcaa | gacgcagcaa | atatcaggca | ggaatttctg | 600 |
| tcaagcttgg | agggtttcgt | gaacgtcttg | tcaggagccc | aagagtccct | caaagaaaaa | 660 |
| gtgaatctcc | ggaaatgcga | tatcctggag | ctgaagacgc | tcaaggagcc | cactgactat | 720 |
| ttgactttgg | caaataatcc | agagacgctt | ggaaaaatcg | aggattgtat | gaaagtctgg | 780 |
| attaagcaga | cggagcaagt | ccttgccgaa | aataaccaac | tgctgaaaga | ggcagacgat | 840 |
| gtgggtccca | gagctgaact | cgaacactgg | aagaaacgcc | tgtcgaagtt | taactacctt | 900 |
| ctggaacagc | ttaagtcgcc | ggatgtcaaa | gcggtgctcg | cagtcctcgc | ggccgcgaag | 960 |
| tccaagcttt | tgaaaacctg | gagggagatg | acatccgca | tcacggatgc | tactaatgag | 1020 |
| gccaaagaca | acgtgaagta | tttgtatact | cttgaaaagt | gctgcgaccc | tttgtactcg | 1080 |
| tcggacccgc | tgtcaatgat | ggacgctatc | cccacgttga | ttaatgcgat | taagatgatc | 1140 |
| tactccattt | cgcattacta | caatacgtcc | gagaagatta | cctcactgtt | cgtcaaagtg | 1200 |
| acgaaccaga | tcatttcagc | gtgtaaagcg | tacattacca | caacggcac | cgctagcatt | 1260 |
| tggaatcaac | cccaagacgt | ggtggaggag | aagatccttt | ccgcgatcaa | gcttaagcag | 1320 |
| gagtatcaat | tgtgctttca | caaaactaaa | caaaagctta | agcagaatcc | taacgccaag | 1380 |
| cagttcgatt | tttcagaaat | gtacatcttc | ggaaagtttg | aaacgttcca | cagacgcctc | 1440 |
| gccaaaatca | ttgatatctt | tacgaccctc | aagacctata | gcgtgctgca | ggattcgacg | 1500 |
| atcgagggc | ttgaggatat | ggctactaag | taccaaggaa | tcgtcgctac | tattaaaaag | 1560 |
| aaggaatata | actttctcga | ccaacgcaaa | atggacttcg | atcaggacta | cgaggaattc | 1620 |
| tgtaaacaga | ctaatgatct | gcataatgaa | cttagaaagt | ttatggacgt | cactttcgct | 1680 |
| aaaattcaaa | acactaatca | agcactcaga | atgctgaaaa | aatttgaacg | gttgaatatc | 1740 |
| ccaaatctgg | gcattgatga | taaatatcaa | cttatcctcg | agaactatgg | ggcagacatc | 1800 |
| gacatgatct | ccaagttgta | tactaagcaa | aaatacgacc | cccccttgc | tcgcaaccaa | 1860 |
| cccccaattg | caggaaaaat | cctgtgggcc | aggcagctct | tccaccggat | ccaacagcca | 1920 |
| atgcagctct | ttcagcaaca | tcccgctgtg | cttagcaccg | cagaagccaa | acctatcatc | 1980 |
| aggtcataca | accgcatggc | taaggtgctg | ctggaatttg | aagtcctttt | ccatcgggct | 2040 |
| tggcttagac | aaatcgagga | gattcacgtc | ggactcgaag | cctcccttct | ggtgaaagca | 2100 |

```
ccgggaacgg gggagctgtt cgtgaatttt gatccccaaa ttttgatctt gttccgggaa    2160
acggagtgca tggctcaaat gggtcttgaa gtctcaccac tcgctaccag cctctttcag    2220
aagagagata gatacaaacg gaacttttcc aacatgaaaa tgatgctcgc ggagtatcaa    2280
agggtgaaga gcaaaatccc tgccgcaatt gaacagttga tcgtcccgca cctggccaag    2340
gtggacgaag ccctccagcc cggacttgca gctttgacgt ggacgtcact taatattgag    2400
gcgtatctgg aaaatacgtt cgcgaagatc aaggacctgg agctcttgct cgatcgggtc    2460
aatgatctca tcgaatttag gattgatgca atcctcgagg agatgtccag cactcctctt    2520
tgtcaacttc ctcaggagga gcccttgact tgcgaggagt ttctgcagat gacgaaagat    2580
ctctgtgtca acggtgcaca aatcttgcac tttaagagca gccttgtgga agaagcagtc    2640
aatgagcttg tcaatatgtt gcttgacgtg gaagtcctct ccgaggaaga gagcgagaag    2700
atttccaacg aaaactccgt caattacaag aatgaatcaa gcgctaaacg cgaggaaggg    2760
aatttcgaca ctctcacgtc atcgatcaac gctcgggcca acgctcttct cctgaccact    2820
gtcacgagaa agaagaaaga aacggagatg ctgggagaag aggccagaga attgctttcg    2880
cactttaatc accaaaatat ggatgccctg ctcaaggtca ccaggaacac cctggaggcc    2940
attagaaaac ggattcacag ctcacatacc atcaacttta gggattccaa tagcgcttcg    3000
aatatgaagc agaactcatt gccaatcttc cgcgcttccg tgaccctggc gattcctaac    3060
attgtgatgg ccccggcatt ggaagacgtg cagcagactc tgaataaggc cgtcgaatgt    3120
atcatttcgg tccctaaagg ggtgcgccag tggtcgtcag aactcctgag caagaaaaag    3180
atccaggaga gaaaaatggc ggccttgcaa tcgaatgagg attcggattc agatgtcgaa    3240
atgggtgaga atgaactcca agacacgctt gagatcgcct cggtcaatct cccaatccct    3300
gtccaaacta aaaactacta taagaacgtc tccgaaaaca aggaaattgt gaaattggtg    3360
tcggtcttga gcactatcat taactcaacg aaaaaagagg tcatcaccag catggattgc    3420
tttaaaagat ataatcatat ttggcagaag ggtaaggaag aggccatcaa gacctttatt    3480
acccaatcac ctctgctctc ggaattcgag tcgcaaatcc tgtacttcca aaatctggag    3540
caagagatta atgctgagcc agaatatgtc tgcgtcggca gcattgcgct gtataccgct    3600
gatctgaagt ttgcattgac ggcggaaact aaagcttgga tggtcgtgat tgggcgccat    3660
tgtaacaaaa aatataggtc ggaaatggaa aacatcttca tgttgatcga ggagtttaat    3720
aagaagctca ataggcccat caaagacctg gacgatatta ggattgccat ggcagccctc    3780
aaggaaatta gagaggaaca aatctcaatt gacttccagg tcggacccat tgaagagtca    3840
tatgcgctgc ttaatcgcta cggattgttg attgcccggg aagagatcga taaagtggac    3900
actcttcatt acgcatggga gaaactcctc gctagggccg gtgaagtgca gaataagctt    3960
gtcagcctcc aacccagctt caaaaaagaa ctgatctccg cagtcgaggt cttcttgcag    4020
gattgccacc agttttactt ggattatgat ctgaatggtc ccatggcatc cggcttgaag    4080
cctcaggaag ccagcgatcg cctcattatg ttccagaacc agtttgataa tatttacaga    4140
aagtacatta cctataccgg aggcgaagag cttttttggct tgcctgctac ccaatatccg    4200
cagttgctcg aaattaaaaa gcagctcaat ctgcttcaga aaatttacac cttgtataac    4260
tcagtgattg aaacggtgaa ctcgtactac gatattctct ggagcgaggt gaatattgag    4320
aaaatcaaca cgaactcct tgaattccaa aaccggtgta gaaagctgcc cagggcgctg    4380
aaagattggc aggccttctt ggacctgaag aaaattattg atgacttctc agaatgctgc    4440
cccctcttgg agtatatggc atcaaaagcc atgatggaaa gacattggga acgcattacg    4500
```

```
acgcttacgg gacactccct tgacgtgggc aatgaatcct tcaagcttcg gaacatcatg    4560
gaagctccct tgttgaagta caagaagag atcgaagata tctgcatttc agccgtcaaa    4620
gaaagggaca tcgagcagaa gcttaaacag gtgattaacg aatgggacaa caaaacgttt    4680
actttcggga gcttcaagac caggggcgag ctgcttcttc gcggtgactc aacttcagag    4740
attatcgcaa atatggaaga cagccttatg cttctcgggt cactcctctc gaatcggtat    4800
aacatgccct ttaaagccca aattcaaaag tgggtccaat acctttccaa ctcgactgat    4860
attattgagt cctggatgac cgtccaaaac ttgtggattt acctcgaagc cgtcttcgtc    4920
ggtggagaca tcgccaagca actccccaag gaggccaaga ggttctcaaa cattgataag    4980
tcctgggtca aaatcatgac tcgggcacac gaggtcccgt cagtggtcca gtgctgtgtc    5040
ggcgacgaaa ctcttgggca gctccttccg caccttctcg atcaattgga gatttgtcaa    5100
aaatccttga ctggctacct tgaaaagaaa cggttgtgtt ttccacgctt tttctttgtc    5160
agcgatcctg cgttgctgga atcttgggt caggcgtcgg actcgcacac cattcaggca    5220
cacctgctta atgtctttga taatattaaa agcgtgaaat tccatgagaa gatctatgac    5280
agaattttga gcatttcgtc acaagaaggt gagactattg aactcgataa accagtcatg    5340
gctgaaggta acgtcgaggt ctggcttaat tcactcttgg aagagtcgca gtccagcttg    5400
cacctggtca ttagacaagc ggcggcaaac attcaagaga ctggttttca acttaccgag    5460
tttttgtcct ccttccccgc tcaagtgggt ctgttgggga ttcagatgat ttggactagg    5520
gatagcgaag aggcgcttcg gaatgcgaaa tttgataaaa aaatcatgca gaaaactaac    5580
caagcgtttc tcgaacttct taatacccctg atcgacgtca cgaccagaga cctgagctcg    5640
actgaaagag tcaagtacga aaccctgatt acgattcacg tccaccagag ggatatctt    5700
gatgacttgt gccacatgca tatcaaatca ccgatggatt ttgaatggct caagcagtgc    5760
agattctatt tcaatgagga tagcgataaa atgatgatcc atatcactga cgtggcgttc    5820
atctatcaga acgagtttct tggctgcact gatagactgg tcatcactcc tctgactgat    5880
cgctgttaca ttacccttgc ccaagcccctt ggtatgtcca tgggcggtgc tccagctggg    5940
cccgcgggca cgggaaagac cgaaactacg aaggacatgg gcaggtgtct gggaaagtat    6000
gtcgtcgtgt tcaattgctc cgatcagatg gacttccggg gcctcggcag aattttaag    6060
ggcctggctc agtcgggttc atgggggtgc ttcgacgaat tcaatcggat tgacttgcca    6120
gtgttgtcag tggcggcgca acagattagc attattttga cgtgtaaaaa agagcacaag    6180
aaatcgttta tcttcactga cggcgataac gtcacgatga atcccgaatt tggcttgttc    6240
ttgactatga atcccgggta cgcaggtcgc caggaacttc cggaaaatct taaaattaat    6300
tttaggagcg tcgcgatgat ggtgccagat cgccagatca ttatccgggt caaattggcc    6360
tcgtgtggat tcattgataa cgtggtgctg gcgagaaaat ttttaccct ttataaattg    6420
tgcgaggaac agctctcgaa gcaggtcac tacgacttcg gactccgcaa tattctttca    6480
gtcttgagaa ctctgggtgc agctaaaagg gcaaacccga tggacacgga aagcactatt    6540
gtcatgaggg tgcttcggga tatgaacctt tccaaattga ttgacgaaga cgaacctttg    6600
tttctcagcc tgattgaaga tctcttcccg aatattctcc tggacaaggc cggctaccct    6660
gaattggagg cagccatttc ccggcaggtc gaagaagccg gcttgatcaa ccatcctcca    6720
tggaagctca aagtgatcca gctcttcgag actcaacggg tgcggcacgg tatgatgacg    6780
cttggtccgt cgggtgccgg taaaaccact tgcatccaca ctctcatgag ggcgatgact    6840
```

```
gactgtggca aaccgcaccg cgaaatgcgc atgaatccga aagcgattac tgctccccaa    6900
atgttcggac ggttggatgt cgcgactaac gactggaccg atggcatctt ctcgacgttg    6960
tggcgcaaaa cgctgcgcgc caaaaagggc gagcacattt ggatcattct tgacggtcct    7020
gtggacgcga tttggattga gaatctgaat tccgtgcttg atgacaacaa aaccttgacc    7080
cttgccaacg gtgataggat ccccatggcc ccgaattgca aaattatttt cgaacctcac    7140
aatattgata atgcgtcacc cgctacggtc tcccgcaacg gcatggtctt tatgagctcg    7200
tcaatcctgg attggtcacc tatcctcgaa ggattcttga agaagcgctc cccccaagag    7260
gcagagattc tccggcaact ctataccgaa agcttcccg acctgtatcg cttttgtatt     7320
cagaacttgg agtacaaaat ggaagtcctt gaggcctttg tcattacgca atcgattaac    7380
atgcttcaag gccttattcc tttgaaagag caaggaggag aggtgtccca agcacatctg    7440
gggaggttgt tgtgtttgc gcttctttgg tcagcgggcg ccgcgttgga actggacggc     7500
cgcagacggc tcgagttgtg gctccgctcg agacctactg gtacgttgga actcccgcct    7560
cccgcaggtc ctggggacac cgcgtttgat tattacgtgg ctcccgacgg tacctggact    7620
cactggaaca ctaggaccca agagtacctc tacccttcag acacgacccc tgaatacggg    7680
tcgattcttg tgcccaatgt cgacaatgtc aggaccgact ttctcatcca gacgattgca    7740
aaacagggta aagcagtcct gctgatcggg gaacagggca cggcaaaaac tgtgatcatt    7800
aagggtttca tgtccaagta tgatccagag tgtcacatga ttaagtcatt gaacttttca    7860
tcggcgacta cgccgctcat gttccaaaga acgatcgagt cgtacgtgga caaacgcatg    7920
ggaaccactt atgcccacc agccgggaaa aagatgactg tgtttattga cgacgtgaat     7980
atgcctatta ttaatgagtg gggcgatcag gtcaccaacg aaattgtgag caacttatg     8040
gagcagaatg ggttttataa cctcgaaaag ccagggaat tcacttccat cgtcgacatc      8100
caattcctcg ctgccatgat tcatccaggg ggaggtagaa acgatatccc ccagcggctg    8160
aaacggcaat tttcaatctt taattgcacg ctgcccagcg aggcctcagt ggacaagatc    8220
tttggggtca ttggggtcgg acactactgc acgcaacgcg gatttcaga agaagtccgg     8280
gactcggtga ccaagctcgt cccgcttacc cgccggcttt ggcaaatgac caaaatcaag    8340
atgcttccaa ccccccgcaaa gtttcactac gtcttcaatc ttcgcgatct ttcacgggtg   8400
tggcaaggga tgctgaacac tacgtcgagg gtgattaagg agcccaacga cttgctcaaa   8460
ttgtggaaac atgaatgtaa gcgggtgatt gcagacaggt ttactgtgtc cagcgacgtc    8520
acgtggttcg ataaggctct cgtctccctg gtcgaagaag agttcggcga ggaaaaaaaa    8580
ctgcttgtcg attgcgggat tgatacctat ttcgtggact tcctgcggga tgccccagag    8640
gcggcgggag agacttccga agaggctgac gcggagaccc ctaagatcta tgaacctatc    8700
gaaagctttt cacacctcaa ggaacgcttg aacatgtttc tccaactgta caatgaatcg    8760
attagaggcg ccggcatgga catggtgttc ttcgccgacg cgatggtcca tctcgtgaaa    8820
atctcgcggg tcattcgcac ccctcaaggt aacgcgcttt tggtcggtgt cggcggcagc    8880
ggaaagcaga gcttgacccg cttggcttcc tttatcgcgg ggtatgtctc gtttcaaatc    8940
acgctgacca gatcgtataa tacttccaat ttgatggaag accttaaagt cctttataga    9000
actgcagggc aacaaggcaa gggtatcact tttatcttca ccgacaacga aattaaggac    9060
gaatccttcc tggaatatat gaataatgtg ctttcgagcg gggaggtgag caatctttt     9120
gccccgcgacg aaatcgatga aatcaatagc gaccttgcga gcgtcatgaa gaaggagttc    9180
ccaagatgtt tgcctacgaa cgaaaacctt catgactact tcatgtcacg ggtgaggcag    9240
```

```
aacttgcata tcgtcctgtg tttttccccg gtgggtgaga agtttcgcaa tcgcgcactg   9300
aaatttccgg cattgattag cggctgcacg atcgactggt tctcgcggtg gcctaaagac   9360
gcattggtgg cggtgagcga gcattttctg acctcatatg acatcgactg ttccctggaa   9420
attaaaaaag aagtcgtcca atgcatggga agcttccagg acggtgtcgc cgagaagtgc   9480
gtggattact tccagcggtt tcgccgctcg actcatgtca ctccaaaaag ctacttgtcc   9540
ttcattcaag gatataagtt tatctatggt gagaaacacg tggaggtgag gacccttgcc   9600
aatcgcatga acactggcct ggaaaaactg aaggaagcaa gcgagtccgt ggctgcgttg   9660
tcgaaagaac tcgaggcgaa agaaaaagaa ctccaagtcg ctaatgataa agcggacatg   9720
gtgctcaaag aggtgacgat gaaggctcaa gcagcagaga aagtcaaggc ggaggtccaa   9780
aaagtgaagg accgcgccca ggcgatcgtc gattcgattt ccaaagataa ggctatcgcc   9840
gaagaaaaat tggaggccgc gaagcctgct cttgaagagg ctgaagcagc acttcaaacc   9900
attagaccct cggacattgc cacggtgcgg actctgggca gacctccgca ccttatcatg   9960
agaatcatgg attgcgtctt gctgttgttc caaagaaaag tctccgcagt caaaatcgat  10020
ctcgaaaaat cgtgtacgat gccgtcctgg caggagtccc tcaaactgat gaccgcgggt  10080
aacttccttc aaaatctgca gcaattccct aaagacacta tcaacgagga agtgatcgaa  10140
ttcctgtcgc cgtactttga aatgcctgat tacaatatcg agaccgctaa aagagtgtgc  10200
gggaacgtgg ccggtctctg cagctggacc aaggcgatgg cttcgttctt ctcgattaat  10260
aaggaggtgc ttcccctcaa agccaacctc gtcgtccagg agaacaggca tctgctggcc  10320
atgcaagatc tccaaaaagc ccaagcagaa ttggatgaca agcaggcaga gcttgacgtc  10380
gtccaagccg agtacgagca agcaatgacg gaaaagcaaa ctcttctcga agacgcggaa  10440
aggtgtcggc acaaaatgca aaccgcttcc actcttatct cagggttggc aggagaaaag  10500
gaacgctgga ccgaacaaag ccaagaattt gcggctcaaa cgaagagatt ggtcggcgat  10560
gtgttgctcg caaccgcgtt tctgtcgtat tccggcccct ttaatcagga gtttcgcgat  10620
ttgctcctca atgattggcg gaaagagatg aaggcaagga agatcccgtt cggcaagaac  10680
ctgaatctct cggagatgct catcgacgct cctactatct cggagtggaa tctccaagga  10740
ctgcctaacg atgacctctc cattcaaaat gggattattg tcacgaaggc gagccgctac  10800
ccccttctga tcgatcccca gactcaaggg aagatctgga tcaagaacaa agaatcgcgc  10860
aatgagctcc aaaattacttc cctcaaccat aagtactttc gcaaccacct cgaagactcg  10920
ctttcattgg gcaggccact cttgatcgaa gatgtgggag aagaactgga ccctgccctt  10980
gataacgtgc tggaacgcaa cttcattaag acgggatcaa ctttcaaagt gaaagtgggt  11040
gataaggaag tggatgtgct cgacggattc agactttaca ttactacgaa gctccctaat  11100
ccagcctaca cgcctgagat ctccgctcgg acttcaatca tcgatttcac ggtgacgatg  11160
aagggccttg aggaccaact gttgggcaga gtcattctca ccgagaaaca ggaactcgaa  11220
aaggagcgga cgcatcttat ggaggacgtg acggccaata agcgccggat gaaggaattg  11280
gaagataact tgctctacag gctcactagc acgcagggta gcctcgtgga ggacgaaagc  11340
ctgattgtgg tcctcagcaa cacgaaaagg acggccgagg aggtgaccca aaagttggaa  11400
atttcagctg aaacggaggt gcagatcaat tcagcaaggg aagagtatag gcctgtggcg  11460 acgaggggggt caatcttgta tttcctgatt acggaaatgc gccttgtcaa cgaaatgtac  11520
cagacgtcat tgcgccaatt tctcgggctt tttgacctgt cgctcgctag gtcggtcaaa  11580
```

```
tcccctatca cgtccaaacg cattgcaaac attattgaac atatgacgta cgaggtgtac   11640
aagtatgcag cacggggact gtacgaggaa cacaaattcc ttttcaccct tctgctcacc   11700
ttgaagattg acattcagag gaatagagtc aaacacgagg agttcctcac tctcatcaaa   11760
ggtggggcgt cgctcgactt gaaggcttgt ccgcctaaac catccaagtg gattctggat   11820
attacgtggc tcaatctcgt cgaattgtca aaattgagac aattttcaga tgtgctcgat   11880
cagatttccc gcaacgagaa gatgtggaaa atctggttcg ataaagagaa tcccgaggag   11940
gagccccttc caaatgcgta tgacaaatcg ctggactgct tcggaggtt gctcctgatt   12000
cgctcgtggt gtccagatag aaccatcgcc caggcgcgga agtatattgt ggattcgatg   12060
ggtgaaaaat acgctgaagg agtcattttg gatctggaaa agacgtggga agagtcggac   12120
ccacgcaccc cgctcatctg cctccttagc atgggctcgg acccaactga ttcgattatt   12180
gccttgggga aaaggctcaa aattgaaacc aggtacgtca gcatgggtca gggtcaagag   12240
gtgcacgctc ggaaactgtt gcaacagacc atggcaaacg gcggatgggc tctgctccag   12300
aactgccacc tcgggttgga cttcatggac gaactgatgg acattatcat cgaaaccgaa   12360
ctggtgcacg atgcttttcg cctctggatg acgaccgagg cccataagca atttcccatc   12420
acgctcctcc aaatgagcat taaatttgcg aatgatccgc cacaggggct gagagctggt   12480
ttgaagcgga cttatagcgg agtcagccag gatctgttgg atgtctccag cggaagccag   12540
tggaagccca tgttgtatgc agtggccttt ttgcattcaa ctgtccagga gaggcggaag   12600
ttcggcgccc tcgggtggaa catcccgtat gaatttaacc aggcggattt caacgcgact   12660
gtgcagttta ttcagaacca tctggatgat atggatgtca aaaagggagt gtcctggacg   12720
accatcaggt atatgattgg tgagatccaa tatggtggga gggtcacgga cgattatgac   12780
aagaggcttc tcaacacctt tgcgaaagtg tggttttccg aaaacatgtt cgggcctgac   12840
tttagctttt accagggtta caatatcccc aaatgtagca ccgtggacaa ttacctgcaa   12900
tacattcaga gccttcccgc atacgacagc ccggaggtgt tcggttttgca tccgaatgca   12960
gatattacgt atcaatccaa gctcgcaaaa gacgtcttgg acacgatcct cggaattcaa   13020
cctaaagaca cgtccggcgg cggcgatgaa acccgcgaag ccgtcgtcgc gcggcttgcg   13080
gacgatatgt tggagaaatt gccacccgat tacgtcccctt ttgaagtcaa ggaaaggctt   13140
cagaagatgg gccctttttca acccatgaat atcttcctta ggcaggaaat tgaccgcatg   13200
cagagggtgt tgtcgctcgt ccggtcgacg cttaccgagt tgaagcttgc gatcgatggg   13260
accatcatta tgtccgaaaa tctcagagac gctctcgact gtatgttcga tgccaggatc   13320
ccagcttggt ggaaaaaggc gagctggatc agctccactt tgggcttttg gttcacggag   13380
ctcattgaga gaaactcgca gtttacttcg tgggtgttca acggcagacc acactgtttt   13440
tggatgactg gattctttaa tccccagggc tttttgactg ctatgaggca ggaaattact   13500
cgggctaaca aaggttgggc attggataac atggtgcttt gtaacgaagt cacgaagtgg   13560
atgaaggacg acatctcggc cccccccact gagggggtgt acgtgtacgg gttgtacctg   13620
gaaggcgcgg gctgggacaa aagaaacatg aagctcattg aatcaaagcc caaggtcctt   13680
ttcgaactca tgcctgtcat tcgcatctat gccgagaata acactctcag agatcctagg   13740
ttctattcgt gtccgatcta caaaaagccc gtgagaaccg atcttaatta cattgctgca   13800
gtggacttga gaacggctca aactcccgaa cactgggtcc tgagaggcgt ggcactcttg   13860
tgcgatgtca aatag                                                   13875
```

<210> SEQ ID NO 16
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 16

| | | | | | |
|---|---|---|---|---|---|
| atgttcagaa | ttgggcggcg | gcaactttgg | aagcatagcg | taacacgggt | gctgactcag | 60 |
| agactgaaag | gagaaaagga | ggcgaaaagg | gccttgctgg | acgcccgcca | taactacctc | 120 |
| ttcgcgattg | tggcctcatg | cctggacctg | aataagactg | aagtcgagga | cgctatcctc | 180 |
| gagggcaacc | aaatagagcg | catcgaccaa | ttgttcgccg | tgggtggact | tcggcacctg | 240 |
| atgttctact | accaagacgt | ggaagaagcg | gaaaccgggc | agctgggatc | actgggggc | 300 |
| gtgaacctcg | tgagcggaaa | gatcaagaag | cccaaggtgt | tcgtcaccga | aggcaacgat | 360 |
| gtggcgctca | ccggggtgtg | cgtgttttc | attcgcactg | acccatcaaa | ggccattact | 420 |
| cccgataaca | tccatcaaga | ggtgtccttc | aacatgctgg | acgctgccga | tgaggactg | 480 |
| ctcaacagcg | tgcgccggct | cctctcggac | atttcatcc | ccgccctgag | agctaccagc | 540 |
| catggatggg | gggaactcga | gggactacag | gacgcggcaa | acattcgcca | gaattcctg | 600 |
| tcctcattgg | agggcttcgt | gaacgtgctc | agcggagctc | aggaaagcct | caagaaaaa | 660 |
| gtcaacctcc | gcaagtgcga | catcctagag | ctcaaaacgc | tgaaggagcc | cacagactac | 720 |
| ctcactctcg | ccaataaccc | agaaaccctc | ggaaagatcg | aggactgcat | gaaggtctgg | 780 |
| attaagcaaa | cagaacaagt | cctggcggag | aacaaccagc | tccttaagga | ggcggacgac | 840 |
| gtcggcccga | gggcggagtt | agaacactgg | aagaaacgcc | tcagcaagtt | taattacctc | 900 |
| ctggagcaat | tgaagtcccc | tgacgtgaag | gccgtgctcg | cagtgttggc | agcggccaaa | 960 |
| tcgaagctgc | tgaaaacttg | gcgggagatg | gacattgaa | ttactgacgc | gactaacgag | 1020 |
| gccaaggata | acgtcaaata | cttgtacacc | ctcgagaagt | gttgcgaccc | gttgtatagc | 1080 |
| tcagacccac | tgagcatgat | ggacgccatc | cccaccctca | ttaacgccat | taagatgatt | 1140 |
| tactcaatct | cccattacta | caacacctca | gagaagatta | cttcactctt | cgtgaaggtg | 1200 |
| accaaccaaa | ttatctcggc | ctgcaaggct | tacattacta | taacgggac | agcttccatc | 1260 |
| tggaaccagc | cgcaagatgt | cgtggaagag | aagatcctgt | cggccatcaa | acttaaacag | 1320 |
| gagtaccaac | tctgctttca | caaaaccaag | cagaagctga | agcaaaatcc | gaacgccaag | 1380 |
| caattcgact | tctccgaaat | gtacatcttc | ggaaagttcg | aaaccttcca | ccggagactg | 1440 |
| gccaagatca | ttgacatttt | cactactctt | aagacctaca | gcgtgctcca | ggacagcact | 1500 |
| atcgagggac | tggaggacat | ggcaacgaag | taccaaggca | tcgtcgccac | cattaaaaaa | 1560 |
| aaggaataca | acttcctgga | tcagcggaag | atggacttcg | atcaggatta | tgaggagttc | 1620 |
| tgcaaacaga | ccaacgacct | ccacaacgaa | ctgcgcaagt | ttatggacgt | gaccttcgca | 1680 |
| aagatccaaa | acacgaacca | ggcgctgcg | atgctcaaga | gttcgagag | attgaacatc | 1740 |
| ccgaatctcg | gcatcgacga | taagtaccaa | ctcatcctgg | aaaactacgg | ggccgacatc | 1800 |
| gacatgatct | ccaagctgta | tactaagcag | aagtacgacc | cgccactggc | gagaaaccag | 1860 |
| ccccccattg | ccggcaagat | cctctgggcc | cgacagcttt | tccaccgaat | ccagcaaccc | 1920 |
| atgcagcttt | tccagcaaca | ccccgccgtg | ctctcaaccg | ccgaggccaa | gcccatcatt | 1980 |
| aggagctaca | acagaatggc | gaaggtcctg | ctcgaattcg | aagtcttgtt | ccaccgcgca | 2040 |
| tggttgcgcc | agatcgagga | aatacacgtg | ggactggaag | cgtcgctgct | cgtgaaggca | 2100 |

```
cctgggaccg gagaactgtt cgtcaacttc gacccgcaaa tcctgatcct gttccgcgaa    2160
actgaatgca tggctcagat gggattggaa gtcagccccc tggcgacttc cctcttccaa    2220
aagagagata gatacaaacg gaacttctcc aacatgaaga tgatgctggc ggaataccag    2280
cgcgtgaaat ccaagattcc ggccgctatc gagcagctca tcgtgcctca ccttgccaag    2340
gtcgacgaag cactgcagcc tggcctggcc gctctcactt ggaccagcct caacatcgag    2400
gcctacttgg aaaacacctt cgccaagatc aaggacctcg aactcctcct cgaccgggtg    2460
aacgacttga tcgagtttag gattgatgcc attctggagg agatgagctc cactccgctg    2520
tgtcaactgc cacaggagga acccctcaca tgcgaggaat cctgcaaat gactaaggac     2580
ctgtgcgtca acggggccca atcctgcac ttcaaatcct ccctggtcga ggaggcagtc     2640
aacgagctcg tgaacatgct cctggatgtg gaagtgctgt ccgaggagga gtccgagaag    2700
atctccaacg aaaatagcgt gaactataag aacgaatcca gcgccaagcg ggaagagggg    2760
aatttcgata ccctgacttc cagcatcaac gccaggggca acgccctctt actaactacc    2820
gtgactagaa agaagaaaga aaccgaaatg ctgggcgagg aggcacgcga actcctgtcc    2880
cactttaacc atcagaacat ggacgcccctt cttaaggtca cccggaacac tttggaggcg   2940
attcgcaaga gaatccacag cagccacacc attaacttcc gcgacagcaa ctcggcatcc    3000
aacatgaagc agaattcact gccgatcttc agggccagcg tgactttggc tatcccgaat    3060
attgtcatgg cgcctgctct ggaggacgtc cagcaaaccc tgaacaaggc cgtcgagtgc    3120
atcatcagcg tgccgaaggg tgtccggcag tggtccagcg aattgttgtc taaaaagaag    3180
attcaagaga ggaagatggc tgcgctccaa tccaatgaag atagcgacag cgacgtggag    3240
atgggcgaga acgaactgca ggacacctc gagatcgcgt ccgtcaacct tcctatcccg     3300
gtccagacca agaactacta caagaatgtc tcggaaaaca aggagatcgt gaagctcgtg    3360
tcggtcctgt ccaccattat caactccaca aagaaggagg tcattacttc catggactgc    3420
ttcaagaggt ataaccacat ttggcaaaag gggaaggaag aggccatcaa gacctttatc    3480
acccagtcgc cactcttgag cgagtttgag tcacagattc tgtacttcca gaacctggaa    3540
caggagatta atgctgaacc agagtacgtg tgcgtgggct ccattgcgct gtatactgcg    3600
gacctcaagt tcgcgttgac tgcagagact aaggcctgga tggtggtcat tggcagacac    3660
tgcaacaaga agtacaggag cgaaatggag aacattttca tgttgatcga agagttcaac    3720
aagaagctca accggccaat caaggacctc gatgatattc gcattgccat ggcggccctc    3780
aaggaaatcc gggaggagca gatctccatc gacttccagg tcggccctat tgaagagagc    3840
tacgcactgc tcaaccgcta tggactgtta atcgcccggg aagaaattga taggtggat    3900
accctgcatt acgcttggga aaagttgctg gcccgggcag gagaggtgca gaacaagctc    3960
gtcagcctcc aaccctcctt caaaaaggaa ttgatcagcg cggtggaggt ctttctccaa    4020
gactgccacc agttctactt ggattatgat ctgaacggcc ccatggctag cggcctgaag    4080
cctcaagagg cctcagaccg gctgatcatg tttcagaacc aattcgataa catctaccgg    4140
aagtacatta cctatactgg cggagaggag ttgtttggat tgccggcaac ccagtaccct    4200
cagctcctgg agatcaagaa gcagctgaac ttgctgcaga gatctacac cctctacaac    4260
tccgtcatag agactgtgaa ctcctactac gacattcttt ggagcgaagt aaacatcgaa    4320
aagatcaata cgagctctt ggaatttcag aaccgatgca ggaagctgcc ccgggccctg    4380
aaagactggc aggctttctt ggaccttaag aagattattg atgacttctc agaatgctgc    4440
cccctcctgg agtacatggc ctccaaggcc atgatggaac gccactggga gcggatcact    4500
```

```
accctgacgg gacacagcct ggatgtcggc aacgagagct tcaaactgag aaacatcatg   4560
gaagcgccac tcctgaagta caaggaagag attgaggata tttgcatttc cgccgtgaaa   4620
gaaagggaca ttgaacagaa acttaagcaa gtcatcaacg agtgggacaa caaaaccttc   4680
acgttcggct ccttcaaaac ccgcggcgag ctcctcctga ggggagactc aaccagcgaa   4740
atcatcgcca acatggagga tagcctgatg ctcctgggat cgctgctgtc gaacagatat   4800
aacatgccct tcaaggccca gattcagaag tgggtgcagt acctctccaa ctccaccgac   4860
atcatcgagt cctggatgac tgtgcagaac ttgtggatct acctcgaggc cgtgttcgtc   4920 ggagggata tcgcaaaaca acttcctaag gaagccaaga ggttcagcaa tattgacaag   4980
agctgggtga agatcatgac ccgggcacac gaagtgcctt cggtggtgca atgttgcgtg   5040
ggggatgaaa ccctcggaca gttgctgcct cacctccttg accaactcga gatttgtcaa   5100
aagtccctga ctggatacct cgagaagaaa cgcttgtgct cccaaggtt tttcttcgtg   5160 tccgatcctg ccctcttgga aatcctgggt caggcctccg actcacacac catccaagcc   5220
cacctcctta acgtctttga taacattaag agcgtcaagt tccatgagaa aatctacgac   5280
cggatcctct ccatttcgtc ccaagaggga gaaacgattg agctggataa gccagtgatg   5340
gccgaaggaa atgtcgaggt gtggctcaac agcctgctgg aagagtcaca aagctccctt   5400
catcttgtga tccggcaggc agccgccaat atccaggaaa ccggattcca actcaccgag   5460
ttcctcagct ccttccccgc acaagtggga ctgctgggca ttcaaatgat ctggacgcgg   5520
gactccgagg aagccctgag gaacgcaaag ttcgacaaga gatcatgca aaaaaccaac   5580 caggctttcc tcgaacttct caacaccctg atcgatgtga ccactagaga tctctcctcg   5640
acggaacggg tgaaatacga aaccctcatc accatccacg tgcaccagcg ggatattttc   5700
gacgacctct gccacatgca tattaagagc ccaatggatt ttgaatggtt gaaacagtgc   5760 cggtttttact tcaacgagga cagcgacaag atgatgatcc atatcaccga cgtcgccttc   5820
atctaccaga acgaattcct gggatgcacc gataggctgg tgattacccc gctgactgac   5880
cggtgctaca ttacgctggc ccaggccctg ggaatgtcga tgggcggcgc ccctgccgga   5940
ccggctggca ccggcaagac cgaaaccacc aaggatatgg gacggtgtct cggaaagtac   6000
gtggtggtgt ttaactgctc ggaccagatg gacttccgcg gacttggaag gattttcaaa   6060
ggcctcgccc aaagcggttc atggggatgc ttcgacgagt tcaaccgcat tgatttgccg   6120
gtgctgtccg tcgcagcgca gcaaatttcg atcatcctga cctgtaaaaa ggaacacaaa   6180
aagtcgttca tttttaccga cggagacaac gtcacaatga cccggagtt cgggttgttc   6240 ctgactatga accctgggta cgccgggcgc caggaactcc ctgaaaacct gaaaattaac   6300
ttccgctcag tggcaatgat ggtgcctgac agacagatca ttattcgggt gaagctggcg   6360
agctgcggct tcatcgataa cgtggtgctg gcgcggaagt ttttcacact gtacaaactt   6420
tgcgaggagc agctctccaa acaggtgcac tacgatttcg gactgagaaa tatcctgagc   6480
gtgctcagga ccctgggggc cgctaagcgc gcgaaccca tggatactga atccaccatt   6540
gtgatgaggg tgctgagaga catgaacctg tccaagctca tcgacgagga tgaaccctg    6600 ttcctgtccc tgattgaaga tctgttccca aacatcctcc tggacaaggc gggatacccc   6660
gagctggaag cagccatttc cagacaagtg gaggaggccg gactcatcaa ccacccaccc   6720
tggaagctca aggtcatcca gctgttcgaa acgcagagag tgcgacacgg catgatgaca   6780
ctggggccgt caggggcagg aaagaccacg tgcatccaca ccttgatgcg ggcgatgacc   6840
```

```
gactgcggga agccgcaccg ggagatgcgc atgaacccga aggcgattac tgcccctcaa    6900
atgttcggac ggctcgacgt ggccactaac gactggaccg acggcatttt ctcgacattg    6960
tggcgcaaga ccctaagagc caagaaggga gagcatatct ggatcatcct ggatggtcca    7020
gtggatgcga tttggatcga gaaccttaac tccgtgctgg acgacaacaa gaccctgaca    7080
ctggctaacg gcgaccggat ccctatggcg cccaactgca aaatcatctt cgagcctcac    7140
aacattgaca acgcctcgcc cgccaccgtg tcgcggaacg gcatggtgtt catgtcgtcg    7200
tccatcctgg actggtcccc cattctcgaa ggcttcctga agaagcgcag ccctcaagaa    7260
gccgagatac tccggcaact ctacaccgag tcgttccccg atctttaccg gttctgtatc    7320
cagaacttgg agtacaaaat ggaagtcctt gaggccttcg tgatcaccca gtcgatcaac    7380
atgctgcagg gactcatccc cctgaaagaa cagggaggtg aagtatccca ggctcacctg    7440
ggccgcctgt tcgtgtttgc gttgctttgg agcgcggggg ctgcgctcga gctggacggg    7500
cgacgccgcc tggagctctg gctccgcagt aggccgaccg gaaccctgga actcccgccc    7560
ccggccggcc ctggagacac cgccttcgac tactacgtgg cccccgacgg gacctggact    7620
cactggaaca cgagaaccca agaatacctg taccctccg acaccactcc ggaatacgga    7680
agcatccttg tgccgaacgt ggacaacgtg cgcactgact tcctaattca gaccatcgcc    7740
aaacagggga aggcagtgct gcttattgga gaacaaggta ccgcaaagac cgtgatcatc    7800
aagggattca tgtccaagta cgatcctgag tgtcacatga tcaagtcact taacttctcc    7860
agcgctacta cccctctgat gttccagaga accatcgaaa gctacgtcga caagcgcatg    7920
ggaaccacgt acggtccccc ggccggaaag aagatgaccg tattcatcga cgacgtgaac    7980
atgccgatca ttaacgaatg gggggatcag gtcaccaacg aaatcgtgcg gcaattaatg    8040
gagcagaacg gattctacaa cctggaaaag cccggagagt tcacttcaat cgtggacatt    8100
cagttcctgg ccgccatgat ccacccgggc ggaggaagaa acgacatccc gcagagactc    8160
aaaagacaat tctcaatctt caactgcacc ctgccgtccg aggcctcagt cgataagatt    8220
ttcggagtga tcggagtggg ccactactgc acgcagaggg gtttcagcga ggaggtccgc    8280
gactccgtga ccaaattggt cccactcact cgaaggctgt ggcagatgac caagattaag    8340
atgctcccca ctcctgccaa gtttcattac gtgtttaacc ttcgggactt gtcccgggtc    8400
tggcagggaa tgctgaatac gacctccgaa gtgattaagg aaccaaatga cctcctgaag    8460
ctctggaaac acgaatgcaa gagggtgatc gcggatagat tcacggtgtc ctccgacgtg    8520
acctggttcg acaaggccct cgtgtccttg gtggaagaag agttcggtga agagaagaag    8580
ctcctggtgg actgcggaat cgacacctac tttgtcgact tcttgagaga tgccccggag    8640
gctgcgggaa aaacctcaga agaggccgat cgggagactc cgaagattta cgaacccatc    8700
gaatccttca gccacttgaa ggaaaggctc aacatgttcc tgcagctcta caacgaaagc    8760
atccggggag ctgggatgga catggtgttc ttcgccgacg ccatggtgca ccttgtcaag    8820
atctcccggg tcattcgaac gccccaggga aacgcattgc tcgtgggtgt cggaggatcc    8880
ggaaaacagt ccctgacgag gctggcgtcc ttcattgcgg ggtacgtgag cttccaaatt    8940
actctcaccc gctcctacaa tacttccaac cttatggagg acttgaaggt cttgtaccgc    9000
accgccggac aacagggaaa ggggatcacc ttcatcttca ccgacaacga aatcaaggac    9060
gagagcttcc tggagtacat gaacaacgtc ctttcgtccg gagaagtgtc caacctcttc    9120
gcacgcgatg aaatcgacga gattaactcc gacttggcca gcgtcatgaa aaagaattc    9180
cctcgctgtc tccccaccaa cgagaacctc catgattact ttatgagccg ggtccgccaa    9240
```

```
aacttgcaca ttgtgctgtg cttctcgccc gtgggggaga aatttcggaa ccgggcgctg   9300
aagttccccg cgctgattag cggatgtact atcgactggt tctcgagatg gcccaaagac   9360
gccctggtcg ccgtgagcga acacttcctg acttcgtatg atatcgactg cagcctcgaa   9420
attaagaagg aagtggtgca gtgcatgggg tcatttcagg atggagtggc cgagaagtgc   9480
gtcgactact tccagagatt ccggcggtca actcatgtga cgcccaaaag ctacctttcg   9540
ttcatccagg gttacaagtt catatacggg gaaaagcacg tcgaagtgcg gaccctggcc   9600
aaccgcatga acaccggcct tgagaagttg aaagaggcct cggaatccgt ggcggcgctc   9660
agcaaggaac tggaggccaa agagaaggaa ctccaagtcg cgaatgataa agcagacatg   9720
gtgctgaagg aagtgacgat gaaagcccag gccgccgaga aggtcaaggc cgaggtccag   9780
aaagtgaagg accgcgctca agcaatcgtg gattcgattt ccaaggacaa agcaatcgca   9840
gaggagaagc tggaggccgc aaagcccgcg ctcgaagagg ctgaagcggc actgcagact   9900
atccggccgt ccgacattgc caccgtgaga accctgggcc gccccccaca cctcatcatg   9960
cgcatcatgg actgcgtcct cttgctctttt caacggaagg tgtccgccgt caagatcgac   10020
cttgagaaat catgcaccat gccatcgtgg caggagtccc tgaaactcat dacagccggc   10080
aacttcctgc agaatctgca acagttcccc aaagacacca tcaacgaaga agtgatcgag   10140
ttcttgtccc cgtacttcga aatgcctgat tataacattg aaaccgccaa gcgcgtgtgc   10200
ggaaatgtcg cgggcctgtg ctcctggact aaggccatgg cctccttctt tagcattaac   10260
aaggaagtgc tcccactgaa ggccaacctc gtggtgcagg aaaatcgcca cttgctggcc   10320
atgcaggatc tccagaaggc tcaagcggag ctggacgata acaggccga acttgacgtg   10380 gtgcaggcgg agtacgagca ggctatgacg gaaaagcaga ccttgctgga agatgcagaa   10440
agatgcaggc acaagatgca gaccgcctcc acccttattt ccggcctggc cggcgaaaag   10500
gaacggtgga ccgagcagtc ccaggaattc gcagctcaga ccaagaggct cgtgggcgat   10560
gtgctgctgg ccactgcctt cttgagctac tcaggcccct ttaaccagga atttcgggac   10620
ctcctgctga acgattggag gaaggaaatg aaggcgcgga agatcccatt cgggaagaac   10680
ttgaacctct ccgaaatgct catcgacgct cccaccatta gcgagtggaa cctccaggga   10740
ctgcccaacg acgaccttag cattcaaaac gggatcatcg tgaccaaggc ctcgcgctac   10800
cccctcctta tcgacccaca aactcaagga aagatttgga ttaagaacaa ggagtcacgc   10860
aacgagctgc agatcaccct cctgaaccat aagtacttca gaaaccatct cgaggattcc   10920
ctgagcctgg gcagaccct tctgatcgag gacgtgggcg aggagctcga tccggccctg   10980
gacaacgtcc tggagagaaa cttcatcaag actggatcca ccttcaaggt caaggtcggc   11040
gataaggaag tcgatgtcct ggatggcttc aggctgtata tcaccaccaa attgcctaac   11100
cccgcataca ccccggaaat ctcagcgcgc acctcgatca ttgactttac tgtcaccatg   11160
aaaggactgg aggatcaact gctgggcaga gtcattctca ccgaaaagca agagctcgaa   11220
aaggaacgca cccatctcat ggaggacgtg accgcgaaca agcggcggat gaaagagctt   11280
gaggataact tgctgtaccg cctgacctcg actcaggggt ccctcgtcga agatgagtcc   11340
ctgatcgtcg tcctgagcaa tactaagagg accgccgagg aagtaaccca gaagctcgag   11400
atcagcgcgg aaaccgaagt gcagatcaac agcgcaagag aagaatatag acccgtagct   11460
acgaggggga gcattctgta cttcctcatc acggagatga gacttgtcaa cgaaatgtac   11520
cagacctcat tgcggcaatt cctcggactg ttcgacctgt ccctcgctcg gtccgtcaag   11580
```

```
tcccctatca cttcaaagcg cattgcgaac attatcgagc acatgaccta cgaagtgtac    11640
aagtacgcgg ccagggggtt gtatgaggag cacaagtttc tcttcaccct cctgctgacc    11700
ttgaagatcg acattcaaag gaatcgcgtg aagcatgaag aattcctgac cctcatcaaa    11760
ggcggcgctt ccctcgatct gaaggcttgc ccaccgaaac cgagcaaatg gatcctggac    11820
atcacgtggc tgaaccttgt cgaacttagc aagctgcggc aattctccga cgtcctggac    11880
cagatctccc ggaacgagaa aatgtggaag atctggttcg acaaagaaaa ccccgaggag    11940
gagcctctgc ccaacgcgta tgacaaaagc ctggactgct tccggcggct cctcctcatt    12000
cgctcgtggt gtcccgaccg gaccattgca caggcccgca agtacatcgt ggactccatg    12060
ggggagaagt acgctgaggg cgtgatcctt gacctggaga aaacttggga ggaaagcgac    12120
ccgaggacgc ctctgatttg cctgctttca atgggaagcg acccgaccga tagcatcatc    12180
gcgctgggaa agaggcttaa gattgaaact cgctacgtca gcatgggggca aggccaggaa    12240 gtgcacgccc ggaagctgct ccagcagacc atggccaacg gaggctgggc gctgctgcag    12300
aactgccacc ttggactgga cttcatggac gaactcatgg acatcattat cgagactgaa    12360
cttgtccacg acgccttcag actgtggatg actaccgagg cccataagca gttccccatc    12420
acactcctcc agatgagcat caaattcgcc aacgatcctc cacagggcct gcgcgccgga    12480
ttgaaaagga cgtactcagg ggtgtcccag gacctcctgg acgtgtcctc cggctcccaa    12540
tggaagccaa tgctctacgc agtggcattc ctgcacagca ctgtgcagga gaggcggaag    12600
tttggagccc tgggatggaa cattccatac gagttcaacc aggccgactt caacgcgact    12660
gtgcaattca tccagaacca cctggacgat atggatgtga aaaggggggt gtcctggacg    12720
accattcgct acatgatcgg ggagatccag tacgggggaa gagtgaccga tgattacgac    12780
aagaggctcc tgaacacttt cgctaaggtc tggttctccg aaaacatgtt cggccccgac    12840
ttctcgttct accaggggta taacattcca aagtgctcga cggtggataa ctacctccag    12900
tacatccagt cgctgccggc ctacgattcc cccgaggtgt tcggcctcca ccccaacgcc    12960
gacattacct accagagcaa gctggctaaa gacgtgctgg acaccatact ggggatccaa    13020
ccgaaggata cctccggagg aggggacgaa acccgcgaag cagtggtggc acgccttgcc    13080
gacgacatgc tggaaaaact gccccctgac tacgtcccct ttgaggtcaa ggaacgcctc    13140
cagaagatgg gaccttttcca gccaatgaac atttttcttgc gacaagagat cgaccggatg    13200
cagcgcgtcc tctccctcgt gcgctcaacc ctcaccgagc tcaagctggc aatcgacggt    13260
accattatca tgtcggaaaa cctccgggac gcactggact gcatgttcga tgcgcggatc    13320
ccagcgtggt ggaagaaagc ctcctggatt tcgtcgaccc tggggttctg gttcaccgag    13380
ctgattgaaa ggaactccca attcacctcc tgggtctttta acggcagacc gcactgcttc    13440
tggatgaccg gcttttttaa ccccccaggga tttctcaccg ccatgcgcca agagatcacc    13500
agggcgaaca agggctgggc gttggataac atggtgctgt gcaacgaagt gactaagtgg    13560
atgaaagatg acatttcagc cccgccaacc gaaggcgtct acgtctacgg gctctacttg    13620
gaaggggccg gatgggacaa gagaaatatg aaactcattg agtccaagcc gaaggtgctg    13680
ttcgagctga tgccagtgat ccgcatctac gctgaaaata acactctccg ggatcccagg    13740
ttctactcgt gcccaattta caagaagccc gtgcggaccg acctgaacta catcgccgcc    13800
gtcgaccttc gcactgccca gactccggag cactgggtgc tgcggggagt cgccctgctt    13860
tgcgacgtga agtag                                                     13875
```

-continued

```
<210> SEQ ID NO 17
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 17
atgtttagga ttggaaggag acaattgtgg aaacacagcg tgaccagggt gctcactcaa     60
cgccttaaag gggagaagga ggctaaacgg gcgctgctcg acgctaggca taactacctc    120
ttcgccatcg tggcatcctg ccttgatctt aacaagacgg aagtggagga cgctattctt    180
gagggcaacc aaatcgagag aatcgaccag ctgttcgccg tgggaggcct gcgccacctt    240
atgttctact atcaggacgt ggaggaggcc gagactggac agctggggtc tttgggagga    300
gtcaatttgg tcagcggcaa aatcaagaag ccaaaagtgt tgtcacggaa ggcaatgac    360 gtcgcgctga ctggggtctg cgtgttcttc atccggaccg accctctaa ggccatcacc    420 ccagataaca ttcaccagga ggtgtctttc aacatgctgg acgccgcaga tggaggcctg    480
ctgaactccg tgaggaggct cctcagcgac atcttcattc ccgccctgcg cgccacctcg    540
catggatggg gagaactgga ggggcttcaa gacgccgcga acattcggca agaattcctg    600
tcctccctgg aaggattcgt gaacgtgctg agcggcgcac aggaatccct caaggagaaa    660
gtcaacttga gaaagtgcga catcctcgaa ctcaagactt tgaaggagcc taccgattac    720 ctcacccctcg cgaacaaccc tgaaaccttg gaaagatcg aagattgtat gaaggtctgg    780
attaagcaga ctgaacaggt gctggctgag aacaaccaac tgctgaagga ggccgacgat    840
gtcgggccgc gggcggaact cgaacattgg aaaaagagac tctccaagtt taattacctc    900
ctggaacagc ttaaatcccc ggatgtgaag gcggtgctgg cagtcctggc ggccgccaag    960
tccaagctgc tcaagacttg gcgcgagatg gacatccgca ttaccgatgc caccaacgag   1020
gcaaaggaca acgtgaaata tctgtacacc ctcgagaagt gctgcgaccc tttgtactca   1080
agcgatccac tctcaatgat ggacgccatt ccgactttga ttaacgccat taagatgatt   1140
tactccattt cgcattacta caatacctcg gaaaagatca cttcgttgtt cgtgaaggtg   1200
accaaccaga tcattagcgc ctgcaaggca tacatcacaa ataacggaac cgcctccatt   1260
tggaaccaac cgcaggacgt ggtggaggaa aagattttgt cagcaatcaa gttgaagcag   1320
gagtaccagc tctgtttcca taagactaag cagaagttga agcagaatcc caatgccaag   1380
caattcgact tctccgaaat gtacatcttc ggcaagtttg agactttcca ccggcggctg   1440
gcaaagatca ttgatatctt caccacgctt aagacctaca gcgtcctcca ggattcgact   1500
atcgaagggt tggaagatat ggcgaccaag tatcaaggaa ttgtcgctac catcaagaag   1560
aaggagtaca acttcctcga ccagagaaaa atggacttcg atcaggacta cgaggagttc   1620
tgtaagcaaa ccaacgatct gcataacgag cttcggaagt tcatggacgt cacgtttgcc   1680
aagattcaga ataccaacca agccctgagg atgcttaaga agtttgaacg gctcaacatt   1740
cccaacctcg gcatcgacga caagtaccaa ctcattctcg aaaattatgg ggcagacatt   1800
gatatgatca gcaagctgta caccaagcag aagtacgacc ctccactagc caggaatcag   1860
cctcctatcg ccggcaagat cctgtgggcg agacaactct tccacagaat tcagcagcca   1920
atgcaactgt tccagcagca tcccgcggtg ctgtcgactg cggaagccaa gcctatcatc   1980
cgctcctaca ataggatggc caaggtcctg ctggagttcg aagtgctgtt ccatagagct   2040
tggctccgcc agatcgaaga aattcacgtc ggccttgaag catccctcct ggtcaaggcc   2100
```

-continued

```
cccggcaccg gtgaactctt cgtcaacttc gaccctcaga tcctcatcct gtttagagag    2160
actgagtgca tggcccagat gggactcgaa gtttcgccgc ttgccactag cttatttcaa    2220
aagcgggatc ggtataagcg gaacttctcc aacatgaaga tgatgctggc cgagtatcaa    2280
cgggtgaaat ccaagattcc cgcggcgatt gaacagctca ttgtgccgca cctcgccaaa    2340
gtggatgagg ccttgcagcc gggacttgca gcactgacct ggacttcgct caacattgaa    2400
gcctacttgg agaacacttt cgccaagatc aaagacctgg aactgttgct cgataggtg    2460 aacgacctca ttgagttccg gatcgacgcc atcctcgaag aaatgtccag cactcccctg    2520
tgtcaactcc cccaagagga acccctcact tgcgaagaat ttctgcagat gacgaaggat    2580
ctttgcgtca acggggcaca gattctgcac ttcaagtcat cacttgtgga agaggccgtg    2640
aacgaacttg ttaacatgtt gcttgacgtc gaggtcttga gcgaggagga atccgagaaa    2700
atctccaatg aaaactcggt gaactataag aacgagtcct ccgccaagag ggaagaggga    2760
aacttcgaca ccctgacctc gtccatcaac gccaggcca atgccctgtt gctgactact    2820
gtgaccagaa agaagaagga gactgaaatg ctggggagg aagcaaggga gctcctcagc    2880
cacttcaacc atcaaaacat ggacgccctg ctcaaggtga ccaggaatac ccttgaggcc    2940
attcggaagc ggattcactc gagccacacc attaacttcc gcgatagcaa ctcagccagc    3000
aacatgaagc agaacagtct ccccatcttc agagcctccg tgactctggc cattccgaac    3060
attgtcatgg ccccgctttt ggaggatgtc cagcagactc ttaacaaggc cgtggagtgc    3120
atcatttccg tacccagggg cgtgcgccaa tggtctagcg aactcctgtc caagaagaag    3180
attcaggaac gcaagatggc cgccctccag agtaatgaag atagcgactc cgatgtggaa    3240
atgggggaaa acgaactcca ggatactctt gagatcgcct cggtgaactt gccgattccc    3300
gtccagacta agaactacta caagaacgtc agcgaaaaca agaaatcgt gaagctcgtg    3360 tcggtgctga gcacgatcat taacagcact aagaaggaag tgattactag tatggactgc    3420
ttcaagcggt ataaccacat ttggcagaag ggcaaggaag aggctattaa gaccttcatc    3480
acccaatccc ccctgctgag cgagttcgag tcccagatct tgtacttcca gaacctcgaa    3540
caagaaatta tgccgagcc cgagtacgtc tgcgtgggct ccatcgcgct gtacaccgcc    3600
gatctgaagt ttgccctgac cgccgagact aaggcctgga tggtcgtgat cggcagacac    3660
tgcaacaaga agtaccgctc ggagatggaa aacattttta tgcttattga agagttcaac    3720
aagaaattga accgccctat caaggatctc gacgacattc gaatagctat ggccgccctg    3780
aaggaaatcc gggaagaaca gatctcaatt gacttccagg tcgggcccat cgaagaaagc    3840
tacgcactcc ttaatcgcta cggactactc attgccaggg aagagatcga caaggtcgac    3900
accctccatt acgcatggga gaagctgctc gctcgcgctg gcgaagtgca gaacaaactc    3960
gtcagcctgc agccgagctt taagaaggaa ctgatctccg ccgtggaagt gtttctgcaa    4020
gactgccacc aattctacct tgattacgac ctcaatggtc caatggcctc gggcctgaag    4080
ccccaagagg cctcggaccg gctgatcatg ttccaaaacc agttcgacaa catctaccgg    4140
aagtacatta cctacactgg tggcgaagaa cttttcggcc tgccagctac ccagtatccg    4200
cagctcctgg agatcaagaa gcaactgaac ttgttacaaa agatctacac tctctacaat    4260
agcgtcattg aaaccgtcaa ctcctactac gacatcctgt ggagcgaagt gaatattgaa    4320
aaaattaata cgagctgct tgagttccag aacagatgcc gcaagctccc gcgggcactc    4380
aaggactggc aagcattctt ggacctcaag aaaattatcg acgatttcag cgagtgctgc    4440
ccgctcctgg agtacatggc ctccaaggcg atgatggaac gccattggga gcggatcact    4500
```

-continued

```
accctgacgg ggcacagcct ggacgtgggc aacgagagct ttaagctccg gaacattatg    4560
gaagccccgt tgctgaagta taaggaagag atcgaggata tttgcatcag cgccgtgaag    4620
gaaagggaca tcgagcagaa actaaagcaa gtgatcaacg agtgggacaa caagacgttc    4680
acgttcggct cgttcaagac tagaggagaa ctcctcctga gaggagactc cacttccgaa    4740
atcatcgcga acatggagga tagccttatg cttctcggct ccctacttag caacagatac    4800
aacatgccgt tcaaggcgca gatccaaaag tgggtgcaat acctgagcaa ctccaccgat    4860
attattgaat cctggatgac cgtgcagaac ttgtggatct acctcgaagc cgtgttcgtg    4920
ggtggagaca ttgccaagca actgcccaaa gaggcgaagc ggttttccaa cattgacaag    4980
agctgggtga agattatgac cagggcccac gaagtgccga gcgtggtgca gtgctgtgtc    5040
ggtgacgaga ctctcggcca gctgctccct catctcctgg atcagctgga gatttgtcag    5100
aagtcgttga ccggatacct tgaaaagaaa aggctctgct tcccgcgctt cttcttcgtg    5160
agcgaccccg cgctgttgga gattttgggt caagcgtccg attcccacac catccaagcc    5220
cacctcctca acgtctttga taacattaag tcagtgaagt tccatgagaa gatctacgac    5280
agaattctta gcatctcgtc ccaggagggc gagacaatcg agctggacaa gccggtgatg    5340
gccgagggta acgtcgaggt ctggcttaac tcgttgctgg aagagagcca gtcaagcctg    5400
cacttggtca ttcgccaagc cgcggccaac atccaggaga ctggattcca gctcaccgag    5460
ttcctgagca gcttcccggc tcaagtcgga ctcctgggca tccaaatgat ttggacgaga    5520
gactctgagg aggcgttgcg caacgccaag tttgacaaga aaattatgca aaagacaaac    5580
caggccttcc ttgaattgct aaacacccct attgacgtga ccaccagaga tctcagctcg    5640
actgagcgcg tgaagtacga aaccctgatc actatccacg tgcaccagag agacatcttc    5700
gacgacttgt gtcacatgca tattaagtcg ccgatggact tcgaatggct caagcagtgt    5760
agattctact tcaacgagga ctcggataaa atgatgattc atattactga tgtggcgttt    5820
atctaccaaa acgaattctt gggctgcact gataggttgg tgatcactcc cctgactgac    5880
agatgctata tcaccctggc ccaggcgttg gaatgtcaa tgggaggcgc ccctgccgga    5940
ccggctggca ctgaaagac cgaaacgact aaggatatgg ggagatgctt gggaaaatac    6000
gtcgtagtgt tcaactgctc cgaccagatg gacttccgcg gcctgggcag aattttttaag    6060 ggcctcgccc agtcagggtc gtgggggtgc ttcgacgagt tcaatagaat tgacttgccc    6120
gtcctgtcgg tggccgccca gcaaattagc atcatattga cgtgcaagaa ggaacataag    6180
aaatccttca tctttaccga cggggacaat gtcactatga atccagagtt cggtcttttc    6240
ctaaccatga acccaggcta cgctggcaga caggagctgc ctgagaactt gaagatcaat    6300
ttcagaagcg tggcgatgat ggtccccgac cgacaaatca ttatacgcgt caaactggcc    6360
tcgtgtggct tcatcgacaa cgtcgtcctg gcccggaagt ttttcaccct ctacaagctc    6420
tgtgaggagc agctcagcaa acaagtgcat tacgatttcg ggcttcggaa catcctgagc    6480
gtcctccgga ccctcggagc cgccaagaga gccaacccaa tggacaccga gtcaaccatt    6540
gtgatgcgcg tcttgcgaga tatgaacttg tccaagctca tcgacgagga cgagcccctc    6600
ttcctgagcc tgattgagga cctgttccct aacatcctcc tggataaggc cggctaccct    6660
gaactggagg cggccattag cagacaggtg gaggaggcgg ggctgatcaa ccatccccct    6720
tggaagctca aggtcatcca gttgttcgag actcagcgcg tgcggcacgg catgatgacc    6780
ctgggaccgt ccggcgcagg caaaactacg tgcattcaca ccctcatgcg ggcgatgacc    6840
```

```
gactgtggca agccccacag agaaatgaga atgaatccca aagccattac tgctccccaa      6900
atgtttggcc ggctggacgt ggccaccaat gactggacgg acggaatctt tagcaccttg      6960
tggcggaaaa ccctgagagc taagaagggc gaacacattt ggatcattct cgacggccct      7020
gtggacgcga tttggattga aaatctgaat agcgtgctgg atgacaataa gactctcacg      7080
cttgccaacg gtgatcggat tcccatggcc ccgaattgta agattatttt cgagcctcat      7140
aacatcgata acgcttcgcc tgcgactgtc tcaagaaatg gcatggtgtt tatgtcctct      7200
tccattctgg actggtcccc gattctcgag ggcttcctga agaaaaggtc accacaagag      7260
gctgaaattt tgaggcaact gtacactgag tccttcccag acctgtaccg gttttgcatc      7320
cagaacctcg agtacaaaat ggaagtcttg gaagccttcg tcattactca gtcaatcaac      7380
atgctccagg ggctcatccc cctcaaggag caggggggag aggtcagcca ggcgcacctc      7440
ggacggctgt tcgtgttcgc actcctgtgg agcgcggggg ctgcactgga actggatggg      7500
aggaggcggt tggagttgtg gctgagaagc agaccgacgg gtaccctgga actaccccc       7560
cccgcgggtc cgggagacac cgccttcgat tactacgtcg cgcccgatgg cacttggacc      7620
cattggaaca ctcgcaccca agagtatttg tacccttccg atactacgcc tgaatacggc      7680
agcatcctcg tgcctaacgt ggacaacgtc cggacagact tccttatcca aaccattgcc      7740
aaacagggca aggccgtgct cttgattggg gagcaaggca ctgccaagac ggtgatcatt      7800
aagggcttca tgtcgaagta cgacccagaa tgccatatga tcaaatcact gaacttcagc      7860
agcgccacta ccccactcat gttccaacgc acaattgagt cgtacgtcga taaaagaatg      7920
ggcaccacct acgacctcc ggccggaaaa aaatgaccg tgtttatcga cgatgtgaat       7980
atgcctatta tcaacgagtg gggtgaccaa gtgaccaacg aaatcgtgcg ccagcttatg      8040
gaacagaacg gattttacaa cctggagaag cctggggagt ttacctctat cgtggacatc      8100
caattcctgg ccgcaatgat tcacccggga ggaggtcgga acgacatccc gcagcgactg      8160
aagcggcaat tctcgatctt caactgtact ctcccgtcgg aggcgtcagt ggacaagatc      8220
tttggagtca tcggggtggg ccattactgt acccagaggg gtttcagcga agaggtgcgc      8280
gattccgtga ccaagctggt gccccttacc agacgcctgt ggcaaatgac caagatcaaa      8340
atgcttccca ctcccgcgaa gttccactac gtgtttaacc tccgcgatct gtcccgggtc      8400
tggcagggca tgttgaacac taccagtgaa gtcatcaagg agccgaacga cttgctcaag      8460
ctgtggaagc acgaatgcaa gcgcgtcatc gccgaccggt ttacggtgtc ctccgacgtg      8520
acctggttcg acaaagcgtt ggtgtcattg gtcgaagagg aattcggtga ggaaaaaaag      8580
ctcctggtgg attgtgggat tgacacttac tttgtcgatt ttctccgcga cgcccctgaa      8640
gcggccggtg aaaccagcga ggaagccgac gccgaaaccc cgaagatcta cgagccgatt      8700
gaatcgttca gccatctcaa agagcggctc aacatgttcc tccagctgta caacgaatca      8760
atcaggggcg ctggaatgga catggtgttc ttcgccgatg ccatggtcca ccttgtcaag      8820
atctcgcgcg tgatccggac ccctcaagga aacgccctct tggtcggtgt cggagggtca      8880
ggaaagcaga gcctgacccg gctcgcgtcg ttcattgccg gttacgtgag cttcaaatt      8940
actctcaccc ggtcgtataa cacctcgaac ttgatggagg acctgaaggt cctctatcgc      9000
accgccgggc agcaaggcaa aggaatcacc ttcatcttca ccgacaacga aattaaggat      9060
gaatcatttc tggaatacat gaacaatgtc ctgagcagcg gagaagtgtc caacttgttc      9120
gctcgcgatg agatcgatga aattaactcc gacctggcct ccgtgatgaa gaaggagttc      9180
cctaggtgcc tgccgaccaa cgaaaaacctc catgactact tcatgtccag ggtccggcaa      9240
```

```
aatctgcata ttgtgctgtg tttctcaccc gtgggggaaa aatttcgcaa tcgcgcgctg   9300
aagttccccg cactgatcag cggctgcacc atcgactggt tctcccggtg gccgaaggat   9360
gccctggtgg cagtcagcga acacttcctg actagctacg atattgactg tagcctcgaa   9420
attaagaagg aggtggtcca atgcatgggg tcattccagg atggtgtcgc agaaaaatgc   9480
gtggattatt tccaaaggtt ccggagaagc acccatgtga cgccgaagtc gtacttgtcg   9540
ttcattcagg gctacaaatt catctatggc gaaaaacacg tcgaagtgcg gaccctggct   9600
aacagaatga acaccggcct ggaaaaactg aaggaagcta gcgaaagcgt ggccgcgctc   9660
agcaaggaac ttgaagcgaa ggaaaaagaa ctgcaagtgg ctaacgacaa agcggacatg   9720
gtgttgaaag aggtgaccat gaaggcccag gcagcagaga aggtgaaggc cgaggtgcaa   9780
aaggtcaaag accgggccca ggccattgtg gactcgatct ccaaggataa ggctatcgct   9840
gaggagaagt tggaagcggc taagccagcc ctggaagagg ccgaggccgc cctgcaaacc   9900
atcaggccgt ccgacatcgc gaccgtgcgc accttgggca gaccgcccca cctcatcatg   9960
cggatcatgg actgtgtact cctcctgttc cagcgcaagg tgtccgcagt caagatcgat  10020
ctggaaaagt catgcacgat gcccagctgg caggaaagtc ttaaactcat gactgccggt  10080
aacttcctgc aaaaccttca acaatttccc aaggacacca ttaacgaaga agtcatcgaa  10140
ttcctgtcgc cgtacttcga aatgcctgac tacaatattg agactgccaa acgcgtgtgc  10200
ggaaacgtcg ccggactttg ctcctggacg aaggccatgg catccttctt cagcattaac  10260
aaggaggtcc tgccgctgaa ggcgaacctc gtggtccagg aaaaccgcca ccttctggcc  10320
atgcaagatc tccaaaaagc acaagccgaa ctggacgaca agcaggcgga acttgacgtg  10380
gtccaggccg agtacgagca agcaatgacc gagaagcaga cttgctgga ggacgcagaa  10440 cgctgccggc acaagatgca gacggcgtca acgttgatct cgggcctcgc cggagaaaag  10500
gaaagatgga ccgagcagag ccaagaattc gcagcgcaga ctaagagact tgtcggagat  10560
gttctcctgg ccaccgcctt tctgtcctac agcgggccat tcaaccagga attcagagat  10620
ctgctgctga acgactggcg caaggaaatg aaggctcgca agattccgtt cgggaagaat  10680
ctcaatctct cggaaatgct tatcgacgca ccaaccatct ctgaatgaa tctgcaaggc  10740 ctgccgaacg acgaccttag catccagaac ggaatcatcg tgactaaggc ctccaggtac  10800
cccctcctga tcgaccccca gactcaggga agatctgga ttaagaacaa ggaatcgcgg  10860
aacgaactcc agatcacctc actcaaccac aagtacttcc gcaaccatct cgaggattca  10920
ctcagcctgt gtcggccct gcttattgag gacgtcggag aggagctgga tcctgccctc  10980
gacaacgtcc tcgagagaaa cttcatcaag acgggatcaa ccttcaaggt gaaggtcgga  11040
gacaaggaag tcgacgtgct ggatggattc aggctctaca tcaccactaa gctccccaac  11100
cccgcctaca ctccggagat ttcggcccgc acctccatca tcgactttac cgtcaccatg  11160
aagggactcg aagatcagct cctcgggaga gtgatcctga cagaaaagca ggaactggaa  11220
aaagaaagaa cgcatctgat ggaggatgtg actgcgaata gcggagaat gaaggaactc  11280 gaagataact tgctgtatag acttacgagc acccaagggt ccctggtcga ggacgagtca  11340
ttgatcgtgg tgctgtccaa caccaagcgc accgccgagg aggtgacgca gaagctcgaa  11400
atctcggcgg aaacggaagt ccagattaat tcggctcgcg aggaatatcg cccggtcgca  11460
actcggggat cgatcctgta cttcctgatc actgaaatgc ggctcgtcaa cgaaatgtac  11520
cagacatcgc tgcggcaatt cctgggactt tttgacctga gcctggcccg gtccgtcaag  11580
```

-continued

```
tcgccgatca cctcaaagag aattgcgaac atcattgaac acatgaccta cgaagtgtac    11640
aagtacgccg cccgtggatt gtacgaggag cacaaattcc tgtttacctt gctgcttacc    11700
cttaagatag acatccagag gaacagagtg aagcacgaag agttccttac gctgattaag    11760
ggcggagcct cactcgactt gaaggcatgc cccccgaagc catcaaagtg gattctcgac    11820
atcacctggc tgaacctggt ggagctctcc aagctccggc agttctcgga cgtcctggac    11880
caaatatcga gaaacgaaaa aatgtggaag atttggtttg acaaggaaaa cccggaagag    11940
gagccccttc ccaatgccta tgacaagtcg ctggactgct ttcggcgcct cctcctgatt    12000
aggtcctggt gccctgatag gactattgcc caggccagaa agtacattgt ggactcaatg    12060
ggagagaagt acgccgaagg agtcatcctt gacctcgaaa agacttggga ggaatcagac    12120
cctcgcaccc cgctgatttg tctcctttcg atgggctcgg atcctacaga tagcatcatc    12180
gccctgggaa agcgcctcaa gatcgaaact cggtacgtgt ccatgggaca aggtcaggaa    12240
gtccatgccc ggaagctgct tcaacagact atggcgaacg gtggatgggc cctgcttcag    12300
aactgccacc ttgggctcga tttcatggac gaattgatgg acattattat cgaaacggag    12360
ctggtgcacg acgcttttag actctggatg accactgagg cccataagca attccccatt    12420
acgctgctcc aaatgtctat caaattcgcc aatgatcccc gcaaggtct gcgggctggt    12480 cttaaaagga cgtactccgg agtgtcccag gacttgctgg atgtctccag cgggtcgcag    12540
tggaaaccaa tgctttacgc cgtcgccttc cttcactcga ccgtgcagga acgccggaag    12600
ttcggcgccc ttggctggaa cattccctac gaattcaatc aagccgactt caatgccact    12660
gtgcaattca tccagaacca cttagacgat atggacgtca aaaagggagt gagctggacc    12720
accatccgct acatgattgg tgaaatccag tacgcggac gggtcacgga cgattatgac    12780
aaacggctcc tcaacacctt cgcgaaagtg tggttcagcg agaacatgtt cggtccggac    12840
ttctccttct accaaggcta taatattcca aagtgctcga ctgtggataa ctacctccag    12900
tacattcaga gccttcctgc atatgactcc cctgaagtgt tcggattgca tccgaacgcc    12960
gatattactt accagagcaa gctggcaaag gacgtgctgg acaccattct gggcatccag    13020
cccaaggata cgagcggagg aggagatgaa acccgcgaag ccgtcgtcgc acgcttggca    13080
gacgacatgc tggagaaact gcctcccgac tacgtgccgt ttgaggtgaa ggaacggctg    13140
cagaaaatgg gaccatttca gccgatgaat attttcctgc ggcaggaaat cgaccggatg    13200
caacgcgtgc tttccctcgt ccgcagcacc ctgaccgagc tgaaacttgc tatcgatgga    13260
accattatca tgagcgagaa cttgcgcgac gccttagact gtatgttcga tgcgagaatc    13320
ccggcgtggt ggaagaaagc cagttggatc tcgtcgacac tggggttctg gttcaccgag    13380
cttatcgaaa ggaactccca attcacgtcc tgggtgttca acggtagacc gcattgcttc    13440
tggatgactg gattcttcaa cccgcagggc ttcctgaccg ccatgcggca ggagatcacc    13500
agagccaaca aaggatgggc tttggacaac atggtgctct gcaacgaagt cacaaagtgg    13560
atgaaggacg atatctccgc cccgcctacg gagggcgtat acgtctacgg gctctacttg    13620
gaaggagccg gatgggacaa gagaaatatg aagctgatcg aaagcaagcc gaaggtgcta    13680
ttcgaactga tgccagtgat ccgcatttac gccgagaaca cacacttcg cgatccgcga    13740 ttctacagct gccctatcta caaaaagccc gtgaggactg acctgaacta tatcgcagca    13800
gtggaccttc gcaccgccca aaccccgaa cactgggtgt tgagggggt ggcgctgctc    13860 tgcgacgtga agtag                                                    13875
```

<210> SEQ ID NO 18
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 18

| | | | | | |
|---|---|---|---|---|---|
| atgttccgga | tcggacggcg | ccaactttgg | aagcattccg | tcacccgcgt gctgactcag | 60 |
| cgcctcaagg | gtgaaaaaga | ggccaaaagg | gccctgctcg | atgctagaca taactactta | 120 |
| tttgccattg | tcgcatcctg | cctggatctg | aataagaccg | aagtcgagga cgcgattctg | 180 |
| gaagggaacc | aaatcgagcg | atcgaccaa | ctcttcgccg | tgggtgggct gcgccatctc | 240 |
| atgttctact | accaggatgt | ggaagaagca | gaaaccggcc | aattgggatc actgggaggt | 300 |
| gtcaatctcg | tatccggcaa | gattaagaaa | cctaaggtgt | tcgtgactga gggaaacgac | 360 |
| gtcgcgctta | cgggcgtctg | cgtcttttc | attcggaccg | atccttcgaa ggccatcacc | 420 |
| ccggacaaca | tccaccaaga | agtgtccttc | aacatgcttg | acgcagccga cggcgggctt | 480 |
| ttaaacagcg | tcagacggct | cctgagcgac | attttcattc | ctgccctgcg ggccactagc | 540 |
| cacggctggg | gagaattgga | gggacttcag | gacgctgcta | atattagaca agaattcctc | 600 |
| tcctcgttgg | aaggattcgt | gaacgtgcta | agcggcgccc | aggaaagcct gaaagagaag | 660 |
| gtcaacttga | ggaagtgcga | catcctcgaa | ttgaaaacac | tgaaggagcc tactgattac | 720 |
| ctgacactgg | caaacaatcc | tgagactctc | gggaaaatcg | aggattgtat gaaggtctgg | 780 |
| atcaagcaga | ccgagcaagt | gctcgccgaa | aacaatcaac | tcctcaagga ggcggatgac | 840 |
| gtgggtccta | gggcagaatt | ggagcattgg | aaaaaaagac | tctccaagtt caactacttg | 900 |
| ctcgaacagc | tgaaatcgcc | tgacgtgaag | gccgtccttg | ccgtgctggc cgctgccaag | 960 |
| agcaaactcc | tgaaaacttg | gcgggaaatg | acattcgga | tcactgatgc caccaacgag | 1020 |
| gctaaggaca | atgtgaagta | cttgtacaca | ctcgagaagt | gttgcgaccc gctgtattcg | 1080 |
| agcgatccac | tcagcatgat | ggacgcgatc | ccgaccctca | ttaacgcaat taagatgatc | 1140 |
| tactcgataa | gccattatta | caacacctct | gaaaagatca | cctccctttt cgtgaaggtg | 1200 |
| acgaaccaga | ttatttcagc | ctgcaaggct | tacattacta | caacggcac tgcctccatc | 1260 |
| tggaatcagc | tcaggacgt | cgtggaggag | aaaatcctgt | ccgcgatcaa gctgaagcaa | 1320 |
| gaataccagc | tgtgcttcca | caagaccaag | caaaagctca | aacagaaccc caatgctaaa | 1380 |
| caattcgact | tttcggagat | gtacatcttc | ggaaagtttg | aaaccttcca tcggaggctc | 1440 |
| gcgaagatta | tcgacatctt | caccaccctc | aagacttaca | gcgtgctcca ggatagcact | 1500 |
| atcgaaggcc | tagaagatat | ggctaccaaa | taccaaggaa | ttgtggcaac catcaagaag | 1560 |
| aaggaataca | acttcctgga | ccagcgcaaa | atggatttcg | atcaggatta tgaggagttt | 1620 |
| tgtaagcaga | ccaacgatct | gcataatgaa | ctgaggaagt | tcatggacgt gacgttcgct | 1680 |
| aagatccaaa | atactaatca | agccctgagg | atgctgaaga | gtttgaacg cctgaacatc | 1740 |
| cccaacctcg | gaatcgacga | taaataccaa | ctcatcctcg | aaaactacgg agcagatatc | 1800 |
| gacatgatct | ccaagttgta | cacgaagcag | aagtatgacc | ctcctctcgc ccggaaccag | 1860 |
| cctccgattg | cgggaaagat | cctttgggcc | cgccagctct | tcaccggat ccagcagcca | 1920 |
| atgcagctct | ttcagcaaca | tcctgcggtc | cttagcaccg | ccgaagccaa acctattatc | 1980 |
| agatcataca | accgcatggc | caaagtgttg | ttggagttcg | aggtcctgtt ccatcgcgcc | 2040 |
| tggctgaggc | agatcgaaga | gatccacgtc | ggcctcgagg | cgtccctgct tgtcaaggcc | 2100 |

```
ccgggtactg gggaactctt cgtgaatttt gaccccncaga tcttgatcct tttccgcgag    2160
acagagtgca tggcgcaaat gggactggaa gtctcgccgt tggccacttc gttgttccag    2220
aagcgggata ggtacaagcg aaacttcagc aacatgaaga tgatgctggc agaataccaa    2280
cgtgtgaagt cgaaaattcc cgccgcaatc gaacagctca tcgtgcccca cttggctaaa    2340
gtggacgagg ccctgcagcc gggactcgct gcgctgacct ggaccagcct caacattgaa    2400
gcctacctcg agaacacctt cgctaagatc aaggatctcg agctcctcct cgatagagtc    2460
aacgacctga ttgaattcag gattgacgca attctggagg aaatgagctc aactcccctc    2520
tgtcagctcc cccaagaaga accgctgact tgcgaagaat ttctccagat gaccaaagac    2580
ctgtgcgtca atgggcgca gatcctccac tttaagagtt cactcgtcga ggaggccgtg    2640
aacgaactcg tgaacatgct gctggatgtg aagtgctgt cggaggaaga gtcggagaag    2700
atttccaacg aaaacagcgt gaattacaaa acgagtcat cagcaaagcg cgaagagggg    2760
aacttcgata ccctgaccag cagcatcaac gccagggcca acgctttgct cctcacgacc    2820
gtgacccgaa gaagaaaga aaccgagatg ctcggagagg aagcgcggga attgctgtcg    2880
cacttcaacc accagaacat ggacgcactc cttaaagtga ctcggaacac tttggaggcg    2940
atccggaaga ggatccattc ctcccatacc atcaacttca gggacagcaa cagcgcgtcg    3000
aacatgaagc agaactcact cccaattttc agagcgtcgg tgacacttgc cattccgaac    3060
atcgtcatgg ctcccgcact ggaggatgtc caacagaccc tgaacaaggc agtggagtgt    3120
atcatttcgg tccccaaagg ggtgcggcag tggagctccg aacttctttc caaaaaaaag    3180
atccaagaac ggaagatggc ggccctccaa tccaacgaag attcggactc agacgtcgaa    3240
atgggtgaaa acgaattgca agacactctg gaaattgcca gcgtgaatct ccctatcccc    3300
gtccaaacta gaattactaa caagaacgtg agcgagaaca aggagattgt gaagctggtg    3360
tccgtcttga gcactatcat caattcgacc aagaaggagg tgatcaccag tatggattgc    3420
ttcaagcgct acaaccatat ctggcaaaag ggaaaggagg aggccatcaa gaccttcatc    3480
acccaaagcc ctcttctctc cgaattcgaa tcgcagatcc tctatttcca aaacttggaa    3540
caggaaatca acgccgagcc tgagtacgtg tgcgtggggt caatcgccct gtatactgcg    3600
gacctgaaat tcgcgctgac tgccgaaact aaggcctgga tggtggtcat ggccggcac    3660 tgcaacaaaa aataccgcag cgagatggag aacatcttca tgctcatcga ggaattcaac    3720
aagaagctga acagaccgat caaggacctc gatgatatca ggattgccat ggcggccctt    3780
aaggaaatcc gggaggaaca aattagcatc gatttccagg tcggcccaat cgaggaatcc    3840
tacgccttgc tgaaccgcta tggcctgctg attgcacggg aagagatcga caaggtggac    3900
acccttcatt atgcgtggga gagctgcttt gcgcgggcgg gagaagtcca aaacaagctg    3960
gtgtccctgc agccttcctt caaaaaggag ctgatctcag ccgtggaagt gttcttgcaa    4020
gattgtcatc aattctacct cgactacgac ttgaatggac ccatggcatc aggcctgaaa    4080
ccacaggagg cgtcagaccg gctgatcatg ttccagaacc aattcgacaa catttacagg    4140
aagtatatca cgtacactgg aggagaggaa ttgttcggcc ttcctgccac tcagtacccg    4200
caactgctgg aaattaagaa gcaacttaac ctcctccaga gatctatac tctctacaat    4260 tcagtgattg agactgtgaa ctcgtactac gacattctgt ggtcagaggt gaacatcgaa    4320
aagatcaata cgagttgct ggaatttcag aaccgctgca gaaagctccc tagagccctc    4380
aaagactggc aggccttctt ggacctgaag aaaattatcg acgacttctc cgaatgctgc    4440
ccgctgcttg agtacatggc ctccaaagcg atgatggaac gccattggga acggatcacg    4500
```

```
actttgactg gacacagcct ggatgtgggg aacgaatcct ttaaactgag gaacatcatg    4560
gaagctccgc tgctcaaata taaagaagaa atcgaggaca tttgcatcag cgccgtcaag    4620
gaaagggaca ttgaacagaa gctgaaacag gtcatcaacg agtgggacaa taagactttc    4680
accttcggca gcttcaagac tcggggcgaa ctcctcctga gaggagattc gacgagcgag    4740
attattgcga acatggagga ttcgctgatg ctccttggaa gcctcctctc gaatagatac    4800
aacatgccgt ttaaggcaca gatccaaaag tgggtccagt acctctcgaa ctccaccgac    4860
attatcgagt cctggatgac cgtgcaaaac ctctggatct atctcgaagc agtattcgtc    4920
ggggggata tcgccaaaca actgcctaaa gaggccaaga gattctccaa catcgataag    4980
tcgtgggtga aaattatgac tcgggcacat gaggtgccca gcgtggtcca atgctgcgtc    5040
ggtgacgaaa ctctcggtca actgcttcca cacttgctgg accaactgga gatttgccag    5100
aagtcactca ctggatatct cgaaaagaag cggctctgtt tcccccgctt cttttttcgtg   5160
agcgaccctg ccttgttgga aatcttgggg caggcctccg actcgcacac catccaggcc    5220
cacctcctga acgtctttga caacatcaag tccgtgaagt ttcatgagaa gatctacgac    5280
cgcatcctga gcatttcgtc acaggaaggt gaaactatcg aactggataa acctgtcatg    5340
gcggaaggga acgtggaagt gtggctgaac agcctgctgg aggagtcaca gagctcgctc    5400
cacctggtca ttcggcaggc cgccgcgaat atccaagaga ctggattcca gctgacggag    5460
ttcctgagca gcttcccggc ccaagtgggc ctgctgggaa ttcaaatgat ctggacccgg    5520
gacagcgaag aggccctgag aaacgctaag ttcgacaaaa aaatcatgca gaaaacgaac    5580
caggccttcc tggaattgct gaacaccctc attgacgtca ccactcgcga ccttagctcc    5640
accgagaggg tgaaatacga aactctgatt accatccacg tgcatcaacg cgatattttc    5700
gacgacctct gccacatgca cattaagtcg ccgatggatt tcgagtggct gaagcagtgt    5760
agattctact ttaacgagga ttcggacaag atgatgatcc acatcaccga tgtcgccttt    5820
atctaccaga atgagttcct gggatgcacc gacagactcg tgatcacccc actgaccgac    5880
agatgctaca tcacccttgc gcaggctctg ggcatgtcga tgggtggggc cccggcgggc    5940
cctgcaggca ccggcaagac ggaaaccacc aaggatatgg gaaggtgcct tgggaagtac    6000
gtggtcgtgt tcaactgctc agaccagatg gacttccgcg ggctgggacg catttttcaag   6060
ggcctggccc agtcgggctc gtgggggttgc ttcgacgagt tcaacaggat cgacttgccg    6120
gtcctgtccg tggctgcaca gcagatttcg attatcctca cttgcaagaa ggagcacaag    6180
aagtccttca ttttcaccga cggagacaac gtcaccatga atccggaatt cggccttttc    6240
ctgactatga accctgggta cgcgggaagg caggaactgc cagaaaacct caagattaat    6300
tttcgcagcg tggctatgat ggtgccggac cggcaaatca ttattagagt gaagctcgca    6360
tcgtgcggat tcatcgacaa cgtcgtgctc gcaagaaagt tcttcactct gtacaagctg    6420
tgcgaggaac agcttagcaa acaggtgcac tacgattttg gcctccggaa cattctctca    6480
gtgctccgga ccctgggagc cgcgaagagg gccaaccccca tggacaccga atcaaccatt    6540
gtgatgcggg tcctgagaga catgaacttg tccaagctca tcgacgagga cgaacccctg    6600
ttcttgagct tgatcgagga cctgttccct aacatcctcc tggataaagc aggctacccg    6660
gaattggaag ccgccattag cagacaagtg gaggaagccg gattgattaa tcatccaccg    6720
tggaagctga aagtcatcca gttattcgaa acccaacgcg tgcgccatgg aatgatgacc    6780
ctcggcccctt ccggagccgg caaaaccacg tgcatccaca ccctcatgcg cgccatgact    6840
```

```
gactgtggca agccacaccg ggaaatgagg atgaacccga aagctattac cgcgccacag    6900
atgttcggac gcctggacgt ggccactaac gattggacgg atgggatctt ctcgacccct    6960
tggcgcaaaa ctctgcgcgc aagaaggga  gaacacatct ggatcattct tgacggacct    7020
gtggacgcca tttggattga aaatctgaac tcggtgcttg acgacaacaa gactctcacc    7080
ttggcaaatg gcgaccgaat tcctatggcc ccgaactgca agattatttt cgagcctcac    7140
aatattgata acgcttcgcc agcgactgtc tcccgcaacg gatggtgtt  catgtcaagc    7200
tcgatcctgg attggagccc aatcctcgag ggctttttaa aaaagcggtc gcctcaggaa    7260
gcggaaatcc ttcggcagct ttacaccgag tcgttcccgg atctctaccg cttctgcatt    7320
cagaacctcg aatacaagat ggaagtgctc gaagccttcg tgatcacaca gtccattaac    7380
atgctgcagg gcctgatccc cctgaaggag caaggaggag aagtgtccca ggcccatctg    7440
ggtagacttt tcgtgttcgc gctcctgtgg tccgccggtg ccgcgctcga acttgacggc    7500
cgaaggcggc tggaactgtg gctgaggtcg aggccgaccg gaactttgga gctgcctcca    7560
cccgccggac ctgcgacac  tgcctttgac tactacgtcg cccctgacgg aacctggacc    7620
cactggaaca ccaggactca ggagtacctc tacccttccg acacgactcc cgagtacggg    7680
tcaattttgg tgccgaacgt ggataacgtg cggacagact ttctgatcca gactatcgcg    7740
aagcagggaa aggcagtcct gctgatcggc gaacaaggaa cggcaaagac ggtcattatt    7800
aagggcttca tgagcaagta cgaccctgag tgccatatga tcaagtcact gaatttctcc    7860
agcgcgacga ccccccttat gtttcaaaga accattgagt cgtacgtcga caagagaatg    7920
ggcactacgt atgggcctcc cgccggaaaa aagatgaccg tgttcatcga cgatgtgaac    7980
atgccgatta tcaacgaatg gggggaccaa gtcacgaacg agatcgtgag gcagcttatg    8040
gaacagaacg gtttctacaa tcttgagaag ccggagagat tcacttccat cgtcgatatt    8100
cagttcctgg ccgccatgat ccacccagga ggaggccgga atgatatccc tcagcgcctg    8160
aaaaggcagt tctcgatctt taattgcacc ttgccgtcag aagcctcggt ggacaagatc    8220
ttcggcgtga tcggcgtggg gcattactgc actcagcgcg gcttctcgga ggaggtccgg    8280
gactcggtca ccaagctggt gccactgacc cgcaggctct ggcaaatgac caagattaag    8340
atgctgccta ccccccgccaa gttccattat gtgttcaacc tcagggacct ctcacgggtg    8400
tggcaaggaa tgctgaatac tacttccgaa gtgatcaaag agcctaacga ccttttgaag    8460
ttgtggaagc acgagtgcaa gcgcgtcatt gccgaccggt tcaccgtgtc ctcagacgtg    8520
acttggttcg acaaggccct cgtgtccctg gtcgaagagg agtttggaga agaaaaaaag    8580
ctccttgtgg actgcggtat cgatacctac ttcgtggact ttcttcggga cgcaccggaa    8640
gcagccggag aaactagcga agaagctgac gccgaaactc cgaagatcta tgagcctatc    8700
gagagctttt cgcacctgaa ggaacggctg aacatgttcc tccagcttta taatgagagc    8760
attcgcggtg ccgggatgga tatggtgttc ttcgccgacg cgatggtgca ccttgtgaag    8820
atttcacggg tcattcggac cccacaagga aacgcgctgc tggtcggtgt cggggatcc    8880
gggaaacagt cactgacgag attggcgagc ttcattgccg gatacgtgag cttccagatc    8940
acgctgacca ggtcctacaa taccagcaac ttgatggagg atttgaaggt gctgtaccgc    9000
accgcgggcc aacaagggaa ggggattact ttcattttca ctgacaacga aatcaaggac    9060
gaatcgttcc tggaatacat gaataacgtc ctctcgagcg gggaagtgtc caacctgttc    9120
gccagggatg agattgacga gatcaatagc gaccttgcaa gcgtcatgaa gaaggaattc    9180
cctcgctgcc tccccacaaa cgaaaacctc cacgattact tcatgagccg ggtcagacag    9240
```

```
aacctccata ttgtgctgtg cttctcacct gtgggtgaaa agtttcggaa ccgcgcactg    9300
aaattccccg cactgatctc ggggtgcacc atcgactggt tttcccggtg gcctaaggac    9360
gccctggtcg ccgtgtccga gcacttcctc actagctatg atatagattg cagcttggaa    9420
atcaagaagg aggtagtcca gtgcatggga tcgttccaag atggcgtcgc ggaaaagtgc    9480
gtggattact tccagaggtt tcggagatcg acccacgtga ccccgaagtc atacctgagc    9540
tttattcaag gttataagtt tatttacggc gaaaagcacg tcgaagtccg caccctcgcc    9600
aaccgaatga caccgggct ggaaaagctc aaggaagcct cagaatccgt ggccgcactg    9660
agcaaggaac tcgaggctaa agaaaaagag ttgcaagtgg ccaacgacaa agcggacatg    9720
gtgcttaaag aagtgaccat gaaggcccaa gcagcggaaa aggtgaaggc cgaagtgcag    9780
aaggtcaagg acagggcgca agcaatcgtg gactcgatca gcaaagacaa ggctattgcg    9840
gaggagaagc tcgaggccgc caagcctgca ctggaggaag cagaagccgc tctccagacc    9900
atcagaccta gcgacatcgc caccgtgcgg actcttggcc ggcctcccca cttgattatg    9960
cgcatcatgg actgcgtgct gctgctcttt cagcggaagg tgtcggcggt gaagatcgac   10020
ttggaaaagt cgtgtactat gccttcgtgg caagaatcac tcaaactcat gaccgcaggc   10080
aacttcctac agaacctcca acaattccca aaggatacca tcaacgaaga agtcattgaa   10140
ttcctctctc cgtatttcga aatgcccgat tacaacattg aaacggccaa acgcgtgtgc   10200
ggcaacgtgg cgggactgtg ctcatggact aaggcgatgg cgtccttctt ctcgattaac   10260
aaggaagtgc ttccacttaa ggcgaacctg gtggtccagg agaatcgaca cctcctggcg   10320
atgcaggacc ttcagaaggc ccaggccgaa cttgacgaca gcaggcaga actggacgtg   10380 gtgcaggccg aatacgagca ggctatgact gagaagcaaa cgctgctgga ggatgccgag   10440
cggtgccggc ataaaatgca gaccgcctcg accttatttt ccggactcgc tggagagaag   10500
gaacgctgga ctgaacagag ccaggaattt gccgcgcaaa ccaagagact tgtgggcgac   10560
gtcctgctcg caactgcctt cctgtcctac tccggcccat tcaatcagga attccgcgac   10620
ctgttgctta atgactggcg gaaagagatg aaagcccgca agatccccttt cgggaagaac   10680 cttaacctct ccgagatgct gatcgacgca ccgaccatta gcgaatggaa cctccaagga   10740
ttgccaaatg acgatctaag tatccagaac gggatcatcg tgacgaaggc ctccaggtac   10800
cctcttctga tcgatccgca gacccaagga aagatctgga tcaagaataa ggagagcaga   10860
aatgaactgc agataaacctc actcaatcac aagtacttta ggaaccacct tgaggattca   10920
ctgagcttgg gacggccgct gttgatcgag gatgtggggg aggaactgga tccagcgttg   10980
gataacgtcc tggagcgcaa cttcatcaag accggatcga ccttcaaggt gaaggttggc   11040
gataaggaag tggacgtgct ggacgggttt agactctaca taaccactaa gctccccaac   11100
cctgcctaca cgcctgaaat ttccgccaga acctcaatta tcgacttcac cgtcactatg   11160
aagggactcg aggaccagtt gctgggtcgc gtcatcctga ctgaaaagca ggaactggag   11220
aaggaacgga ctcatctcat ggaggatgtg accgccaata agcgccggat gaaggaattg   11280
gaagataact tgctgtatag acttacttcc acccaaggct ccctcgtgga ggacgaaagc   11340
ctcattgtgg tcctgtccaa tactaagcgc actgccgaag aagtcactca aaagctggaa   11400
atttcagcgg agactgaggt gcagatcaac tcggccagag aggaataccg gcccgtggct   11460
actcgcggga gcatcctgta cttcctcatt actgagatgc gcctggtgaa cgagatgtat   11520
cagacctccc tccgacaatt ccttggtctt ttcgacttga gccttgctcg ctcggtcaag   11580
```

```
agccccatta ctagcaaacg catcgcgaac atcatcgagc acatgactta cgaagtgtac    11640
aagtacgcgg ctagaggact gtacgaggag cacaagttcc ttttcacact cctcctcacc    11700
ctcaagatcg atattcaacg gaacagagtc aagcacgaag aattcctgac tctcatcaag    11760
ggaggagcct cgctcgatct caaggcctgc cctccgaagc catccaagtg gatcttggat    11820
attacctggc tgaacctcgt ggagcttagc aaactgcggc aattcagcga cgtgctggac    11880
cagatttcca gaaacgaaaa gatgtggaag atttggtttg acaaggagaa ccccgaggaa    11940
gaaccattgc cgaatgccta tgataaaagc ctggactgct ttaggcggct gctcctgatc    12000
agatcatggt gccctgatcg taccatcgcc caagcgcgca agtatatcgt cgactccatg    12060
ggtgaaaagt acgctgaggg ggtgatcctc gacctggaaa agacgtggga agagagcgac    12120
ccacgcaccc cgctcatttg cctcttaagc atgggatccg accccaccga tagcattatt    12180
gctctgggca aaaggctcaa aatcgaaacg cggtacgtga gcatggggca gggtcaggag    12240
gtgcacgccc ggaagctgct ccagcaaact atggcgaacg gcggatgggc gcttcttcag    12300
aactgccatc tcggcctcga cttcatggat gagctgatgg atattattat tgaaaccgag    12360
ctggtccacg acgcattcag gctctggatg accaccgagg cccacaaaca attccccatc    12420
acgctgttgc agatgtccat caagttcgct aacgatcccc ctcaaggact tagggctggg    12480
ctcaagcgga cgtattcagg agtctcacag gatctccttg atgtgtcaag cggctcacaa    12540
tggaaaccca tgctctacgc tgtggctttc cttcactcca cggtgcagga acggcgcaag    12600
ttcggagcct tggggtggaa tatcccctac gaattcaacc aagcggactt caacgctacc    12660
gtgcaattca tccaaaatca tcttgacgac atggatgtga agaagggagt gagctggacc    12720
accattagat acatgattgg cgagatccag tacgggggc gcgtgaccga cgactatgac    12780
aaacggctct tgaacacgtt cgcaaaagtg tggtttagcg agaacatgtt cggcccagac    12840
ttctctttct accaaggtta caatatcccg aagtgctcca ccgtcgataa ctacctccag    12900
tacatccaaa gccttcccgc ctacgactcg cccgaggtgt tcggtctgca tccgaacgcg    12960
gacatcacct accaatccaa actggctaag gacgtccttg atacgattct gggtattcag    13020
ccaaaagaca cgagcggagg aggggacgaa accagagaag ccgtggtcgc ccgcttggct    13080
gacgacatgc tggaaaaact tccgccggac tacgtgccgt ttgaagtgaa agaacgcttg    13140
cagaagatgg gtcccttcca accaatgaac atattcttga caagagat tgatagaatg      13200
cagcgggtgc tgagcttggt gcggtcgacc ctcacagaac ttaaactggc gattgacggg    13260
acgatcatta tgagcgagaa tctgcgcgac gccttggact gcatgtttga tgctcggatc    13320
cccgcgtggt ggaagaaggc ttcttggatc tcgagcacgc tcgggttttg gtttaccgaa    13380
ctcatcgagc ggaattcgca gttcacttca tgggtctttta acgggcgacc ccactgcttc    13440
tggatgacgg gcttcttcaa cccgcaaggt tttctcaccg ccatgcggca ggagatcact    13500
agagccaaca aaggctgggc gttggacaat atggtcctgt gcaacgaagt gaccaagtgg    13560
atgaaggacg acatctccgc gcccccacc gagggcgttt atgtctacgg actttacttg      13620
gaaggtgccg gatgggacaa gcggaacatg aagctcatcg agagcaaacc gaaggtgctg    13680
tttgagctca tgcccgtgat ccgcatctat gccgaaaata acacattgag agatccccgc    13740
ttctactcgt gccccatcta taagaagcct gtcagaaccg acttgaacta cattgccgcc    13800
gtcgacctga gaacggccca gactcccgag cattgggtcc tgagggagt ggcgctgctg      13860
tgcgatgtga agtag                                                     13875
```

<210> SEQ ID NO 19
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 19

| | | | | | |
|---|---|---|---|---|---|
| atgtttagaa | ttggcaggcg | ccagctgtgg | aagcactcag | tgacccgggt | gctaacgcag | 60 |
| cggcttaagg | gcgagaagga | ggcgaagcgg | gccttgctgg | acgccaggca | caactacctc | 120 |
| ttcgcgattg | tggcgtcgtg | ccttgacctg | aacaaaaccg | aggtcgagga | cgcgattttg | 180 |
| gaagggaacc | agatcgaaag | gatcgaccaa | ttgtttgccg | tcggaggtct | gcggcacctg | 240 |
| atgttctact | accaggatgt | ggaggaggcc | gaaaccggcc | agctaggctc | cctcggagga | 300 |
| gtgaacctgg | tgtcgggaaa | aatcaagaag | cccaaggtgt | tcgtcaccga | aggcaatgat | 360 |
| gtcgctctga | ccggcgtgtg | cgtgttcttc | attcggaccg | accccctcaaa | agcaatcacc | 420 |
| ccggacaata | tccaccagga | ggtttccttc | aacatgctcg | acgcggctga | cggtggactg | 480 |
| cttaacagcg | tccggaggct | cctctcggac | attttcattc | ccgccctgcg | ggctactagc | 540 |
| catggctggg | gagaactgga | ggggcttcag | gacgccgcta | atattagaca | ggaattcctg | 600 |
| tcctcgctgg | agggattcgt | gaacgtcctg | tcgggcgccc | aggaaagtct | caaagaaaag | 660 |
| gtcaacctca | gaaagtgcga | catcttggaa | ctgaaaacgc | ttaaagaacc | gaccgattac | 720 |
| ctgaccctgg | ctaacaaccc | ggaaaccctg | gcaagatcg | aagattgcat | gaaagtgtgg | 780 |
| atcaagcaaa | cagaacaggt | cctggctgaa | acaaccagc | tgctgaagga | agccgatgat | 840 |
| gtggggccca | gagccgaact | ggagcactgg | aagaagaggt | taagcaagtt | caactacctt | 900 |
| ctggaacagc | ttaaatcccc | ggatgtgaag | gccgtgctgg | ccgtgctggc | cgccgccaag | 960 |
| agcaagctcc | tcaagacttg | gagagagatg | gacatccgga | tcacggacgc | tacgaacgaa | 1020 |
| gccaaggata | atgtcaagta | cctttacacc | ttggagaagt | gctgcgaccc | actgtacagc | 1080 |
| agcgatcctc | tgagcatgat | ggatgctatc | ccgaccctta | tcaacgcgat | caagatgatt | 1140 |
| tacagcatca | gccactatta | caacacaagc | gaaaaaatta | cttcactgtt | cgtgaaggtc | 1200 |
| actaaccaga | ttatttccgc | ttgtaaggcc | tacatcacta | caacggaac | tgccagcatc | 1260 |
| tggaaccagc | cacaggacgt | ggtggaggag | aagatcctga | gcgccatcaa | gctgaaacaa | 1320 |
| gagtatcagc | tgtgctttca | caagacgaaa | cagaagctga | acagaaccc | aaacgctaag | 1380 |
| cagttcgatt | tctcagaaat | gtacatcttc | ggcaagttcg | aaaccttcca | caggcgcctc | 1440 |
| gccaagatta | ttgacatctt | cactaccctt | aaaacgtaca | gcgtcctcca | agactccacc | 1500 |
| attgaaggc | tggaggatat | ggccaccaag | taccagggga | tcgtggccac | catcaagaag | 1560 |
| aaggaataca | acttccttga | ccaacggaag | atggacttcg | accaggacta | tgaggagttc | 1620 |
| tgcaaacaaa | ccaacgattt | gcacaatgaa | ctcaggaagt | tcatggatgt | gacctttgcc | 1680 |
| aagatccaga | atactaacca | ggccctgcgc | atgctgaaga | agttcgaacg | gctgaatatt | 1740 |
| ccgaacttgg | ggatcgacga | caagtaccaa | tcatcctgg | aaaactacgg | cgctgacatt | 1800 |
| gacatgatct | cgaaactcta | caccaagcag | aaatacgacc | caccgctggc | tcggaaccag | 1860 |
| ccgcctatcg | cgggaaagat | cctgtgggcg | agacagctgt | ccataggat | tcagcagcca | 1920 |
| atgcagcttt | tccagcagca | tccggccgtg | ctcagcaccg | ccgaggcgaa | acctatcatt | 1980 |
| cggtcataca | acaggatggc | caaagtgttg | ctggaattcg | aagtgctgtt | ccaccggcg | 2040 |
| tggctccggc | agatcgagga | gatccacgtc | gggctagagg | cctccctcct | cgtgaaggct | 2100 |

```
cccggaaccg gggagctgtt cgtcaacttt gaccctcaaa tcttgatcct tttccgggag    2160
actgaatgca tggcccagat gggattggag gtgtcaccat tggctacttc gctctttcaa    2220
aagcgggacc gctacaaaag gaatttcagc aacatgaaga tgatgctcgc agaataccag    2280
cgcgtcaagt ccaagatccc tgccgccatc gaacagctca tcgtcccgca ccttgccaaa    2340
gtggacgaag cgcttcagcc cggactggcg gctctgacgt ggactagcct taacatcgaa    2400
gcgtatttag agaacaccct tcgccaagat caaggacctgg agctgctctt ggataggtg    2460 aacgacctga tcgagttcag aatcgacgct atactggagg aaatgagctc aacgccgctg    2520
tgccagctcc ctcaggaaga acccttgact tgtgaagaat tcctgcagat gactaaggac    2580
ttgtgcgtga acggtgcgca gattctgcat tttaagtcat ccttggtgga ggaggcggtg    2640
aacgagcttg tcaacatgct cctggacgtg gaggtgctgt cagaggagga atcggaaaaa    2700
atctccaacg aaaacagcgt caactacaag aacgaatcga gtgccaagcg ggaagagggt    2760
aacttcgaca ccctcacctc gagcattaac gcgcgggcga acgccctcct tctcaccact    2820
gtgacgcgga agaagaagga gactgaaatg cttggcgagg aagccagaga actcctgtcc    2880
cattttaatc atcaaaatat ggatgcactg ctcaaggtca ctcgcaacac tctcgaggcc    2940
atccgcaaac gaatccacag ctcacacact atcaacttcc gggattccaa ctccgcaagc    3000
aacatgaagc agaactcact gccgattttt cgggcttcag tcactctggc gatcccgaat    3060
attgtgatgg ccccggccct ggaagatgtc cagcaaaccc tcaacaaggc ggtggaatgt    3120
atcatctcag tgcctaaggg tgtgaggcaa tggagcagcg agcttctctc caagaagaag    3180
atccaggagc gcaagatggc ggctctccag agcaacgaag attcggactc cgacgtggag    3240
atgggcgaaa acgaactgca agacacgctg gaaattgcat cagtgaacct cccaattcct    3300
gtgcaaacta aaaactacta taaaaacgtc agcgaaaata aggagatcgt caagctggtc    3360
agcgtcctgt cgaccattat taactccacg aagaagaag tgataaccag catggactgc    3420
tttaagcgct acaaccacat ttggcagaag ggaaaggagg aagccattaa gactttcatt    3480
acccagtccc cgctcttgag cgagttcgag tcccagatcc tgtacttcca gaacctcgag    3540
caggagatta cgctgagcc cgaatacgtc tgcgtgggta gcattgcgct gtatactgcc    3600
gatctcaagt ttgccctcac ggctgaaact aaggcctgga tggtcgtgat cgggaggcat    3660
tgtaacaaga agtaccgctc cgaaatggaa aacattttca tgcttatcga agagttcaac    3720
aagaaactca atcggcccat caaggatttg gacgatatcc ggattgcgat ggccgcgctc    3780
aaggagatcc gagaggaaca gatctcgatt gacttccagg tcgggcctat cgaggagagc    3840
tacgccctgc tgaacagata tggactcctc attgctcggg aagaaattga caaggtggac    3900
actctgcatt atgcctggga gaactgctg gcccgcgcag gggaggtcca gaacaaactg    3960
gtcagcctcc aacctagctt caagaaagag ctgatctccg cagtggaggt gtttctgcag    4020
gactgccatc aattctacct tgattacgac ctcaacggcc cgatggccag cggactcaaa    4080
cctcaagagg catccgaccg gctcatcatg ttccagaacc aattcgacaa catctaccgg    4140
aagtatatca cttataccgg cggagaagaa ctgttcggat tgccggcgac tcagtacccc    4200
caacttctcg aaatcaagaa gcaattgaac ctcctgcaaa agatttacac gctttacaac    4260
agcgtgatcg aaacggtgaa ctcctactac gacatccttt ggtccgaagt gaacatcgaa    4320
aaaatcaaca atgaactgct ggaattccag aacagatgcc gcaagttgcc acgcgctctg    4380
aaggattggc aggccttctt ggacctgaag aagattatcg acgatttag cgaatgctgc    4440 cccttgctgg aatacatggc tagcaaggcc atgatggaga acattggga gcgcatcacg    4500
```

```
accctcactg gccacagcct tgacgtgggc aatgagtcgt tcaagctgag aaacattatg    4560
gaagcaccgc tgctcaagta caaggaagag atcgaagata tttgcattag cgcggtcaag    4620
gaacgggaca ttgagcagaa acttaaacag gtcatcaacg agtgggacaa taagactttt    4680
acctttggat cctttaagac ccggggcgag ctccttctga gaggcgactc gactagcgag    4740
atcatcgcaa atatggagga ttccctgatg ctcctgggat cactcctgag caacagatat    4800
aatatgccct taaggctcaa atccagaag tgggtgcaat acctgtccaa cagcaccgac    4860
attatcgaga gctggatgac cgtccagaac ttgtggatct acctggaagc ggtgttcgtc    4920
ggcggtgata ttgccaagca gctccctaag gaggctaaaa ggttctccaa cattgacaag    4980
agctgggtga agatcatgac tagagcccat gaagtcccga gtgtggtcca atgctgtgtg    5040
ggggacgaga ctctggggca gctgctaccc cacctcctgg accagcttga gatctgtcaa    5100
aagagcctga cgggctacct ggagaagaaa cgcctgtgct ttccgaggtt cttcttcgtg    5160
agcgacccgg ccctgctgga aattctcgga caagcgagcg actcccatac catccaggca    5220
catctgctta acgtgttcga taacatcaag agcgtgaagt tccacgagaa gatctacgac    5280
cggatcctga gcatctcatc gcaggaagga gagactatag agcttgacaa accagtgatg    5340
gccgaaggaa atgtggaggt gtggttgaac tccctgctcg aagagagcca gagctccctg    5400
cacctcgtca ttcgccaggc cgcggcgaat attcaggaaa ccgggttcca acttaccgag    5460
ttcttgtcca gctttccgc gcaagtcgga ctcttgggta ttcaaatgat ttggaccaga    5520
gattccgaag aggccctccg caacgccaag ttcgacaaaa agatcatgca aaaaactaac    5580
caagcattcc tggagctgct taacacccctt atcgatgtga ccaccaggga tctcagctcc    5640
actgagcggg tcaaatacga aacgttgatt actatccacg tgcaccaacg cgacatcttc    5700
gacgacttgt gccacatgca catcaagagc ccgatggatt tcgagtggct caaacagtgc    5760
cggttctact tcaacgagga ttccgacaaa atgatgattc acattaccga tgtggctttc    5820
atttaccaaa acgaattcct gggctgtact gaccggctgg tgatcacgcc gctgaccgac    5880
cgctgctaca tcactctggc acaggctctg ggaatgtcga tgggaggagc tcctgcgggc    5940
ccagcgggaa ctggcaaaac cgaaaccacg aaggatatgg ggcggtgtct ggggaagtac    6000
gtcgtggtgt ttaactgctc agaccagatg gactttaggg gactgggtcg gatctttaag    6060
ggactggccc agtcaggctc ctgggggtgt ttcgatgaat tcaatcggat cgacttgccg    6120
gtgctgtccg tggccgcgca gcaaatttcc atcatcctta cctgtaagaa ggagcacaag    6180
aagtccttca tctttaccga cggggacaac gtgaccatga acccagagtt cggactcttc    6240
ctcactatga atcccgggta cgccggccgc caagagctcc cagagaatct gaagattaat    6300
tttcgctcag tggccatgat ggtcccggat agacaaatca tcatccgggt gaagttggcg    6360
tcctgcggct tcatcgacaa cgtggtgttg gccagaaaat tcttcacgct ctataagttg    6420
tgtgaagaac agctctcaaa acaggtgcac tacgacttcg acttaggaa catcctcagc    6480 gtgttgagaa ctctcggagc ggcgaagcgc gcaaacccca tggataccga gtcgactatc    6540
gtgatgagag tgctgagaga catgaacctt tcaaagctga ttgacgagga cgaaccgctg    6600
ttcctttcct tgatcgagga cctcttcccg aacatcctcc tcgataaggc cggttacccc    6660
gagctcgaag ccgcgatttc acggcaagtt gaagaggctg gactcattaa ccacccacca    6720
tggaagctca aggtcatcca gctgttcgag actcagagag tgcggcatgg aatgatgaca    6780
cttggtccta gcggcgcggg aaagactacg tgtatccaca ccttgatgcg ggcgatgacc    6840
```

```
gattgcggca agccgcacag ggaaatgcgg atgaacccga aggcgatcac cgcaccccaa     6900
atgttcggac ggctcgacgt ggcgaccaac gactggaccg acggcatttt ttcgaccttg     6960
tggcgcaaga ccctgcgggc caagaaagga gaacacatct ggattatcct ggatggcccg     7020
gtggatgcga tctggattga aaaccttaac tcagtgctcg acgacaataa gaccctgacc     7080
ctggctaacg gcgataggat cccgatggct cctaactgca aaatcatctt cgagccgcat     7140
aacattgata tgcatcacc agccaccgtg tcccgcaatg gtatggtgtt catgagctcc      7200
agcatcctgg attggtcgcc cattcttgag ggattcctca agaagcgctc accacaggag     7260
gccgagattt tgaggcagct gtataccgaa tcatttccgg atctctacag attttgtatc     7320
cagaacctcg agtacaagat ggaggtcctt gaagccttcg tcatcaccca aagcattaac     7380
atgctgcagg gacttatccc cttgaaggaa cagggcggag aggtgtcaca ggctcacctg     7440
ggaaggctgt tcgtgtttgc cttgttgtgg tccgccggcg cggccctcga gctggatggc     7500
aggaggcggc tcgagttgtg gctgcggagc cgccccaccg ggactttgga actgccgccc     7560
ccggcgggtc cgggcgacac cgcttttcgac tactacgtcg cgccggacgg aacttggact     7620
cactggaata ccagaaccca agaataccttta tatccatcgg atactacccc tgaatatggt    7680
agcatcctcg tccctaacgt ggacaacgtc cgaacggact tcctcatcca aactatcgcc     7740
aagcagggca aggcagtcct gctgatcggc gaacaaggca ctgccaagac cgtcattatc     7800
aaaggctttta tgagcaaata cgatccggag tgccatatga tcaagagcct gaacttctcc     7860
tccgcgacaa ctccgctgat gttccaaaga actattgagt cgtacgtgga taagcgcatg     7920
ggaaccactt acgggccgcc ggccggaaag aagatgaccg tgttcattga tgacgtgaac     7980
atgccgatca tcaacgaatg gggcgaccag gtcactaacg aaatcgtgag acaactgatg     8040
gagcagaacg gattctacaa cctggagaag cccggagagt ttacctccat cgtggatatc     8100
cagttcctgg ccgccatgat ccatccgggc ggagggcgga acgacatccc acaaagactg     8160
aagagacagt tctccatctt taattgcacc ttgccctcgg aggcctcagt ggataagatt     8220
tttggagtga ttggcgtggg ccactactgc acccagcggg gtttcagcga ggaggtcagg     8280
gatagcgtga ccaagctcgt gccccttgacc agacggctgt ggcagatgac gaagattaag     8340
atgctgccca ccccggcgaa gttccactac gtgttcaatc tgagggactt gtcccgcgtg     8400
tggcagggaa tgctgaacac cacgagcgaa gtgatcaagg agccgaacga cttgctcaaa     8460
ttgtggaaac acgaatgcaa aagagtgatt gcggaccgct tcaccgtgag ctccgacgtg     8520
acctggttcg acaaggctct cgtgtccctg gtggaagagg agttcggcga agaaaaaaag     8580
ctcctggtgg attgcggcat cgatacgtac ttcgtggact tcctgagaga tgcacccgag     8640
gccgcaggag aaacttccga ggaagcagac gccgaaaccc ccaaaattta cgagcccatc     8700
gagtcctttt cacacctgaa ggaacgcctg aacatgttcc tccagctcta caacgaatcg     8760
atccgcggcg caggaatgga catggtgttc ttcgcggacg ccatggtgca tctcgtgaag     8820
atctccagag tgatcagaac tccccagggc aacgctctgc tggtcggagt gggggggatcg     8880
gggaagcaat cgctcaccag actggccagc ttcatcgcgg gctacgttag cttccaaatc     8940
accctcacca ggagctacaa tacctcgaac ctgatggagg atctgaaggt cctctacagg     9000
actgcgggac agcaggggaa gggtattacc ttcatctttta ccgataacga gataaaggat     9060
gagagttttc tcgagtacat gaacaatgtg ctgtcgtcgg gggaagtgtc aaacctcttc     9120
gccccgcgatg aaatcgacga gatcaacagc gacttagcta gcgtgatgaa aaaggagttt     9180
ccgagatgct tgccgaccaa tgagaacttg catgactact ttatgtcaag ggtccgccaa     9240
```

```
aacctccaca tcgtgctttg tttctcgcca gtgggagaga agttccgcaa ccgcgcactt    9300
aaattccccg ccctgatctc cggttgtacc attgactggt tctcccgctg gcctaaagat    9360
gcactcgtgg cagtctcgga gcacttcctg acttcgtacg atattgactg ctccttggag    9420
attaagaaag aggtcgtcca gtgtatgggg agcttccagg acggagtcgc cgaaaaatgc    9480
gtggactact ttcagagatt caggcggagc acccatgtca cccccaagtc atacctcagc    9540
tttatccaag gctacaagtt catctacggc gaaaagcatg tcgaggtccg caccctggca    9600
aacagaatga ataccggtct ggagaagctc aaggaagcgt cggagtcagt ggctgccttg    9660
tcaaaggaac tcgaagccaa ggaaaaggaa ttacaggtgg cgaacgacaa ggccgacatg    9720
gtgctgaaag aagtgactat gaaggcccag gcggcggaga aggtgaaggc cgaagtgcag    9780
aaggtcaagg accgcgccca agctatcgtg gactcgatct cgaaggacaa ggcgattgct    9840
gaggagaagc tcgaagccgc caagccggct ctggaggaag ccgaagcggc attgcaaacc    9900
attagacctt cagacatcgc tacggtcagg actctgggaa ggcccccca tttgatcatg    9960 cggatcatgg actgcgtgct cctcctgttc caaagaaaag tgagcgccgt gaagatcgat    10020
cttgagaaat cctgcacgat gccctcatgg caggagtcgc tcaagctcat acggccggt    10080 aacttcctgc aaaacctcca gcagtttcct aaggatacaa tcaacgaaga ggtgattgaa    10140
ttcctcagcc cgtactttga gatgcccgac tacaacatcg aaactgcgaa acgcgtgtgc    10200
gggaacgtgg ccggactgtg tagctggacc aaggccatgg cctccttctt ctccatcaac    10260
aaggaagtgc tgcctctaaa ggcaaacttg gtcgtgcagg aaaaccggca ccttctcgca    10320
atgcaggacc ttcagaaggc acaagcggag ctggacgaca agcaggctga gctggacgtg    10380
gtccaggctg agtacgagca ggcgatgact gagaagcaaa cgctactgga ggacgcagag    10440
cgctgtagac ataaaatgca gaccgcatcc accctgatct ccgggctcgc cggcgaaaag    10500
gagaggtgga ctgaacagtc acaagaattt gctgctcaaa caaagcgcct ggtcggtgat    10560
gtcctgcttg ccactgcctt cctgagctac agcggtcctt ttaaccaaga gttccgcgac    10620
ctcctcctca atgactggag aaaggaaatg aaggctcgga agatccccgtt cggcaagaac    10680 ctcaatctta gcgagatgct cattgacgca cctactatca gcgaatggaa cttgcaagga    10740
ctgccgaacg acgacctgtc cattcaaaac ggaatcatcg tcaccaaggc ttcgcggtat    10800
ccactcctca ttgacccgca gactcagggc aagatatgga ttaaaaacaa ggaaagccgc    10860
aatgaactgc aaattacctc cctgaaccac aagtacttcc gcaaccacct cgaggacagc    10920
ctcagccttg gcgcccatt gctcatcgag gacgtcggcg aggaactgga tccggccctg    10980
gacaacgtcc tggaaagaaa cttcatcaag accggctcga catttaaagt caaggtgggc    11040
gacaaggaag tggacgtgct ggatggcttt agactctaca ttaccaccaa attaccgaac    11100
ccggcctaca ccccagaaat tcggcgcgcg acctccatca ttgactttac tgtgactatg    11160
aagggcctgg aggaccagct cctcggccgg gtgatcctga ctgaaaaaca agagctcgaa    11220
aaggaaagga ctcacctcat ggaggacgtg acggcgaaca aaagacggat gaaggaattg    11280
gaggataatc tcctgtatag actcactagc actcaagggt ccctggtcga agatgagtcc    11340
cttattgtgg tcctttcgaa tacaaaacgg accgcggaag aggtcactca gaaactcgag    11400
atctccgcgg aaactgaagt gcagatcaac agcgctcgag aggaatacag gccagtggca    11460
accaggggct ccatactcta cttcctcatc accgaaatgc gcctcgtcaa tgagatgtac    11520
caaacctcgc tgcggcaatt cttggggctt ttcgacctct cactcgcacg gtcggtgaaa    11580
```

```
tcgccgatta ctagcaagag aattgccaat atcatcgagc acatgaccta cgaggtgtac    11640
aagtacgcag ccagggggact gtacgaggaa cacaagttcc tgtttaccct tctcctgaca    11700
ctgaagattg acattcagag aaacagagtg aaacatgagg aatttctcac cctcatcaaa    11760
ggaggggcta gccttgattt gaaggcgtgc ccgccgaaac cttcgaagtg gatcctggat    11820
atcacctggc tcaacctggt ggagctgtca aagctgcggc agttttccga cgtgctggac    11880
caaatttcgc gcaacgagaa gatgtggaag atctggttcg acaaagagaa ccccgaagag    11940
gagccgctgc ccaacgctta tgacaagtca cttgactgct tccgccgcct cctgctcata    12000
cggagctggt gcccagaccg gaccattgcc caggcgcgaa agtacatcgt cgatagcatg    12060
ggggaaaagt acgcggaggg tgtgattctc gacctcgaga aaacttggga ggaatcagac    12120
cctcgcaccc ccttgatttg cctcctgtcc atgggctccg atcccactga cagcatcatt    12180
gcactcggga agaggctgaa gatcgaaacg cgctacgtgt caatgggaca gggacaagaa    12240
gtccacgctc ggaagctcct ccagcaaacg atggcgaacg gtggttgggc cctgttgcag    12300
aattgccatc tggggctgga cttcatggat gaactcatgg acattattat cgaaacggaa    12360
ctggtccacg atgcctttag actttggatg acgactgaag cccataaaca attccctatc    12420
accctgcttc aaatgtcgat caagttcgcc aatgaccctc gcaggggct ccgggccggc    12480 ctcaaaagga cttactccgg ggtgtcacag gaccttcttg acgtgtcctc cggaagccaa    12540
tggaagccaa tgctttacgc cgtcgcgttc ctccactcca cggtgcagga acggcggaag    12600
ttcggagctc tgggctggaa tattccgtac gaattcaacc aggcagattt caatgcaacc    12660
gtccagttca tccaaaacca tctcgatgat atggatgtga agaaaggagt gtcatggact    12720
accattagat acatgatcgg ggagatccag tacgggggac gagtgactga cgattacgat    12780
aagcgccttc tgaacacttt cgctaaggtc tggtttagcg aaaacatgtt tggtccagac    12840
ttctccttct accaagggta taacatcccg aagtgctcca ccgtggacaa ctacctccag    12900
tacattcagt cgctcccccgc ttatgattca ccagaagtct ttggcttgca cccaaatgcc    12960
gatatcacct accaaagcaa actcgcgaag gacgtcctgg acaccatact ggggatccag    13020
ccgaaagata cctcgggggg cggcgatgag actcgcgaag cagtcgtggc gagactggcg    13080
gacgacatgc ttgaaaagct gcctcctgac tacgtgccat ttgaagtgaa agaaagattg    13140
cagaagatgg gcccttttcca gcctatgaac attttcctga ggcaggagat tgaccgcatg    13200
caacgggtgc tcagcctcgt gcgatccacc ctcactgagt tgaagctcgc catcgatggg    13260
accatcatca tgagcgaaaa cttgcgggat gcactcgact gcatgttcga cgctaggatc    13320
ccagcgtggt ggaaaaaggc atcatggatt agctccaccc tgggcttctg gttcaccgaa    13380
ctcatcgaga ggaactccca gttcacctcc tgggtgttca acggacggcc tcattgcttt    13440
tggatgaccg gcttcttcaa cccccaaggt tttctcacgg ccatgcgcca ggaaattacc    13500
cgggcaaaca agggggtggc cctcgacaac atggtgcttt gtaacgaggt tactaagtgg    13560
atgaaggacg acatctcagc ccccccctacc gagggagtct acgtgtacgg cctgtacctg    13620
gagggcgcag gatgggataa acggaacatg aagctgatcg agtcgaagcc gaaagtcctg    13680
ttcgagctca tgcccgtcat tcgcatctac gccgagaaca cacccctgcg cgacccaaga    13740
ttctacagct gcccgattta caaaaagccc gtccggacgg acttgaacta tatcgcggcc    13800
gtcgatctgc ggactgcgca gacccctgag cactgggtgc tgcggggagt ggcgctgctc    13860
tgcgacgtca agtag                                                    13875
```

<210> SEQ ID NO 20
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 20

| | | | | | | |
|---|---|---|---|---|---|---|
| atgttccgga | tcggacgcag | gcagctctgg | aaacatagcg | tcacgagagt | gctgacccag | 60 |
| cgcctcaagg | gggagaagga | agcgaagcgg | gccctgctcg | acgccagaca | caattacttg | 120 |
| ttcgccattg | tcgcctcctg | cctggatctg | aacaagactg | aggtcgaaga | tgccatcctc | 180 |
| gagggaaacc | aaatcgaaag | aattgaccaa | ttattcgccg | tgggcgggtt | gcgccatttg | 240 |
| atgttctact | accaagacgt | tgaggaggca | gagactggac | agcttggttc | cttgggtgga | 300 |
| gtgaacttag | tgtcggggaa | gatcaagaag | ccgaaagtgt | tcgtgactga | aggcaacgat | 360 |
| gtggctctga | ctggagtgtg | cgtgttcttt | attcgcactg | acccctctaa | ggccattacg | 420 |
| ccggacaaca | ttcatcagga | ggtgtcattc | aacatgctgg | acgccgcgga | tggcggcctg | 480 |
| ctcaacagcg | tgcgccggct | gctttccgac | attttcattc | ctgcattgag | agcgacttcg | 540 |
| catggttggg | gtgaactgga | agggctgcaa | gacgctgcca | acatccgaca | ggaattcctg | 600 |
| agctccctgg | aaggtttcgt | gaacgtcctc | agcggcgccc | aggaaagcct | caaggaaaag | 660 |
| gtcaacctga | gaaagtgtga | catcctggaa | ctgaaaacgc | tgaaggagcc | cacagattac | 720 |
| cttaccttgg | ccaataaccc | ggaaaccctc | gggaagatcg | aggactgcat | gaaggtctgg | 780 |
| atcaagcaga | ctgaacaagt | gctcgcagag | aacaaccaac | tcctgaagga | agccgacgac | 840 |
| gtcgggcctc | gggcagagct | cgagcactgg | aagaagcggc | tgagcaagtt | caactacctc | 900 |
| ctggaacagt | tgaagtcgcc | ggacgtgaag | gcggtgctcg | ccgtgttggc | cgccgccaag | 960 |
| agcaagctgc | tcaaaacttg | gcgggagatg | gacattagga | tcaccgacgc | caccaacgaa | 1020 |
| gcaaaggaca | atgtgaagta | cttatacacc | ctcgagaagt | gctgcgatcc | gctctactcg | 1080 |
| tcggaccccc | tgtcgatgat | ggatgctatc | ccgacgctca | tcaacgcaat | caagatgata | 1140 |
| tattccatca | gccactacta | caatacgagc | gagaagatta | cttccctgtt | cgtgaaggtt | 1200 |
| accaaccaga | ttatctccgc | gtgcaaggcc | tacattacca | caacggaac | tgccagtatc | 1260 |
| tggaatcaac | ctcaagacgt | ggtcgaagag | aagatactct | cggctatcaa | gctgaagcag | 1320 |
| gaataccaac | tgtgctttca | caagaccaag | caaaagctga | agcagaaccc | aaacgccaaa | 1380 |
| cagttcgatt | tcagcgagat | gtacatcttc | gggaagttcg | agacttttca | ccgccggctg | 1440 |
| gccaagatca | tcgacatctt | caccaccctc | aagacgtact | ccgtgctgca | agactcgact | 1500 |
| atcgagggat | tggaggatat | ggccacgaag | tatcaaggca | ttgtggcaac | catcaagaag | 1560 |
| aaagaataca | actttctcga | ccagagaaag | atggatttcg | accagatta | tgaagagttc | 1620 |
| tgcaagcaaa | ccaatgacct | tcataacgaa | ctccggaagt | tcatggatgt | caccttcgcg | 1680 |
| aagatccaga | acacgaacca | agcactgaga | atgctcaaga | agttcgaacg | ccttaacatt | 1740 |
| ccaaacctcg | ggattgatga | caagtaccaa | cttatcctgg | agaattacgg | tgccgacatc | 1800 |
| gacatgatct | ccaaattgta | caccaaacaa | aagtacgatc | ctccactggc | gcgcaaccaa | 1860 |
| cccccccatcg | ccggaaagat | cctgtgggca | agacaattat | tccacagaat | ccagcagccg | 1920 |
| atgcaactgt | ttcagcagca | tcccgctgtc | cttagcacgg | cggaagccaa | gcctatcatc | 1980 |
| agatcgtata | atcgcatggc | aaaggtgctg | ctggaattcg | aggtcctctt | ccaccgggcg | 2040 |
| tggctgaggc | agattgagga | gattcacgtg | ggacttgagg | cgagcctgct | tgtcaaagct | 2100 |

```
ccgggcaccg gagagctgtt cgtgaatttc gacccacaaa tcttgatcct gttccgggaa   2160
actgagtgca tggcccagat gggcctcgag gtgtcaccac tggccacgtc attgttccaa   2220
aagcgggaca gatacaagcg caatttttcg aacatgaaaa tgatgctggc cgaataccaa   2280
cgggtgaaat ccaagattcc cgctgccatt gaacaactca tcgtgcctca tcttgcgaaa   2340
gtcgatgagg ccctgcaacc gggactggcg gcgctgactt ggacttccct taacattgag   2400
gcatacctcg agaacacctt cgcaaagatt aaagacctag agctcctcct cgaccgcgtg   2460
aacgacctta tcgagttccg gatcgatgcc atcctggaag agatgtcgtc cactccactt   2520
tgccaacttc cccaggagga accgttgact tgtgaagaat tcttgcagat gaccaaagac   2580
ctttgcgtca acggcgccca gatcctgcac tttaagtcta gcctggtgga ggaagcggtg   2640
aacgagctcg tcaacatgct tctcgacgtg gaagtgctgt cggaagagga atccgagaaa   2700
atctccaacg aaaatagcgt gaactacaaa aatgagtcat cagccaagag ggaagagggt   2760
aacttcgata cgctgactag cagcattaac gccagggcaa acgccctgct cctgaccacc   2820
gtgactcgga agaagaaaga gactgagatg ctggagaaag aagctcggga gcttctgagc   2880
cacttcaacc accaaaacat ggatgccctg cttaaggtga cccggaacac actggaggcg   2940
atccggaagc ggatccactc gagccatacc attaattttc gggattcgaa cagcgcctcg   3000
aacatgaagc aaaattccct gccgattttt agagcgagcg tcaccctggc catccccaac   3060
atcgtgatgg cgcccgcatt ggaggacgtg cagcagaccc ttaacaaggc ggtggagtgt   3120
atcattagcg tccctaaggg cgtccgccaa tggagctcag agttgctctc gaagaagaaa   3180
atccaggagc ggaagatggc ggctctccag tccaacgagg actccgattc ggacgtggag   3240
atgggtgaaa atgagttgca agacactctc gagatcgcct ccgtcaatct gccgattccc   3300
gtccaaacca agaactacta caaaaacgtg agcgagaaca agagatcgt gaagctcgtc   3360
agcgtgctca gcactatcat taactcaacg aagaaagaag tgatcactag catggactgc   3420
tttaagcggt acaaccatat ctggcagaaa ggcaaggaag aagccatcaa gaccttcatc   3480
acccaatccc ccttgttgtc ggaattcgag tcacagattt tgtacttcca gaatctcgag   3540
caggagatca atgcggagcc agaatacgtg tgcgtggggt ccattgcgct atacaccgcc   3600
gaccttaaat tcgcgctgac ggccgaaacc aaggcctgga tggttgtgat cggccgccat   3660
tgtaacaaga agtacaggag cgaaatggag aatatcttca tgctgatcga agagttcaac   3720
aagaagttga accggcccat taaggacctg gatgatattc gcattgccat ggccgcccct   3780
aaggagatcc gcgaagaaca gatctccatc gactttcagg tcggccctat cgaagagagc   3840
tacgccctcc tgaaccgcta cgggctcctc attgccaggg aagaaattga caaggtcgat   3900
accettcact acgcatggga gaagttgctg gcgcgcgccg gagaggtcca aaacaagttg   3960
gtgtccctgc aaccctcctt caagaaggaa ctgatttcgg cagtcgaggt gttcttgcaa   4020
gactgccatc aattttacct ggactacgac ctgaatggac ccatggcgtc cggcctcaag   4080
ccccaagagg cctcagacag actgatcatg tttcagaacc aattcgacaa catctaccgg   4140
aagtatatca cgtataccgg tggagaagaa ctgttcggac tcccggccac gcaatacccg   4200
cagctcctcg agattaagaa gcagcttaac cttcttcaga agatttacac gctgtacaat   4260
agcgtcatcg agactgtgaa ttcctattat gacatccttt ggagcgaagt caatatcgag   4320
aaaatcaaca acgaactcct cgagttccag aacaggtgcc ggaaattgcc ccgcgccctg   4380
aaggactggc aggcgttctt ggatctgaaa aagattattg acgacttctc cgaatgctgt   4440
cctttgctcg agtacatggc ctctaaggct atgatggagc gacattggga acgcatcacc   4500
```

```
accctcaccg  gacacagcct  cgacgtcggc  aatgagtcct  tcaagttgag  aaatattatg     4560
gaggcgcctc  tgctgaagta  caaagaagag  atcgaggaca  tttgcatttc  ggcggtcaag     4620
gagagggaca  ttgaacagaa  gctcaagcaa  gtcatcaatg  agtgggataa  taagaccttc     4680
acatttggga  gctttaagac  ccgcggcgag  ctactcctgc  gcggcgactc  gaccagcgaa     4740
atcattgcca  acatggaaga  ttcactcatg  ctgctgggtt  ccttgctctc  gaacagatat     4800
aacatgccct  tcaaagcgca  gatacagaag  tgggtgcagt  acctgtctaa  tagcaccgac     4860
attatcgaat  cctggatgac  tgtgcagaac  ctctggattt  acctggaggc  cgtgttcgtc     4920
ggcggagaca  tcgcgaagca  actgccgaag  gaggctaaaa  gattctccaa  tatcgataag     4980
tcgtgggtga  aaatcatgac  gcgcgcacac  gaggtcccat  cagtggtgca  gtgctgtgtc     5040
ggtgacgaga  ctttgggtca  actgctgccg  cacctcctcg  accagctcga  gatttgccaa     5100
aagtccttga  cgggatacct  ggaaaagaag  cggctttgct  tcccccgctt  cttcttcgtg     5160
tccgaccccg  cgctgctcga  gatcctgggc  caggctagcg  actcacacac  cattcaggcg     5220
catctcctga  acgtgttcga  caacattaag  tcagtgaagt  tccacgaaaa  aatttacgac     5280
cgcatcctga  gcatcagctc  gcaggagggg  gagactattg  aactcgacaa  gcccgtcatg     5340
gccgagggga  acgtggaggt  gtggttgaac  tcactcctgg  aggaaagcca  atcctcgctc     5400
cacctcgtga  ttcgccaggc  cgcagcgaac  atccaggaga  ctggatttca  gctcaccgag     5460
ttcctctcga  gctttcctgc  acaagtcggc  ctgcttggca  ttcagatgat  ttggacccgc     5520
gacagcgaag  aggccctgag  aaacgccaag  ttcgacaaga  agatcatgca  aaagactaat     5580
caggcattct  tggaactgct  gaacactctg  atcgatgtca  ccactcggga  tctgtcgagc     5640
actgagcgcg  tgaagtacga  gactttgatt  accattcatg  tgcaccagcg  ggacatcttc     5700
gacgacctgt  gccatatgca  tattaaaagc  ccgatggatt  ttgagtggct  gaagcaatgc     5760
agattctact  tcaatgagga  ctcagacaag  atgatgattc  atatcaccga  cgtggccttt     5820
atctaccaaa  acgaattcct  gggttgtact  gataggttag  tgatcactcc  gctcaccgac     5880
aggtgctata  tcaccctggc  acaggccctg  ggaatgtcga  tgggaggggc  ccccgccggc     5940
ccggccggaa  ccgggaaaac  tgaaactact  aaagatatgg  ggcggtgcct  tgggaagtac     6000
gtcgtggtgt  tcaattgcag  cgatcaaatg  gatttccggg  gacttggacg  cattttcaag     6060
ggtctggcgc  aaagcggcag  ctgggatgc   ttcgacgaat  tcaaccggat  cgacttgccc     6120
gtgctctccg  tcgcagccca  acaaatctcc  atcatcctga  cttgcaagaa  ggagcacaag     6180
aagtcgttca  tcttcaccga  cggagacaat  gtcactatga  acccagagtt  tggcctattc     6240
ctgacgatga  acccgggcta  tgccggcagg  caggagctgc  ctgagaatct  gaagatcaac     6300
ttccggagcg  tggctatgat  ggtgcctgat  cgccaaatca  ttatccgcgt  gaaactggcc     6360
tcgtgtggat  tcatcgacaa  tgtggtgttg  gctaggaagt  ttttcactct  ctacaagctc     6420
tgtgaagaac  agctcagcaa  acaggtccat  tacgacttcg  gcctccggaa  cattcttagc     6480
gtgctccgga  ctcttggagc  cgccaagcgg  gcgaacccga  tggacaccga  gtccaccatt     6540
gtgatgaggg  tgttgcggga  tatgaacctc  tccaaactga  tcgacgaaga  tgaaccttg     6600 ttcctgagcc  tcatcgagga  tctgtttcct  aacatcctgc  tcgacaaagc  cggatatccc     6660
gaactcgaag  ccgctatcag  ccgccaggtg  gaggaagcgg  ggctcatcaa  ccatcctccg     6720
tggaagctca  aggtcattca  gctgtttgaa  acgcagagag  tgcggcacgg  catgatgacc     6780
ctgggaccga  gcggtgccgg  aaaaacgact  tgcatccaca  ccctcatgag  agccatgacc     6840
```

```
gattgtggca agccgcaccg ggaaatgcgg atgaacccaa aagcgattac ggcccccccag    6900 atgtttggac ggttggatgt ggcaaccaac gactggactg atgggatttt ctcaactctg    6960
tggcgcaaga cgctgcgcgc gaaaaagggg gaacacattt ggatcattct tgacggtccg    7020
gtggacgcca tttggattga aaatttgaac agcgtgctgg atgataacaa gacgctgact    7080
ttggccaacg gagacagaat ccccatggcc ccaaactgca agatcatctt cgaacctcac    7140
aacatcgaca atgcctcgcc cgcgaccgtg agccgcaacg gaatggtctt tatgagtagc    7200
agcattttgg actggagccc tatcctcgag ggattcctga agaagcgctc accgcaggag    7260
gcggagatcc tgaggcagct ttacactgaa agtttccccg atctctaccg cttctgcatc    7320
cagaaccttg aatacaagat ggaggtgctc gaggccttcg tcatcaccca gtccatcaac    7380
atgctccaag ggctcatccc gctgaaggag caaggcggag aggtgtcaca agcgcacctc    7440
ggcagactgt ttgtgtttgc cctgttgtgg agcgccggag cagctttgga gcttgatggg    7500
cggcggcgcc tggaattgtg gctgcgctcc cggcctaccg ggactttgga actcccacct    7560
cccgccggcc ccggcgacac agcgttcgat tattacgtgg cccccgacgg cacctggacc    7620
cactggaaca cccgcactca agaatacctg tacccttcgg acaccactcc agagtatgga    7680
tccattcttg tgcctaacgt ggacaatgtc cggacggact ttttaatcca gaccattgct    7740
aagcagggaa aggcggtgct gctcattgga gagcaaggga cagcaaagac cgtgatcatc    7800
aaggggttca tgtcgaagta tgacccggaa tgccatatga taaagtcact gaatttcagc    7860
agcgctacaa ccccactcat gttccaaaga accatcgagt catacgtcga caagagaatg    7920
ggcactactt acgcccacc ggccggaaag aagatgaccg tgttcatcga tgatgtgaac    7980
atgccaatca ttaacgagtg gggcgaccag gtcaccaacg agattgtccg gcagctcatg    8040
gagcaaaacg gcttctacaa cctggagaag cccggagagt ttacctcaat cgtggatatt    8100
cagttccttg cagcgatgat ccacccgggc ggaggtcgca atgacatccc cagaggctt    8160 aaaagacagt tctcgatttt taactgcacc ttacccagcg aagcgtcggt ggataagatc    8220
ttcggagtca tcggcgtggg gcactattgc acccagagag cttttccga ggaagtccgg    8280 gactccgtca cgaagctcgt gccttttgacc cgccgcctgt ggcagatgac caaaattaag    8340
atgctcccta cgccggctaa atttcactac gtgttcaacc tacgggacct gtcccgggtg    8400
tggcaaggca tgctgaacac aaccagcgaa gtcatcaaag agccgaacga cttgctcaag    8460
ctctggaaac acgaatgcaa gcgcgtgatc gcggaccggt ttaccgtcag cagcgacgtg    8520
acctggttcg acaaggcgct cgtgtcgttg gtcgaagagg agtttgggga agaaaaaaag    8580
ctccttgtgg actgtggcat cgacacctac ttcgtggatt tcctgcggga tgccccagag    8640
gcggcgggag aaaccagcga agaagccgac gcagaaactc caaagattta cgagccgatt    8700 gaatcgttttt cgcacctcaa agaacgcctc aacatgttcc tccagcttta taacgaatcc    8760
atccggggag cgggcatgga tatggtgttc ttcgctgacg caatggtcca ccttgtgaag    8820
atctcgcgcg tcatccgcac cccacagggg aacgccctct ggtgggggt cggaggctcc    8880 ggaaagcaaa gcctgacccg gcttgcctcc ttcattgccg gctacgtcag ttttcaaatc    8940
acgctgaccc gctcctataa caccagcaac cttatggaag atctcaaagt cttgtaccgg    9000
accgctggcc agcagggcaa gggtatcacc ttcatcttca ctgacaatga gattaaagat    9060
gagagttttc tcgaatacat gaacaatgtg ctgtcaagcg gcgaagtctc caacctttt    9120 gcgcgggatg agattgatga aattaactcg gacctggcaa gcgtgatgaa gaaggagttc    9180
ccgaggtgct tgccgaccaa cgaaaacttg cacgactact tcatgagccg cgtgagacag    9240
```

```
aacttgcata tcgtgctgtg cttctcgccg gtcggagaga agttccgaaa ccgcgcgctc    9300
aagtttcctg cactgatctc gggctgcacc attgattggt tctcacgctg gccaaaggac    9360
gccctggtgg ctgtctccga gcacttcctc acctcctacg atattgactg cagcctcgag    9420
attaaaaagg aggtggtgca gtgcatgggt agcttccaag acggggtcgc cgaaaagtgc    9480
gtggactatt ttcaacggtt caggcggagc actcacgtca ctccgaagtc ctacttgtcg    9540
ttcatccagg gctacaagtt tatctacggc gaaaagcacg tggaggtcag aactctcgcc    9600
aataggatga acaccgggct ggagaagtta aggaggcct cggaaagcgt ggccgccctc    9660
tcaaaggagc tggaagctaa ggagaaggag ctgcaagtcg ctaacgataa ggccgacatg    9720
gtgctgaagg aggtcaccat gaaggcccag gcggccgaaa aagtgaaggc cgaagtgcaa    9780
aaagtcaaag acagagcgca ggctatcgtc gacagcatct cgaaggataa ggccattgcc    9840
gaggagaagc tcgaggctgc aaagcctgcc ctggaggaag cggaagcagc actgcagacc    9900
atcagacctt ccgatatcgc caccgtcagg accctgggaa ggcctcctca cctcatcatg    9960
cggatcatgg attgcgtcct gttgctttc caacggaagg tgtccgccgt caagatcgac    10020
ttggagaagt cgtgcaccat gccatcatgg caggagtcac tgaagctcat gactgcagga    10080
aactttctcc agaaccttca gcaattccca aaggatacca tcaacgaaga ggtgatcgag    10140
ttcttgtcgc cgtatttcga aatgccggat tacaatatcg aaactgcaaa acgcgtgtgc    10200
ggtaacgtgg caggcttgtg ctcctggacc aaggccatgg ctagcttttt ctcgattaac    10260
aaggaagtac tgccactcaa ggcaaacttg gtggtgcagg aaaatagaca tcttctcgcg    10320
atgcaggatc tgcaaaaggc tcaagccgag ctggatgata agcaggccga actggatgtc    10380
gtgcaggccg aatacgagca ggccatgact gaaaagcaaa cgctgctgga ggacgcggaa    10440
cgctgcagac acaagatgca gacagcttcc accttgattt cgggcctcgc tggagagaaa    10500
gagagatgga cggagcagag ccaggagttt gccgcgcaaa ctaaacgcct ggtgggcgac    10560
gtgctgctgg ccacagcgtt ccttagctac agcggcccat ttaaccagga attccgggac    10620
ttgctcctga atgactggag gaaagaaatg aaggcgcgca agattccttt cggcaagaac    10680
ctgaacttgt ccgagatgct tatcgacgcc ccgaccattt cagagtggaa tctgcaaggg    10740
ctccccaatg acgatctgag catccagaac ggcatcattg tgacaaaggc ctcgcgctac    10800
ccgctgctca tcgatccgca gactcaaggg aagatctgga ttaagaataa ggagagccgg    10860
aacgaactgc agatcaccag cttgaaccac aagtacttta gaaaccacct ggaggattca    10920
ctgagcctgg gccgccctct gctcatcgaa gatgtcggag aggaactgga tccggccctt    10980
gacaacgtcc tggagcggaa ctttatcaaa actgggtcga ctttcaaggt caaggtcggc    11040
gacaaagagg tcgacgtgct ggacgggttc aggctttaca tcaccactaa actccccaat    11100
cctgcctaca ctcctgagat ctccgcccgc acctcgatta tcgacttcac agtgaccatg    11160
aaagggcttg aggaccagct ccttggacgc gtgatcctga ctgaaaagca agaactggaa    11220
aaggaacgga cccacttgat ggaggacgtc accgccaaca aaagacgcat gaaggaattg    11280
gaagataatc tcctgtatag acttaccagc actcagggta gtctggtgga agatgaatcc    11340
ctcatcgtcg tgttgtccaa caccaagcgc actgcggaag aagtcaccca gaagctggaa    11400
atttcggcag aaaccgaggt tcagattaac tcggcaaggg aagaataccg gcctgtggcc    11460
acccggggtt ccattctcta cttcctcatc accgaaatga ggctggtcaa tgaaatgtac    11520
cagacctcac tccgccagtt cctgggactg ttcgatctga gcctggcccg ctcggtgaag    11580
```

```
tcgcctatca cgtcaaagag gatcgcaaac atcatcgagc acatgaccta tgaggtctac    11640
aaatacgccg cccggggcct ttacgaggaa cataagtttt tgttcacgct cttgcttact    11700
ctcaagattg acatccagcg gaaccgggtc aaacacgagg aattcctgac cctgatcaag    11760
ggtggtgcct ccttggatct gaaggcatgc cctcctaagc ctagcaagtg gattcttgac    11820
atcacttggc tgaacctggt ggagctgagc aaactgaggc agttttcgga cgtgctcgac    11880
cagatttcaa ggaacgaaaa gatgtggaag atctggttcg acaaagagaa cccggaggaa    11940
gaaccgctgc ctaacgccta tgacaagtca ctggactgtt tccggagatt gctgctgatc    12000
aggtcctggt gcccggatag aaccattgcg caggccagga agtacattgt ggattcgatg    12060
ggagaaaaat acgccgaggg agtgatcctc gatctggaaa agacctggga agagagcgat    12120
cctcgcaccc ctctgatttg cctcctttcg atgggaagcg acccgactga tagcatcatt    12180
gcactgggga aacgcttgaa aatcgaaact cgatatgtgt caatgggaca gggacaggaa    12240
gtgcacgcaa gaaagctctt gcagcagact atggccaacg ggggatgggc gctcctccag    12300
aactgccact tgggactgga cttcatggat gaactcatgg atattatcat tgagactgaa    12360
ctcgtgcatg acgcttttcag attgtggatg actacggagg cccacaagca gttccctatc    12420
acccttttac aaatgtccat caaattcgcc aacgaccccc cccagggcct gcgggccggg    12480
ttgaaacgaa cttactccgg agtgtcgcag gacctactgg acgtcagctc cggctcacag    12540
tggaagccaa tgctgtatgc cgtggccttc ttgcactcca ctgtgcagga cgcagaaag    12600
ttcggtgcct tgggctggaa cattccctac gaatttaacc aagccgactt caacgccacc    12660
gtgcagttca tccagaacca cctggacgat atggacgtca agaagggtgt cagctggact    12720
accatcaggt acatgattgg tgaaattcaa tacggcggac gcgtgacgga cgactacgac    12780
aagaggctcc tcaacacctt cgctaaggtc tggttctcgg aaaacatgtt tggaccagac    12840
ttttcattct accaaggata caatatcccg aagtgctcga cggtggataa ctacttgcag    12900
tatattcaaa gccttcctgc ctacgattcg ccagaagtgt ttgggttgca tcctaacgcg    12960
gatattacct accagtcgaa acttgcaaag gatgtgctcg acacgatcct gggcattcaa    13020
ccgaaagaca ccagcggggg aggcgacgag actcgggagg cggtggtggc tcgcctggcg    13080
gacgacatgc tggaaaagct cccgcccgat tacgtgccgt ttgaagtcaa agagcgcctt    13140
caaaaaatgg gacccttcca gcctatgaac attttcctaa gacaggagat cgacagaatg    13200
caacgggtcc tgagccttgt gcgcagcact ctcactgagc tcaagttggc gatcgacggg    13260
accatcatta tgtcggaaaa ccttagagat gcgctcgact gcatgttcga tgcgagaatt    13320
ccagcttggt ggaagaaggc ctcatggata tcatccaccc tcgggttctg gtttactgag    13380
ctgattgaac ggaactccca gttcacgtcg tgggtgttca acggaaggcc gcactgcttc    13440
tggatgacag ggttctttaa tccgcaaggt ttccttactg cgatgcgcca agagattacc    13500
cgcgcgaaca aggggtgggc gctggacaat atggtgctct gcaacgaagt gaccaagtgg    13560
atgaaggacg acatatcggc ccccctacc gagggcgtct acgtgtacgg attgtacctg    13620
gaagggcgg gctgggacaa gcgaaacatg aaattaatcg aatcgaagcc caaggtgctt    13680
tttgaactga tgcccgtgat ccggatttat gctgaaaata acactctgcg cgacccgcgc    13740
ttttactcat gcccaattta caaaaagccg gtcagaacgg acctcaacta catcgccgct    13800
gtggacctca gaacggccca gaccccgag cactgggtgc tgagaggtgt cgcgctgctt    13860
tgcgacgtga agtag                                                    13875
```

```
<210> SEQ ID NO 21
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 21
atgtttcgca ttggtaggcg gcagctctgg aagcactcgg tgactagagt gctgactcaa      60
cgcctcaagg gcgagaagga agcaaagcgc gctctgctgg atgctcggca caactacctc     120
ttcgcgatag tcgccagctg cctcgacctg aataagaccg aagtcgagga cgccatcctg     180
gagggcaacc aaatcgaaag aattgatcaa ctgttcgccg tgggcggact gagacacctg     240
atgttctatt accaggatgt ggaagaggcg gagactggac aactaggatc gctcggtggt     300
gtcaacctcg tcagcggaaa gatcaagaag cccaaagtgt tcgtgaccga aggaaacgat     360
gtggccctga ctggggtgtg cgtgttcttt attagaaccg acccttcgaa ggcgatcact     420
cccgacaaca ttcaccagga ggtgtccttt aacatgcttg acgccgcaga tggaggcctg     480
ctgaactcag tcagaaggct gctttcagac attttatcc ctgccctgag agccacttct     540
catggttggg gagaattgga aggcttgcaa gacgctgcca atattcgcca agaattcttg     600
tcctcattgg aaggattcgt gaacgtgctc agtggagccc aggaaagcct gaaagaaaag     660
gtcaacttgc gaaagtgcga catcctcgag ctcaaaaccc tgaaggagcc cactgattac     720
ctcaccttag ccaacaatcc cgaaacctg ggcaaaatcg aggactgcat gaaggtctgg     780
atcaaacaga cggagcaagt cctcgccgaa acaaccaat tgctgaagga ggctgacgat     840
gtgggcccta gggccgaact cgagcattgg aagaagagac tgtcgaaatt taactacttg     900
ctggaacagc ttaagagccc tgacgtcaag gctgtgctgg cggtgctggc cgcagccaag     960
tccaagttac tcaaaacgtg gagagagatg gatataagaa tcaccgacgc cacgaacgag    1020
gctaaggaca cgtgaagta cttgtatact ctcgagaagt gctgcgatcc cctgtactct    1080
tccgaccctt tgagcatgat ggacgcgatc ccgaccctga tcaacgcgat taagatgatc    1140
tatagcatct cccactacta caacacttcc gaaaagatta cgtccctctt cgtcaaggtg    1200
accaaccaga ttatttccgc ctgtaaggcg tatattacta caacggaac cgcctcgatc    1260
tggaaccagc cgcaggacgt cgtggaagag aagatcctga gcgccatcaa gttgaagcag    1320
gaataccaac tgtgcttcca taagaccaaa cagaagctca agcaaaatcc aaatgccaaa    1380
caattcgact ctctccgaaat gtacatttc ggcaagttcg aaactttcca ccggaggctc    1440
gcgaagatta tcgacatttt cactacccctt aaaacctaca gcgtgcttca agattctacc    1500
atcgaaggac tcgaggacat ggccacgaag taccagggta ttgtggcaac catcaagaag    1560
aaagaatata acttcctgga ccagcgcaaa atggattttg accaggatta tgaggagttc    1620
tgcaaacaga ctaacgacct ccacaatgaa ctcagaaagt ttatggacgt gaccttcgcc    1680
aagatccaga cacgaacca agccctgagg atgcttaaga gttcgaacg cttgaacatt    1740
ccgaacctcg gcatcgatga caaataccaa ctcatcttgg aaaattacgg cgcggatatt    1800
gatatgatct caaagttgta cactaagcag aagtacgatc cgccgctggc ccggaaccaa    1860
ccgcctatcg cgggcaagat cctgtgggcc cggcagttgt tcaccggat tcagcagccg    1920
atgcagcttt ttcaacaaca tcccgcggtg ctctcgaccg ctgaagctaa gcctattatt    1980
cggagctaca accgcatggc taaggtgctg ctggagtttg aggtcttgtt ccatcgggca    2040
tggctcagac agatcgagga aatccacgtc ggactggagg cttccctgct cgtcaaagcg    2100
```

```
ccaggcacgg gcgaactttt cgtgaatttc gatccgcaaa tcctgattct gttccgcgaa    2160
acggagtgca tggcgcaaat gggattggaa gtgtcgcccc ttgccacttc cctgttccaa    2220
aagcgcgacc gctacaagcg gaatttcagc aatatgaaga tgatgctcgc cgaataccag    2280
cgggtgaaaa gcaagatccc agccgccatc gagcaactca tcgtgcctca cctcgccaag    2340
gtcgacgagg ccctgcaacc gggtttggcc gcactgactt ggacctcgtt aaacatcgaa    2400
gcctacttgg aaaacacttt cgcgaagatc aaggatcttg aacttctgct ggaccgcgtg    2460
aacgacctaa tcgagttccg gatcgatgcc atcctggaag agatgagttc cacccccctc    2520
tgccagttgc cacaagaaga acctctgaca tgcgaagaat tcctccaaat gactaaggac    2580
ttgtgcgtca cggggcaca gatccttcac ttcaaatcct ccctggtcga ggaggccgtg    2640
aacgagctag tgaacatgct ccttgatgtg gaggtcctca gcgaggaaga gtccgaaaag    2700
atcagcaacg aaaactccgt gaactacaaa acgagagca gcgctaaaag gaggaggga     2760 aatttcgaca ccctgacttc ctccatcaac gcgagagcga atgcactcct cctgactact    2820
gtgacaagga agaagaaaga gactgaaatg ctcggcgagg aggccagaga actgttgtcg    2880
cacttcaacc accagaacat ggacgccctg ctcaaggtga cccgaaacac cctggaagcg    2940
atcagaaaga gaatccacag cagccacacc attaacttta gggacagcaa ctcagcctca    3000
aatatgaagc agaattcact gcccatcttc cgcgcgtcag tgaccctggc catcccgaac    3060
atcgtcatgg cgcccgcatt ggaggacgtg cagcagactc tgaacaaggc cgtcgagtgt    3120
attattagcg ttcccaaggg agtgcggcag tggagctccg aactgttgtc gaaaaagaag    3180
atccaggaac gcaagatggc cgccctgcaa tctaacgaag attcggactc agacgtggag    3240
atgggagaga acgaattgca ggatactctg gagattgctt cggtgaactt gcccatcccg    3300
gtgcagacga aaaattacta caagaatgtc agcgagaaca aagagattgt taagctcgtg    3360
tcggtgctct caaccatcat caactcaact aaaaaggaag tcattaccag catggattgc    3420
ttcaaacggt ataaccacat ttggcagaag gggaaggaag aggccattaa gaccttcata    3480
acccaatcac cgctcctgtc cgagtttgag tcgcagatcc tgtactttca aaacttggaa    3540
caggaaatca cgccgaacc cgaatacgtc tgcgtgggta gcatcgccct gtatactgcg    3600
gacctcaagt tcgcgcttac tgctgaaacc aaggcatgga tggtggtcat cggtaggcat    3660
tgtaacaaga agtaccgcag cgagatggaa aatatcttca tgctgattga agaattcaac    3720
aaaaaactga acagacctat caaagacctg gacgatatta aatcgccat ggcggccctg    3780 aaggagattc gggaggaaca gatttccatc gacttccaag tgggcccctat cgaagagagc    3840 tacgccttat tgaacagata tggattgttg atcgcacggg aagagatcga caaagtcgac    3900
actttgcact acgcatggga aaagctgctc gcccgagccg gggaggtcca gaacaaactt    3960
gtgtcgcttc agccctcctt caagaaggag ctgatcagcg cggtggaagt gttcctccaa    4020
gattgccatc aattctacct ggactacgat ttgaacggac ctatggctag cggcctgaag    4080
ccccaggagg cgtccgacag acttatcatg tttcagaacc agtttgacaa cattttacaga   4140 aagtacatta cctacactgg tggcgaagaa ctcttcggac ttccggccac ccagtacccc    4200
cagctccttg agatcaagaa gcaactgaac ttgctgcaga gatctacac tctgtataat    4260 tccgtgattg aaacggtgaa ctcctactac gacattctct ggagcgaggt gaacatcgaa    4320
aagatcaaca cgaattgctc gaatttcaa acagatgcc ggaagctgcc cagggcactc     4380
aaggactggc aagcgttcct cgacttgaaa aaaattattg atgatttctc ggagtgctgc    4440
ccgctgctcg aatacatggc aagcaaggcg atgatggagc ggcactggga acggattacc    4500
```

```
accctgactg gacactcgct cgatgtggga aatgagtcct ttaagctgcg gaacatcatg    4560
gaagcccctc ttctgaagta taaggaggaa atcgaggata tttgcatctc cgctgtcaag    4620
gagcgcgata tcgagcagaa gctcaagcaa gtcattaatg aatgggataa caagaccttc    4680
acttttggct ccttcaagac tcgcggcgaa ctgcttcttc ggggcgactc aacgagcgaa    4740
attatcgcga acatggagga ttcactgatg ctcctgggat cgctgctctc aaacaggtat    4800
aacatgccct ttaaggctca gatccagaag tgggtgcagt acctgtcaaa ttccactgac    4860
ataattgaat cgtggatgac cgtgcaaaac ctttggatct acctggaggc cgtgttcgtg    4920
ggtggcgata ttgctaagca actccctaaa gaagctaaaa ggttcagcaa catcgataag    4980
agctgggtca agatcatgac cagagcccat gaagtgcctt cggtggtgca gtgctgcgtg    5040
ggcgatgaaa cgctgggaca gctcctgcct cacctcctgg accaattgga gatttgtcag    5100
aagtcgctga ctgggtacct tgaaaagaaa agactttgct cccacgctt cttctttgtc    5160
tccgacccgg cgcttcttga gattctggga caggccagcg actcccatac catccaagcc    5220
cacttgctca acgtgttcga taacattaaa tcagtgaagt tccatgagaa aatttacgac    5280
cgaatcctgt cgatctccag ccaggagggc gaaaccatcg agttggataa acccgtgatg    5340
gccgaaggaa acgtggaagt gtggttgaac tccttgctgg aagagagcca gagctccctc    5400
cacctggtga tccgccaggc ggcggccaac attcaggaaa cggggttcca gctcaccgag    5460
tttctgagct cgttccctgc ccaggtggga ctcctgggca tccaaatgat ctggacccgg    5520
gattcggagg aagccctgag aaatgcgaaa tttgacaaga agattatgca aaagactaac    5580
caggcctttc ttgaattgct gaatactctg atcgacgtga ccacccggga cctttcgtcc    5640
acggaaaggg ttaagtacga aactttaatt actatccacg ttcaccaaag ggacattttc    5700
gatgatctct gtcacatgca catcaagagc ccaatggact tgagtggct gaagcaatgc    5760
cggttttact tcaacgaaga tagcgacaag atgatgatcc acatcaccga tgtcgcgttt    5820
atctaccaaa acgaattcct gggttgcact gaccgcctcg tgatcacccc gctgaccgat    5880
aggtgttaca tcaccctggc acaagcattg gggatgtcca tggggggagc tccagccggg    5940
cctgccggca ccggcaaaac cgaaacgaca aaggacatgg ggagatgcct tgggaagtac    6000
gtggtggtgt tcaattgcag cgaccaaatg gacttccgcg ggctgggacg gatcttcaag    6060
ggtctggctc aaagcggaag ctgggggtgc ttcgatgaat tcaatagaat tgacctcccc    6120
gtgctgtcgg tggccgcgca gcagatcagc atcatcctta cttgcaagaa ggagcacaag    6180
aagtcattca ttttcactga cggagataac gtgactatga cccggaatt cggcctgttc    6240
ttaaccatga acccggcta cgcgggccgg caggagctgc cagaaaacct gaaaatcaac    6300
tttcggagtg tcgctatgat ggtcccggac agacagatca tcatcagagt gaaactcgcg    6360
tcgtgcggtt tcatcgataa cgtcgtgctg gcccgcaaat tcttcaccct ctacaagttg    6420
tgcgaagaac agctctccaa gcaagtgcac tacgacttcg gactgcgcaa cattcttagc    6480
gtgcttcgca cgctcggagc cgcaaagaga gcgaacccta tggacacgga atccaccatc    6540
gtcatgcggg tgctgcgcga catgaacctg tccaagctca tcgacgaaga tgagccgctc    6600
tttttgtccc tgatcgagga cctgttccct aacatccttc ttgacaaggc cggctaccct    6660
gagcttgaag ccgccatttc cagacaggtg aagaagccg gccttattaa tcatccccca    6720
tggaaactca aagtgatcca gctctttgag actcaaaggg tccggcacgg gatgatgaca    6780
ctcggaccta gcggtgccgg caagactact tgtatccaca ccctcatgcg cgccatgacc    6840
```

```
gactgtggaa aaccccacag agagatgaga atgaaccta aggccatcac tgcaccgcag    6900
atgttcggcc ggctggacgt ggccacgaat gactggactg acggcatctt cagcaccctc    6960
tggaggaaaa ccttgagagc gaagaagggc gaacacattt ggatcatcct cgatgggcct    7020
gtggatgcga tttggattga gaacctcaat agcgtcctcg atgacaacaa gaccctgacc    7080
ctcgccaacg gggaccggat ccccatggcc cccaactgca agatcatctt cgagccgcat    7140
aacattgaca atgctagccc ggccacggtg tcccggaacg ggatggtctt tatgagctca    7200
tccatcctgg attggtcccc tatcctcgaa gggttcctca agaagcggtc ccctcaggaa    7260
gccgaaatcc tgcggcagct ctacacggag agcttcccgg acttgtaccg gttctgcatt    7320
cagaacttgg aatacaagat ggaagtcttg gaggccttcg tcattaccca gagcatcaac    7380
atgctgcagg ggctcattcc actcaaggaa cagggcggag aggtgtcgca ggcccatctc    7440
gggaggcttt tcgtattcgc actgctgtgg tctgcaggag ctgccctgga actggacggc    7500
cgcaggaggc tggagctctg gctgcgctca cggcccacgg gcacccttga actgcctccc    7560
cccgcgggtc cggagatac cgccttcgac tactacgtcg ctccggacgg cacatggacg    7620
cactggaata cccgcactca ggagtatctc taccttccg acactactcc ggaatacggc    7680
agcatcctcg tgccgaacgt ggacaacgtg agaacggact tccttatcca aactattgct    7740
aagcaaggaa aagccgtctt gcttatcggc gagcaaggca ccgcaaagac cgtgatcatc    7800 aagggggttta tgagcaagta cgacccagaa tgccacatga tcaaaagcct caactttagc    7860
tccgccacca ctccactgat gtttcagcgc actattgagt cgtacgtcga caagcgcatg    7920
ggaaccactt acgtccacc ggccggaaag aagatgactg tgtttattga cgatgtgaac    7980
atgcccatca tcaacgaatg gggcgatcaa gtgactaacg agattgtgcg ccagctgatg    8040
gaacaaaacg gattctacaa cctggaaaag ccgggcgaat tcacctcgat tgtcgacatc    8100
caattcctgg cagccatgat tcatcccgga ggcggaagaa acgacattcc tcagaggctc    8160
aagcggcaat tctccatttt caattgcacc ctgccgtcgg aagcctccgt ggacaaaatt    8220
ttcggcgtca ttggagtggg gcactactgc acccagcggg gcttcagcga agaagtgaga    8280
gattccgtca ccaagctggt gccactcacc agacggcttt ggcaaatgac caagatcaaa    8340
atgctgccta ccccggccaa atttcactac gtctttaacc tccgggatct cagccgggtg    8400
tggcagggaa tgctcaatac tacttccgag gtgatcaagg aacccaatga cctcctgaaa    8460
ctgtggaagc acgaatgcaa gcgcgtgatt gctgaccgct ttaccgtgag cagcgacgtg    8520
acgtggtttg acaaagcgct cgtgtcactc gtcgaggaag aatttggcga ggagaagaag    8580
ttgttggtgg actgtggaat tgatacctac ttcgtggatt ccttcgggaa cgcccctgaa    8640
gcggccggag aaacttccga agaagcagat gccgaaaccc caaagattta cgaaccgatt    8700
gagtcgtttt cacacctcaa agaacgcctc aacatgttcc ttcagctgta caacgagtca    8760
atccggggtg ccggaatgga catggtgttt tcgcgacg ccatggtaca cctcgtgaag    8820
atctcgcgcg tgattagaac gccacagggg aacgccctgc tggtcggtgt ggggggtagc    8880
ggaaagcagt cattgacccg gctggcctcg ttcattgcgg gatacgtgtc attccagata    8940
acccttacca gatcgtacaa cacctccaac ctgatggagg acctgaaggt gctgtatcgc    9000
actgccgggc agcaagggaa aggaataact ttcattttca ctgacaatga gattaaggat    9060
gagagcttcc ttgaatacat gaacaacgtc ctttcatccg gggaagtcag caacctttc    9120 gccccgcgacg agatcgacga gattaacagc gatcttgcgt ccgtcatgaa gaaggaattc    9180
cctagatgct tgccgaccaa cgaaaaccta cacgattact tcatgtcaag agtgcgccaa    9240
```

```
aacctccaca tcgtgctgtg tttcagcccg gtgggcgaga agttcagaaa cagggctttg   9300
aaattccccg cactgatttc cggttgtacg attgattggt tctcacgctg gccgaaggac   9360
gccctggtgg ccgtcagcga gcacttcctg accagctacg acattgactg cagcctcgag   9420
atcaagaagg aggtggtcca gtgtatgggc tccttccaag atggagtggc cgaaaagtgc   9480
gtggactact tccagagatt cagacgctcc actcacgtga ctcccaaatc ctacttgtcc   9540
ttcatccaag gttataagtt catttacggc gaaaagcatg tcgaggtccg gactctggcc   9600
aaccggatga acaccggact ggagaagctg aagaagccag gcgagtcggt ggccgctctc   9660
tcaaaggaac tggaggccaa ggagaaggag ctccaggtgg cgaacgacaa ggcggacatg   9720
gtcctgaagg aggtgaccat gaaggcccag gccgctgaga agtgaaggc ggaggtgcag    9780
aaggtcaaag atagggcgca ggccatcgtc gattccatca gcaaggacaa ggccattgcg   9840
gaagagaagc tggaggctgc aaagccggcg cttgaagaag ccgaggccgc gctgcaaacc   9900
attcgcccca gcgacatcgc caccgtgagg actctgggac gacccccaca ccttatcatg   9960
cggatcatgg attgcgtgct cctcctgttc cagcgcaaag tgtcggcagt caagatcgac  10020
ctggagaaat catgcactat gccttcatgg caggagtcct tgaagctgat gacggcaggc  10080
aacttcctgc aaaacttgca gcagtttccg aaggatacca tcaacgaaga agtgatcgag  10140
ttcctttcgc cgtactttga gatgcccgat tacaacattg aaaccgcaaa gagggtctgc  10200
ggcaacgtgg cagggctgtg cagctggacc aaggcaatgg cctcgttctt ctcgattaac  10260
aaggaagtgc tgccgctgaa ggcgaacctg gtcgtacagg agaacaggca ccttctggcc  10320
atgcaagacc tccaaaaggc acaagccgaa ttggacgaca gcaggccga gctcgatgta   10380
gtccaggctg aatacgaaca ggccatgacc gagaaacaga ctctgctgga agatgccgag  10440
cggtgccgcc acaagatgca gaccgcttcg accctcatta gcgggctggc cggcgaaaag  10500
gagaggtgga ccgaacagtc acaagaattc gccgcccaga cgaaacgcct ggtcggcgac  10560
gtcctcctcg ccaccgcctt cctgagctac agcgggcctt tcaaccagga attcagagat  10620
ctccttctga cgactggcg gaaggaaatg aaggccagaa agatcccgtt cggcaagaac   10680
ctgaacctct cggagatgct gattgacgct ccgacaattt cagagtggaa ccttcagggt  10740
ctgccaaatg atgacctgag cattcaaaat ggcatcatcg tgaccaaggc atccaggtac  10800
cctctcctta ttgatcccca aacccagggg aagatctgga tcaagaacaa agagtccaga  10860
aacgaactgc agattaccag cctcaaccat aaatactttc gcaatcacct ggaagattcc  10920
ctgagcctcg ggaggcccct gctcatcgag gatgtgggag aggaactgga ccccgcgctc  10980
gataacgtgc tggagcgcaa tttcatcaag accggaagca ccttcaaagt caaggtcggc  11040
gataaggagg tggatgtcct ggatggtttc cggctctaca ttactacgaa actcccgaac  11100
cctgcctata cgccggaaat ctcagcccga accagcatca tcgacttcac tgtgactatg  11160
aaaggcctgg aggaccagct cctccggacg gtgatcctga cggagaagca agagctggag  11220
aaggagagga ctcatctcat ggaggatgtc accgcgaaca aaagacggat gaaggagctg  11280
gaggacaacc tgttgtacag gctgacgtca actcagggat cactggtgga agatgagtcc  11340
ctcatcgtcg ttctgtccaa caccaagcgg accgccgagg aagtcaccca gaagctcgag  11400
attagcgctg aaaccgaagt ccagattaac tccgccagag aggaataccg gcccgtggct  11460
actcgggggct ctatcctgta cttcctcatc accgagatgc gcttggtcaa cgaaatgtac  11520
cagacttccc ttcggcaatt cctgggactg ttcgatttga gcctcgccag atccgtgaag  11580
```

```
tcgcccatca cttcaaagag gattgcgaac atcatcgaac acatgactta cgaggtgtac    11640
aagtacgccg cacgaggcct gtacgaagaa cacaagttcc tgttcacttt actgttgacg    11700
cttaagatcg acatccagcg gaacagagtg aagcacgagg agttcctcac gcttattaag    11760
ggcggtgctt ccctggacct gaaggcctgt cctcccaagc ctagcaagtg gatcctggat    11820
atcacgtggc tgaacttggt ggagctctcc aaacttagac agttctccga cgtcttggac    11880
cagatttcaa ggaatgagaa aatgtggaag atctggttcg acaaggagaa cccggaagag    11940
gagcccttgc cgaacgctta cgacaagtcc ctggactgtt tcaggagact gttgctcatt    12000
cggtcctggt gtccggatag gaccatcgcc caggcccgca agtacatcgt ggatagcatg    12060
ggtgaaaagt acgctgaagg cgtcattctt gacctggaaa agacttggga ggaaagcgac    12120
ccgcgcaccc cactgatttg cctcctctcg atgggaagcg atcctacgga ctccatcatt    12180
gcccttggta aaagacttaa gatcgagact cgctatgtct cgatgggcca ggggcaggag    12240
gtccacgccc ggaagttgct tcagcagact atggccaatg gaggttgggc gctgctccag    12300
aactgccatc tgggtttgga cttcatggac gaattaatgg atatcatcat tgaaaccgaa    12360
ctggtgcatg acgctttccg gctgtggatg accaccgaag cccataagca atttccaatt    12420
accctcctcc aaatgagcat caagtttgcc aacgacccac cacaaggttt gcgcgcgggc    12480
cttaagcgga cttactccgg agtcagccag gacttgctcg acgtcagcag cggatcacag    12540
tggaagccca tgctctacgc agtggccttt ttgcacagca ctgtgcagga gagaaggaag    12600
tttggagcgc tggggtggaa tattccgtac gaattcaacc aagcggactt taatgctacg    12660
gtccagttca tccagaacca ccttgacgat atggacgtca aaaagggcgt gtcgtggacg    12720
acgatcaggt acatgatcgg ggaaatccag tacggcggaa gagtcactga cgattacgac    12780
aagaggctcc tgaacacttt tgccaaagtg tggtttttcag agaacatgtt cgggccggac    12840
ttctccttct accaaggata caatatcccc aaatgcagca ccgtggacaa ctacttgcaa    12900
tacatccaga gcctgccagc atacgactcc ccagaagtct ttggactgca cccgaacgcc    12960
gacattacct accagagcaa gttggcgaag gacgtcttgg acactattct tggtatccag    13020
ccgaaagaca cctcgggggg gggggacgaa accagagagg cagtggtcgc gcggctcgct    13080
gacgacatgc tggaaaagct gccccccgga tacgtcccgt tcgaggtcaa ggagaggctg    13140
cagaagatgg gaccattcca gcctatgaat attttcctga ggcaggagat cgaccggatg    13200
cagcgcgtcc tgtcactcgt gcgcagcact ctcaccgagt tgaaactggc aatcgatggc    13260
acgattatca tgtcggaaaa ccttcgcgat gcactggact gcatgtttga cgccagaatt    13320
cccgcttggt ggaagaaggc ttcatggata agctccacct tgggattctg gttcacagag    13380
ctcattgaac gcaacagcca gttcacttcc tgggtgttca atggcagacc ccactgcttc    13440
tggatgaccg gattcttcaa cccccagggg ttcctgaccg ctatgcggca ggagattact    13500
cgggcgaata agggatgggc cctggacaac atggtgctct gcaacgaagt gaccaaatgg    13560
atgaaggatg atattagcgc gccgccgact gagggagtgt acgtctacgg actttacttg    13620
gagggcgcgg ggtgggataa aaggaacatg aagttgatcg agtcaaaacc caaggtgctc    13680
tttgaattga tgccggtgat ccgcatctac gccgaaaaca cactctcag agatcccaga    13740
ttctactcgt gtcctattta caagaagccc gtccgcaccg acttgaacta tatcgccgcg    13800
gtcgatttga gaactgccca gactcccgag cactgggtgc ttcggggagt cgcgctgctt    13860
tgcgatgtga agtag                                                    13875
```

<210> SEQ ID NO 22
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 22

| | | | | | |
|---|---|---|---|---|---|
| atgttccgca | tcggccgccg | ccagctctgg | aagcatagcg | tgactagagt ccttacccaa | 60 |
| cgcctgaagg | gtgaaaaaga | ggccaagcgc | gccctgctgg | acgcccggca taattacctg | 120 |
| tttgccattg | tcgcctcatg | cctggacctg | aataagactg | aggtcgagga tgccatcctt | 180 |
| gaagggaacc | aaatcgagag | aatcgatcaa | ctcttcgccg | tgggggggct gcggcatctc | 240 |
| atgttctact | accaggacgt | ggaagaagca | gaaaccggcc | agcttggctc ccttggtggg | 300 |
| gtgaacctcg | tgtcgcggaa | gatcaaaaag | cctaaggtgt | tcgtgaccga gggcaacgac | 360 |
| gtggcgctta | ccggagtgtg | cgtgttcttc | ataaggacgg | atccatcaaa ggccattacc | 420 |
| cctgataaca | ttcatcaaga | ggtcagcttc | aacatgctcg | atgccgcgga tggaggtttg | 480 |
| ctgaatagcg | tgcgcagatt | gctctcagac | attttcatcc | ctgcgctccg cgccacctcc | 540 |
| cacggttggg | gagaacttga | ggggctccag | gatgccgcca | acattagaca ggaattcctg | 600 |
| agcagcctgg | aaggattcgt | gaacgtgctg | tccggggcac | aagagagcct caaagaaaag | 660 |
| gtcaatttga | aaaatgcga | catcctcgaa | ctcaagactc | tgaaggaacc gactgattat | 720 |
| ctgactctcg | cgaataaccc | agaaaccctc | ggaaagatcg | aggactgcat gaaggtctgg | 780 |
| attaaacaaa | cggagcaagt | gctggctgag | aataaccagc | ttctcaagga agccgatgac | 840 |
| gtcggcccga | gagcagagct | tgaacattgg | aagaagagac | tttccaagtt caactacctc | 900 |
| ctcgaacagc | tgaagtcccc | ggacgtcaag | gccgtgctcg | ccgtgctggc cgctgccaag | 960 |
| agcaagctgc | tcaagacttg | gcgggaaatg | acatcagga | tcaccgacgc aacgaacgag | 1020 |
| gccaaagata | acgtcaagta | cctttatacc | ttggagaagt | gctgtgatcc gctttactcg | 1080 |
| agcgaccctc | tgtcgatgat | ggacgccatc | ccaactctga | ttaacgccat taagatgatt | 1140 |
| tatagcatca | gccactacta | caatacctcc | gaaaaaatca | cctcgttgtt cgtgaaggtc | 1200 |
| accaatcaga | ttatttccgc | ttgcaaggcg | tacattacca | ataacggtac cgcgagcatc | 1260 |
| tggaaccagc | cgcaggacgt | ggtgaagaa | aaaattctga | gcgcaattaa gctgaaacaa | 1320 |
| gagtaccagt | tgtgctttca | caagaccaag | cagaagttga | agcagaaccc aaacgccaag | 1380 |
| cagtttgatt | tttccgaaat | gtacatttc | gggaagtttg | agactttcca ccggagactc | 1440 |
| gcgaagatta | ttgacatttt | caccacccct | aagacttaca | gcgtgctaca ggactcgacc | 1500 |
| attgagggggc | tcgaggatat | ggccaccaag | taccagggaa | ttgtggccac aattaagaag | 1560 |
| aaggaataca | acttcctcga | ccagcgcaag | atggacttcg | accaagacta cgaggagttt | 1620 |
| tgcaagcaga | ctaatgacct | tcataatgag | ctgcggaagt | tcatggatgt gaccttcgcg | 1680 |
| aaaatccaga | acaccaacca | ggccctgcgg | atgctcaaga | aattcgaacg cctgaacatt | 1740 |
| cctaacctcg | ggatcgacga | caaataccaa | ctcattttgg | agaactatgg gcggatatc | 1800 |
| gatatgatct | ccaaactcta | caccaaacag | aagtacgacc | cgcccttggc tcggaaccag | 1860 |
| ccacccatcg | cgggaaagat | cctgtgggcc | cgccaacttt | ccatcgcat ccagcagcct | 1920 |
| atgcagctgt | tccagcagca | tcccgccgtg | ctctccacgg | ccgaagcaaa gccgattatt | 1980 |
| cgctcctata | accggatggc | caaagtgctg | ctcgagttcg | aagtgctgtt ccatcgcgca | 2040 |
| tggctccggc | agatcgagga | gattcacgtg | ggcctcgaag | ctagcttgct cgtgaaggct | 2100 |

```
cctggcactg gagaactttt cgtgaacttt gaccctcaaa tcctgatcct gttcagggag    2160
actgagtgca tggcgcagat gggcttggag gtgtcaccct tggccacgag cctgtttcag    2220
aagagagaca ggtacaagcg caacttttcc aacatgaaga tgatgctggc cgaataccag    2280
cgcgtgaaat ccaagatacc ggcggccatc gaacaactta ttgtgcccca cctcgcaaag    2340
gtggacgagg cgcttcaacc cggactcgcc gcgctcacat ggacgtcgct gaacatcgag    2400
gcctacttgg agaacaccct tgccaagatc aaggacctgg aactgttgct agatcgcgtg    2460
aacgacctga ttgaattccg gattgatgct attttggaag agatgtcgtc gaccccgctg    2520
tgtcagctgc cccaggagga gcctctcact tgcgaagagt tcttacaaat gacgaaggac    2580
ttgtgcgtga acggtgccca atcctgcac ttcaagtcct cgctcgtcga ggaggccgtg     2640
aacgagctcg tgaatatgct tcttgatgtc gaggtgctga gcgaggaaga atcagagaaa    2700
atttcgaatg agaatagcgt caattacaag aacgagagta gcgcgaagcg cgaggagggg    2760
aattttgaca ctcttacctc ctccatcaac gcccgggcaa atgcactcct tctgactacc    2820
gtgacccgga agaagaagga aaccgagatg ctgggagaag aagcaagaga gctccttagc    2880
cacttcaacc accagaacat ggacgcgctc ctgaaagtga cccggaacac cctggaggct    2940
atccggaagc ggatccatag cagccacacc attaatttcc gcgacagcaa cagcgcaagc    3000
aacatgaagc agaactcact gccaatcttc cgcgcctccg tgactctcgc cattccaaac    3060
atcgtgatgg ctcctgcctt ggaggatgtc cagcaaaccc tgaataaggc cgtggaatgc    3120
atcatctccg tgccgaaggg agtcaggcag tggtcgtcag agctcctgtc aaaaaagaag    3180
atccaagagc ggaagatggc cgccctgcaa tccaacgaag atagcgattc ggacgtggag    3240
atgggagaga acgagttgca ggatacctc gagatcgcct ccgtgaatct gccaatccca    3300
gtgcagacta gaattatta caagaacgtg agcgaaaaca aagaaattgt caaactcgtg    3360
agcgtcctga gcaccattat caattccact aagaaggaag tcatcaccag catggactgc    3420
ttcaagaggt acaaccatat ttggcagaag ggaaaggaag aggcgattaa gaccttcatc    3480
actcaatccc ccctcctcag cgagttcgaa tcgcagattc tgtacttcca aaacttggag    3540
caggaaatta cgccgagcc tgaatacgtg tgcgtgggct ccatcgccct gtacaccgcg    3600
gatctcaagt tcgcgctcac cgcagaaacc aaggcgtgga tggtggtgat cgggagacac    3660
tgcaacaaaa agtaccggtc cgaaatggaa aacatcttca tgctgattga ggaattcaac    3720
aagaaactga accggccgat aaaggacctc gacgacatca ggatagccat ggcagccttg    3780
aaggaaatcc gcgaggagca gatcagcatt gacttccagg tcggaccgat tgaggagtcc    3840
tacgccctgc tgaatagata cggtctgcta atcgccagag aagagatcga caaggtggac    3900
accttgcact acgcttggga aaagctcctt gcccgggccg gggaagtgca gaacaagctg    3960
gtcagcttac agccatcctt taaaaaggaa ttgatctccg ccgtggaagt gttcttgcaa    4020
gattgccacc agttctacct ggactacgac ctcaacggac cgatggctag cggccttaag    4080
ccacaggagg catcagaccg gctgatcatg tttcagaacc aattcgacaa catctacaga    4140
aagtacatta cctacaccgg gggcgaggaa ttgttcggcc tgccggcaac ccaatacccc    4200
cagcttctcg agattaagaa acaattgaac ttgctccaga gatctacac gctctataac    4260 tccgtgatcg agactgtgaa ctcgtactat gacattctct ggtcagaggt caacatcgaa    4320
aagattaata cgaactgct ggaatttcaa aatcggtgca ggaagctccc tagggctctg    4380
aaggattggc aggccttcct ggaccttaag aagatcattg acgacttctc ggaatgctgc    4440
ccactcctgg agtatatggc tagcaaggct atgatggaga ggcattggga gcgcatcacc    4500
```

```
actttgactg gccacagcct tgacgtgggc aatgaatcct tcaaactgcg caacatcatg    4560
gaggcaccat tgttgaaata caaggaagaa atcgaagata tctgcatcag cgccgtcaag    4620
gaacgcgata tcgaacagaa gctcaaacag gtcattaacg agtgggacaa caagacgttc    4680
accttcggga gcttcaagac taggggagaa ctgctgttga gaggagactc cacttcggag    4740
atcattgcca acatggaaga tagcctcatg ttgctgggct ccttgctctc gaaccgctat    4800
aacatgccat tcaaggcaca aatccagaag tgggtccaat acctctccaa tagcacagac    4860
atcatcgaat cgtggatgac cgtccaaaac ctgtggatct acctggaagc cgtgttcgtg    4920
ggcggagata ttgcgaagca gttgcctaag gaggcaaaaa gattcagcaa tatcgacaag    4980
tcgtgggtga agatcatgac cagagcccac gaggttcctt ccgtggtgca gtgctgcgtc    5040
ggagatgaga ctctgggcca gctcctcccg caccttctgg atcaactgga aatctgccaa    5100
aagtccctga ctggctacct ggaaaaaaaa agactgtgct ttcctcggtt cttcttcgtg    5160
tccgaccccg ctctgctgga aatcctcgga caggcgtccg actcccacac tatccaggcc    5220
caccttctca acgtgttcga taatatcaag tcggtcaaat tccatgagaa gatctacgac    5280
agaatccctgt ccatctcgtc acaagagggc gagactatcg agcttgataa gccagtcatg    5340
gccgaaggca acgtcgaagt ctggctcaat tcactcctgg aagaatcaca gtcgtccttg    5400
catctggtca ttcgccaagc cgccgctaac attcaggaga ctggtttcca acttactgag    5460
ttcttgtcgt cattccccgc ccaagtgggc ctgctgggca ttcagatgat ttggacgagg    5520
gattccgaag aggcccttcg caatgcaaaa ttcgacaaga aaattatgca gaaaaccaat    5580
caagccttcc tggaacttct gaacactttg attgatgtga ctactcggga tctcagctcc    5640
accgaaagag tcaaatacga gactctcatc accatccacg tgcatcaacg cgacattttc    5700
gacgacttgt gccacatgca tatcaaatcc ccgatggatt tcgagtggct gaagcagtgt    5760
cgctttttact tcaacgaaga ttccgacaaa atgatgattc acatcaccga tgtggccttt    5820
atttaccaaa acgaattctt gggctgtact gaccggctgg tgattactcc tttgactgat    5880
cgctgctaca ttaccccttgc ccaggctctg gaatgtcca tgggagggc gcctgccggc    5940
ccggccggaa ctgaaaagac cgaaaccacg aaggacatgg tcggtgcct gggcaagtac    6000
gtggtggtgt tcaactgcag cgaccaaatg gactttcggg gactgggaag aatcttcaag    6060
ggactcgccc agtcggggtc atggggctgc tttgacgaat tcaacaggat tgacctcccg    6120
gtcctgtccg tcgccgccca acaaatttca atcattctca cctgtaagaa agaacataag    6180
aagtcattca tcttcaccga cggagacaac gtgaccatga ccctgaatt tggactgttc    6240
ctcaccatga acccgggata tgcgggccgg caggagctgc cagagaacct taagattaat    6300
ttccggtccg tcgcgatgat ggtgccggac cggcaaatta tcatccgggt aaagctggct    6360
tcatgcgggt tcatcgataa cgtcgtcctc gcccggaaat ttttcacccct ttataagctg    6420
tgcgaagaac agctttcgaa acaggtgcat tacgattttg gtctgcggaa catcctgagc    6480
gtcctccgga ctctgggagc cgcgaagagg gctaatccga tggacactga gtccactatc    6540
gtcatgagag tcctgcgcga catgaacctt tccaagctca tcgacgagga tgagcctctc    6600
ttcctgagcc tgatcgagga cctgttcccc aacatcctgc tcgacaaggc gggatatcct    6660
gaactggagg cggccatcag cagacaggtc gaggaggccg gcctaatcaa ccaccctccc    6720
tggaagctca aggtgatcca gctgtttgag acacaacggg tgcggcatgg aatgatgacc    6780
ctggggccgt ccggggctgg aaaaactact tgtatccata ctctcatgcg cgccatgacc    6840
```

```
gattgtggaa aacctcaccg cgagatgaga atgaatccca aggcgattac tgcccccag    6900
atgtttgggc ggctggacgt cgccactaac gactggacgg acggaatttt ctccaccctc    6960
tggcgcaaaa cactgagagc caagaaggga gagcatatct ggatcattct ggacggtcca    7020
gtcgatgcga tttggatcga gaacctgaac tccgtcttgg acgataacaa gacgctcacc    7080
ctggctaacg gcgatagaat cccaatggcc ccaaattgta agatcatctt cgagccacac    7140
aacattgata acgcgtcacc ggccaccgtc agccggaacg gaatggtgtt tatgagcagc    7200
tcgattcttg actggagccc gatcctcgaa ggtttcctca aaagagatc  cccccaggag    7260
gcagagattc tcaggcagct ctacaccgag tcattcccgg atctgtacag gttctgcatt    7320
cagaatctgg aatacaagat ggaagtcctt gaagccttcg tgatcaccca atcgattaac    7380
atgcttcagg ggctgatccc actcaaagaa caagggggag aggtgtctca ggcgcacctg    7440
ggccgcttgt tcgtgtttgc tttgctttgg agcgcgggcg ccgcccttga actggatggc    7500
cgcaggcgcc tcgagctctg gctgagaagc agacctacgg gaaccttga  actccctccc    7560
cccgctggcc ccggagatac cgccttcgac tactacgtgg ccccggacgg gacttggact    7620
cattggaaca ccagaactca agagtacctt tatccgtccg atactactcc ggagtacgga    7680
tccatcctgg tccctaacgt ggacaacgtg cgaaccgact tcctgattca gacaatcgcc    7740
aagcagggaa aggcggtgct gcttatcgga gaacaaggaa cagccaagac tgtcatcatc    7800
aagggattta tgagcaagta tgatcctgag tgccacatga tcaagagctt gaacttctcg    7860
tcggccacta ctcccctcat gttccaaaga accatcgagt cctacgtgga caaaagaatg    7920
ggaaccacgt acgggccccc tgccgggaag aagatgaccg tctttatcga tgacgtgaac    7980
atgcccatca tcaacgagtg gggtgatcaa gtcaccaacg aaatcgtgcg gcagctcatg    8040
gaacagaacg gattctacaa cctggaaaag ccagggaat  tcacctccat cgtggatatt    8100
cagttcctgg ccgccatgat ccatccaggc ggaggccgca atgacattcc gcaacgcctg    8160
aagcggcagt tctcaatctt caattgcacc ctcccgtcgg aagctagcgt ggataagatt    8220
tttggtgtca tcggagtcgg acactactgc acccaacgag gctttagcga agaggtcaga    8280
gatagcgtca cgaaactcgt gccgttgact cgccgccttt ggcagatgac caagatcaag    8340
atgctaccca ccccgctaa  gttccactac gttttcaatt tgcgggactt gagccgggtg    8400
tggcagggaa tgctgaacac cacctcgaa  gtcatcaaag aacctaacga cttgctgaag    8460
ctctggaagc acgaatgcaa gcgcgtgatc gccgaccgct tcactgtgag cagcgacgtg    8520
acgtggtttg ataaggctct ggtcagcctg tcgaggagg  agttcgggga agagaagaag    8580
ctcctggtcg actgtggcat cgacacgtat ttcgtggact ttctcagaga tgcgcccgaa    8640
gccgcgggcg aaacctcgga agaagcagac gctgagactc caagatcta  cgagccgatt    8700
gagagcttca gccacttgaa ggagagactt aacatgtttc tgcagctcta caacgaaagc    8760
attcggggcg ctgggatgga catggtgttt ttcgctgacg ccatggttca cttagtgaaa    8820
atctcccgcg taattaggac cccgcagggt aatgccctgc ttgtaggcgt gggcggatcc    8880
ggaaagcagt cactgacccg gcttgcatca ttcatcgcgg gctacgtgag cttccagatc    8940
actcttacta gatcatataa cacgtccaat ctcatggagg acctgaaagt gctgtatagg    9000
accgcgggcc agcaggggaa gggtatcacc ttcattttta ccgacaacga aatcaaagat    9060
gagtccttct tggagtacat gaacaacgtg ctctccagcg gcgaagtgag caaccttttc    9120
gccccgcgatg agatcgatga aattaactcc gacctggcct cagtgatgaa gaaggaatt   9180
ccgcgctgcc tccctacgaa cgaaaatctg cacgattact tcatgtcaag agtccggcag    9240
```

```
aatctccaca tcgtgctgtg cttttcaccg gtgggagaga agtttcgcaa ccgcgcactg   9300
aagttcccgg ccctgatttc gggatgcacg attgattggt tctcgcggtg gcctaaagat   9360
gccctcgtgg cggtgtccga gcacttcctt acttcctacg acatcgattg ctccctggag   9420
atcaagaaag aggtggtgca gtgtatgggt tcattccagg acggggtcgc agagaagtgc   9480
gtggactact ttcagagatt cagacgctcc actcacgtca ctccgaaatc ctacctgagc   9540
ttcatccagg atacaagtt tatatacggc gaaaagcacg tcgaagtgag aacactcgcc   9600
aacaggatga acactggttt ggaaaagctc aaggaggcgt ccgaatcggt ggccgcactg   9660
tcaaaggagc tcgaagcgaa ggagaaagaa ctccaggtcg cgaacgacaa ggccgacatg   9720
gtgttgaagg aagtaaccat gaaggcccag ccgccgaga aggtgaaggc cgaagtgcaa   9780
aaggtcaagg atagggcaca agccatcgtc gactcaattt cgaaggacaa ggcaatcgcc   9840
gaagaaaagt tggaggccgc gaagccggcc ctcgaagaag cggaggcggc gctgcagacc   9900
atcaggcctt cagatatcgc tacggtccgc accctgggtc gccctcctca cctcattatg   9960
agaatcatgg actgcgtgct gcttttgttc cagcgcaaag tctcagcagt gaagatcgat  10020
ctcgaaaagt catgcaccat gccatcatgg caggagagcc tgaagctaat gaccgctgga  10080
aatttccttc aaaatctgca gcaattccca aaggacacta ttaacgaaga agtgatcgaa  10140
ttcctctcgc cttacttcga gatgcccgac tacaacatcg aaaccgccaa agagtgtgc   10200 ggcaacgtcg ccgggctttg ctcctggacg aaggcaatgg ccagcttctt ctcaatcaac  10260
aaagaggtgc tgcccttgaa ggccaacttg gtggtccagg aaaacaggca ccttctcgcc  10320
atgcaagatc tccaaaaggc ccaagccgag ctcgatgaca agcaggccga gctggatgtg  10380
gtgcaggcgg agtacgagca ggcgatgaca gaaaagcaga cgttgcttga ggacgccgag  10440
agatgccggc acaaaatgca gaccgcctcc accctgatct cggggctggc aggcgaaaaa  10500
gaaagatgga ccgagcaatc gcaggagttt gccgctcaaa ccaagaggtt ggtgggcgac  10560
gtgttgttgg caaccgcatt cctgagctac agcggaccat tcaaccaaga gttccgcgac  10620
ctgttgctga cgactggag aaaggagatg aaggcccgca agatcccatt cggcaagaac  10680
cttaatctca gcgaaatgct gattgatgcc cctacaattt ccgagtggaa tctgcaggga  10740
cttccaaacg acgacctgag catccaaaat ggcatcatcg tgaccaaggc ttcacggtac  10800
cccctcctca tcgacccgca gactcaagga agatttggga tcaagaataa ggaaagccgg  10860
aacgagctgc agatcacttc ccttaaccac aagtacttta gaaaccacct cgaggactcc  10920 cttttccttgg gtcggccgct cctcattgag gacgtgggcg aggaattaga cccagccctc  10980
gacaacgtgc tggaaagaaa cttcattaag accggatcca cctttaaggt gaaagtcgga  11040
gataaggaag tcgacgtcct ggacggcttc agactctaca ttacgactaa gctcccaaac  11100
cctgcctata ccccggagat ctccgcgcgc actagcatta ttgacttcac cgtcacgatg  11160
aagggactgg aggaccagct gctggggagg gtgatcctga cggaaaagca ggaactcgag  11220
aaggagcgga cgcatttgat ggaggacgtg actgcgaaca agcggcgcat gaaggagctg  11280
gaggataacc tgttgtaccg gctgaccagc acccagggct cactggtcga ggacgaaagc  11340
cttatcgtgg tgctgtcgaa cactaagcgg actgccgagg aggtcactca gaagctggag  11400
atctccgctg agacagaagt ccagattaac tccgcccgcg aagagtacag gcctgtcgcc  11460
actagaggat ccatcctgta cttcttgatt accgaaatga gactcgtcaa cgagatgtac  11520
caaacctccc tgagacaatt cctgggcctg ttcgacctga gcctggcccg gtcggtaaag  11580
```

```
tcccctatca ccagcaagcg catcgctaat atcattgagc acatgaccta tgaggtgtac    11640
aagtacgccg cccgggggct ctacgaagaa cataagttcc tgtttaccct tctgctcacc    11700
cttaagatcg acattcagcg gaaccgcgtg aagcacgagg aattcctgac ccttatcaag    11760
ggaggagcct cactcgactt gaaagcgtgt cccccaaagc cctcgaagtg gatactggac    11820
attacctggc tgaaccttgt ggagctctcc aaactccggc aattttcaga cgtcttggat    11880
caaatttcaa ggaacgaaaa aatgtggaag atctggttcg acaaggaaaa tccggaggaa    11940
gaaccactgc cgaacgccta cgacaagagc ctcgactgct ttcggcggct gctgctcatt    12000
agaagctggt gcccggatcg gaccatcgcg caggccagga agtatatagt ggattcgatg    12060
ggggagaagt acgcggaagg cgtgattctc gatcttgaaa agacgtggga ggaatcggat    12120
cccaggacgc ccctcatttg cctgctgtcg atgggcagcg atcccacaga ctccatcatt    12180
gcactgggca agcggctcaa gattgaaact agatacgtgt cgatgggtca gggtcaagag    12240
gtgcacgcca gaaagttgct tcaacaaacc atggcaaacg gaggttgggc cctgcttcaa    12300
aattgccacc tgggactgga tttcatggac gaactcatgg atattattat cgaaaccgag    12360
ctggtccacg acgccttcag actgtggatg accaccgagg cccacaagca gtttccgatc    12420
acgctgctgc aaatgtcgat caagttcgcg aatgatccgc cgcaaggact ccgggccgga    12480
ttgaagagga cctactcggg agtctcacag gacctcctcg acgtttcgag cggctcacaa    12540
tggaagccca tgctgtacgc ggtcgctttc ctgcacagca ccgtgcaaga acggcggaag    12600
ttcggcgcgc ttgggtggaa tatcccgtac gaattcaacc aagccgactt taacgccacc    12660
gtgcagttta tccagaacca cctcgatgat atggatgtca aaaagggagt ctcgtggacc    12720
accattcggt acatgattgg agaaattcag tacggggac gcgtcaccga tgattacgac    12780
aagaggcttc tcaacacctt cgccaaagtg tggttctcgg aaaatatgtt tggaccggac    12840
ttctcgtttt accagggtta caacatcccg aaatgctcaa ccgtcgataa ctacctccaa    12900
tacatccaat cgctgcccgc gtatgactcg ccagaggtct ttggactgca tcctaacgcc    12960
gatattacct accagtccaa actggcgaag gacgtcctcg ataccatcct cgggatccaa    13020
ccaaaggaca cgagcggagg aggcgacgaa acccgcgagg cagtggtggc tcgcctggcc    13080
gatgatatgc ttgaaaagct gcccccagac tatgtgccgt tcgaggtcaa ggaaagattg    13140
caaaagatgg gacccttcca accgatgaac atcttcctga cacaggagat cgacaggatg    13200
cagcgcgtgc tatcgctggt cagatcgacg ctgaccgagc tgaaattggc aattgacgga    13260
acgattatca tgagcgaaaa ccttcgggac gcccttgatt gcatgttcga cgccagaatt    13320
ccggcttggt ggaaaaaagc gtcatggatt agctcaaccc tcgggttttg gttcacggag    13380
ctcattgaga ggaactccca gttcacttca tgggtgttta atggacggcc tcattgcttc    13440
tggatgactg gattctttaa tcctcaaggt ttcctgactg cgatgcggca ggagattact    13500
cgggccaata aggttgggc cctggataac atggtgttgt gcaacgaagt gactaaatgg    13560
atgaaggatg acatcagcgc accgcccacg gaaggcgtgt acgtctacgg attgtatctc    13620
gaaggagcgg gttgggacaa aaggaacatg aagctgatcg agtccaaacc aaaagtgctc    13680
tttgagctga tgcccgtgat ccggatctac gcagagaaca cacccctgcg ggatccccgc    13740
ttttattcat gcccgattta caagaagccc gtgaggaccg acctcaacta catcgcagcc    13800
gtggatttgc gcaccgccca aaccccggag cactgggtgc tgagggggt cgcattgttg    13860
tgcgatgtga aatag                                                    13875
```

```
<210> SEQ ID NO 23
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 23
atgttccgga ttgggaggag acagctttgg aagcactcag tcactagggt gctgacccaa      60
agactgaagg gcgaaaagga agcgaagaga gctttgctcg atgcgcgcca caattaccct     120
ttcgcgattg tggcctcatg cctggatctc aacaaaaccg aggtcgagga cgcgatcctc     180
gagggtaacc aaatcgaacg catcgaccag ttgtttgccg tgggtggact gcggcacttg     240
atgttctact accaggatgt cgaagaggct gaaacgggcc agctgggttc actcggagga     300
gtgaatcttg tcagcgggaa gatcaaaaag ccgaaagtgt tcgtcaccga aggtaacgat     360
gtagccctga ccggagtgtg tgtgttcttt atccggaccg atccgtccaa ggcgatcact     420
cctgataata ttcaccagga ggtgtcgttc aacatgctgg acgctgctga cggaggactg     480
cttaacagcg tcaggagact cctgtccgac atcttcattc ctgccctgcg ggcaaccagc     540
cacggatggg gagagctcga gggattgcag gacgcggcaa acattaggca ggaattcctg     600
agctccttgg agggcttcgt gaacgtcctt agcggagccc aagagtcctt gaaggaaaaa     660
gtgaacttgc ggaaatgcga tatcctggag ctcaagactc tcaaggagcc gaccgattat     720
ctgacgctgg ccaataatcc agagactctc ggcaagatcg aggattgtat gaaggtctgg     780
attaagcaga ctgagcaagt gctcgctgaa aataaccaac tgctgaagga agcggatgat     840
gtgggaccgc gcgctgaact ggaacactgg aagaaacgcc tgtcgaagtt taactacctc     900
ctggaacagc tcaagagccc ggatgtgaag gcagtgctcg cagtgttggc ggccgcgaag     960
tcaaagctcc ttaagacttg gcgggagatg acatccggat cactgatgc gaccaacgaa    1020
gccaaagaca acgtgaaata cttgtacact ctggaaaagt gctgcgaccc attgtactcc    1080
agcgacccgc tgtcaatgat ggacgctatc cccacgttga ttaacgcgat taagatgatc    1140
tactcaatca gccactacta caacacctcc gaaaagatta cctcactctt cgtcaaagtg    1200
acgaaccaga tcatctcagc gtgcaaggcg tacattacta caacggcac cgccagcatt    1260
tggaatcaac ctcaagacgt cgtggaggag aagatcttga gcgccatcaa gctgaagcag    1320
gagtaccaac tatgctttca caaaaccaag caaaagctca gcagaaccc taacgccaag    1380
caattcgact ctccgaaat gtacatcttc ggcaagtttg aaactttcca caggcgcctc    1440
gccaaaatca tcgacatctt caccaccctc aaaacttaca gcgtgctgca ggattccact    1500
atcgagggac ttgaagatat ggctaccaag taccaaggaa tcgtggccac cattaagaag    1560
aaggaataca attttctgga ccaacgcaaa atggacttcg accaggatta cgaggagttc    1620
tgcaagcaga ctaacgatct gcacaatgag ctccggaagt tcatggacgt gactttcgca    1680
aagatccaaa acaccaacca agccctccgc atgctgaaga aattcgaaag actcaatatc    1740
cctaacctgg gcattgacga taaataccaa cttatcctcg agaactatgg cgcggatatc    1800
gacatgatct cgaaactgta cactaagcag aaatacgacc cgcccttgc tcgcaatcag    1860
cccccgattg ccggaaagat cctgtgggcc cggcagctct tcacagaat caacagcca    1920
atgcagctct ttcagcaaca tcccgccgtg ctttccaccg cggaggctaa gcctatcatc    1980
cggtcctaca accggatggc taaggtcctc cttgagttcg aagtcctgtt ccaccgggcc    2040
tggcttagac aaatcgaaga gattcacgtg ggactcgaag ctagcttgct cgtaaaagca    2100
```

```
ccgggaacgg gggagctttt cgtcaacttt gacccccaaa tcctgatcct gttccgcgaa   2160
accgagtgca tggctcaaat gggacttgag gtgtccccac tcgcgactag cctctttcag   2220
aagagagaca gatacaagcg caacttctcc aacatgaaaa tgatgctggc tgagtatcaa   2280
cgcgtgaagt cgaaaattcc agccgccatt gaacagctga ttgtgcctca cctggccaaa   2340
gtggatgaag ccctgcagcc cggtctggcc gctttgacgt ggaccagcct caacatcgaa   2400
gcgtacttag agaacacttt cgccaagatc aaggatctcg aactcctcct ggaccgagtc   2460
aatgacctca tcgaattcag gatcgatgcc attttggaag agatgtccag cactcccctt   2520
tgccagcttc cccaggagga gccgcttact tgcgaggagt tcctccagat gactaaggat   2580
ctctgcgtga acggtgctca aatcctgcac tttaagtcct ccctggtgga agaagccgtc   2640
aatgagctgg tgaacatgtt gcttgacgtg gaggtcctgt cggaggaaga gagcgagaag   2700
atttccaacg aaaacagcgt caattacaag aacgagagta gcgccaaacg cgaggaagga   2760
aacttcgaca ctctgacatc ctcaatcaac gcccgcgcta atgctctcct cctgaccact   2820
gtcacgagaa agaagaagga aaccgagatg ctcggggagg aggctagaga gctcctgagc   2880
cactttaacc accaaaacat ggacgcgctg cttaaggtga cccgcaacac cctcgaggcg   2940
atcagaaagc ggatccactc gtcacacacc attaactttc gagactccaa ttccgcatcg   3000
aacatgaagc aaaattcact accgatcttc agagcctcgg tgactttggc aattcccaac   3060
atcgtcatgg ctcctgcact cgaggatgtc cagcaaaccc tcaataaggc cgtcgagtgt   3120
atcatcagcg tgccgaaggg agtgcgccag tggtcgtcag aactcctcag caagaaaaag   3180
atccaggaaa gaaagatggc cgcgctccag tctaacgaag atagcgactc cgacgtggaa   3240
atgggagaga acgagctgca agacactctg gaaatcgcca gcgtcaatct ccctatcccc   3300
gtccagacca gaactactga taagaacgtc agcgaaaaca aggaaatcgt gaagttggtg   3360
tccgtcttgt ccacgatcat caactcgacc aaaaaggagg tgatcaccag catggattgc   3420
tttaagagat acaaccacat ttggcagaag ggcaaggagg aggctatcaa gaccttcatt   3480
acccagtccc cactgttgtc ggaattcgaa tcgcagatcc tgtacttcca gaatctggaa   3540
caggagatta tgccgagcc cgagtacgtc tgcgtcggca gcatcgcgct gtacaccgcc   3600
gatttgaagt tcgccttgac tgccgagact aaggcctgga tggtggtgat tggccgccat   3660
tgcaacaaga agtataggag cgaaatggaa aatattttca tgttgatcga ggaattcaat   3720
aagaagctga atagaccaat caaggacctc gacgacatta ggattgccat ggcagccctg   3780
aaggaaattc gcgaggaaca aatcagcatt gacttccagg tcggcccaat cgaagaaagc   3840
tacgccctgc ttaaccgcta cggactgctc attgcccgcg aagagatcga caaagtggac   3900
acgttacatt acgcttggga gaaactcctg gctcgcgccg gagaggtgca aaacaagctg   3960
gtcagcctcc aacccagctt caagaaggag ctgatctccg ccgtcgaggt gttcttgcag   4020
gattgccacc aattttacct ggattacgac ctgaacggac cgatggcgtc cggcctcaag   4080
ccgcaagagg ctagcgacag gctgatcatg tttcagaacc aattcgacaa catttacaga   4140
aagtacatca cttacaccgg aggcgaggag cttttcggcc tgcccgccac tcagtaccca   4200
caattgctgg agatcaagaa gcagctcaat ctgctgcaga aaatttacac cttgtacaac   4260
tcagtgattg aaactgtgaa cagctactac gacatcctgt ggagcgaggt caacattgaa   4320
aagatcaata tgaactgct ggagttccag aaccggtgcc gcaagctgcc tagggcgctg   4380
aaggactggc aggcgttcct ggacctgaag aagattatcg acgatttctc agaatgctgc   4440
ccactgctcg agtacatggc ctcgaaggcc atgatggaac ggcactggga gcgcatcacg   4500
```

-continued

```
actttgactg  gacatagcct  tgacgtgggc  aatgagtcct  tcaagctgcg  gaacatcatg  4560
gaagctccct  tgctcaagta  caaggaagaa  atcgaagata  tctgcatctc  cgccgtgaag  4620
gaacgcgaca  tcgaacagaa  actgaaacag  gtcatcaacg  aatgggacaa  caagactttt  4680
actttcggga  gcttcaagac  cagggcgag  ctccttcttc  ggggtgactc  aacctcagag  4740
attatcgcca  atatggaaga  tagcctcatg  cttctcggaa  gcctcctgtc  caaccgctat  4800
aacatgccct  ttaaggccca  aatccaaaag  tgggtccaat  acttatctaa  cagcaccgat  4860
attatcgaat  cgtggatgac  cgtgcagaac  ctttggattt  acctggaggc  cgtgttcgtc  4920
ggcggagata  ttgccaagca  actgcccaag  gaggccaagc  gcttctcaaa  catcgacaag  4980
tcctgggtca  aaatcatgac  tcgggcccac  gaagtcccct  cagtggtcca  gtgctgtgtc  5040
ggcgacgaaa  ccttggggca  gctcctgccg  caccttctcg  accagttgga  gatttgtcaa  5100
aagtccttga  ccggctacct  tgaaaaaaag  aggttgtgct  tcccacgctt  tttctttgtg  5160
agcgaccccg  cgctcctcga  gatcctgggt  caggcgagcg  actcccacac  catccaggcg  5220
cacctcctga  acgtgttcga  caacattaag  agcgtcaaat  tccatgaaaa  gatctacgac  5280
agaatcctga  gcatctccag  ccaagagggt  gaaaccatcg  aactcgacaa  gccagtgatg  5340
gctgagggaa  acgtcgaggt  ctggctgaat  tcattgctgg  aagaatcgca  gagcagcttg  5400
cacctcgtga  tccgccaggc  cgcggcgaac  attcaggaga  ctggctttca  gttgaccgag  5460
tttttgagct  ccttccccgc  gcaagtgggc  ctgctgggga  tccagatgat  ttggactagg  5520
gattccgaag  aggcgctgag  aaatgccaag  tttgacaaaa  aaattatgca  gaaaaccaac  5580
caggcctttc  tcgagcttct  gaacactttg  atcgacgtca  ctacacgcga  tctgagctcg  5640
actgagcgcg  tcaagtatga  aaccctgatt  accatccacg  tccatcaacg  ggatattttc  5700
gatgacctct  gccacatgca  tatcaaatca  ccgatggatt  ttgaatggct  caaacagtgc  5760
cgcttctact  tcaatgaaga  tagcgacaag  atgatgattc  atatcaccga  tgtggccttc  5820
atctaccaga  acgaattcct  tggctgcact  gacagactgg  tcatcactcc  tctgaccgat  5880
agatgctata  ttaccettgc  ccaggcctta  ggaatgtcga  tgggcggtgc  tccagccggg  5940
cccgcgggca  ccggaaagac  agagactacg  aaggatatgg  gaaggtgcct  gggcaagtac  6000
gtcgtcgtgt  tcaattgcag  cgaccagatg  gatttccggg  gcctgggccg  cattttcaag  6060
ggccttgcgc  agtcgggatc  gtgggggtgc  ttcgatgaat  tcaatcggat  cgacttgcca  6120
gtgttgagcg  tcgcgcccca  acagatttca  atcatactaa  cctgtaaaaa  ggagcacaag  6180
aaatccttca  ttttcacgga  cggggacaac  gtgacgatga  acccagaatt  tggcctcttc  6240
ctcactatga  atccagggta  cgccggtcgg  caggaacttc  ccgaaaatct  gaaaattaac  6300
ttcaggagcg  tcgccatgat  ggtcccagat  cggcaaatca  tcattagggt  caaactggct  6360
tcgtgcggat  tcattgataa  cgtggtgctg  gccagaaagt  tcttcaccct  ttacaaattg  6420
tgcgaggaac  agctctcgaa  gcaagtgcac  tacgactttg  gcctcagaaa  catcctaagc  6480
gtgctgcgca  ctctggggc  agccaaaaga  gccaacccaa  tggacaccga  gagcactatt  6540
gtgatgaggg  tccttcgcga  catgaacctc  tcaaaactta  tcgacgagga  cgagccgcta  6600
ttcctcagcc  tgatcgaaga  tctgttcccc  aacatcctgc  tggacaaggc  gggctaccct  6660
gaactggagg  ccgccatttc  ccgccaagtc  gaagaggccg  gcttgattaa  ccatcctccc  6720
tggaagctca  aggtgatcca  gttattcgag  actcagcgcg  tacggcacgg  gatgatgacg  6780
ctgggtccgt  cgggtgccgg  aaagactact  tgtatccaca  ccctcatgag  ggctatgacc  6840
```

-continued

```
gattgtggaa aaccccaccg ggaaatgcgc atgaacccga aggcgattac ggctccgcag   6900
atgtttggac gcctggatgt cgccactaac gactggaccg atgggatttt ctccacgctg   6960
tggagaaaaa ccttgcgcgc caaaaagggc gaacacattt ggatcattct tgacggaccg   7020
gtggacgcga tctggatcga aaatctgaat tccgtcctgg acgataacaa aactctcacc   7080
ctggctaacg gtgatcggat ccctatggcg ccgaattgta aaattatctt cgaacctcat   7140
aacattgaca atgctagccc cgcaacggtc agccgcaatg gcatggtgtt tatgtcatcg   7200
tccatcctgg attggtcacc gatcctcgag ggattcctca agaagcgctc ccctcaagag   7260
gccgaaattc tccggcagct ctacaccgag tcgttcccag atttgtacag gttctgtatt   7320
cagaacctgg aatacaagat ggaagtgttg gaagcattcg tgatcacgca gtcgatcaac   7380
atgctgcaag gtctgattcc tttgaaggag cagggcggcg aggtgtccca agcgcacctg   7440
ggacggttgt tcgtatttgc cttgctgtgg tccgccgggg ccgccctgga actggacggg   7500
cgccgccgcc tggagctctg gctccggtcc agacctaccg gaacgttgga actgcccccc   7560
ccggccggtc ccggggacac cgcctttgac tactacgtgg ctcccgacgg cacttggact   7620
cattggaaca cccggactca agagtacctg tacccttcag acacaactcc cgagtacggt   7680
tcaatccttg tgccaaacgt cgacaacgtg cgcaccgact ttctcattca gaccattgcc   7740
aagcaaggaa aggcagtcct gctcatcgga gagcagggca cggccaagac cgtgatcatc   7800
aagggattca tgagcaagta tgaccctgag tgtcatatga tcaagtcact gaacttttcg   7860
agcgctacta caccgctcat gttccagcgg actatcgaaa gctacgtgga caaaagaatg   7920
ggaaccactt acggaccgcc agccggaaag aagatgaccg tgttcattga cgatgtgaac   7980
atgcccatta tcaacgaatg gggcgaccag gtcaccaacg aaatcgtgag gcaattgatg   8040
gagcagaacg gattttataa cctcgaaaag ccaggcgaat tcacctccat cgtggatatc   8100
cagttcctgg ccgcaatgat ccatcccggc ggcggtagaa acgacatccc gcaacgcctg   8160
aagcggcaat tctcaatttt caattgtact ctccccctccg aggcctccgt ggacaagatc   8220
tttggagtca ttggggtggg ccactactgc acccagagag cttttccga ggaagtccgg   8280
gactcggtca ccaagctggt gccgcttacc cgcaggctct ggcaaatgac caaaatcaag   8340
atgcttccta ccccggccaa gtttcactac gtgttcaacc tccgcgatct gtcacgcgtg   8400
tggcagggga tgctcaacac cacttccgag gtcatcaagg aaccgaacga cctcctgaaa   8460
ctgtggaaac atgaatgcaa aagagtcatt gctgaccgct tcaccgtgag tagcgacgtc   8520
acatggttcg acaaggcact ggtcagcctg gtcgaagagg agttcggcga ggaaaaaaaa   8580
ctgcttgtgg actgtgggat cgatacttat ttcgtggatt tcctgaggga tgccccagag   8640
gcggccggcg aaacatccga agaagcagac gccgaaaccc ctaagatcta cgagcccatt   8700
gaatcctttt cccacttaaa ggaacgcctg aacatgttcc tgcagctgta caatgaaagc   8760
attcgcggcg ccgggatgga catggttttc ttcgccgatg ccatggtgca cctcgtgaag   8820
ataagccggg tcattagaac ccctcaaggg aacgccctgt tggtcggtgt cggcggctcg   8880
gggaagcaga gcttgactcg gctcgccagc tttatcgccg ggtatgtctc atttcaaatc   8940
accctgaccc gctcctacaa cactagcaac ctgatggagg acctgaaggt gctgtacaga   9000
actgccgggc agcagggcaa gggtatcacg tttattttca ccgataacga aattaaggat   9060
gagagctttc tcgaatacat gaacaacgtg ctgagttccg gggaggtgtc caaccttttt   9120
gcaagggacg aaatcgatga gatcaactcc gacttggcca gcgtgatgaa gaaggaattc   9180
ccaagatgcc tcccaactaa cgaaaatctc cacgactatt tcatgtcaag agtccgacaa   9240
```

```
aacttgcaca tcgtgctgtg ctttagtcct gtgggagaga agttccgaa ccgggctctg    9300
aagtttcccg ccctgattag cggatgcacc attgactggt tctcccggtg cccaaagat    9360
gcgctggttg ctgtgtcgga acacttcctg acctcgtacg atattgactg ttccctggaa   9420
atcaagaagg aagtcgtcca atgcatggga agtttccagg acggtgtcgc cgaaaagtgc   9480
gtggattact ttcaaaggtt ccgccgcagt actcatgtca cccccaaaag ctacctgtca   9540
ttcattcagg ggtacaaatt catctacgga gagaaacacg tggaggtgcg gactctggcc   9600
aatcgcatga acaccgggct ggagaagctc aaggaagcga gcgagagcgt ggccgccttg   9660
tccaaggaac tcgaggccaa ggaaaaagag ctccaggtag ccaatgacaa ggccgatatg   9720
gtgctgaagg aggtcaccat gaaagcacag gcagcagaga agtcaaggc ggaagtccaa    9780
aaggtgaagg accgggccca ggccatcgtc gactcgatct ccaaggataa ggccattgcc   9840
gaggaaaaat tagaggcggc gaagccggct ctcgaggaag cggaagctgc cctgcaaacc   9900
atcagaccct ccgacatcgc caccgtgagg actctgggcc gccctccgca tcttatcatg   9960
cggatcatgg actgcgtcct gctcctgttc cagcgaaagg tgtccgccgt gaagatcgat  10020
ctcgagaagt cgtgtaccat gccctcgtgg caggaatcgc tcaaattgat gacgccgga   10080
aacttcctgc aaaatctgca gcagttccct aaagacacta tcaacgagga agtgatcgaa  10140
ttcctctcgc cgtacttcga gatgccggac tacaacatcg aaaccgctaa acgggtctgc  10200
ggcaacgtcg ccggtctttg ctcctggacc aaggcgatgg cctccttctt ctcgattaac  10260
aaggaggtgc tgcctctcaa ggccaacctc gtcgtgcaag aaaacagaca cctactagcg  10320
atgcaagacc ttcagaaggc acaggccgag ctggacgaca agcaagcaga actggacgtc  10380
gtgcaggccg agtacgagca agccatgacc gagaagcaga ctctgctaga ggacgccgag  10440
cgctgtcggc acaaaatgca aaccgcgtcc acccttattt cgggattggc aggagaaaag  10500
gaacggtgga ctgaacagag ccaagaattt gccgcgcaaa ccaagagact tgtgggcgac  10560
gtgctcctgg ccactgcctt cctgagctat tccggacctt tcaatcagga attccgcgac  10620
ctcctgctga tgactggcg gaaggagatg aaggcacgca agatcccttt cggaaagaac  10680
ttgaacctct ccgagatgct tatcgacgcg cctaccattt ccgaatggaa cctccaggga  10740
ctgccgaatg acgatctcag cattcaaaac gggatcatcg tgacgaaggc cagccgctac  10800
ccctgctca tcgaccccca gactcagggg aagatttgga tcaagaacaa ggaaagccgg   10860
aacgaactcc aaattaccag ccttaaccac aagtactttc gcaaccacct cgaggacagc  10920
cttttccttgg gcagaccttt actgatcgag gatgtgggag aggaactgga ccctgccctt  10980
gataacgtac tggaaagaaa ctttatcaag actggctcta ctttcaaagt gaaagtgggt  11040
gacaaggaag tggatgtgct ggacgggttc cggctgtaca tcaccaccaa gctccccaat  11100
ccagcctaca cccctgaaat ctccgcccgg actagcatca ttgatttcac cgtgactatg  11160
aagggccttg aggaccaact gctgggcaga gtcattctga ccgagaaaca ggaactggaa  11220
aaggaaagga cgcatcttat ggaggacgtc actgcgaaca agcggcggat gaaggagttg  11280
gaagataact tgctctaccg gctgaccagc acccagggaa gcctcgtgga ggatgaatca  11340
ctcatcgtgg tcctcagcaa caccaagagg actgcagagg aagtgaccca gaagttggaa  11400
attagcgcag aaacggaggt gcagatcaat agtgctcggg aggaatacag gcccgtcgcg  11460
accagggga gcatcctgta cttcctgatt actgaaatgc gcctggtcaa tgaaatgtac   11520
cagacgtccc tgcgccaatt cctggggctt tttgacttgt ccctcgctag gtcggtgaag  11580
```

-continued

```
tcccctatca cgtccaaaag aattgcaaac attattgaac acatgacgta cgaagtctac    11640
aagtatgcag ccagaggtct gtacgaggaa cacaagttcc ttttcaccct tctgctgacc    11700
ctgaagattg atatccagcg caataggtg aaacatgaag agttcctcac cctgatcaaa     11760
ggtggcgctt ccctcgattt gaaggcatgt ccgcctaagc cttcaaagtg gatcctggat    11820
attacgtggc tcaatctcgt ggaactgtcc aagttgcgac agtttagtga cgtgctggac    11880
cagatttccc gcaatgaaaa gatgtggaag atctggttcg ataaggaaaa ccccgaagag    11940
gagccgctgc ccaacgccta cgacaagtcg ctggattgct ttcggaggtt actcctgatt    12000
agatcgtggt gcccggatcg caccatcgct caggccagga agtacatagt ggactcgatg    12060
ggggaaaaat acgccgaagg agtcattttg gacctcgaaa agacttggga ggagtccgac    12120
cctcgcactc cgctgatctg cctgcttagc atgggctcgg accctactga ttcgatcatt    12180
gccttgggga agcgcctcaa gatcgaaacc agatacgtgt cgatgggcca aggtcaagag    12240
gtgcacgcgc ggaaactcct ccagcagacc atggcgaacg cggctgggc gctgctgcag     12300
aactgccacc tcgggctgga cttcatggac gagctgatgg acatcattat cgaaaccgag    12360
ctggtgcacg acgcgttccg cctttggatg accaccgagg cccataagca atttcccatc    12420
acactcctcc aaatgtccat caagtttgcc aacgaccctc cgcagggtct gcgggctggt    12480
ctgaagagga cttattccgg agtcagccag gacctcctag atgtcagcag cggatcccaa    12540
tggaagccaa tgttgtacgc cgtggccttt ttgcactcca ccgtccagga aggaggaag     12600
ttcggagcct tagggtggaa tatcccgtac gaattcaacc aggccgattt caatgctact    12660
gtccagttca tccagaatca tctggacgat atggacgtaa agaagggagt gtcgtggacg    12720
acgattcgct acatgattgg tgagattcag tacgggggc gggtcactga cgactatgat     12780
aagaggcttc tcaataccct tgcgaaggtc tggttctccg aaaacatgtt cggcccgat    12840
ttctccttct accaaggtta caatatcccg aagtgctcga ccgtggacaa ctacctccag    12900
tacattcaga gccttcctgc ctacgactcc ccggaagtgt tcggcctgca ccctaacgcg    12960
gacattacgt atcaaagcaa gctggccaaa gacgtgctgg acactattct cggaatccag    13020
cctaaggaca catcgggagg aggcgatgaa acccgcgaag ccgtggtggc gcggctggcg    13080
gatgacatgt tggagaagtt gccaccggac tacgtgccat tcgaagtgaa agaaaggctg    13140
caaaagatgg gaccgtttca acccatgaac attttcctta gacaggaaat tgatagaatg    13200
caaagggtcc tgtcgctcgt tagatccacg ctgaccgagt taaagctggc tatcgacggc    13260
accattatca tgagcgagaa tctccgggac gctctcgact gcatgttcga tgcaaggatt    13320
ccggcttggt ggaagaaggc gagctggatt agctccactt tgggcttttg gttcactgaa    13380
ctcattgaac ggaactccca gtttacttcg tgggtcttta acggtaggcc acactgcttt    13440
tggatgactg gattctttaa cccccagggc ttccttaccg ctatgcggca ggagattacc    13500
agagccaaca agggttgggc actgacaaac atggtgcttt gtaacgaagt gaccaagtgg    13560
atgaaggacg atattagcgc tcccccgacc gaagggtct acgtctacgg actctacctg     13620
gaaggggccg gttgggacaa aagaaacatg aagctcattg agtctaagcc caaggtcctc    13680
ttcgaactca tgccagtcat tcgcatttac gccgaaaata acactctccg cgatcctcgg    13740
ttctactcat gcccgatcta caagaagccc gtgagaactg acttgaatta catcgctgcc    13800
gtggacctca gaacggccca gaccccgaa cactgggtcc tgagagggt ggcactgctg      13860
tgcgatgtca agtag                                                     13875
```

<210> SEQ ID NO 24
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 24

| | | | | | |
|---|---|---|---|---|---|
| atgttcagaa | tcggaaggag | acaactatgg | aagcacagcg | tgacgcgggt acttacccaa | 60 |
| cgtctaaagg | gggagaagga | ggcgaagcgg | gcactgctag | acgcgcgtca taattacctc | 120 |
| tttgcaatag | ttgccagctg | cctcgacctc | aacaagacgg | aggtagagga cgccatatta | 180 |
| gagggcaacc | agattgagcg | gatcgatcag | ctatttgccg | tgggcgggct ccggcatcta | 240 |
| atgttttact | accaggacgt | cgaggaagct | gagaccgggc | aactgggatc cctgggaggc | 300 |
| gtcaacctcg | tctccggcaa | gataaaaaag | cctaaggttt | tcgttacaga gggcaacgac | 360 |
| gtagcgctga | ctggtgtatg | cgtcttcttc | atacggacag | accccagcaa ggcgattacg | 420 |
| ccagacaaca | tccaccagga | ggtctcgttt | aacatgctcg | acgccgccga tggcgggctg | 480 |
| ctgaactcgg | tgcgccggct | gctctcggat | atctttatcc | ccgcgcttcg ggcgacgagc | 540 |
| cacgggtggg | gtgagctgga | aggcctacag | gacgcggcca | atattcgtca ggagttccta | 600 |
| tccagcctgg | aaggttttgt | taacgtgctg | tccggcgccc | aggagtcgct taaggagaag | 660 |
| gtgaacttac | gaaagtgtga | tatattagag | ctgaaaaccc | tgaaggaacc tacagactat | 720 |
| ctcacccteg | caaacaaccc | cgaaaccctc | ggcaaaattg | aagattgcat gaaggtgtgg | 780 |
| attaagcaga | cggaacaagt | cctggcagag | aacaaccaac | tcttgaagga ggccgacgac | 840 |
| gtgggcccgc | gcgctgagct | ggagcactgg | aagaagaggc | tcagcaagtt taactatctt | 900 |
| cttgagcagc | tgaagagccc | ggacgttaag | gcggtactag | cggtcctcgc ggctgcgaag | 960 |
| tcgaagctgc | tcaagacctg | gcgtgagatg | gacatacgca | tcacggacgc aaccaacgaa | 1020 |
| gctaaggaca | acgttaagta | tttgtatacc | ctcgagaagt | gctgcgaccc cctctactca | 1080 |
| tctgatccgc | tcagtatgat | ggatgccatc | cccacgctaa | ttaacgccat taagatgatc | 1140 |
| tactcgatat | cgcactatta | caacacgtct | gaaaaaatca | ccagcctctt cgtaaaagtg | 1200 |
| actaaccaaa | tcattagcgc | ctgcaaggct | tacatcacta | caacggcac cgccagtata | 1260 |
| tggaaccagc | cccaggacgt | cgtggaggag | aagatcctat | cggccataaa gctgaagcag | 1320 |
| gagtatcagc | tgtgcttcca | caaaccaag | cagaaactca | agcagaaccc aaatgctaag | 1380 |
| cagttcgact | ttctgagat | gtatatttc | gggaagtttg | aaacatttca tcgccgcctg | 1440 |
| gccaaaatca | tcgacatatt | caccactctg | aagacctact | cagtcctaca agacagcact | 1500 |
| atagaagggc | tagaggatat | ggccacaaag | taccagggca | tcgtggccac tatcaaaaag | 1560 |
| aaggagtaca | acttcttaga | ccagcgtaaa | atggatttcg | accaggacta tgaagaattc | 1620 |
| tgcaaacaaa | cgaatgattt | gcacaacgag | cttcggaaat | tcatggatgt gacttttgcc | 1680 |
| aaaatacaga | ataccaacca | agctcttagg | atgttaaaga | aatttgaaag gctcaatatt | 1740 |
| cctaatttgg | gcattgatga | caaataccag | ttgatactcg | aaaattatgg agcagatatt | 1800 |
| gatatgatct | ctaaactgta | cacaaaacaa | aaatatgatc | ccccgctagc tagaaatcaa | 1860 |
| cctccgattg | ctggtaagat | actctgggcc | agacagctct | tcaccgcat ccagcagccc | 1920 |
| atgcagctgt | ttcagcagca | ccctgcggtg | ctgtccaccg | ccgaagcgaa acccattatt | 1980 |
| cgatccttata | accgcatggc | caaggttctg | ttagagtttg | aagttttgtt ccaccgtgcc | 2040 |
| tggttacgtc | agatcgagga | gatccatgtg | ggactggagg | cctctctcct agtcaaggcc | 2100 |

```
cccggcacag gcgaactctt tgtcaatttt gatccccaga ttctaatact cttccgggaa    2160
accgagtgca tggcccagat gggcttagag gttagtcctc tggctacttc tctgttccag    2220
aagagagacc gctataaacg gaatttcagc aatatgaaga tgatgctcgc tgaatatcag    2280
agggtcaagt ccaaaatccc cgctgcgatc gagcagctga tagtgccaca cctggccaaa    2340
gtagatgagg ccctacaacc aggactggcc gcgctgacgt ggacctctct gaatatcgaa    2400
gcgtatttgg agaacacctt tgccaagatt aaggacctgg agcttttact ggacagagtg    2460
aacgatctca ttgaattccg catagacgcg attttagagg agatgtcttc cacgccacta    2520
tgccagcttc ctcaggagga gcctttaaca tgtgaagagt tccttcagat gactaaggac    2580
ctctgcgtga atggcgctca gatactacat ttcaagtcta gcttggtcga ggaggcagtg    2640
aacgaattgg ttaacatgtt actggatgta aagtcctta gcgaggagga atccgaaaag    2700
atcagcaacg aaaattcggt gaactataag aacgaatcta gcgccaagcg ggaggagggc    2760
aactttgata cactcacttc ttccatcaat gcgagggcta atgctctctt gttgacgacc    2820
gttaccagaa aaaaaagga gactgagatg cttggggaag aggcaaggga gttgctgtcc    2880
cacttcaacc atcagaatat ggacgccctc ttaaaggtta cccgaaacac gttagaggca    2940
attaggaagc gtattcactc aagccacacg ataaacttcc gcgactcaaa ctcagcatca    3000
aatatgaagc aaaactcctt gccgatcttc agagccagcg tcaccctggc catacctaac    3060
atcgttatgg caccggcact tgaggacgta caacaaacct tgaacaaagc agtagagtgc    3120
atcatcagcg tccctaaagg agttcgccaa tggtccagtg aactgctatc caagaagaag    3180
atccaggagc gtaaaatggc tgcgttacag agtaacgaag attcggactc tgacgttgaa    3240
atgggtgaaa acgagctcca agacacactg gagattgcga gcgttaacct gcctataccc    3300
gtccagacca agaactacta caaaaacgtg tccgaaaaca aggagatcgt caagctcgtt    3360
tctgtgctca gcaccataat aaattcgact aagaagaag ttataacttc catggattgt    3420
ttcaaacggt ataaccacat ctggcagaaa ggcaaggaag aagctatcaa gacatttatt    3480
acccagagcc cactactaag cgagttcgag tctcagatcc tctacttcca gaatcttgag    3540
caggagatca acgctgagcc cgaatatgtg tgcgtcggct cgatagccct gtacacggct    3600
gatctgaaat ttgcgctgac cgctgagacg aaggcttgga tggtggtgat tggccgacac    3660
tgcaacaaga gtaccggtc tgaaatggag aacatcttta tgctaatcga ggaatttaac    3720
aaaaagctga accgtcccat taaggatctg gacgacatca ggattgccat ggcggcccta    3780
aaggaaatta gagaggagca gatatccatt gattttcagg ttggccccat cgaagaatca    3840
tatgcccttc tgaatcgata cggtctatta atcgcccgag aggaaataga taaggtggac    3900
acacttcatt atgcatggga gaaactctta gcgcgggccg gcgaagtgca gaataagctc    3960
gtatcgctgc agccatcatt taagaaggag ctcatcagtg ctgtcgaggt ctttctgcag    4020
gactgccacc agttctatct ggattatgac ctgaacggtc cgatggcgag tggtctgaag    4080
ccccaagagg cttcagaccg gcttatcatg ttccaaaatc agttcgacaa tatttaccga    4140
aagtatatca cctatacagg gggtgaagaa ttgtttggtc tcccagccac ccagtatcca    4200
caattattgg aaataaagaa gcagctgaac cttcttcaaa aaatctacac tctctataat    4260
tcggtaattg aaactgttaa ttcctactac gatattctct ggagcgaggt caacattgag    4320
aaaattaata cgaactctt ggagttccaa aacagatgcc gcaagttgcc gagagcgctg    4380
aaggactggc aggcttttct cgaccttaag aaaataatcg atgatttcag tgaatgcgtt    4440
cctctcttag aatacatggc gagtaaggct atgatggaga gacactggga gaggattacg    4500
```

```
actctgacgg ggcattcttt ggacgttggc aacgagtcct tcaagctgcg taatataatg   4560
gaggctccac ttctcaagta caaagaggaa atagaagaca tctgtatatc tgctgtcaaa   4620
gagcgcgaca tagaacagaa actaaagcag gtaattaacg aatgggacaa taaaacgttt   4680
acatttggca gtttcaagac acgtggagaa ttattgcttc gaggcgactc cacctcggaa   4740
attatcgcta acatggagga ctctctcatg ttactcggct cgctgttatc gaaccggtat   4800
aatatgccat tcaaagcaca gatccagaag tgggtgcagt atctatctaa tagtacggat   4860
ataatagaga gctggatgac cgtccagaat ctctggatct acctggaggc ggtgtttgtg   4920
ggaggtgata tagcgaagca gcttccaaag gaggccaaaa gattctccaa cattgacaaa   4980
tcctgggtca agattatgac tcgggcccac gaagtgccct ccgtggtgca gtgctgcgtc   5040
ggggacgaaa ccttgggcca gctgttgccc cacctgttgg atcaattgga aatctgccaa   5100
aagagcctga ctggctacct agagaaaaag cgtctgtgct ttccccggtt cttcttcgtt   5160
tctgaccctg cactactcga aatcttgggt caggcctctg attctcacac aattcaggct   5220
catttgttaa atgtgtttga acatcaaaa agtgtgaaat tcatgaaaaa gatttatgac   5280
aggatcttgt ccatttcatc ccaagaggga gaaaccattg agcttgataa gcctgtgatg   5340
gcagagggaa acgtggaggt ctggcttaac agtctcctgg aagagtccca gtcctcactg   5400
cacctggtca tccgccaggc ggcggctaat atccaggaga caggattcca gctcacggaa   5460
ttccttagtt cgtttccggc gcaagtgggg ctcctcggca ttcagatgat ctggacgaga   5520
gattcggagg aagccctccg caacgccaag tttgacaaga agattatgca gaaaactaac   5580
caagccttcc tagagctcct caacactctg atcgatgtca caactcgtga tctatcgtct   5640
accgagcggg tcaagtatga gacactgatt accatacacg ttcaccagcg tgatatattc   5700
gatgatctat gccacatgca cataaagagt cccatggact tcgaatggct aaaacagtgc   5760
aggttctact ttaatgaaga ctcggataag atgatgatcc atatcacaga tgtagcgttt   5820
atttaccaaa acgagttcct tggctgcaca gacaggttag tcataactcc gttaactgat   5880
cgctgctaca ttacactcgc ccaagcgctt ggaatgtcca tgggtggagc ccccgcaggg   5940
ccggcgggga caggtaagac cgaaacaact aaagatatgg gccgttgcct cgggaagtat   6000
gtagtagttt ttaactgctc agaccaaatg gatttccgag ggctgggccg tatctttaaa   6060
gggctggcgc aatccggttc ctgggctgt tttgacgagt tcaatcgtat tgatttaccg   6120
gtgctaagtg ttgccgcaca gcaaattagt ataattttga catgtaagaa agaacacaag   6180
aaaagtttta tatttactga cggcgacaac gtcactatga atcctgaatt cgggcttttc   6240
ttgactatga acccagggta tgctggccgt caagaacttc ctgaaaatct gaaaatcaac   6300
tttcgatcgg tggctatgat ggtaccggac cgccagatca tcatccgggt aaaactggcc   6360
tcgtgtggct tcatcgacaa cgtcgtactt gctcgaaagt tcttcaccct ttacaagcta   6420
tgtgaggagc agtatcgaa acaagttcat tacgactttg ggctccggaa tatcttgtcc   6480
gtcttacgca cactcggagc ggctaaacgt gcaaatccca tggacactga gagtacgatt   6540
gtgatgcgag tgttaaggga tatgaatctc tcaaaattaa tagacgagga cgagcctctt   6600
tttctcagcc ttatagagga tctgttccca aacatcctcc tggacaaggc tggatatccc   6660
gagttggaag cggcgattag caggcaggtg gaggaggccg gattgattaa tcacccgccc   6720
tggaaactga aagtcatcca gctgttcgag actcagcggg tccgacacgg tatgatgact   6780
ttaggcccat ctggcgcggg gaaaaccacc tgcatccaca ccctgatgag ggctatgacc   6840
```

```
gattgtggga agcctcaccg tgagatgcgg atgaacccga aggcgatcac agcgcccaa      6900
atgtttgggc gtctggatgt ggcgacaaat gactggaccg atggaatctt ttccacactc    6960
tggaggaaga ccctgcgcgc aaaaaaagga gagcacatct ggatcattct cgatggcccc    7020
gttgacgcta tttggatcga aaacttaaac agcgtgctcg acgacaacaa gaccctgaca    7080
ttggcaaatg gtgaccggat tcctatggct cccaattgca aaatcatttt tgaacctcac    7140
aacatcgaca acgccagtcc ggctacggtg tcccgcaacg gtatggtttt catgagcagt    7200
tccatactgg attggagtcc gatattggaa ggatttctca agaaacgcag tccccaggag    7260
gcggaaattc tgcggcaact gtatacgaaa agttttcctg acctgtaccg tttctgtatt    7320
caaaatctcg agtataagat ggaggtgttg gaggccttcg tcatcacaca gtccattaac    7380
atgcttcagg gcttgatccc cttgaaggag caaggagggg aagtcagcca ggcacatcta    7440
gggcggcttt tcgttttcgc ccttctctgg tccgcgggtg ctgctctcga gctagacggt    7500
cgccggcgct tggagttgtg gctgaggtct cgcccgaccg ggacactcga gctgccgccg    7560
ccagccggac ccgggacaca ggcattcgac tactacgttg ctccggacgg cacctggacc    7620
cactggaaca cccgtacgca ggagtatctc tatcccagcg atacaactcc tgagtatggt    7680
agcatactcg ttccgaacgt agacaacgtc agaaccgact ttctgatcca gaccattgct    7740
aagcagggca aggcagtcct attgatcgga gagcaaggga ccgcgaaaac cgtgattatc    7800
aagggcttca tgagtaaata tgacccagag tgtcatatga ttaagtccct caacttcagt    7860
tctgctacca caccactcat gtttcagcgt actatcgaat cctacgtgga caagcggatg    7920
ggcaccacct acgggccgcc tgccgggaag aagatgacgg tatttataga cgacgttaac    7980
atgcccatca tcaacgagtg gggagatcaa gtgacaaacg aaatcgttcg gcaacttatg    8040
gaacaaaacg ggttctataa cctcgagaag ccgggcgagt tcacctcaat agtagacatt    8100
caatttctgg cagctatgat ccatcccgga ggaggacgga acgacattcc ccagcggctc    8160
aagcgccaat tcagcatctt caactgcacg ctgccaagtg aagcatcggt agacaaaatc    8220
ttcggcgtca tcggggtggg tcactactgc acccagcgcg gcttttcaga ggaagtccga    8280
gattctgtta ctaaactggt tccttttgact agaaggctgt ggcagatgac caaaattaag    8340
atgcttccta ctccagctaa attccactac gtgttcaatc tgcgagactt atccagggta    8400
tggcaaggta tgcttaatac cacctctgag gtaattaaag aaccgaacga tctgctgaaa    8460
ctgtggaagc acgaatgtaa gagagttatt gcagataggt ttactgtttc gtcagatgtt    8520
acctggttcg ataaagccct ggtgtctttg gtcgaagaag agtttgggga agagaagaag    8580
ctactcgtcg attgcgggat cgacacttac tttgtggact tcttaagaga cgcccctgag    8640
gctgccggcg aaacatcgga agaggcagac gctgagactc ctaagatcta tgagccgatc    8700
gagagcttta gccacctcaa ggaacgtctg aatatgtttt tacaattgta taatgagagc    8760
attcgtggtg ctgggatgga tatggtgttc ttcgcggatg caatggtgca tctggtaaag    8820
atttctcggg tgattcgcac gccacaggga aacgcgctac tggtcggggt gggtgggtca    8880
ggaaagcaat cgttaactcg tttggcatcc tttatcgcgg gatatgtgag ttttcaaatc    8940
accctgacaa ggtcctataa tacatccaac ctgatggagg atcttaaagt tctctacagg    9000
acggcgggac aacagggcaa aggaataacc ttcatcttca cagataacga aattaaagac    9060
gaatcattct tggagtatat gaacaacgtc ttatcaagcg gcgaagtttc gaacctcttc    9120
gcgcgggacg aaatcgatga gatcaactct gatctcgctt ctgtcatgaa gaaagaattc    9180
ccccggtgtt tgccgacgaa tgagaacttg catgactatt tcatgtcccg tgtgcggcag    9240
```

```
aatttgcaca ttgtgctttg cttttcaccg gtgggggaga agttccgaaa tagagctttg    9300
aagttccctg ctttgatttc tgggtgcact attgactggt tttcccgttg gcccaaggac    9360
gctctggtcg ccgtgtccga gcactttta accagctatg atatcgactg cagcctcgaa    9420
attaagaagg aagtagttca gtgtatgggc tctttccaag acggtgtggc agagaagtgc    9480
gtcgactatt tccagaggtt tcgccgatct actcatgtca cacctaagag ctacttgtcc    9540
ttcatacagg ggtacaagtt tatatatggg gagaaacacg ttgaagtaag gactctggca    9600
aaccgtatga atactggctt agagaagctc aaggaggcct cagaaagtgt ggctgctctc    9660
tcaaaggagc ttgaagctaa ggagaaggaa ctccaagttg cgaacgataa agcggatatg    9720
gttctaaaag aagtgactat gaaagcacaa gcggctgaaa aggttaaggc ggaggtacag    9780
aaggtgaagg atcgcgccca ggcaatagtc gattccattt ccaaagacaa ggccatcgcg    9840
gaagaaaagc tagaagccgc caagccggcc ttagaagagg cagaggctgc cttgcaaacc    9900
ataagaccga gtgacatcgc gacggtacga acccttggtc gtcctcctca tttgattatg    9960
aggattatgg actgtgtcct gcttttattt caacgtaaag tatctgcagt taagattgat   10020
ttggaaaaat cctgtaccat gccctcatgg caggaatccc tgaaattgat gaccgcgggc   10080
aatttccttc aaaatctaca acaattcccc aaggacacca ttaacgaaga ggtcatagaa   10140
tttttatctc catattttga gatgccagat tacaatattg aaacagcgaa gcgcgtctgt   10200
ggtaacgtag caggtctctg ttcgtggacc aaagctatgg cctccttctt tagtatcaat   10260
aaagaggtac ttccactgaa agccaacctg gtggtacagg agaaccggca tctgcttgct   10320
atgcaggatc ttcagaaggc ccaggccgaa ttagacgaca acaggctga gcttgacgtt   10380 gtgcaagcag aatacgaaca agctatgact gaaaagcaga ctttattaga ggacgctgaa   10440
cgctgcagac ataagatgca gactgcaagc accctcatat ccgggttggc tggagaaaaa   10500
gaacggtgga cagagcagtc gcaagaattc gctgctcaaa ccaaaaggtt ggttggagac   10560
gttctactcg cgacagcttt tctctcctat tctggtcctt tcaaccagga attccgggac   10620
cttttgctga atgactggag aaaagaaatg aaggctcgca aaataccatt tggtaagaat   10680
ttgaacttgt ctgaaatgct tattgacgca cccactatat cagagtggaa tcttcaggga   10740
cttccaaatg acgatctgtc catccaaaac ggaattattg taaccaaggc gagtcgctac   10800
cctctgctca ttgacccgca gacacagggc aagatctgga ttaaaaataa ggaaagcagg   10860
aacgaactcc agatcacaag tctcaaccac aagtacttcc gtaaccacct cgaagatagt   10920
ctgtccctgg gacggccgtt gctaatcgag gacgttggag aagagctgga ccccgcatta   10980
gacaacgtcc ttgaaagaaa ttttatcaag acaggatcaa ctttaaagt taaagtagga   11040 gataaagaag tggatgtgtt agatggcttc cgcctatata tcacaactaa actcccgaat   11100
cccgcctata ctccagagat cagcgctaga actagcatca tagatttcac tgtaactatg   11160
aaggggttag aagatcaatt attaggacgc gtgatcctga cggagaaaca ggaattgaa   11220 aaagagcgta cacacctcat ggaagacgtg acagctaaca aacgacggat gaaggaactg   11280
gaggacaatt tactgtatcg gttgacatca acacagggct cccttgttga ggacgagagt   11340
ctgatcgtgg tcctgtctaa cacaaagagg actgctgaag aagtaactca gaaattggag   11400
atttctgccg aaactgaagt tcagattaac tccgctagag aagagtatcg tccagtcgct   11460
actcggggct ctatcctata cttcctcata actgagatgc gcttggtcaa tgaaatgtac   11520
cagacttcac tccggcaatt cctgggcttg tttgacttgt cgctggcaag atcagtaaaa   11580
```

```
tctccaatta ccagcaagag aatcgcaaac atcattgagc acatgacgta cgaggtgtat  11640
aaatacgcgg cgagggtct  ttatgaagag cataagttcc tcttcaccct actattaacg   11700
ttgaagatag atattcagag gaaccgggtg aagcacgagg agtttctaac tctaataaaa  11760
ggaggagcta gtttagattt gaaagcctgt ccaccgaaac cttctaagtg gattttagac  11820
ataacatggc tgaatttagt ggagttgtcc aagttacgtc agttcagtga cgtattggat  11880
cagatatcca ggaacgagaa gatgtggaag atctggttcg ataaagagaa tccgaggag    11940
gagcccttgc caaatgctta tgataaatca ctagactgct tcaggaggtt gttgctcatc   12000
cgctcctggt gccccgaccg cactattgcc caagctagga aatacattgt ggactccatg  12060
ggggagaagt atgccgaggg agtcatactc gacctggaaa agacttggga agagtcagat  12120
ccgaggacgc ccctcatttg tcttctttcc atgggttctg atcccacgga ctctattata   12180
gcactcggga aaagactaaa gatcgagaca cgctatgtta gcatgggaca ggggcaagag  12240
gtccatgccc gcaaactact acagcaaact atggctaatg gaggttgggc tctgttacag   12300
aactgtcact taggcctgga ttttatggac gaattgatgg acataataat tgagacggag   12360
ctagtccacg acgcatttcg cttatggatg acgactgaag cacacaagca gtttccgatt   12420
accctgttgc agatgtccat caagttcgca aatgaccctc tcagggcct  tagggcaggt   12480
ctcaaaagga cctacagcgg cgtttcccag gatttacttg acgtcagctc cggatcccag   12540
tggaagccca tgctctacgc tgtggctttc cttcacagca cagttcaaga aaggcggaag  12600
tttggtgcgc taggctggaa catcccctac gagttcaacc aagctgattt taatgcaaca  12660
gtacagttta ttcaaaatca tctggatgac atggatgtta aaaaaggtgt gtcatggact  12720
acaataaggt acatgattgg ggagattcag tacggaggac gggtaactga tgattatgac  12780
aagcggctac tgaacacatt cgctaaagtg tggttttctg agaatatgtt cggtccagat   12840
ttcagcttct accaaggtta caatatacc  aagtgctcca cggtcgacaa ctaccttcag   12900
tacatccaga gcttgcccgc gtacgacagc ccggaagtct tcggactcca ccccaacgcc  12960
gacatcacgt accagagcaa gctggccaag gacgtgcttg acaccattct cggcatccag   13020
ccgaaggaca cgtccggcgg gggggacgag acgcgggagg ccgtcgtcgc gcgcttggca  13080
gatgacatgc tggagaagct ccccccccgat tacgtcccgt ttgaggtcaa ggaaaggctc  13140
cagaagatgg gcccgttcca gcccatgaac atcttcctcc gccaggagat cgaccggatg  13200
cagcgcgtgc ttagcctggt gcgctcaacg ctgaccgagc tgaagctggc catcgacggg  13260
acgatcatta tgtcggagaa cctccgggac gcgctggact gcatgttcga cgcgcgtatc  13320
ccggcctggt ggaagaaggc gtcgtggatc tccagcaccc tggggttctg gttcacggag  13380
ctgatcgagc gcaactcgca attcacctcc tgggtgttca acgggcggcc ccactgcttc  13440
tggatgacgg gcttctttaa cccgcagggc ttcctgacgg ctatgcggca ggaaatcacc  13500
cgggcgaaca agggttgggc gctcgacaat atggtgctct gcaacgaggt cacgaagtgg  13560
atgaaggacg acatctcggc gcctcccacc gaagggtct  acgtctatgg cctgtacctc   13620
gagggggcgg gctgggacaa gcgtaacatg aagctgatcg agtcgaagcc caaggtcctg  13680
ttcgagctga tgcccgtcat ccgcatctac gcagaaaaca cacgctgcg  cgacccgcgg   13740
ttctactcgt gccccatcta caagaagccg gtgcggacgg acctcaacta catcgccgcc  13800
gtcgacctcc gcaccgcgca gaccccccgag cactgggtgc tgcggggggt cgcactgctc  13860
tgcgacgtca agtag                                                    13875
```

<210> SEQ ID NO 25
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 25

| | | | | | |
|---|---|---|---|---|---|
| atgttcagaa | tcggaaggag | acaactatgg | aagcacagcg | tgacgcgggt | acttacccaa | 60 |
| cgtctaaagg | gggagaagga | ggcgaagcgg | gcactgctag | acgcgcgtca | taattacctc | 120 |
| tttgcaatag | ttgccagctg | cctcgacttg | aacaagacgg | aggtagagga | cgccatatta | 180 |
| gagggcaacc | agattgaacg | gatcgatcag | ctatttgccg | tgggcgggct | ccggcatcta | 240 |
| atgttttact | accaggacgt | cgaggaagct | gagaccggcc | aactgggatc | cctgggaggc | 300 |
| gtcaacctcg | tctccggcaa | gataaaaaag | cctaaggttt | tcgttacaga | gggcaacgac | 360 |
| gtagcgctga | ctggtgtatg | cgtcttcttc | atacggacag | accccctcaaa | ggcaattacg | 420 |
| ccagacaaca | tccaccagga | ggtctcgttt | aacatgctcg | acgccgccga | tggcgggctg | 480 |
| ctgaactcgg | tgcgccggct | gctctcggat | atctttatcc | ccgcgcttcg | ggcgacgagc | 540 |
| cacgggtggg | gtgagctgga | aggcctacag | gacgcggcca | atattcgtca | ggagttccta | 600 |
| tccagcctgg | aaggttttgt | taacgtgtta | tccggcgccc | aggagtcgct | taaggagaag | 660 |
| gtgaacttac | gaaagtgtga | tatattagag | ctgaaaaccc | tgaaggaacc | tacagactat | 720 |
| ctcacccctcg | caaacaaccc | cgaaacactc | ggcaaaattg | aagattgcat | gaaggtgtgg | 780 |
| attaagcaga | cggaacaagt | cctggcagag | aacaaccaac | tcttgaagga | ggccgacgac | 840 |
| gtgggcccgc | gcgctgagct | ggagcactgg | aagaagaggc | tcagcaagtt | taactatctt | 900 |
| cttgagcagc | tgaagagccc | ggacgttaag | gcggtactag | cggtcctcgc | ggctgcgaag | 960 |
| tcgaagctcc | tcaagacctg | gcgtgagatg | gacatacgca | tcacggacgc | gaccaacgaa | 1020 |
| gctaaggaca | acgttaagta | tttgtatacc | ctcgagaagt | gctgcgaccc | cctctactca | 1080 |
| tctgatccgc | tcagtatgat | ggatgccatc | cccacgttga | ttaacgccat | taaaatgatc | 1140 |
| tactcgatat | cgcactatta | caacacgtct | gaaaaaatca | ccagcctctt | cgtaaaagtg | 1200 |
| actaaccaaa | tcattagcgc | ctgcaaggct | tacatcacta | caacggcac | cgccagtata | 1260 |
| tggaaccagc | cccaggacgt | cgtggaggag | aagatcctat | cggccataaa | gctgaagcag | 1320 |
| gagtatcagc | tgtgcttcca | caaaaccaag | cagaaactca | gcagaaccc | aaatgctaag | 1380 |
| cagttcgact | tctctgagat | gtacattttc | gggaagtttg | aaacatttca | tcgccgcctg | 1440 |
| gccaaaatca | tcgacatatt | caccactctg | aagacctact | cagtcctaca | agatagcact | 1500 |
| atagaagggc | tagaggatat | ggccacaaag | taccagggca | tcgtggccac | tatcaaaaag | 1560 |
| aaggagtaca | acttcttaga | ccagcgtaaa | atggatttcg | accaggacta | tgaagaattc | 1620 |
| tgcaaacaaa | cgaatgattt | gcacaacgag | cttcggaaat | tcatggatgt | gacttttgcc | 1680 |
| aaaatacaga | ataccaacca | agctcttagg | atgttaaaga | aatttgaaag | gctcaatatt | 1740 |
| cctaatttgg | gcattgatga | caaataccag | ttgatactcg | aaaattatgg | agcagatatt | 1800 |
| gatatgatct | ctaaactgta | cacaaaacaa | aaatatgatc | ccccgctagc | tagaaatcaa | 1860 |
| cctccgattg | ccggtaagat | actctgggcc | agacagctct | tcaccgcat | ccagcagccc | 1920 |
| atgcagctgt | tcagcagca | ccctgcggtg | ctgtccaccg | ccgaagcgaa | acccattatt | 1980 |
| cgatccttata | accgcatggc | caaggttctt | ttagagtttg | aagttttgtt | ccaccgtgcc | 2040 |
| tggttacgtc | agatcgagga | gatccatgtg | ggactggagg | cctctctcct | agtcaaggcc | 2100 |

-continued

```
cccggcacag gcgaactctt tgtcaatttt gatccccaga ttctaatact cttccgggaa    2160
accgagtgca tggcccagat gggcttagag gttagtcctc tggctacttc tctgttccag    2220
aagagagacc gctataaacg gaatttcagc aatatgaaga tgatgctcgc tgaatatcag    2280
agggtcaagt ccaaaatccc cgctgcgatc gagcagctga tagtgccaca cctggccaaa    2340
gtagatgagg ccctacaacc aggactggcc gcgctgactt ggacctctct gaatatcgaa    2400
gcgtatttgg agaacacctt tgcaaagatt aaggacctgg agcttttact ggacagagtg    2460
aacgatctca ttgaattccg catagacgcg attttagagg agatgtcttc cacgccacta    2520
tgccagcttc ctcaggagga gcctttaaca tgtgaagagt tccttcagat gactaaggac    2580
ctctgcgtga atggcgctca gatactacat ttcaagtcta gcttggtcga ggaggcagtg    2640
aacgaattgg ttaacatgtt actggatgta gaagtcctta gcgaggagga atccgaaaag    2700
atcagcaacg aaaattcggt gaactataag aacgaatcta gcgccaagcg ggaggagggc    2760
aactttgata cactcacttc ttccatcaat gcgagggcta atgctctctt gttgacgacc    2820
gttaccagaa aaaaaagga gactgagatg cttggggaag aggcacgtga gttgctgtcc    2880
cacttcaacc atcagaatat ggacgccctc ttaaaggtta cccgaaacac gctagaggca    2940
attaggaagc gtattcactc aagccacacg ataaacttcc gcgactcaaa ctcagcatca    3000
aatatgaagc aaaactcctt gccgatcttc agagccagcg tcaccctggc catacctaac    3060
atcgttatgg caccggcact tgaggacgta caacaaacct tgaacaaagc agtcgagtgc    3120
atcatcagcg tccctaaagg agttcgccaa tggtccagtg aactgctatc caagaagaag    3180
atccaggagc gtaaaatggc tgcgttacag agtaacgaag attcggacag cgacgttgaa    3240
atgggtgaaa acgagctcca agacacactg gagattgcga gcgttaacct gcctataccc    3300
gtccagacca agaactacta caaaaacgtg tccgaaaaca aggagatcgt caagctcgtt    3360
tctgtgctca gcaccataat aaattcgact aagaagaag ttataacttc catggattgt    3420
ttcaaacggt ataaccacat ctggcagaaa ggtaaggaag aagctatcaa gacatttatt    3480
acccagagcc cactactaag cgagttcgag tctcagatcc tctacttcca gaatttagag    3540
caggagatca acgctgagcc cgaatatgtg tgcgtcggct cgatagccct gtacacggct    3600
gatctgaaat ttgcgctgac cgctgagacg aaggcttgga tggtggtgat tggccgacac    3660
tgcaacaaga agtaccggtc tgaaatggag aacatcttta tgctaatcga ggaatttaac    3720
aaaaagctga accgtcccat taaggatctg gacgacatca ggattgccat ggcggcccta    3780
aaggaaatta gagaggagca gatatccatt gattttcagg ttggccccat cgaagaatca    3840
tatgcccttc tgaatcgata cggtctatta atcgcccgag aggaaataga taaggtggac    3900
acacttcatt atgcatggga gaaactctta gcgcgggccg gcgaagtgca gaataagctc    3960
gtatcgctgc agccatcatt taagaaggag ctcatcagtg ctgtcgaggt ctttctgcag    4020
gactgccacc agttctatct ggattatgac ctgaacggtc cgatggcgag tggtctgaag    4080
ccccaagagg cttcagaccg gcttatcatg ttccaaaatc agttcgacaa tatttaccga    4140
aagtatatca cctatacagg gggtgaagaa ttgtttggtc tcccagccac ccagtatcca    4200
caattattgg aaataaagaa gcagttgaac cttctccaaa aatctacac tctctataat    4260 tcggtaattg aaactgttaa ttcctactac gatattctct ggagcgaggt caacattgag    4320
aaaattaata cgaactcttt ggagttccaa aacagatgcc gcaagttgcc gagagcgctg    4380
aaggactggc aggcttttct cgaccttaag aaaaataatcg atgatttcag tgaatgcgtgt    4440 cctctcttag aatacatggc gagtaaggct atgatggaga gacactggga gaggattacg    4500
```

```
actctgacgg ggcattcttt ggacgttggc aacgagtcct tcaagctgcg taatataatg    4560
gaggctccac ttctcaagta caaagaggaa atagaagata tctgtatatc tgctgtcaaa    4620
gagcgcgaca tagaacagaa actaaagcag gtaattaacg aatgggacaa taaaacgttt    4680
acatttggca gtttcaagac acgtggagaa ttattgcttc gaggcgactc cacttcggaa    4740
attatcgcta acatggagga ctctctcatg ttactcggct cgctgttatc gaaccggtat    4800
aatatgccat tcaaagcaca gatccagaag tgggtgcagt atctatctaa tagtacggat    4860
ataatagaga gctggatgac cgtccagaat ctgtggatct acctggaggc ggtgttcgtg    4920
ggaggtgata tagcgaagca gcttccaaag gaggccaaaa gattctccaa cattgacaaa    4980
tcctgggtca agattatgac tcgggcccac gaagtgccct ccgtggtgca gtgctgcgtc    5040
ggggacgaaa ccttgggcca gctgttgccc cacctgttgg atcaattgga aatctgccaa    5100
aagagcctga ctggctacct agagaaaaag cgtctgtgct tccccggtt cttcttcgtt     5160
tctgaccctg cactactcga aatcttgggt caggcctctg attccacac aattcaggct      5220
catttgttaa atgtgtttga acatcaaa agtgtgaaat tcatgaaaaa gatttatgac       5280
aggatcttgt ccatttcatc ccaagaggga gaaaccattg agcttgataa gcctgtgatg    5340
gcagagggaa acgtggaggt ctggcttaac agtctcctgg aagagtccca gtcctcactg     5400
cacctggtca tccgccaggc ggcggctaat atccaggaga caggattcca gctcacggaa    5460
ttccttagtt cgtttccggc gcaagtgggg ctcctcggca ttcagatgat ctggacgaga    5520
gattcggagg aagccctccg caacgccaag tttgacaaga gattatgca gaaaactaac      5580
caagccttcc tagagctcct caacactctg atcgatgtca caactcgtga tctatcgtct    5640
accgagcggg tcaagtatga gacactgatt accatacacg ttcaccagcg tgatatattc    5700
gatgatctat gccacatgca cataaagagt cccatggact tcgaatggct aaaacagtgc    5760
aggttctact ttaatgaaga ctcggataag atgatgatcc atatcacaga tgtagcgttt    5820
atttaccaaa acgagttcct tggctgcaca gacaggttag tcataactcc gttaactgat    5880
cgctgctaca ttcacactcgc ccaagcgctt ggaatgtcca tgggtggagc ccccgcaggg   5940
ccggcgggga caggtaagac cgaaacaact aaagatatgg gccgttgcct cggaaagtat    6000
gtagtagttt ttaactgctc agaccaaatg gatttccgag ggctggggcg tatctttaaa    6060
gggctggcgc aatccggttc ctggggctgt tttgacgagt tcaatcgtat tgatttaccg    6120
gtgctaagtg ttgccgcaca gcaaattagt ataattttga catgtaagaa agaacacaag    6180
aaaagttta tatttaccga cggcgacaac gtcactatga atcctgaatt cgggcttttc      6240
ttgactatga acccagggta tgctggacgt caagaacttc ctgaaaatct gaaaatcaac     6300
tttcgatcgg tggctatgat ggtaccggac cgccagatca tcatccgggt aaaactggcc    6360
tcgtgtggct tcatcgacaa cgtcgtactt gctcgaaagt tcttcacccct ttacaagcta    6420
tgtgaggagc agttatcgaa acaagttcat tacgactttg ggctccggaa tatcttgtcc    6480
gtcttacgca cactcggagc ggctaaacgt gccaatccca tggacactga gagtacgatt    6540
gtgatgcgag tgttaaggga tatgaatctc tcaaaactga tagacgagga cgagcctctt    6600
tttctcagcc ttatagagga tctgttccca aacatcctcc tcgacaaggc tggatatccc    6660
gagttggaag cggcgattag caggcaggtg gaggaggccg gattgattaa tcacccgccc    6720
tggaaactga aagtcatcca gctgttcgag actcagcggg tccgacacgg tatgatgact   6780
ttaggcccat ctggcgcggg gaaaaccacc tgcatccaca ccctgatgag ggctatgacc    6840
```

```
gattgtggga agcctcaccg tgagatgcgg atgaacccga aggccatcac agcgccgcaa    6900
atgtttgggc gtctggatgt ggcgacaaat gactggaccg atggaatctt ttccacactc    6960
tggaggaaga ccctgcgcgc aaaaaaagga gagcacatct ggatcattct cgatggcccc    7020
gttgacgcta tttggatcga aaacttaaac agcgtgctcg acgacaacaa gacccctgaca   7080
ttggcaaatg gtgaccggat tccaatggct cccaattgca aaatcatttt cgaacctcac    7140
aacatcgaca acgccagtcc ggctacggtg tcccgcaacg gtatggtttt catgagctca    7200
tccatactgg attggagtcc gatattagaa ggatttctca agaagcgcag tccccaggag    7260
gcggaaattc tgcggcaact gtatacgaaa agttttcctg acctgtaccg tttctgtatt    7320
caaaatctcg agtataagat ggaggtgttg gaggccttcg tcatcacaca gtccattaac    7380
atgcttcagg gtttgatccc cttgaaggag caaggagggg aagtcagcca ggcacatcta    7440
gggcggcttt tcgttttcgc ccttctctgg tccgcgggtg ctgctctcga gctagacggt    7500
cgccggcgct ggagttgtg gctgaggtct cgcccgaccg ggacactcga gctgccgccg     7560
ccagccggac cggggggacac ggcattcgac tactacgttg ctccggacgg cacctggacc   7620
cactggaaca cccgtacgca ggagtacctc tatcccagcg atacaactcc tgagtatggt    7680
agcatactcg ttccgaacgt agacaacgtc cgtaccgact ttctgatcca gaccattgct    7740
aagcagggca aggcagtcct attgatcgga gagcaaggga ccgcgaaaac cgtgattatc    7800
aagggcttca tgagtaaata tgacccagag tgtcatatga ttaagtccct caacttcagt    7860
tctgctacca caccactcat gtttcagcgt actatcgaat cctacgtgga caagcggatg    7920
ggcaccacct acgggccgcc tgccgggaag aagatgacgg tatttataga cgacgttaac    7980
atgcccatca tcaacgagtg gggagatcaa gtgacaaacg aaatcgttcg gcaacttatg    8040
gaacaaaacg ggttctataa cctcgagaag ccgggcgagt tcacctcaat agtagacatt    8100
caatttctgg cagctatgat ccatcccgga ggagggcgga acgacattcc acagcggctc    8160
aagcgccaat tcagcatctt caactgcacg ctgccaagtg aagcatcggt agacaaaatc    8220
ttcggcgtca tcggggtggg tcactactgc acccagcgcg gcttttcaga ggaagtccga    8280
gattctgtta ctaaactggt tccttttgact agaaggctgt ggcagatgac caaaattaag   8340
atgcttccta ctccagctaa attccactac gtgttcaatc tgcgagactt atcgagggta    8400
tggcaaggta tgcttaatac cacctctgag gtaattaaag aaccgaacga tctgctgaaa    8460
ctgtggaagc acgaatgtaa gagagttatt gcagataggt ttactgtttc gtcagatgtt    8520
acctggttcg ataaagccct ggtttctttg gtcgaagaag agtttgggga agagaagaag    8580
ctactcgtcg attgcgggat cgacacttac tttgtggact tcttaagaga cgcccctgag    8640
gctgccggcg aaacatcgga agaggcagac gctgagactc ctaagatcta tgagccgatc    8700
gagagcttta gccacctcaa ggaacgtctg aatatgtttt tacaattgta taatgagagc    8760
attcgtggtg ctgggatgga tatggtgttc ttcgcggatg ccatggtgca tctggtaaag    8820
atttctcggg tgattcgcac gccacaggga aacgcgctac tggtcggggt gggtgggtca    8880
ggaaagcaat cgttaactcg tttggcatcc tttatcgcgg gatatgtgag ttttcaaatc    8940
accctgacaa ggtcctataa tacatccaac ctgatggagg atcttaaagt tctctacagg    9000
acggcgggac aacagggcaa aggtataacc ttcatcttca cagataacga aattaaagac    9060
gaatcattct ggagtatat gaacaacgtc ttatcaagcg gcgaagtttc gaacctcttc     9120
gctagggacg aaatcgatga gatcaactct gatctcgctt ctgtcatgaa gaaagaattc    9180
ccccggtgtt tgccgacgaa tgagaacttg catgactatt tcatgtcccg tgtgcggcag    9240
```

```
aatttgcaca ttgtgctttg cttttcaccg gtgggggaga agttccgaaa tagagctttg   9300
aagttccctg cgttgatttc tgggtgcact atcgactggt tttcccgttg gcccaaggac   9360
gctctggtcg ccgtgtccga gcactttta accagctatg atatcgactg cagcctcgaa    9420
attaagaagg aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt tatatatggg gagaaacacg ttgaagtaag gactctggca   9600
aaccgtatga atactggctt agagaagctc aaggaggcct cagaaagtgt ggctgctctc   9660
tcaaaggagc ttgaagctaa ggagaaggaa ctccaagttg cgaacgataa agcggatatg   9720
gttctaaaag aagtgactat gaaagcacaa gcggctgaaa aggttaaggc ggaggtacag   9780
aaggtgaagg atcgcgccca ggcaatagtc gattccattt ccaaagacaa ggccatcgcg   9840
gaagaaaagc tagaagccgc caagccggcc ttagaagagg cagaggctgc cttgcaaacc   9900
ataagaccga gtgacatcgc gacggtacgc acccttggtc gtcctcctca tttgattatg   9960
aggattatgg actgtgtcct gctcttgttc cagcggaagg tgagcgcggt gaaaatcgac  10020
ctagaaaaga gctgtacgat gccgagctgg caggagtccc tcaagctcat gaccgccggg  10080
aacttcttac agaacttgca gcagttcccg aaggacacca taaacgagga ggtgatcgag  10140
tttcttagcc cctactttga gatgcccgac tacaacatcg agaccgcgaa gcgcgtctgc  10200
gggaacgtgg ccggtctctg ctcgtggacc aaggctatgg cctccttctt ttcgataaat  10260
aaggaggtcc tgccgctcaa ggccaacctc gtcgtgcagg agaaccgtca cctactcgct  10320
atgcaggacc tccagaaggc gcaggcggag ttggacgaca acaggccga gctggacgtc   10380 gtgcaagccg agtacgaaca ggctatgacg gagaagcaga cgctgctaga agacgcggag  10440
cggtgccggc ataaaatgca gacggcgagc acactgattt cgggcctagc aggggagaaa  10500
gagcggtgga cggagcagtc gcaagagttc gccgcccaaa ctaagcgact ggtgggcgac  10560
gtgctcctgg ctactgcttt tttgtcctat tcgggcccct tcaatcaaga gttccgggac  10620
ttgctactca cgactggcg taaggagatg aaggcccgca agatccccctt cgggaagaac   10680 ctgaacctca gtgaaatgct gatagacgcc cccactatct ctgagtggaa tctccagggg  10740
ctgcctaacg acgacctgag catacagaac gggatcatag tcaccaaggc gtcgcgctac  10800
cccctgctga tcgatccgca aacccagggg aagatctgga tcaagaacaa ggagtcccgg  10860
aacgagttgc aaatcacgtc cctcaatcac aagtactttc ggaaccacct agaggactcg  10920
ctgtcgttgg ggcgcccgct tctgattgag gacgttggcg aggagctgga tcctgcgctg   10980
gacaacgttc ttgagcgcaa cttcatcaag accgggtcca ccttcaaggt aaaggtggga  11040
gacaaggagg tcgacgtgct ggacggcttt cgcctatata tcaccacgaa gctgcctaac  11100
ccggcgtaca cgcccgagat cagtgcgcgt acgagcatca ttgacttcac cgtgactatg  11160
aaaggcctcg aagatcagct gctcggtcgc gtcattctca cggaaaagca ggagctggag  11220
aaggagcgaa cacacctgat ggaggacgtg acggccaaca agcggcgtat gaaagagcta  11280
gaggacaacc tgctgtaccg cttgacatca acccaggggt cgctggtcga ggacgaatcc  11340
ctgatcgtgg tgctgagtaa taccaaacgg acagcagaag aggtcacgca gaaactcgag  11400
atctcggcgg agaccgaggt gcagatcaac tccgcgcggg aagagtaccg cccggtggcc  11460
acccgcggga gcatcttgta cttcctgatc actgagatgc ggcttgtgaa tgagatgtac  11520
cagacaagcc tgcggcagtt ccttggcctg ttcgatcttt cgctggcccg gtccgtcaag  11580
```

```
tctccgatta cctccaagcg gatcgctaac ataattgaac acatgacgta cgaggtgtac    11640
aagtacgcgg cgcgaggcct ctacgaagag cacaagttcc tgttcacgct gctcctcacg    11700
ctcaagatcg acatccagcg caaccgcgtc aagcacgagg agtttctcac cctgataaag    11760
ggtggagcgt ccctggacct gaaggcctgt ccgccgaagc cgtcgaagtg gatcctggac    11820
ataacgtggc tcaaccttgt cgagctgtcc aagctccgtc agttctcgga cgtgctcgac    11880
cagatttcgc ggaacgagaa gatgtggaaa atttggttcg acaaggaaaa tccagaggag    11940
gagcccttgc ccaacgcgta tgacaagtcg ctcgactgct tccgtcgcct gctgctgatc    12000
cgcagctggt gccccgaccg gacgatcgcg caggcgagga agtacatcgt ggacagtatg    12060
ggtgagaaat atgcggaggg cgttattctg gatctggaga agacttggga ggagagcgac    12120
ccccgcaccc ccctgatctg cctgctgtct atggggtccg acccgaccga tagcatcatt    12180
gcgctgggga acggctcaa gatcgagacc cggtacgtgt ccatgggtca ggggcaggag    12240
gtgcatgccc gcaagctcct gcagcagact atggcgaacg ggggttgggc gctcttacag    12300
aactgccatc tggggctcga cttcatggat gaactcatgg atatcatcat cgagacggaa    12360
ctcgtgcacg acgcattccg cctgtggatg accaccgagg cgcacaagca gttcccgatc    12420
acgttgctgc agatgtccat caagttcgcc aacgaccctc cgcagggcct ccgggcgggc    12480
ctgaagcgca cgtatagcgg cgtgtctcag gatctccttg atgtcagctc ggggagccag    12540
tggaagccga tgctctatgc cgtggcattt ctacactcga ccgtccagga gcggcgaaag    12600
tttggagcgc tggggtggaa cataccctac gagtttaacc aggccgactt caacgccacc    12660
gtacagttca tccagaacca tttggacgat atggatgtga agaaggggt gtcctggacg    12720 accatacggt acatgatcgg cgagatccag tatgggggcc gggtcacgga cgactacgac    12780
aagcggttgc tgaacacgtt cgcgaaggtc tggttcagcg agaatatgtt cgggcccgat    12840
ttttcctttt accagggcta caatataccc aagtgctcca cggtagacaa ctatcttcag    12900
tacatccaga gccttcccgc gtacgacagc ccggaagtct tcggactcca ccccaacgcc    12960
gacatcacgt accagagcaa gctggccaag gacgtgctcg acaccattct cggcatccag    13020
ccgaaggaca cgtccggcgg gggggacgag acgcgggagg ccgtcgtcgc gcgcttggca    13080
gatgacatgc tggagaagct cccccccgat tacgtcccgt tcgaggtcaa ggaaaggctc    13140
cagaagatgg gcccgttcca gcccatgaac atcttcctcc gccaggagat cgaccggatg    13200
cagcgcgtgc ttagcctggt ccgctcaacg ctgacggagc tgaagctggc catcgacggg    13260
acgatcatta tgtcggagaa cctccgggac gcgctggact gcatgttcga cgcgcgtatc    13320
ccggcctggt ggaagaaggc gtcgtggatc tccagcaccc tggggttctg gttcacggag    13380
ctgatcgagc gcaactcgca attccactcc tgggtcttca acgggcggcc ccactgcttc    13440
tggatgacgg gcttcttcaa cccgcagggc ttcctgacgg ctatgcggca ggaaatcacc    13500
cgggcgaaca agggttgggc gctcgacaat atggtgctct gcaacgaggt cacgaagtgg    13560
atgaaggacg acatctcggc gcctcccacc gaagggtct acgtatacgg cctgtacctc    13620 gaggggcgg gctgggacaa gcgtaacatg aagctgatcg agtcgaagcc caaggtcctg    13680
ttcgagctga tgcccgtcat ccgcatctac gcagagaaca cacgctgcg cgacccgcgg    13740 ttctactcgt gccccatcta caagaagccg gtgcggacgg acctcaacta catcgccgcc    13800
gtcgacctcc gcaccgcgca gacccccgag cactgggtgc tgcgggggt cgcactgctc    13860 tgcgacgtca agtag                                                    13875
```

<210> SEQ ID NO 26
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 26

| | | | | | |
|---|---|---|---|---|---|
| atgttcagaa | tcggaaggcg | tcaactatgg | aaacacagcg | tcaccagagt actgactcaa | 60 |
| cggctcaaag | gagaaaaaga | ggcgaagcga | gcgcttctcg | acgcccgaca caattatcta | 120 |
| ttcgcgattg | tagcatcgtg | tcttgacctc | aataagacgg | aggtggaaga cgccatatta | 180 |
| gaaggaaacc | agattgagcg | gatcgaccaa | ttgtttgcgg | ttggtggact cagacattta | 240 |
| atgttttact | atcaagacgt | tgaagaagcg | gaaactgggc | aactcgggtc acttggtgga | 300 |
| gttaacctcg | tcagcggtaa | aattaaaaag | ccaaaagtat | ttgtcacaga gggaaacgac | 360 |
| gttgcactca | caggtgtatg | tgtattcttt | attcggactg | atccctcaaa agccataaca | 420 |
| ccagataata | tacaccagga | agtcagcttt | aacatgctcg | acgccgccga cggcgggctg | 480 |
| ctgaactcgg | tgcgccggct | gctctcggat | atctttatcc | ccgcgcttag agcgacgagc | 540 |
| cacgggtggg | gtgagctgga | aggcctacag | gacgcggcca | atatcaggca ggaattcctg | 600 |
| tcatccctgg | aaggttttgt | gaacgtgctc | agcggcgcac | aggagtcatt gaaagaaaag | 660 |
| gtgaacttgc | ggaagtgtga | cattctggaa | ttaaagactt | tgaaggagcc aaccgactat | 720 |
| ctcaccttgg | cgaacaatcc | ggagactcta | gggaaaatag | aggactgcat gaaggtgtgg | 780 |
| ataaaacaga | ccgagcaagt | tttagcagaa | ataaccagc | tgctgaagga ggcggacgac | 840 |
| gtaggccctc | gggcggaact | tgaacattgg | aagaagcggc | tgtctaagtt taattacctt | 900 |
| ttagaacagt | taaaatctcc | agatgtcaaa | gcagtgcttg | cagtcctcgc agctgcaaag | 960 |
| tccaaactgc | tgaagacgtg | gcgtgagatg | gacatacgga | taactgacgc gaccaatgaa | 1020 |
| gccaaggata | acgttaagta | cctatacacc | ctagagaagt | gttgtgatcc tctatattcc | 1080 |
| tctgatccgc | tgtctatgat | ggatgcaata | cctacgttga | tcaacgctat taagatgatt | 1140 |
| tacagtatct | ctcactatta | taatacaagc | gaaaaaataa | cttccttatt cgtaaaagtc | 1200 |
| acgaaccaaa | ttatatcagc | ctgtaaagca | tatataacca | ataacggcac ggcatctata | 1260 |
| tggaatcagc | cccaagacgt | ggttgaggaa | aaaattctta | gtgctataaa actaaagcaa | 1320 |
| gagtatcaat | tgtgcttcca | taagactaag | cagaagctaa | agcagaaccc aaacgctaag | 1380 |
| cagttcgact | ctctgagat | gtatattttt | gggaagtttg | aaaccttcca ccgacgtcta | 1440 |
| gccaaaatta | tcgacatctt | tacgacgtta | aaaacttaca | gcgtgctgca agattctacg | 1500 |
| atagaagggc | tagaagatat | ggccacaaag | taccagggca | tcgtggccac tatcaaaaag | 1560 |
| aaggagtaca | acttcttaga | ccagcgtaaa | atggatttcg | accaggacta tgaagaattc | 1620 |
| tgcaaacaaa | cgaatgattt | gcacaacgag | cttcggaaat | tcatggatgt gactttttgcc | 1680 |
| aaaatacaga | acaccaacca | agctcttagg | atgttaaaaa | aatttgaaag gctcaatatt | 1740 |
| cctaatttgg | gcattgatga | caaataccag | ttgatactcg | aaaattatgg agcagatatt | 1800 |
| gatatgatct | ctaaactgta | caccaaacaa | aaatatgatc | accgctagc tagaaatcaa | 1860 |
| cctccgattg | ctggtaagat | actctgggcc | agacaactct | tcaccgcat ccagcagccc | 1920 |
| atgcagctgt | tcagcagca | ccctgcggtg | ctttccaccg | ccgaggcgaa accattatt | 1980 |
| cgatcttata | accgcatggc | caaggttctg | ttagagtttg | aagttttgtt ccacagagcc | 2040 |
| tggttacgtc | agatagagga | gatccatgtg | ggactggagg | cctctctcct agtcaaggcc | 2100 |

```
cccggcacag gcgaactctt tgtcaatttt gatccccaga ttctaatact cttccgggaa   2160
accgagtgca tggcccagat gggcttagag gtttcgcctc tggctacttc tctgttccag   2220
aaaagagacc gctataaacg gaatttcagc aatatgaaga tgatgctcgc tgaatatcag   2280
agggtcaagt ccaagatccc cgctgcgatc gagcagctga tagtgccaca cctggcaaaa   2340
gtagatgagg ccctacaacc aggactggct gcgctgacgt ggacctctct gaatatcgaa   2400
gcgtatcttg agaacacctt tgccaagatt aaagacctgg agcttttact ggacagagtg   2460
aacgatctca ttgaattccg catagacgcg attttagagg agatgtctag cacgccacta   2520
tgccagcttc ctcaggagga gcctttaact tgtgaagagt tccttcagat gactaaggat   2580
ctctgcgtga atggcgctca gatactacat ttcaagtcta gcttggtcga ggaggcagta   2640
aacgaattgg ttaacatgtt actggatgta gaagtcctta gcgaggagga aagcgaaaag   2700
atcagcaacg aaaattcggt gaactataag aacgaatcta gcgccaagcg ggaggagggc   2760
aactttgata cactcacttc ttccatcaat gcgagggcta atgctctctt gttgacgacg   2820
gttaccagga aaaaaagga gactgagatg cttggtgaag aggcaaggga gctactgtcc   2880
cacttcaacc atcagaatat ggacgccctc ttaaaggtta cccgaaacac gttagaggca   2940
attaggaagc gtattcactc aagccacacg ataaacttcc gagactcaaa ctcagcatca   3000
aatatgaagc aaaactccct gccgatcttc agagccagcg tcaccctggc catacctaac   3060
atcgttatgg caccggcact tgaggacgta caacaaacct tgaacaaagc agtagagtgc   3120
atcatcagcg tccctaaagg agttcgccaa tggtccagtg aactgctatc caagaagaag   3180
atccaggagc gtaaaatggc tgcgttacag agtaacgaag attcggactc tgacgttgaa   3240
atgggtgaaa acgagctcca agacacactg gagattgcga gcgttaaccct gcctatacca   3300 gtccagacca agaactacta caaaaacgtg tccgaaaaca aggagatcgt caagctcgtt   3360
tctgtgctca gcaccatcat aaattcgact aagaagaag ttataacttc catggattgt   3420
ttcaaacggt ataaccacat ctggcagaaa ggcaaggagg aagctatcaa gacatttatt   3480
acccagagcc cactactaag cgagttcgag tctcagatcc tctacttcca gaatcttgag   3540
caggagatca acgctgagcc cgaatatgtg tgcgtcggct cgatagccct gtacacggct   3600
gatctgaaat ttgcgctgac cgctgagacg aaggcttgga tggtggtgat tggccgacac   3660
tgcaacaaga agtaccgatc tgaaatggag aacatcttta tgctaatcga ggaatttaac   3720
aaaaagctga accgtcccat taaagatctg gacgacatca ggattgccat ggcggcccta   3780
aaggaaatta gagaggagca gatatccatt gattttcagg ttggccccat cgaagaatca   3840
tatgcccttc tgaatcgata cggtctatta atcgccaggg aggaaataga taaggtggac   3900
acactacatt atgcatggga gaaactctta gcgcgggccg gcgaagtgca gaataagctc   3960
gtatcgttac aaccatcatt taagaaggag ctcatcagtg ctgtcgaggt ctttctgcag   4020
gactgccatc agttctatct ggattatgac ctgaacggtc cgatggcgag tggtctgaag   4080
ccccaagagg cttcagaccg gcttatcatg ttccaaaatc agtttgacaa tatttacagg   4140
aagtatatca cctatacagg gggtgaagaa ttgtttggtc tcccagccac ccagtatcca   4200
caattattgg aaataaagaa gcagctgaac cttcttcaaa aatctacac tctctataat   4260 tcggtaattg aaactgttaa ttcctactac gatattctct ggagcgaggt caacattgag   4320
aaaattaata cgaactcttt ggagtttcaa aaccgatgcc gcaagttgcc gagagcgctg   4380
aaggactggc aggcttttct cgaccttaag aaaataatcg atgatttcag tgaatgctgt   4440
cctctcttag aatacatggc gagtaaggct atgatggaga gacactggga gaggattacg   4500
```

```
actctgaccg gccattcttt ggacgttggc aacgagtcct tcaagctgcg taatataatg    4560
gaggctccac ttctcaagta caaagaggaa atagaagaca tctgtatatc tgctgtcaaa    4620
gagcgcgaca tagaacagaa actaaagcag gtaattaacg aatgggacaa taaaacgttt    4680
acatttggca gtttcaagac acgtggagaa ttattgcttc gtggcgactc cacctcggaa    4740
attatcgcta acatggagga ctctctcatg ttactcggct cgctgttatc gaaccggtat    4800
aatatgccat tcaaagcaca gatccaaaag tgggtgcagt atctatctaa tagtacggat    4860
attatagaga gctggatgac cgtccagaat ctctggatct acctggaggc ggtgtttgtg    4920
ggaggtgata ttgcgaagca gcttccaaag gaggccaaaa gattctccaa cattgacaag    4980
tcctgggtca agattatgac tcgggcccac gaagtgccgt ccgtggtgca atgctgcgtt    5040
ggggacgaaa ccttgggcca gctgttgccc cacctgttgg atcaattgga aatctgccaa    5100
aagagcctga ctggctacct agaaaaaaag cgtctgtgct ttccccggtt cttttttcgtt    5160 tctgaccctg cactcctcga aatcttgggt caggcctcag attctcacac aattcaggct    5220
catttgttaa atgtgtttga acacatcaaa agtgtgaagt tcatgaaaaa gatttatgac    5280
aggatcttgt ccatttcatc ccaagagggg gaaaccattg agcttgataa gcctgtgatg    5340
gcagagggaa acgtggaggt ctggcttaac agtctcctgg aagagtccca gtcctcactg    5400
cacctggtca tccgccaggc ggcggctaac atccaggaga caggattcca gctcacggaa    5460 ttccttttcct cgtttccggc gcaagtgggg ctcctcggca ttcagatgat ctggacgaga    5520
gattcggagg aagccctccg caacgccaag tttgacaaga agattatgca gaaaactaac    5580
caagccttcc tagagctcct caacaccctg atcgatgtca caacacgtga tctatcgtct    5640
accgagcggg tcaagtatga gacactgatt accattcacg tgcaccagcg tgatatattc    5700
gatgatctct gccacatgca cataaagagt cccatggact tcgaatggct aaaacagtgc    5760
aggttctact ttaatgaaga ctcggataag atgatgatcc atatcacaga tgtagcgttt    5820
atttaccaaa acgagttcct tggctgcaca gacaggttag tcataactcc gttaactgat    5880
cgctgctaca ttcacactcgc ccaagcgctt ggaatgtcca tgggtggagc ccccgcaggg    5940
ccggcgggga ctggtaagac cgaaacaacg aaagatatgg gccgttgcct cgggaagtat    6000
gtagtagttt ttaactgttc agaccaaatg gatttccgag ggctgggccg tatctttaaa    6060
gggctggcgc aatccggttc ctgggctgt tttgacgagt tcaatcgtat tgatttaccg    6120
gtgctatcgg ttgccgcaca gcaaattagt ataattttga cttgtaagaa agaacacaag    6180
aaaagtttta tatttactga tggcgacaac gtcactatga atcctgaatt cgggcttttc    6240
ttgactatga acccagggta tgctggccgt caagaacttc ctgaaaatct gaagatcaac    6300
ttccgatcgg tggctatgat ggtaccggat cgccagatca ttatacgggt aaaactggcc    6360
tcgtgtggct tcatcgacaa cgtcgtactt gctagaaagt tcttcacccct ttataagcta    6420 tgtgaggagc agtatcgaa gcaagttcat tacgactttg ggctccggaa tatcttgtcc    6480
gtcttacgca cactcggagc ggctaaacgt gcaaatccca tggacactga gagtacgatt    6540
gtgatgcgag tgttaaggga tatgaatctc tcaaaattaa tagacgagga cgagcctctt    6600
tttctcagcc ttatagagga tctgtttcca aacatcctcc tggacaaggc gggatatccc    6660
gagttggaag cggccattag caggcaggtg gaggaggccg gattgattaa tcacccgccc    6720
tggaaactga agtcatcca gctgttcgag actcagcggg tccgacacgg tatgatgact    6780
ttaggcccat ctggtgcggg caaaactacc tgcatccaca ccctgatgag ggctatgacc    6840
```

```
gattgtggga agcctcaccg tgagatgcgg atgaacccca aggcgatcac tgcgcccaa    6900 atgtttgggc gtctggatgt ggcgacaaat gactggaccg atggaatctt ttccacactc    6960
tggaggaaga ccctgcgcgc aaaaaaagga gagcacatct ggatcattct cgatggcccc    7020
gttgacgcta tttggatcga aaacttaaac agcgtgctcg acgacaacaa gaccctgaca    7080
ttggcaaatg gtgaccgaat tcctatggct cccaactgca aaatcatttt tgaacctcac    7140
aacatcgaca acgccagtcc ggctacggtg tcccgcaacg gtatggtttt catgagcagt    7200
tccatactgg attggagtcc gatattggaa ggatttctca agaaacgcag tccccaggag    7260
gcggaaattc tgagacaact gtatacgaaa agttttcctg acctgtaccg cttctgtatt    7320
caaaatctcg agtataagat ggaggtgttg gaggccttcg tcatcacaca gtccattaac    7380
atgcttcagg ggttgatccc cttgaaggaa caaggagggg aagtcagcca ggcacatcta    7440
gggcggcttt tcgttttcgc cctgctatgg tccgcgggtg ctgctctcga gctagacggt    7500
cgccggcgct tggagttgtg gctgaggtct cgcccgaccg ggacactcga gctgccgccg    7560
ccagccggac ccgggacac tgcattcgac tactacgtag ctccggacgg cacctggacc    7620
cactggaaca cccgtacgca ggagtacctc tatcccagcg atacaactcc tgagtatgga    7680
agcatactcg ttccgaacgt agacaacgtc agaaccgact ttctgatcca gaccattgct    7740
aagcagggca aggcagtcct attgatcgga gagcaaggga ccgcgaaaac cgtgattatc    7800
aagggcttca tgtctaaata tgacccagag tgtcatatga ttaagtcgct caacttcagt    7860
tctgctacca caccactcat gtttcagcgt actatcgaat cctacgtgga caagcggatg    7920
ggcaccacct acgggccacc tgccgggaag aagatgacgg tatttataga cgacgttaac    7980
atgcccatca tcaacgagtg gggagatcaa gtgaccaacg agatcgttcg gcaacttatg    8040
gaacaaaacg ggttctataa cctcgagaaa ccgggcgagt tcacctcaat agtggacatt    8100
caatttctgg cagctatgat ccaccccgga ggaggacgga acgacattcc ccagcggctc    8160
aagcgccaat tcagcatctt caactgcacg ctgccaagtg aagcatcggt agacaaaatc    8220
ttcggcgtca tcggggtggg tcattactgc acccagcgcg gcttttcaga ggaagtccga    8280
gattctgtta ctaaactggt tcctttgact agaaggttat ggcagatgac caaaattaaa    8340
atgcttccta ctccagctaa attccactac gtgttcaatc tgcgagactt atccagggta    8400
tggcaaggta tgcttaatac cacctctgag gtaattaaag aaccgaacga tctgctgaaa    8460
ctgtggaagc acgaatgtaa gagagttatt gcagacaggt ttactgtatc gtcagatgtt    8520
acctggttcg ataaagcact ggtgtctttg gtggaagaag agtttgggga agagaagaag    8580
ctactcgtcg attgcgggat cgacacttac ttcgtggact tcttaagaga cgcccctgag    8640
gctgccggcg aaacatcgga agaggcagac gctgagactc ctaagatcta tgagccgatc    8700
gagagcttta gccacctcaa ggaacgtctg aatatgtttt tacaattgta taacgagagc    8760
attcgtggtg ctgggatgga tatggtgttc ttcgcggatg caatggtgca tctggttaag    8820
atttctcggg tgattcgcac gccacaggga aacgcgctac tggtcggggt gggtgggtca    8880
ggaaagcaat cgttgactcg tctcgcatcc tttatcgcgg gatatgtgag ttttcaaatc    8940
accctgacaa ggtcctataa tacatccaac ctgatggagg atcttaaagt tctctacagg    9000
acggcgggac aacaaggcaa aggaataacc ttcatcttca ctgataacga aattaaagac    9060
gaatcattct ggagtatat gaacaacgtc ttatcaagcg gcgaagtttc gaacctcttc    9120
gcgcgggacg aaatcgatga gatcaactct gatctcgctt ctgtcatgaa gaaagaattc    9180
ccacgctgtt tgccgacgaa tgagaacttg catgactatt tcatgtcccg tgtgcggcag    9240
```

```
aatttgcaca ttgtgctttg cttttcaccg gtgggggaga agttccgaaa tagagctttg   9300
aagttccctg ctttgatttc tgggtgtact attgactggt tttcccgttg gcccaaggac   9360
gctctggtcg ccgtgtccga gcactttta accagctatg atatcgactg cagcctcgaa    9420
attaagaagg aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt tatatatggg gagaaacacg ttgaagtaag gactctggca   9600
aaccgtatga atactggctt agagaagctc aaggaggcct cagaaagtgt ggctgctctc   9660
tcaaaggagc ttgaagctaa ggagaaggaa ctccaagttg cgaacgataa agcggatatg   9720
gttctaaaag aagttactat gaaagcacaa gcggctgaaa aggttaaggc ggaggtacag   9780
aaggtgaagg atcgcgccca ggcaatagtc gatagcattt ccaaggacaa ggcgatcgcg   9840
gaagagaagc tcgaggccgc gaagcctgcg ctggaggagg ccgaggccgc gctgcagacc   9900
atccgcccct ccgacatcgc gacggttcgc acgttgggc ggccacctca ccttatcatg     9960
cgcattatgg actgcgttct gctcttgttc cagcggaagg tgagcgcggt gaaaatcgac  10020
ctggaaaaga gctgtaccat gccgagctgg caggagtccc tcaagctcat gacggccggg  10080
aacttcttac aaaacctgca gcagttcccg aaggacacca taaacgagga ggtgatcgag  10140
tttcttagcc cctactttga gatgcccgac tacaacatcg agaccgcgaa gcgcgtatgc  10200
gggaacgtgg ccggtctctg ctcgtggacc aaggctatgg cgtccttctt ttcgataaat  10260
aaggaggtct tgccgctcaa ggccaacctc gtcgtgcagg agaaccgtca cctactcgct  10320
atgcaggacc tccagaaagc gcaggcggag ttggacgaca aacaggccga gctggacgtc  10380
gtgcaagccg agtacgaaca ggctatgacg gagaagcaga cgctgctaga agacgcggag  10440
cggtgccggc ataaaatgca gacggcgagc acactgatta gtggcctagc aggggagaaa  10500
gagcggtgga cggagcagtc gcaagagttc gccgcccaaa ctaagcgact ggtgggcgac  10560
gtgctcctgg ctactgcttt tttgtcctat tcgggcccct tcaatcaaga gttccgggac  10620
ttgctactca cgactggcg taaggagatg aaggcccgca agatcccctt cgggaagaac    10680
ctgaacctca gtgaaatgct gatcgacgcc cccactatct ctgagtggaa tctccagggg  10740
ctgcccaacg acgacctgtc gatacaaaac ggaataatag tcaccaaggc gtcgcgctac  10800
cccctgctga tcgatccgca aacccagggg aagatctgga tcaagaacaa ggagtcccgg  10860
aacgagttgc aaatcacgtc cctcaatcac aagtactttc ggaaccacct cgaggactcg  10920
ctgtcgttgg ggcgcccgct tctgatcgag gacgttggcg aggagctgga tcctgcgctg  10980
gacaacgttc ttgagcgcaa cttcatcaag accgggtcca ccttcaaggt aaaggtggga  11040
gataaggagg tcgacgtgct ggacggcttt cgcctatata tcaccacgaa gctgcctaac  11100
ccggcgtaca cgcccgagat cagtgcgcgt acgagcatca ttgacttcac cgtgactatg  11160
aaaggcctcg aagatcagct gctcggtcgc gtgattctca cggaaaagca ggagctggag  11220
aaggagcgaa cacacctgat ggaggacgtg acggccaaca agcggcgtat gaaagagcta  11280
gaggacaacc tgctgtaccg ccttacgtca acccagggt cgctggtcga ggacgaatcc    11340
ctgatcgtgg tgctgagtaa taccaagcgg acagctgagg aggtcacgca gaaactcgag  11400
atctcggccg agaccgaggt gcagatcaac agcgcgcggg aggagtaccg cccggtggcc  11460
acccgcggga gcatcttgta cttcctgatc actgagatgc gccttgtgaa tgagatgtac  11520
cagacaagcc tgcggcagtt ccttggcctg ttcgatcttt cgctggcccg gtccgtcaag  11580
```

```
tctccgatta cctccaagcg gatcgctaac ataattgaac acatgacgta cgaggtgtac    11640
aagtacgcgg cgcggggcct ctacgaagag cacaagttcc tgttcacgct cctcctcacg    11700
ctcaagatcg acatccagcg caaccgcgtc aagcacgagg agtttctcac cctgataaag    11760
gggggagcgt ccttagacct gaaggcctgt ccgccgaagc cgtcgaagtg gatcctggac    11820
ataacgtggc tcaacctcgt cgagctgtcc aagctccgtc agttctcgga cgtgctcgac    11880
cagatttcgc ggaacgagaa gatgtggaaa atatggttcg acaaggagaa tccagaggag    11940
gagcccttgc ccaatgcgta tgacaagtcg ctcgactgct tccgtcgcct gctgctgatc    12000
cgcagctggt gccccgaccg gacgatcgcg caggcgagga agtacatcgt tgacagtatg    12060
ggtgagaaat acgcggaggg cgttattctg gatctggaga agacttggga ggagagcgac    12120
ccccgcaccc ccctgatttg ccttctgtct atggggtccg acccgaccga tagcatcatt    12180
gcgctgggga acggctcaa gatcgagacc cggtacgtgt ctatgggaca ggggcaggag     12240
gtgcatgccc gcaagctcct gcagcagact atggcgaacg ggggttgggc gctcttacag    12300
aactgccatc tggggctcga cttcatggat gaactgatgg acatcatcat cgagacggaa    12360
ctcgtgcacg acgcattccg cctgtggatg accaccgagg cgcacaagca gttcccgatc    12420
acgttgctgc agatgtccat caagttcgcc aacgaccctc cgcagggcct ccgggcgggc    12480
ctgaagcgca cgtattcggg cgtgtctcaa gatctcctag atgtcagctc ggggtcccag    12540
tggaagccga tgctctatgc cgtggcattt ctacactcga ccgtccagga gcggcgaaag    12600
tttggagcgc tggggtggaa catacccctac gagtttaacc aggccgactt caacgccacc    12660
gtacagttca tccagaacca tttgacgat atggatgtta agaagggggt gtcctggacg     12720
accatacggt atatgattgg cgagatccag tatgggggc gggtcacgga cgactacgac    12780
aagcggttac tgaacacgtt cgcgaaggtc tggttctccg agaatatgtt cgggcccgat    12840
ttttcctttt accagggcta taatataccc aagtgctcca cggtcgacaa ctaccttcag    12900
tacatccaga gcctacccgc gtacgacagc ccggaagtct tcggactcca ccccaacgcc    12960
gacatcacgt accagagcaa gctggccaag gacgtgctcg acaccatact cggcatccag    13020
ccgaaggaca cgtccggcgg gggggacgag acgcgggagg ccgtcgtcgc gcgcttggca    13080
gatgacatgc tggagaagct cccccccgat tacgtcccgt tcgaggtcaa ggaaaggctc    13140
cagaagatgg gcccgttcca gcccatgaac atcttcctcc gccaggagat cgaccggatg    13200
cagcgcgtgc ttagcctggt gcgctcaacg ctgacggagc tgaagctggc catcgacggg    13260
acgatcatta tgtcggagaa cctccgggac gcgctggact gcatgttcga cgcgcgtatc    13320
ccggcctggt ggaagaaggc gtcgtggatc tccagcaccc tggggttctg gttcacggag    13380
ctgatcgagc gtaattctca atttacatct tgggtgttta atggtcgtcc ccattgtttt    13440
tggatgactg gtttttttaa tccacaagga tttttaactg ctatgagaca ggaaataact    13500
cgtgcgaata agggttgggc attagataat atggttttgt gtaatgaagt aactaagtgg    13560
atgaaagacg atataagtgc accacctact gaaggtgttt atgtatatgg tttatattta    13620
gaaggagctg gatgggataa acgtaatatg aaattaatag aatcgaaacc aaaagttttta   13680 tttgaactga tgccagttat tagaatttat gcagaaaata atacattaag agatcctaga    13740
ttttatagtt gtccgatttta taaaaaacct gtaagaacag atttaaatta tatagcagcc   13800
gtcgatctta gaactgctca aacaccagaa cattgggtat taagaggagt agctttactt    13860
tgtgatgtta aatag                                                     13875
```

```
<210> SEQ ID NO 27
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 27
```

| | | | | | |
|---|---|---|---|---|---|
| atgttcagaa | taggcagacg | acagttatgg | aaacacagtg | tgactagggt | tctaacacag | 60 |
| agactaaaag | gagagaaaga | ggcaaaaaga | gcgctactcg | atgcaagaca | taactatcta | 120 |
| ttcgctattg | tggcgtcgtg | tttagattta | aataaaactg | aagtagagga | cgccattctc | 180 |
| gagggaaatc | aaatagaacg | catcgaccaa | ttattcgcgg | ttggaggact | tagacatttg | 240 |
| atgttttact | atcaagacgt | tgaagaagcg | gaaactgggc | aactcgggtc | actaggtgga | 300 |
| gttaatttag | tctcaggtaa | gatcaaaaag | ccaaaagtat | ttgtaacaga | aggaaacgac | 360 |
| gttgcactaa | caggtgtttg | cgtgtttttt | attagaactg | atccgtctaa | agccataaca | 420 |
| cccgacaaca | tccatcagga | agtttcgttt | aacatgctgg | atgcggccga | cggaggacta | 480 |
| ctgaattcag | tgcgtcgcct | gctatctgac | attttcattc | ctgctttgcg | tgcgaccagt | 540 |
| cacgggtggg | gggagttaga | aggactccag | gacgccgcga | atatccggca | ggaattcctg | 600 |
| tccagcctgg | aaggttttgt | taacgtcctg | tccggcgccc | aggagagcct | taaggagaag | 660 |
| gtgaacttac | gaaagtgcga | catactcgag | ctcaaaaccc | tgaaggaacc | tacagactac | 720 |
| ctcacccctcg | caaacaaccc | cgaaaccctc | ggcaaaattg | aagattgcat | gaaggtttgg | 780 |
| attaagcaga | cggaacaagt | cctggccgag | aacaaccaac | tcctaaagga | ggccgacgac | 840 |
| gtgggcccgc | gcgctgagct | ggagcactgg | aagaagaggc | tcagcaagtt | taactatctt | 900 |
| cttgagcagc | tgaagagccc | ggacgttaag | gcggtactag | ccgtcctcgc | ggctgcgaag | 960 |
| tcgaaactgc | tcaagacctg | gcgtgagatg | gatatacgca | ttacggacgc | aaccaacgaa | 1020 |
| gctaaggaca | acgttaagta | cttgtatacc | ctcgagaagt | gctgcgaccc | actctactca | 1080 |
| tctgacccgc | tcagtatgat | ggatgccatc | cccacgctaa | ttaacgcaat | taagatgatc | 1140 |
| tactcgatat | cgcactatta | caacacgtct | gaaaaaataa | ccagcctctt | cgtaaaagtg | 1200 |
| accaaccaga | tcatttcagc | ctgtaaggct | tacatcacaa | acaacggcac | cgcctccata | 1260 |
| tggaaccagc | cccaggacgt | cgtggaagag | aagatcctat | cggccataaa | gctgaagcag | 1320 |
| gagtaccagc | tgtgcttcca | caaaaccaag | cagaaactca | agcagaaccc | caatgctaag | 1380 |
| cagttcgact | tctctgagat | gtatattttc | gggaagtttg | aaaccttcca | ccgccgcctg | 1440 |
| gcgaagatca | tcgacatatt | cacaactctg | aagacctaca | gtgttctaca | agacagcact | 1500 |
| atagagggtc | tcgaggatat | ggccactaag | taccagggca | ttgtcgcaac | tatcaagaag | 1560 |
| aaagaatata | atttcctcga | tcagcgtaag | atggacttcg | accaggacta | cgaagaattc | 1620 |
| tgcaagcaga | cgaatgattt | gcataacgaa | ctccggaagt | tcatggacgt | aacgtttgcc | 1680 |
| aagattcaaa | acacaaatca | ggcgttgcgg | atgctaaaga | agttcgagcg | tctgaacatc | 1740 |
| cctaatctag | ggattgacga | caagtaccaa | cttatactgg | aaaactacgg | ggctgacatc | 1800 |
| gatatgatct | ccaagctata | taccaagcaa | aagtatgacc | cgccgttagc | tcggaatcag | 1860 |
| cccccgatcg | ccgggaagat | cctgtgggca | cggcagcttt | tcaccgcat | tcagcagcct | 1920 |
| atgcagctgt | tccagcagca | cccggcggtt | ctctccaccg | ccgaggctaa | gccaattata | 1980 |
| cgtagctaca | accgcatggc | gaaagtcctg | ctcgagtttg | aggtcttgtt | ccaccgagcg | 2040 |
| tggcttcggc | agatcgaaga | gatccacgtc | gggctcgagg | cctcgctcct | ggttaaggcg | 2100 |

```
ccggggaccg gtgagctgtt cgtaaacttc gacccgcaaa tactaatcct gttccgtgaa    2160
accgagtgca tggcccagat gggcctcgag gtctcacctt tggccacgag cctgttccag    2220
aagcgcgacc gctacaagcg gaacttctct aacatgaaga tgatgcttgc cgagtaccag    2280
agggttaagt cgaagatccc tgctgccatc gagcagctca tcgtgccaca tctggccaag    2340
gttgacgagg cactccaacc gggcttggcg gccctgacgt ggacctccct aaacattgag    2400
gcctacttgg aaaatacttt cgcgaagatt aaggatctcg aattactact ggatcgtgtg    2460
aatgacctca tagaattccg gatagacgcg atcctagagg agatgtcgag cacccccctc    2520
tgtcagctcc cgcaggagga gccgctcaca tgcgaggaat ttctccagat gactaaggac    2580
ctctgcgtta acggggccca gatactccat ttcaagtcgt ccctcgttga ggaggcggtg    2640
aatgaactgg ttaatatgct cttggatgtg gaagtgctct cggaggaaga atccgagaag    2700
attagcaacg agaatagcgt gaactacaag aacgagagct cagcaaaacg ggaggagggg    2760
aattttgata cgctgacttc ctccatcaac gcgcgggcca acgctctctt gctgacaaca    2820
gtaacgcgca aaagaagga gactgagatg ctaggagagg aggcgcgcga gctgctgtcc    2880
catttcaacc accaaaatat ggatgcgctt ctcaaagtca cccggaatac cctcgaggcg    2940
atacgcaagc gcatccattc gagccatacg ataaacttca gggacagcaa ctccgcgtca    3000
aatatgaagc agaactcgtt gccgatattc cgggcctcgg tgacgctggc gatcccgaac    3060
attgtgatgg caccggccct cgaggacgta cagcagaccc ttaacaaggc ggtggagtgc    3120
atcatctccg ttcccaaggg cgtccgccag tggtcctcgg agctgctcag caagaaaaag    3180
attcaggagc gtaaaatggc ggcccttcaa tcgaacgaag actccgactc tgacgttgag    3240
atgggagaga acgagctaca ggataccttg gaaatcgcct ccgtgaacct ccctatcccg    3300
gtgcagacga aaaactacta caagaacgtc agcgaaaaca aggaaatcgt aaagctggtg    3360
agcgtcctga gtaccatcat taacagcaca aagaaggaag tgataacctc gatggactgc    3420
tttaagcgct acaaccacat ttggcagaaa ggcaaggagg aggctataaa aacgttcatc    3480
acgcagagcc ccctgctctc ggagttcgag tcacaaatcc tctacttcca aaatctggag    3540
caggagatca acgctgagcc ggaatatgtg tgcgtcggct cgatagccct gtacacggct    3600
gatctgaaat ttgcgctgac cgctgagacg aaggcttgga tggtggtgat tggccgacac    3660
tgcaacaaga agtaccggtc tgaaatggag aacatcttta tgctaatcga ggaatttaac    3720
aaaaagctga accgtcccat taaggatctg gacgacatcc gaattgccat ggcggcccta    3780
aaggaaatta gagaggagca gatatccatt gactttcagg ttggccccat cgaagaatca    3840
tatgcccttc tgaatcgata cggtctatta atcgcccgag aggaaataga taaggtggac    3900
acacttcatt atgcatggga gaaactctta gcgcgggccg gcgaagtgca gaataagctc    3960
gtatcgctgc aaccatcatt taagaaggag ctcatcagtg ctgtcgaagt ctttctgcag    4020
gactgccacc agttctatct ggattatgac ctgaacggtc cgatggcgag tggtctgaag    4080
ccccaagagg cttcagaccg gcttattatg ttccaaaatc agtttgataa tatttaccgg    4140
aagtatatca cctatacagg gggtgaagaa ttgtttggtc tcccagccac ccagtaccca    4200
caattattgg aaataaagaa gcagctgaac cttcttcaaa aaatctacac tctctataat    4260
tcggtaattg aaactgttaa ttcctactac gatattctct ggagcgaggt caacattgag    4320
aaaattaaca cgaactctt ggagtttcaa aacagatgcc gcaagttgcc cagagcgctg    4380
aaggactggc aggcttttct cgaccttaaa aaaataatcg atgatttcag tgaatgctgt    4440
cctctcttag aatacatggc ctcaaaggct atgatggaga gacactggga gaggattacg    4500
```

```
actctcacgg ggcattcttt ggacgttggc aacgagtcct tcaagctgcg taatataatg    4560
gaggctccac ttctcaagta caaagaggaa atagaagaca tctgtatatc tgctgtcaaa    4620
gagcgcgata tagaacagaa actaaagcag gtaattaacg aatgggacaa taaaacgttt    4680
acatttggca gtttcaagac acgtggagaa ttattgcttc gtggcgactc cacctcggaa    4740
attatagcta acatggagga ctctctcatg ttactcggct cgctgttatc gaaccggtat    4800
aatatgccat tcaaagcaca gattcagaag tgggtgcagt atctatctaa tagtacggat    4860
attatagaga gctggatgac cgtccagaat ctctggatct acctggaggc ggtgtttgtg    4920
ggtggtgata ttgcgaagca gcttccaaag gaggccaaaa gattctccaa cattgacaaa    4980
tcctgggtca agattatgac tcgggcccac gaagtgccct ccgtggtgca gtgctgcgtt    5040
ggcgacgaaa ccttgggcca gctgttgccc cacctgttgg atcaattgga aatctgccaa    5100
aagagcctga ctggctacct agaaaaaaag cgtctgtgct ttccccggtt cttttcgtt     5160 tctgaccctg cactactcga aatcttgggt caggcctcag attctcacac aattcaggct    5220
catttgttaa atgtgtttga acatcaaaa agtgtgaaat tcatgaaaa gatttatgac       5280 aggatcttgt ccatttcatc ccaagagggg gaaaccattg agcttgataa gcctgtgatg    5340
gcagagggaa acgtggaggt ctggttaaac agtctcctgg aagagtccca gtcctcactg    5400
cacctggtaa tccgccaggc ggcggctaat atccaggaga caggattcca gctcacggaa    5460
ttccttagtt cgtttccggc gcaagtgggg ctcctcggca ttcagatgat ctggacgaga    5520
gattcggagg aagccctcag aaacgccaag tttgacaaga agattatgca gaaaactaac    5580
caagccttcc tagagctcct caacaccctg atcgatgtca caacacgtga tctatcgtct    5640
accgagcggg tcaagtatga gacactgatt accatacacg tgcaccagcg tgatatattc    5700
gatgatctct gccacatgca cataaagagt cccatggact tcgaatggct aaaacagtgc    5760
cgcttctact ttaatgaaga ctcggataag atgatgatcc atatcacaga tgtagcgttt    5820
atttaccaaa acgagttcct tggctgcaca gacaggttag tcataactcc gttaactgat    5880
cgctgctaca ttcacactcgc ccaagcgctt ggaatgtcca tgggtggagc ccccgcaggg    5940
ccggcgggga ctggtaagac cgaaacaact aaagatatgg gccgttgcct cgggaagtat    6000
gtggtagttt ttaactgctc agaccaaatg gatttccgag ggctgggccg tatctttaaa    6060
gggctggcgc aatcaggttc ctggggctgt tttgacgagt tcaatcgtat tgatttaccg    6120
gtgctaagtg ttgccgcaca gcaaattagt ataattctaa cttgtaagaa agaacacaag    6180
aaaagtttta tatttactga tggcgacaac gtcactatga atcctgaatt cgggcttttc    6240
ttgactatga acccagggta tgctggccgt caagaacttc ctgaaaatct gaagatcaac    6300
tttcgatcgg tggctatgat ggtaccggat cgccagatca ttatccgagt aaaactggct    6360
tcgtgtggct tcatcgacaa cgtcgtactt gctcgaaagt tcttcacccc ttacaagcta    6420
tgtgaggagc agttatcgaa acaagttcat tacgactttg ggctccggaa tatcttgtcc    6480
gtcctccgca cactcggagc ggctaaacgt gcaaatccca tggacactga gagtacgatt    6540
gtgatgcgag tgttaaggga tatgaatctc tcaaaattaa tcgacgagga cgagcctctt    6600 ttttaagcc ttatagagga tctgttccca aacatcctcc tggacaaggc gggatatccc       6660
gagttggaag cggccattag caggcaggtg gaggaggccg gattgattaa tcacccgccc    6720
tggaaactga agtcatcca gctgttcgag actcagcggg tccgacacgg tatgatgact      6780
ttaggcccat ctggcgcggg caaaaccacc tgcatccaca ccctgatgag ggctatgacc    6840
```

```
gattgtggga agcctcaccg tgagatgcgg atgaacccga aggcgatcac tgcgcccaa    6900
atgtttgggc gtctggatgt ggcgacaaat gactggaccg atggaatctt tagcacactc   6960
tggaggaaga ccctgcgcgc caaaaaagga gagcacatct ggatcattct cgatggcccc   7020
gttgacgcta tttggatcga aaacttaaac agcgtgctcg acgacaacaa gaccctgaca   7080
ttggcaaatg gtgaccggat tcctatggct cccaattgca aaatcatttt tgaacctcac   7140
aacatcgaca acgccagtcc ggctacggtg tcccgcaacg gtatggtttt catgagcagt   7200
tccatactgg attggagtcc gatattggaa ggatttctca agaaacgcag tccccaggag   7260
gcggaaattc tgcggcaact gtatacgaaa agttttcctg acctgtaccg cttctgtatt   7320
caaaatctcg agtataagat ggaggtgttg gaggccttcg tcatcacaca gtccattaac   7380
atgcttcagg gcttgatccc cttgaaggag caaggagggg aagtcagcca ggcacatcta   7440
gggcggcttt tcgttttcgc ccttctctgg tccgcgggtg ctgctctcga gctagacgga   7500
cgccggcgct tggagttgtg gctgaggtct cgcccgaccg ggacactcga gctcccgccg   7560
ccagccggac ccgggacac tgcattcgac tactacgtag ctccggacgg cacctggacc   7620
cactggaaca cccgtacgca ggagtatctc tatcccagcg atacaactcc tgagtatggt   7680
agcatactcg ttccgaacgt agacaacgtc agaaccgact ttctgatcca gaccattgct   7740
aagcagggca aggcagtcct acttatcgga gagcaaggga ccgcgaaaac cgtgattatc   7800
aagggcttca tgagtaaaata tgacccagag tgtcatatga ttaaatccct caacttctcc   7860
tctgctacca caccactcat gtttcagcgc actatcgaat cctacgtgga caagcggatg   7920
ggcaccacct acgaccgcc tgccgggaag aagatgacgg tatttataga cgacgttaac   7980
atgcccatca tcaacgagtg gggagatcaa gtgaccaacg aaatcgttcg gcaacttatg   8040
gaacaaaacg ggttctataa cctcgagaag ccgggcgagt tcacctcaat agtagacatt   8100
caatttctgg cagctatgat ccaccccgga ggaggacgga acgacattcc ccagcggctc   8160
aagcgccaat tcagcatctt caactgcacg ctgccaagtg aagcatcggt tgacaaaatc   8220
ttcggcgtca tcggggtggg tcactactgc acccagcgcg gcttttcaga ggaagtccga   8280
gattctgtta ctaaactggt tcctttgact agaaggctgt ggcagatgac caaaattaaa   8340
atgcttccta ctccagctaa attccactac gtgttcaatc tgcgagactt atccagggta   8400
tggcaaggta tgcttaatac cacctctgag gtaattaaag aaccgaacga tctgctgaaa   8460
ctgtggaagc acgaatgtaa gagagttatt gcagataggt ttactgtatc gtcagatgtt   8520
acctggttcg ataaagcact ggtgtctttg gtcgaagaag agtttgggga agagaagaag   8580
ctactcgtcg attgcgggat agacacttac tttgtggact tcttaagaga cgcccctgag   8640
gctgccggcg aaacatcgga agaggcagac gctgagactc ctaagatcta tgagccgatc   8700
gagagcttta gccacctcaa ggagcgtctg aatatgtttt tacaattgta taacgagagc   8760
attcgtggtg ctgggatgga tatggtgttc ttcgccgatg caatggtgca tctggttaag   8820
attagccggg tgattcgcac gccacaggga aacgcgctac tggtcggggt gggtgggtca   8880
ggaaagcaat cgttaactcg tttggcatcc tttatcgcgg gatatgtgag ttttcaaatc   8940
accctgacga ggtcctataa tacatccaac ctgatggagg atcttaaagt tttgtacagg   9000
acggcgggac aacagggcaa aggaataacc ttcatcttca cagataacga aattaaagac   9060
gaatcattct ggagtatat gaacaacgtc ttatcaagcg gcgaagtttc gaacctcttc   9120
gcgcgggacg aaatcgatga gatcaactct gatctcgctt ctgtcatgaa gaaagaattc   9180
ccccgctgtt tgccgacgaa tgagaacttg catgactatt tcatgtcccg tgtgcggcag   9240
```

```
aatttgcaca ttgtgctatg tttttcaccg gtgggggaga agttccgaaa tagagctttg    9300
aagttccctg ctttgatttc tgggtgtact attgactggt tttcccgttg gcccaaggac    9360
gctctggtcg ccgtgtccga gcactttta accagctatg atatcgactg cagcctcgaa    9420
attaagaagg aagtagttca gtgtatgggc tctttccaag acggtgtggc agagaagtgc    9480
gtcgactatt tccagaggtt tcgccgatct actcatgtca cacctaagag ctacttgtcc    9540
ttcatacagg ggtacaagtt tatatatggg gagaaacacg ttgaagtaag gactctggca    9600
aaccgtatga atactggctt agagaagctc aaggaggcct cagaatccgt ggctgctctc    9660
tcaaaggagc ttgaagctaa ggagaaggaa ctccaagttg ctaacgataa agcggatatg    9720
gttctaaagg aagtcactat gaaagcacaa gcggctgaaa aggttaaggc ggaggtacag    9780
aaggtgaagg atcgcgccca ggcaatagtc gattccattt ccaaagacaa ggccatcgcg    9840
gaagaaaagc tagaagcggc gaagccggcc ttagaagagg cagaggctgc cttgcaaacc    9900
ataagaccca gtgacatcgc cacgtacga acccttggtc gtcctcctca tttgattatg    9960
aggattatgg actgtgtcct gcttttattt caacgtaaag tatctgcagt taagattgat   10020
ttggaaaaat cctgtaccat gccctcatgg caggaatccc tgaaattgat gaccgcgggc   10080
aatttccttc aaaatttgca acaattcccc aaggacacca ttaacgaaga ggtcatagaa   10140 ttttatctc catattttga gatgccagac tacaatattg aaacagcgaa gcgcgtctgt   10200
ggtaacgttg caggtctctg ttcgtggacc aaagctatgg cctccttctt tagtatcaat   10260
aaagaggtac taccactgaa agccaacctg gtggtacagg agaaccggca tctgcttgct   10320
atgcaggatc ttcagaaggc ccaggccgaa ttagacgaca agcaggctga gcttgacgtt   10380
gtgcaagcag aatacgaaca agctatgaca gaaaagcaga ctttattaga agacgctgaa   10440
cgctgcagac ataagatgca gactgcaagc accctcatat ccggtttggc tggagaaaaa   10500
gagcggtgga cagagcagtc gcaagaattc gctgctcaaa ccaaaaggtt ggttggagac   10560
gttctactcg cgacagcgtt tctctcctat tctggtcctt tcaaccagga attccgggac   10620
cttttgctga atgactggag aaaagaaatg aaggctcgca aaataccatt tggaaagaat   10680
ttgaacttgt ctgaaatgct tattgacgca cccactatat cagagtggaa tcttcaggga   10740
cttccaaatg acgatctgtc catccaaaac ggaattattg taaccaaggc gagccgctac   10800
cctctgctaa ttgacccgca gacacagggc aagatctgga ttaaaaataa ggaaagcagg   10860
aacgagctcc agatcactag tctcaaccac aagtacttcc gtaaccacct cgaagatagt   10920
ctgtccctgg gacggccgtt gctaatcgag gacgtcggag aagagctgga ccccgcatta   10980
gacaacgttc ttgaaagaaa ttttatcaag acaggatcaa cttcaaagt taaagtagga   11040 gataaagaag tggatgtgtt agatggcttc cgcctatata tcacgactaa actcccgaat   11100
cccgcctata ctccagagat cagcgctaga actagcatca tagatttcac tgtaactatg   11160
aaggggttag aagatcaatt attaggacgc gtcatcctga cggagaaaca ggaacttgaa   11220
aaagagcgta cacacctcat ggaagacgtg acagctaaca acgtcggat gaaggaactg   11280 gaggacaatt tactgtatcg gttgacatca acacagggct cccttgttga ggacgagagt   11340
ctgatcgtgg tcctgtctaa cacaaagagg actgctgaag aagtcactca gaaattggag   11400
atttctgccg aaactgaagt tcagattaac tccgctagag aagagtatcg tccagtcgct   11460
actcggggct ctatcctata cttcctcata actgagatgc gcttggtcaa tgagatgtac   11520
cagacttcac tccggcaatt cctgggcttg tttgacttgt cgctggcaag atcagtaaaa   11580
```

```
tctccaatta ccagcaagag aatcgcaaac atcattgagc acatgacgta cgaggtgtat   11640
aaatacgcgg cgaggggtct ttatgaagag cataagttcc tcttcaccct actattaacg   11700
ttgaagatag atattcagag gaaccgggtg aagcacgagg agtttctaac tctaataaaa   11760
ggaggagctt ctttagatct taaagcctgt ccaccgaaac cttctaagtg gattttagac   11820
ataacatggc tgaatttagt ggagttgtcc aagttacgtc agttcagtga cgttttggat   11880
cagatatcta ggaacgagaa gatgtggaag atctggttcg ataaagagaa tccggaggag   11940
gagcccttgc caaatgctta tgataaaagc ctagactgct tcaggaggct tttgctcatc   12000
cgctcctggt gccccgaccg cactattgcc caagctagga aatacattgt ggactccatg   12060
ggggagaagt atgccgaagg agtcatactc gacttggaga agacttggga agagtcagat   12120
ccgaggacgc ccctcatttg tcttctttcc atgggttctg atcccacgga ctctattata   12180
gcactcggga aaagactaaa gatcgagaca cgctatgtta gcatgggaca ggggcaagag   12240
gtccatgccc gcaaactact acagcagact atggctaatg gaggttgggc tctgttacag   12300
aactgtcact taggccttga ttttatggac gaattgatgg acatcataat tgagacggag   12360
ctagttcacg acgcatttcg cttatggatg acgactgaag cacacaagca gtttccgata   12420
accctgttgc agatgtccat caagttcgcc aacgaccctc cccagggcct tagggcaggt   12480
ctcaaaagga cctacagcgg cgtttcccag gatttacttg acgtctccag cggatcccag   12540
tggaagccca tgttgtacgc cgtggctttc cttcacagca cagttcagga aaggcggaag   12600
tttggtgcgc taggctggaa catcccctac gagttcaacc aggctgactt taatgcaaca   12660
gtacagttta ttcaaaatca tctggatgac atggatgtca aaaaaggtgt gtcatggact   12720
acaataaggt acatgattgg ggagatacag tacggaggcc gggtaactga tgattatgat   12780
aaaagattgt taaacacttt tgctaaagtt tggtttagtg aaaatatgtt tggacctgat   12840
tttagttttt atcaaggtta taatatacct aagtgctcaa ctgtagataa ttatttacaa   12900
tatattcaaa gtttacctgc atatgatagt cctgaagttt ttggtttgca tcctaatgca   12960
gatataacat accaatcaaa attagcaaaa gacgtcttag atacaatact tggtatccag   13020
cctaaggaca ccagtggggg cggtgacgag actcgcgagg ctgtggtggc ccggctcgct   13080
gatgacatgc tagagaaact tcccccggac tacgtcccct tgaggtcaa agagcggctg   13140 cagaaaatgg ggcccttcca gcccatgaac atattcttgc gccaggagat agaccgtatg   13200
caacgagtcc tgagcctggt ccgctcgact ctaaccgagc tcaagctggc catcgatggg   13260
acgatcatta tgtctgagaa tttgagggac gcgctcgatt gcatgtttga cgccaggatc   13320
ccagcctggt ggaaaaaagc tagttggatc tcatctaccc tggggttctg gttcacagag   13380
ttgatagagc gcaactcgca attcacctcc tgggtgttca acgggcggcc ccactgcttc   13440
tggatgacgg gcttcttcaa cccgcagggc ttcctgacgg ctatgcggca ggaaatcacc   13500
cgggcgaaca agggttgggc gctcgacaat atggtgctct gcaacgaggt cacgaagtgg   13560
atgaaggacg acatctcggc gcctcccacc gaagggtct acgtatacgg cctgtacctc   13620
gagggggcgg gctgggacaa gcgtaacatg aagctgatcg agtcgaagcc caaggtgctg   13680
ttcgagctga tgcccgtcat ccggatctac gcagagaaca cacgctgcg cgacccgcgg   13740 ttctactcgt gccccatcta caagaagccg gtgcggacgg acctcaacta catcgccgcc   13800
gtcgacctcc gcaccgcgca gaccccgag cactgggtgc tgcgggggt cgcattgctc   13860 tgcgacgtca agtag                                                   13875
```

```
<210> SEQ ID NO 28
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 28
```

| | | | | | |
|---|---|---|---|---|---|
| atgttcagaa | taggcagacg | acagttatgg | aaacacagtg | tgactagggt tctaacacag | 60 |
| agactaaaag | gagagaaaga | ggcaaaaaga | gcgctactcg | atgcaagaca taactatcta | 120 |
| ttcgctattg | tggcgtcgtg | tttagattta | aataaaactg | aagtagagga cgccattctc | 180 |
| gagggaaatc | aaatagaacg | catcgaccaa | ttattcgcgg | ttggaggact tagacatttg | 240 |
| atgttttact | atcaagacgt | tgaagaagcg | gaaactgggc | aactcgggtc actaggtgga | 300 |
| gttaatttag | tctcaggtaa | gatcaaaaag | ccaaaagtat | ttgtaacaga aggaaacgac | 360 |
| gttgcactaa | caggtgtttg | cgtgtttttt | attagaactg | atccgtctaa agccataaca | 420 |
| cccgacaaca | tccatcagga | agtttcgttt | aacatgctgg | atgcggccga cggaggacta | 480 |
| ctgaattcag | tgcgtcgcct | gctatctgac | attttcattc | ctgctttgcg tgcgaccagt | 540 |
| cacgggtggg | gggagttaga | aggactccag | gacgccgcga | atatccggca ggaattcctg | 600 |
| tccagcctgg | aaggttttgt | taacgtcctg | tccggcgccc | aggagagcct taaggagaag | 660 |
| gtgaacttac | gaaagtgcga | catactcgag | ctcaaaaccc | tgaaggaacc tacagactac | 720 |
| ctcacccctcg | caaacaaccc | cgaaaccctc | ggcaaaattg | aagattgcat gaaggtttgg | 780 |
| attaagcaga | cggaacaagt | cctggccgag | aacaaccaac | tcctaaagga ggccgacgac | 840 |
| gtgggcccgc | gcgctgagct | ggagcactgg | aagaagaggc | tcagcaagtt taactatctt | 900 |
| cttgagcagc | tgaagagccc | ggacgttaag | gcggtactag | ccgtcctcgc ggctgcgaag | 960 |
| tcgaaactgc | tcaagacctg | gcgtgagatg | gatatacgca | ttacggacgc aaccaacgaa | 1020 |
| gctaaggaca | acgttaagta | cttgtatacc | ctcgagaagt | gctgcgaccc actctactca | 1080 |
| tctgacccgc | tcagtatgat | ggatgccatc | cccacgctaa | ttaacgcaat taagatgatc | 1140 |
| tactcgatat | cgcactatta | caacacgtct | gaaaaaataa | ccagcctctt cgtaaaagtg | 1200 |
| accaaccaga | tcatttcagc | ctgtaaggct | tacatcacaa | caacggcac cgcctccata | 1260 |
| tggaaccagc | cccaggacgt | cgtggaagag | aagatcctat | cggccataaa gctgaagcag | 1320 |
| gagtaccagc | tgtgcttcca | caaaaccaag | cagaaactca | agcagaaccc caatgctaag | 1380 |
| cagttcgact | ctctctgagat | gtatattttc | gggaagtttg | aaaccttcca ccgccgcctg | 1440 |
| gcgaagatca | tcgacatatt | cacaactctg | aagacctaca | gtgttctaca agacagcact | 1500 |
| atagagggtc | tcgaggatat | ggccactaag | taccagggca | ttgtcgcaac tatcaagaag | 1560 |
| aaagaatata | atttcctcga | tcagcgtaag | atggacttcg | accaggacta cgaagaattc | 1620 |
| tgcaagcaga | cgaatgattt | gcataacgaa | ctccggaagt | tcatggacgt aacgtttgcc | 1680 |
| aagattcaaa | acacaaatca | ggcgttgcgg | atgctaaaga | agttcgagcg tctgaacatc | 1740 |
| cctaatctag | ggattgacga | caagtaccaa | cttatactgg | aaaactacgg gctgacatc | 1800 |
| gatatgatct | ccaagctata | taccaagcaa | aagtatgacc | cgccgttagc tcggaatcag | 1860 |
| cccccgatcg | ccgggaagat | cctgtgggca | cggcagcttt | tcaccgcat tcagcagcct | 1920 |
| atgcagctgt | tccagcagca | cccggcggtt | ctctccaccg | ccgaggctaa gccaattata | 1980 |
| cgtagctaca | accgcatggc | gaaagtcctg | ctcgagtttg | aggtcttgtt ccaccgagcg | 2040 |
| tggcttcggc | agatcgaaga | gatccacgtc | gggctcgagg | cctcgctcct ggttaaggcg | 2100 |

```
ccggggaccg gtgagctgtt cgtaaacttc gacccgcaaa tactaatcct gttccgtgaa    2160
accgagtgca tggcccagat gggcctcgag gtctcacctt tggccacgag cctgttccag    2220
aagcgcgacc gctacaagcg gaacttctct aacatgaaga tgatgcttgc cgagtaccag    2280
agggttaagt cgaagatccc tgctgccatc gagcagctca tcgtgccaca tctggccaag    2340
gttgacgagg cactccaacc gggcttggcg gccctgacgt ggacctccct aaacattgag    2400
gcctacttgg aaaatacttt cgcgaagatt aaggatctcg aattactact ggatcgtgtg    2460
aatgacctca tagaattccg gatagacgcg atcctagagg agatgtcgag cacccccctc    2520
tgtcagctcc cgcaggagga gccgctcaca tgcgaggaat ttctccagat gactaaggac    2580
ctctgcgtta acggggccca gatactccat ttcaagtcgt ccctcgttga ggaggcggtg    2640
aatgaactgg ttaatatgct cttggatgtg gaagtgctct cggaggaaga atccgagaag    2700
attagcaacg agaatagcgt gaactacaag aacgagagct cagcaaaacg ggaggagggg    2760
aattttgata cgctgacttc ctccatcaac gcgcgggcca acgctctctt gctgacaaca    2820
gtaacgcgca aaagaagga gactgagatg ctaggagagg aggcgcgcga gctgctgtcc    2880
catttcaacc accaaaatat ggatgcgctt ctcaaagtca cccggaatac cctcgaggcg    2940
atacgcaagc gcatccattc gagccatacg ataaacttca gggacagcaa ctccgcgtca    3000
aatatgaagc agaactcgtt gccgatattc cgggcctcgg tgacgctggc gatcccgaac    3060
attgtgatgg caccggccct cgaggacgta cagcagaccc ttaacaaggc ggtggagtgc    3120
atcatctccg ttcccaaggg cgtccgccag tggtcctcgg agctgctcag caagaaaaag    3180
attcaggagc gtaaaatggc ggcccttcaa tcgaacgaag actccgactc tgacgttgag    3240
atgggagaga acgagctaca ggataccta gaaatcgcct ccgtgaacct ccctatcccg    3300
gtgcagacga aaaactacta caagaacgtc agcgaaaaca aggaaatcgt aaagctggtg    3360
agcgtcctga gtaccatcat taacagcaca aagaaggaag tgataacctc gatggactgc    3420
tttaagcgct acaaccacat ttggcagaaa ggcaaggagg aggctataaa aacgttcatc    3480
acgcagagcc ccctgctctc ggagttcgag tcacaaatcc tctacttcca aaatctggag    3540
caggagatca acgctgagcc ggaatatgtg tgcgtcggct cgatagccct gtacacggct    3600
gatctgaaat ttgcgctgac cgctgagacg aaggcttgga tggtggtgat tggccgacac    3660
tgcaacaaga agtaccggtc tgaaatggag aacatcttta tgctaatcga ggaatttaac    3720
aaaaagctga accgtcccat taaggatctg gacgacatcc gaattgccat ggcggcccta    3780
aaggaaatta gagaggagca gatatccatt gactttcagg ttggccccat cgaagaatca    3840
tatgcccttc tgaatcgata cggtctatta atcgcccgag aggaaataga taaggtggac    3900
acacttcatt atgcatggga gaaactctta gcgcgggccg gcgaagtgca gaataagctc    3960
gtatcgctgc aaccatcatt taagaaggag ctcatcagtg ctgtcgaagt ctttctgcag    4020
gactgccacc agttctatct ggattatgac ctgaacggtc cgatggcgag tggtctgaag    4080
ccccaagagg cttcagaccg gcttattatg ttccaaaatc agtttgataa tatttaccgg    4140
aagtatatca cctatacagg gggtgaagaa ttgtttggtc tcccagccac ccagtaccca    4200
caattattgg aaataaagaa gcagctgaac cttcttcaaa aaatctacac tctctataat    4260
tcggtaattg aaactgttaa ttcctactac gatattctct ggagcgaggt caacattgag    4320
aaaattaaca cgaactctt ggagtttcaa aacagatgcc gcaagttgcc cagagcgctg    4380
aaggactggc aggcttttct cgaccttaaa aaaataatcg atgatttcag tgaatgctgt    4440
cctctcttag aatacatggc ctcaaaggct atgatggaga gacactggga gaggattacg    4500
```

```
actctcacgg ggcattcttt ggacgttggc aacgagtcct tcaagctgcg taatataatg    4560
gaggctccac ttctcaagta caaagaggaa atagaagaca tctgtatatc tgctgtcaaa    4620
gagcgcgata tagaacagaa actaaagcag gtaattaacg aatgggacaa taaaacgttt    4680
acatttggca gtttcaagac acgtggagaa ttattgcttc gtggcgactc cacctcggaa    4740
attatagcta acatggagga ctctctcatg ttactcggct cgctgttatc gaaccggtat    4800
aatatgccat tcaaagcaca gattcagaag tgggtgcagt atctatctaa tagtacggat    4860
attatagaga gctggatgac cgtccagaat ctctggatct acctggaggc ggtgtttgtg    4920
ggtggtgata ttgcgaagca gcttccaaag gaggccaaaa gattctccaa cattgacaaa    4980
tcctgggtca agattatgac tcgggcccac gaagtgccct ccgtggtgca gtgctgcgtt    5040
ggcgacgaaa ccttgggcca gctgttgccc cacctgttgg atcaattgga aatctgccaa    5100
aagagcctga ctggctacct agaaaaaaag cgtctgtgct ttccccggtt cttttcgtt     5160 tctgaccctg cactactcga aatcttgggt caggcctcag attctcacac aattcaggct    5220
catttgttaa atgtgtttga caacatcaaa agtgtgaaat tcatgaaaaa gatttatgac    5280
aggatcttgt ccatttcatc ccaagagggg gaaaccattg agcttgataa gcctgtgatg    5340
gcagagggaa acgtggaggt ctggttaaac agtctcctgg aagagtccca gtcctcactg    5400
cacctggtaa tccgccaggc ggcggctaat atccaggaga caggattcca gctcacggaa    5460
ttccttagtt cgtttccggc gcaagtgggg ctcctcggca ttcagatgat ctggacgaga    5520
gattcggagg aagccctcag aaacgccaag tttgacaaga agattatgca gaaaactaac    5580
caagccttcc tagagctcct caacaccctg atcgatgtca caacacgtga tctatcgtct    5640
accgagcggg tcaagtatga gacactgatt accatacacg tgcaccagcg tgatatattc    5700
gatgatctct gccacatgca cataaagagt cccatggact tcgaatggct aaaacagtgc    5760
cgcttctact ttaatgaaga ctcggataag atgatgatcc atatcacaga tgtagcgttt    5820
atttaccaaa acgagttcct tggctgcaca gacaggttag tcataactcc gttaactgat    5880
cgctgctaca ttacactcgc ccaagcgctt ggaatgtcca tgggtggagc ccccgcaggg    5940
ccggcgggga ctggtaagac cgaaacaact aaagatatgg gccgttgcct cgggaagtat    6000
gtggtagttt ttaactgctc agaccaaatg gatttccgag gctgggccg tatctttaaa     6060 gggctggcgc aatcaggttc ctggggctgt tttgacgagt tcaatcgtat tgatttaccg    6120
gtgctaagtg ttgccgcaca gcaaattagt ataattctaa cttgtaagaa agaacacaag    6180 aaaagttta tatttactga tggcgacaac gtcactatga atcctgaatt cgggcttttc     6240
ttgactatga acccagggta tgctggccgt caagaacttc ctgaaaatct gaagatcaac    6300
tttcgatcgg tggctatgat ggtaccggat cgccagatca ttatccgagt aaaactggct    6360
tcgtgtggct tcatcgacaa cgtcgtactt gctcgaaagt tcttcaccct ttacaagcta    6420
tgtgaggagc agttatcgaa acaagttcat tacgactttg ggctccggaa tatcttgtcc    6480
gtcctccgca cactcggagc ggctaaacgt gcaaatccca tggacactga gagtacgatt    6540
gtgatgcgag tgttaaggga tatgaatctc tcaaaattaa tcgacgagga cgagcctctt    6600 ttttaagcc ttatagagga tctgttccca aacatcctcc tggacaaggc gggatatccc     6660
gagttggaag cggccattag caggcaggtg gaggaggccg gattgattaa tcacccgccc    6720
tggaaactga aagtcatcca gctgttcgag actcagcggg tccgacacgg tatgatgact    6780
ttaggcccat ctggcgcggg caaaaccacc tgcatccaca ccctgatgag ggctatgacc    6840
```

```
gattgtggga agcctcaccg tgagatgcgg atgaacccga aggcgatcac tgcgcccaa    6900 atgtttgggc gtctggatgt ggcgacaaat gactggaccg atggaatctt tagcacactc    6960
tggaggaaga ccctgcgcgc caaaaaagga gagcacatct ggatcattct cgatggcccc    7020
gttgacgcta tttggatcga aaacttaaac agcgtgctcg acgacaacaa gacccctgaca   7080 ttggcaaatg gtgaccggat tcctatggct cccaattgca aaatcatttt tgaacctcac    7140
aacatcgaca acgccagtcc ggctacggtg tcccgcaacg gtatggtttt catgagcagt    7200
tccatactgg attggagtcc gatattggaa ggatttctca agaaacgcag tccccaggag    7260
gcggaaattc tgcggcaact gtatacgaaa agttttcctg acctgtaccg cttctgtatt    7320
caaaatctcg agtataagat ggaggtgttg gaggccttcg tcatcacaca gtccattaac    7380
atgcttcagg gcttgatccc cttgaaggag caaggagggg aagtcagcca ggcacatcta    7440
gggcggcttt tcgttttcgc ccttctctgg tccgcgggtg ctgctctcga gctagacgga    7500
cgccggcgct tggagttgtg gctgaggtct cgcccgaccg ggacactcga gctcccgccg    7560
ccagccggac ccggggacac tgcattcgac tactacgtag ctccggacgg cacctggacc    7620
cactggaaca cccgtacgca ggagtatctc tatcccagcg atacaactcc tgagtatggt    7680
agcatactcg ttccgaacgt agacaacgtc agaaccgact ttctgatcca gaccattgct    7740
aagcagggca aggcagtcct acttatcgga gagcaaggga ccgcgaaaac cgtgattatc    7800
aagggcttca tgagtaaata tgacccagag tgtcatatga ttaaatccct caacttctcc    7860
tctgctacca caccactcat gtttcagcgc actatcgaat cctacgtgga caagcggatg    7920
ggcaccacct acgaccgcc tgccgggaag aagatgacgg tatttataga cgacgttaac     7980
atgcccatca tcaacgagtg gggagatcaa gtgaccaacg aaatcgttcg gcaacttatg    8040
gaacaaaacg ggttctataa cctcgagaag ccgggcgagt tcacctcaat agtagacatt    8100
caatttctgg cagctatgat ccacccccgga ggaggacgga acgacattcc ccagcggctc    8160
aagcgccaat tcagcatctt caactgcacg ctgccaagtg aagcatcggt tgacaaaatc    8220
ttcggcgtca tcggggtggg tcactactgc acccagcgcg gcttttcaga ggaagtccga    8280
gattctgtta ctaaactggt tccttttgact agaaggctgt ggcagatgac caaaattaaa    8340
atgcttccta ctccagctaa attccactac gtgttcaatc tgcgagactt atccagggta    8400
tggcaaggta tgcttaatac cacctctgag gtaattaaag aaccgaacga tctgctgaaa    8460
ctgtggaagc acgaatgtaa gagagttatt gcagataggt ttactgtatc gtcagatgtt    8520
acctggttcg ataaagcact ggtgtctttg gtcgaagaag agtttgggga agagaagaag    8580
ctactcgtcg attgcgggat agacacttac tttgtggact tcttaagaga cgcccctgag    8640
gctgccggcg aaacatcgga agaggcagac gctgagactc ctaagatcta tgagccgatc    8700
gagagcttta gccacctcaa ggagcgtctg aatatgtttt tacaattgta taacgagagc    8760
attcgtggtg ctgggatgga tatggtgttc ttcgccgatg caatggtgca tctggttaag    8820
attagccggg tgattcgcac gccacaggga aacgcgctac tggtcggggt gggtgggtca    8880
ggaaagcaat cgttaactcg tttggcatcc tttatcgcgg gatatgtgag ttttcaaatc    8940
accctgacga ggtcctataa tacatccaac ctgatggagg atcttaaagt tttgtacagg    9000
acggcgggac aacagggcaa aggaataacc ttcatcttca cagataacga aattaaagac    9060
gaatcattct ggagtatat gaacaacgtc ttatcaagcg gcgaagtttc gaacctcttc     9120
gcgcgggacg aaatcgatga gatcaactct gatctcgctt ctgtcatgaa gaaagaattc    9180
ccccgctgtt tgccgacgaa tgagaacttg catgactatt tcatgtcccg tgtgcggcag    9240
```

```
aatttgcaca ttgtgctatg tttttcaccg gtgggggaga agttccgaaa tagagctttg   9300
aagttccctg ctttgatttc tgggtgtact attgactggt tttcccgttg gcccaaggac   9360
gctctggtcg ccgtgtccga gcactttta accagctatg atatcgactg cagcctcgaa   9420
attaagaagg aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt tatatatggg gagaaacacg ttgaagtaag gactctggca   9600
aaccgtatga atactggctt agagaagctc aaggaggcct cagaatccgt ggctgctctc   9660
tcaaaggagc ttgaagctaa ggagaaggaa ctccaagttg ctaacgataa agcggatatg   9720
gttctaaagg aagtcactat gaaagcacaa gcggctgaaa aggttaaggc ggaggtacag   9780
aaggtgaagg atcgcgccca ggcaatagtc gattccattt ccaaagacaa ggccatcgcg   9840
gaagaaaagc tagaagcggc gaagccggcc ttagaagagg cagaggctgc cttgcaaacc   9900
ataagaccca gtgacatcgc cacggtacga acccttggtc gtcctcctca tttgattatg   9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatttgca acaattcccc aaggacacca ttaacgaaga ggtcatagaa  10140
tttttatctc catattttga gatgccagac tacaatattg aaacagcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca gcaggctga gcttgacgtt  10380 gtgcaagcag aatacgaaca agctatgaca gaaaagcaga ctttattaga agacgctgaa  10440
cgctgcagac ataagatgca gactgcaagc accctcatat ccggtttggc tggagaaaaa  10500
gagcggtgga cagagcagtc gcaagaattc gctgctcaaa ccaaaaggtt ggttggagac  10560
gttctactcg cgacagcgtt tctctcctat tctggtcctt tcaaccagga attccgggac  10620
cttttgctga atgactggag aaaagaaatg aaggctcgca aaataccatt tggaaagaat  10680
ttgaacttgt ctgaaatgct tattgacgca cccactatat cagagtggaa tcttcaggga  10740
cttccaaatg acgatctgtc catccaaaac ggaattattg taaccaaggc gagccgctac  10800
cctctgctaa ttgacccgca gacacagggc aagatctgga ttaaaaataa ggaaagcagg  10860
aacgagctcc agatcactag tctcaaccac aagtacttcc gtaaccacct cgaagatagt  10920
ctgtccctgg gacggccgtt gctaatcgag gacgtcggag aagagctgga ccccgcatta  10980
gacaacgttc ttgaaagaaa ttttatcaag acaggatcaa ctttcaaagt taaagtagga  11040
gataaagaag tggatgtgtt agatggcttc cgcctatata tcacgactaa actcccgaat  11100
cccgcctata ctccagagat cagcgctaga actagcatca tagatttcac tgtaactatg  11160
aaggggttag aagatcaatt attaggacgc gtcatcctga cggagaaaca ggaacttgaa  11220
aaagagcgta cacacctcat ggaagacgtg acagctaaca acgtcggat gaaggaactg  11280 gaggacaatt tactgtatcg gttgacatca acacagggct cccttgttga ggacgagagt  11340
ctgatcgtgg tcctgtctaa cacaaagagg actgctgaag aagtcactca gaaattggag  11400
atttctgccg aaactgaagt tcagattaac tccgctagag aagagtatcg tccagtcgct  11460
actcggggct ctatcctata cttcctcata actgagatgc gcttggtcaa tgagatgtac  11520
cagacttcac tccggcaatt cctgggcttg tttgacttgt cgctggcaag atcagtaaaa  11580
```

```
tctccaatta ccagcaagag aatcgcaaac atcattgagc acatgacgta cgaggtgtat   11640
aaatacgcgg cgaggggtct ttatgaagag cataagttcc tcttcaccct actattaacg   11700
ttgaagatag atattcagag gaaccgggtg aagcacgagg agtttctaac tctaataaaa   11760
ggaggagctt ctttagatct taaagcctgt ccaccgaaac cttctaagtg gattttagac   11820
ataacatggc tgaatttagt ggagttgtcc aagttacgtc agttcagtga cgttttggat   11880
cagatatcta ggaacgagaa gatgtggaag atctggttcg ataaagagaa tccggaggag   11940
gagcccttgc caaatgctta tgataaaagc ctagactgct tcaggaggct tttgctcatc   12000
cgctcctggt gccccgaccg cactattgcc caagctagga aatacattgt ggactccatg   12060
ggggagaagt atgccgaagg agtcatactc gacttggaga agacttggga agagtcagat   12120
ccgaggacgc ccctcatttg tcttctttcc atgggttctg atcccacgga ctctattata   12180
gcactcggga aaagactaaa gatcgagaca cgctatgtta gcatgggaca ggggcaagag   12240
gtccatgccc gcaaactact acagcagact atggctaatg gaggttgggc tctgttacag   12300
aactgtcact taggccttga ttttatggac gaattgatgg acatcataat tgagacggag   12360
ctagttcacg acgcatttcg cttatggatg acgactgaag cacacaagca gtttccgata   12420
accctgttgc agatgtccat caagttcgcc aacgaccctc cccagggcct tagggcaggt   12480
ctcaaaagga cctacagcgg cgtttcccag gatttacttg acgtctccag cggatcccag   12540
tggaagccca tgttgtacgc cgtggctttc cttcacagca cagttcagga aaggcggaag   12600
tttggtgcgc taggctggaa catcccctac gagttcaacc aggctgactt taatgcaaca   12660
gtacagttta ttcaaaatca tctggatgac atggatgtca aaaaaggtgt gtcatggact   12720
acaataaggt acatgattgg ggagatacag tacggaggcc gggtaactga tgattatgat   12780
aaaagattgt taaacacttt tgctaaagtt tggtttagtg aaaatatgtt tggacctgat   12840
tttagttttt atcaaggtta atatacct aagtgctcaa ctgtagataa ttatttacaa   12900
tatattcaaa gtttacctgc atatgatagt cctgaagttt ttggtttgca tcctaatgca   12960
gatataacat accaatcaaa attagcaaaa gacgtcttag atacaatact tggtatccag   13020
cctaaggaca ccagtggggg cggtgacgag actcgcgagg ctgtggtggc ccggctcgct   13080
gatgacatgc tagagaaact tcccccggac tacgtcccct ttgaggtcaa agagcggctg   13140
cagaaaatgg ggcccttcca gcccatgaac atattcttgc gccaggagat agaccgtatg   13200
caacgagtcc tgagcctggt ccgctcgact ctaaccgagc tcaagctggc catcgatggg   13260
acgatcatta tgtctgagaa tttgagggac gcgctcgatt gcatgtttga cgccaggatc   13320
ccagcctggt ggaaaaaagc tagttggatc tcatctaccc tggggttctg gttcacagag   13380
ttgatagagc gcaactcgca attcacctcc tgggtgttca acgggcggcc ccactgcttc   13440
tggatgacgg gcttcttcaa cccgcagggc ttcctgacgg ctatgcggca ggaaatcacc   13500
cgggcgaaca agggttgggc gctcgacaat atggtgctct gcaacgaggt cacgaagtgg   13560
atgaaggacg acatctcggc gcctcccacc gaagggtct acgtatacgg cctgtacctc   13620 gaggggggcgg gctgggacaa gcgtaacatg aagctgatcg agtcgaagcc caaggtgctg   13680
ttcgagctga tgcccgtcat ccggatctac gcagagaaca cacgctgcg cgacccgcgg   13740 ttctactcgt gccccatcta caagaagccg gtgcggacgg acctcaacta catcgccgcc   13800
gtcgacctcc gcaccgcgca gaccccgag cactgggtgc tgcggggggt cgcattgctc   13860
tgcgacgtca agtag                                                    13875
```

```
<210> SEQ ID NO 29
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 29
atgttcagaa tcgggcggcg acaattatgg aaacactcag tcactagagt tctaacacaa      60
aggttaaaag gagaaaaaga agcaaaaaga gcgctattgg acgcaagaca taattatttg     120
ttcgcgatag tcgcatcgtg tttagattta aataaaactg aagtagaaga cgctattttg     180
gaaggaaatc aaatcgaacg gatcgaccaa ttattcgcgg ttggaggact ccgtcattta     240
atgtttact  accaagacgt ggaggaagcg gaaactgggc aactcgggtc acttggggga     300
gttaacttag tctcaggtaa aattaagaag ccaaaagtat ttgtaacaga aggaaacgac     360
gttgcactaa caggtgtttg cgtatttttt attcgaactg atccgtcaaa agccattaca     420
ccagataata ttcatcagga gtttcatttt aacatgctag atgctgctga tggaggttta     480
ctaaattccg tacgtaggtt gctaagcgat attttcattc ctgccctaag agcaacttct     540
cacggatggg gtgagttaga aggtttacaa gacgctgcaa acatacgtca agaattcctt     600
tcaagtcttg agggatttgt caatgtgctc tcaggagccc aagaatcact aaaggagaaa     660
gtaaatttga gaaagtgtga tattcttgaa ttgaaaacct aaaagaacc  taccgattat     720
ctaacgcttg caaataatcc tgagacatta ggtaaaatcg aggattgtat gaaagtgtgg     780
atcaaacaga ctgaacaagt cttagcagaa aataaccagt tattaaaaga agcggatgac     840
gttggaccgc gagcagaact agaacactgg aagaagaggc taagtaaatt taattatctt     900
cttgaacaac tgaagtctcc agatgttaag gcggttctcg cggtgttagc agctgcaaaa     960
tcaaaactcc ttaaaacgtg gcgtgaaatg gatataagga ttactgatgc aactaacgaa    1020
gcaaagata  acgtaaaata tttgtatacg ctcgaaaagt gttgtgatcc tttatattca    1080
tcagatccac ttagtatgat ggacgctata cctacattaa ttaacgctat taaaatgatt    1140
tatagtatct ctcattatta aatacaagc  gaaaaaataa cttccttatt cgtaaaagtc    1200
acgaaccaga ttatatcagc gtgtaaagca tatataacta caacggtac  tgcatctata    1260
tggaatcagc cccaagacgt ggttgaggaa aaaattttga gtgctataaa attaaaacaa    1320
gaatatcaat tgtgctttca taaaactaaa caaaaactga agcaaaatcc aaatgcaaaa    1380
caatttgact tttctgaaat gtatatattc ggtaaattcg aaacgtttca ccgtcgatta    1440
gccaaaatta tcgacatctt tacgacgtta aaaacttaca gcgtgctaca agattctacg    1500
atagaagggc tagaggatat ggccacaaag taccagggca tcgtggccac tatcaagaag    1560
aaggagtaca acttcttaga ccagcgtaaa atggatttcg accaggacta tgaagaattc    1620
tgcaaacaaa cgaatgatct gcacaacgag ctgcggaaat tcatggatgt gacttttgcc    1680
aaaatacaga ataccaacca agctcttagg atgttaaaga aatttgaaag gctcaacatt    1740
cctaatttgg gcattgatga caaataccag ttgatactcg aaaattatgg agcagatatt    1800
gatatgatct ctaaaactata cacaaaacaa aaatatgatc ctccgttagc tagaaatcaa    1860
ccgccgatt  ctggtaagat actctgggcc agacaactct tcaccgcat  ccagcagccc    1920
atgcagctgt ttcagcagca ccctgcggtg ctctccaccg ccgaggcgaa accattatt    1980
cgatcttata accgcatggc caaggttctg ttagagtttg aagttttgtt ccaccgtgcc    2040
tggttacgtc agatcgagga gatccatgtg ggactggagg cctctctcct agtcaaggcc    2100
```

```
cccggcaccg gcgaactctt tgtcaatttt gatccccaga ttctaatact cttccgggaa     2160
accgagtgca tggcccagat gggtttagag gttagtcctc tggctacttc actgttccag     2220
aagagggacc gctataaacg gaatttcagc aatatgaaga tgatgctcgc tgagtatcag     2280
agggtcaagt ccaaaatccc cgctgcgatc gagcagctga tcgtgccaca cctggccaaa     2340
gtagatgagg ccctacaacc aggactggct gcgctgacgt ggacctctct gaatatcgaa     2400
gcgtatcttg aaaacacctt tgccaagatt aaagacctgg agctttttact ggacagagtg     2460
aacgacctca ttgaattccg catagacgcg attttagagg agatgtcttc cacgccacta     2520
tgtcagcttc ctcaggagga gcctctcaca tgtgaagagt tccttcagat gactaaggat     2580
ctctgcgtga atggcgctca gatactacat ttcaaatcta gcttggtcga ggaggcagtg     2640
aacgaattgg ttaacatgtt actggatgta gaagtcctta gcgaggagga atccgaaaag     2700
atcagcaacg aaaattcggt gaactataag aacgaatctt ctgccaagcg ggaggagggc     2760
aactttgata cactcacatc ttccatcaat gcgcgcgcta atgcactctt gttgacgacg     2820
gttaccagga aaagaagga gactgagatg cttgggaag aggcaaggga gttactgtcc     2880
cacttcaacc atcagaatat ggacgccttg ttaaaggtta cccgaaacac gttagaggca     2940
attcgtaagc gtattcactc aagccacacg ataaacttcc gagactcaaa ctcagcatca     3000
aatatgaagc aaaactcctt gccgatcttc agagccagcg tcaccctggc catacctaac     3060
atcgttatgg caccggcact tgaggacgta caacaaacct tgaacaaagc agtagagtgc     3120
atcatcagcg tccctaaagg agttcgccaa tggtccagtg aactgctatc caagaagaag     3180
atccaggagc gtaaaatggc tgcgttacag agtaacgaag attcggactc tgacgttgaa     3240
atgggtgaaa acgagctcca agacacactg gagattgcga gcgttaacct gcctataccc     3300
gtccagacca agaactacta caaaaacgtg tccgaaaaca aggagatcgt caagctcgtt     3360
tctgtgctca gcaccatcat aaattcgact aagaaagaag ttataacttc catggattgt     3420
ttcaaacggt ataaccacat ctggcagaaa ggcaaggagg aagctatcaa gacatttatt     3480
acccagtccc cactactaag cgagttcgag tctcagatcc tttacttcca gaatcttgag     3540
caggagatca acgcggagcc cgaatatgtg tgcgtcggct cgatagccct gtacacggct     3600
gatctgaaat ttgcgctgac cgcggagacg aaggcttgga tggtggtgat tggccgacac     3660
tgcaacaaga agtaccggtc tgaaatggag aacatcttta tgctaatcga ggaatttaac     3720
aaaaagctga accgtcccat taaggatctg gacgacatca ggattgccat ggcggcccta     3780
aaggaaatta gagaggagca gatatccatt gattttcagg ttggccccat cgaagaatca     3840
tatgcccttc tgaatcgata cggtctatta atcgcccgag aggaaataga taaggtggac     3900
acacttcatt acgcatggga gaaactctta gcgcgggccg gcgaagtgca gaataagctc     3960
gtatcgctgc aaccatcatt taagaaggag ctcatcagtg ctgtcgaggt ctttctgcag     4020
gactgccacc agttctatct ggattatgac ttaaacggtc cgatggcgag tggtctgaag     4080
ccccaagagg cttcagaccg gcttatcatg ttccaaaatc agtttgacaa tatttaccga     4140
aagtatatca cctatacagg gggtgaagaa ttgtttggtc tcccagccac ccagtatcca     4200
caattattgg aaataaaaaa gcagctgaac cttttacaaa aaatctacac tctctataat     4260
tcggtaattg aaactgttaa ttcctactac gatattctct ggagcgaggt caacattgag     4320
aaaattaata acgaactctt ggagtttcaa aacagatgcc gcaagttgcc gagagcgctg     4380
aaggactggc aggcttttct cgaccttaag aaaataatcg atgatttcag tgaatgctgt     4440
cctctcttag aatacatggc gagtaaggct atgatggaga cacactggga gaggattacg     4500
```

```
actctgacgg ggcattcttt agacgttggc aacgagtcct tcaagctgcg taatataatg   4560
gaggctccac ttctcaaata caaagaggaa atagaagaca tctgtatctc tgctgtcaaa   4620
gagcgcgaca tagaacagaa actaaagcag gtcattaacg aatgggacaa taaaacgttt   4680
acatttggca gtttcaagac acgtggagaa ttattgcttc gtggcgactc cacctcggaa   4740
attatcgcta acatggagga ctctctcatg ttactcggct cgctgttatc gaaccggtat   4800
aatatgccat tcaaagcaca gatccagaag tgggtgcagt atctatctaa tagcacggat   4860
attatagaga gctggatgac cgtccaaaat ctctggatct acctggaggc ggtgtttgtg   4920
ggaggtgata ttgcgaagca gcttccaaag gaggccaaaa gattctccaa catcgacaag   4980
tcctgggtca agattatgac tcgggcccac gaagtgccct ccgtggtgca gtgctgcgtt   5040
ggggacgaaa ccttgggcca gctgttgccc cacctgttgg atcaattgga aatctgccaa   5100
aagagcctga cgggctacct agaaaaaaag cgtctgtgct ttccccggtt cttttcgtt    5160
tctgaccctg cactactcga aatcttgggt caggcctcag attctcacac aattcaggct   5220
catttgttaa atgtgtttga caatatcaaa agtgtgaaat tcatgaaaaa gatttatgac   5280
aggatcttgt ccatttcatc ccaagagggg gaaaccattg agcttgataa gcctgtgatg   5340
gcagagggaa acgtggaggt ctggcttaac agtctcctgg aagagtccca gtcctcactg   5400
cacctggtca tccgccaggc ggcggctaat atccaggaga caggattcca gctcacggaa   5460
ttccttagtt cgtttccggc gcaagtgggg ctcctcggaa ttcagatgat ctggacgaga   5520
gattcggagg aagccctccg caacgccaag tttgacaaga agattatgca gaaaactaac   5580
caagccttcc tagagctcct caacaccctg atcgatgtca caacacgtga tctatcgtct   5640
accgagcggg tcaagtatga gacactgatt accatacacg tgcaccagcg tgatatattc   5700
gacgatctct gccacatgca cataaagagt cccatggact tcgaatggct aaaacagtgc   5760
aggttctact ttaacgaaga ctcggataag atgatgatcc atatcacaga tgtagcgttt   5820
atttaccaaa acgagttcct tggctgcaca gacaggttag tcataactcc gttaactgat   5880
cgctgctaca ttacactcgc ccaagcgctt ggaatgtcca tgggtggagc ccccgcaggg   5940
ccggcgggga ctggtaagac cgaaacaact aaagatatgg gccgttgcct cgggaagtat   6000
gtagtagttt ttaactgctc agaccaaatg gatttccgag ggctgggccg tatctttaaa   6060
gggctggcgc aatccggttc ctgggctgt tttgacgagt tcaatcgtat tgatttaccg    6120
gtgctaagtg ttgccgcaca gcaaattagt ataatattga cttgtaagaa agaacacaag   6180
aaaagtttta tatttactga tggcgacaac gtcactatga atcctgaatt cgggcttttc   6240
ttgactatga acccagggta tgctggccgt caagaacttc ctgaaaatct gaagatcaac   6300
tttcgatcgg tggctatgat ggtaccggat cgccagatca ttatccgggt aaaactggcg   6360
tcgtgtggct tcatcgacaa cgtggtactt gctcgaaagt tcttcaccct ttacaagcta   6420
tgtgaggagc agttatcgaa acaagttcat tacgactttg ggctccggaa tatcttgtcc   6480
gtcttacgca cactcggagc ggctaaacgt gcaaatccca tggacactga gagtacgatt   6540
gtgatgaggg tgttaaggga tatgaatctc tcaaaattaa tagacgagga cgagcctctt   6600
tttctctccc ttatagagga tctgttccca aacattctcc tggacaaggc gggatatccc   6660
gagttggaag cggcgatcag caggcaggtg gaggaggccg gattgattaa tcacccgccc   6720
tggaaactga agtcatcca gctgttcgag actcagcggg tccgacacgg tatgatgact   6780
ttaggcccct ctggcgcggg gaaaaccacc tgcatccaca ccctgatgag ggctatgacc   6840
```

```
gattgtggga agcctcaccg tgagatgcgg atgaacccga aggcgatcac agcgcccaa      6900
atgtttgggc gtctggatgt ggcgacaaat gactggaccg atggaatctt ttccacactc     6960
tggaggaaga ccctgcgcgc aaaaaaagga gagcacatct ggatcattct cgatggcccc    7020
gttgacgcta tttggatcga aaacttaaac agcgtgctcg acgacaacaa gaccctgaca    7080
ttggcaaatg gtgaccggat tcctatggct cccaattgca aaatcatttt tgaacctcac    7140
aacatcgaca acgccagtcc ggctacggtg tcccgcaacg gtatggtttt catgagcagt    7200
tccatactgg attggagtcc gatattggaa ggatttctca agaaacgcag tccccaggag    7260
gcggaaattc tgcggcaact gtatacgaaa agtttccctg acctgtaccg cttctgtatt    7320
caaaatctcg agtataagat ggaggtgttg gaggccttcg tcatcacaca gtccattaac    7380
atgcttcagg gcttgatccc cttgaaggag caaggagggg aagtcagcca ggcacatcta    7440
gggcggcttt tcgttttcgc ccttctctgg tccgcgggtg ctgctctcga gctagacggt    7500
cgccggcgct tggagttgtg gctgaggtct cgcccgaccg ggacactcga gctgccgccg    7560
ccagccggac ccgcgacac  tgcattcgac tactacgtag ctccggacgg cacctggacc    7620
cactggaaca cccgtacgca ggagtatctc tatcccagcg atacaactcc tgagtatggt    7680
agcatactcg ttccgaacgt agacaacgtc agaaccgact ttctgatcca gaccattgct    7740
aagcagggca aggcagtcct attgatcgga gagcaaggga ccgcgaaaac cgtgattatc    7800
aagggcttca tgagtaaata tgacccagag tgtcatatga ttaagtccct taacttcagt    7860
tctgctacca caccactcat gtttcagcgt actatcgaat cctacgtgga caagcggatg    7920
ggcaccacct acgggccgcc tgccgggaag aagatgacgg tatttataga cgacgttaac    7980
atgcccatca tcaacgagtg gggagatcaa gtgaccaacg aaatcgttcg gcaacttatg    8040
gaacaaaacg ggttctataa cctcgagaag ccgggcgagt tcacctcaat agtagacatt    8100
caatttctgg cagctatgat ccaccccgga ggaggacgga acgacattcc ccagcggctc    8160
aagcgccaat tcagcatctt caactgcacg ctgccaagtg aagcatcggt agacaaaatc    8220
ttcggcgtca tcggggtggg tcactactgc acccagcgcg gcttttcaga ggaagtccga    8280
gattctgtta ctaaactggt tcctttgact agaaggctgt ggcagatgac caaaattaaa    8340
atgcttccta ctccagctaa attccactac gtgttcaatc tgcgagactt atccagggta    8400
tggcaaggta tgcttaatac cacctctgag gtaattaaag aaccgaacga tctgctgaaa    8460
ctgtggaagc acgaatgtaa gagagttata gcagataggt ttactgtatc gtcagatgtt    8520
acctggttcg ataaagcact ggtgtctttg gtcgaagaag agtttgggga agagaagaag    8580
ctactcgtcg attgcgggat cgacacttac tttgtggact tcttaagaga cgcccctgag    8640
gctgccggcg aaacatcgga agaggcagac gctgagactc ctaagatcta tgagccgatc    8700
gagagcttta gccacctcaa ggagcgtctg aatatgtttt tacaattgta taacgagagc    8760
attcgtggtg ctgggatgga tatggtgttc ttcgcggatg caatggtgca tctggttaag    8820
atttctcggg tcattcgcac gccacaggga aacgcgctac tggtcggggt gggtgggtca    8880
ggaaagcaat cgttaactcg tttggcatcc tttatcgcgg gatatgtgag ttttcaaatc    8940
acactgacaa ggtcctataa tacatccaac ctgatggagg atcttaaagt tctttacagg    9000
acggcgggac aacagggcaa aggaataacc ttcatcttca cagataacga aattaaagac    9060
gaatcattct ggagtatat  gaacaacgtc ttatcaagcg gcgaagtttc gaacctcttt    9120
gcgcgggacg aaatcgatga gatcaactct gatctcgctt ctgtcatgaa gaaagaattc    9180
ccccgctgtt tgccgacgaa cgagaacttg catgactatt tcatgtcccg tgtgcggcag    9240
```

```
aatttgcaca ttgtgctttg cttttcaccg gtgggcgaga agttccgaaa tagagctttg   9300
aagttccctg ctttgatttc tgggtgtact attgactggt tttcccgttg gcccaaggac   9360
gctctggtcg ccgtgtccga gcactttta accagctatg atatcgactg cagcctcgaa   9420
attaagaagg aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt tatatacggg gagaaacacg ttgaagtaag gactctggcg   9600
aaccgtatga atactggctt agagaagctc aaggaggcct cagaaagtgt ggctgctctc   9660
tcaaaggaac ttgaagctaa ggagaaggaa ctccaagttg cgaacgataa agcggatatg   9720
gttctaaaag aagtcactat gaaagcacaa gcggctgaaa aggttaaggc ggaggtacag   9780
aaggtgaaaa atcgcgccca ggcaatagtc gattccattt ccaaagacaa ggccatcgcg   9840
gaagaaaagc tagaagccgc caagccggcc ttagaagagg cagaggctgc cttgcaaacc   9900
ataagaccga gcgacatcgc gacggtacga acccttggtc gtcctcctca tttgattatg   9960
aggattatgg actgtgtcct gcttttattt caacgtaaag tatctgcagt taagattgat  10020
ttggagaaat cctgtaccat gccctcatgg caggaatccc tgaaattgat gaccgcgggc  10080
aatttccttc aaaatctaca acaattcccc aaggacacca ttaacgaaga ggtcatagaa  10140
tttttatctc catattttga gatgccagat tacaatatag aaacagcgaa gcgcgtctgt  10200
ggaaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatatgaaca agctatgact gaaaagcaga ctttattaga ggacgctgaa  10440
cgctgcagac ataagatgca gactgcaagc accctcatat ccgggttggc tggagaaaaa  10500
gagcggtgga cagagcagtc gcaagaattc gctgctcaaa ccaaaaggtt ggttggagac  10560
gttctactcg cgacagcttt cctctcctat tctggtcctt tcaaccagga attccgggac  10620
cttttgctga atgactggag aaaagaaatg aaggctcgca agataccatt tggtaagaat  10680
ttgaacttgt ctgaaatgct tattgacgca cccactatat cagagtggaa tcttcaggga  10740
cttccaaatg acgatctgtc catccaaaac ggaattattg taaccaaggc gagtcgctac  10800
cctctgctca ttgacccgca gacacagggc aagatctgga ttaaaaataa ggaaagcagg  10860
aacgaattgc agatcactag tctcaaccac aagtacttcc gtaaccacct cgaagatagt  10920
ctgtccctgg gaaggccgct tctgatcgag gacgttggcg aggagctgga tcctgcgctg  10980
gacaacgttc ttgagcgcaa cttcatcaag accgggtcca ccttcaaggt aaaggtggga  11040
gacaaggagg tggacgtgct ggacggcttt cgcctatata tcaccacgaa gctgcctaac  11100
ccggcgtaca cgcccgagat cagtgcgcgt acgagcatca ttgacttcac cgtgactatg  11160
aaaggcctcg aagatcagct gctcggtcgc gtcattctca cggaaaagca ggagctggag  11220
aaggagcgaa cgcacctgat ggaggacgtg acggccaaca agcggcgtat gaaagagcta  11280
gaggacaacc tgctgtaccg cctcacgtca acccaggggt cgctggtcga ggacgaatcc  11340
ctgatcgtgg tgctgagtaa taccaagcgg acagcagagg aggtcacgca gaaactcgag  11400
atctcggcgg agaccgaggt gcagatcaac agcgcgcggg aggagtacag gccggtggcc  11460
acccgcggga gcatcttata cttcctgatc actgagatgc gccttgtgaa tgagatgtac  11520
cagacaagcc tgcggcagtt ccttggcctg ttcgatcttt cgctggcccg gtccgtcaag  11580
```

```
tctccgatta cctccaagcg gatcgctaac ataattgaac acatgacgta cgaggtgtac    11640
aagtacgcgg cgaggggcct ctacgaagag cacaagttcc tgttcacgct gctcctcacg    11700
ctcaagatcg acatccagcg caaccgcgtc aagcacgagg agtttctcac cctgataaag    11760
gggggagcgt ccctggacct gaaggcctgt ccgccgaagc cgtcgaagtg gatcctggac    11820
ataacgtggc tcaacctcgt cgagctgtcc aagctccgtc agttttcgga cgtgctcgac    11880
cagatttcgc ggaacgagaa gatgtggaaa atatggttcg acaaggagaa tccagaggag    11940
gagcccttgc ccaacgcgta tgacaagtcg ctcgactgct tccgtcgcct gctgctgatc    12000
cgcagctggt gccccgaccg gacgatcgcg caggcgagga agtacatcgt tgacagtatg    12060
ggtgagaaat acgcggaggg cgttattctg gatctggaga agacttggga ggagagcgac    12120
ccccgcaccc ccctgatctg ccttctgtct atggggtccg acccgaccga tagcatcatt    12180
gctctgggga agcggctcaa gatcgagacc cggtacgtgt ccatgggaca ggggcaggag    12240
gtgcatgccc gcaagctcct gcagcagact atggcgaacg ggggttgggc gctcttacag    12300
aactgccatc tggggctcga cttcatggat gaactcatgg acatcatcat cgagacggaa    12360
ctcgtgcacg acgcattccg cctgtggatg accaccgagg cgcacaagca gttcccgatc    12420
acgttgctgc agatgtccat caagttcgcc aacgaccctc cgcagggcct ccgggcgggc    12480
ctgaagcgca cgtatagcgg cgtgtctcag gatctccttg atgtcagctc ggggagccag    12540
tggaagccga tgctctatgc cgtggcattt ctacactcga ccgtccagga gcggcgaaag    12600
tttggagcgc tggggtggaa catacccctac gagtttaacc aggccgactt caacgccacc    12660
gtgcagttca tccagaacca tttgacgat atggatgtga agaaggggg gtcctggacg    12720 accatacggt atatgatcgg cgagatccag tatgggggc gggtcacgga cgactacgac    12780
aagcggttgc tgaacacgtt cgcgaaggtc tggttcagcg agaatatgtt cgggcccgat    12840
tttccttttt accagggcta caatataccc aagtgctcca cggtcgacaa ctaccttcag    12900
tacatccaga gcttgcccgc atacgacagc ccggaagtct tcggactcca ccccaacgcc    12960
gacatcacgt accagagcaa gctggccaag gacgtgctcg acaccattct cggcatccag    13020
ccgaaggaca cgtccggcgg gggggacgag acgcgggagg ccgtcgtcgc gcgcttggca    13080
gatgacatgc tggagaagct cccccccgat tacgtcccgt tcgaggtcaa ggaaaggctc    13140
cagaagatgg gcccgttcca gcccatgaac atcttcctcc gccaggagat cgaccggatg    13200
cagcgcgtgc ttagcctggt gcgctcaacg ctgacggagc tgaagctggc catcgacggg    13260
acgatcatta tgtcggagaa cctccgggac gcgctggact gcatgttcga cgcgcgtatc    13320
ccggcctggt ggaagaaggc gtcgtggatc tccagcaccc tggggttctg gttcacggag    13380
ctgatcgagc gcaactcgca attccactcc tgggtgttca acgggcggcc ccactgcttc    13440
tggatgacgg gcttcttcaa cccgcagggc ttcctgacgg ctatgcggca ggaaatcacc    13500
cgggcgaaca aggttgggc gctcgacaat atggtgctct gcaatgaggt cacgaagtgg    13560
atgaaggacg acatctcggc gcctcccact gaagggtct acgtctacgg cctgtacctc    13620 gaggggcgg gctgggacaa gcgtaacatg aagctgatcg agtcgaagcc caaggtcctg    13680
ttcgagctga tgcccgtcat ccgcatctac gccgagaaca cacgctgcg cgacccgcgg    13740 ttctactcgt gccccatcta caagaagccg gtgcggacgg acctcaacta catcgccgcc    13800
gtcgacctcc gcaccgcgca gaccccccgag cactgggtgc tgcgggggt cgcactgctc    13860 tgcgacgtca agtag                                                     13875
```

```
<210> SEQ ID NO 30
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 30
atgttcagaa taggaaggag acaactatgg aagcacagcg tgacgcgggt acttacccaa      60
cgtctaaagg gggagaagga ggcgaagcgg gcactgctag acgcgcgtca taattaccte     120
tttgcaatag ttgccagctg cctcgacctc aacaagacgg aggtagagga cgccatatta     180
gagggcaacc agattgagcg gatcgatcag ctatttgccg tgggcgggct ccggcatcta     240
atgtttact accaggacgt cgaggaagct gagaccgggc aactgggatc cctgggaggc      300
gtcaacctcg tctccggcaa gataaaaaag cctaaggttt tcgttacaga gggcaacgac     360
gtagcgctga ctggtgtatg cgtcttcttc atccggacag accccagcaa ggcaattacg     420
ccagacaaca tccaccagga ggtctcgttt aacatgctcg acgctgccga tggcgggctg     480
ctgaactcgg tgcgccggct gctctcggat atctttatcc ccgcgcttcg ggcgacgagc     540
cacgggtggg gtgagctgga aggcctacag gacgcggcca atattcgtca ggagttccta     600
tccagcctgg aaggttttgt taacgtgctg tccggcgccc aggagtcgct taaggagaag     660
gtgaacttac gaaagtgtga tatattagag ctgaaaaccc tgaaggaacc tacagactat     720
ctcacccteg caaacaaccc cgaaaccctc ggcaaaattg aagattgcat gaaggtgtgg     780
attaagcaga cggaacaagt cctggcagag aacaaccaac tcttgaagga ggccgacgac     840
gtgggcccgc gcgctgagct ggagcactgg aagaagaggc tcagcaagtt taactatctt     900
cttgagcagc tgaagagccc ggacgttaag gcggtactag cggtcctcgc ggctgcgaag     960
tcgaagctgc tcaagacctg gcgtgagatg gacatacgca tcacggacgc aaccaacgaa    1020
gctaaggaca acgttaagta tttgtatacc ctcgagaagt gctgcgaccc cctctactca    1080
tctgatccgc tcagtatgat ggatgccatc cccacgctaa ttaacgccat taagatgatc    1140
tactcgatat cgcactatta caacacgtct gaaaaaatca ccagcctctt cgtaaaagtg    1200
actaaccaaa tcatcagcgc ctgcaaggct tacatcacta caacggcac cgccagtata     1260
tggaaccagc cccaggacgt cgtggaggag aagatcctat cggccataaa gctgaagcag    1320
gagtatcagc tgtgcttcca caaacaaag cagaaactca gcagaaccc aaatgctaag      1380
cagttcgact ttctgagat gtacattttc gggaagtttg aaacatttca tcgccgcctg    1440
gccaaaatca tcgacatatt caccactctg aagacctact cagtcctaca agacagcact    1500
atagaagggc tagaggatat ggccacaaag taccagggca tcgtggccac tatcaaaaag    1560
aaggagtaca acttcttaga ccagcgtaaa atggatttcg accaggacta tgaagaattc    1620
tgcaaacaaa cgaatgattt gcacaacgag cttcggaaat tcatggatgt gactttgcc    1680
aaaatacaga ataccaacca agctcttagg atgttaaaga aatttgaaag gcttaatatt    1740
cctaatttgg gcattgatga caaataccag ttgatactcg aaaattatgg agcagatatt    1800
gatatgatct ctaagctgta cacaaaacaa aaatatgatc ccccgctagc tagaaatcaa    1860
cctccgattg ctggtaagat actctgggcc agacagctct tcaccgcat ccagcagccc     1920
atgcagctgt tcagcagca ccctgcggtg ctgtccaccg ccgaagcgaa acccattatt     1980
cgatcttata accgcatggc caaggttctg ttagagtttg aagttttgtt ccaccgtgcc    2040
tggttacgtc agatcgagga gatccatgtg ggactggagg cctctctcct agtcaaggcc    2100
```

```
cccggcacag gcgaactctt tgtcaatttt gatccccaga ttctaatact cttccgggaa    2160
accgagtgca tggcccagat gggcttagag gttagtcctc tggctacttc tctgttccag    2220
aagagagacc gctataaacg gaatttcagc aatatgaaga tgatgctcgc tgaatatcag    2280
agggtcaagt ccaaaatccc cgctgcgatc gagcagctga tagtgccaca cctggccaaa    2340
gtagatgagg ccctacaacc aggactggcc gcgctgacgt ggacctctct gaatatcgaa    2400
gcgtatttgg agaacacctt tgccaagatc aaggacctgg agcttttact ggacagagtg    2460
aacgatctca ttgaattccg catagacgcg attttagagg agatgtcttc cacgccacta    2520
tgccagcttc ctcaggagga gccgttaaca tgtgaagagt tcctgcagat gactaaggac    2580
ctctgcgtga atggcgctca gatactacat ttcaagtcta gcttggtcga ggaggcagtg    2640
aacgaattgg ttaacatgtt actggatgta gaagtccttt ccgaggagga atccgaaaag    2700
atcagcaacg aaaattcggt gaactataag aacgaatcta gcgccaagcg ggaggagggc    2760
aactttgata cactcacttc ttccatcaat gcgagggcta atgctctctt gttgacaacc    2820
gttaccagaa aaaaaagga gactgagatg cttggggaag aggcaaggga gttgctgtcc    2880
cacttcaacc atcagaatat ggacgccctc ttaaaggtta cccgaaacac gttagaggca    2940
attaggaagc gtattcactc aagccacacg ataaacttca gagactcaaa ctctgcatca    3000
aatatgaagc aaaactcctt gccgatcttc agagccagcg tcaccctggc catacctaac    3060
atcgttatgg caccggcact tgaggacgta caacaaacct tgaacaaagc agtagagtgc    3120
atcatcagcg tccctaaagg agttcgccaa tggtccagtg aactgctatc caagaagaag    3180
atccaggagc gtaaaatggc tgcgttacag agtaacgaag attcggactc tgacgttgaa    3240
atgggtgaaa acgaactcca agacacactg gagattgcga gcgttaacct gcctataccc    3300
gtccagacca agaactacta caaaaacgta tccgaaaaca aggagatcgt caagctcgtt    3360
tctgtgctca gcaccataat aaattcgact aagaaagagg ttataacttc catggattgt    3420
ttcaaacggt ataaccacat ctggcagaaa ggcaaggaag aagctatcaa gacatttatt    3480
acccagagcc cactactaag cgagttcgag tctcagatcc tctacttcca gaatcttgag    3540
caggagatca acgctgagcc cgaatatgtg tgcgtcggct cgatagccct gtacacggct    3600
gatctgaaat ttgccctgac cgctgagact aaggcttgga tggtggtgat tggccgacac    3660
tgcaacaaga agtaccggtc tgaaatggag aacatcttta tgctaatcga ggaatttaac    3720
aaaaagctga accgtcccat taaggatctg gacgacatca ggattgccat ggcggcccta    3780
aaggaaatta gagaggagca gatatccatt gattttcagg ttggccccat cgaagaatca    3840
tatgcccttc tgaatcgata cggtctatta atcgcccgag aggaaataga taggtggac    3900 acacttcatt atgcatggga gaaactctta gcgcgggccg gcgaagtgca gaataagctc    3960
gtatcgctgc agccatcatt taagaaggag ctcatcagtg ctgtcgaggt ctttctgcag    4020
gactgccacc agttctatct ggattatgac ctgaacggtc cgatggcgag tggtctgaag    4080
ccccaagagg cttcagaccg gcttatcatg ttccaaaatc agttcgacaa tatttaccga    4140
aagtatatca cctatacagg gggtgaagaa ttgtttggtc tcccagccac ccagtatcca    4200
caattattgg aaataaagaa gcagctgaac cttcttcaaa aaatctacac tctctataat    4260
tcggtaattg aaactgttaa ttcctactac gatattctct ggagcgaggt caacattgag    4320
aaaattaata cgaactctt ggagttccaa aacagatgcc gcaagctgcc gagagcgctg    4380
aaggactggc aggcttttct cgaccttaag aaaataatcg atgatttcag tgaatgctgt    4440
cctctcttag aatacatggc gagtaaggct atgatggaga cactgggaga ggattacg    4500
```

```
actctgacgg ggcattcttt ggacgttggc aacgagtcct tcaagctgcg taatataatg    4560
gaggctccac ttctcaagta caaagaggaa atagaagaca tctgtatatc tgctgtcaaa    4620
gagcgcgaca tagaacagaa actaaagcag gtaattaacg agtgggacaa taaaacgttt    4680
acatttggca gtttcaagac acgtggagaa ttattgcttc gaggtgactc cacctcggaa    4740
attatcgcta acatggagga ctctctcatg ttactcggct cgctgttatc gaaccggtat    4800
aatatgccat tcaaagcaca gatccagaag tgggtgcagt atctatctaa tagtacggat    4860
attatagaga gctggatgac cgtccagaat ctctggatct acctggaggc ggtgtttgtg    4920
ggaggtgata tagcgaagca gcttccaaag gaggccaaaa gattctccaa cattgacaaa    4980
tcctgggtca agattatgac tcgggcccac gaagtgccct ccgttgtgca gtgctgcgtc    5040
ggggacgaaa ccttgggcca gctgttgccc cacctgttgg atcaattgga aatctgccaa    5100
aagagcctga ctggctacct agagaaaaag cgtctgtgct ttccccggtt cttcttcgtt    5160
tctgaccctg cactactcga aatcttgggt caggcctctg attctcacac aattcaggct    5220
catttgttaa atgtgtttga caacatcaaa agtgtgaaat tcatgaaaaa gatttatgac    5280
aggatcttgt ccatttcatc ccaagaggga gaaaccattg agcttgataa gcctgtgatg    5340
gcagagggaa acgtggaagt ctggcttaac agtctcctgg aagagtccca gtcctcactg    5400
cacctggtca tccgccaggc ggcggctaat atccaggaga caggattcca gctcacggaa    5460
ttccttagtt cgtttccggc gcaagtgggg ctcctcggca ttcagatgat ctggacgaga    5520
gattcggagg aagccctccg caacgccaag tttgacaaga agattatgca gaaaactaac    5580
caagccttcc tagagctcct caacactctg atcgatgtca caactcgtga tctatcgtct    5640
accgagcggg tcaagtatga gacactcatt accatacacg ttcaccaacg tgatatattc    5700
gatgatctat gccacatgca cataaagagt cccatggact tcgaatggct aaaacagtgc    5760
aggttctact ttaatgaaga ctctgataaa atgatgatac acatcacaga tgttgctttt    5820
atctatcaaa acgaattttt aggttgtacc gacagactag taatcactcc attgacagat    5880
agatgttata ttacacttgc tcaggctcta ggtatgagta tgggtggagc accagcgggt    5940
ccggcaggaa caggtaaaac agaaacgaca aaggatatgg gacgttgttt aggtaaatat    6000
gtagtcgtat ttaactgttc tgaccaaatg gattttcgtg gtcttggtag aattttttaaa    6060
ggtttagctc aatcaggttc ttggggttgt tttgacgaat ttaatcggat agatttgcct    6120
gttttatctg tcgcggctca acaaatctcc ataattttaa cttgtaaaaa gaacataaaa    6180
aaaagtttca tttttaccga tggtgataac gttacgatga ccctgaatt tggtttgttc    6240
ttaactatga atccaggata cgccggccgt caagagttac ctgaaaattt gaaaataaac    6300
tttagatcag tggctatgat ggttcctgat cgccagatta ttatccgagt caaattagca    6360
agttgtggat ttattgataa cgttgtttta gcaagaaagt tttttacact atacaaatta    6420
tgtgaggaac aattgtctaa acaagtacat tacgattttg gtctaagaaa tatattatca    6480
gtattgcgaa cattaggagc agctaagaga gcaaatccaa tggatactga atcaactatt    6540
gtaatgcgcg ttttaagaga tatgaattta tcaaagttaa ttgatgaaga cgaacctctt    6600
tttctcagcc ttatagagga tctgtttcca aacattctcc tggacaaggc gggatatccc    6660
gagttggaag cggccattag caggcaggtg gaggaggccg gattgattaa tcacccgccc    6720
tggaaactga agtcatcca gctgttcgag actcagcggg tccgacacgg tatgatgact    6780
ttaggcccat ctggcgcggg caaaaccacc tgcatccaca cccttatgag ggctatgacc    6840
```

```
gactgtggga agcctcaccg tgagatgcgg atgaacccga aggcgatcac tgcgcccaa    6900
atgtttgggc gtctggatgt ggcgacaaat gactggaccg atgggatctt ttccacactc   6960
tggaggaaga ccctgcgcgc caaaaaagga gagcacatct ggatcattct cgatggcccc   7020
gttgacgcta tttggatcga aaacttaaac agcgtgctcg acgacaacaa gaccctgaca   7080
ttggcaaatg gtgaccggat tcctatggct cctaattgca aaataatttt tgaacctcac   7140
aacatcgaca acgccagtcc ggctacggtg tcccgcaacg gtatggtttt catgagcagt   7200
tccatactgg attggagtcc gatattggaa ggatttctca agaaacgcag tccccaggag   7260
gcggaaattc tgcggcaact gtatacgaaa agttttcctg acctgtaccg cttctgcatt   7320
caaaatctcg agtataagat ggaggtgttg gaggccttcg tcatcacaca gtccattaac   7380
atgcttcagg gcttgatccc cttgaaggag caagggggg aagtcagcca ggcacatcta    7440
gggcggcttt ttgttttcgc cctgctctgg tccgcgggtg ctgctctcga gctagacggt   7500
cgccggcgct tggagttgtg gctgaggtct cgcccgaccg ggacactcga gctgccgccg   7560
ccagccggac ccggggacac tgcattcgac tactacgtag ctccggacgg cacctggacc   7620
cactggaaca cccggacgca ggagtatctc tatcccagcg atacaactcc tgagtatggt   7680
agcatactcg ttccgaacgt agacaacgtc agaaccgact ttctgatcca gaccattgct   7740
aagcaaggca aggcagtcct attgatcgga gagcaaggga ccgcgaaaac cgtgattatc   7800
aagggcttca tgagtaaata tgacccagag tgtcatatga ttaagtcact caacttcagt   7860
tctgctacca caccactcat gtttcagcgt actatcgaat cctacgtgga caagcggatg   7920
ggcaccacct acgggccgcc tgccgggaag aagatgacgg tatttataga cgacgttaac   7980
atgcccatca tcaacgagtg gggagatcaa gtgaccaacg aaatcgttcg gcaacttatg   8040
gaacaaaacg ggttctacaa cctcgagaag ccgggcgagt tcacctcaat agtagacatt   8100
caatttctgg cagctatgat ccaccccgga ggaggacgaa acgacattcc ccagcggctg   8160
aagcgccaat tcagcatctt caactgcacg ctgccaagcg aagcatcggt agacaaaatc   8220
ttcggcgtca tcggggtggg tcactactgc acccagcgcg gcttttcaga ggaagtccga   8280
gattctgtta ctaaactggt tccttttgact agaaggctgt ggcagatgac caaaattaaa   8340
atgcttccta ctccagctaa attccactac gtgttcaatc tgcgagactt atccagggta   8400
tggcaaggta tgcttaatac cacctctgag gtaattaaag aaccgaacga tctgctgaaa   8460
ctgtggaagc acgaatgtaa gagagtcatt gcagataggt ttactgtatc gtcagatgta   8520
acctggttcg ataaagcact ggtgtctttg gtcgaagaag agtttgggga agagaagaag   8580
ctactcgtcg attgcgggat cgacacttac tttgtagact tcttaagaga cgcccctgag   8640
gctgccggtg aaacatcgga agaggcagac gctgagactc ctaagatcta tgagccgatc   8700
gagagcttta gccacctcaa ggagcgtctg aatatgtttt tacaactcta taacgagagc   8760
attcgtggtg ctgggatgga tatggtgttc ttcgcggatg caatggtgca tctggtcaag   8820
atctctcggg tgattcgcac gccacaggga aacgcgctac tggtcggggt gggtgggtca   8880
ggaaagcaat cgttaactcg tttggcatcc tttatcgcgg atatgtgtc atttcaaatc    8940
accctgacaa ggtcctataa tacatccaac ctgatggagg atcttaaagt tctctacagg   9000
acggcgggac aacagggcaa aggaataacc ttcatcttca cagataacga aattaaagac   9060
gaatcattct tggagtatat gaacaacgtc ttatcaagcg gcgaagtttc gaacctcttc   9120
gcgcgggacg aaatagatga gatcaactct gatctcgctt ctgtcatgaa gaaagaattc   9180
ccccgctgtt tgccgacgaa tgagaacttg catgactatt tcatgtcccg tgtgcggcag   9240
```

```
aatttgcaca ttgtgctttg cttttcaccg gtgggggaga agttccgaaa tagagctttg   9300
aagttccctg ctttgattag cgggtgtact attgactggt tttcccgttg gcccaaggac   9360
gctctggtcg ccgtgtccga gcactttta acctcttatg atatcgactg cagcctcgaa    9420
attaagaaag aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt catatatggg gagaaacacg ttgaagtaag gactctggca   9600
aaccgtatga atactggctt agagaagctc aaggaggcct cagaaagtgt ggctgctctc   9660
tcaaaggagc ttgaagctaa ggagaaggaa ctccaagttg cgaacgataa agcggatatg   9720
gttctaaaag aagtcactat gaaagcacaa gcggctgaaa aggttaaggc ggaggtacag   9780
aaggttaagg atcgcgccca ggcaatagtc gattccattt ccaaagacaa ggccatcgcg   9840
gaagaaaagc tagaagccgc caagcctgcc ttagaagagg cagaggctgc cttgcaaacc   9900
ataagaccga gtgacatcgc gacggtacga acccttggtc gtcctcctca tttgattatg   9960
aggattatgg actgtgtcct gcttttattt caacgtaaag tatctgcagt taagattgat  10020
ttggaaaaat cctgtaccat gccctcatgg caggagtccc tgaaattgat gaccgcgggc  10080
aatttccttc aaaatctaca acaattcccc aaggacacca ttaacgaaga ggtcatagaa  10140
tttttatctc catattttga gatgccagat tacaatattg aaactgcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tttgcttgct  10320
atgcaggatc ttcagaaggc acaggccgaa ttagacgaca agcaggctga gcttgacgtt  10380
gtgcaagcag aatacgaaca agctatgact gaaaagcaga ctttattaga ggacgctgaa  10440
cgctgcagac ataagatgca gactgcaagc accctcatat ccgggttggc tggagaaaaa  10500
gagcggtgga cagagcagtc gcaagaattt gctgctcaaa ccaaaaggtt ggttggagac  10560
gtgctactcg cgacagcttt tctctcctat tctggtcctt tcaaccagga attccgggac  10620
cttttgctga atgactggag aaaagaaatg aaggctcgca aaataccatt tggtaagaat  10680
ttgaacttgt ctgaaatgct tattgacgca cccactatat cagagtggaa tcttcaggga  10740
cttccgaatg acgacctgtc tatccaaaac ggaattattg taaccaaggc gagtcgctac  10800
cctctgctca ttgacccgca gacacagggc aagatctgga ttaaaaataa ggaaagcagg  10860
aacgaactcc agatcactag tctcaaccac aagtacttcc gtaaccacct cgaagatagt  10920
ctgtccctgg gacggccatt gctaatcgag gacgtcggag aagagctgga ccccgcatta  10980
gacaacgtcc ttgaaagaaa tttcatcaag acaggatcaa cttcaaagt taaagtagga   11040
gataaagaag tggatgtgtt agatggcttc cgcctatata tcacaactaa actcccgaat  11100
cccgcctata ctccagagat cagcgctaga actagcatca tagatttcac tgtaactatg  11160
aagggggttag aagatcaatt attaggacgc gtgatcctga cggagaaaca ggaattgaaa  11220
aaagagcgta cacatctcat ggaagacgtg acagctaaca aacgtcgaat gaaggaactg  11280
gaggacaatt tactgtatcg gttgacatca acacagggct cccttgttga ggacgagagt  11340
ctgatcgtgg tcctgtctaa cacaaagagg actgctgaag aagtaactca gaaattggag  11400
atttctgccg aaactgaagt tcagattaac tccgctagag aagagtatcg tccagtcgct  11460
actcggggct cgatcctata cttcctcata actgagatgc gcttggtcaa tgagatgtat  11520
cagacttcac tccggcaatt cctgggcttg tttgacttgt cgctggcaag atcagtgaaa  11580
```

```
tctccaatta ccagcaagag aatcgcaaac atcattgagc acatgacgta cgaggtgtat    11640
aaatacgcgg caaggggact ttacgaagag cataagttcc tcttcaccct actattaacg    11700
ttgaagatag atattcagag gaaccgggtg aagcacgagg agtttctaac tctaataaaa    11760
ggaggagctt ctttggattt gaaagcctgt ccaccgaaac cttctaagtg gattttagac    11820
ataacatggc tgaatctcgt ggagttgtcc aagctccgtc agttcagtga cgttttggat    11880
cagatatcca ggaacgagaa gatgtggaag atctggttcg ataaagagaa tccggaggaa    11940
gagcccttgc caaatgctta tgataaaagc ctagactgct tcaggaggct tttgctcatc    12000
cgctcctggt gccccgaccg cactattgcc caggctagga atacattgt ggactccatg     12060
ggggagaagt atgccgaagg agtcatactc gacttggaga agacttggga agagtcagat    12120
ccgaggacgc ccctcatttg tcttctttcc atgggttctg atcccacgga ctctattata    12180
gcactcggga aaagactaaa gatcgagaca cgctatgtta gcatgggaca ggggcaagag    12240
gtccatgccc gcaaactact acagcagact atggctaatg gaggttgggc tctgttacag    12300
aactgtcact taggcttaga ttttatggac gaattgatgg acatcataat tgagacggag    12360
ctagtccacg acgcatttcg cttatggatg acgactgaag cacacaagca gtttccgata    12420
accctgttgc agatgtccat caagttcgcc aatgaccctc cccagggcct tagggcaggt    12480
ctcaaaagga cctacagcgg cgtttcccag gatttacttg acgtctcctc cggatcccag    12540
tggaagccca tgttgtacgc tgtggctttc cttcacagca cagttcagga aaggcggaag    12600
tttggtgcgc taggctggaa catcccctac gagttcaacc aggctgactt taatgcaaca    12660
gtacagttta ttcaaaatca tctggatgac atggatgtta aaaaaggtgt gtcatggact    12720
acaataaggt acatgattgg ggagatacag tacggaggcc gggtaactga tgattatgac    12780
aagcggctac tgaacacttt cgctaaagtg tggttttctg agaatatgtt cggtccagat    12840
ttcagcttct accaaggtta taacattcca aagtgctcca cagtcgacaa ctacctccaa    12900
tatattcaaa gtttacctgc atatgatagt cctgaagttt ttggtttgca tcctaatgca    12960
gatataacat atcaaagtaa attagcaaaa gacgtcttag atacaatact aggaatccaa    13020
ccaaaagata catccggtgg gggagacgaa actcgagaag ccgttgttgc aagattagca    13080
gatgatatgt tagaaaaatt acctcctgac tatgtacctt ttgaagttaa agaacgtttg    13140
caaaaaatgg gaccttttca accaatgaat atctttctaa ggcaggagat tgatcgaatg    13200
caaagggttt tatccttagt acgatctact ttaacagaac ttaaactagc tatagatggt    13260
actataatta tgagtgaaaa tttaagagac gcattagatt gtatgtttga tgcaaggatt    13320
ccagcttggt ggaaaaaagc atcttggata tcatcaacat tgggattttg gtttactgaa    13380
ttgatagaac gtaattctca atttacaagt tgggtattta atggtcgtcc acattgtttt    13440
tggatgactg gttttttttaa tccacaagga ttttttaactg ccatgagaca ggaaataact    13500
agagcaaata agggttgggc attagataat atggttttgt gtaatgaagt aactaagtgg    13560
atgaaagacg atataagtgc accaccaact gagggtgttt atgtatatgg tttatattta    13620
gaaggagctg gatgggataa acgtaatatg aaattaatag aatcgaaacc aaaagtttta    13680
tttgaattaa tgccagttat cagaatttat gcagagaata atacattaag agatcctaga    13740
ttttatagtt gtccaattta taaaaaacct gtcagaacag atcttaatta tatagcagcc    13800
gtcgatctta gaactgctca aacaccagaa cattgggtat taagaggagt agctttactt    13860
tgtgatgtta aatag                                                     13875
```

<210> SEQ ID NO 31
<211> LENGTH: 13875
<212> TYPE: DNA
<213> ORGANISM: Artificial Sequence
<220> FEATURE:
<223> OTHER INFORMATION: Synthetic polynucleotide

<400> SEQUENCE: 31

```
atgttcagaa tcggaaggcg gcaattatgg aagcattcag taactagagt cttgacacag      60
aggctcaaag gtgaaaaaga ggcaaagcgt gcgctattgg atgcacggca taattacttg     120
ttcgcgatag tagcaagttg tttagatcta aacaaaactg aagtagaaga cgccattctc     180
gaaggaaatc aaattgagcg gattgaccaa ttattcgctg ttggaggcct cagacattta     240
atgtttact atcaagacgt tgaagaagcg gaaactgggc aactcgggtc actaggtggc      300
gttaatttag tctcaggtaa aattaaaaag ccaaaagtat ttgttactga gggcaacgac     360
gtggccctaa ctggagtatg tgtgttttt attcggaccg acccgagtaa ggccattacg      420
ccagacaata ttcatcaaga ggtatcattt aacatgctag atgctgctga tggtggactt     480
ctgaatagcg tgcgtcgcct gctatctgac attttcattc ctgctttacg cgcgaccagt     540
cacgggtggg gggagcttga aggcctccag gacgccgcca atatcaggca ggaattcctg     600
tcctccttag aaggttttgt gaatgttctc agcggtgccc aggagtcact aaaagaaaag     660
gtgaacttgc ggaagtgtga cattcttgaa ttaaagactc tgaaggagcc aaccgattac     720
ctcacgttag ctaacaaccc ggagactcta ggcaaaatcg aggactgcat gaaggtgtgg     780
atcaaacaga ctgagcaagt tttagcagaa acaaccagc tccttaagga agcggatgac     840
gtaggccctc gggcggaact tgaacattgg aagaagcggt tgtctaagtt taattatctt     900
cttgaacagc ttaaatctcc tgatgtcaaa gcagtgcttg cagtcctcgc tgcagcaaag     960
tccaagctgc ttaagacctg gcgtgaaatg gacataagga taactgacgc taccaatgaa    1020
gctaaggata cgttaagta cctatacaca ctagagaagt gttgtgatcc tttatactcc    1080
tctgatccac tgtctatgat ggatgcaata cctacgctaa tcaacgctat taagatgatt    1140
tatagtatct ctcactatta taacacatct gagaaaatta cttccctttt cgtgaaagtt    1200
acgaaccaga ttattagcgc ctgcaaggct tacataacca ataacggtac agcgagcata    1260
tggaatcagc cacaggacgt cgttgaagag aagattttgt ccgccatcaa attgaaacag    1320
gagtaccagc tgtgcttcca taaaacaaag cagaagctga gcagaaccc aaacgctaag    1380
cagttcgact ctctgagat gtatatttt gggaaatttg aaaccttcca ccgacgtcta    1440
gccaaaatta tcgacatctt tacgacgtta aaaacttaca gcgtgctgca agattctacg    1500
atagaagggc tagaggatat ggccacaaag taccagggca tcgtggccac tatcaaaaag    1560
aaggagtaca acttcttaga ccagcgtaaa atggatttcg accaagacta tgaagaattc    1620
tgcaaacaaa cgaatgattt gcacaacgag cttcggaaat tcatggatgt gacttttgcc    1680
aaaatacaga ataccaacca agctcttagg atgttgaaga aatttgaaag ttgaatatt    1740
cctaatttgg gcattgatga caaataccag ttgatactcg aaaattatgg agcagatatt    1800
gatatgatct ctaaactgta cacaaaacaa aaatatgatc ccccgctagc tagaaatcaa    1860
cctccgattc tggtaagat actctgggcc agacaactct ttcaccgcat ccagcagccc    1920
atgcagctgt ttcagcagca ccctgcggtg ctctccaccg ccgaggcgaa acccattatt    1980
cgatcttata accgcatggc caaggttctg ttagagtttg aagttttgtt ccaccgtgcc    2040
tggttacgtc agatcgagga gatccatgtg ggactggagg cctctctcct agtcaaggcc    2100
```

```
cccggcacag gcgaactctt tgtcaatttt gatccccaga ttttaatact cttccgggag    2160
accgagtgca tggcccagat gggcttagag gttagtcctc tggctacttc tctgttccag    2220
aagagagacc gctataaacg gaatttcagc aatatgaaga tgatgctcgc tgaatatcag    2280
agggtcaagt ccaaaatccc cgctgcgatc gagcagctga tagtgccaca cctggccaaa    2340
gtagatgagg ccctacaacc aggactggcc gcgctgacgt ggacctctct gaatatcgaa    2400
gcgtatttgg agaacacgtt tgccaagatt aaggacctgg agcttttact ggacagagtg    2460
aacgatctca ttgaattccg catagacgcg attttagagg agatgtcttc cacgccacta    2520
tgccagcttc ctcaggagga gcctttaaca tgtgaagagt tccttcagat gactaaggac    2580
ctctgcgtga atggcgctca gatactacat ttcaagtcta gcttggtcga ggaggcagtg    2640
aacgaattgg ttaacatgtt actggatgta gaagtcctta gcgaggagga atccgaaaag    2700
atcagcaacg aaaattcggt gaactataag aacgaatcta gcgccaagcg ggaggagggg    2760
aactttgata ctctcacttc ttccatcaat gcgagggcta atgctctctt gttgacgacc    2820
gttaccagaa aaaaaagga gactgagatg cttggggaag aggcaaggga gttgctgtcc    2880
catttcaacc atcagaatat ggacgccctc ttaaaggtta cccgaaacac gttagaagcc    2940
attaggaagc gtattcactc aagccacacg ataaatttcc gcgactcaaa ctcagcatca    3000
aatatgaagc aaaactcctt gccgatcttc agagccagcg tcaccctggc catacctaac    3060
atcgttatgg caccggcact tgaggacgta caacaaacct tgaacaaagc agtagagtgc    3120
atcatcagtg tccctaaagg agttcgccaa tggtccagtg aactgctatc caagaagaag    3180
atccaggagc gtaaaatggc tgcgttacag agtaacgaag attcggactc tgacgttgaa    3240
atgggtgaaa acgagctcca agacacactg gagattgcga gcgttaaccc gcctatacct    3300
gtccagacca agaactacta caaaaacgtg tcggaaaaca aggagattgt caagctcgtt    3360
tctgtgctca gcaccataat aaattcaact aagaaagaag ttataacttc catggattgt    3420
ttcaaacggt ataaccacat ctggcagaaa ggcaaggaag aagctatcaa aacatttatt    3480
acccagagcc cactactaag cgaattcgag tctcagatcc tctacttcca gaatcttgag    3540
caggagatca acgctgagcc cgaatatgtg tgcgtcggct cgatagccct gtacacggct    3600
gatctgaaat ttgcgctgac cgctgagaca aaggcttgga tggtggtgat tggccgacac    3660
tgcaacaaga agtaccggtc tgaaatggag aacattttta tgctaatcga ggaatttaac    3720
aaaaagctga accgtcccat taaggatctg gacgacatca ggattgccat ggcggcccta    3780
aaggaaatta gagaggagca gatatccatt gattttcagg taggccccat cgaagaatca    3840
tatgcccttc tgaatcgata cggtctatta atcgcccgag aggaaataga taaggtggac    3900
acacttcatt atgcatggga gaaactctta gcgcgggccg gcgaagtgca gaataagctc    3960
gtatcgctgc agccatcatt taagaaggag ctcatcagtg ctgtcgaggt ctttctgcag    4020
gactgccacc agttctatct ggattatgac ctgaacggtc cgatggcgag tggtctgaag    4080
ccccaagagg cttcagaccg gcttatcatg ttccaaaatc agttcgacaa tatttacagg    4140
aagtatatca cctatacagg gggtgaagaa ttgttcggtc tcccagccac ccagtatcca    4200
caattattgg aaataaagaa gcagttaaac cttcttcaaa aaatctacac tctctataat    4260
tcggtaatag aaactgttaa ttcctactac gatattctct ggagcgaggt caatattgag    4320
aaaattaata cgaactcttt ggagttccaa aacagatgcc gcaagttgcc gagagcgctg    4380
aaggactggc aggcttttct cgaccttaag aaaataatcg atgatttcag tgaatgctgt    4440
cctctcttag aatacatggc gagtaaggct atgatggaga gacactggga gaggattacg    4500
```

```
actctgacgg ggcattcttt ggacgttggc aacgagtcct tcaagctgcg taatataatg    4560
gaggctccac ttctcaagta caaagaggag atagaggaca tctgtatatc tgctgtcaaa    4620
gagcgcgaca tagaacagaa actaaagcag gtaattaacg aatgggacaa caaaacgttt    4680
acatttggca gtttcaagac acgtggagaa ttattgcttc gaggcgactc cacctcggaa    4740
attatcgcta acatggagga ctctctcatg ttacttggct cgctgttatc gaaccggtat    4800
aatatgccat tcaaagcaca gatccagaag tgggtgcagt atctatctaa tagtacggat    4860
ataatagaga gctggatgac cgtccagaat ctctggatct acttggaggc ggtgtttgtg    4920
ggaggtgata tagcgaagca gcttcccaag gaggccaaaa gattctccaa cattgacaaa    4980
tcctgggtca agattatgac tcgggcccac gaagtgccct ccgtggtgca gtgctgcgta    5040
ggggacgaaa ccttgggcca gctgttgccc cacctgttgg atcaactcga aatctgccaa    5100
aagtctctga ctggctacct agagaaaaag cgtctgtgct ttccccggtt cttcttcgtt    5160
tctgatcctg cactactcga aatcttgggt caggcctctg attctcacac aattcaggct    5220
catttgttaa atgtgtttga acatcaaaa agtgtgaaat tcatgaaaaa gatttatgac    5280
aggatcttgt ccatttcatc ccaagaggga gaaaccattg agcttgataa gcctgtgatg    5340
gcagagggaa acgtggaggt ctggcttaac agtctcttgg aagagtccca gtcctcactg    5400
cacctggtca tccgccaggc ggcggctaat atccaggaga caggattcca gctcacggaa    5460
ttccttagtt cgtttccggc gcaagtgggg ctcctcggca ttcagatgat ctggacgaga    5520
gattcggagg aagccctccg caacgccaag tttgacaaga agattatgca gaaaactaac    5580
caagccttcc tagagctcct caacactctg atcgatgtca caactcgtga cctatcgtct    5640
accgagcggg tcaagtatga gacactgatt acaatccacg ttcaccagcg tgatatattc    5700
gatgatctat gccacatgca cataaaaagt cccatggact tcgaatggct aaaacagtgc    5760
aggttctact ttaatgaaga cagtgataag atgatgatcc atatcacaga tgtagcgttt    5820
atttaccaaa acgagttcct tggctgtaca gacaggttag tcataactcc gttaactgat    5880
cgctgctaca ttacactcgc ccaagcgctt ggaatgtcca tgggtggagc ccccgcaggg    5940
ccggcgggga caggtaagac cgaaacaact aaagatatgg gccgttgcct cgggaagtat    6000
gttgtagtat ttaactgctc agaccaaatg gatttccgag ggctgggccg tatctttaaa    6060
gggctggcgc aatccggttc ctggggctgt tttgacgagt tcaatcgtat tgatttaccg    6120
gtgctaagtg ttgccgcaca gcaaattagt ataattttga catgtaagaa agaacacaag    6180
aaaagtttta tatttactga cggcgacaac gtcactatga atcctgaatt cgggcttttc    6240
ttgactatga acccagggta cgctggccgt caagaacttc ctgaaaatct gaaaatcaac    6300
tttcgatcgg tggctatgat ggtaccggac cgccagatca tcatccgggt aaaactggcc    6360
tcgtgtggct tcatcgacaa cgtcgtactt gctcgaaagt tcttcaccct ttacaagcta    6420
tgtgaggagc agttatcgaa acaagttcat tacgactttg ggctccggaa tatcttgtcc    6480
gtcttacgca cactcggagc ggctaaacgt gcaaatccca tggacactga gagtacgatt    6540
gtgatgcgag tgttaaggga tatgaatctc tcgaagttaa tagacgagga cgagcctctt    6600
tttctcagcc ttatagagga tctgttccca aacatcctcc tggacaaggc tggatatccc    6660
gagttggaag cggcgattag caggcaggtg gaggaggccg gattgattaa tcacccgccc    6720
tggaaactga aagtcatcca gctgttcgag actcagcggg tccgacacgg tatgatgact    6780
ttaggcccat ctggcgcggg gaaaaccacc tgcatccaca ccctgatgag ggctatgacc    6840
```

```
gattgtggga agcctcaccg tgagatgcgg atgaacccga aggcgatcac agcgcccaa      6900 atgtttgggc gtctggatgt ggcgacaaat gactggaccg atggaatctt ttccacactc      6960
tggaggaaga ccctgcgcgc aaaaaagga gagcacatct ggatcattct cgatggcccc      7020
gttgacgcta tttggatcga aaacttaaac agcgtgctcg acgacaacaa gaccctgaca      7080
ttggcaaatg gtgaccggat tcctatggct cccaattgca aaatcatttt tgaacctcac      7140
aacatcgaca acgccagtcc ggctacggtg tcccgcaacg gtatggtttt catgagcagt      7200
tccatactgg attggagtcc gatattggaa ggatttctca agaaacgcag tccccaggag      7260
gcggaaattc tgcggcaact gtatacgaaa agttttcctg acctgtaccg cttctgtatt      7320
caaaatctcg agtataagat ggaggtgttg gaggccttcg tcatcacaca gtccattaac      7380
atgcttcagg gcttgatccc cttgaaggag caaggagggg aagtcagcca ggcacatcta      7440
gggcggcttt tcgttttcgc ccttctctgg tccgcgggtg ctgctctcga gctagacggt      7500
cgccggcgct tggagttgtg gctgaggtct cgcccgaccg ggacactcga gctgccgccg      7560
ccagcgggac ccgggacac tgcattcgac tactacgtag ctccggacgg cacctggacc      7620
cactggaaca cccgtacgca ggagtatctc tatcccagcg atacaactcc tgagtatggt      7680
agcatactcg ttccgaacgt agacaacgtc agaaccgact ttctgatcca gaccattgct      7740
aagcagggca aggcagtcct attgatcgga gagcaaggga ccgcgaaaac cgtgattatc      7800
aagggcttca tgagtaaaata tgacccagag tgtcatatga ttaagtccct caacttcagt      7860
tctgctacca caccactcat gtttcagcgt actatcgaat cctacgtgga caagcggatg      7920
ggcaccacct acgggccgcc tgccgggaag aagatgacgg tatttataga cgacgttaac      7980
atgcccatca tcaacgagtg gggagatcaa gtgaccaacg aaatcgttcg gcaacttatg      8040
gaacaaaacg ggttctataa cctcgagaag ccgggcgagt tcacctcaat agtagacatt      8100
caatttctgg cagctatgat ccaccccgga ggaggacgga acgacattcc ccagcggctc      8160
aagcgccaat tcagcatctt caactgcacg ctgccaagtg aagcatcggt agacaaaatc      8220
ttcggcgtca tcggggtggg tcactactgc acccagcgcg gcttttcaga ggaagtccga      8280
gattcagtta ctaaactggt tccttttgact agaaggctgt ggcagatgac caaaattaaa      8340
atgcttccta ctccagctaa attccactac gtgttcaatc tgcgagactt atccagggta      8400
tggcaaggta tgcttaatac cacctctgag gtaattaaag aaccgaacga tctgctgaaa      8460
ctgtggaagc acgaatgtaa gagagttatt gcagataggt ttactgtatc gtcagatgtt      8520
acctggttcg ataaagcact ggtgtctttg gtcgaagaag agtttgggga agagaagaag      8580
ctactcgtcg attgcgggat cgacacttac tttgtggact tcttaagaga cgcccctgag      8640
gctgccggcg aaacatcgga agaggcagac gctgagactc ctaagatcta tgagccgatc      8700
gagagcttta gccacctcaa ggagcgtctg aatatgtttt tacaattgta taacgagagc      8760
attcgtggtg ctgggatgga tatggtgttc ttcgcggatg caatggtgca tctggttaag      8820
atttctcggg tgattcgcac gccacaggga aacgcgctac tggtcggggt gggtgggtca      8880
ggaaagcaat cgttaactcg tttggcatcc tttatcgcgg gatatgtgag ttttcaaatc      8940
accctgacaa ggtcctataa tacatccaac ctgatggagg atcttaaagt tctctacagg      9000
acggcgggac aacagggcaa aggaataacc ttcatcttca cagataacga aattaaagac      9060
gaatcattct tggagtatat gaacaacgtc ttatcaagcg gcgaagtttc gaacctcttc      9120
gcgcgggacg aaatcgatga gatcaactct gatctcgctt ctgtcatgaa gaaagaattc      9180 cccccgctgtt tgccgacgaa tgagaacttg catgactatt tcatgtcccg tgtgcggcag      9240
```

```
aatttgcaca ttgtgctttg cttttcaccg gtgggggaga agttccgaaa tagagctttg   9300
aagttccctg ctttgatttc tgggtgtact attgactggt tttcccgttg gcccaaggac   9360
gctctggtcg ccgtgtccga gcactttta accagctatg atatcgactg cagcctcgaa    9420
attaagaagg aagtagttca gtgtatgggc tctttccaag acggtgtggc agagaagtgc   9480
gtcgactatt tccagaggtt tcgccgatct actcatgtca cacctaagag ctacttgtcc   9540
ttcatacagg ggtacaagtt tatatatggg gagaaacacg ttgaagtaag gactctggca   9600
aaccgtatga atactggctt agagaagctc aaggaggcct cagaaagtgt ggctgctctc   9660
tcaaaggagc ttgaagctaa ggagaaggaa ctccaagttg cgaacgataa agcggatatg   9720
gttctaaaag aagtcactat gaaagcacaa gcggctgaaa aggttaaggc ggaggtacag   9780
aaggtgaagg atcgcgccca ggcaatagtc gattccattt ccaaagacaa ggccatcgcg   9840
gaagaaaagc tagaagccgc caagccggcc ttagaagagg cagaggctgc cttgcaaacc   9900
ataagaccga gtgacatcgc gacggtacga acccttggtc gtcctcctca tttgattatg   9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatctaca acaattcccc aaggacacca ttaacgaaga ggtcatagaa  10140
tttttatctc catattttga gatgccagat tacaatattg aaacagcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatacgaaca agctatgact gaaaagcaga cttttattaga ggacgctgaa  10440 cgctgcagac ataagatgca gactgcaagc accctcatat ccgggttggc tggagaaaaa  10500
gagcggtgga cagagcagtc gcaagaattc gctgctcaaa ccaaaaggtt ggttggagac  10560
gttctactcg cgacagcttt tctctcctat tctggtcctt tcaaccagga attccgggac  10620
cttttgctga atgactggag aaaagaaatg aaggctcgca aaataccatt tggtaagaat  10680
ttgaacttgt ctgaaatgct tattgacgca cccactatat cagagtggaa tcttcaggga  10740
cttccaaatg acgatctgtc catccaaaac ggaattattg taaccaaggc gagtcgctac  10800
cctctgctca ttgacccgca gacacagggc aagatctgga ttaaaaataa ggaaagcagg  10860
aacgaactcc agatcactag tctcaaccac aagtacttcc gtaaccacct cgaagatagt  10920
ctgtccctgg gacggccgtt gctaatcgag gacgtcggag aagagctgga ccccgcatta  10980
gacaacgttc ttgaaagaaa ttttatcaag acaggatcaa cttcaaagt taaagtagga   11040 gataaagaag tggatgtgtt agatggcttc cgcctatata tcacaactaa actcccgaat  11100
cccgcctata ctccagagat cagcgctaga actagcatca tagatttcac tgtaactatg  11160
aaggggttag aagatcaatt attaggacgc gtgatcctga cggagaaaca ggaattgaaa  11220
aaagagcgta cacacctcat ggaagacgtg acagctaaca acgtcggat gaaggaactg   11280 gaagacaatt tactgtatcg gttgacatca acacagggct cccttgttga ggacgagagt  11340
ctgatcgtgg tcctgtctaa cacaaagagg actgctgaag aagtaactca gaaattggag  11400
atttctgccg aaactgaagt tcagattaac tccgctagag aagagtatcg tccagtcgct  11460
actcggggct ctatcctata cttcctcata actgagatgc gcttggtcaa tgagatgtac  11520
cagacttcac tccggcaatt cctgggcttg tttgacttgt cgctggcaag atcagtaaaa  11580
```

```
tctccaatta ccagcaagag aatcgcaaac atcattgagc acatgacgta cgaggtgtat    11640
aaatacgcgg cgaggggtct ttatgaagag cataagttcc tcttcaccct actattaacg    11700
ttgaagatag atattcagag gaaccgggtg aagcacgagg agtttctaac tctaataaaa    11760
ggaggagctt ctttagattt gaaagcctgt ccaccgaaac cttctaagtg gattttagac    11820
ataacatggc tgaatttagt ggagttgtcc aagttacgtc agttcagtga cgttttggat    11880
cagatatcca ggaacgagaa gatgtggaag atctggttcg ataaagagaa tccgggaggag   11940
gagcccttgc caaatgctta tgataaaagc ctagactgct tcaggaggct tttgctcatc    12000
cgctcctggt gccccgaccg cactattgcc caagctagga aatacattgt ggactccatg    12060
ggggagaagt atgccgaagg agtcatactc gacttggaga agacttggga agagtcagat    12120
ccgaggacgc ccctcatttg tcttctttcc atgggttctg atcccacgga ctctattata    12180
gcactcggga aaagactaaa gatcgagaca cgctatgtta gcatgggaca ggggcaagag    12240
gtccatgccc gcaaactact acagcagact atggctaatg gaggttgggc tctgttacag    12300
aactgtcact taggccttga ttttatggac gaattgatgg acatcataat tgagacggag    12360
ctagtccacg acgcatttcg cttatggatg acgactgaag cacacaagca gtttccgata    12420
accctgttgc agatgtccat caagttcgcc aatgaccctc cccagggcct tagggcaggt    12480
ctcaaaagga cctacagcgg cgtttcccag gatttacttg acgtctcctc cggatcccag    12540
tggaagccca tgttgtacgc tgtggctttc cttcacagca cagttcagga aaggcggaag    12600
tttggtgcgc taggctggaa catcccctac gagttcaacc aggctgactt taatgcaaca    12660
gtacagttta ttcaaaatca tctggatgac atggatgtta aaaaaggtgt gtcatggact    12720
acaataaggt acatgattgg ggagatacag tacggaggcc gggtaactga tgattatgac    12780
aagcggctac tgaacacttt cgctaaagtg tggttttctg agaatatgtt cggtccagat    12840
ttcagcttct accaaggtta taacattcca aagtgctcca cagtcgacaa ctacctccag    12900
tacatccaat cgttaccagc atacgacagc ccggaagttt ttggcctgca cccaaacgcg    12960
gacatcactt atcagtcgaa gctggcaaag gacgtgctcg acaccatcct tggtatacag    13020
cctaaggaca ccagtggggg cggtgacgag actcgcgagg ctgtggtggc ccggctcgct    13080
gatgacatgc tagagaaact tcccccggac tacgtcccct ttgaggtcaa agagcggctg    13140
cagaaaatgg ggcccttcca gcccatgaac atattcttgc gccaggagat agaccgtatg    13200
caacgggtcc tgagcctggt ccgctcgact ctaaccgagc tcaagctggc catcgatggg    13260
acgattatta tgtctgagaa tttgagggac gcgctcgatt gcatgtttga tgccaggatc    13320
ccagcctggt ggaaaaaagc tagttggatc tcatctactc tggggttttg gtttacagag    13380
ttgatagaac ggaacagcca gtttacttct tgggtattca atggtaggcc tcactgtttt    13440
tggatgacag gcttctttaa ccccccagggt ttcctcactg cgatgagaca agagattacg    13500
cgagccaata agggctgggc actagataac atggtcctgt gtaatgaagt gaccaaatgg    13560
atgaaagacg acatatcagc gccccccacc gagggtgtgt acgtatatgg cctctatttg    13620
gaagggggctg gatgggacaa gcgtaacatg aaactgatag aatccaagcc taaggtcctc    13680
tttgagctaa tgccggttat acgaatctac gccgagaaca atacattgag agatccaaga    13740
ttttattctt gtcccatata caagaagcct gtccgtacag atttgaatta cattgctgcc    13800
gtcgacctgc gcaccgcaca aactcccgag cactgggtgc tgcgggggt cgcactgctc    13860
tgcgacgtca agtag                                                    13875
```